US012630498B2

(12) United States Patent
Liao et al.

(10) Patent No.: US 12,630,498 B2
(45) Date of Patent: May 19, 2026

(54) ARYLAMIDES AND METHODS OF USE THEREOF

(71) Applicant: Genzyme Corporation, Cambridge, MA (US)

(72) Inventors: Junkai Liao, Bridgewater, NJ (US); Mark Munson, Bridgewater, NJ (US); Zhongli Gao, Bridgewater, NJ (US); Gregory Hurlbut, Bridgewater, NJ (US); Hans Peter Nestler, Bridgewater, NJ (US); Helen Yeoman, Bridgewater, NJ (US); Martin Smrcina, Bridgewater, NJ (US); Ronghua Li, Bridgewater, NJ (US); Ryan Hartung, Bridgewater, NJ (US); William Wire, Bridgewater, NJ (US); Bertrand Vivet, Bridgewater, NJ (US); Nina Ma, Bridgewater, NJ (US); William Bock, Bridgewater, NJ (US); Aleksandra Weichsel, Bridgewater, NJ (US); Andrew Scholte, Bridgewater, NJ (US)

(73) Assignee: Genzyme Corporation, Cambridge, MA (US)

( * ) Notice: Subject to any disclaimer, the term of this patent is extended or adjusted under 35 U.S.C. 154(b) by 766 days.

(21) Appl. No.: 17/832,384

(22) Filed: Jun. 3, 2022

(65) Prior Publication Data

US 2023/0159438 A1 May 25, 2023

Related U.S. Application Data

(63) Continuation of application No. PCT/US2020/063586, filed on Dec. 7, 2020.

(Continued)

(51) Int. Cl.

| | |
|---|---|
| ***C07C 235/66*** | (2006.01) |
| ***A61K 31/198*** | (2006.01) |
| ***A61K 31/337*** | (2006.01) |
| ***A61K 31/36*** | (2006.01) |
| ***A61K 31/415*** | (2006.01) |
| ***A61K 31/42*** | (2006.01) |
| ***A61K 31/426*** | (2006.01) |
| ***A61K 31/428*** | (2006.01) |
| ***A61K 31/44*** | (2006.01) |
| ***A61K 45/06*** | (2006.01) |
| ***A61P 11/00*** | (2006.01) |
| ***C07C 235/44*** | (2006.01) |

(Continued)

(52) U.S. Cl.

CPC .......... *C07C 235/66* (2013.01); *A61K 31/198* (2013.01); *A61K 31/337* (2013.01); *A61K 31/36* (2013.01); *A61K 31/415* (2013.01); *A61K 31/42* (2013.01); *A61K 31/426* (2013.01); *A61K 31/428* (2013.01); *A61K 31/44* (2013.01); *A61K 45/06* (2013.01); *C07C 317/14* (2013.01); *C07C 321/28* (2013.01); *C07D 213/30* (2013.01); *C07D 231/12* (2013.01); *C07D 261/08* (2013.01); *C07D 277/24* (2013.01); *C07D 277/30* (2013.01); *C07D 277/64* (2013.01); *C07D 305/06* (2013.01); *C07D 317/54* (2013.01); *C07C 2601/02* (2017.05); *C07C 2601/04* (2017.05); *C07C 2601/08* (2017.05); *C07C 2601/14* (2017.05); *C07C 2601/16* (2017.05); *C07C 2602/10* (2017.05)

(58) Field of Classification Search

CPC ... C07C 235/66; C07C 317/14; C07C 321/28; C07C 2601/02; C07C 2601/08; C07C 2601/14; C07C 2601/16; C07C 2601/10; C07C 235/44; A61K 31/198; A61K 31/337; A61K 31/36; A61K 31/415; A61K 31/42; A61K 31/426; A61K 31/428; A61K 31/44; A61P 11/00

See application file for complete search history.

(56) References Cited

U.S. PATENT DOCUMENTS

| | | | |
|---|---|---|---|
| 4,172,896 | A | 10/1979 | Uno et al. |
| 5,358,970 | A | 10/1994 | Ruff et al. |

(Continued)

FOREIGN PATENT DOCUMENTS

| | | | |
|---|---|---|---|
| EP | 0699438 | A2 | 3/1996 |
| EP | 0790057 | A1 | 8/1997 |

(Continued)

OTHER PUBLICATIONS

Azam S., et al., The Ageing Brain: Molecular and Cellular Basis of Neurodegeneration, Front Cell Dev Biol, 9:683459 (2021).

(Continued)

*Primary Examiner* — Kamal A Saeed
*Assistant Examiner* — Sagar Patel
(74) *Attorney, Agent, or Firm* — Goodwin Procter LLP

(57) ABSTRACT

The present disclosure relates to substituted aryl amide compounds, according to Formula (I):

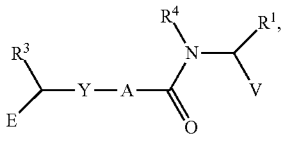

pharmaceutically acceptable salts thereof, and pharmaceutical preparations thereof. Also described herein are compositions and the use of such compounds in methods of treating diseases and conditions mediated by deficient CFTR activity, in particular cystic fibrosis.

57 Claims, No Drawings

Related U.S. Application Data

(60) Provisional application No. 62/944,141, filed on Dec. 5, 2019.

(51) Int. Cl.

| | |
|---|---|
| ***C07C 317/14*** | (2006.01) |
| ***C07C 321/28*** | (2006.01) |
| ***C07D 213/30*** | (2006.01) |
| ***C07D 231/12*** | (2006.01) |
| ***C07D 261/08*** | (2006.01) |
| ***C07D 277/24*** | (2006.01) |
| ***C07D 277/30*** | (2006.01) |
| ***C07D 277/64*** | (2006.01) |
| ***C07D 305/06*** | (2006.01) |
| ***C07D 317/54*** | (2006.01) |

(56) References Cited

U.S. PATENT DOCUMENTS

| | | | |
|---|---|---|---|
| 5,427,798 | A | 6/1995 | Ludwig et al. |
| 5,449,783 | A | 9/1995 | Saita et al. |
| 5,541,231 | A | 7/1996 | Ruff et al. |
| 5,731,000 | A | 3/1998 | Ruff et al. |
| 5,763,493 | A | 6/1998 | Ruff et al. |
| 5,856,347 | A | 1/1999 | Hashiguchi et al. |
| 6,110,973 | A | 8/2000 | Young |
| 8,999,976 | B2 | 4/2015 | Binch et al. |
| 9,790,219 | B2 | 10/2017 | Bastos et al. |
| 2007/0022507 | P1 | 1/2007 | Scully |
| 2009/0233975 | A1 | 9/2009 | Suetsugu et al. |
| 2010/0184739 | A1 | 7/2010 | Sheth et al. |
| 2011/0184177 | A1* | 7/2011 | Hachtel .............. C07D 207/325 546/281.1 |
| 2013/0186801 | A1 | 7/2013 | Verwijs |
| 2015/0005275 | A1 | 1/2015 | Plas et al. |
| 2015/0045327 | A1 | 2/2015 | Van Der Plas et al. |
| 2016/0095858 | A1 | 4/2016 | Miller et al. |
| 2016/0120841 | A1 | 5/2016 | Kym et al. |
| 2016/0122331 | A1 | 5/2016 | Kym et al. |
| 2016/0355480 | A1 | 12/2016 | Altenbach et al. |
| 2019/0248809 | A1 | 8/2019 | Clemens et al. |
| 2023/0137585 | A1 | 5/2023 | Gao et al. |
| 2023/0147360 | A1 | 5/2023 | Liao et al. |
| 2023/0159438 | A1 | 5/2023 | Liao et al. |
| 2023/0159439 | A1 | 5/2023 | Liao et al. |
| 2024/0002374 | A1 | 1/2024 | Liao et al. |
| 2025/0197420 | A1 | 6/2025 | Liao et al. |
| 2025/0197422 | A1 | 6/2025 | Liao et al. |
| 2025/0248975 | A1 | 8/2025 | Liao et al. |
| 2025/0255859 | A1 | 8/2025 | Hurlbut |

FOREIGN PATENT DOCUMENTS

| | | | |
|---|---|---|---|
| EP | 3464282 | A1 | 4/2019 |
| JP | H07149745 | A | 6/1995 |
| JP | 2007504255 | A | 3/2007 |
| JP | 2017074057 | A | 4/2017 |
| WO | WO-9616650 | A1 | 6/1996 |
| WO | WO-98024782 | A2 | 6/1998 |
| WO | WO-03039451 | A2 | 5/2003 |
| WO | WO-2005075435 | A1 | 8/2005 |
| WO | WO-2005120497 | A2 | 12/2005 |
| WO | WO-2006002421 | | 1/2006 |
| WO | WO-2006069656 | A1 | 7/2006 |
| WO | WO-2006113704 | A2 | 10/2006 |
| WO | WO-2007056341 | A1 | 5/2007 |
| WO | WO-2007087066 | A2 | 8/2007 |
| WO | WO-2008000408 | A1 | 1/2008 |
| WO | WO-2008147952 | A1 | 4/2008 |
| WO | WO-2008121877 | A2 | 10/2008 |
| WO | WO-2009074575 | A2 | 6/2009 |
| WO | WO-2009076593 | A1 | 6/2009 |
| WO | WO-2010048526 | A2 | 4/2010 |
| WO | WO-2010048564 | A1 | 4/2010 |
| WO | WO-2010048573 | A1 | 4/2010 |
| WO | WO-2010151747 | A1 | 12/2010 |
| WO | WO-2011072241 | A1 | 6/2011 |
| WO | WO-2011113894 | A1 | 9/2011 |
| WO | WO-2012170889 | A1 | 12/2012 |
| WO | WO-2013003837 | A1 | 1/2013 |
| WO | WO-2013038373 | A1 | 3/2013 |
| WO | WO-2013038378 | A1 | 3/2013 |
| WO | WO-2013038381 | A1 | 3/2013 |
| WO | WO-2013038386 | A1 | 3/2013 |
| WO | WO-2013038390 | A1 | 3/2013 |
| WO | WO-2013043720 | A1 | 3/2013 |
| WO | WO-2014180562 | A1 | 11/2014 |
| WO | WO-2014186704 | A2 | 11/2014 |
| WO | WO-2015018823 | A1 | 2/2015 |
| WO | WO-2015138909 | A1 | 9/2015 |
| WO | WO-2015138934 | A1 | 9/2015 |
| WO | WO-2016130929 | A1 | 8/2016 |
| WO | WO-2016130943 | A1 | 8/2016 |
| WO | WO-2016183173 | A1 | 11/2016 |
| WO | WO-2017062581 | A1 | 4/2017 |
| WO | WO-2017173274 | A1 | 10/2017 |
| WO | WO-2017208115 | A1 | 12/2017 |
| WO | WO-2018042316 | A1 | 3/2018 |
| WO | WO-2018167690 | A1 | 9/2018 |
| WO | WO-2019161078 | | 8/2019 |
| WO | WO-2020206080 | A1 | 10/2020 |
| WO | WO-2021097054 | A1 | 5/2021 |
| WO | WO-2021097057 | A1 | 5/2021 |
| WO | WO-2021113808 | A1 | 6/2021 |
| WO | WO-2021113809 | A1 | 6/2021 |
| WO | WO-20210113806 | A1 | 6/2021 |
| WO | WO-2022032068 | | 2/2022 |
| WO | WO-2022076622 | | 4/2022 |
| WO | WO-2022109573 | A1 | 5/2022 |
| WO | WO-2023034946 | A1 | 3/2023 |
| WO | WO-2023034992 | | 3/2023 |
| WO | WO-2024054840 | A1 | 3/2024 |
| WO | WO-2024054845 | A1 | 3/2024 |
| WO | WO-2024054851 | A1 | 3/2024 |
| WO | WO-2024097227 | A1 | 5/2024 |
| WO | WO-2025189008 | A1 | 9/2025 |

OTHER PUBLICATIONS

Chiba, T., Emerging Therapeutic Strategies in Alzheimer's Disease, Intech, 181-225 (2013).

Damia, G., et al., Contemporary pre-clinical development of anti-cancer agents—What are the optimal preclinical models?, Eur J Cancer, 45(16):2768-2781 (2009).

Derichs, Targeting a genetic defect: cystic fibrosis transmembrane conductance regulator modulators in cystic fibrosis, European Respiratory Review, 22:127, 58-65 (2013).

Felis, A., et al., Current and Investigational Therapeutics for Fabry Disease, Kidney Int Rep, 5(4):407-413 (2020).

Ghelani, D.P., et al., Emerging Cystic Fibrosis Transmembrane Conductance Regulator Modulators as New Drugs for Cystic Fibrosis: A Portrait of in VitroÂ Pharmacology and Clinical Translation, ACS Pharmacol Transl Sci., 3(1):4-10 (2019).

Gregory, R. J. et al., Expression and charaterization of the cystic fibrosis transmembrane conductance regulator, Nature, 347:382-386 (1990).

Guan, X., et al., Dysregulated Chemokine Signaling in Cystic Fibrosis Lung Disease: A Potential Therapeutic Target, Curr Drug Targets, 17(13): 1535-1544 (2016).

Hitchin, et al., Development and evaluation of selective, reversible LSD1 inhibitors derived from fragments, MEDCHEMCOMM, 4(11): 1513 (2013).

Hitchin, J.R., et al., Development and evaluation of selective, reversible LSD1 inhibitors derived from fragments, MedChemComm, 4(11): 1513-1522 (2013).

Jenkins et al., A 3D similarity method for scaffold hopping from the known drugs or natural ligands to new chemotypes, J. Medical Chemistry, 47(25): 6144-6159 (2004).

Jenkins, J.L., et al., A 3D similarity method for scaffold hopping from known drugs or natural ligands to new chemotypes, J Med Chem, 47(25): 6144-59 (2004).

(56) References Cited

OTHER PUBLICATIONS

Johnson, J.I., et al., Relationships between drug activity in NCI preclinical in vitro and in vivo models and early clinical trials, Br J Cancer, 84(10):1424-1431 (2001).
Ledford, H., US cancer institute overhauls cell lines, Nature, 530(7591):391 (2016).
Lopes-Pacheco, M., CFTR Modulators: The Changing Face of Cystic Fibrosis in the Era of Precision Medicine, Front Pharmacol., 10:1662 (2020).
Ivacaftor Prescribing Information, 17 pages, Vertex Pharmaceuticals, Feb. 2017.
Makrilakis, K., Pathophysiology of Type 2 diabetes, Chapter 3 in Diabetes in Clinical Practice: Questions and Answers from Case Studies, Nicholas Katsilambros et al. eds. John Wiley & Sons: 2006, pp. 43-58.
Ocana, A., et al., Preclinical development of molecular targeted agents for cancer, Nat Rev Clin Oneal, 8(4):200-209 (2011).
PCT/US2020/060176 International Preliminary Report on Patentability mailed May 27, 2022, 9 pages.
PCT/US2020/060176 International Search Report and Written Opinion mailed Jan. 29, 2021, 12 pages.
PCT/US2020/060180 International Preliminary Report on Patentability mailed Mar. 27, 2022, 9 pages.
PCT/US2020/060180 International Search Report and Written Opinion mailed Feb. 24, 2021, 13 pages.
PCT/US2020/063586 International Preliminary Report on Patentability mailed Jun. 16, 2022.
PCT/US2020/063586 International Search Report and Written Opinion mailed Feb. 15, 2021.
PCT/US2020/063589 International Preliminary Report on Patentability mailed Jun. 16, 2022.
PCT/US2020/063589 International Search Report and Written Opinion mailed Feb. 11, 2021.
PCT/US2020/063590 International Preliminary Report on Patentability mailed Jun. 16, 2022.
PCT/US2020/063590 International Search Report and Written Opinion mailed Feb. 15, 2021.
PCT/US2024/060181 International Search Report and Written Opinion mailed Mar. 25, 2025.
Rich, D. P. et al., Expression of cystic fibrosis transmembrane conductance regulator corrects defective chloride channel regulation in cystic fibrosis airway epithelial cells, Nature, 347:358-362 (1990).
Riordan, J. R. et al., Identification of the Cystic Fibrosis Gene: Cloning and Characterization of Complementary DNA, Science, 245:1066-1073 (1989).
Saikachi et al., "Synthesis of the Furan Derivatives. XLVII. Synthesis of 5, 6-Bis (5-nitro-2-furyl)-2-aminopyrazine and Its Related Compound", Yakugaku Zasshi. 89(8):1071-1077 (1969).
Sharma, S.V., et al., Cell line-based platforms to evaluate the therapeutic efficacy of candidate anticancer agents, Nat Rev Cancer, 10(4):241-53 (2010).
Stavrou, M., et al., Genetic mechanisms of peripheral nerve disease, Neurosci Lett, 742:135357 (2021).
Types of CFTR Mutations, Online: "https://www.cff.org/research-clinical-trials/types-cftr-mutations", accessed Jun. 2, 2025.
University of Cambridge John van Geest Centre for Brain Repair School of Clinical Medicine "Alzheimer's disease and tauopathy" Online "http://www.brc.cam.ac.uk/research/alzheimers-disease-and-tauopathy/" accessed Sep. 10, 2015.
Van Goor, F., et al., Correction of the F508del-CFTR protein processing defect in vitro by the investigational drug VX-809, Proc Natl Acad Sci USA, 108(46):18843-8 (2011).
Wang, et al., Synthesis and biological evaluation of diarylthiazole derivatives as antimitotic and antivascular agents with potent antitumor activity, Bioorganic & Medicinal Chemistry, 23: 3337-3350 (2015).
Weijlard et al., Some New Aminopyrazines and their Sulfanilamide Derivatives, J. Am. Chem. Soc., 67:802-806 (1945).
Yoshii et al., "Antiviral and Antibacterial Activities of 3-(Substituted benzenesulfonylamino)-5, 6-di(p-substituted phenyl)-1, 2, 4-triazines", Yakugaku Zasshi. 108(1):50-57 (1988).
Bartlett, P.A., Exploiting Chemical Diversity for Drug Discovery, Edited by Paul A Bartlett and Michael Entzeroth, The Royal Society of Chemistry: 113-118 (2006).
Find ETDs Home > Thesis Resources > Find ETDs, retrieved Jan. 31, 2023 from https://ndltd.org/thesis-resources/find-etds/.
He, et al., Restoration of NBD1 thermal stability is necessary and sufficient to correct F508 CFTR folding and assembly, J Mol Biol., 427(1): 106-120 (2015).
Irwin, J.J., et al., ZINC—A Free Database of Commercially Available Compounds for Virtual Screening, J. Chem. Inf. Model., 45: 177-182 (2005).
Kim, S. et al. PubChem in 2021: new data content and improved web interfaces, Nucleic Acids Research, 49 (2021).
Patani, G.A., et al., Bioisosterism: a rational approach in drug design, Chem Rev, 96(): 3147-3176 (1996).
PCT/US2023/073543 International Preliminary Report on Patentability mailed Mar. 20, 2025.
PCT/US2023/073543 International Search Report and Written Opinion mailed Nov. 21, 2023.
PCT/US2023/073551 International Preliminary Report on Patentability mailed Mar. 20, 2025.
PCT/US2023/073551 International Search Report and Written Opinion mailed Nov. 21, 2023.
PCT/US2023/073558 International Preliminary Report on Patentability mailed Mar. 20, 2025.
PCT/US2023/073558 International Search Report and Written Opinion mailed Oct. 26, 2023.

* cited by examiner

ARYLAMIDES AND METHODS OF USE THEREOF

CROSS-REFERENCE TO RELATED APPLICATIONS

This application claims the benefit of and priority to U.S. Provisional Patent Application No. 62/944,141, filed Dec. 5, 2019, the entire disclosures of which are incorporated by reference herein.

BACKGROUND

Cystic fibrosis (CF), an autosomal recessive disorder, is caused by functional deficiency of the cAMP-activated plasma membrane chloride channel, cystic fibrosis transmembrane conductance regulator (CFTR), which can result in damage to the lung, pancreas, and other organs. The gene encoding CFTR has been identified and sequenced (See Gregory, R. J. et al. (1990) Nature 347:382-386; Rich, D. P. et al. (1990) Nature 347:358-362; Riordan, J. R. et al. (1989) Science 245:1066-1073). CFTR, a member of the ATP binding cassette (ABC) superfamily is composed of two six membrane-spanning domains (MSD1 and MSD2), two nucleotide binding domains (NBD1 and NBD2), a regulatory region (R) and four cytosolic loops (CL1-4). Normally, CFTR protein is located primarily in the apical membrane of epithelial cells where it functions to conduct anions, including chloride, bicarbonate and thiocyanate into and out of the cell. CFTR may have a regulatory role over other electrolyte channels, including the epithelial sodium channel ENaC.

In cystic fibrosis patients, the absence or dysfunction of CFTR leads to exocrine gland dysfunction and a multisystem disease, characterized by pancreatic insufficiency and malabsorption, as well as abnormal mucociliary clearance in the lung, mucostasis, chronic lung infection and inflammation, loss of lung function and ultimately respiratory failure.

While more than 1,900 mutations have been identified in the CFTR gene, a detailed understanding of how each CFTR mutation may impact channel function is known for only a subset. (Derichs, European Respiratory Review, 22:127, 58-65 (2013)). The most frequent CFTR mutation is the in-frame deletion of phenylalanine at residue 508 (ΔF508) in the first nucleotide binding domain (NBD1). Over 80% of cystic fibrosis patients have the deletion at residue 508 in at least one CFTR allele. The loss of this key phenylalanine renders the CFTR NBD1 domain conformationally unstable at physiological temperature and compromises the integrity of the interdomain interface between NBD1 and CFTR's second transmembrane domain (ICL4). The ΔF508 mutation causes production of misfolded CFTR protein which, rather than traffic to the plasma membrane, is instead retained in the endoplasmic reticulum and targeted for degradation by the ubiquitin-proteasome system.

The loss of a functional CFTR channel at the plasma membrane disrupts ionic homeostasis and airway surface hydration leading to reduced lung function. Reduced periciliary liquid volume and increased mucus viscosity impede mucociliary clearance resulting in chronic infection and inflammation. In the lung, the loss of CFTR-function leads to numerous physiological effects downstream of altered anion conductance that result in the dysfunction of additional organs such as the pancreas, intestine and gall bladder.

The loss of a functional CFTR channel at the plasma membrane disrupts ionic homeostasis and airway surface hydration leading to reduced lung function. Reduced periciliary liquid volume and increased mucus viscosity impede mucociliary clearance resulting in chronic infection and inflammation. In addition to respiratory dysfunction, because CFTR dysfunction impacts the normal function of additional organs (pancreas, intestine, gall bladder), the loss-of-function likely impacts multiple downstream pathways requiring correction.

Guided, in part, by studies of the mechanistic aspects of CFTR misfolding and dysfunction, small molecule CFTR modulators have been identified that can increase CFTR channel function.

Despite the identification of compounds that modulate CFTR, there is no cure for this fatal disease and identification of new compounds and new methods of therapy are needed as well as new methods for treating or lessening the severity of cystic fibrosis and other CFTR mediated conditions and diseases in a patient.

SUMMARY

Disclosed herein are compounds of Formula (I):

(I)

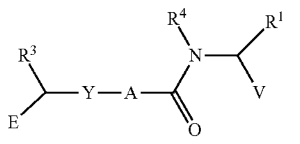

or a pharmaceutically acceptable salt thereof, wherein:

A is

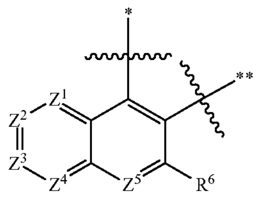

wherein * marks the point of attachment to Y and ** marks the point of attachment to —C(O)—;

$Z^1$, $Z^4$, and $Z^5$ are each independently N or $CR^6$;

$Z^2$ and $Z^3$ are each independently N or $CR^2$;

Y is a bond, —$NR^3$—, —O—, —S—, or —$C(R^4)_2$—;

E is $C_{1-6}$-alkyl, $C_{2-6}$-alkynyl, $C_{3-9}$-cycloalkyl, $C_{4-9}$-cycloalkenyl, $C_{6-10}$-aryl, 3-10 membered heteroaryl, or 3-9 membered heterocycloalkyl, each of which is optionally substituted with one, two, three, four, or five occurrences of $R^5$;

V is —C(O)—O—$R^7$;

$R^1$ is

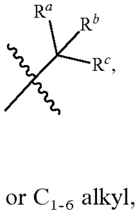

wherein $R^a$ is hydrogen, halo or $C_{1-6}$ alkyl, $R^b$ is hydrogen, halo, $C_{1-6}$ alkyl, halo$C_{1-6}$ alkyl, —OH, —CN, halo $C_{1-6}$ alkyl, thio$C_{1-6}$ alkyl, $C_{2-6}$ alkenyl, $C_{2-6}$ alkynyl, $C_{6-10}$ aryl, —O—$C_{1-6}$ alkyl, —S—$C_{1-6}$ alkylaryl, —S(O)$_2$—$C_{1-6}$ alkyl, or —S—$C_{3-9}$-cycloalkyl, wherein each alkyl, alkenyl, alkynyl, cycloalkyl and aryl is optionally substituted with one, two, three, four, or five occurrences of $R^9$;

$R^c$ is $C_{1-6}$ alkyl, halo$C_{1-6}$ alkyl, aryl$C_{1-6}$ alkyl, $C_{3-9}$-cycloalkyl, $C_{6-10}$ aryl, 3-10 membered heteroaryl, or 3-9 membered heterocycloalkyl, each of which is optionally and independently substituted with one, two, three, four, or five occurrences of $R^{10}$;

$R^a$ and $R^c$, taken together with the atoms to which they are attached, form a $C_{3-8}$ cycloalkyl, an aryl or a $C_{3-8}$ heterocycloalkyl ring, or $R^a$, $R^b$, and $R^c$ are taken together with the atoms to which they are attached to form a bridged $C_{5-9}$ cycloalkyl;

each $R^2$ is independently hydrogen, halo, —CN, —OH, —$NH_2$, —N—($C_{1-6}$ alkyl)$_2$, $C_{1-6}$ alkyl, halo$C_{1-6}$ alkyl, —O—$C_{1-6}$ alkyl, —O-halo$C_{1-6}$ alkyl, —O—$C_{2-6}$ alkenyl, or 3-10 membered heteroaryl;

$R^3$ is hydrogen or $C_{1-6}$ alkyl;

$R^4$ is hydrogen or $C_{1-4}$ alkyl;

each $R^5$ is independently halo, —CN, —$NO_2$, $C_{1-6}$ alkyl, hydroxy$C_{1-6}$ alkyl, $C_{1-6}$ haloalkyl, $C_{3-9}$-cycloalkyl, $C_2$-s-alkenyl, —O—$C_{1-6}$ alkyl, —O—$C_{1-6}$ haloalkyl, —C(O)—O—$C_{1-6}$ alkyl, —$SF_5$, —S—$C_{1-6}$alkyl, —S—$C_{1-6}$ haloalkyl, —S(O)$_2$—$C_{1-6}$ alkyl, —S(O)$_2$—$C_{1-6}$ haloalkyl, or 3-10 membered heteroaryl; or two $R^5$ moieties, taken together with the atoms to which they are attached, form a 3-8 membered heterocycloalkyl ring, wherein each heterocycloalkyl is substituted with one, two, or three occurrences of $R^8$;

each $R^6$ is independently hydrogen, halo, or $C_{1-6}$-alkyl;

$R^7$ is hydrogen, $C_{1-6}$-alkyl, $C_{6-10}$ aryl, or benzyl;

each $R^8$ is independently hydrogen, halo or $C_{1-6}$-alkyl;

each $R^9$ is independently hydrogen, halo, $C_{1-6}$-alkyl, halo$C_{1-6}$-alkyl, or $C_{3-9}$-cycloalkyl;

each $R^{10}$ is independently hydrogen, halo, —CN, —OH, $C_{1-6}$-alkyl, halo$C_{1-6}$ alkyl, —O—$C_{1-6}$alkyl, —O-halo$C_{1-6}$ alkyl, —O—$C_{2-6}$-alkenyl, $C_{1-4}$-alkylaryl, —O—$C_{1-6}$-alkylaryl, —O—$C_{1-6}$ alkyl-O—$C_{1-6}$alkyl, —C(O)O$C_{1-6}$ alkyl, —S—$C_{1-6}$ alkyl, —N═($NH_2$)$_2$, $C_{6-10}$ aryl, or 3-10 membered heteroaryl; and m is 0, 1, or 2;

provided that when $R^2$ is hydrogen, $R^a$ is hydrogen, and $R^b$ is hydrogen or methyl, then $R^c$ is not $C_{1-2}$ alkyl, halo $C_{1-2}$ alkyl, or 5-membered heteroaryl.

Disclosed herein are methods of treating deficient CFTR activity, thereby treating a disease or condition mediated by deficient CFTR activity. Such diseases and conditions include, but are not limited to, cystic fibrosis, congenital bilateral absence of vas deferens (CBAVD), acute, recurrent, or chronic pancreatitis, disseminated bronchiectasis, asthma, allergic pulmonary aspergillosis, congenital pneumonia, intestinal malabsorption, celiac disease, nasal polyposis, non-tuberculous mycobacterial infection, pancreatic steatorrhea, intestinal atresia, chronic obstructive pulmonary disease (COPD), rhinosinusitis, dry eye disease, protein C deficiency, abetalipoproteinemia, lysosomal storage disease, type 1 chylomicronemia, mild pulmonary disease, lipid processing deficiencies, type 1 hereditary angioedema, coagulation-fibrinolysis, hereditary hemochromatosis, CFTR-related metabolic syndrome, chronic bronchitis, constipation, pancreatic insufficiency, hereditary emphysema, and Sjogren's syndrome. In some embodiments, the disease is cystic fibrosis.

In certain embodiments, the present disclosure provides a pharmaceutical composition suitable for use in a subject in the treatment or prevention of disease and conditions associate with deficient CFTR activity, comprising an effective amount of any of the compounds described herein (e.g., a compound of the disclosure, such as a compound of formula (I)), and one or more pharmaceutically acceptable excipients. In certain embodiments, the pharmaceutical preparations may be for use in treating or preventing a condition or disease as described herein.

Provided herein are combination therapies of compounds of formula (I) with CFTR-active agents that can enhance the therapeutic benefit beyond the ability of the primary therapy alone.

DETAILED DESCRIPTION

Disclosed herein are compounds of Formula (I):

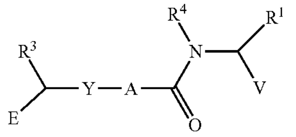

(I)

or a pharmaceutically acceptable salt thereof, wherein:

A is

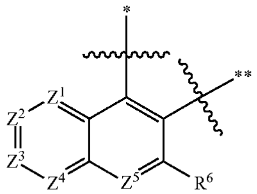

wherein * marks the point of attachment to Y and ** marks the point of attachment to —C(O)—;

$Z^1$, $Z^4$, and $Z^5$ are each independently N or $CR^6$;

$Z^2$ and $Z^3$ are each independently N or $CR^2$;

Y is a bond, —$NR^3$—, —O—, —S—, or —C($R^4$)$_2$—;

E is $C_{1-6}$-alkyl, $C_{2-6}$-alkynyl, $C_{3-9}$-cycloalkyl, $C_{4-9}$-cycloalkenyl, $C_{6-10}$-aryl, 3-10 membered heteroaryl, or 3-9 membered heterocycloalkyl, each of which is optionally substituted with one, two, three, four, or five occurrences of $R^5$;

V is —C(O)—O—$R^7$;

$R^1$ is

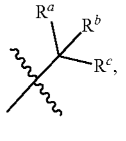

wherein $R^a$ is hydrogen, halo or $C_{1-6}$ alkyl, $R^b$ is hydrogen, halo, $C_{1-6}$ alkyl, halo$C_{1-6}$ alkyl, —OH, —CN, halo $C_{1-6}$ alkyl, thio$C_{1-6}$ alkyl, $C_{2-6}$ alkenyl, $C_{2-6}$ alkynyl, $C_{6-10}$ aryl, —O—$C_{1-6}$ alkyl, —S—$C_{1-6}$ alkylaryl, —S(O)$_2$—$C_{1-6}$ alkyl, or —S—$C_{3-9}$-cycloalkyl, wherein each alkyl, alkenyl, alkynyl, cycloalkyl and aryl is optionally substituted with one, two, three, four, or five occurrences of $R^9$;

$R^c$ is $C_{1-6}$ alkyl, halo$C_{1-6}$ alkyl, aryl$C_{1-6}$ alkyl, $C_{3-9}$-cycloalkyl, $C_{6-10}$ aryl, 3-10 membered heteroaryl, or 3-9 membered heterocycloalkyl, each of which is optionally and independently substituted with one, two, three, four, or five occurrences of $R^{10}$;

$R^a$ and $R^c$, taken together with the atoms to which they are attached, form a $C_{3-8}$ cycloalkyl, an aryl or a $C_{3-8}$ heterocycloalkyl ring, or $R^a$, $R^b$, and $R^c$ are taken together with the atoms to which they are attached to form a bridged $C_{5-9}$ cycloalkyl;

each $R^2$ is independently hydrogen, halo, —CN, —OH, —$NH_2$, —N—($C_{1-6}$ alkyl)$_2$, $C_{1-6}$ alkyl, halo$C_{1-6}$ alkyl, —O—$C_{1-6}$ alkyl, —O-halo$C_{1-6}$ alkyl, —O—$C_{2-6}$ alkenyl, or 3-10 membered heteroaryl;

$R^3$ is hydrogen or $C_{1-6}$ alkyl;

$R^4$ is hydrogen or $C_{1-4}$ alkyl;

each $R^5$ is independently halo, —CN, —$NO_2$, $C_{1-6}$ alkyl, hydroxy$C_{1-6}$ alkyl, $C_{1-6}$ haloalkyl, $C_{3-9}$-cycloalkyl, $C_{2-6}$-alkenyl, —O—$C_{1-6}$ alkyl, —O—$C_{1-6}$ haloalkyl, —C(O)—O—$C_{1-6}$ alkyl, —$SF_5$, —S—$C_{1-6}$alkyl, —S—$C_{1-6}$ haloalkyl, —S(O)$_2$—$C_{1-6}$ alkyl, —S(O)$_2$—$C_{1-6}$ haloalkyl, or 3-10 membered heteroaryl; or two $R^5$ moieties, taken together with the atoms to which they are attached, form a 3-8 membered heterocycloalkyl ring, wherein each heterocycloalkyl is substituted with one, two, or three occurrences of $R^8$;

each $R^6$ is independently hydrogen, halo, or $C_{1-6}$-alkyl;

$R^7$ is hydrogen, $C_{1-6}$-alkyl, $C_{6-10}$ aryl, or benzyl;

each $R^8$ is independently hydrogen, halo or $C_{1-6}$-alkyl;

each $R^9$ is independently hydrogen, halo, $C_{1-6}$-alkyl, halo$C_{1-6}$-alkyl, or $C_{3-9}$-cycloalkyl;

each $R^{10}$ is independently hydrogen, halo, —CN, —OH, $C_{1-6}$-alkyl, halo$C_{1-6}$ alkyl, —O—$C_{1-6}$alkyl, —O-halo$C_{1-6}$ alkyl, —O—$C_{2-6}$-alkenyl, $C_{1-4}$-alkylaryl, —O—$C_{1-6}$-alkylaryl, —O—$C_{1-6}$ alkyl-O—$C_{1-6}$alkyl, —C(O)O$C_{1-6}$ alkyl, —S—$C_{1-6}$ alkyl, —N═($NH_2$)$_2$, $C_{6-10}$ aryl, or 3-10 membered heteroaryl; and m is 0, 1, or 2;

provided that when $R^2$ is hydrogen, $R^a$ is hydrogen, and $R^b$ is hydrogen or methyl, then $R^c$ is not $C_{1-2}$ alkyl, halo $C_{1-2}$ alkyl, or 5-membered heteroaryl.

Disclosed herein are methods of treating deficient CFTR activity in a cell, comprising contacting the cell with a compound of Formula (I):

(I)

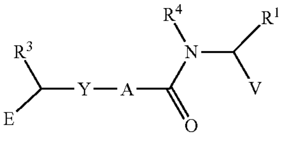

or a pharmaceutically acceptable salt thereof, wherein:

A is

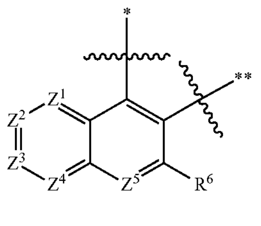

wherein * marks the point of attachment to Y and ** marks the point of attachment to —C(O)—;

$Z^1$, $Z^4$, and $Z^5$ are each independently N or $CR^6$;

$Z^2$ and $Z^3$ are each independently N or $CR^2$;

Y is a bond, —$NR^3$—, —O—, —S—, or —C($R^4$)$_2$—;

E is $C_{1-6}$-alkyl, $C_{2-6}$-alkynyl, $C_{3-9}$-cycloalkyl, $C_{4-9}$-cycloalkenyl, $C_{6-10}$-aryl, 3-10 membered heteroaryl, or 3-9 membered heterocycloalkyl, each of which is optionally substituted with one, two, three, four, or five occurrences of $R^5$;

V is —C(O)—O—$R^7$;

$R^1$ is

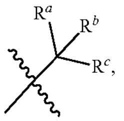

wherein $R^a$ is hydrogen, halo or $C_{1-6}$ alkyl, $R^b$ is hydrogen, halo, $C_{1-6}$ alkyl, halo$C_{1-6}$ alkyl, —OH, —CN, halo $C_{1-6}$ alkyl, thio$C_{1-6}$ alkyl, $C_{2-6}$ alkenyl, $C_{2-6}$ alkynyl, $C_{6-10}$ aryl, —O—$C_{1-6}$ alkyl, —S—$C_{1-6}$ alkylaryl, —S(O)$_2$—$C_{1-6}$ alkyl, or —S—$C_{3-9}$-cycloalkyl, wherein each alkyl, alkenyl, alkynyl, cycloalkyl and aryl is optionally substituted with one, two, three, four, or five occurrences of $R^9$;

$R^c$ is $C_{1-6}$ alkyl, halo$C_{1-6}$ alkyl, aryl$C_{1-6}$ alkyl, $C_{3-9}$-cycloalkyl, $C_{6-10}$ aryl, 3-10 membered heteroaryl, or 3-9 membered heterocycloalkyl, each of which is optionally and independently substituted with one, two, three, four, or five occurrences of $R^{10}$;

$R^a$ and $R^c$, taken together with the atoms to which they are attached, form a $C_{3-8}$ cycloalkyl, an aryl or a $C_{3-8}$ heterocycloalkyl ring, or $R^a$, $R^b$, and $R^c$ are taken together with the atoms to which they are attached to form a bridged $C_{5-9}$ cycloalkyl;

each $R^2$ is independently hydrogen, halo, —CN, —OH, —$NH_2$, —N—($C_{1-6}$ alkyl)$_2$, $C_{1-6}$ alkyl, halo$C_{1-6}$ alkyl, —O—$C_{1-6}$ alkyl, —O-halo$C_{1-6}$ alkyl, —O—$C_{2-6}$ alkenyl, or 3-10 membered heteroaryl;

$R^3$ is hydrogen or $C_{1-6}$ alkyl;

$R^4$ is hydrogen or $C_{1-4}$ alkyl;

each $R^5$ is independently halo, —CN, —$NO_2$, $C_{1-6}$ alkyl, hydroxy$C_{1-6}$ alkyl, $C_{1-6}$ haloalkyl, $C_{3-9}$-cycloalkyl, $C_{2-6}$-alkenyl, —O—$C_{1-6}$ alkyl, —O—$C_{1-6}$ haloalkyl, —C(O)—O—$C_{1-6}$ alkyl, —$SF_5$, —S—$C_{1-6}$alkyl, —S—$C_{1-6}$ haloalkyl, —S(O)$_2$—$C_{1-6}$ alkyl, —S(O)$_2$—$C_{1-6}$ haloalkyl, or 3-10 membered heteroaryl; or two $R^5$ moieties, taken together with the atoms to which they are attached, form a 3-8 membered heterocycloalkyl ring, wherein each heterocycloalkyl is substituted with one, two, or three occurrences of $R^8$;

each $R^6$ is independently hydrogen, halo, or $C_{1-6}$-alkyl;

$R^7$ is hydrogen, $C_{1-6}$-alkyl, $C_{6-10}$ aryl, or benzyl;

each $R^8$ is independently hydrogen, halo or $C_{1-6}$-alkyl;

each $R^9$ is independently hydrogen, halo, $C_{1-6}$-alkyl, halo$C_{1-6}$-alkyl, or $C_{3-9}$-cycloalkyl;

each $R^{10}$ is independently hydrogen, halo, —CN, —OH, $C_{1-6}$-alkyl, halo$C_{1-6}$ alkyl, —O—$C_{1-6}$alkyl, —O-halo$C_{1-6}$ alkyl, —O—$C_{2-6}$-alkenyl, $C_{1-4}$-alkylaryl, —O—$C_{1-6}$-alkylaryl, —O—$C_{1-6}$ alkyl-O—$C_{1-6}$alkyl, —C(O)O$C_{1-6}$ alkyl, —S—$C_{1-6}$ alkyl, —N═($NH_2$)$_2$, $C_{6-10}$ aryl, or 3-10 membered heteroaryl; and m is 0, 1, or 2.

In some embodiments of the compound of Formula (I), $Z^1$, $Z^4$, and $Z^5$ are each independently $CR^6$;

$Z^2$ and $Z^3$ are each independently $CR^2$;

Y is —O—;

E is $C_{2-6}$-alkynyl, $C_{3-9}$-cycloalkyl, $C_{4-9}$-cycloalkenyl, $C_{6-10}$ aryl, 3-10 membered heteroaryl, or 3-9 membered heterocycloalkyl, each of which is optionally and independently substituted with one, two, three, four, or five occurrences of $R^5$;

$R^1$ is

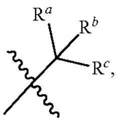

wherein $R^a$ is $C_{1-6}$ alkyl;

$R^b$ is $C_{1-6}$ alkyl or halo $C_{1-6}$ alkyl;

$R^c$ is $C_{1-6}$ alkyl, halo $C_{1-6}$ alkyl, or $C_{6-10}$ aryl, or $R^a$ and $R^c$, taken together with the atoms to which they are attached, form a $C_{3-8}$ cycloalkyl or 3-8 membered heterocycloalkyl ring; and at least one $R^2$ is independently halo, —CN, —N—($C_{1-6}$ alkyl)$_2$, $C_{1-6}$ alkyl, halo$C_{1-6}$ alkyl, —O—$C_{1-6}$ alkyl, —O—$C_{2-6}$ alkenyl, or 3-10 membered heteroaryl.

Variables $Z^1$, $Z^2$, $Z^3$, $Z^4$ and $Z^5$ of Formula (I)

Below are exemplary embodiments of variables $Z^1$, $Z^2$, $Z^3$, $Z^4$ and $Z^5$ of the disclosed compound of Formula (I). The values for the remaining variables are as described above.

In some embodiments, $Z^1$ is N; $Z^2$ and $Z^3$ are each independently $CR^2$; and $Z^4$ and $Z^5$ are each independently $CR^6$. In some embodiments, $Z^2$ is N; $Z^3$ is $CR^2$; and $Z^1$, $Z^4$ and $Z^5$ are each independently $CR^6$. In some embodiments, $Z^3$ is N; $Z^2$ is $CR^2$; and $Z^1$, $Z^4$, and $Z^5$ are each independently $CR^6$. In some embodiments, $Z^4$ is N; $Z^2$ and $Z^3$ are each independently $CR^2$; and $Z^1$ and $Z^5$ are each independently $CR^6$. $Z^1$ and $Z^3$ are each N; $Z^2$ is $CR^2$; and $Z^4$ and $Z^5$ are each independently $CR^6$.

Variables $R^3$, $R^4$, $R^6$, and $R^7$ of Formula (I)

Below are exemplary embodiments of variables $R^3$, $R^6$, $R^7$, and Y of the disclosed compound of Formula (I). The values for the remaining variables are as described above.

In some embodiments, $R^3$ is hydrogen or methyl, such as hydrogen. In some embodiments, $R^3$ is methyl. In some embodiments, $R^4$ is hydrogen. In other embodiments, $R^6$ is hydrogen, while in other embodiments, $R^6$ is fluoro. In some embodiments, $R^7$ is hydrogen, methyl, ethyl or t-butyl, such as hydrogen.

Variables Y and E of Formula (I)

Below are exemplary embodiments of variables Y and E of the disclosed compound of Formula (I). The values for the remaining variables are as described above.

In some embodiments, Y is —O—. In some embodiments, E is $C_{2-6}$-alkynyl, $C_{3-9}$-cycloalkyl, $C_{6-10}$-aryl, or 3-10 membered heteroaryl. In some embodiments, E is isopropyl, cyclopropyl, cyclohexyl, bicycloheptenyl, —O-benzyl, —$CH_2$—S—$CH_3$, —$CO_2$t-butyl, phenyl, benzyl, benzthiazolyl, benzodioxolyl, furanyl, imidazolyl, or pyridyl. In some embodiments, E is cyclohexyl, phenyl or benzthiazolyl. In other embodiments, E is ethyl, phenyl, cyclohexyl, pyrazolyl, benzodioxolyl, cyclohexenyl, thiazolyl, ethynyl, pyridyl, oxazolyl, bicycloheptanyl, or benzthiazolyl. In some embodiments, E is phenyl.

Variables $R^a$, $R^b$, and $R^c$ of Formula (I)

Below are exemplary embodiments of variables $R^a$, $R^b$, and $R^c$ of the disclosed compound of Formula (I). The values for the remaining variables are as described above.

In some embodiments, $R^a$ is hydrogen, methyl, or fluoro, such as hydrogen. In other embodiments, $R^a$ is methyl. In some embodiments, $R^b$ is hydrogen, methyl, ethyl, —$CF_3$, —OH, fluoro, or phenyl. In other embodiments, $R^b$ is hydrogen, methyl, or fluoro, such as hydrogen. In some embodiments, $R^b$ is methyl. In some embodiments, $R^b$ is ethyl. In some embodiments, $R^b$ is —$CF_3$.

In some embodiments, $R^c$ is methyl, ethyl, ethenyl, ethynyl, butyl, t-butyl, —$CF_3$, fluoro, —OH, —OMe, —O-t-butyl, —O-benzyl, —$CH_2$—O—$CH_3$, —S-methyl, —S-cyclopropyl, —S-cyclopentyl, —S— bicycloheptanyl, —$SO_2$Me, cyclopentyl, phenyl, benzodioxolyl, indolyl, imidazolyl, or thiophenyl. In some embodiments, $R^c$ is ethyl, ethynyl, t-butyl, —O-t-butyl, —O-benzyl, —S-methyl, fluoro, cyclopentyl, cyclohexyl, or phenyl. In some embodiments, $R^c$ is t-butyl, —O-benzyl, —S-methyl, cyclopentyl, cyclohexyl, or phenyl. In other embodiments, $R^c$ is methyl, ethyl, propyl, —$CH_2$F, or phenyl. In some embodiments, $R^c$ is methyl or ethyl.

In some embodiments, $R^a$ and $R^c$, taken together with the atoms to which they are attached, form a cyclopropyl, cyclopentyl, cyclohexyl, cycloheptyl, bicyclohexyl, bicycloheptyl or dihydroindenyl. $R^a$ and $R^c$, taken together with the atoms to which they are attached, form a cyclopropyl, cyclobutyl, cyclopentyl, cyclohexyl, bicyclopentyl, bicycloheptyl, or oxiranyl. In some embodiments, In other embodiments, $R^a$ and $R^c$, taken together with the atoms to which they are attached, form a cyclopentyl or cyclohexyl. In certain embodiments, $R^a$, $R^b$, and $R^c$ are taken together with the atoms to which they are attached to form a phenyl, naphthyl or bicyclooctyl.

Variables $R^2$, $R^5$, and $R^{10}$ of Formula (I)

Below are exemplary embodiments of variables $R^2$, $R^5$, and $R^{10}$ of the disclosed compound of Formula (I). The values for the remaining variables are as described above.

In some embodiments, at least one $R^2$ is fluoro, chloro, methyl, —$CF_3$, —OH, —OMe, —O— isopropyl, or —$NH_2$. In some embodiments, at least one $R^2$ is fluoro, chloro, methyl, or —OMe. In certain embodiments, at least one $R^2$ is methyl, chloro, fluoro, bromo, —$CF_3$, —$CHF_2$, —OMe, —O— propenyl, —CN or thiazolyl. In other embodiments, at least one $R^2$ is methyl, chloro, —$CF_3$, —$CHF_2$, or thiazolyl. In some embodiments, at least one $R^2$ is methyl or —$CHF_2$.

In some embodiments, at least one $R^5$ is fluoro, chloro, bromo, methyl, t-butyl, —$CH_2OH$, —$CF_3$, —O—$CF_3$, —$CF_2CF_3$, —CN, —$NO_2$, —$OCF_3$, —$CO_2$Me, —S—$CF_3$, —$SF_5$, —$SO_2$Me, —$SO_2CF_3$, or phenyl. In some embodiments, at least one $R^5$ is fluoro, chloro, —$CF_3$, —O—$CF_3$, —S—$CF_3$, —$SF_5$, or —$SO_2$Me. In some embodiments, $R^5$ is chloro, bromo, —OH, —CN, —$NO_2$, methyl, t-butyl, —$CH_2OH$, —O-iPr, —$CF_3$, —$CF_2CF_3$, —$OCF_3$, —$OCHF_2$, 1-propenyl, —$NH_2$, —$NMe_2$, —$CO_2$Me, —S—$CF_3$, —$SF_5$, —$SO_2$Me, —$SO_2CF_3$, phenyl, cyclopropyl, 1-$CF_3$-cyclopropyl, or 4,4-difluorocyclohexyl. In some embodiments, $R^5$ is t-butyl, —$CF_3$, —$OCF_3$, —S—$CF_3$, or —$SF_5$.

In some embodiments, at least one $R^{10}$ is fluoro, chloro, methyl, —$CH_2$—CH═$CH_2$, —$CF_3$, —CN, —OH, —OMe, —O-t-butyl, —O—$CF_3$, —N═($NH_2$)$_2$, 2,2-difluorocyclopropyl, or phenyl. In some embodiments, at least one $R^{10}$ is chloro, methyl, —$CF_3$, or phenyl.

Variable $R^1$ of Formula (I)

In some embodiments, $R^1$ is in the α-configuration, such that the structure of Formula (I) is that of Formula (IA):

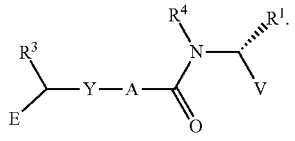
(IA)

In some embodiments, $R^1$ is in the β-configuration, such that the structure of Formula (I) is that of Formula (IB):

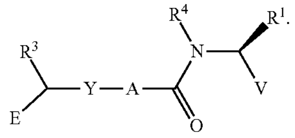
(IB)

Representative compounds, or pharmaceutically acceptable salts thereof, include the following in Table 1:

TABLE 1

| Compound | # |
| --- | --- |
| 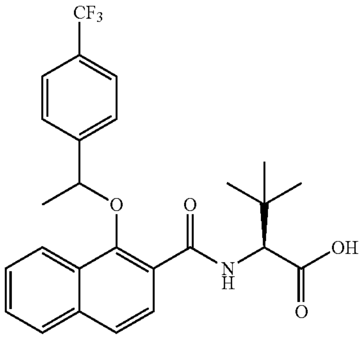 | 71 |
| 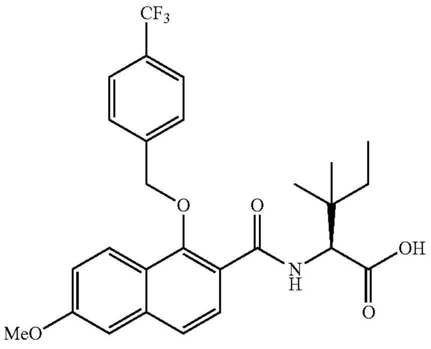 | 83 |

TABLE 1-continued

| Compound | # |
| --- | --- |
| 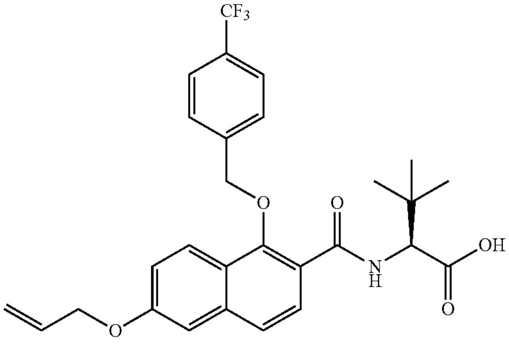 [SMILES: C=CCOc1ccc2c(OCc3ccc(C(F)(F)F)cc3)c(C(=O)N[C@H](C(=O)O)C(C)(C)C)ccc2c1] | 73 |
| 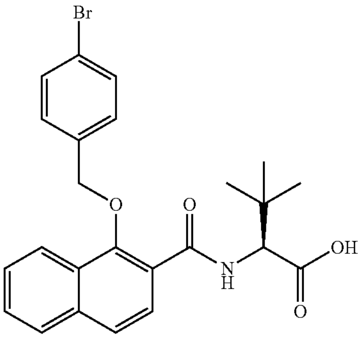 | 46 |
| 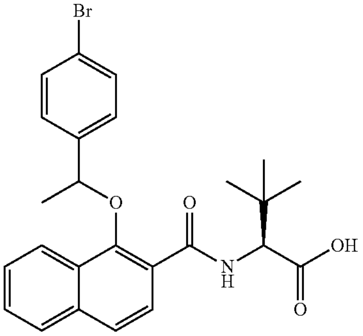 | 42 |
| 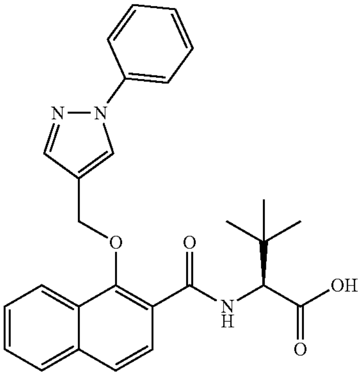 [SMILES: CC(C)(C)[C@H](NC(=O)c1ccc2ccccc2c1OCc1cnn(-c2ccccc2)c1)C(=O)O] | 62 |

TABLE 1-continued
| Compound | # |
| --- | --- |
| 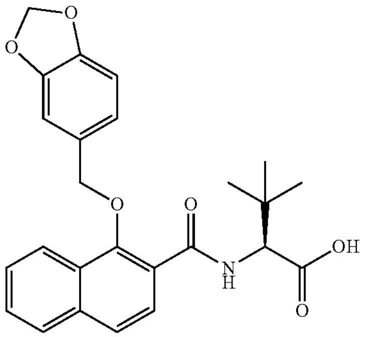 [SMILES: CC(C)(C)[C@H](NC(=O)c1ccc2ccccc2c1OCc1ccc2c(c1)OCO2)C(=O)O] | 79 |
| 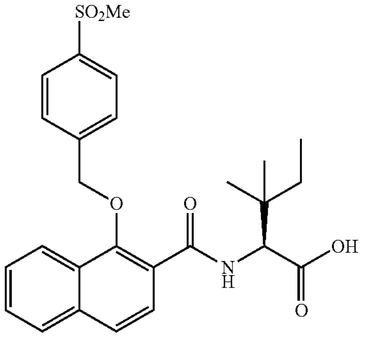 | 53 |
| 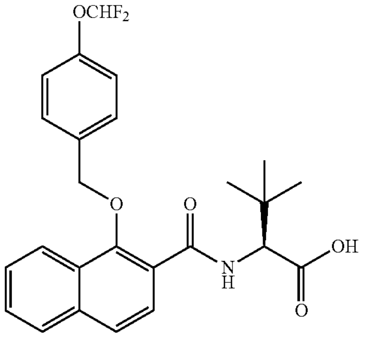 | 12 |
| 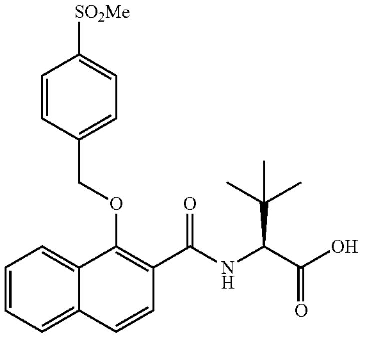 | 66 |
TABLE 1-continued
| Compound | # |
| --- | --- |
| 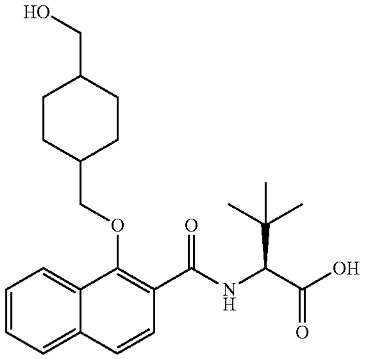 [SMILES: CC(C)(C)[C@H](NC(=O)c1ccc2ccccc2c1OCC1CCC(CO)CC1)C(=O)O] | 29 |
| 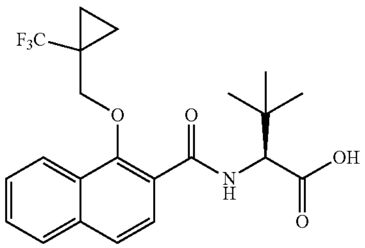 [SMILES: CC(C)(C)[C@H](NC(=O)c1ccc2ccccc2c1OCC1(C(F)(F)F)CC1)C(=O)O] | 268 |
| 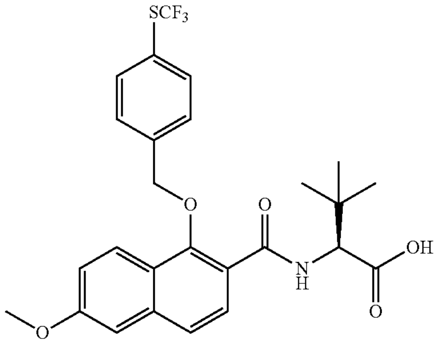 | 63 |
| 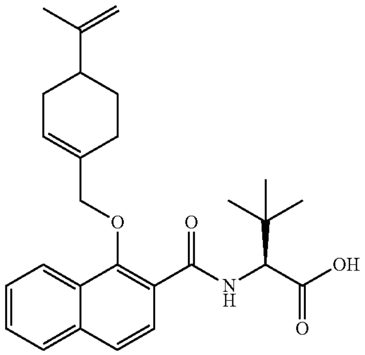 [SMILES: C=C(C)C1CC=C(COc2c(C(=O)N[C@H](C(=O)O)C(C)(C)C)ccc3ccccc23)CC1] | 49 |

TABLE 1-continued
| Compound | # |
|---|---|
| 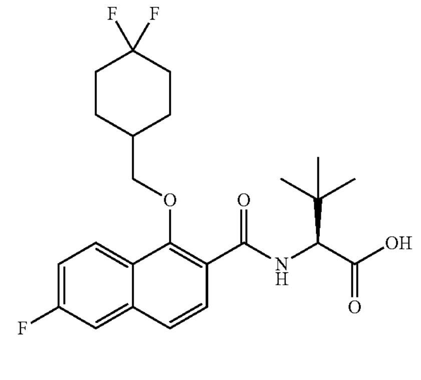 [SMILES: CC(C)(C)[C@H](NC(=O)c1ccc2cc(F)ccc2c1OCC1CCC(F)(F)CC1)C(=O)O] | 76 |
| 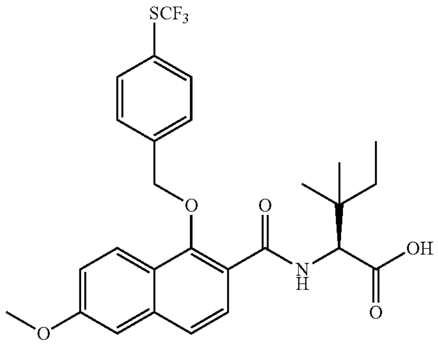 | 32 |
| 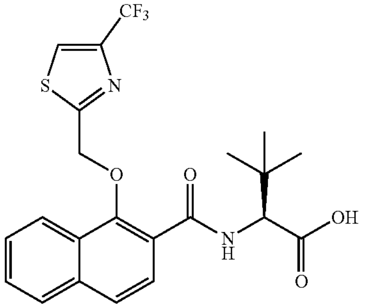 [SMILES: CC(C)(C)[C@H](NC(=O)c1ccc2ccccc2c1OCc1nc(C(F)(F)F)cs1)C(=O)O] | 269 |
| 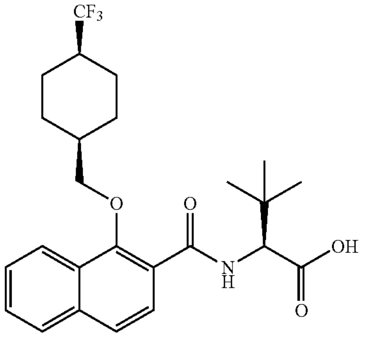 [SMILES: CC(C)(C)[C@H](NC(=O)c1ccc2ccccc2c1OC[C@H]1CC[C@@H](C(F)(F)F)CC1)C(=O)O] | 26 |
TABLE 1-continued
| Compound | # |
|---|---|
| 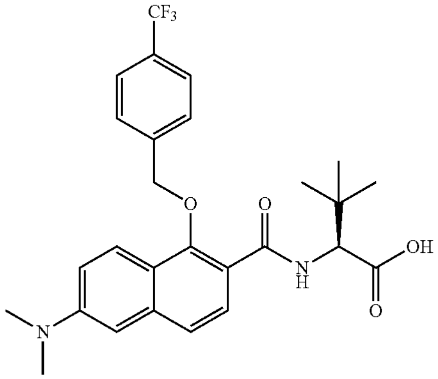 [SMILES: CN(C)c1ccc2c(OCc3ccc(C(F)(F)F)cc3)c(C(=O)N[C@H](C(=O)O)C(C)(C)C)ccc2c1] | 85 |
| 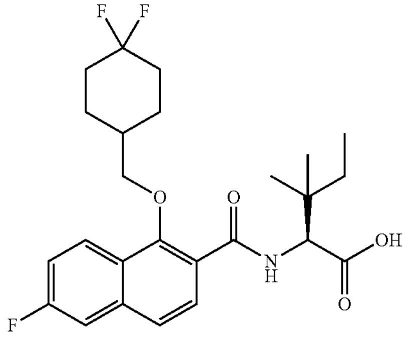 | 34 |
| 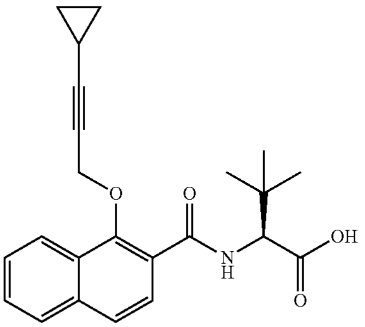 [SMILES: CC(C)(C)[C@H](NC(=O)c1ccc2ccccc2c1OCC#CC1CC1)C(=O)O] | 270 |
| 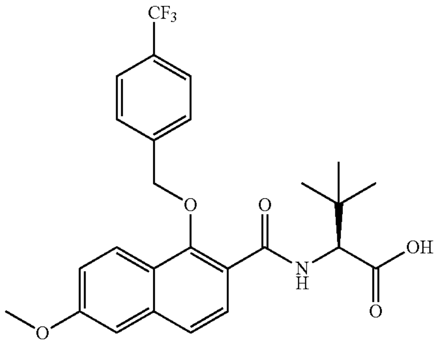 [SMILES: COc1ccc2c(OCc3ccc(C(F)(F)F)cc3)c(C(=O)N[C@H](C(=O)O)C(C)(C)C)ccc2c1] | 38 |

TABLE 1-continued
| Compound | # |
|---|---|
| 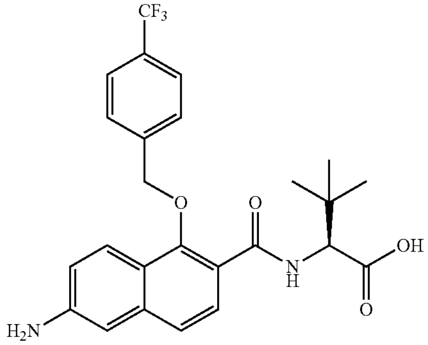 [SMILES: CC(C)(C)[C@H](NC(=O)c1ccc2cc(N)ccc2c1OCc1ccc(C(F)(F)F)cc1)C(=O)O] | 52 |
| 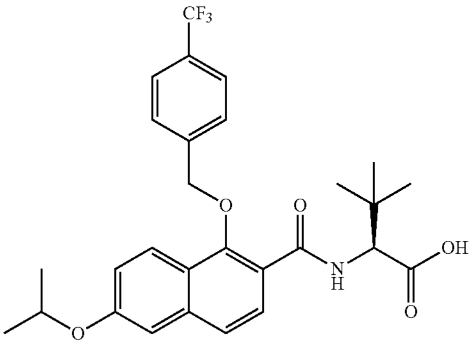 [SMILES: CC(C)Oc1ccc2c(OCc3ccc(C(F)(F)F)cc3)c(C(=O)N[C@H](C(=O)O)C(C)(C)C)ccc2c1] | 260 |
| 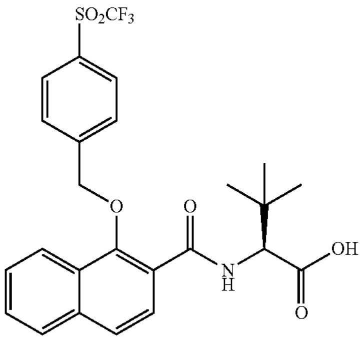 | 57 |
| 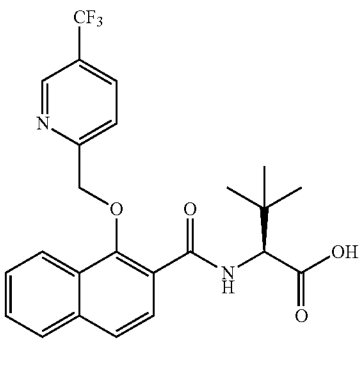 | 2 |
TABLE 1-continued
| Compound | # |
|---|---|
| 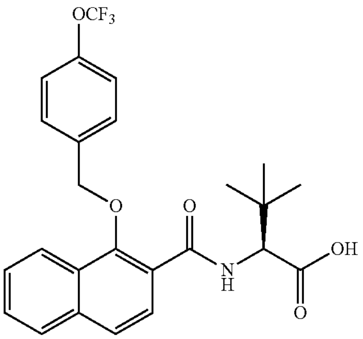 | 65 |
| 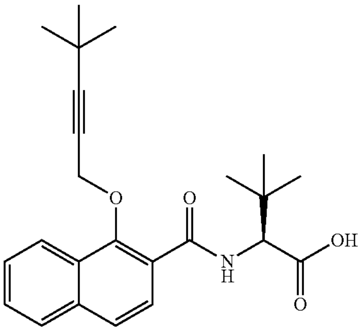 [SMILES: CC(C)(C)C#CCOc1c(C(=O)N[C@H](C(=O)O)C(C)(C)C)ccc2ccccc12] | 267 |
| 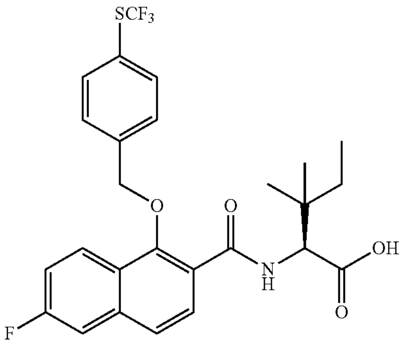 | 84 |
| 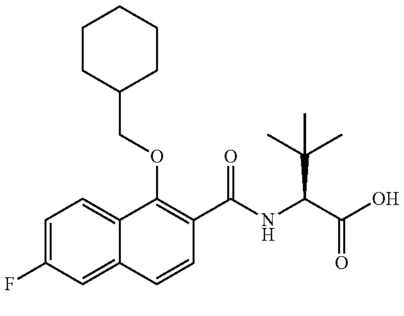 [SMILES: CC(C)(C)[C@H](NC(=O)c1ccc2cc(F)ccc2c1OCC1CCCCC1)C(=O)O] | 45 |

TABLE 1-continued
| Compound | # |
|---|---|
| 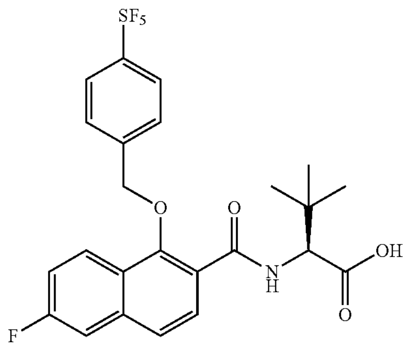 | 81 |
| 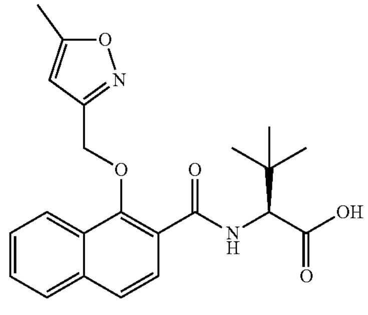 [SMILES: Cc1cc(COc2c(C(=O)N[C@H](C(=O)O)C(C)(C)C)ccc3ccccc23)no1] | 86 |
| 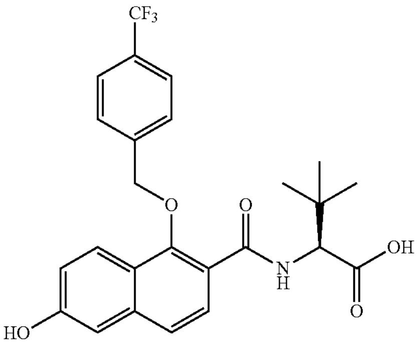 | 59 |
| 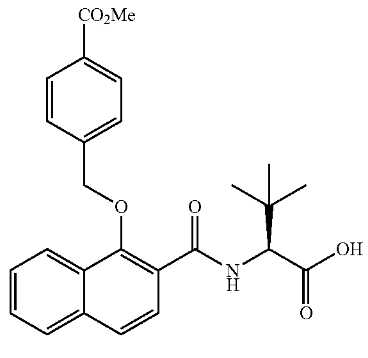 | 28 |
TABLE 1-continued
| Compound | # |
|---|---|
| 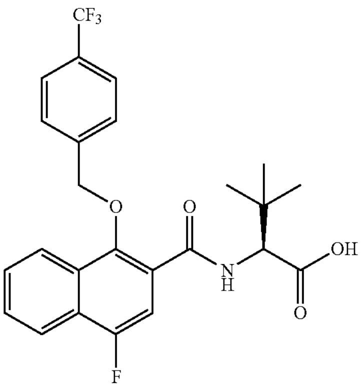 | 64 |
| 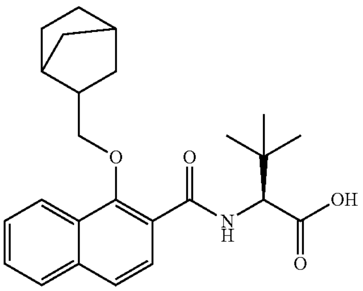 [SMILES: CC(C)(C)[C@H](NC(=O)c1ccc2ccccc2c1OCC1CC2CCC1C2)C(=O)O] | 41 |
| 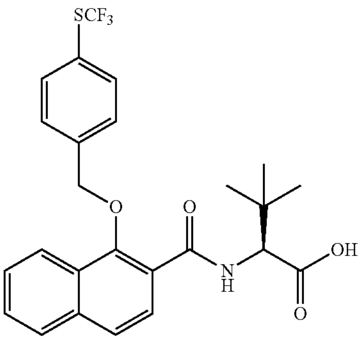 | 35 |
| 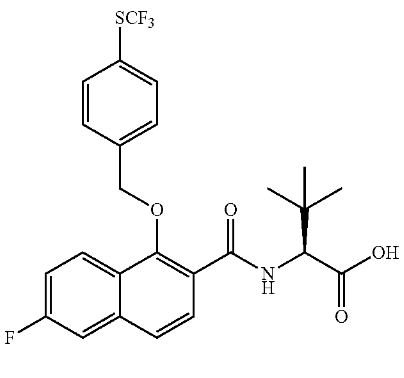 | 75 |

TABLE 1-continued
| Compound | # |
| --- | --- |
| 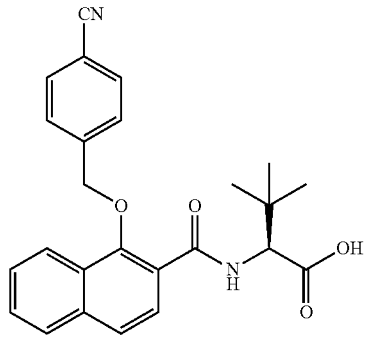 | 31 |
| 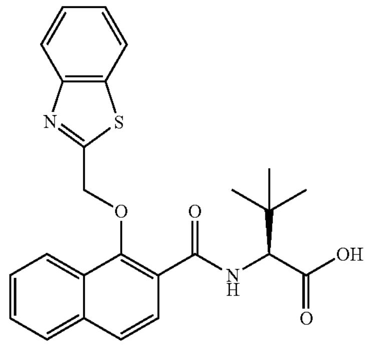 [SMILES: CC(C)(C)[C@H](NC(=O)c1ccc2ccccc2c1OCc1nc2ccccc2s1)C(=O)O] | 58 |
| 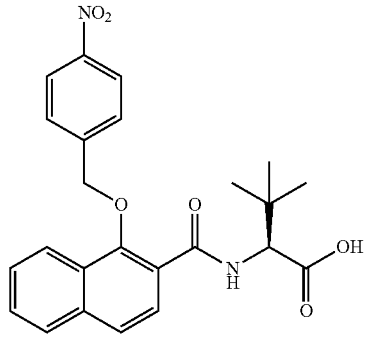 | 231 |
| 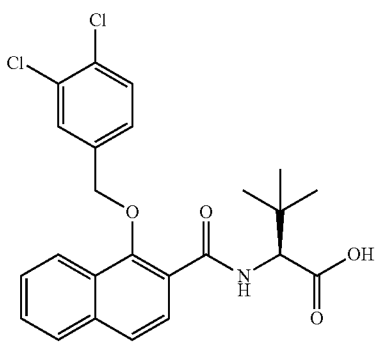 [SMILES: CC(C)(C)[C@H](NC(=O)c1ccc2ccccc2c1OCc1ccc(Cl)c(Cl)c1)C(=O)O] | 47 |
TABLE 1-continued
| Compound | # |
| --- | --- |
| 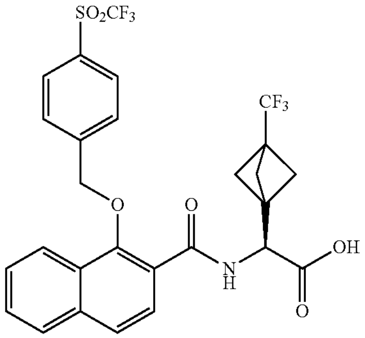 | 3 |
| 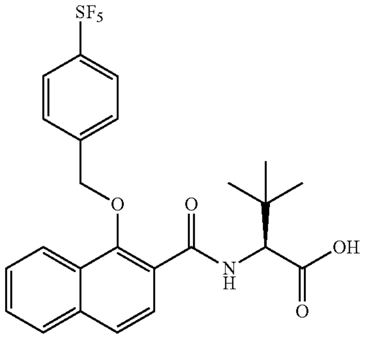 | 67 |
| 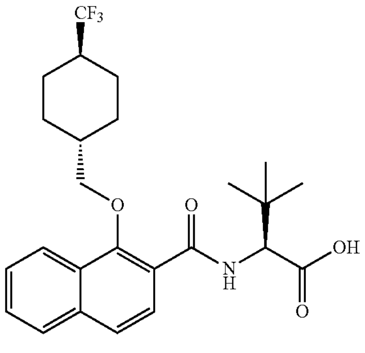 [SMILES: CC(C)(C)[C@H](NC(=O)c1ccc2ccccc2c1OC[C@H]1CC[C@H](C(F)(F)F)CC1)C(=O)O] | 222 |
| 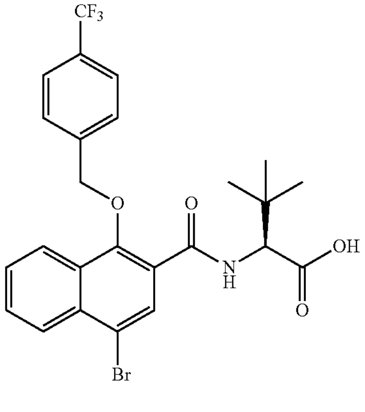 | 51 |

TABLE 1-continued
| Compound | # |
|---|---|
| 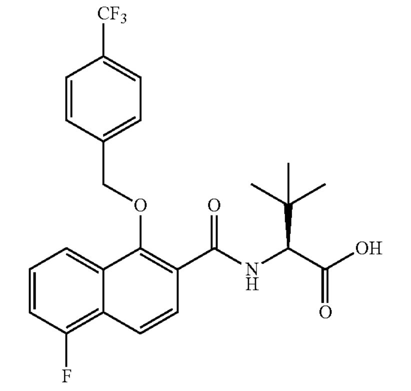 | 236 |
| 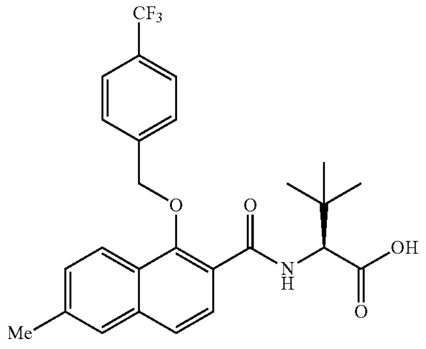 | 233 |
| 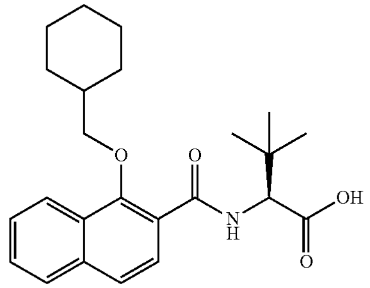 [SMILES: CC(C)(C)[C@H](NC(=O)c1ccc2ccccc2c1OCC1CCCCC1)C(=O)O] | 72 |
| 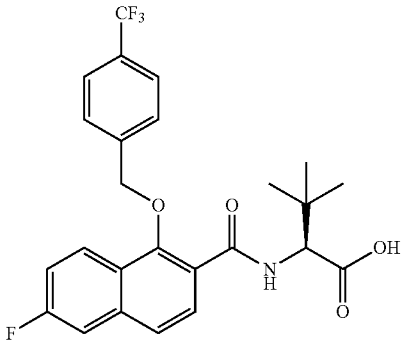 | 27 |
| 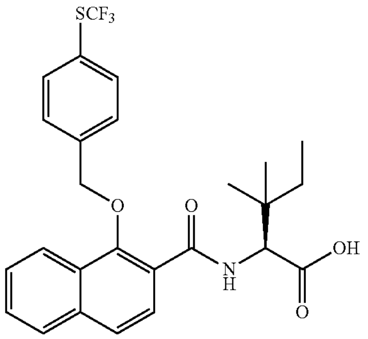 | 55 |
| 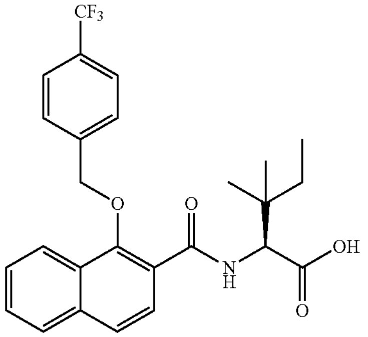 | 78 |
| 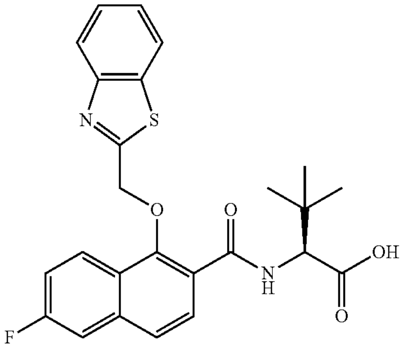 [SMILES: CC(C)(C)[C@H](NC(=O)c1ccc2cc(F)ccc2c1OCc1nc2ccccc2s1)C(=O)O] | 61 |
| 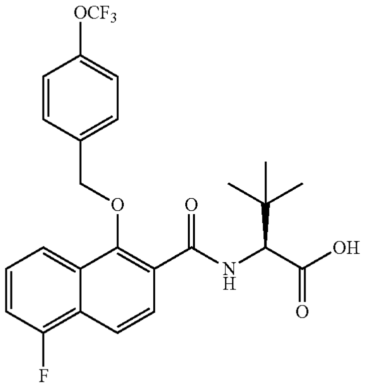 | 221 |

TABLE 1-continued
| Compound | # |
|---|---|
| 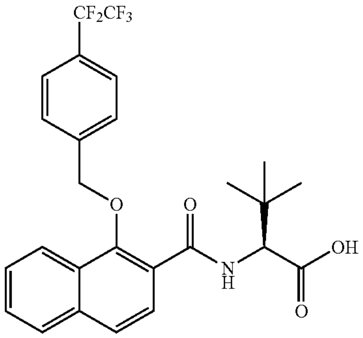 | 37 |
| 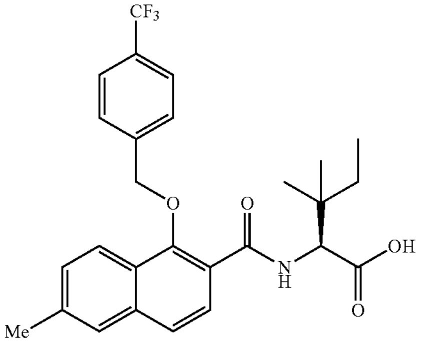 [SMILES: CCC(C)(C)[C@H](NC(=O)c1ccc2cc(C)ccc2c1OCc1ccc(C(F)(F)F)cc1)C(=O)O] | 225 |
| 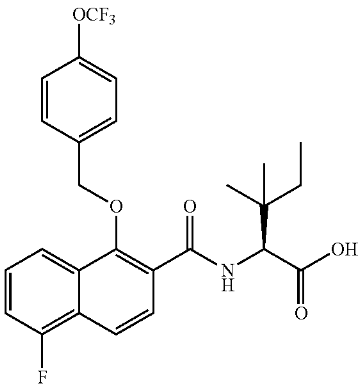 | 226 |
| 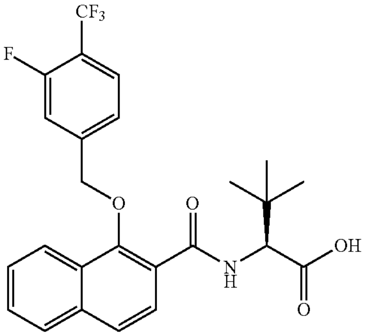 [SMILES: CC(C)(C)[C@H](NC(=O)c1ccc2ccccc2c1OCc1ccc(C(F)(F)F)c(F)c1)C(=O)O] | 25 |
TABLE 1-continued
| Compound | # |
|---|---|
| 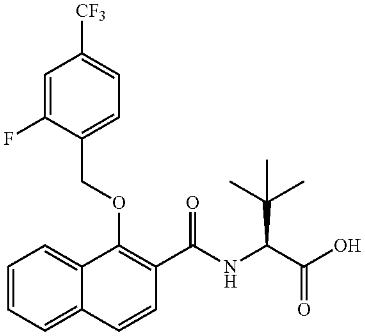 [SMILES: CC(C)(C)[C@H](NC(=O)c1ccc2ccccc2c1OCc1ccc(C(F)(F)F)cc1F)C(=O)O] | 70 |
| 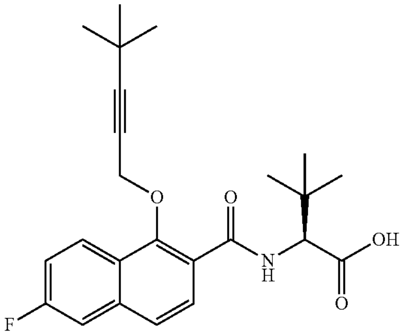 [SMILES: CC(C)(C)C#CCOc1c(C(=O)N[C@H](C(=O)O)C(C)(C)C)ccc2cc(F)ccc12] | 266 |
| 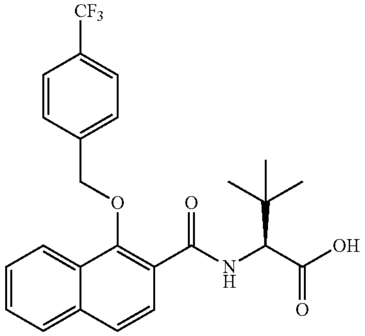 | 74 |
| 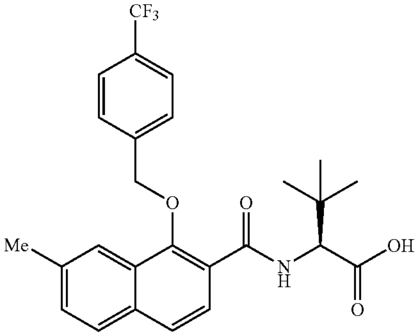 | 279 |

TABLE 1-continued
| Compound | # |
| --- | --- |
| 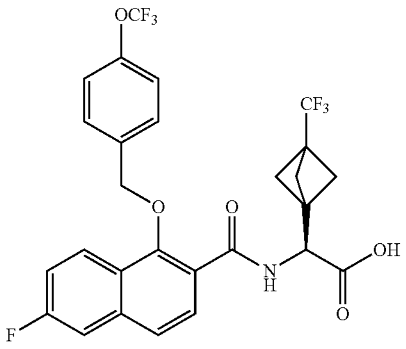 | 4 |
| 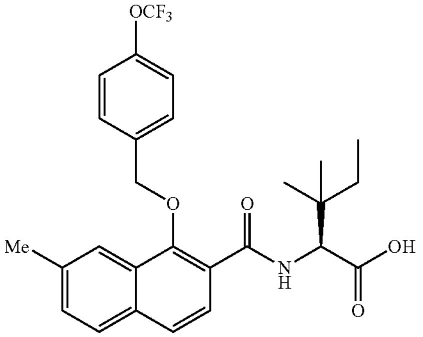 | 280 |
| 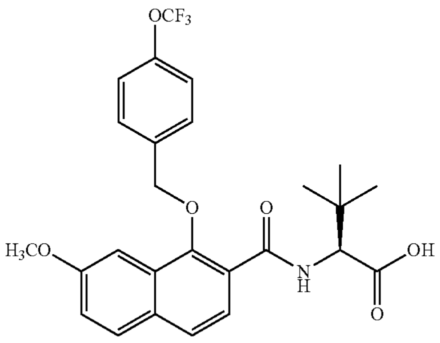 | 310 |
| 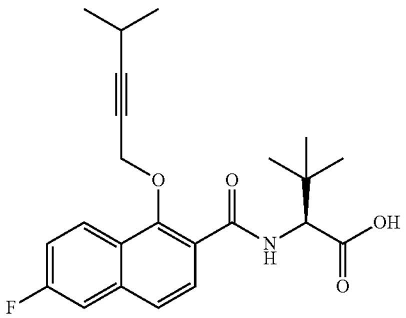 [SMILES: CC(C)C#CCOc1c(C(=O)N[C@H](C(=O)O)C(C)(C)C)ccc2cc(F)ccc12] | 224 |
TABLE 1-continued
| Compound | # |
| --- | --- |
| 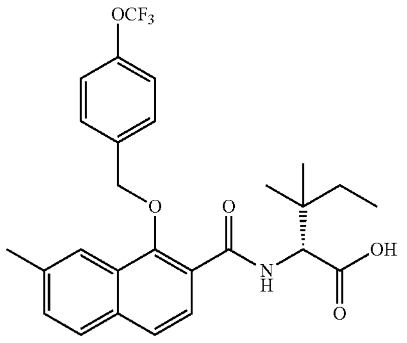 | 312 |
| 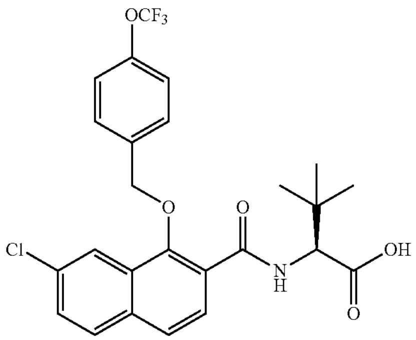 [SMILES: CC(C)(C)[C@H](NC(=O)c1ccc2ccc(Cl)cc2c1OCc1ccc(OC(F)(F)F)cc1)C(=O)O] | 237 |
| 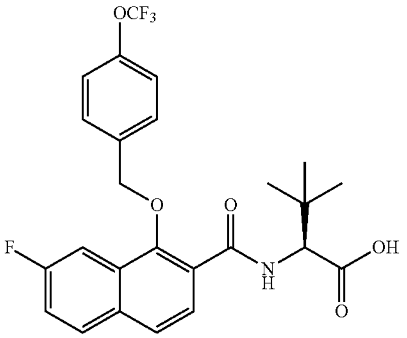 | 239 |
| 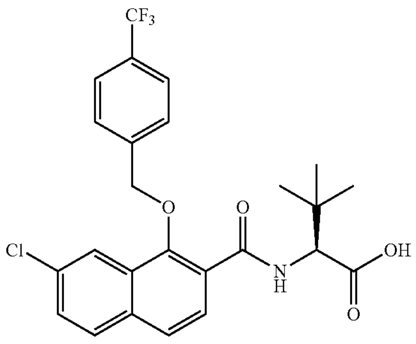 | 286 |

TABLE 1-continued
| Compound | # |
| --- | --- |
| 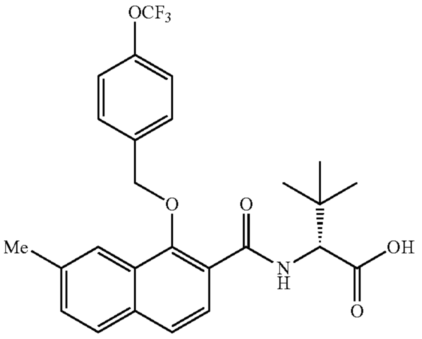 [SMILES: Cc1ccc2ccc(C(=O)N[C@@H](C(=O)O)C(C)(C)C)c(OCc3ccc(OC(F)(F)F)cc3)c2c1] | 289 |
| 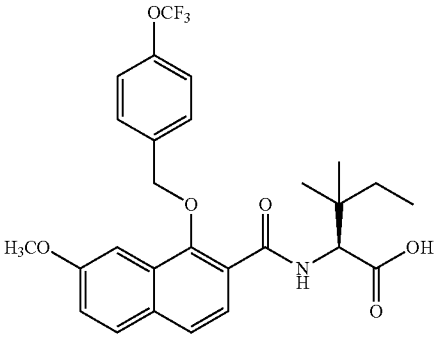 | 311 |
| 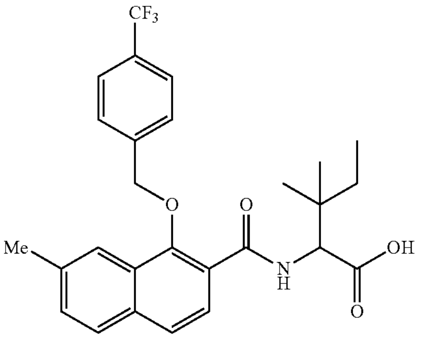 [SMILES: CCC(C)(C)C(NC(=O)c1ccc2ccc(C)cc2c1OCc1ccc(C(F)(F)F)cc1)C(=O)O] | 275 |
| 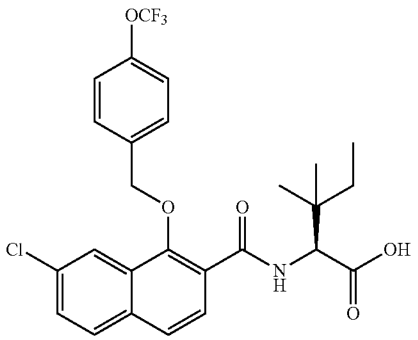 | 277 |
TABLE 1-continued
| Compound | # |
| --- | --- |
| 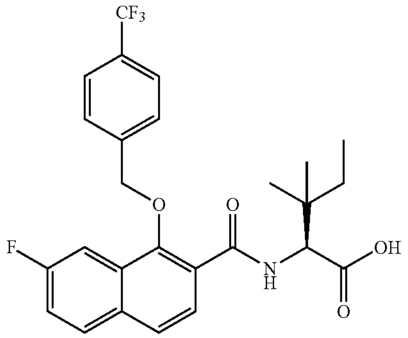 | 274 |
| 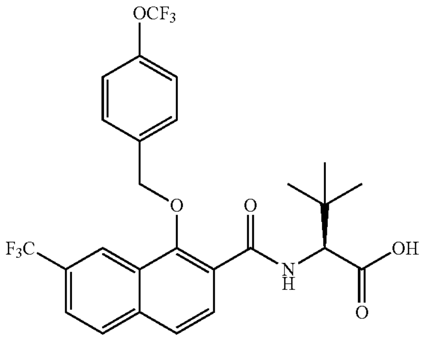 | 292 |
| 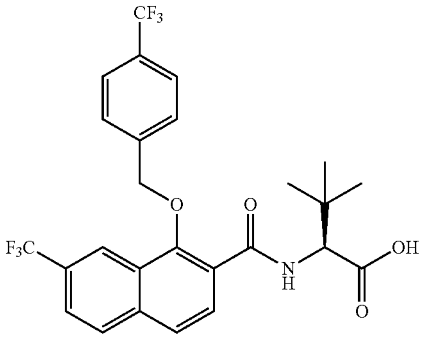 | 293 |
| 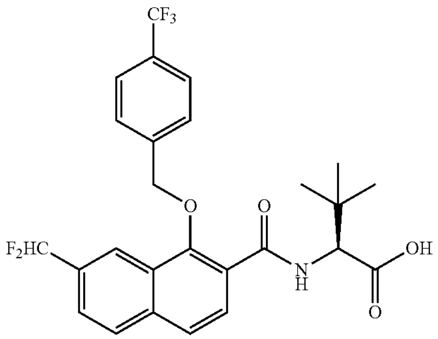 | 244 |

TABLE 1-continued
| Compound | # |
|---|---|
| 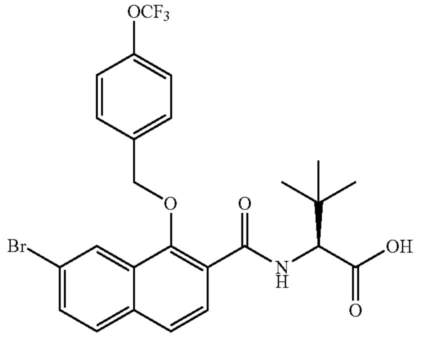 | 247 |
| 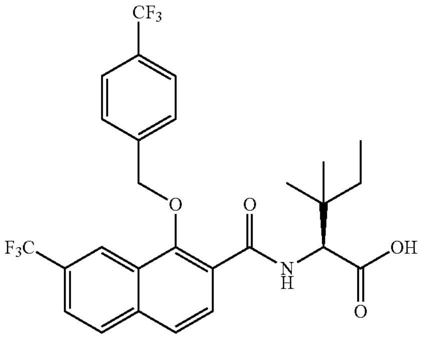 | 295 |
| 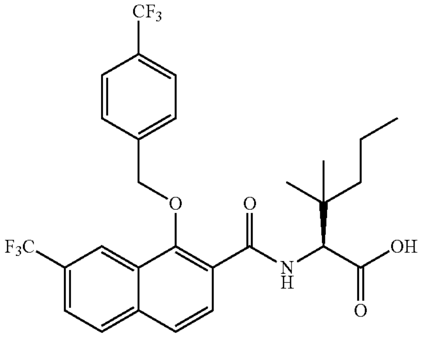 [SMILES: CCCC(C)(C)[C@H](NC(=O)c1ccc2ccc(C(F)(F)F)cc2c1OCc1ccc(C(F)(F)F)cc1)C(=O)O] | 304 |
| 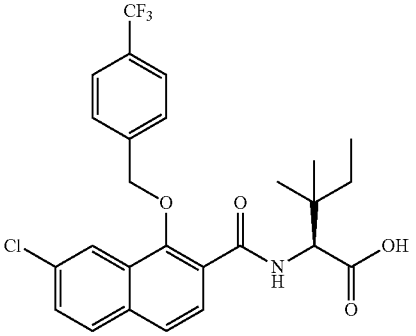 [SMILES: CCC(C)(C)[C@H](NC(=O)c1ccc2ccc(Cl)cc2c1OCc1ccc(C(F)(F)F)cc1)C(=O)O] | 283 |
| 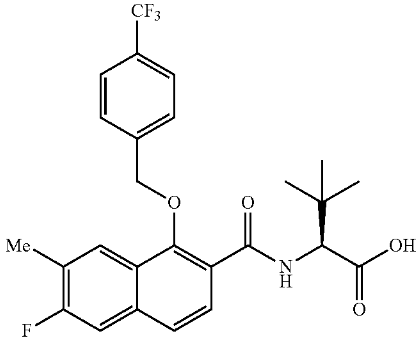 [SMILES: Cc1cc2c(OCc3ccc(C(F)(F)F)cc3)c(C(=O)N[C@H](C(=O)O)C(C)(C)C)ccc2cc1F] | 278 |
| 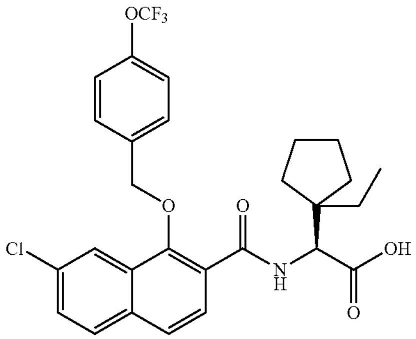 [SMILES: CCC1([C@H](NC(=O)c2ccc3ccc(Cl)cc3c2OCc2ccc(OC(F)(F)F)cc2)C(=O)O)CCCC1] | 293 |
| 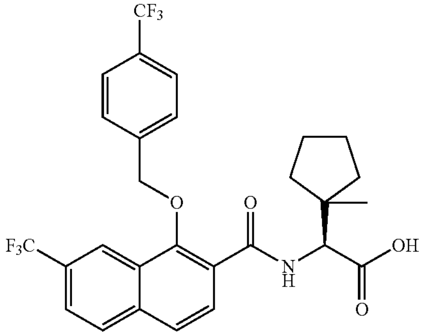 [SMILES: CC1([C@H](NC(=O)c2ccc3ccc(C(F)(F)F)cc3c2OCc2ccc(C(F)(F)F)cc2)C(=O)O)CCCC1] | 301 |
| 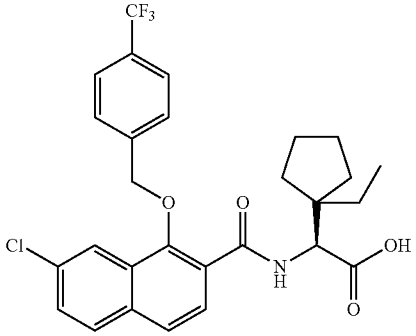 [SMILES: CCC1([C@H](NC(=O)c2ccc3ccc(Cl)cc3c2OCc2ccc(C(F)(F)F)cc2)C(=O)O)CCCC1] | 298 |

TABLE 1-continued
| Compound | # |
|---|---|
| 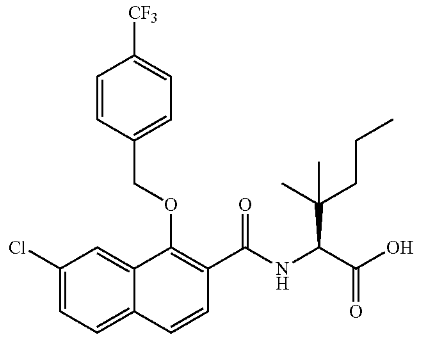 [SMILES: CCCC(C)(C)[C@H](NC(=O)c1ccc2ccc(Cl)cc2c1OCc1ccc(C(F)(F)F)cc1)C(=O)O] | 306 |
| 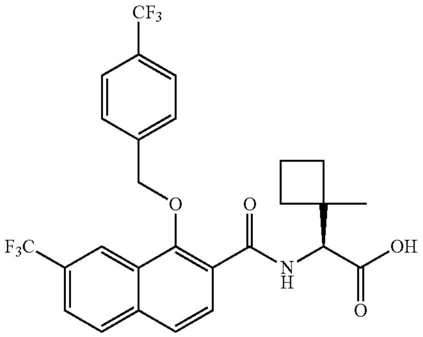 [SMILES: CC1([C@H](NC(=O)c2ccc3ccc(C(F)(F)F)cc3c2OCc2ccc(C(F)(F)F)cc2)C(=O)O)CCC1] | 299 |
| 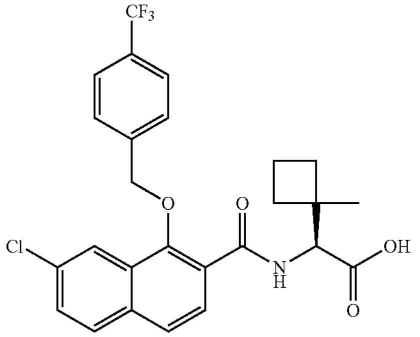 [SMILES: CC1([C@H](NC(=O)c2ccc3ccc(Cl)cc3c2OCc2ccc(C(F)(F)F)cc2)C(=O)O)CCC1] | 300 |
| 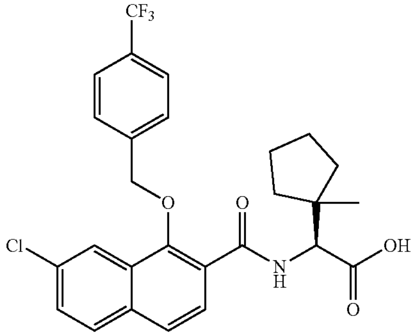 [SMILES: CC1([C@H](NC(=O)c2ccc3ccc(Cl)cc3c2OCc2ccc(C(F)(F)F)cc2)C(=O)O)CCCC1] | 302 |
TABLE 1-continued
| Compound | # |
|---|---|
| 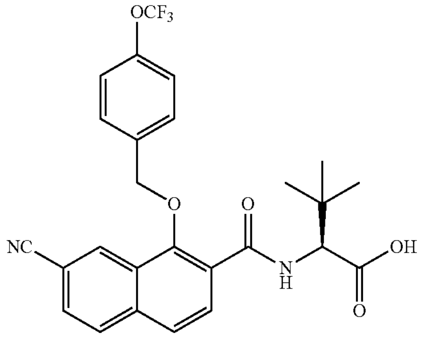 [SMILES: CC(C)(C)[C@H](NC(=O)c1ccc2ccc(C#N)cc2c1OCc1ccc(OC(F)(F)F)cc1)C(=O)O] | 254 |
| 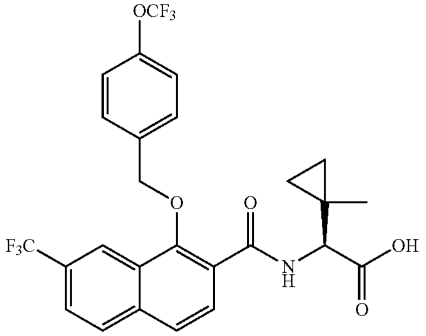 | 297 |
| 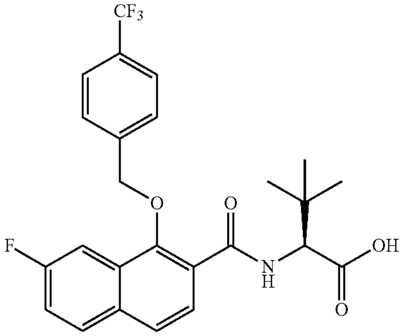 | 241 |
| 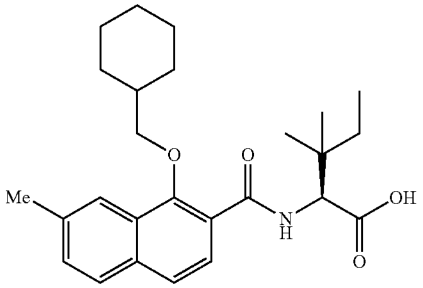 [SMILES: CCC(C)(C)[C@H](NC(=O)c1ccc2ccc(C)cc2c1OCC1CCCCC1)C(=O)O] | 281 |

TABLE 1-continued
| Compound | # |
|---|---|
| 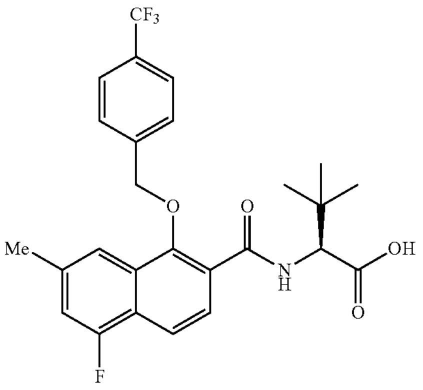 [SMILES: Cc1cc(F)c2ccc(C(=O)N[C@H](C(=O)O)C(C)(C)C)c(OCc3ccc(C(F)(F)F)cc3)c2c1] | 263 |
| 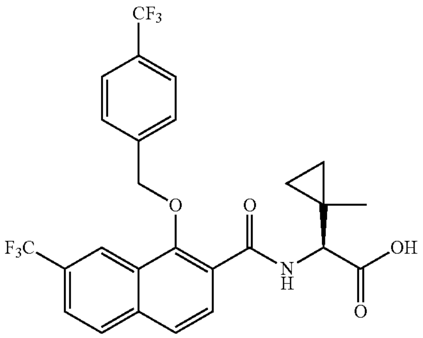 | 298 |
| 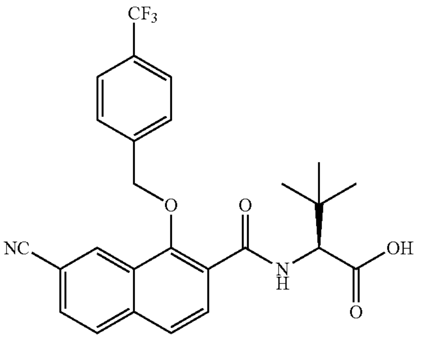 [SMILES: CC(C)(C)[C@H](NC(=O)c1ccc2ccc(C#N)cc2c1OCc1ccc(C(F)(F)F)cc1)C(=O)O] | 248 |
| 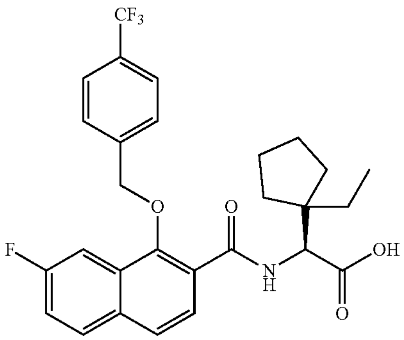 | 314 |
TABLE 1-continued
| Compound | # |
|---|---|
| 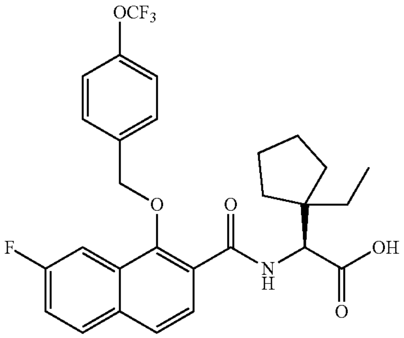 | 313 |
| 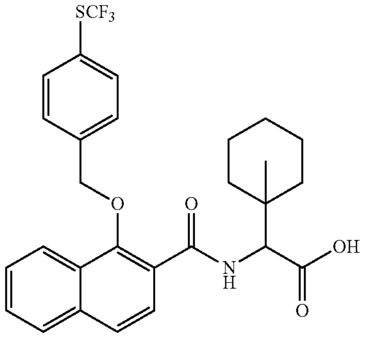 | 36 |
| 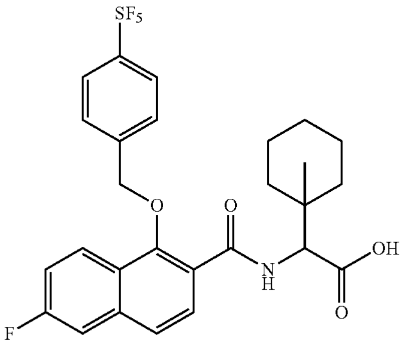 | 50 |
| 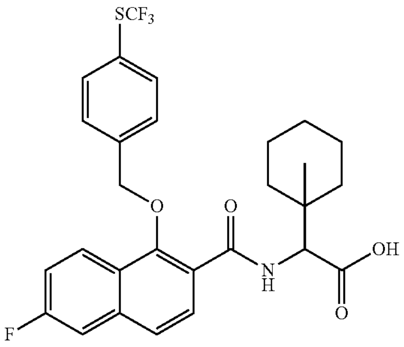 | 69 |

TABLE 1-continued
| Compound | # |
|---|---|
| 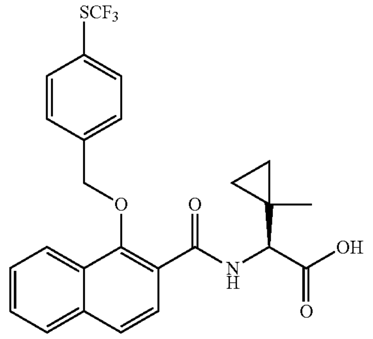 | 82 |
| 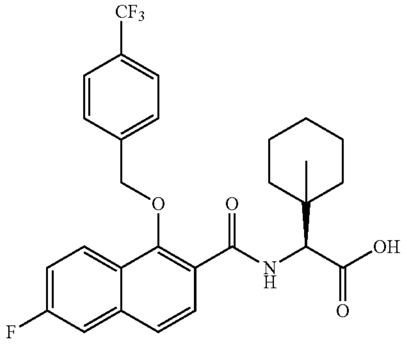 | 40 |
| 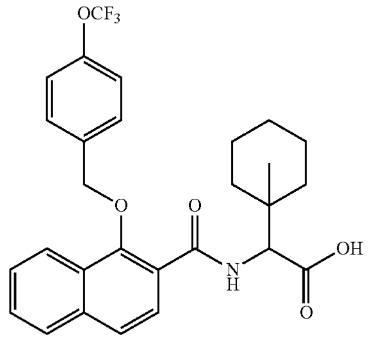 | 1 |
| 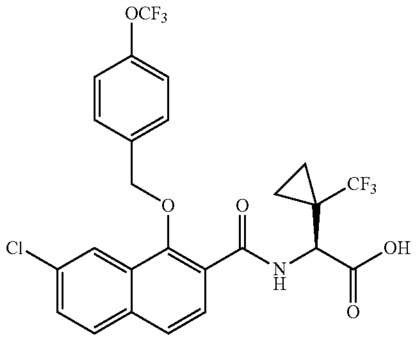 [SMILES: O=C(N[C@H](C(=O)O)C1(C(F)(F)F)CC1)c1ccc2ccc(Cl)cc2c1OCc1ccc(OC(F)(F)F)cc1] | 238 |
TABLE 1-continued
| Compound | # |
|---|---|
| 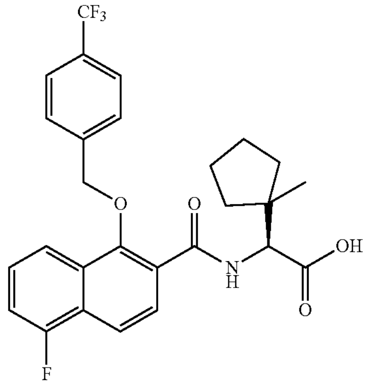 [SMILES: CC1([C@H](NC(=O)c2ccc3c(F)cccc3c2OCc2ccc(C(F)(F)F)cc2)C(=O)O)CCCC1] | 303 |
| 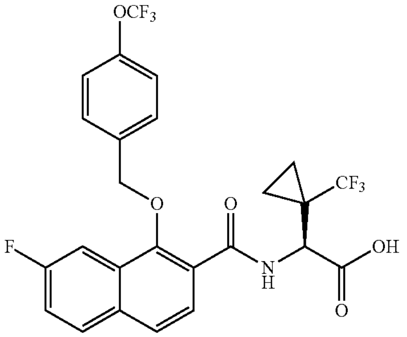 [SMILES: O=C(N[C@H](C(=O)O)C1(C(F)(F)F)CC1)c1ccc2ccc(F)cc2c1OCc1ccc(OC(F)(F)F)cc1] | 240 |
| 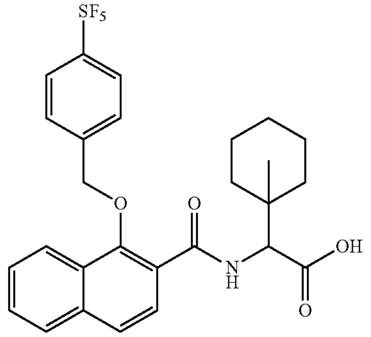 | 48 |
| 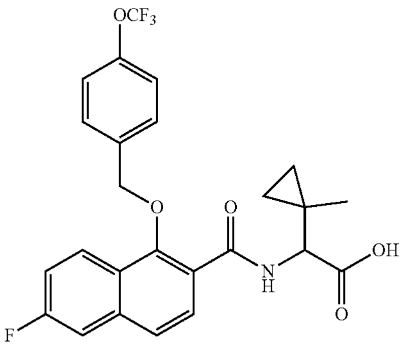 | 30 |

TABLE 1-continued
| Compound | # |
|---|---|
| 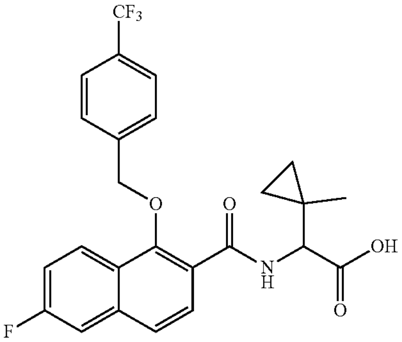 | 60 |
| 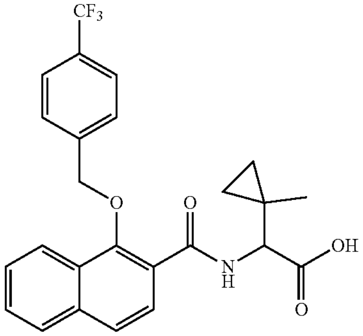 | 56 |
| 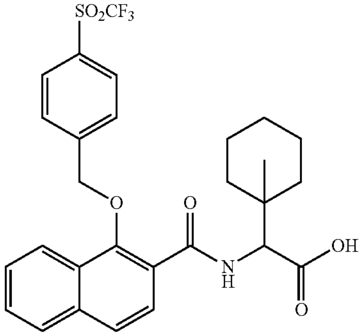 | 77 |
| 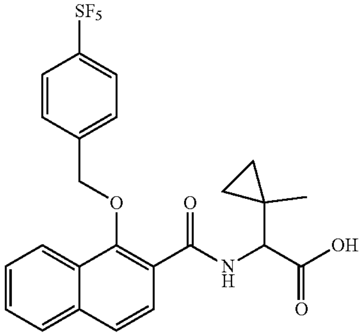 | 68 |
TABLE 1-continued
| Compound | # |
|---|---|
| 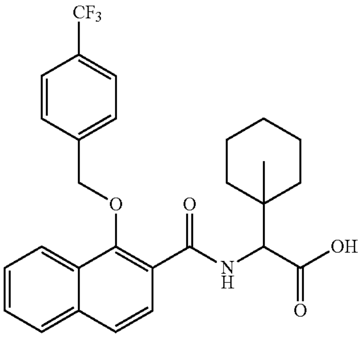 | 80 |
| 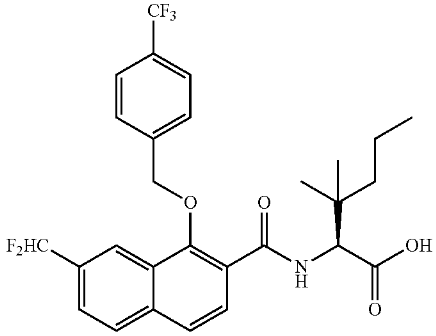 | 246 |
| 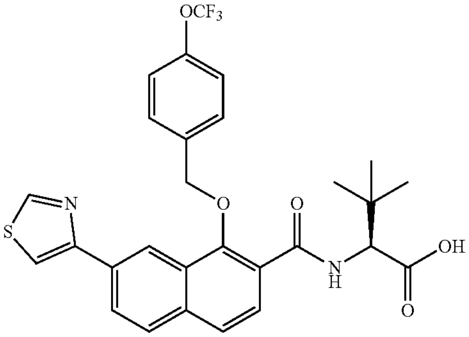 | 292 |
| 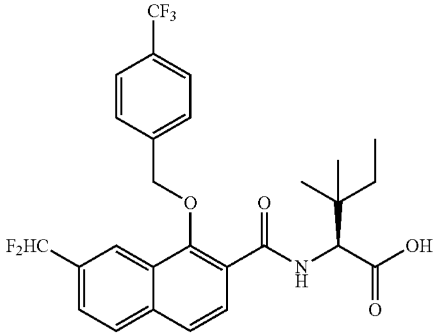 | 242 |

TABLE 1-continued
| Compound | # |
| --- | --- |
| 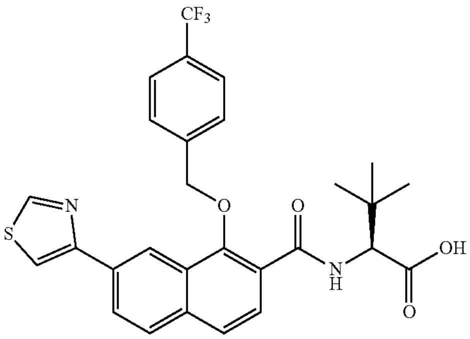 [SMILES: CC(C)(C)[C@H](NC(=O)c1ccc2ccc(-c3cscn3)cc2c1OCc1ccc(C(F)(F)F)cc1)C(=O)O] | 243 |
| 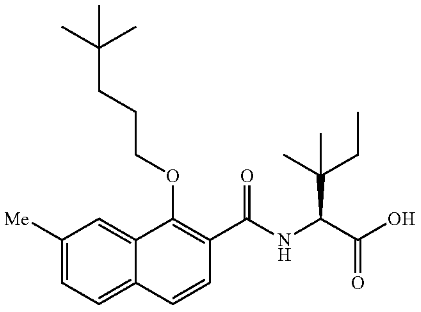 [SMILES: CCC(C)(C)[C@H](NC(=O)c1ccc2ccc(C)cc2c1OCCCC(C)(C)C)C(=O)O] | 257 |
| 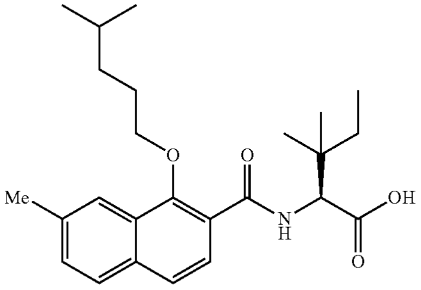 [SMILES: CCC(C)(C)[C@H](NC(=O)c1ccc2ccc(C)cc2c1OCCCC(C)C)C(=O)O] | 294 |
| 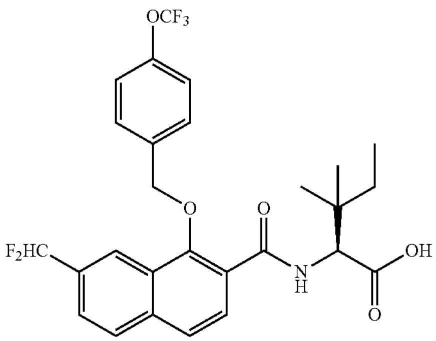 [SMILES: CCC(C)(C)[C@H](NC(=O)c1ccc2ccc(C(F)F)cc2c1OCc1ccc(OC(F)(F)F)cc1)C(=O)O] | 290 |
TABLE 1-continued
| Compound | # |
| --- | --- |
| 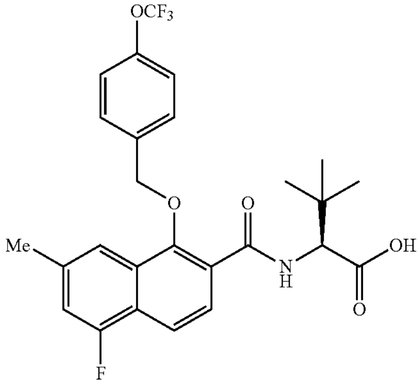 [SMILES: Cc1cc(F)c2ccc(C(=O)N[C@H](C(=O)O)C(C)(C)C)c(OCc3ccc(OC(F)(F)F)cc3)c2c1] | 271 |
| 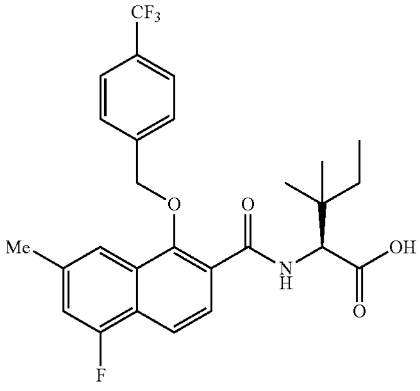 [SMILES: CCC(C)(C)[C@H](NC(=O)c1ccc2c(F)cc(C)cc2c1OCc1ccc(C(F)(F)F)cc1)C(=O)O] | 272 |
| 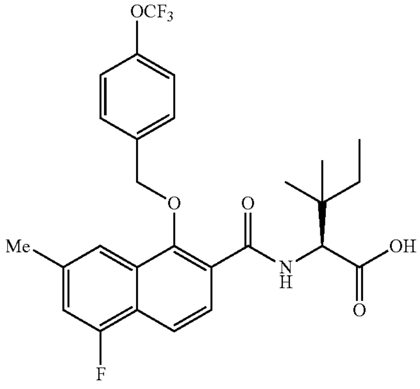 [SMILES: CCC(C)(C)[C@H](NC(=O)c1ccc2c(F)cc(C)cc2c1OCc1ccc(OC(F)(F)F)cc1)C(=O)O] | 273 |
| 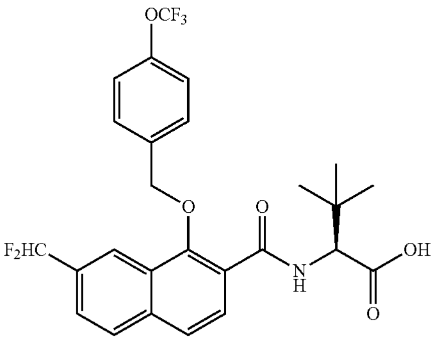 | 245 |

TABLE 1-continued
| Compound | # |
|---|---|
| 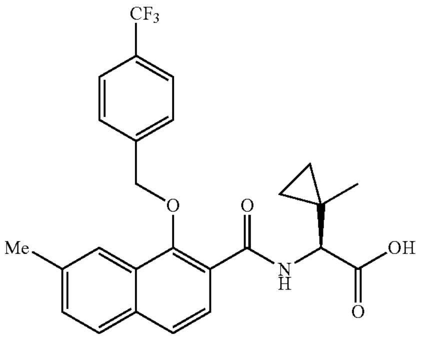 [SMILES: Cc1ccc2ccc(C(=O)N[C@H](C(=O)O)C3(C)CC3)c(OCc3ccc(C(F)(F)F)cc3)c2c1] | 229 |
| 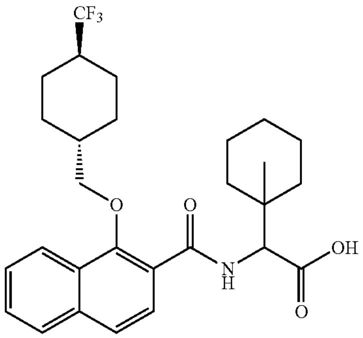 | 43 |
| 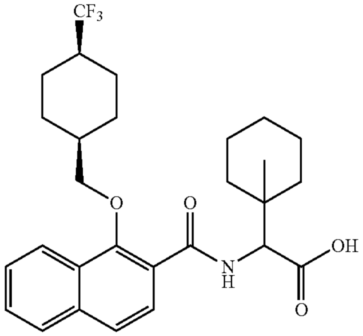 | 39 |
| 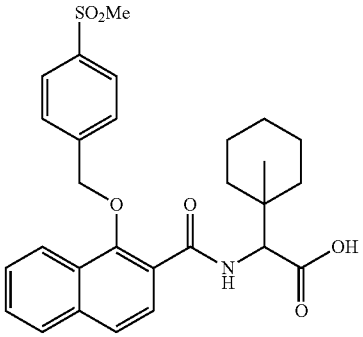 | 44 |
TABLE 1-continued
| Compound | # |
|---|---|
| 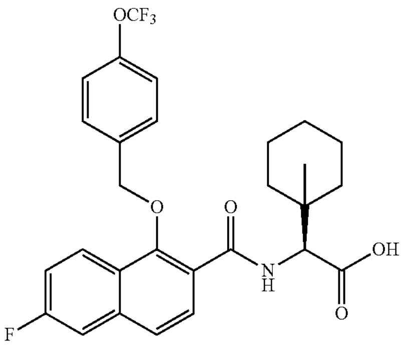 | 33 |
| 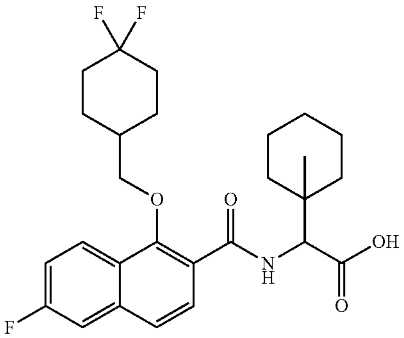 | 54 |
| 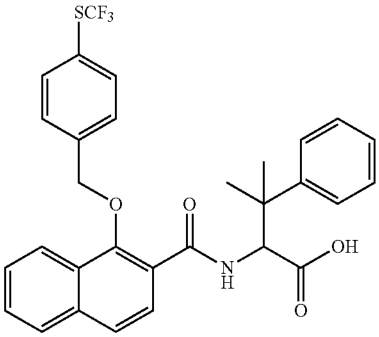 | 5 |
| 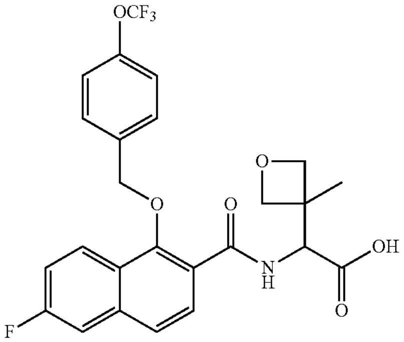 | 6 |

TABLE 1-continued
| Compound | # |
|---|---|
| 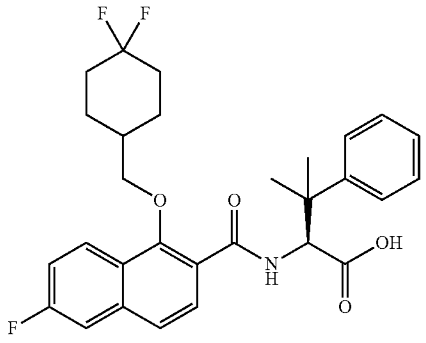 [SMILES: CC(C)(c1ccccc1)[C@H](NC(=O)c1ccc2cc(F)ccc2c1OCC1CCC(F)(F)CC1)C(=O)O] | 7 |
| 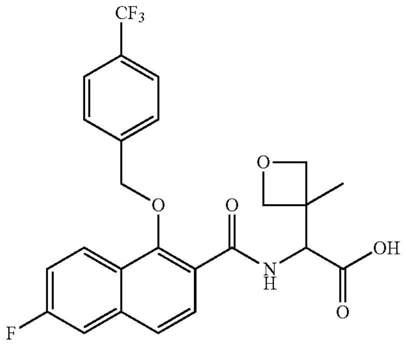 | 8 |
| 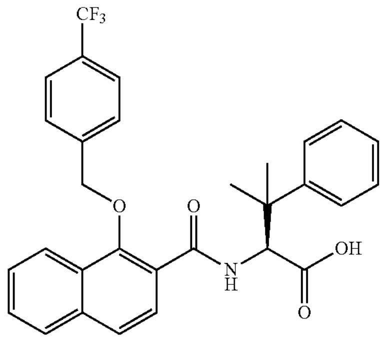 | 9 |
| 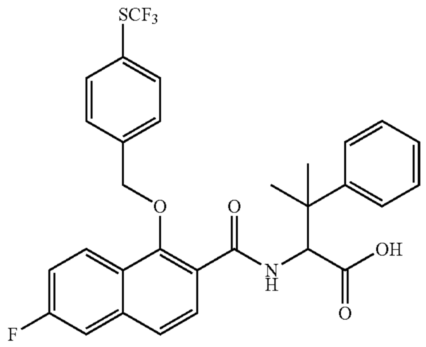 | 10 |
TABLE 1-continued
| Compound | # |
|---|---|
| 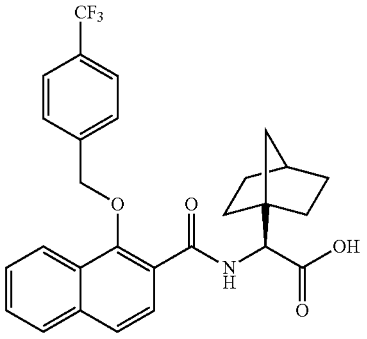 | 11 |
| 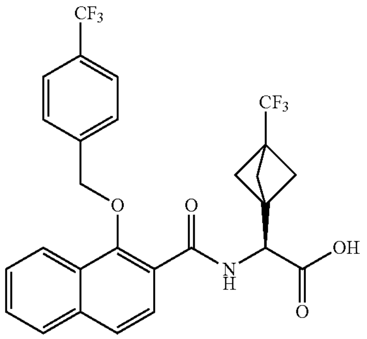 | 13 |
| 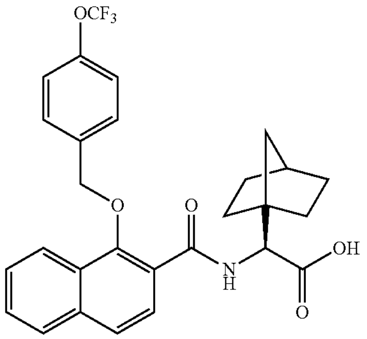 [SMILES: O=C(N[C@H](C(=O)O)C12CCC(CC1)C2)c1ccc2ccccc2c1OCc1ccc(OC(F)(F)F)cc1] | 14 |
| 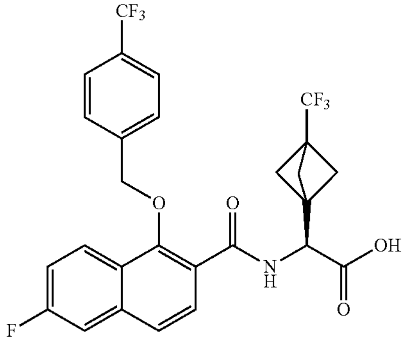 | 15 |

TABLE 1-continued
| Compound | # |
| --- | --- |
| 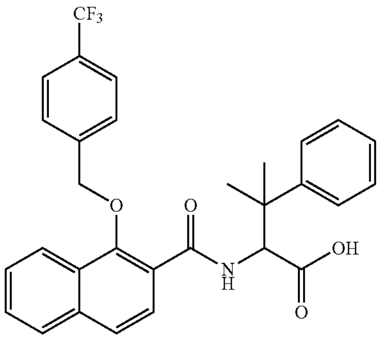 | 16 |
| 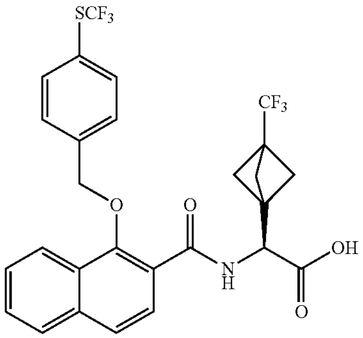 | 17 |
| 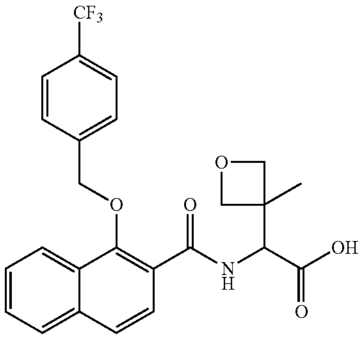 | 18 |
| 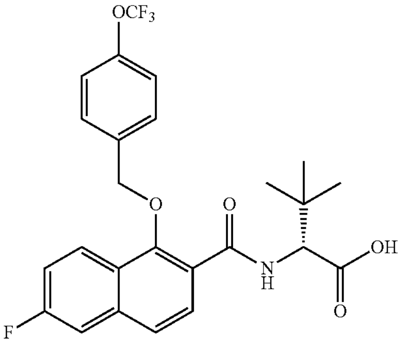 [SMILES: CC(C)(C)[C@@H](NC(=O)c1ccc2cc(F)ccc2c1OCc1ccc(OC(F)(F)F)cc1)C(=O)O] | 19 |
TABLE 1-continued
| Compound | # |
| --- | --- |
| 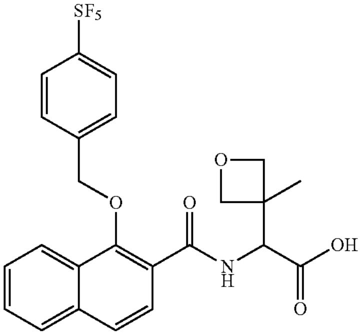 | 20 |
| 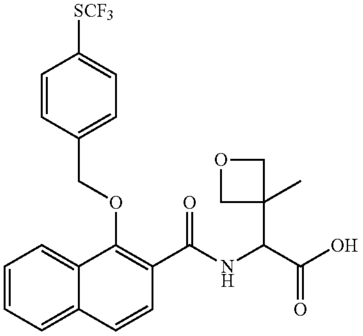 | 21 |
| 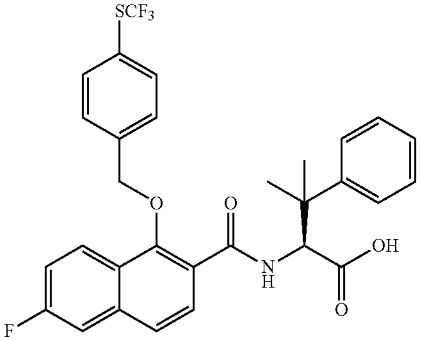 | 22 |
| 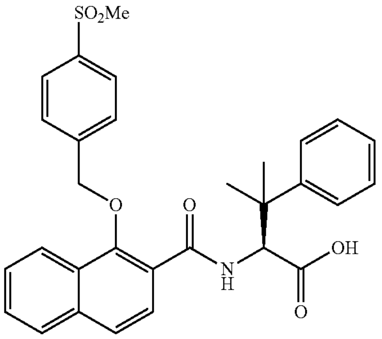 [SMILES: CC(C)(c1ccccc1)[C@H](NC(=O)c1ccc2ccccc2c1OCc1ccc(S(C)(=O)=O)cc1)C(=O)O] | 23 |

TABLE 1-continued
| Compound | # |
| --- | --- |
| 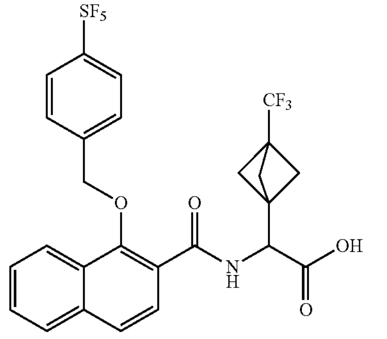 | 24 |
| 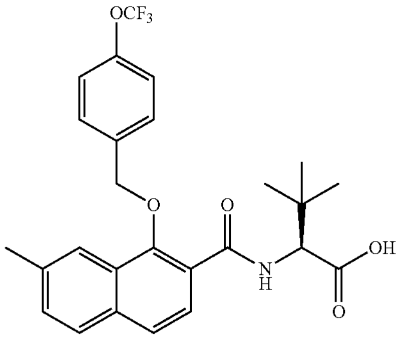 [SMILES: Cc1ccc2ccc(C(=O)N[C@H](C(=O)O)C(C)(C)C)c(OCc3ccc(OC(F)(F)F)cc3)c2c1] | 249 |
| 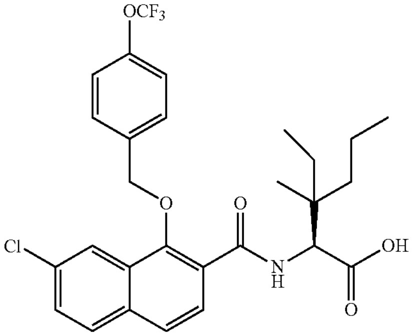 [SMILES: CCCC(C)(CC)[C@H](NC(=O)c1ccc2ccc(Cl)cc2c1OCc1ccc(OC(F)(F)F)cc1)C(=O)O] | 251 |
| 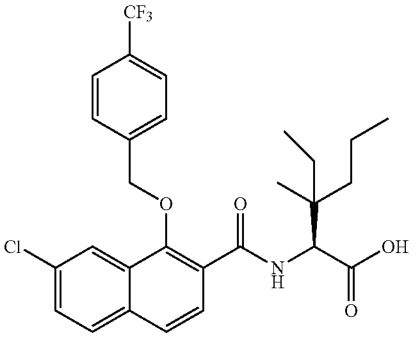 | 255 |
TABLE 1-continued
| Compound | # |
| --- | --- |
| 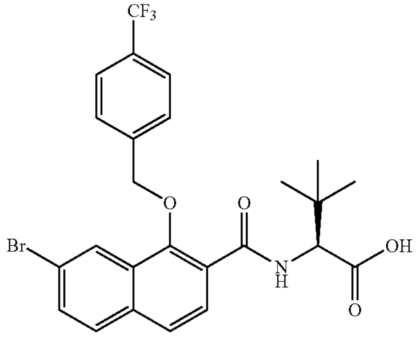 | 256 |
| 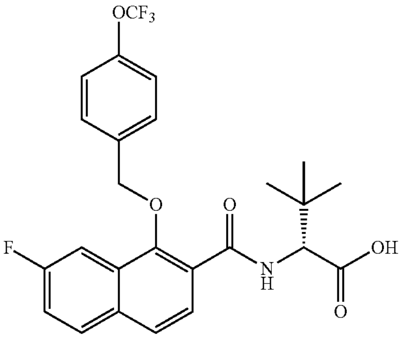 | 259 |
| 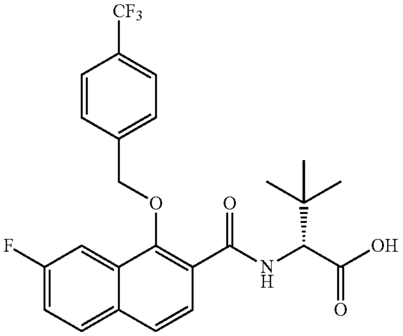 | 261 |
| 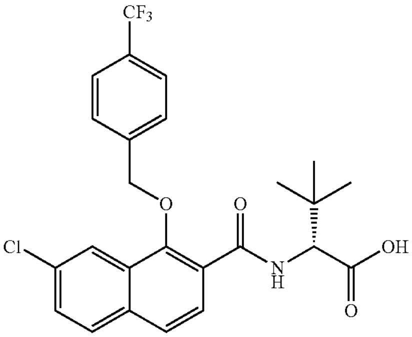 [SMILES: CC(C)(C)[C@@H](NC(=O)c1ccc2ccc(Cl)cc2c1OCc1ccc(C(F)(F)F)cc1)C(=O)O] | 262 |

TABLE 1-continued
| Compound | # |
|---|---|
| 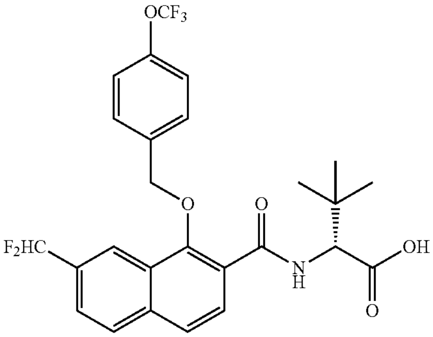 | 264 |
| 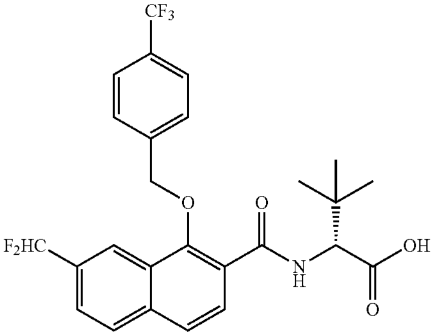 | 265 |
| 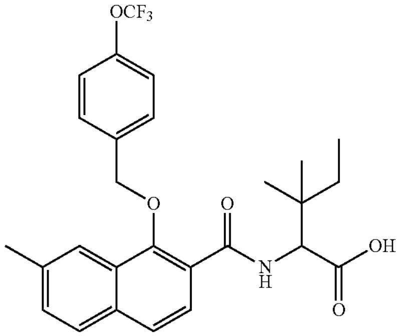 [SMILES: CCC(C)(C)C(NC(=O)c1ccc2ccc(C)cc2c1OCc1ccc(OC(F)(F)F)cc1)C(=O)O] | 276 |
| 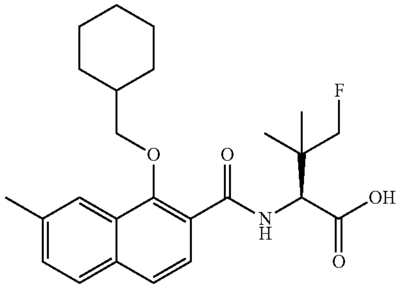 [SMILES: Cc1ccc2ccc(C(=O)N[C@H](C(=O)O)C(C)(C)CF)c(OCC3CCCCC3)c2c1] | 282 |
TABLE 1-continued
| Compound | # |
|---|---|
| 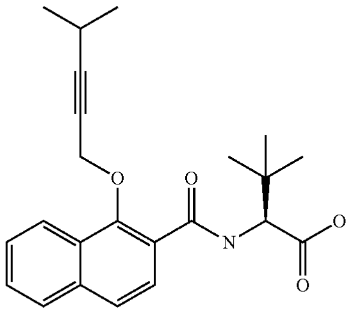 [SMILES: CC(C)C#CCOc1c(C(=O)N[C@H](C(=O)O)C(C)(C)C)ccc2ccccc12] | 235 |
| 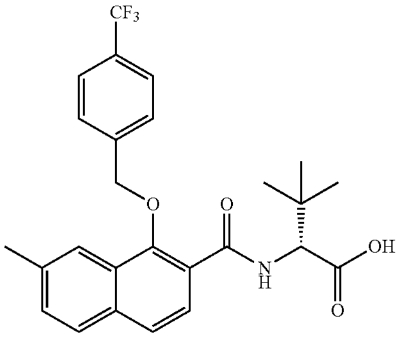 | 284 |
| 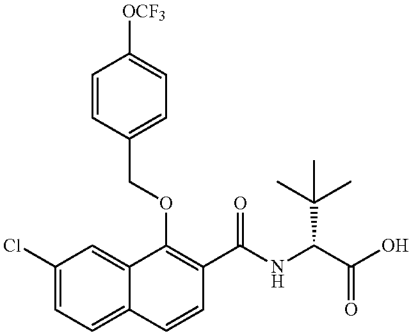 [SMILES: CC(C)(C)[C@@H](NC(=O)c1ccc2ccc(Cl)cc2c1OCc1ccc(OC(F)(F)F)cc1)C(=O)O] | 285 |
| 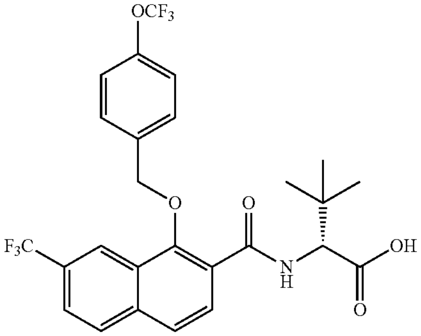 | 287 |

TABLE 1-continued
| Compound | # |
| --- | --- |
| 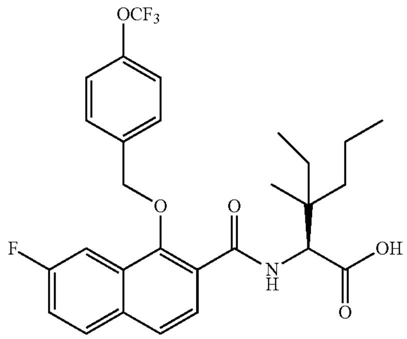 [SMILES: CCCC(C)(CC)[C@H](NC(=O)c1ccc2ccc(F)cc2c1OCc1ccc(OC(F)(F)F)cc1)C(=O)O] | 290 |
| 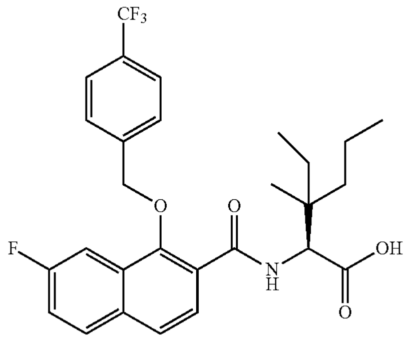 [SMILES: CCCC(C)(CC)[C@H](NC(=O)c1ccc2ccc(F)cc2c1OCc1ccc(C(F)(F)F)cc1)C(=O)O] | 291 |
| 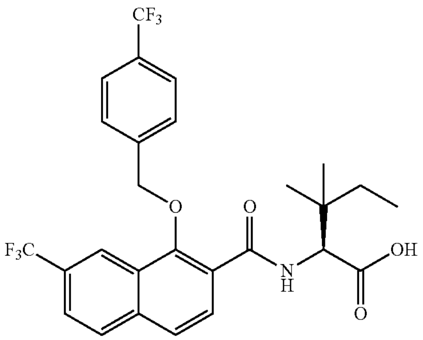 | 295 |
| 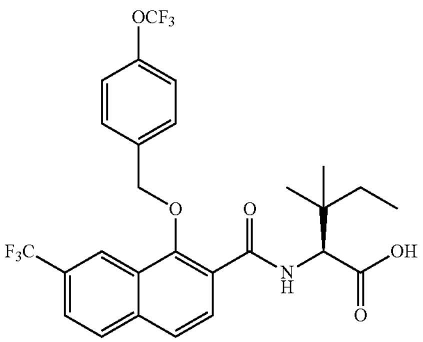 [SMILES: CCC(C)(C)[C@H](NC(=O)c1ccc2ccc(C(F)(F)F)cc2c1OCc1ccc(OC(F)(F)F)cc1)C(=O)O] | 296 |
TABLE 1-continued
| Compound | # |
| --- | --- |
| 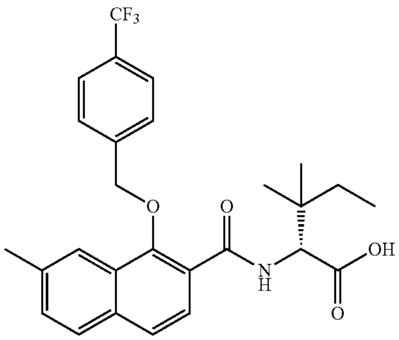 [SMILES: CCC(C)(C)[C@@H](NC(=O)c1ccc2ccc(C)cc2c1OCc1ccc(C(F)(F)F)cc1)C(=O)O] | 305 |
| 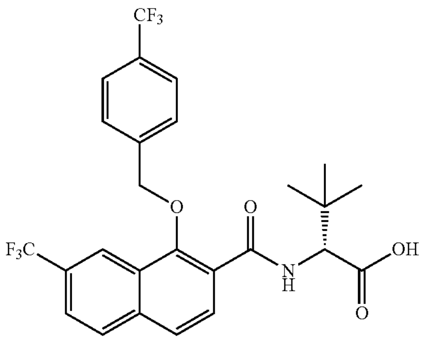 | 307 |
| 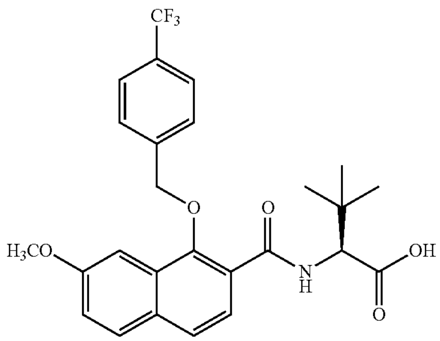 | 308 |
| 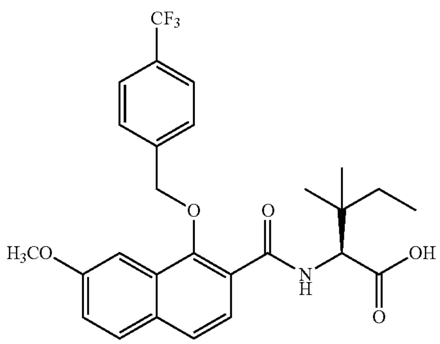 | 988 |

TABLE 1-continued
| Compound | # |
|---|---|
| 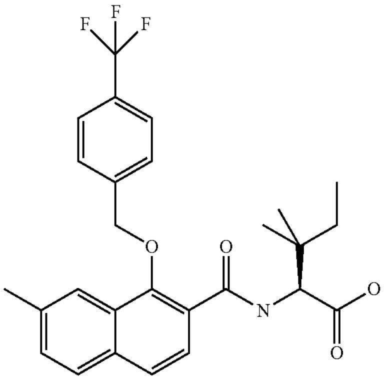 [SMILES: CCC(C)(C)[C@H](NC(=O)c1ccc2ccc(C)cc2c1OCc1ccc(C(F)(F)F)cc1)C(=O)O] | 288 |
| 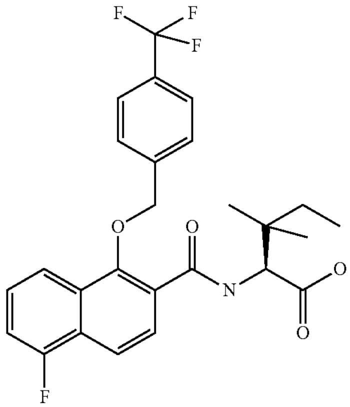 [SMILES: CCC(C)(C)[C@H](NC(=O)c1ccc2c(F)cccc2c1OCc1ccc(C(F)(F)F)cc1)C(=O)O] | 230 |
| 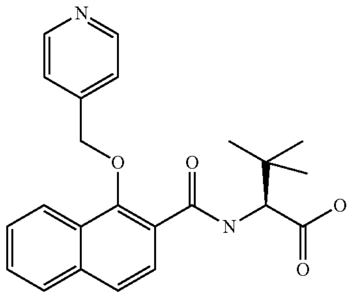 [SMILES: CC(C)(C)[C@H](NC(=O)c1ccc2ccccc2c1OCc1ccncc1)C(=O)O] | 232 |
| 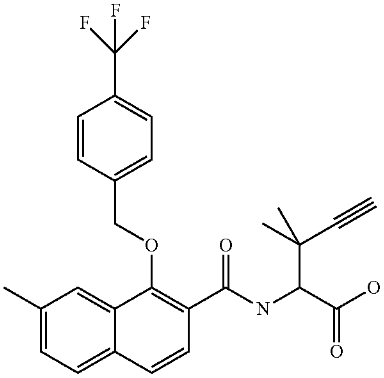 [SMILES: C#CC(C)(C)C(NC(=O)c1ccc2ccc(C)cc2c1OCc1ccc(C(F)(F)F)cc1)C(=O)O] | 219 |
TABLE 1-continued
| Compound | # |
|---|---|
| 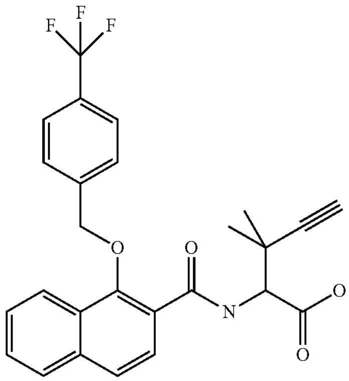 [SMILES: C#CC(C)(C)C(NC(=O)c1ccc2ccccc2c1OCc1ccc(C(F)(F)F)cc1)C(=O)O] | 228 |
| 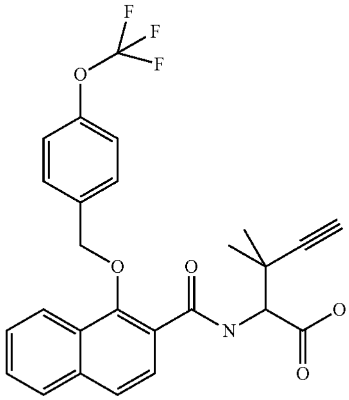 [SMILES: C#CC(C)(C)C(NC(=O)c1ccc2ccccc2c1OCc1ccc(OC(F)(F)F)cc1)C(=O)O] | 234 |
| 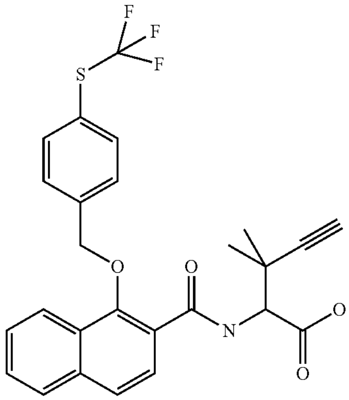 [SMILES: C#CC(C)(C)C(NC(=O)c1ccc2ccccc2c1OCc1ccc(SC(F)(F)F)cc1)C(=O)O] | 227 |
| 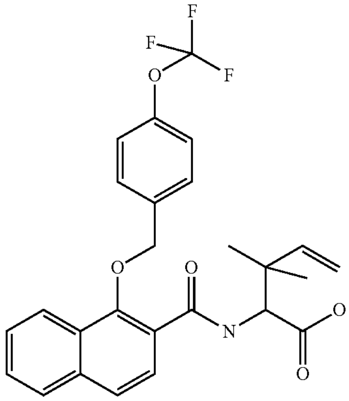 [SMILES: C=CC(C)(C)C(NC(=O)c1ccc2ccccc2c1OCc1ccc(OC(F)(F)F)cc1)C(=O)O] | 220 |

TABLE 1-continued
| Compound | # |
| --- | --- |
| 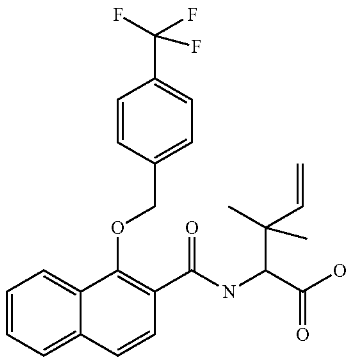 [SMILES: C=CC(C)(C)C(NC(=O)c1ccc2ccccc2c1OCc1ccc(C(F)(F)F)cc1)C(=O)O] | 223 |
In some embodiments, the compound of formula (I) is selected from the following compounds represented in Table 2 below:
TABLE 2
| Compound | # |
| --- | --- |
| 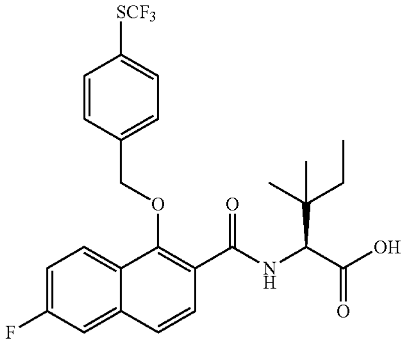 | 84 |
| 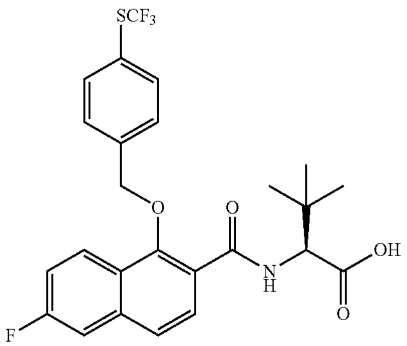 | 75 |
TABLE 2-continued
| Compound | # |
| --- | --- |
| 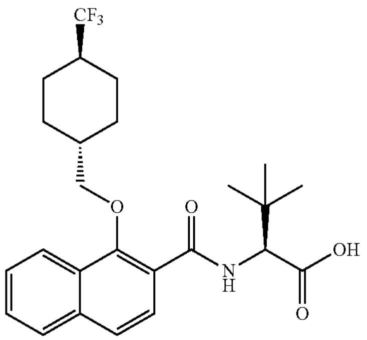 [SMILES: CC(C)(C)[C@H](NC(=O)c1ccc2ccccc2c1OC[C@H]1CC[C@H](C(F)(F)F)CC1)C(=O)O] | 222 |
| 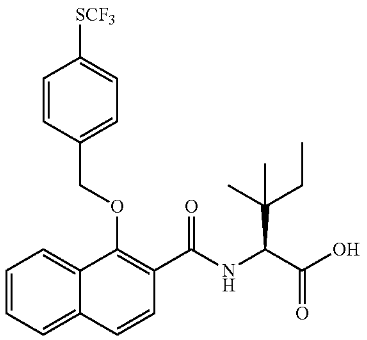 | 55 |
| 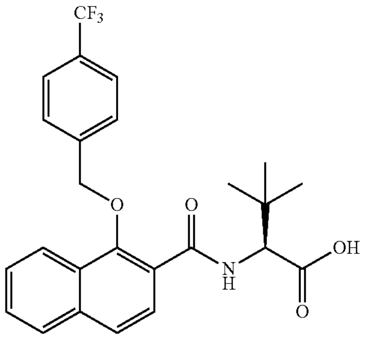 | 74 |
| 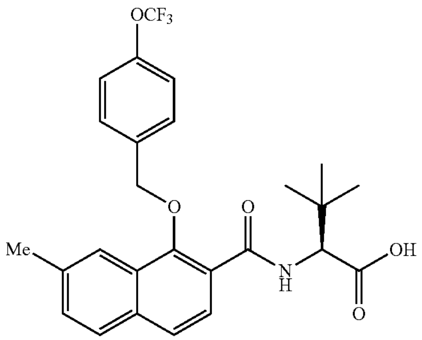 | 249 |

TABLE 2-continued
| Compound | # |
|---|---|
| 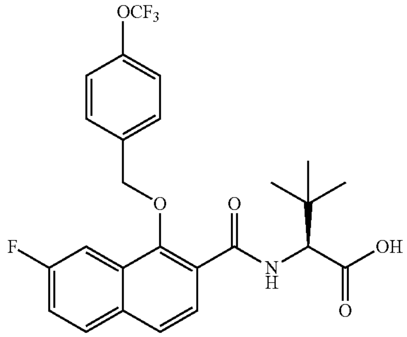 [SMILES: CC(C)(C)[C@H](NC(=O)c1ccc2ccc(F)cc2c1OCc1ccc(OC(F)(F)F)cc1)C(=O)O] | 239 |
| 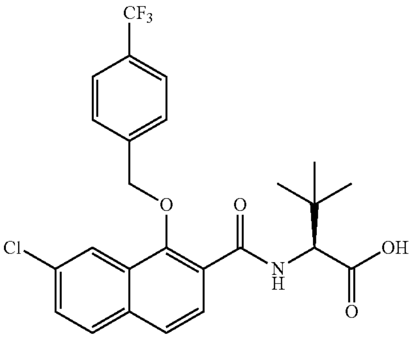 [SMILES: CC(C)(C)[C@H](NC(=O)c1ccc2ccc(Cl)cc2c1OCc1ccc(C(F)(F)F)cc1)C(=O)O] | 286 |
| 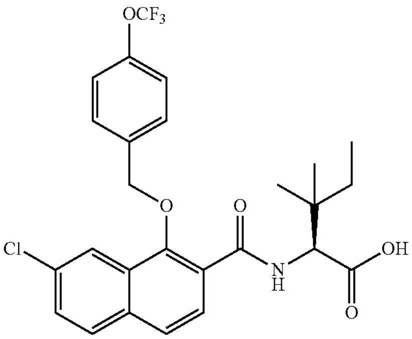 [SMILES: CCC(C)(C)[C@H](NC(=O)c1ccc2ccc(Cl)cc2c1OCc1ccc(OC(F)(F)F)cc1)C(=O)O] | 277 |
| 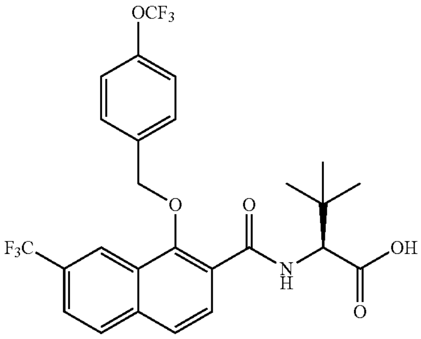 [SMILES: CC(C)(C)[C@H](NC(=O)c1ccc2ccc(C(F)(F)F)cc2c1OCc1ccc(OC(F)(F)F)cc1)C(=O)O] | 292 |
TABLE 2-continued
| Compound | # |
|---|---|
| 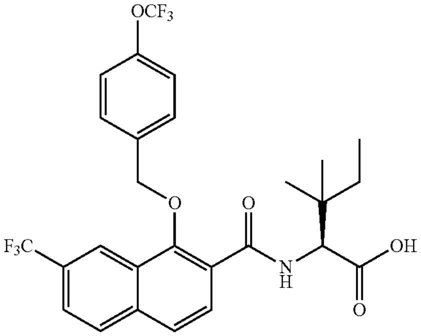 | 296 |
| 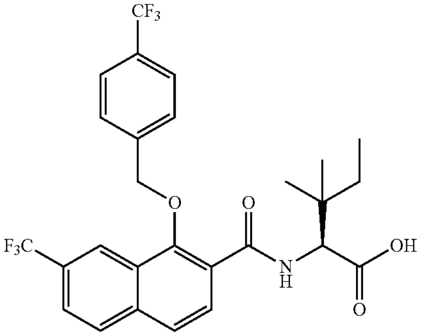 | 295 |
| 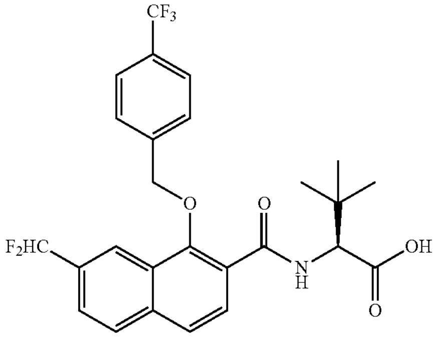 [SMILES: CC(C)(C)[C@H](NC(=O)c1ccc2ccc(C(F)F)cc2c1OCc1ccc(C(F)(F)F)cc1)C(=O)O] | 244 |
| 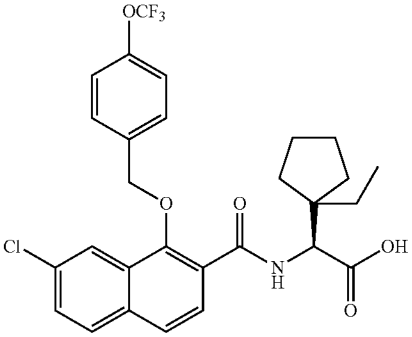 [SMILES: CCC1([C@H](NC(=O)c2ccc3ccc(Cl)cc3c2OCc2ccc(OC(F)(F)F)cc2)C(=O)O)CCCC1] | 253 |

TABLE 2-continued
| Compound | # |
|---|---|
| 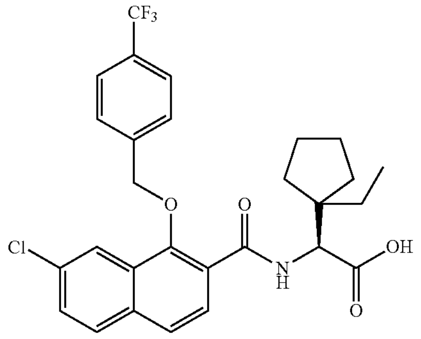 [SMILES: CCC1([C@H](NC(=O)c2ccc3ccc(Cl)cc3c2OCc2ccc(C(F)(F)F)cc2)C(=O)O)CCCC1] | 298 |
| 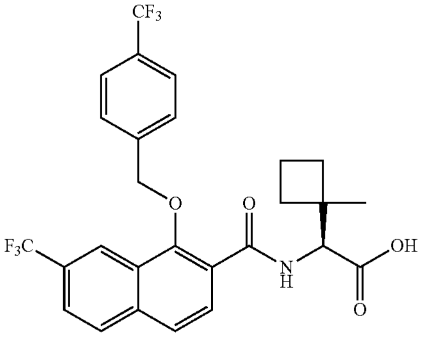 [SMILES: CC1([C@H](NC(=O)c2ccc3ccc(C(F)(F)F)cc3c2OCc2ccc(C(F)(F)F)cc2)C(=O)O)CCC1] | 299 |
| 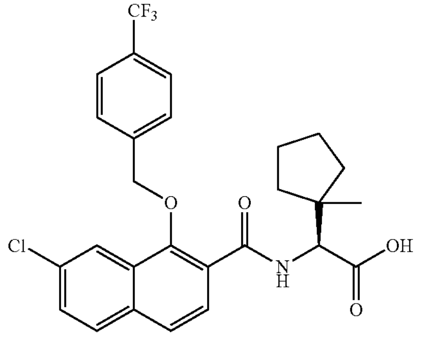 [SMILES: CC1([C@H](NC(=O)c2ccc3ccc(Cl)cc3c2OCc2ccc(C(F)(F)F)cc2)C(=O)O)CCCC1] | 302 |
| 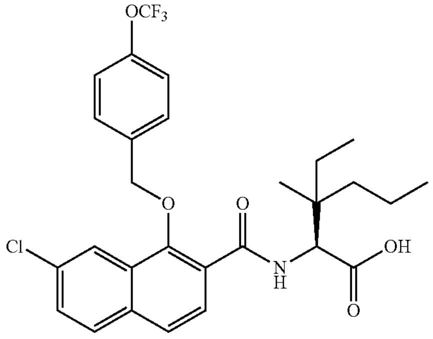 [SMILES: CCCC(C)(CC)[C@H](NC(=O)c1ccc2ccc(Cl)cc2c1OCc1ccc(OC(F)(F)F)cc1)C(=O)O] | 251 |
TABLE 2-continued
| Compound | # |
|---|---|
| 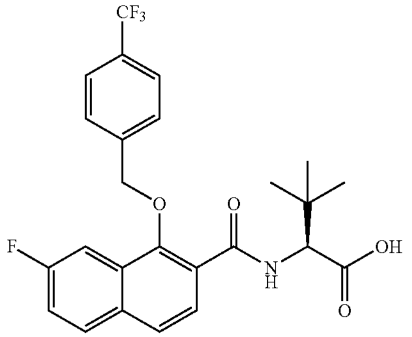 [SMILES: CC(C)(C)[C@H](NC(=O)c1ccc2ccc(F)cc2c1OCc1ccc(C(F)(F)F)cc1)C(=O)O] | 241 |
| 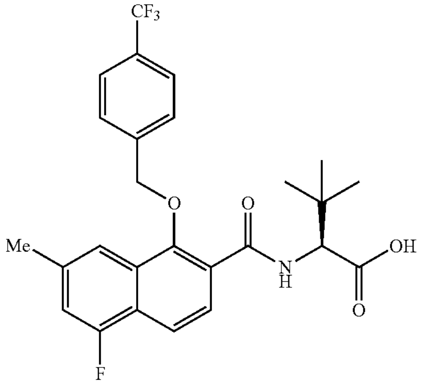 [SMILES: Cc1cc(F)c2ccc(C(=O)N[C@H](C(=O)O)C(C)(C)C)c(OCc3ccc(C(F)(F)F)cc3)c2c1] | 263 |
| 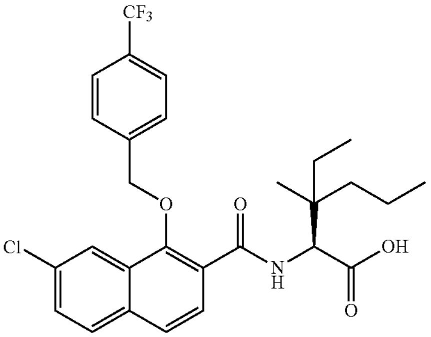 [SMILES: CCCC(C)(CC)[C@H](NC(=O)c1ccc2ccc(Cl)cc2c1OCc1ccc(C(F)(F)F)cc1)C(=O)O] | 255 |
| 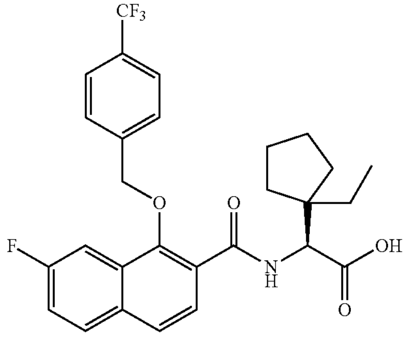 [SMILES: CCC1([C@H](NC(=O)c2ccc3ccc(F)cc3c2OCc2ccc(C(F)(F)F)cc2)C(=O)O)CCCC1] | 314 |

TABLE 2-continued
| Compound | # |
| --- | --- |
| 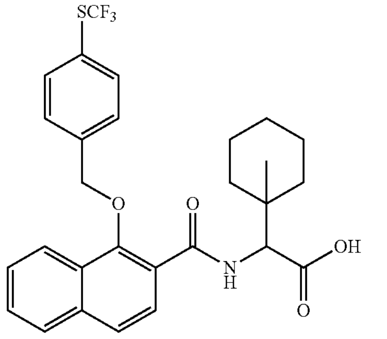 | 36 |
| 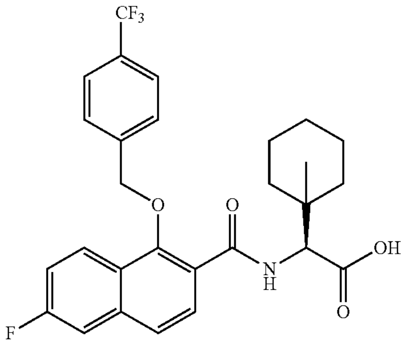 | 40 |
| 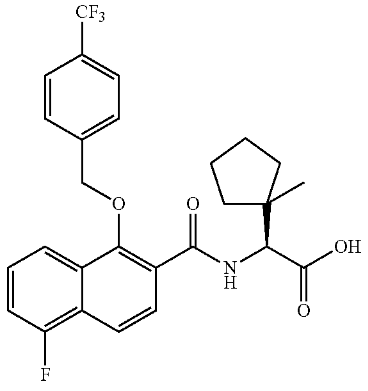 [SMILES: CC1([C@H](NC(=O)c2ccc3c(F)cccc3c2OCc2ccc(C(F)(F)F)cc2)C(=O)O)CCCC1] | 303 |
| 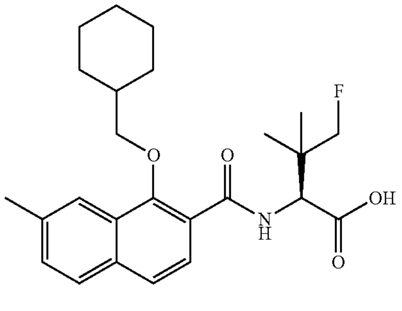 [SMILES: Cc1ccc2ccc(C(=O)N[C@H](C(=O)O)C(C)(C)CF)c(OCC3CCCCC3)c2c1] | 282 |
TABLE 2-continued
| Compound | # |
| --- | --- |
| 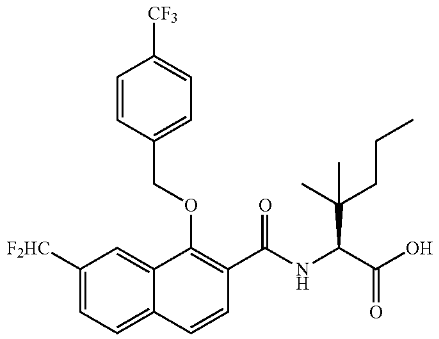 [SMILES: CCCC(C)(C)[C@H](NC(=O)c1ccc2ccc(C(F)F)cc2c1OCc1ccc(C(F)(F)F)cc1)C(=O)O] | 246 |
| 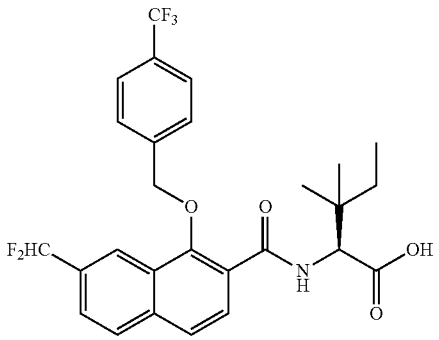 | 242 |
| 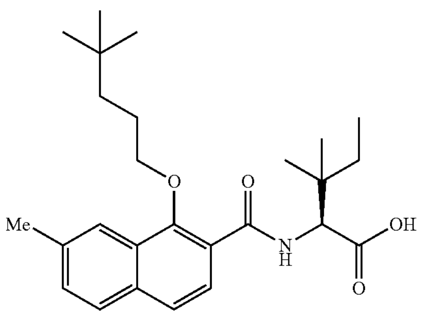 [SMILES: CCC(C)(C)[C@H](NC(=O)c1ccc2ccc(C)cc2c1OCCCC(C)(C)C)C(=O)O] | 257 |
| 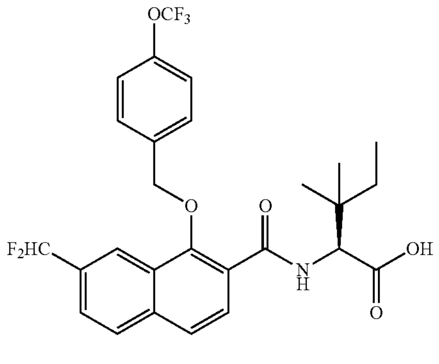 [SMILES: CCC(C)(C)[C@H](NC(=O)c1ccc2ccc(C(F)F)cc2c1OCc1ccc(OC(F)(F)F)cc1)C(=O)O] | 250 |

TABLE 2-continued
| Compound | # |
| --- | --- |
| 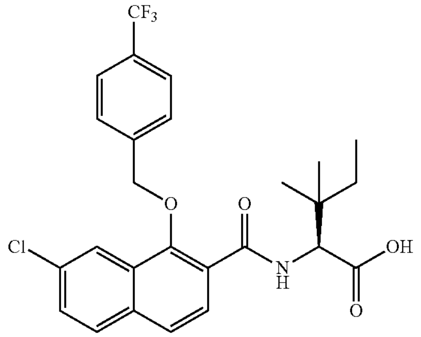 [SMILES: CCC(C)(C)[C@H](NC(=O)c1ccc2ccc(Cl)cc2c1OCc1ccc(C(F)(F)F)cc1)C(=O)O] | 283 |
| 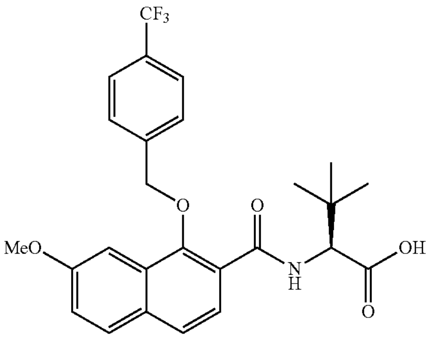 [SMILES: COc1ccc2ccc(C(=O)N[C@H](C(=O)O)C(C)(C)C)c(OCc3ccc(C(F)(F)F)cc3)c2c1] | 308 |
| 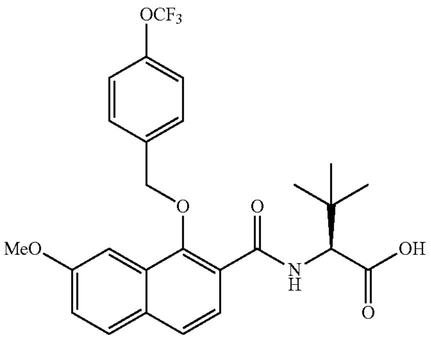 [SMILES: COc1ccc2ccc(C(=O)N[C@H](C(=O)O)C(C)(C)C)c(OCc3ccc(OC(F)(F)F)cc3)c2c1] | 310 |
| 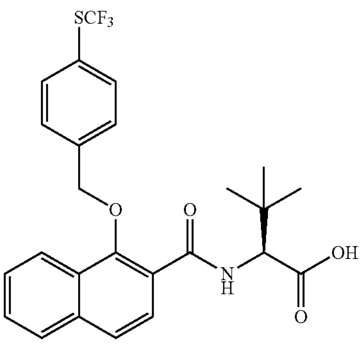 | 35 |
TABLE 2-continued
| Compound | # |
| --- | --- |
| 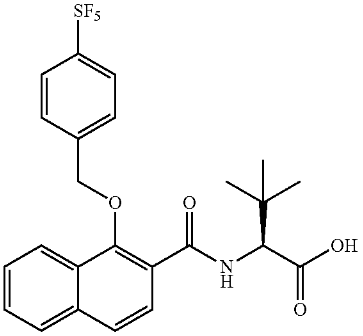 | 67 |
| 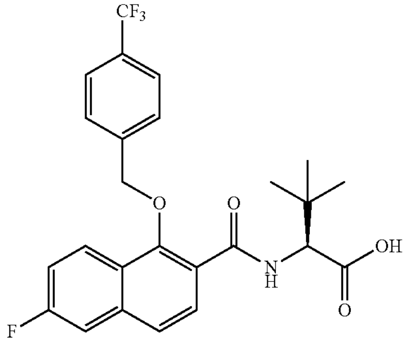 | 27 |
| 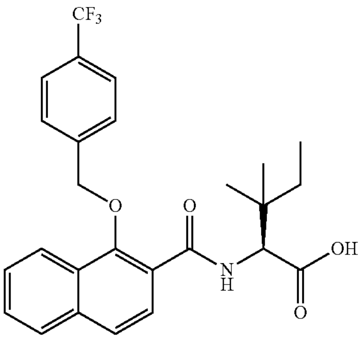 | 78 |
| 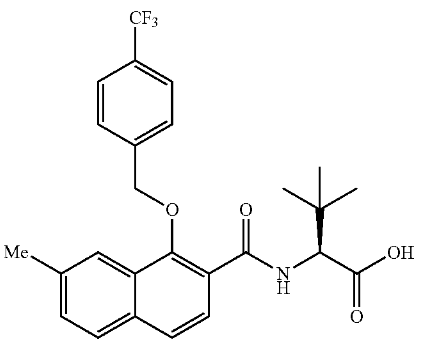 | 279 |

TABLE 2-continued
| Compound | # |
| --- | --- |
| 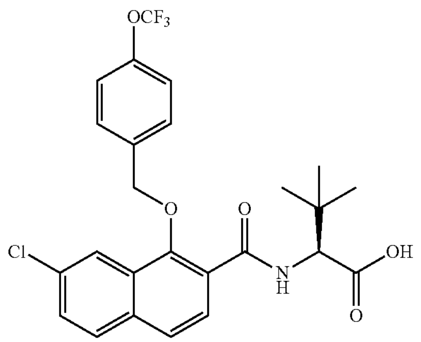 [SMILES: CC(C)(C)[C@H](NC(=O)c1ccc2ccc(Cl)cc2c1OCc1ccc(OC(F)(F)F)cc1)C(=O)O] | 237 |
| 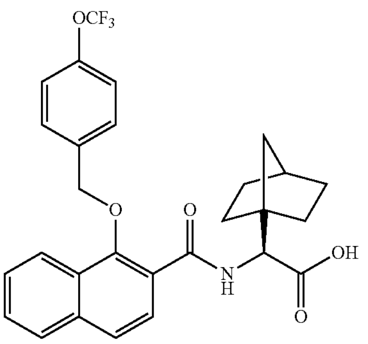 [SMILES: O=C(N[C@H](C(=O)O)C12CCC(CC1)C2)c1ccc2ccccc2c1OCc1ccc(OC(F)(F)F)cc1] | 14 |
| 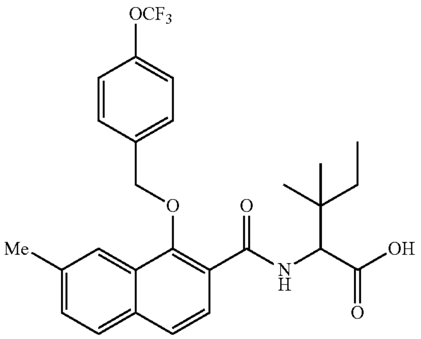 | 280 |
| 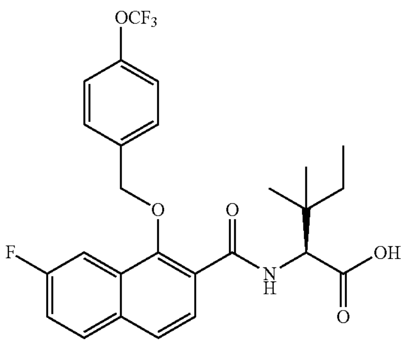 [SMILES: CCC(C)(C)[C@H](NC(=O)c1ccc2ccc(F)cc2c1OCc1ccc(OC(F)(F)F)cc1)C(=O)O] | 274 |
TABLE 2-continued
| Compound | # |
| --- | --- |
| 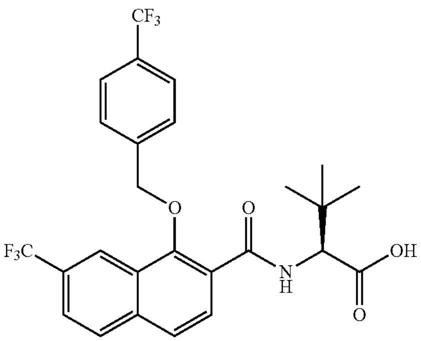 | 293 |
| 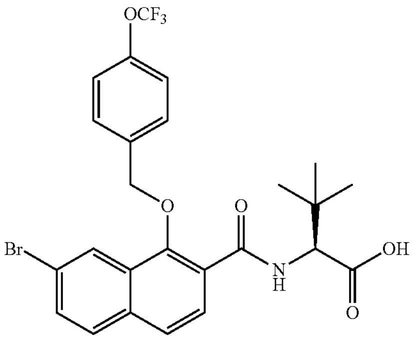 | 247 |
| 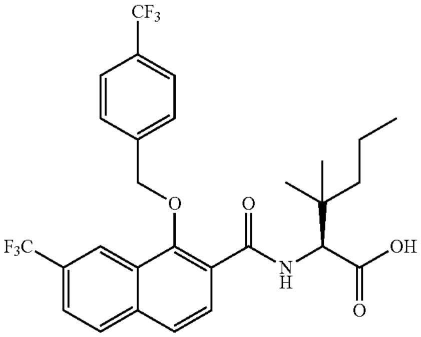 [SMILES: CCCC(C)(C)[C@H](NC(=O)c1ccc2ccc(C(F)(F)F)cc2c1OCc1ccc(C(F)(F)F)cc1)C(=O)O] | 304 |
| 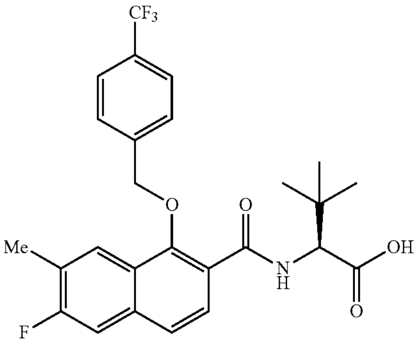 [SMILES: Cc1cc2c(OCc3ccc(C(F)(F)F)cc3)c(C(=O)N[C@H](C(=O)O)C(C)(C)C)ccc2cc1F] | 278 |

TABLE 2-continued
| Compound | # |
|---|---|
| 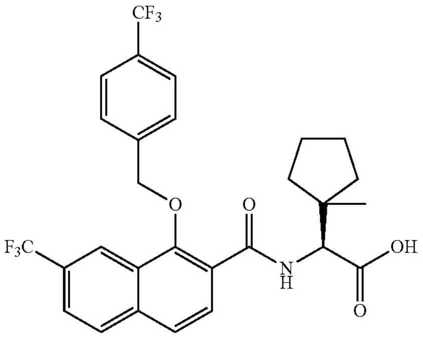 [SMILES: CC1([C@H](NC(=O)c2ccc3ccc(C(F)(F)F)cc3c2OCc2ccc(C(F)(F)F)cc2)C(=O)O)CCCC1] | 301 |
| 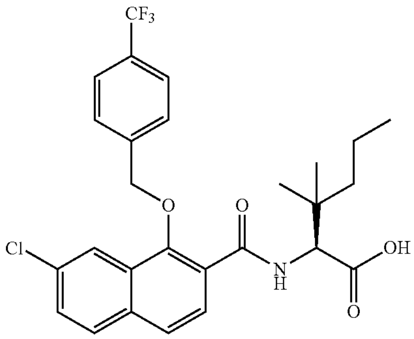 [SMILES: CCCC(C)(C)[C@H](NC(=O)c1ccc2ccc(Cl)cc2c1OCc1ccc(C(F)(F)F)cc1)C(=O)O] | 306 |
| 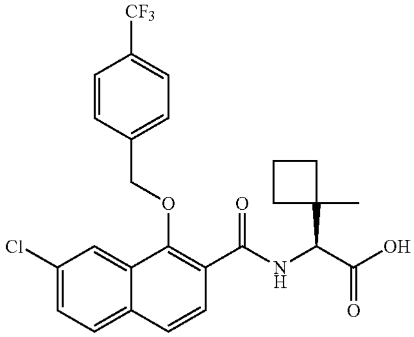 [SMILES: CC1([C@H](NC(=O)c2ccc3ccc(Cl)cc3c2OCc2ccc(C(F)(F)F)cc2)C(=O)O)CCC1] | 300 |
| 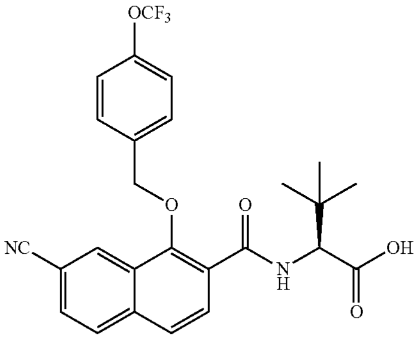 | 254 |
TABLE 2-continued
| Compound | # |
|---|---|
| 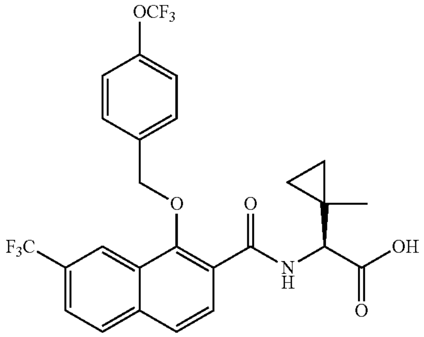 [SMILES: CC1([C@H](NC(=O)c2ccc3ccc(C(F)(F)F)cc3c2OCc2ccc(OC(F)(F)F)cc2)C(=O)O)CC1] | 297 |
| 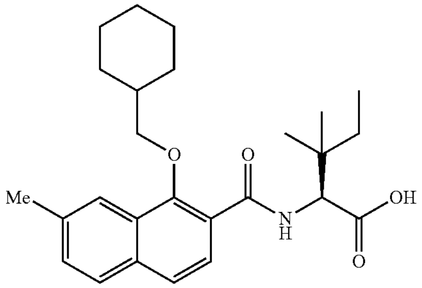 | 281 |
| 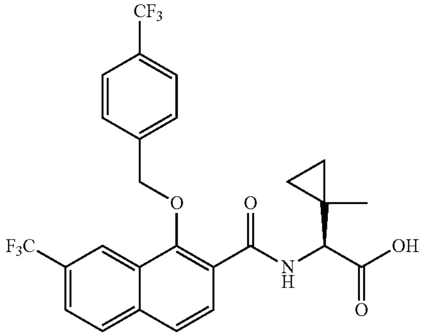 [SMILES: CC1([C@H](NC(=O)c2ccc3ccc(C(F)(F)F)cc3c2OCc2ccc(C(F)(F)F)cc2)C(=O)O)CC1] | 298 |
| 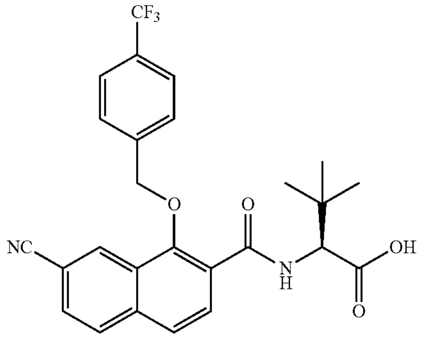 | 248 |

TABLE 2-continued
| Compound | # |
| --- | --- |
| 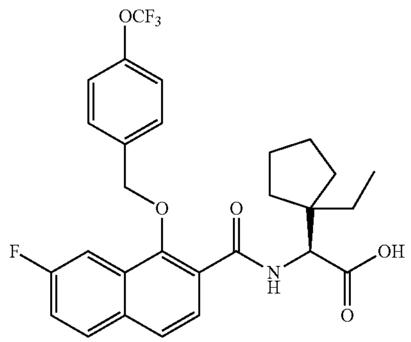 [SMILES: CCC1([C@H](NC(=O)c2ccc3ccc(F)cc3c2OCc2ccc(OC(F)(F)F)cc2)C(=O)O)CCCC1] | 313 |
| 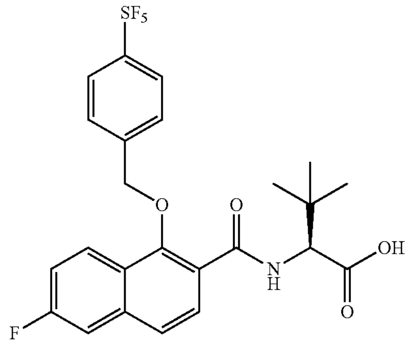 | 81 |
| 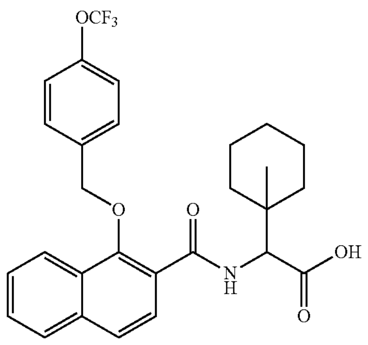 | 1 |
| 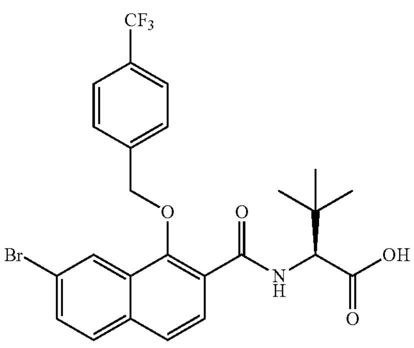 | 256 |
TABLE 2-continued
| Compound | # |
| --- | --- |
| 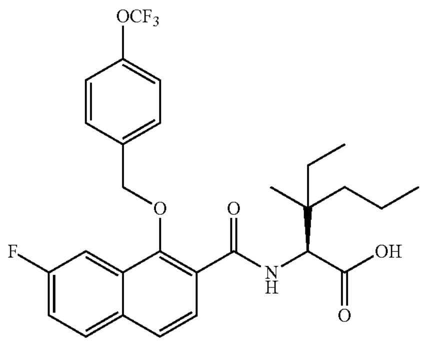 [SMILES: CCCC(C)(CC)[C@H](NC(=O)c1ccc2ccc(F)cc2c1OCc1ccc(OC(F)(F)F)cc1)C(=O)O] | 290 |
| 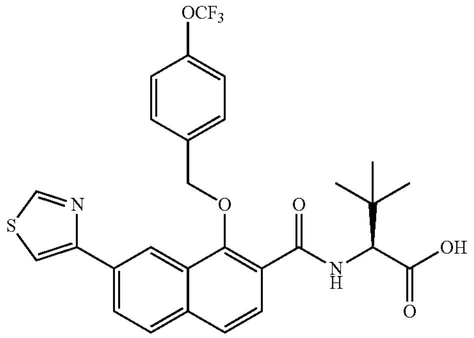 [SMILES: CC(C)(C)[C@H](NC(=O)c1ccc2ccc(-c3cscn3)cc2c1OCc1ccc(OC(F)(F)F)cc1)C(=O)O] | 252 |
| 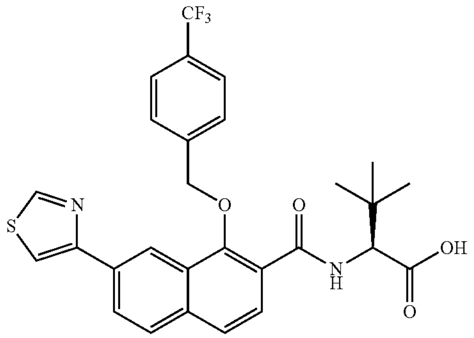 [SMILES: CC(C)(C)[C@H](NC(=O)c1ccc2ccc(-c3cscn3)cc2c1OCc1ccc(C(F)(F)F)cc1)C(=O)O] | 243 |
| 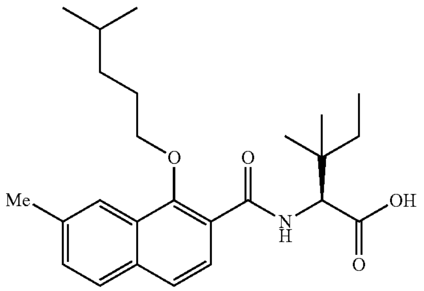 [SMILES: CCC(C)(C)[C@H](NC(=O)c1ccc2ccc(C)cc2c1OCCCC(C)C)C(=O)O] | 294 |

TABLE 2-continued
| Compound | # |
|---|---|
| 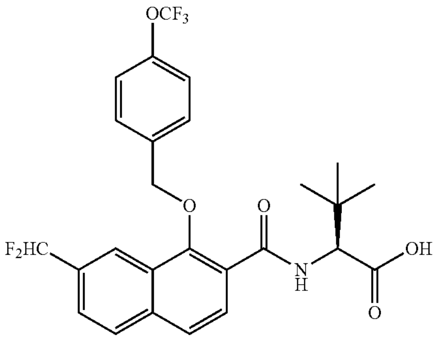 | 245 |
| 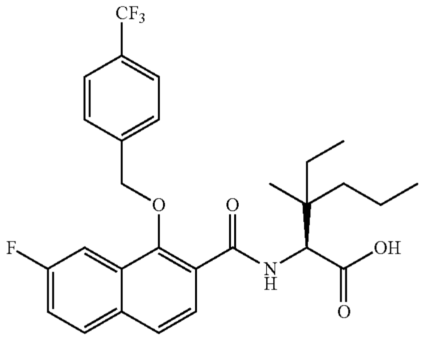 [SMILES: CCCC(C)(CC)[C@H](NC(=O)c1ccc2ccc(F)cc2c1OCc1ccc(C(F)(F)F)cc1)C(=O)O] | 291 |
| 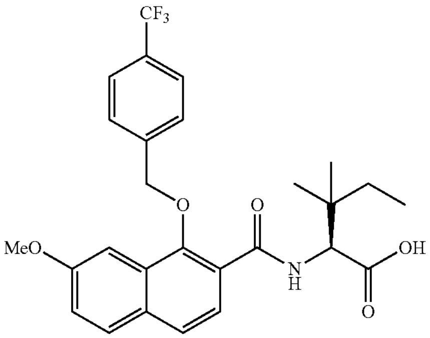 [SMILES: CCC(C)(C)[C@H](NC(=O)c1ccc2ccc(OC)cc2c1OCc1ccc(C(F)(F)F)cc1)C(=O)O] | 309 |
| 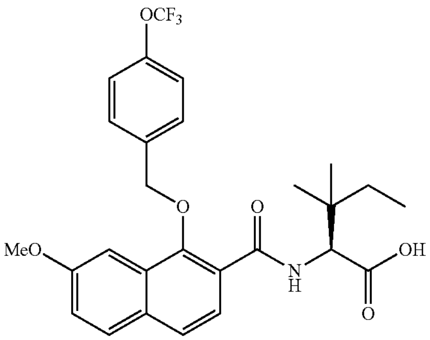 [SMILES: CCC(C)(C)[C@H](NC(=O)c1ccc2ccc(OC)cc2c1OCc1ccc(OC(F)(F)F)cc1)C(=O)O] | 311 |
In some embodiments, the compound of formula (I) is selected from the following compounds represented in Table 3 below:
TABLE 3
| Compound | # |
|---|---|
| 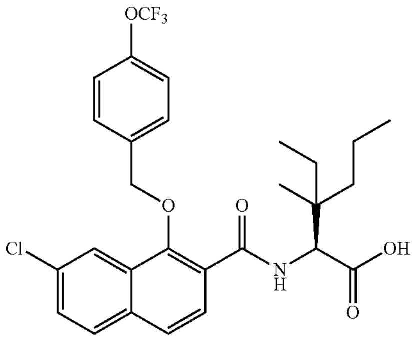 [SMILES: CCCC(C)(CC)[C@H](NC(=O)c1ccc2ccc(Cl)cc2c1OCc1ccc(OC(F)(F)F)cc1)C(=O)O] | 291 |
| 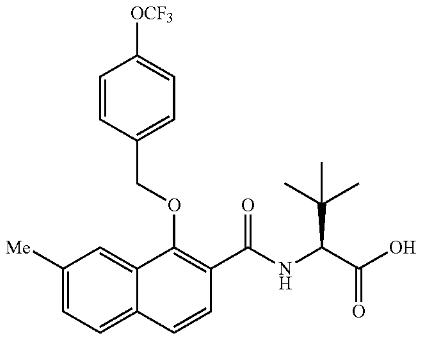 | 249 |
| 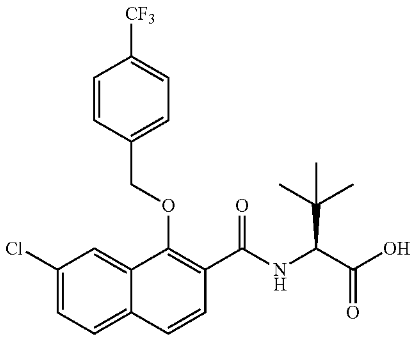 [SMILES: CC(C)(C)[C@H](NC(=O)c1ccc2ccc(Cl)cc2c1OCc1ccc(C(F)(F)F)cc1)C(=O)O] | 286 |
| 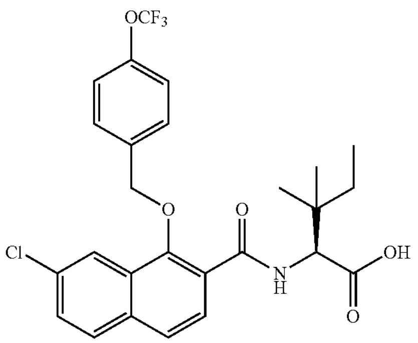 [SMILES: CCC(C)(C)[C@H](NC(=O)c1ccc2ccc(Cl)cc2c1OCc1ccc(OC(F)(F)F)cc1)C(=O)O] | 277 |

TABLE 3-continued
| Compound | # |
| --- | --- |
| 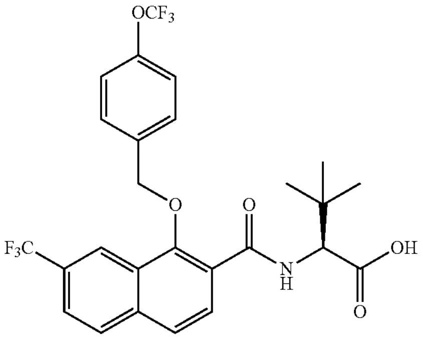 [SMILES: CC(C)(C)[C@H](NC(=O)c1ccc2ccc(C(F)(F)F)cc2c1OCc1ccc(OC(F)(F)F)cc1)C(=O)O] | 292 |
| 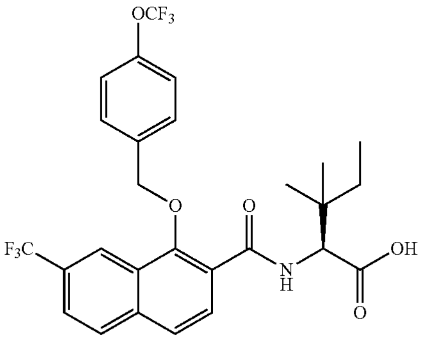 | 296 |
| 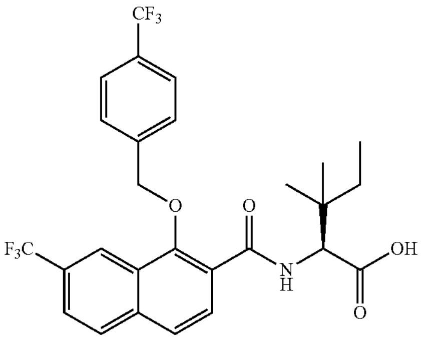 [SMILES: CCC(C)(C)[C@H](NC(=O)c1ccc2ccc(C(F)(F)F)cc2c1OCc1ccc(C(F)(F)F)cc1)C(=O)O] | 295 |
| 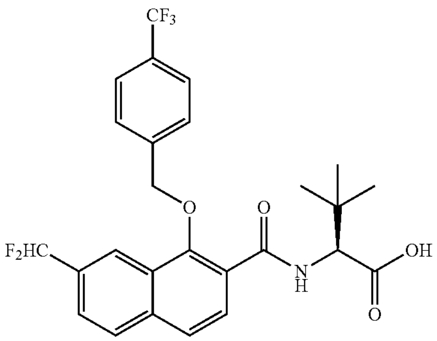 | 244 |
TABLE 3-continued
| Compound | # |
| --- | --- |
| 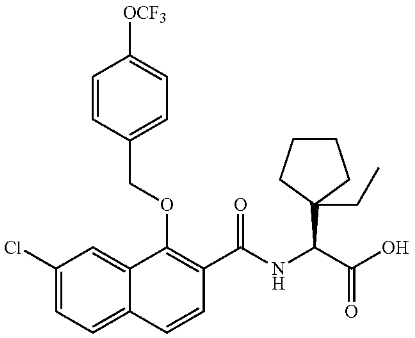 [SMILES: CCC1([C@H](NC(=O)c2ccc3ccc(Cl)cc3c2OCc2ccc(OC(F)(F)F)cc2)C(=O)O)CCCC1] | 253 |
| 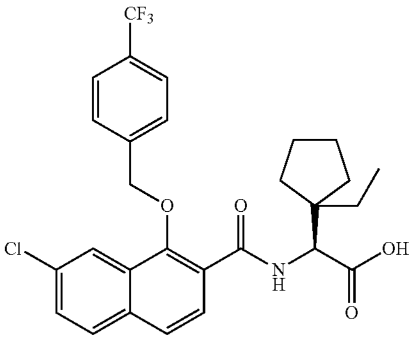 [SMILES: CCC1([C@H](NC(=O)c2ccc3ccc(Cl)cc3c2OCc2ccc(C(F)(F)F)cc2)C(=O)O)CCCC1] | 258 |
| 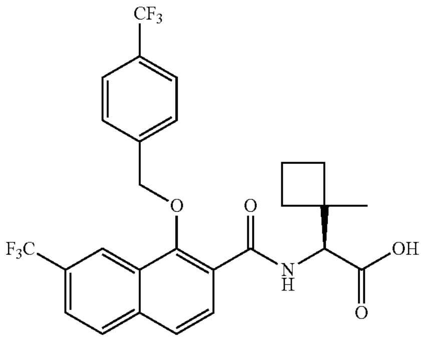 [SMILES: CC1([C@H](NC(=O)c2ccc3ccc(C(F)(F)F)cc3c2OCc2ccc(C(F)(F)F)cc2)C(=O)O)CCC1] | 299 |
| 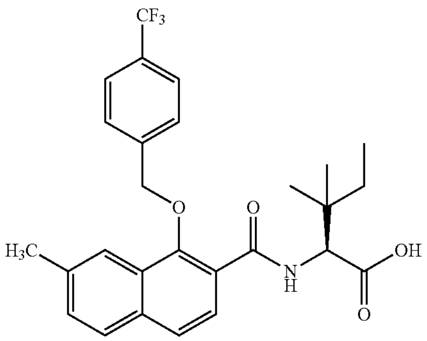 | 288 |

TABLE 3-continued
| Compound | # |
|---|---|
| 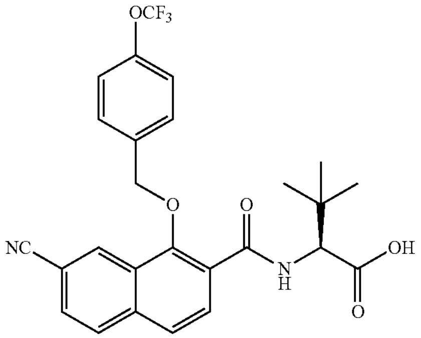 | 254 |
| 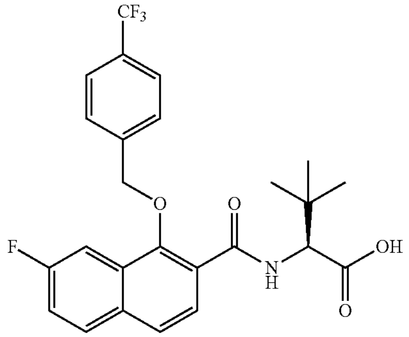 [SMILES: CC(C)(C)[C@H](NC(=O)c1ccc2ccc(F)cc2c1OCc1ccc(C(F)(F)F)cc1)C(=O)O] | 241 |
| 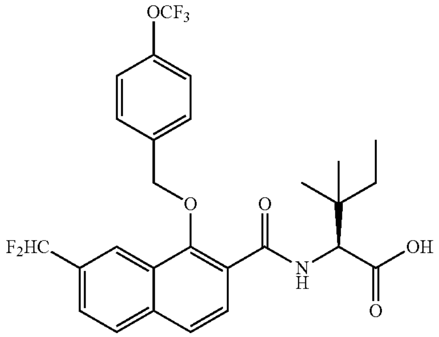 | 290 |
| 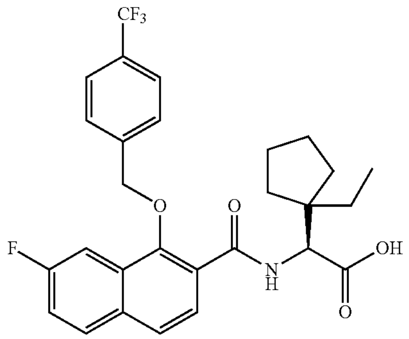 [SMILES: CCC1([C@H](NC(=O)c2ccc3ccc(F)cc3c2OCc2ccc(C(F)(F)F)cc2)C(=O)O)CCCC1] | 314 |
TABLE 3-continued
| Compound | # |
|---|---|
| 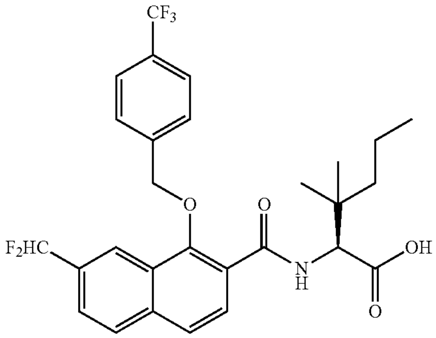 [SMILES: CCCC(C)(C)[C@H](NC(=O)c1ccc2ccc(C(F)F)cc2c1OCc1ccc(C(F)(F)F)cc1)C(=O)O] | 246 |
| 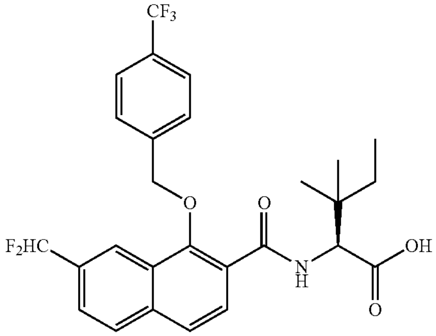 | 242 |
| 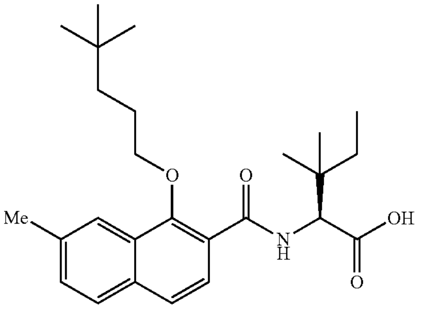 [SMILES: CCC(C)(C)[C@H](NC(=O)c1ccc2ccc(C)cc2c1OCCCC(C)(C)C)C(=O)O] | 257 |
| 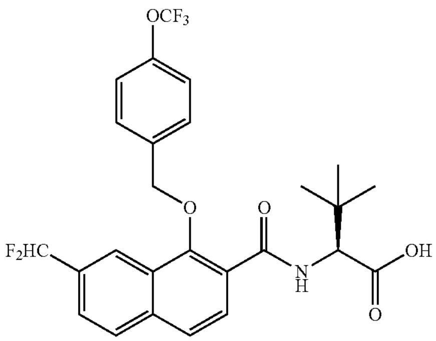 | 245 |

TABLE 3-continued
| Compound | # |
|---|---|
| 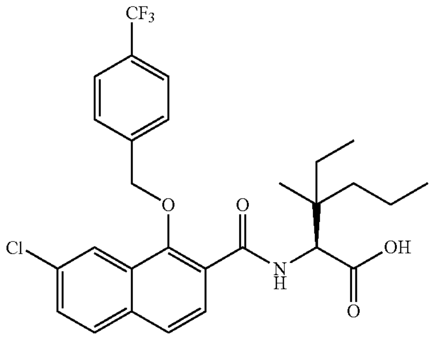 [SMILES: CCCC(C)(CC)[C@H](NC(=O)c1ccc2ccc(Cl)cc2c1OCc1ccc(C(F)(F)F)cc1)C(=O)O] | 255 |
| 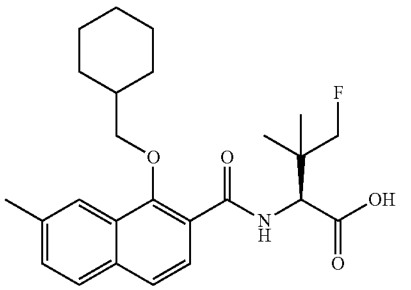 [SMILES: Cc1ccc2ccc(C(=O)N[C@H](C(=O)O)C(C)(C)CF)c(OCC3CCCCC3)c2c1] | 282 |
| 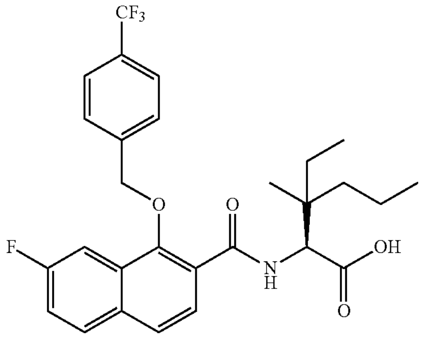 [SMILES: CCCC(C)(CC)[C@H](NC(=O)c1ccc2ccc(F)cc2c1OCc1ccc(C(F)(F)F)cc1)C(=O)O] | 292 |
| 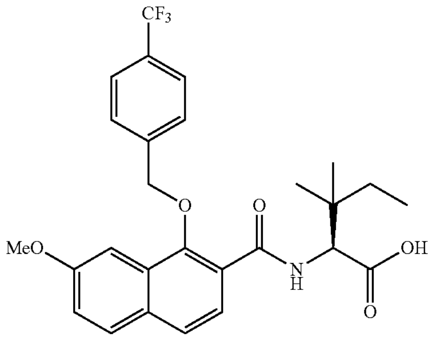 [SMILES: CCC(C)(C)[C@H](NC(=O)c1ccc2ccc(OC)cc2c1OCc1ccc(C(F)(F)F)cc1)C(=O)O] | 309 |
TABLE 3-continued
| Compound | # |
|---|---|
| 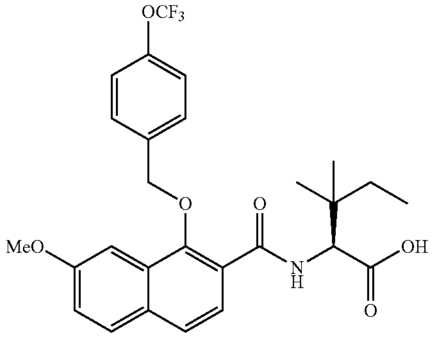 [SMILES: CCC(C)(C)[C@H](NC(=O)c1ccc2ccc(OC)cc2c1OCc1ccc(OC(F)(F)F)cc1)C(=O)O] | 311 |
| 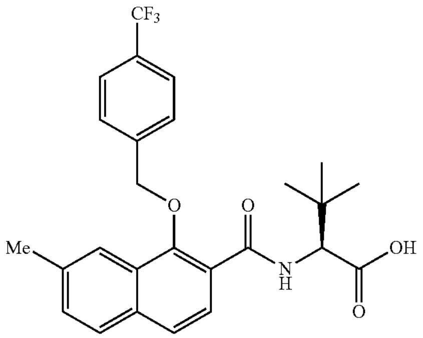 | 229 |
| 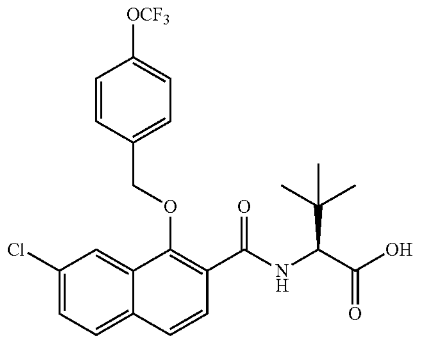 | 237 |
| 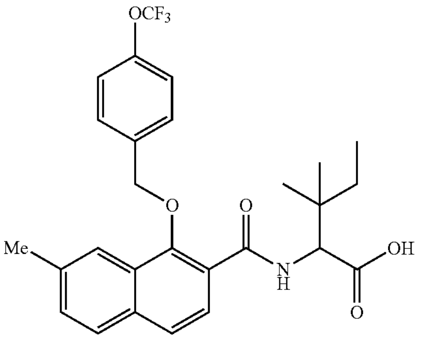 | 280 |

TABLE 3-continued
| Compound | # |
|---|---|
| 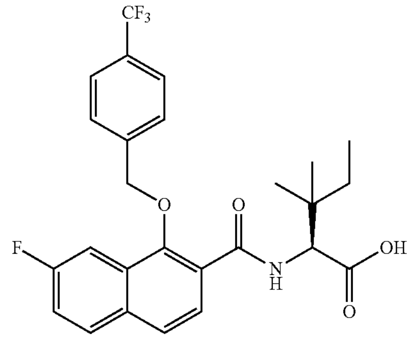 | 274 |
| 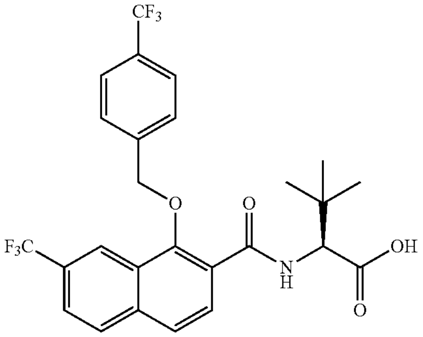 | 293 |
| 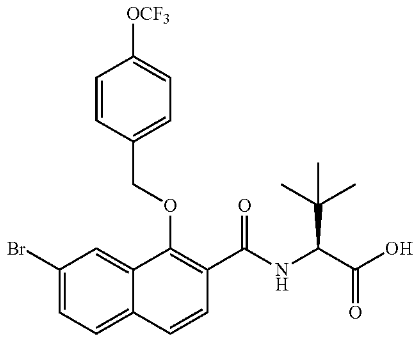 [SMILES: CC(C)(C)[C@H](NC(=O)c1ccc2ccc(Cl)cc2c1OCc1ccc(OC(F)(F)F)cc1)C(=O)O] | 247 |
| 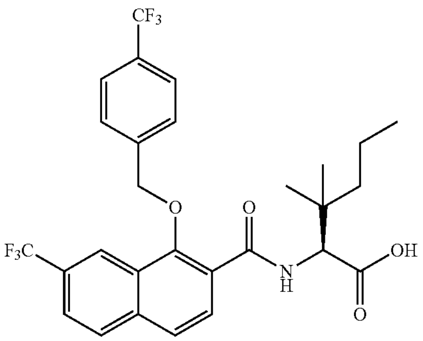 [SMILES: CCCC(C)(C)[C@H](NC(=O)c1ccc2ccc(C(F)(F)F)cc2c1OCc1ccc(C(F)(F)F)cc1)C(=O)O] | 304 |
TABLE 3-continued
| Compound | # |
|---|---|
| 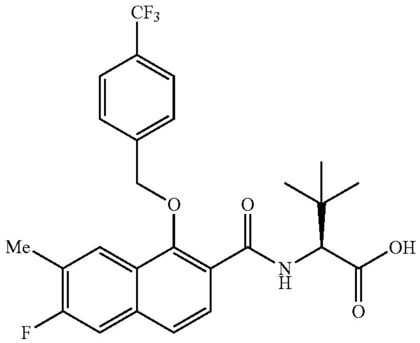 [SMILES: Cc1cc2c(OCc3ccc(C(F)(F)F)cc3)c(C(=O)N[C@H](C(=O)O)C(C)(C)C)ccc2cc1F] | 278 |
| 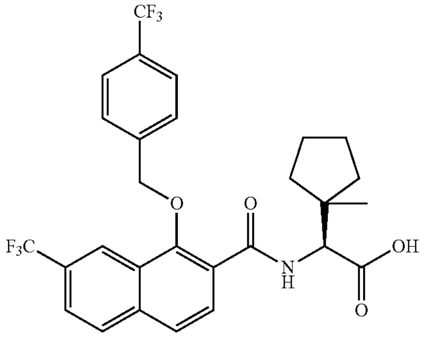 [SMILES: CC1([C@H](NC(=O)c2ccc3ccc(C(F)(F)F)cc3c2OCc2ccc(C(F)(F)F)cc2)C(=O)O)CCCC1] | 301 |
| 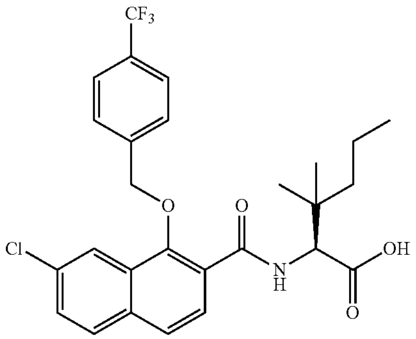 [SMILES: CCCC(C)(C)[C@H](NC(=O)c1ccc2ccc(Cl)cc2c1OCc1ccc(C(F)(F)F)cc1)C(=O)O] | 306 |
| 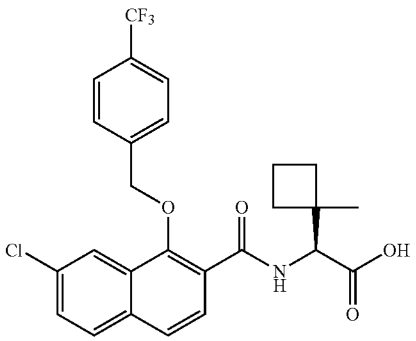 [SMILES: CC1([C@H](NC(=O)c2ccc3ccc(Cl)cc3c2OCc2ccc(C(F)(F)F)cc2)C(=O)O)CCC1] | 300 |

TABLE 3-continued
| Compound | # |
| --- | --- |
| 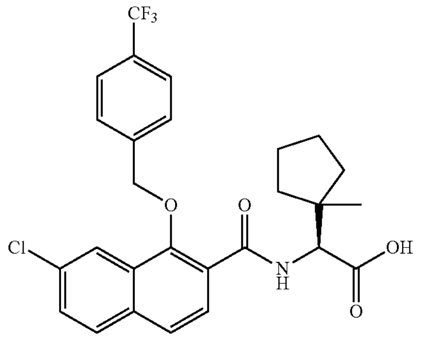 [SMILES: CC1([C@H](NC(=O)c2ccc3ccc(Cl)cc3c2OCc2ccc(C(F)(F)F)cc2)C(=O)O)CCCC1] | 302 |
| 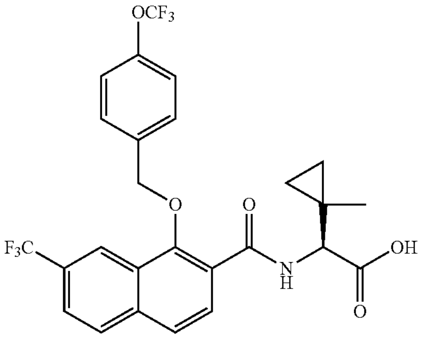 | 297 |
| 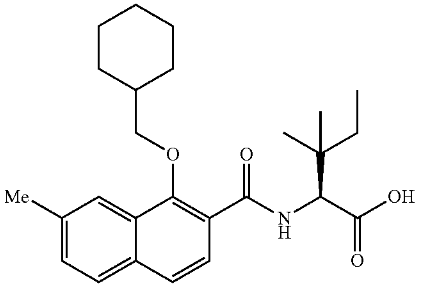 [SMILES: CCC(C)(C)[C@H](NC(=O)c1ccc2ccc(C)cc2c1OCC1CCCCC1)C(=O)O] | 281 |
| 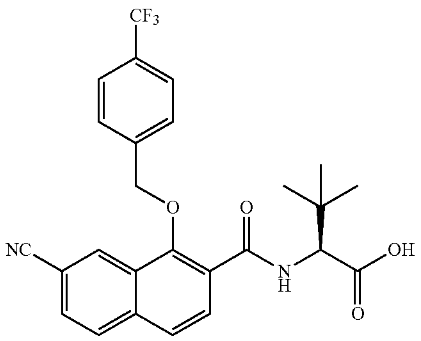 | 248 |
TABLE 3-continued
| Compound | # |
| --- | --- |
| 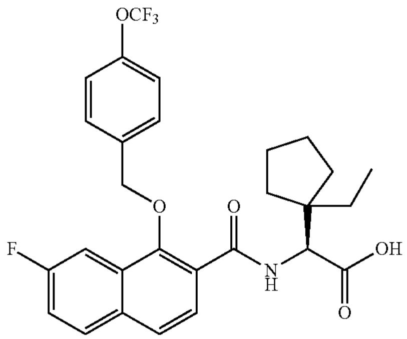 [SMILES: CCC1([C@H](NC(=O)c2ccc3ccc(F)cc3c2OCc2ccc(OC(F)(F)F)cc2)C(=O)O)CCCC1] | 313 |
| 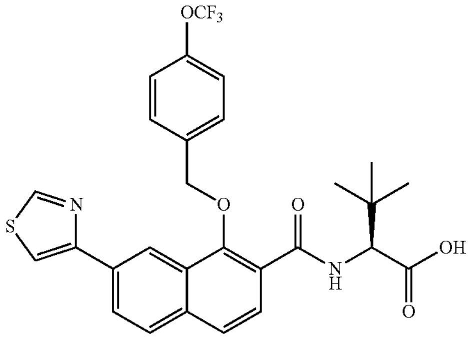 [SMILES: CC(C)(C)[C@H](NC(=O)c1ccc2ccc(-c3cscn3)cc2c1OCc1ccc(OC(F)(F)F)cc1)C(=O)O] | 252 |
| 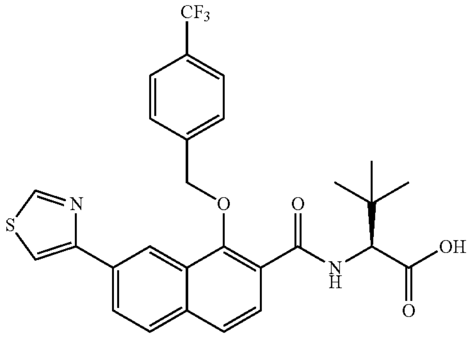 [SMILES: CC(C)(C)[C@H](NC(=O)c1ccc2ccc(-c3cscn3)cc2c1OCc1ccc(C(F)(F)F)cc1)C(=O)O] | 243 |
| 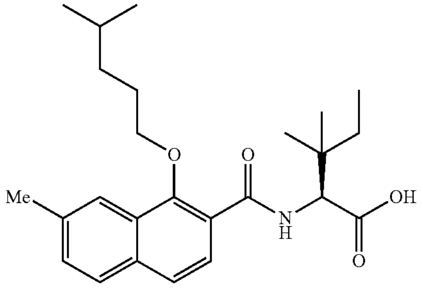 [SMILES: CCC(C)(C)[C@H](NC(=O)c1ccc2ccc(C)cc2c1OCCCC(C)C)C(=O)O] | 294 |

TABLE 3-continued
| Compound | # |
|---|---|
| 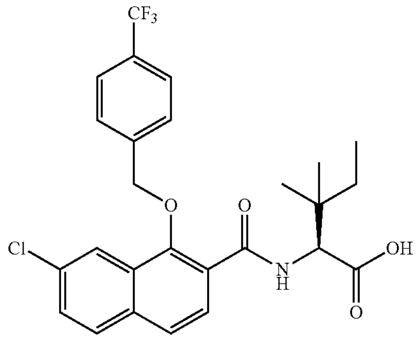 [SMILES: CCC(C)(C)[C@H](NC(=O)c1ccc2ccc(Cl)cc2c1OCc1ccc(C(F)(F)F)cc1)C(=O)O] | 283 |
| 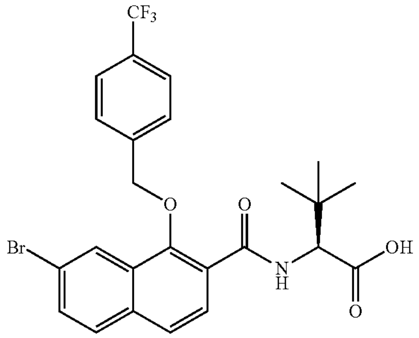 | 256 |
| 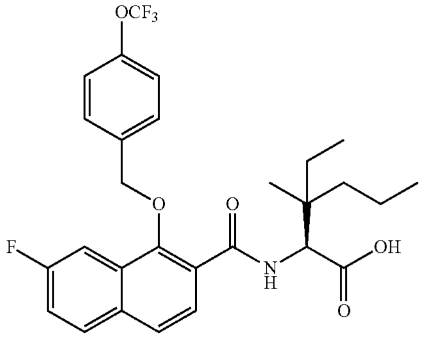 [SMILES: CCCC(C)(CC)[C@H](NC(=O)c1ccc2ccc(F)cc2c1OCc1ccc(OC(F)(F)F)cc1)C(=O)O] | 290 |
| 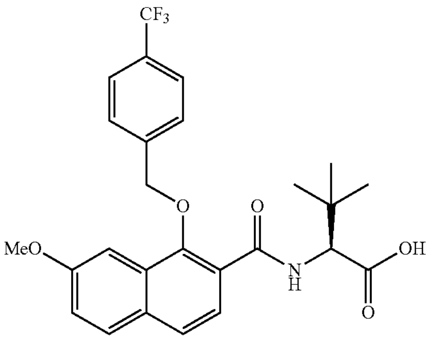 [SMILES: COc1ccc2ccc(C(=O)N[C@H](C(=O)O)C(C)(C)C)c(OCc3ccc(C(F)(F)F)cc3)c2c1] | 308 |
TABLE 3-continued
| Compound | # |
|---|---|
| 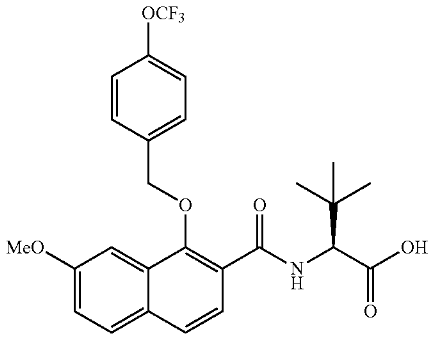 [SMILES: COc1ccc2ccc(C(=O)N[C@H](C(=O)O)C(C)(C)C)c(OCc3ccc(OC(F)(F)F)cc3)c2c1] | 310 |
In some embodiments, the compound of formula (I) is selected from the following compounds represented in Table 4 below:
TABLE 4
| Compound | # |
|---|---|
| 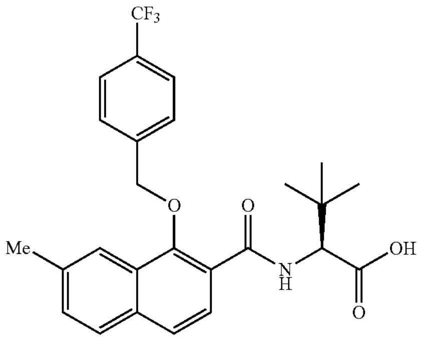 | 279 |
| 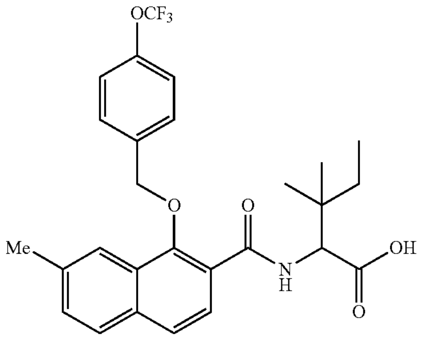 | 280 |
| 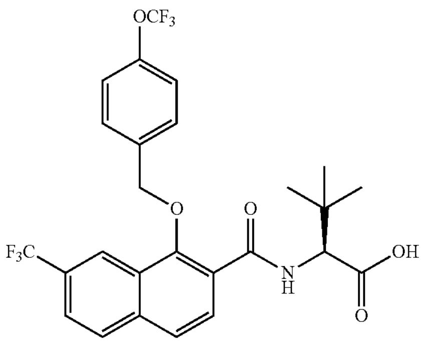 | 292 |

TABLE 4-continued
| Compound | # |
|---|---|
| 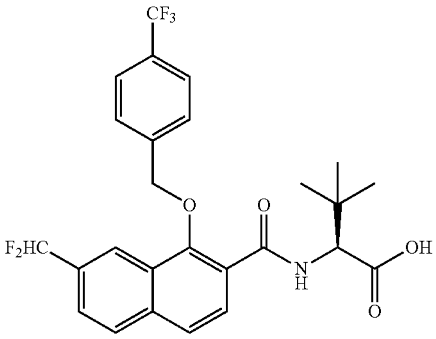 [SMILES: CC(C)(C)[C@H](NC(=O)c1ccc2ccc(C(F)F)cc2c1OCc1ccc(C(F)(F)F)cc1)C(=O)O] | 244 |
| 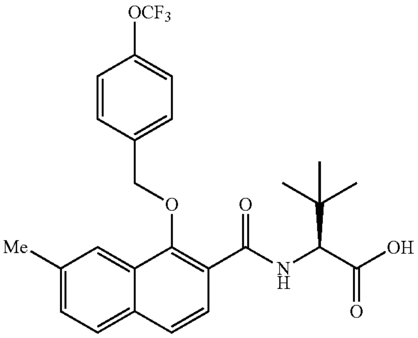 | 249 |
| 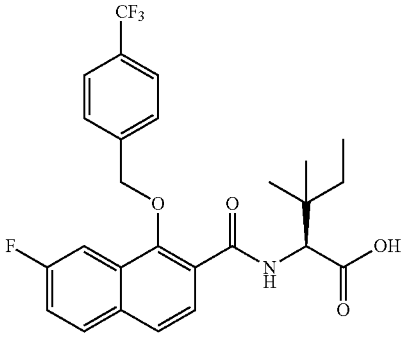 [SMILES: CCC(C)(C)[C@H](NC(=O)c1ccc2ccc(F)cc2c1OCc1ccc(C(F)(F)F)cc1)C(=O)O] | 274 |
| 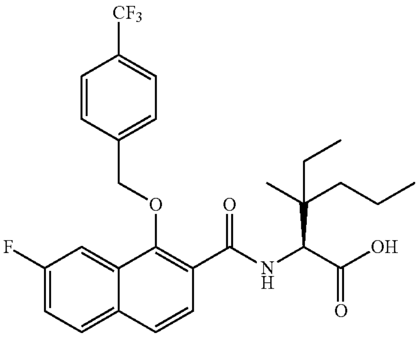 [SMILES: CCCC(C)(CC)[C@H](NC(=O)c1ccc2ccc(F)cc2c1OCc1ccc(C(F)(F)F)cc1)C(=O)O] | 292 |
TABLE 4-continued
| Compound | # |
|---|---|
| 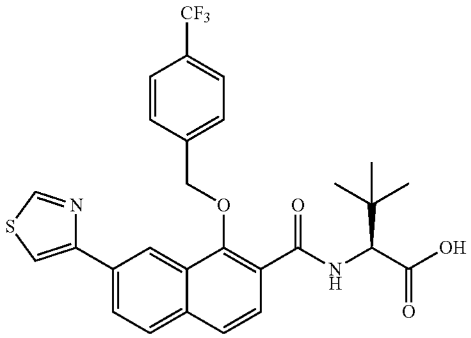 [SMILES: CC(C)(C)[C@H](NC(=O)c1ccc2ccc(-c3cscn3)cc2c1OCc1ccc(C(F)(F)F)cc1)C(=O)O] | 243 |
| 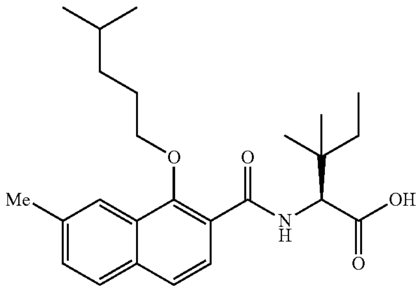 [SMILES: CCC(C)(C)[C@H](NC(=O)c1ccc2ccc(C)cc2c1OCCCC(C)C)C(=O)O] | 294 |
| 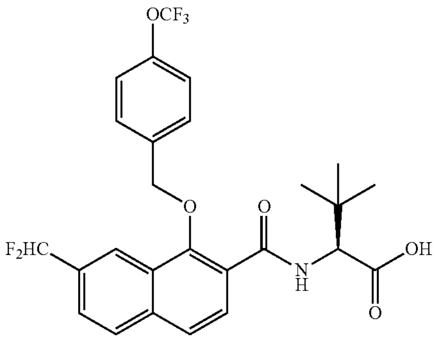 | 245 |
| 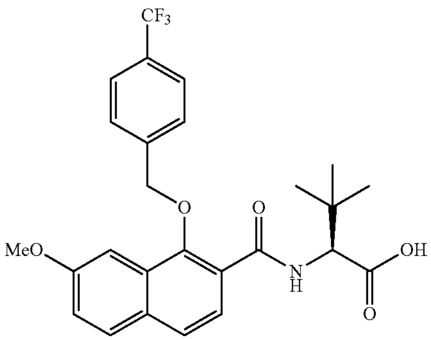 [SMILES: COc1ccc2ccc(C(=O)N[C@H](C(=O)O)C(C)(C)C)c(OCc3ccc(C(F)(F)F)cc3)c2c1] | 308 |

TABLE 4-continued
| Compound | # |
|---|---|
| 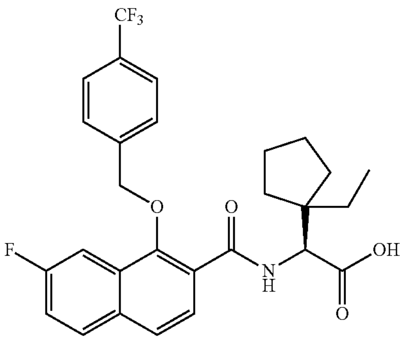 [SMILES: CCC1([C@H](NC(=O)c2ccc3ccc(F)cc3c2OCc2ccc(C(F)(F)F)cc2)C(=O)O)CCCC1] | 314 |
| 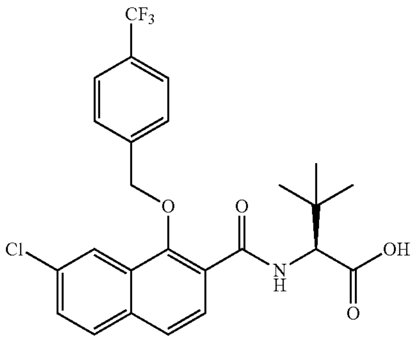 | 286 |
| 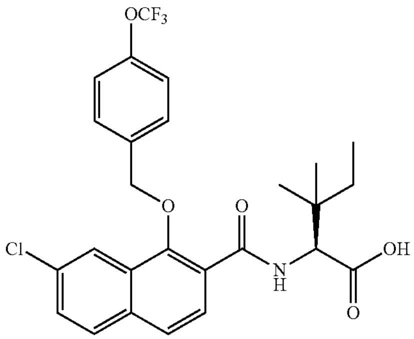 [SMILES: CCC(C)(C)[C@H](NC(=O)c1ccc2ccc(Cl)cc2c1OCc1ccc(OC(F)(F)F)cc1)C(=O)O] | 277 |
| 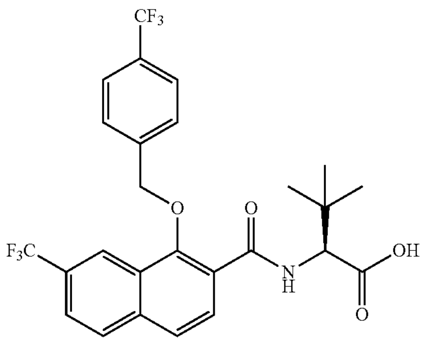 | 293 |
TABLE 4-continued
| Compound | # |
|---|---|
| 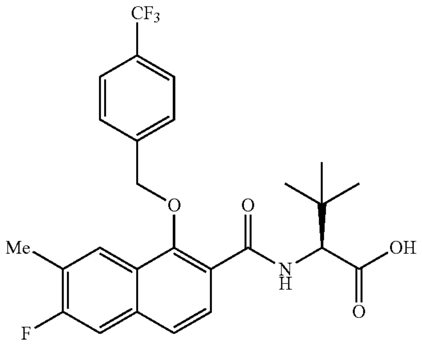 [SMILES: Cc1cc2c(OCc3ccc(C(F)(F)F)cc3)c(C(=O)N[C@H](C(=O)O)C(C)(C)C)ccc2cc1F] | 278 |
| 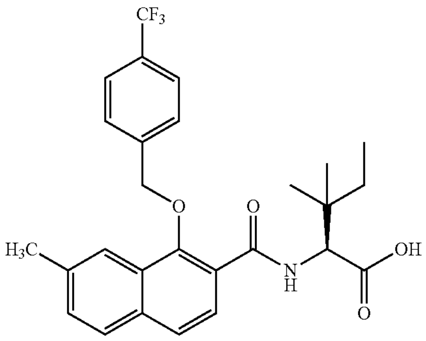 | 288 |
| 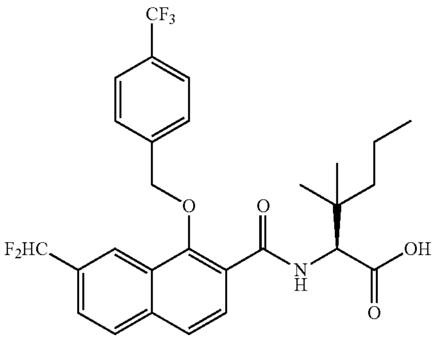 [SMILES: CCCC(C)(C)[C@H](NC(=O)c1ccc2ccc(C(F)F)cc2c1OCc1ccc(C(F)(F)F)cc1)C(=O)O] | 246 |
| 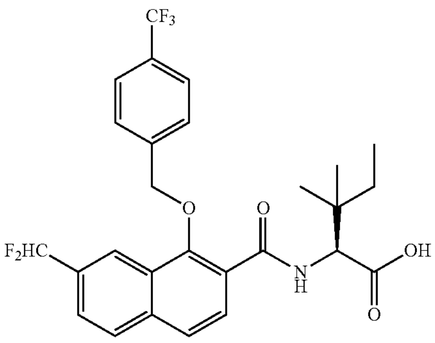 | 242 |

TABLE 4-continued
| Compound | # |
|---|---|
| 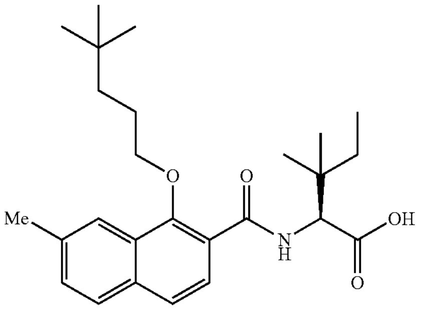 [SMILES: CCC(C)(C)[C@H](NC(=O)c1ccc2ccc(C)cc2c1OCCCC(C)(C)C)C(=O)O] | 257 |
| 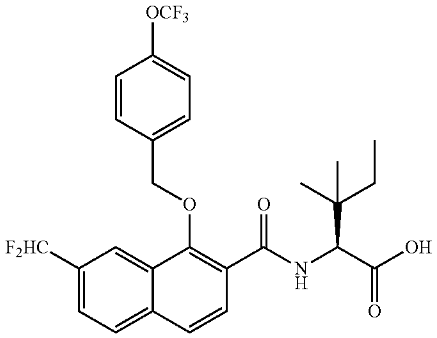 | 250 |
| 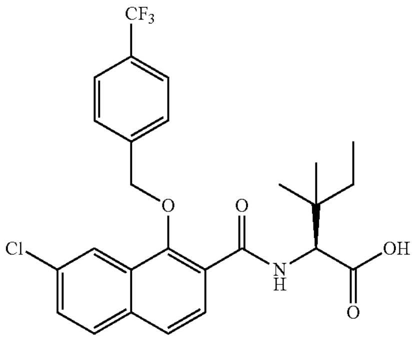 [SMILES: CCC(C)(C)[C@H](NC(=O)c1ccc2ccc(Cl)cc2c1OCc1ccc(C(F)(F)F)cc1)C(=O)O] | 283 |
| 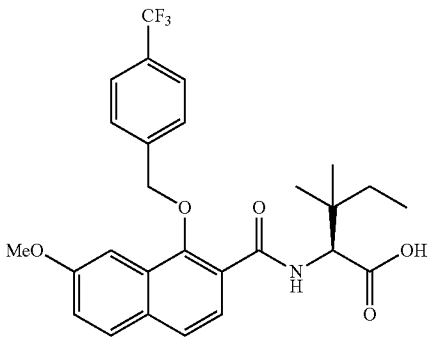 [SMILES: CCC(C)(C)[C@H](NC(=O)c1ccc2ccc(OC)cc2c1OCc1ccc(C(F)(F)F)cc1)C(=O)O] | 309 |
Representative compounds, or pharmaceutically acceptable salts thereof, include the following in Table 5:
TABLE 5
| Compound | # |
|---|---|
| 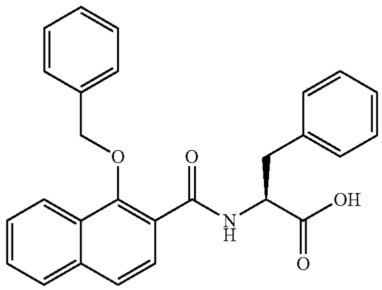 [SMILES: O=C(N[C@@H](Cc1ccccc1)C(=O)O)c1ccc2ccccc2c1OCc1ccccc1] | 317 |
| 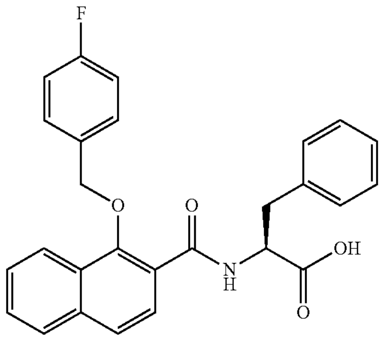 [SMILES: O=C(N[C@@H](Cc1ccccc1)C(=O)O)c1ccc2ccccc2c1OCc1ccc(F)cc1] | 94 |
| 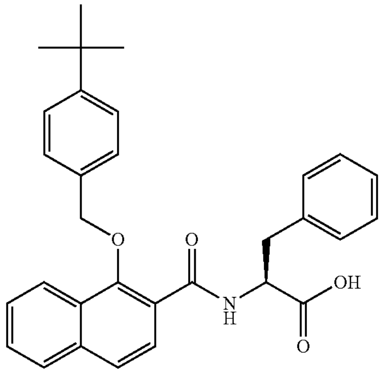 [SMILES: CC(C)(C)c1ccc(COc2c(C(=O)N[C@@H](Cc3ccccc3)C(=O)O)ccc3ccccc23)cc1] | 96 |
| 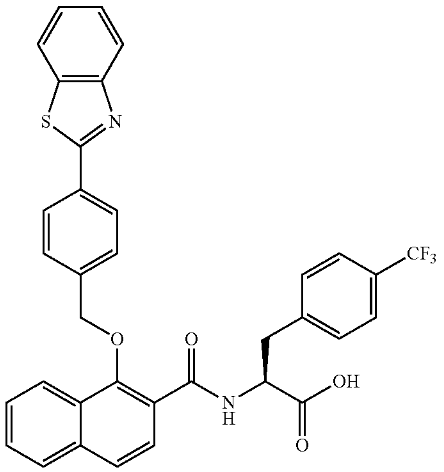 [SMILES: O=C(N[C@@H](Cc1ccc(C(F)(F)F)cc1)C(=O)O)c1ccc2ccccc2c1OCc1ccc(-c2nc3ccccc3s2)cc1] | 213 |

TABLE 5-continued
| Compound | # |
|---|---|
| 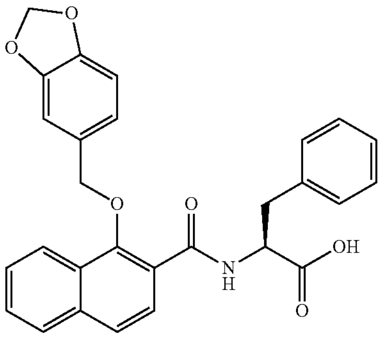 [SMILES: O=C(N[C@@H](Cc1ccccc1)C(=O)O)c1ccc2ccccc2c1OCc1ccc2c(c1)OCO2] | 121 |
| 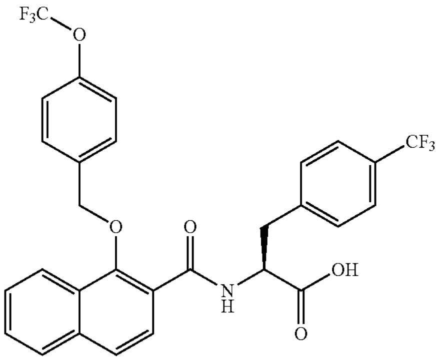 [SMILES: O=C(N[C@@H](Cc1ccc(C(F)(F)F)cc1)C(=O)O)c1ccc2ccccc2c1OCc1ccc(OC(F)(F)F)cc1] | 190 |
| 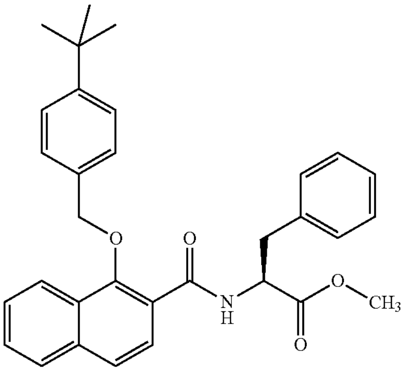 [SMILES: COC(=O)[C@H](Cc1ccccc1)NC(=O)c1ccc2ccccc2c1OCc1ccc(C(C)(C)C)cc1] | 318 |
| 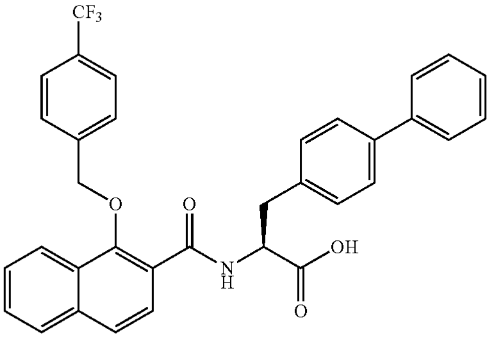 [SMILES: O=C(N[C@@H](Cc1ccc(-c2ccccc2)cc1)C(=O)O)c1ccc2ccccc2c1OCc1ccc(C(F)(F)F)cc1] | 319 |
TABLE 5-continued
| Compound | # |
|---|---|
| 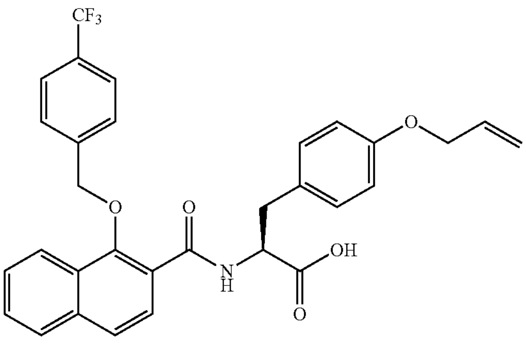 [SMILES: C=CCOc1ccc(C[C@H](NC(=O)c2ccc3ccccc3c2OCc2ccc(C(F)(F)F)cc2)C(=O)O)cc1] | 92 |
| 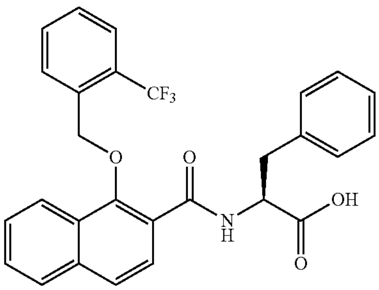 [SMILES: O=C(N[C@@H](Cc1ccccc1)C(=O)O)c1ccc2ccccc2c1OCc1ccccc1C(F)(F)F] | 93 |
| 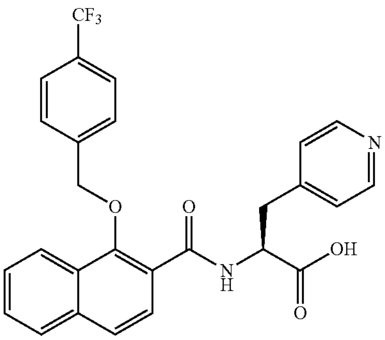 [SMILES: O=C(N[C@@H](Cc1ccncc1)C(=O)O)c1ccc2ccccc2c1OCc1ccc(C(F)(F)F)cc1] | 103 |
| 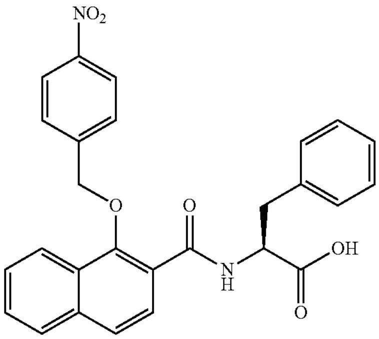 [SMILES: O=C(N[C@@H](Cc1ccccc1)C(=O)O)c1ccc2ccccc2c1OCc1ccc([N+](=O)[O-])cc1] | 91 |

TABLE 5-continued
| Compound | # |
| --- | --- |
| 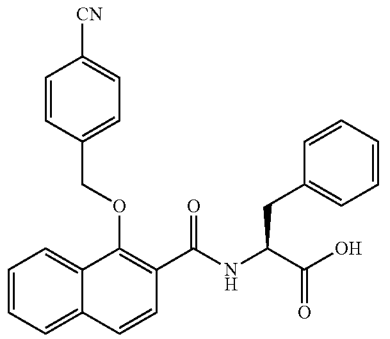 [SMILES: N#Cc1ccc(COc2c(C(=O)N[C@@H](Cc3ccccc3)C(=O)O)ccc3ccccc23)cc1] | 125 |
| 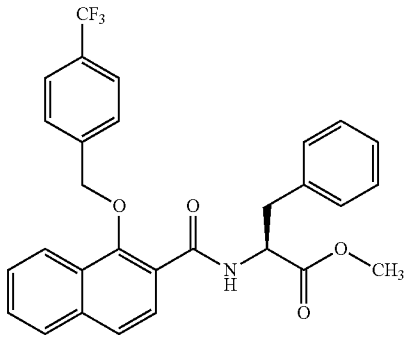 | 323 |
| 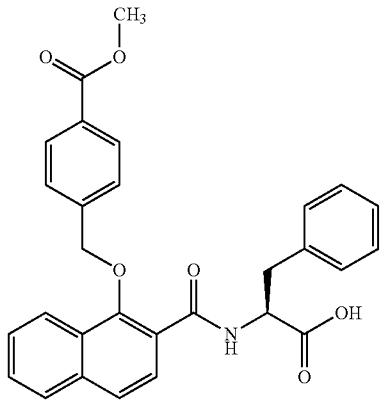 [SMILES: COC(=O)c1ccc(COc2c(C(=O)N[C@@H](Cc3ccccc3)C(=O)O)ccc3ccccc23)cc1] | 120 |
| 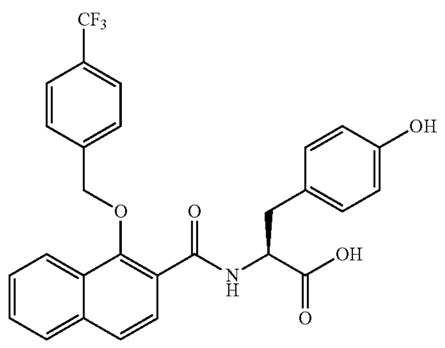 [SMILES: O=C(N[C@@H](Cc1ccc(O)cc1)C(=O)O)c1ccc2ccccc2c1OCc1ccc(C(F)(F)F)cc1] | 324 |
TABLE 5-continued
| Compound | # |
| --- | --- |
| 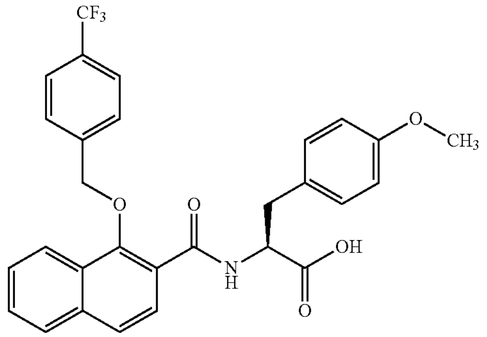 [SMILES: COc1ccc(C[C@H](NC(=O)c2ccc3ccccc3c2OCc2ccc(C(F)(F)F)cc2)C(=O)O)cc1] | 325 |
| 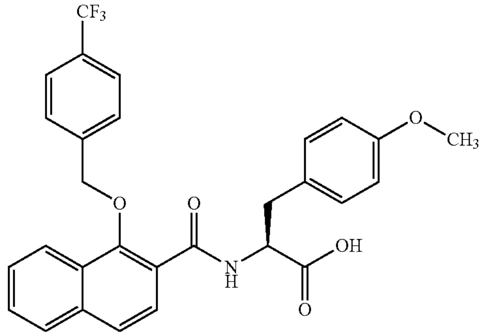 [SMILES: COc1ccc(C[C@H](NC(=O)c2ccc3ccccc3c2OCc2ccc(C(F)(F)F)cc2)C(=O)O)cc1] | 104 |
| 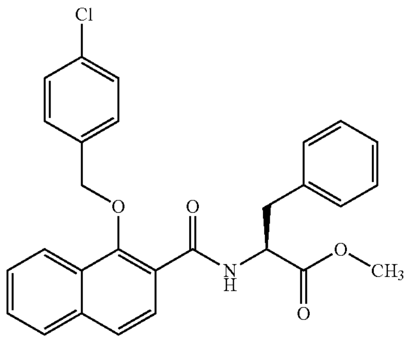 [SMILES: COC(=O)[C@H](Cc1ccccc1)NC(=O)c1ccc2ccccc2c1OCc1ccc(Cl)cc1] | 327 |
| 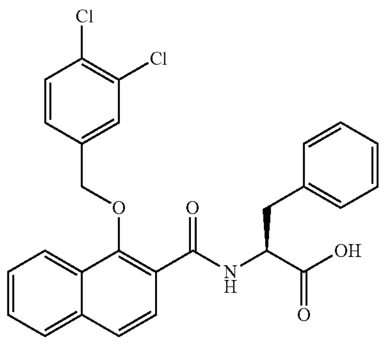 [SMILES: O=C(N[C@@H](Cc1ccccc1)C(=O)O)c1ccc2ccccc2c1OCc1ccc(Cl)c(Cl)c1] | 99 |

TABLE 5-continued
| Compound | # |
| --- | --- |
| 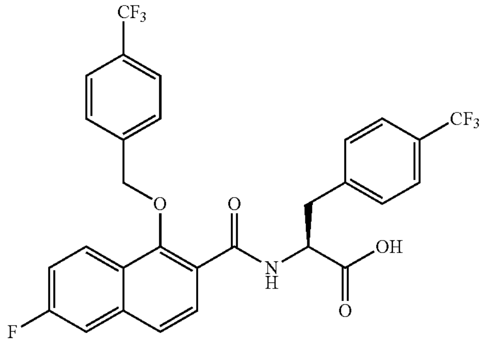 | 197 |
| 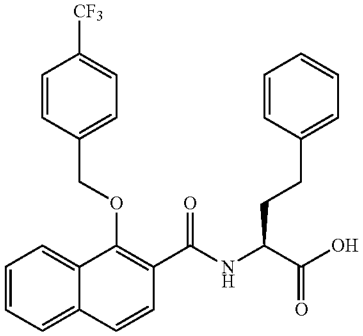 [SMILES: O=C(N[C@@H](CCc1ccccc1)C(=O)O)c1ccc2ccccc2c1OCc1ccc(C(F)(F)F)cc1] | 87 |
| 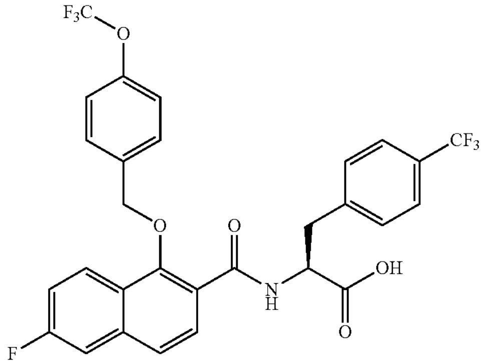 [SMILES: O=C(N[C@@H](Cc1ccc(C(F)(F)F)cc1)C(=O)O)c1ccc2cc(F)ccc2c1OCc1ccc(OC(F)(F)F)cc1] | 194 |
| 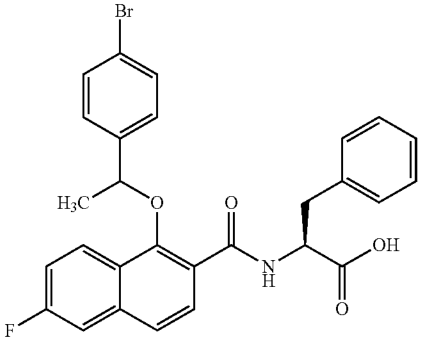 [SMILES: CC(Oc1c(C(=O)N[C@@H](Cc2ccccc2)C(=O)O)ccc2cc(F)ccc12)c1ccc(Br)cc1] | 123 |
TABLE 5-continued
| Compound | # |
| --- | --- |
| 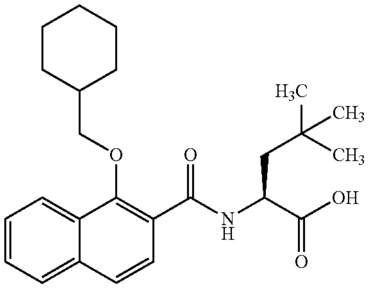 [SMILES: CC(C)(C)C[C@H](NC(=O)c1ccc2ccccc2c1OCC1CCCCC1)C(=O)O] | 201 |
| 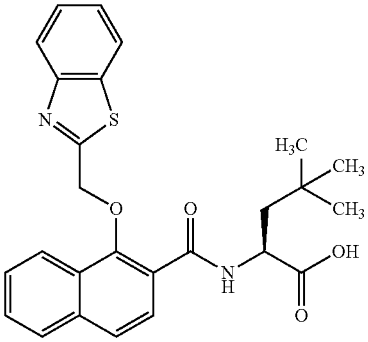 [SMILES: CC(C)(C)C[C@H](NC(=O)c1ccc2ccccc2c1OCc1nc2ccccc2s1)C(=O)O] | 214 |
| 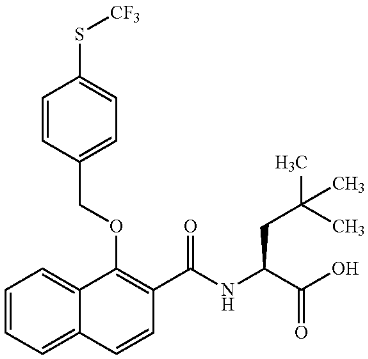 [SMILES: CC(C)(C)C[C@H](NC(=O)c1ccc2ccccc2c1OCc1ccc(SC(F)(F)F)cc1)C(=O)O] | 328 |
| 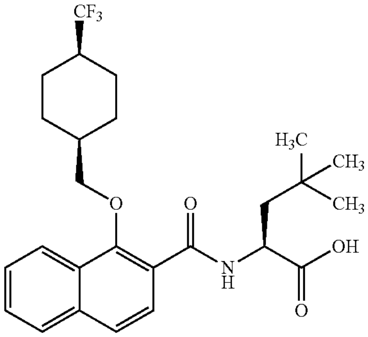 [SMILES: CC(C)(C)C[C@H](NC(=O)c1ccc2ccccc2c1OC[C@H]1CC[C@@H](C(F)(F)F)CC1)C(=O)O] | 180 |

TABLE 5-continued
| Compound | # |
|---|---|
| 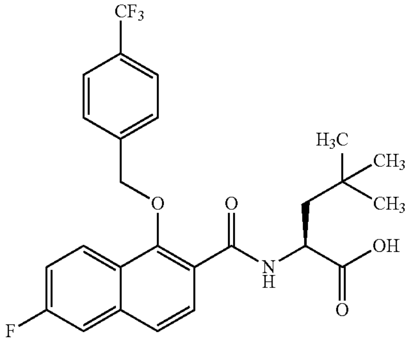 [SMILES: CC(C)(C)C[C@H](NC(=O)c1ccc2cc(F)ccc2c1OCc1ccc(C(F)(F)F)cc1)C(=O)O] | 198 |
| 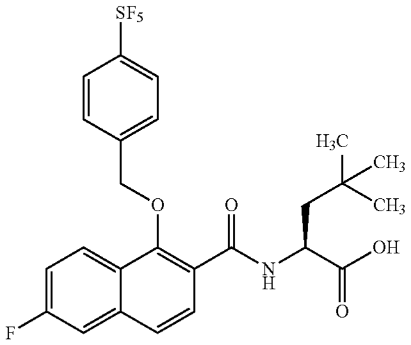 | 112 |
| 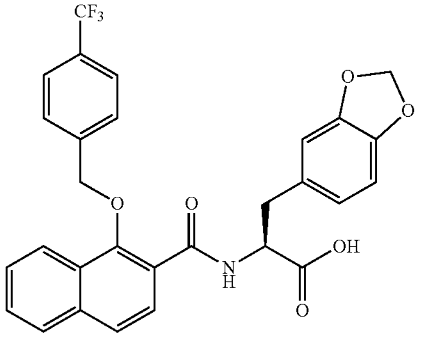 [SMILES: O=C(N[C@@H](Cc1ccc2c(c1)OCO2)C(=O)O)c1ccc2ccccc2c1OCc1ccc(C(F)(F)F)cc1] | 106 |
| 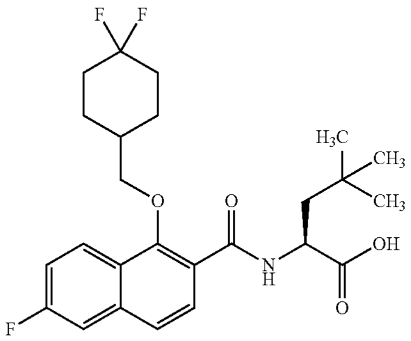 [SMILES: CC(C)(C)C[C@H](NC(=O)c1ccc2cc(F)ccc2c1OCC1CCC(F)(F)CC1)C(=O)O] | 109 |
TABLE 5-continued
| Compound | # |
|---|---|
| 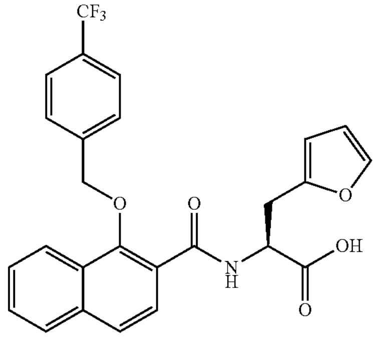 [SMILES: O=C(N[C@@H](Cc1ccco1)C(=O)O)c1ccc2ccccc2c1OCc1ccc(C(F)(F)F)cc1] | 136 |
| 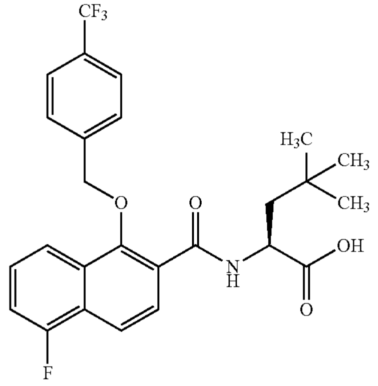 [SMILES: CC(C)(C)C[C@H](NC(=O)c1ccc2c(F)cccc2c1OCc1ccc(C(F)(F)F)cc1)C(=O)O] | 332 |
| 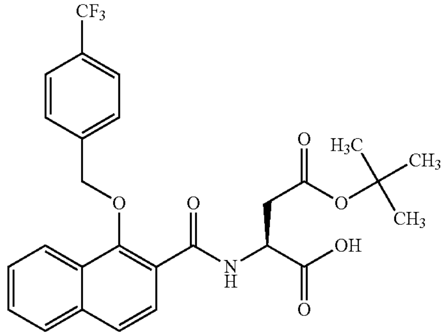 [SMILES: CC(C)(C)OC(=O)C[C@H](NC(=O)c1ccc2ccccc2c1OCc1ccc(C(F)(F)F)cc1)C(=O)O] | 151 |
| 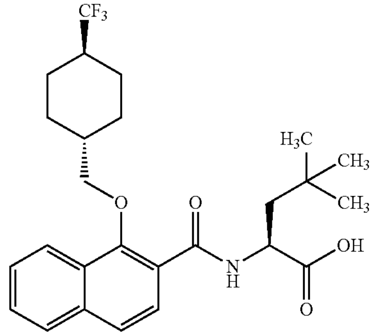 [SMILES: CC(C)(C)C[C@H](NC(=O)c1ccc2ccccc2c1OC[C@H]1CC[C@H](C(F)(F)F)CC1)C(=O)O] | 179 |

TABLE 5-continued
| Compound | # |
|---|---|
| 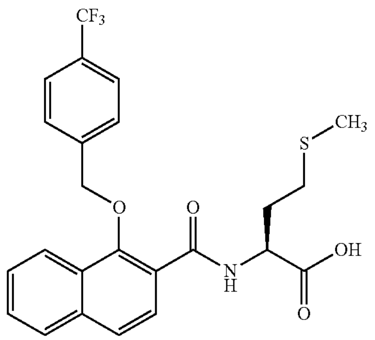 [SMILES: CSCC[C@H](NC(=O)c1ccc2ccccc2c1OCc1ccc(C(F)(F)F)cc1)C(=O)O] | 333 |
| 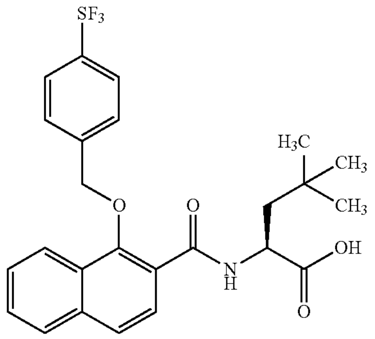 | 115 |
| 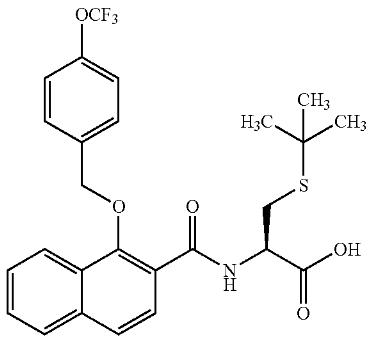 [SMILES: CC(C)(C)SC[C@H](NC(=O)c1ccc2ccccc2c1OCc1ccc(OC(F)(F)F)cc1)C(=O)O] | 337 |
| 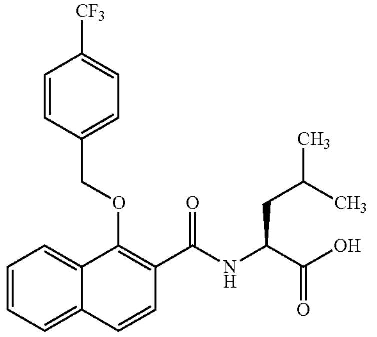 [SMILES: CC(C)C[C@H](NC(=O)c1ccc2ccccc2c1OCc1ccc(C(F)(F)F)cc1)C(=O)O] | 338 |
TABLE 5-continued
| Compound | # |
|---|---|
| 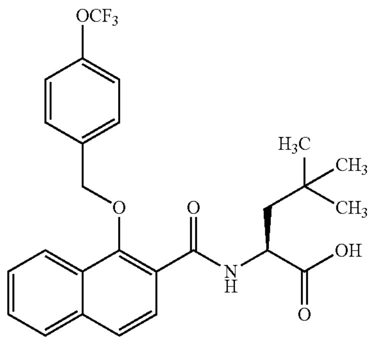 [SMILES: CC(C)(C)C[C@H](NC(=O)c1ccc2ccccc2c1OCc1ccc(OC(F)(F)F)cc1)C(=O)O] | 191 |
| 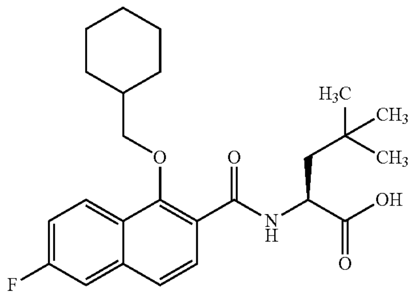 [SMILES: CC(C)(C)C[C@H](NC(=O)c1ccc2cc(F)ccc2c1OCC1CCCCC1)C(=O)O] | 205 |
| 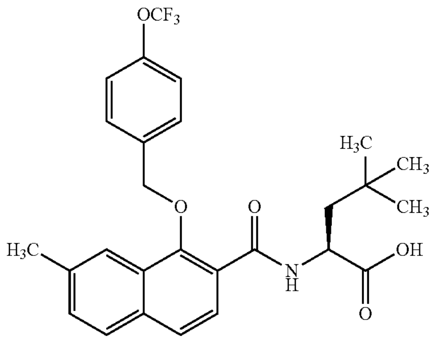 [SMILES: Cc1ccc2ccc(C(=O)N[C@@H](CC(C)(C)C)C(=O)O)c(OCc3ccc(OC(F)(F)F)cc3)c2c1] | 339 |
| 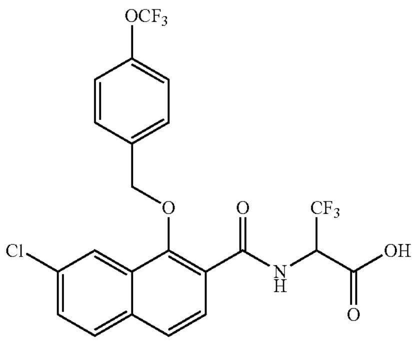 [SMILES: O=C(NC(C(=O)O)C(F)(F)F)c1ccc2ccc(Cl)cc2c1OCc1ccc(OC(F)(F)F)cc1] | 341 |

TABLE 5-continued
| Compound | # |
|---|---|
| 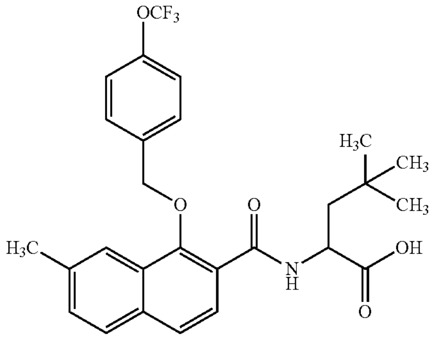 [SMILES: Cc1ccc2ccc(C(=O)NC(CC(C)(C)C)C(=O)O)c(OCc3ccc(OC(F)(F)F)cc3)c2c1] | 342 |
| 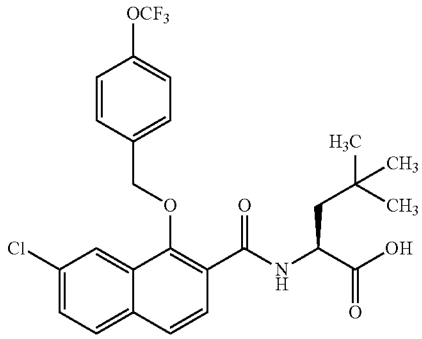 [SMILES: CC(C)(C)C[C@H](NC(=O)c1ccc2ccc(Cl)cc2c1OCc1ccc(OC(F)(F)F)cc1)C(=O)O] | 343 |
| 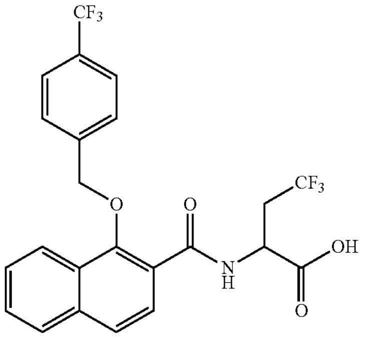 [SMILES: O=C(NC(CC(F)(F)F)C(=O)O)c1ccc2ccccc2c1OCc1ccc(C(F)(F)F)cc1] | 344 |
| 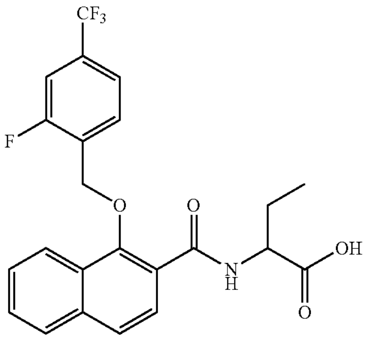 [SMILES: CCC(NC(=O)c1ccc2ccccc2c1OCc1ccc(C(F)(F)F)cc1F)C(=O)O] | 345 |
TABLE 5-continued
| Compound | # |
|---|---|
| 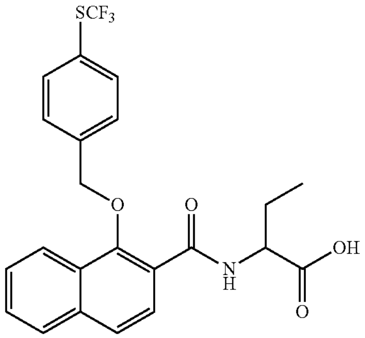 | 351 |
| 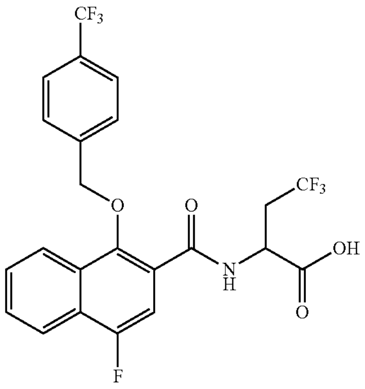 [SMILES: O=C(NC(CC(F)(F)F)C(=O)O)c1cc(F)c2ccccc2c1OCc1ccc(C(F)(F)F)cc1] | 352 |
| 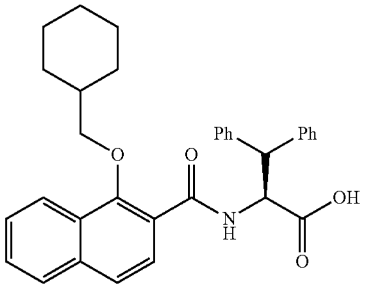 [SMILES: O=C(N[C@H](C(=O)O)C(c1ccccc1)c1ccccc1)c1ccc2ccccc2c1OCC1CCCCC1] | 199 |
| 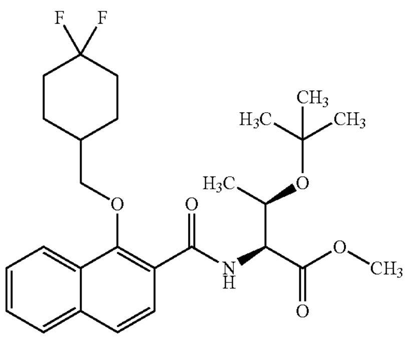 [SMILES: COC(=O)[C@@H](NC(=O)c1ccc2ccccc2c1OCC1CCC(F)(F)CC1)[C@@H](C)OC(C)(C)C] | 353 |

TABLE 5-continued
| Compound | # |
|---|---|
| 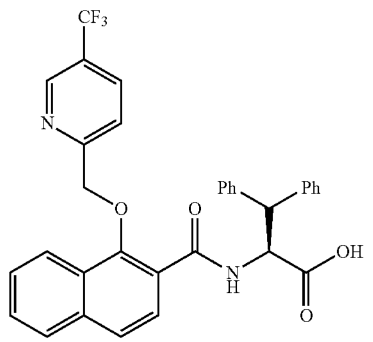 [SMILES: O=C(N[C@H](C(=O)O)C(c1ccccc1)c1ccccc1)c1ccc2ccccc2c1OCc1ccc(C(F)(F)F)cn1] | 132 |
| 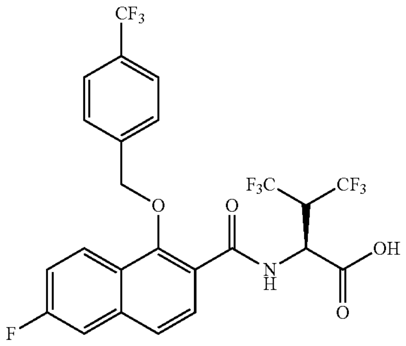 [SMILES: O=C(N[C@H](C(=O)O)C(C(F)(F)F)C(F)(F)F)c1ccc2cc(F)ccc2c1OCc1ccc(C(F)(F)F)cc1] | 182 |
| 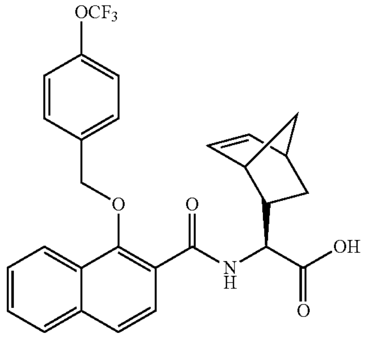 [SMILES: O=C(N[C@H](C(=O)O)C1CC2C=CC1C2)c1ccc2ccccc2c1OCc1ccc(OC(F)(F)F)cc1] | 358 |
| 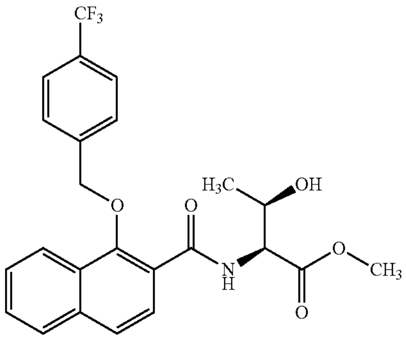 [SMILES: COC(=O)[C@@H](NC(=O)c1ccc2ccccc2c1OCc1ccc(C(F)(F)F)cc1)[C@@H](C)O] | 359 |
TABLE 5-continued
| Compound | # |
|---|---|
| 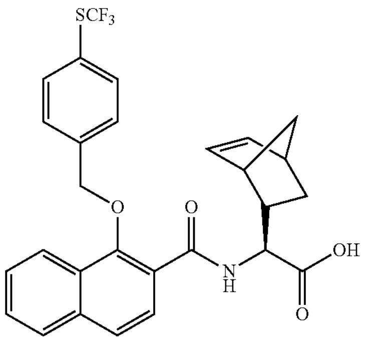 | 360 |
| 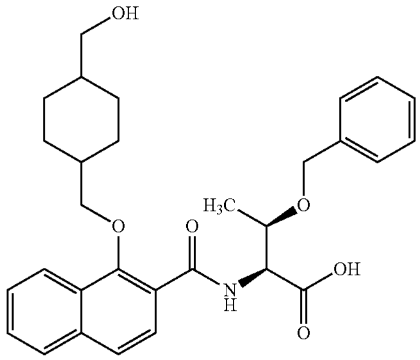 [SMILES: C[C@@H](OCc1ccccc1)[C@H](NC(=O)c1ccc2ccccc2c1OCC1CCC(CO)CC1)C(=O)O] | 146 |
| 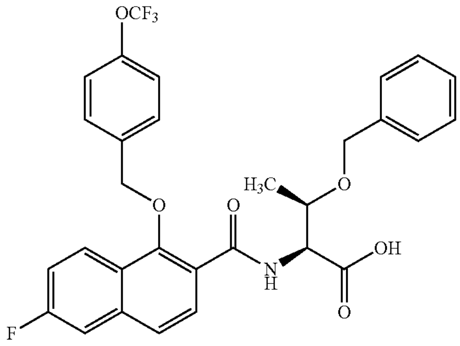 [SMILES: C[C@@H](OCc1ccccc1)[C@H](NC(=O)c1ccc2cc(F)ccc2c1OCc1ccc(OC(F)(F)F)cc1)C(=O)O] | 192 |
| 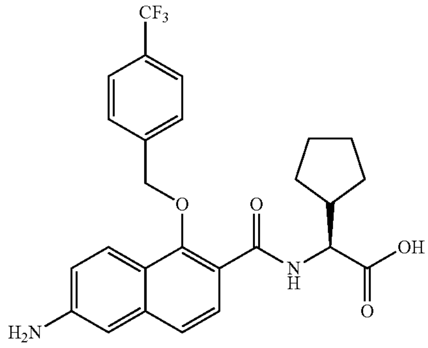 [SMILES: Nc1ccc2c(OCc3ccc(C(F)(F)F)cc3)c(C(=O)N[C@H](C(=O)O)C3CCCC3)ccc2c1] | 187 |

TABLE 5-continued
| Compound | # |
|---|---|
| 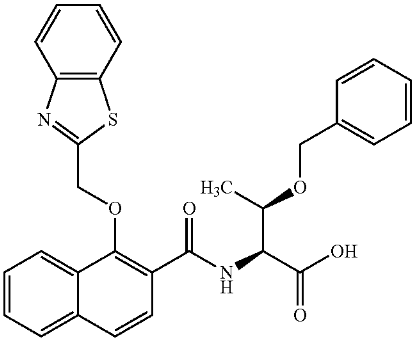 [SMILES: C[C@@H](OCc1ccccc1)[C@H](NC(=O)c1ccc2ccccc2c1OCc1nc2ccccc2s1)C(=O)O] | 148 |
| 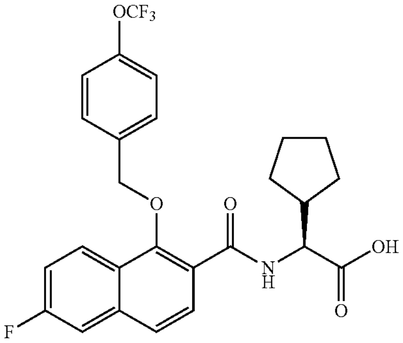 [SMILES: O=C(N[C@H](C(=O)O)C1CCCC1)c1ccc2cc(F)ccc2c1OCc1ccc(OC(F)(F)F)cc1] | 119 |
| 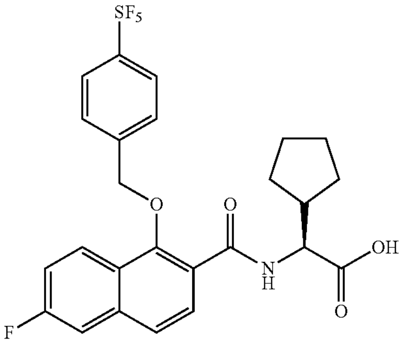 | 113 |
| 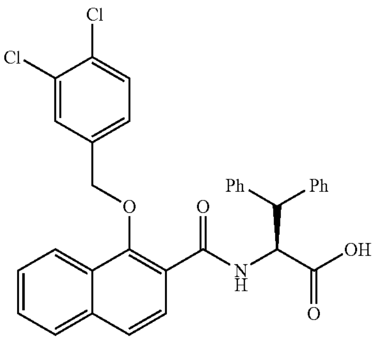 [SMILES: O=C(N[C@H](C(=O)O)C(c1ccccc1)c1ccccc1)c1ccc2ccccc2c1OCc1ccc(Cl)c(Cl)c1] | 207 |
TABLE 5-continued
| Compound | # |
|---|---|
| 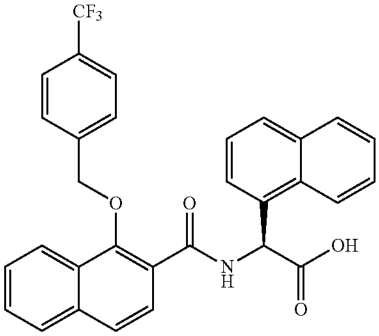 [SMILES: O=C(N[C@H](C(=O)O)c1cccc2ccccc12)c1ccc2ccccc2c1OCc1ccc(C(F)(F)F)cc1] | 142 |
| 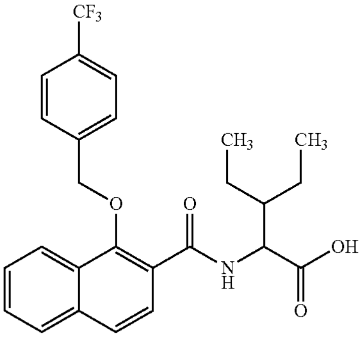 [SMILES: CCC(CC)C(NC(=O)c1ccc2ccccc2c1OCc1ccc(C(F)(F)F)cc1)C(=O)O] | 366 |
| 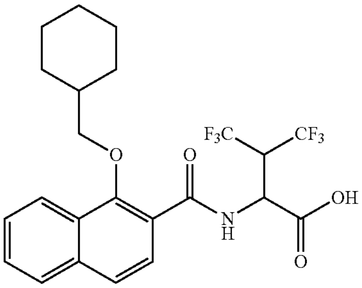 [SMILES: O=C(NC(C(=O)O)C(C(F)(F)F)C(F)(F)F)c1ccc2ccccc2c1OCC1CCCCC1] | 183 |
| 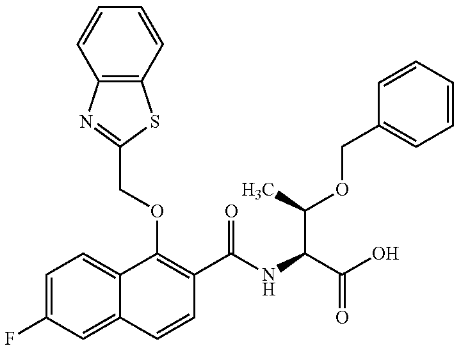 [SMILES: C[C@@H](OCc1ccccc1)[C@H](NC(=O)c1ccc2cc(F)ccc2c1OCc1nc2ccccc2s1)C(=O)O] | 215 |

TABLE 5-continued
| Compound | # |
| --- | --- |
| 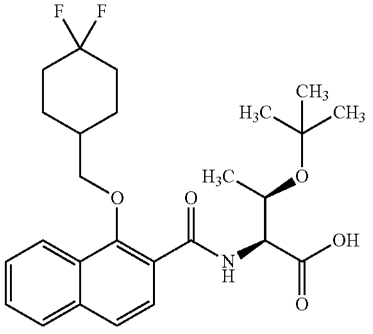 [SMILES: C[C@@H](OC(C)(C)C)[C@H](NC(=O)c1ccc2ccccc2c1OCC1CCC(F)(F)CC1)C(=O)O] | 369 |
| 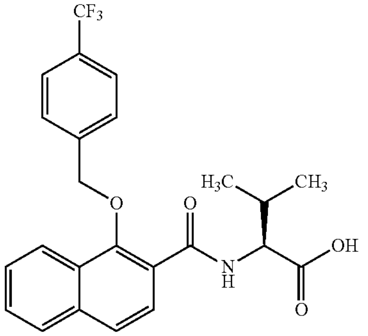 [SMILES: CC(C)[C@H](NC(=O)c1ccc2ccccc2c1OCc1ccc(C(F)(F)F)cc1)C(=O)O] | 370 |
| 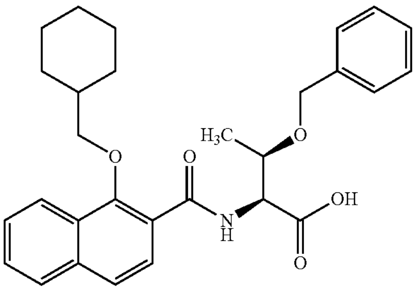 [SMILES: C[C@@H](OCc1ccccc1)[C@H](NC(=O)c1ccc2ccccc2c1OCC1CCCCC1)C(=O)O] | 150 |
| 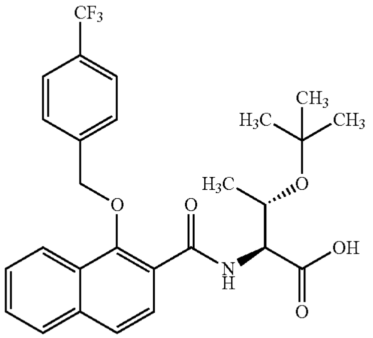 [SMILES: C[C@H](OC(C)(C)C)[C@H](NC(=O)c1ccc2ccccc2c1OCc1ccc(C(F)(F)F)cc1)C(=O)O] | 134 |
TABLE 5-continued
| Compound | # |
| --- | --- |
| 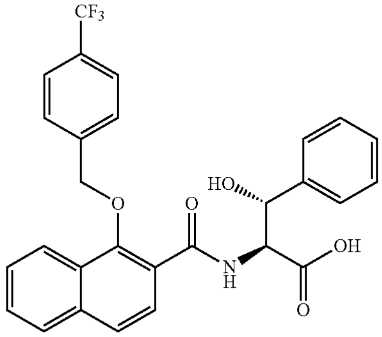 [SMILES: O=C(N[C@H](C(=O)O)[C@H](O)c1ccccc1)c1ccc2ccccc2c1OCc1ccc(C(F)(F)F)cc1] | 129 |
| 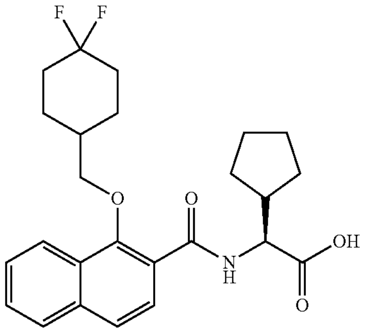 [SMILES: O=C(N[C@H](C(=O)O)C1CCCC1)c1ccc2ccccc2c1OCC1CCC(F)(F)CC1] | 155 |
| 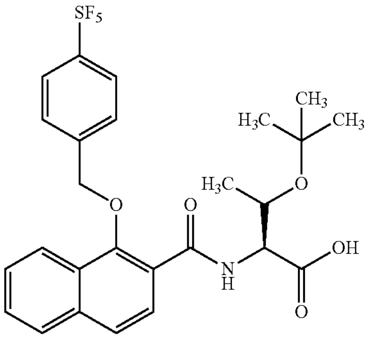 | 371 |
| 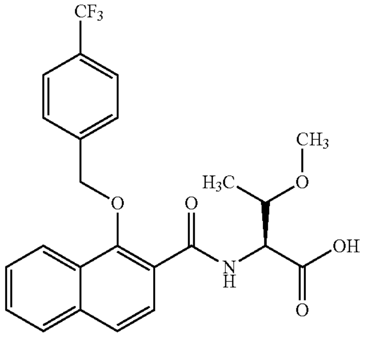 [SMILES: COC(C)[C@H](NC(=O)c1ccc2ccccc2c1OCc1ccc(C(F)(F)F)cc1)C(=O)O] | 135 |

TABLE 5-continued
| Compound | # |
|---|---|
| 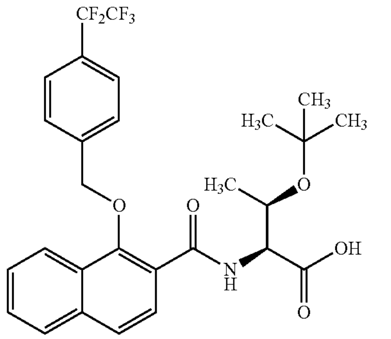 | 372 |
| 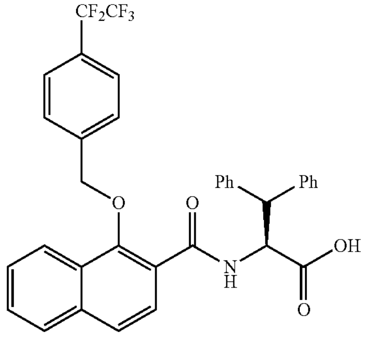 | 131 |
| 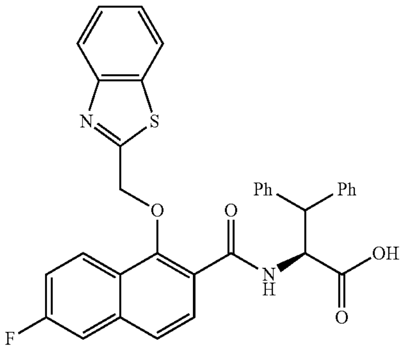 [SMILES: O=C(N[C@H](C(=O)O)C(c1ccccc1)c1ccccc1)c1ccc2cc(F)ccc2c1OCc1nc2ccccc2s1] | 216 |
| 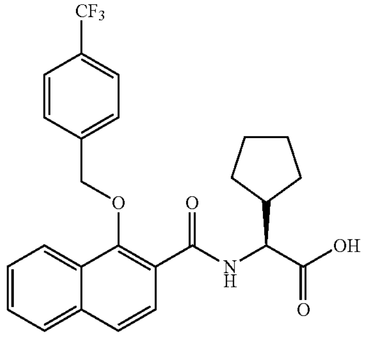 [SMILES: O=C(N[C@H](C(=O)O)C1CCCC1)c1ccc2ccccc2c1OCc1ccc(C(F)(F)F)cc1] | 154 |
TABLE 5-continued
| Compound | # |
|---|---|
| 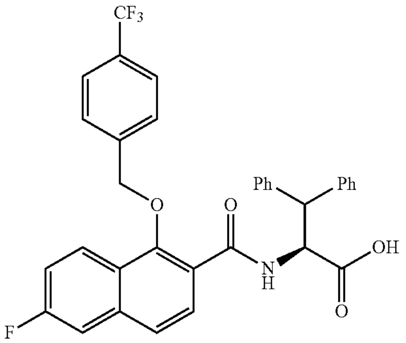 [SMILES: O=C(N[C@H](C(=O)O)C(c1ccccc1)c1ccccc1)c1ccc2cc(F)ccc2c1OCc1ccc(C(F)(F)F)cc1] | 196 |
| 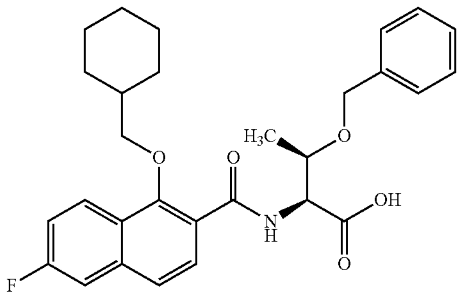 [SMILES: C[C@@H](OCc1ccccc1)[C@H](NC(=O)c1ccc2cc(F)ccc2c1OCC1CCCCC1)C(=O)O] | 202 |
| 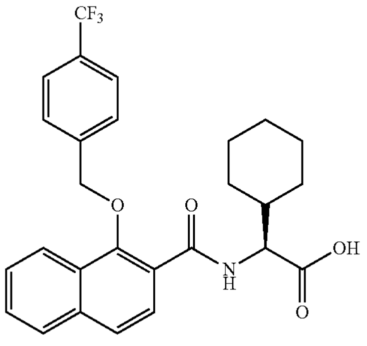 [SMILES: O=C(N[C@H](C(=O)O)C1CCCCC1)c1ccc2ccccc2c1OCc1ccc(C(F)(F)F)cc1] | 128 |
| 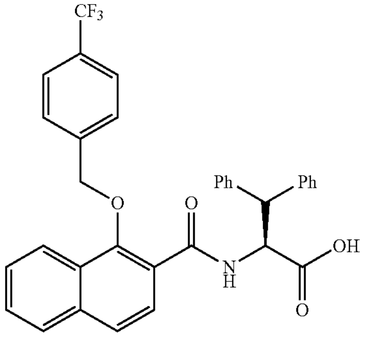 [SMILES: O=C(N[C@H](C(=O)O)C(c1ccccc1)c1ccccc1)c1ccc2ccccc2c1OCc1ccc(C(F)(F)F)cc1] | 126 |

TABLE 5-continued
| Compound | # |
| --- | --- |
| 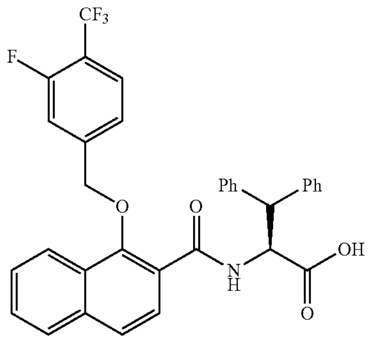 [SMILES: O=C(N[C@H](C(=O)O)C(c1ccccc1)c1ccccc1)c1ccc2ccccc2c1OCc1ccc(C(F)(F)F)c(F)c1] | 130 |
| 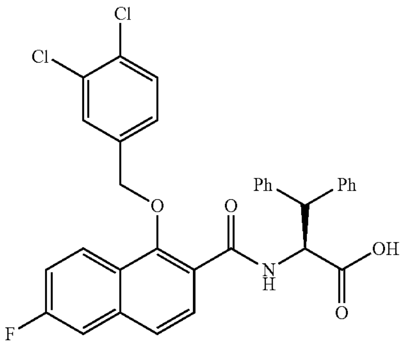 [SMILES: O=C(N[C@H](C(=O)O)C(c1ccccc1)c1ccccc1)c1ccc2cc(F)ccc2c1OCc1ccc(Cl)c(Cl)c1] | 209 |
| 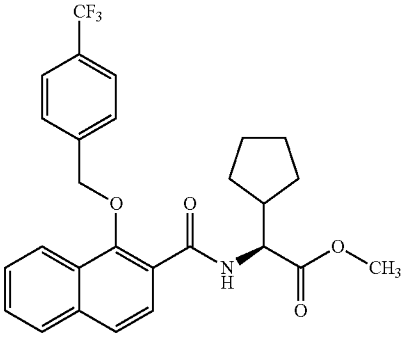 [SMILES: COC(=O)[C@@H](NC(=O)c1ccc2ccccc2c1OCc1ccc(C(F)(F)F)cc1)C1CCCC1] | 376 |
| 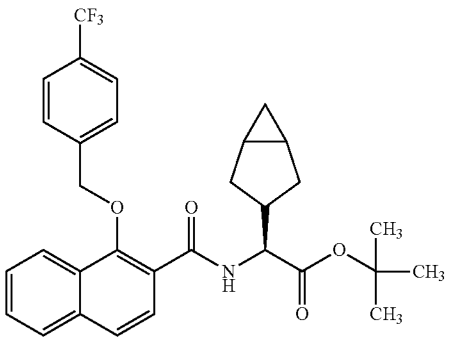 [SMILES: CC(C)(C)OC(=O)[C@@H](NC(=O)c1ccc2ccccc2c1OCc1ccc(C(F)(F)F)cc1)C1CC2CC2C1] | 377 |
TABLE 5-continued
| Compound | # |
| --- | --- |
| 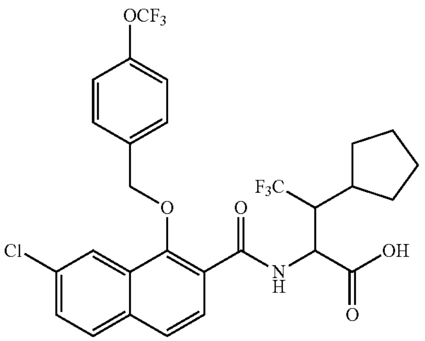 [SMILES: O=C(NC(C(=O)O)C(C1CCCC1)C(F)(F)F)c1ccc2ccc(Cl)cc2c1OCc1ccc(OC(F)(F)F)cc1] | 381 |
| 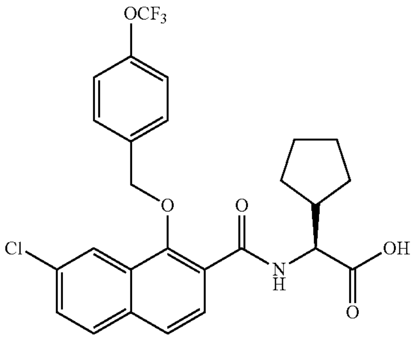 [SMILES: O=C(N[C@H](C(=O)O)C1CCCC1)c1ccc2ccc(Cl)cc2c1OCc1ccc(OC(F)(F)F)cc1] | 382 |
| 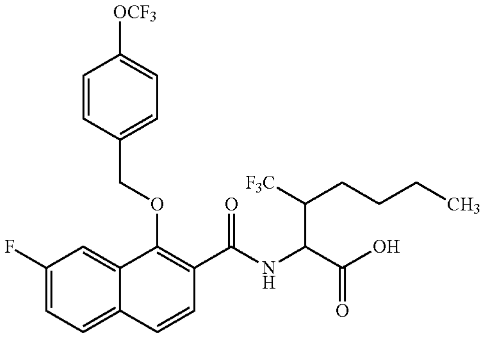 [SMILES: CCCCC(C(NC(=O)c1ccc2ccc(F)cc2c1OCc1ccc(OC(F)(F)F)cc1)C(=O)O)C(F)(F)F] | 383 |
| 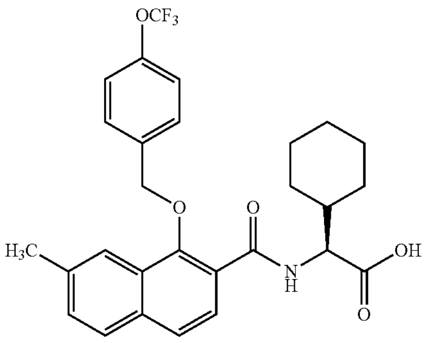 [SMILES: Cc1ccc2ccc(C(=O)N[C@H](C(=O)O)C3CCCCC3)c(OCc3ccc(OC(F)(F)F)cc3)c2c1] | 384 |

TABLE 5-continued
| Compound | # |
|---|---|
| 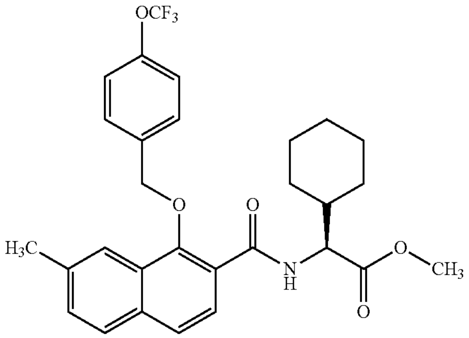 | 385 |
| 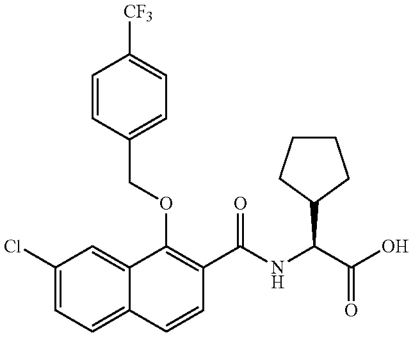 [SMILES: O=C(N[C@H](C(=O)O)C1CCCC1)c1ccc2ccc(Cl)cc2c1OCc1ccc(C(F)(F)F)cc1] | 391 |
| 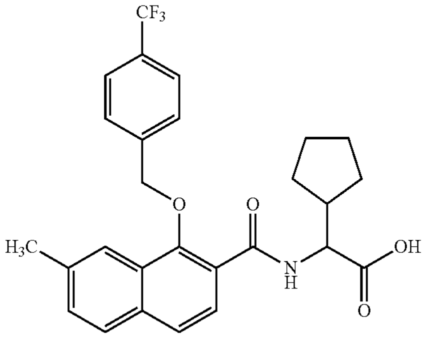 [SMILES: Cc1ccc2ccc(C(=O)NC(C(=O)O)C3CCCC3)c(OCc3ccc(C(F)(F)F)cc3)c2c1] | 392 |
| 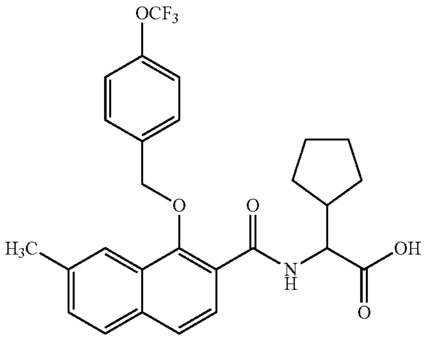 [SMILES: Cc1ccc2ccc(C(=O)NC(C(=O)O)C3CCCC3)c(OCc3ccc(OC(F)(F)F)cc3)c2c1] | 393 |
TABLE 5-continued
| Compound | # |
|---|---|
| 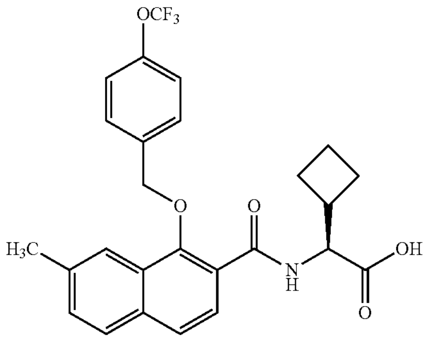 [SMILES: Cc1ccc2ccc(C(=O)N[C@H](C(=O)O)C3CCC3)c(OCc3ccc(OC(F)(F)F)cc3)c2c1] | 394 |
| 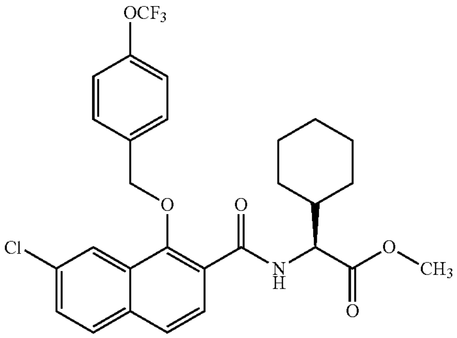 [SMILES: COC(=O)[C@@H](NC(=O)c1ccc2ccc(Cl)cc2c1OCc1ccc(OC(F)(F)F)cc1)C1CCCCC1] | 395 |
| 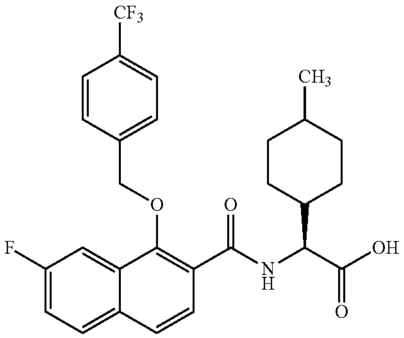 [SMILES: CC1CCC([C@H](NC(=O)c2ccc3ccc(F)cc3c2OCc2ccc(C(F)(F)F)cc2)C(=O)O)CC1] | 401 |
| 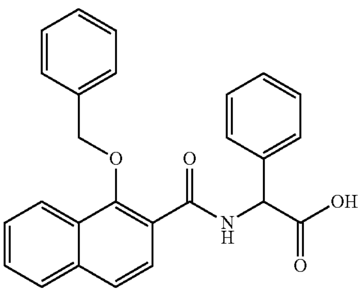 [SMILES: O=C(NC(C(=O)O)c1ccccc1)c1ccc2ccccc2c1OCc1ccccc1] | 402 |

TABLE 5-continued
| Compound | # |
|---|---|
| 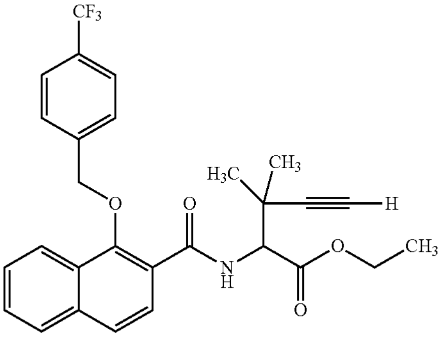 [SMILES: C#CC(C)(C)C(NC(=O)c1ccc2ccccc2c1OCc1ccc(C(F)(F)F)cc1)C(=O)OCC] | 403 |
| 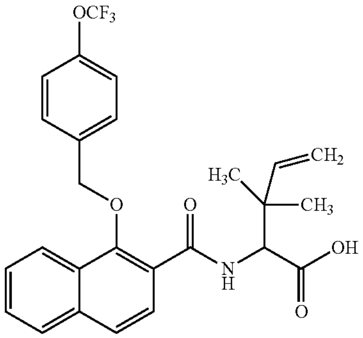 [SMILES: C=CC(C)(C)C(NC(=O)c1ccc2ccccc2c1OCc1ccc(OC(F)(F)F)cc1)C(=O)O] | 220 |
| 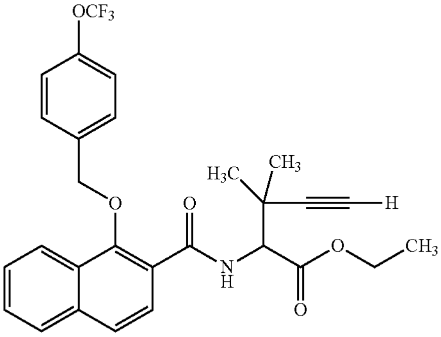 [SMILES: C#CC(C)(C)C(NC(=O)c1ccc2ccccc2c1OCc1ccc(OC(F)(F)F)cc1)C(=O)OCC] | 404 |
| 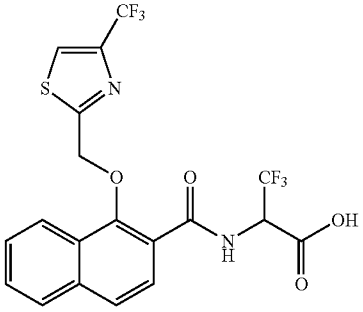 [SMILES: O=C(NC(C(=O)O)C(F)(F)F)c1ccc2ccccc2c1OCc1nc(C(F)(F)F)cs1] | 408 |
TABLE 5-continued
| Compound | # |
|---|---|
| 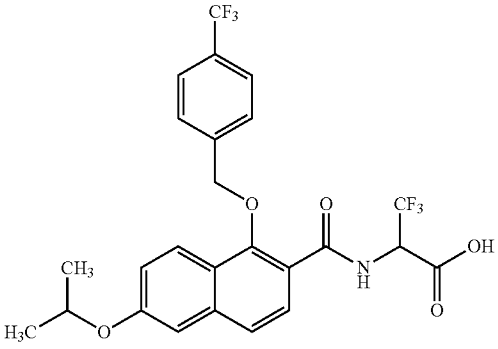 [SMILES: CC(C)Oc1ccc2c(OCc3ccc(C(F)(F)F)cc3)c(C(=O)NC(C(=O)O)C(F)(F)F)ccc2c1] | 409 |
| 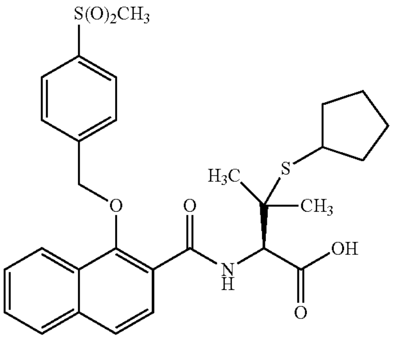 | 171 |
| 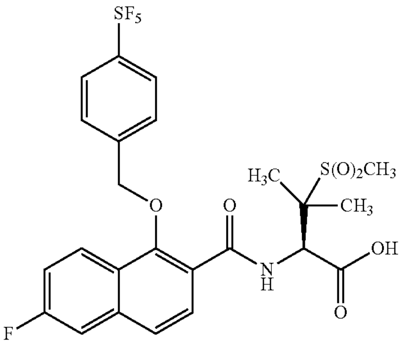 | 410 |
| 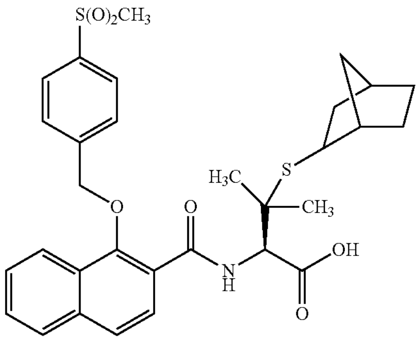 | 176 |

TABLE 5-continued
| Compound | # |
|---|---|
| 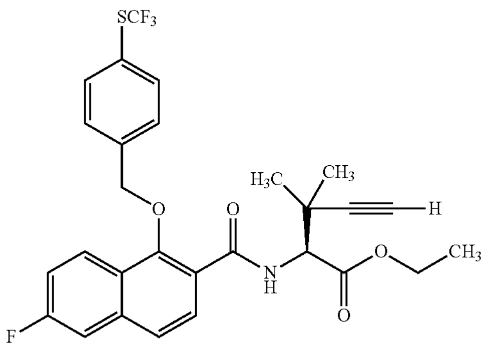 | 415 |
| 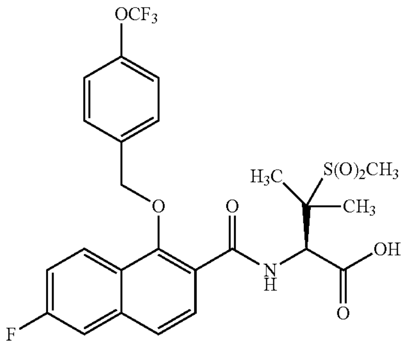 | 416 |
| 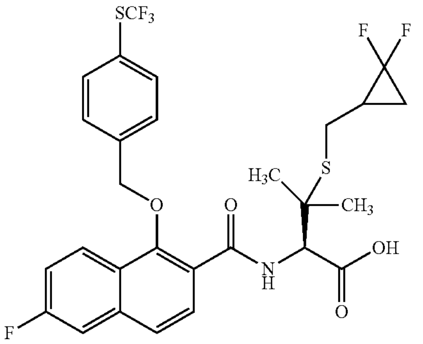 | 167 |
| 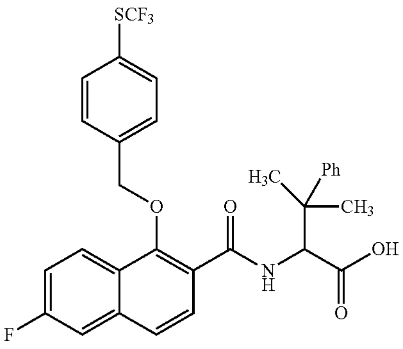 | 10 |
TABLE 5-continued
| Compound | # |
|---|---|
| 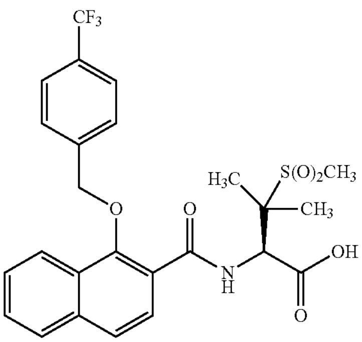 | 417 |
| 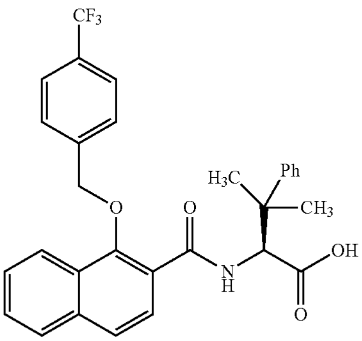 [SMILES: CC(C)(c1ccccc1)[C@H](NC(=O)c1ccc2ccccc2c1OCc1ccc(C(F)(F)F)cc1)C(=O)O] | 9 |
| 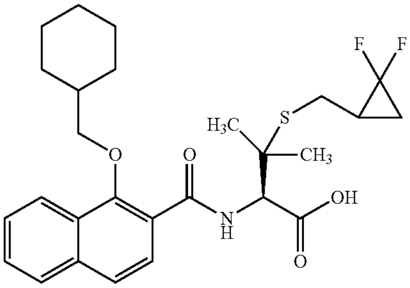 [SMILES: CC(C)(SCC1CC1(F)F)[C@H](NC(=O)c1ccc2ccccc2c1OCC1CCCCC1)C(=O)O] | 165 |
| 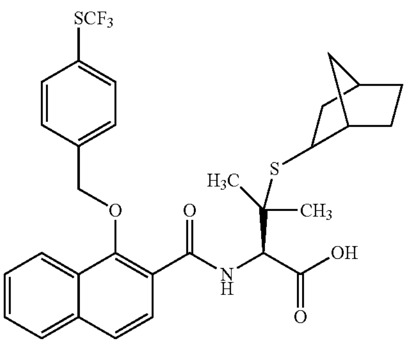 | 174 |

TABLE 5-continued
| Compound | # |
| --- | --- |
| 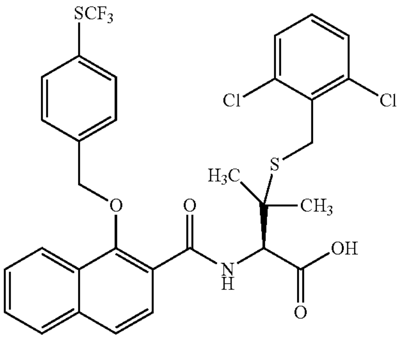 | 418 |
| 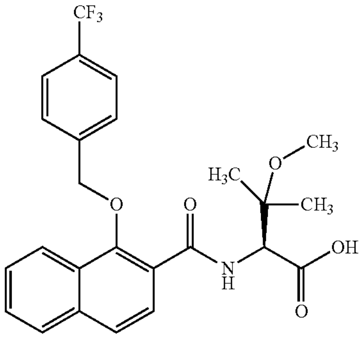 [SMILES: COC(C)(C)[C@H](NC(=O)c1ccc2ccccc2c1OCc1ccc(C(F)(F)F)cc1)C(=O)O] | 139 |
| 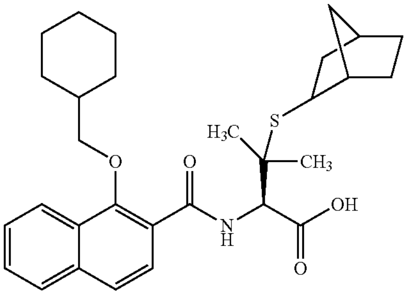 [SMILES: CC(C)(SC1CC2CCC1C2)[C@H](NC(=O)c1ccc2ccccc2c1OCC1CCCCC1)C(=O)O] | 175 |
| 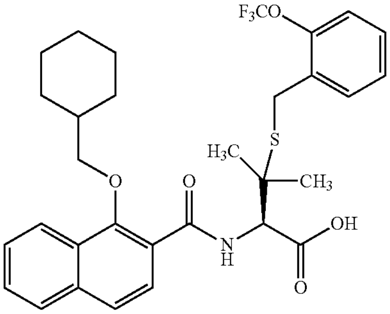 [SMILES: CC(C)(SCc1ccccc1OC(F)(F)F)[C@H](NC(=O)c1ccc2ccccc2c1OCC1CCCCC1)C(=O)O] | 421 |
TABLE 5-continued
| Compound | # |
| --- | --- |
| 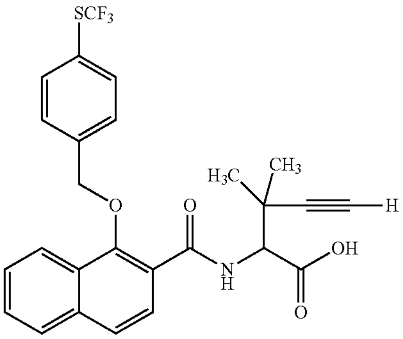 | 221 |
| 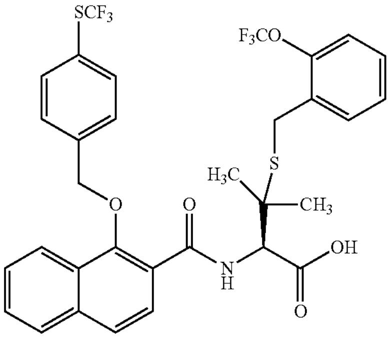 | 422 |
| 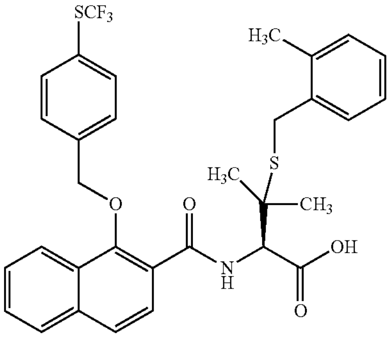 | 423 |
| 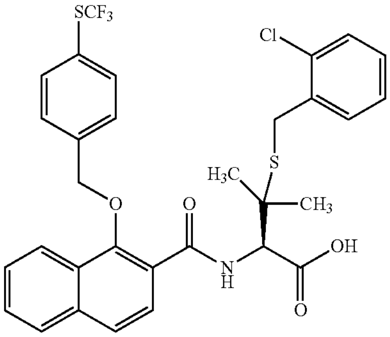 | 424 |

TABLE 5-continued
| Compound | # |
|---|---|
| 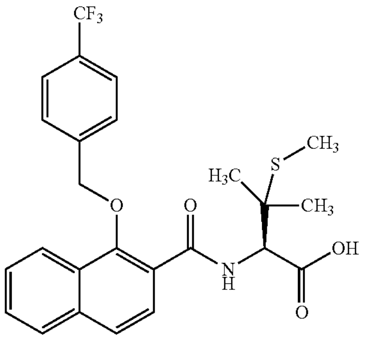 [SMILES: CSC(C)(C)[C@H](NC(=O)c1ccc2ccccc2c1OCc1ccc(C(F)(F)F)cc1)C(=O)O] | 428 |
| 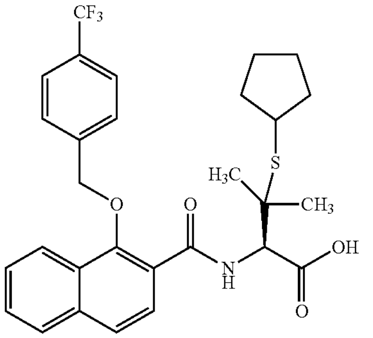 [SMILES: CC(C)(SC1CCCC1)[C@H](NC(=O)c1ccc2ccccc2c1OCc1ccc(C(F)(F)F)cc1)C(=O)O] | 168 |
| 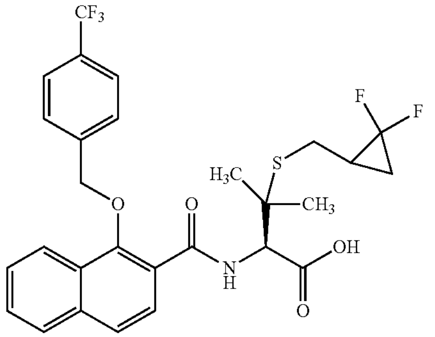 [SMILES: CC(C)(SCC1CC1(F)F)[C@H](NC(=O)c1ccc2ccccc2c1OCc1ccc(C(F)(F)F)cc1)C(=O)O] | 163 |
| 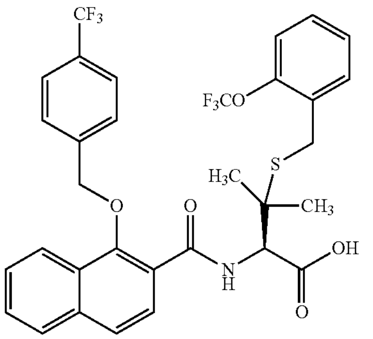 | 429 |
TABLE 5-continued
| Compound | # |
|---|---|
| 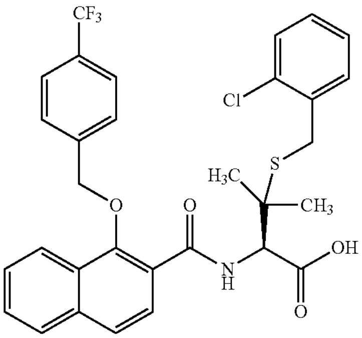 [SMILES: CC(C)(SCc1ccccc1Cl)[C@H](NC(=O)c1ccc2ccccc2c1OCc1ccc(C(F)(F)F)cc1)C(=O)O] | 430 |
| 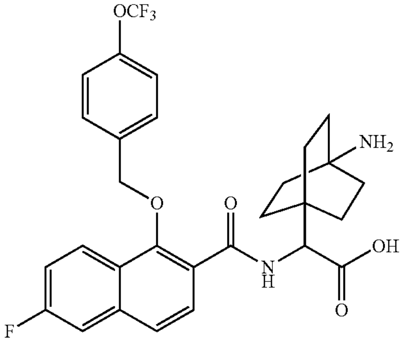 [SMILES: NC12CCC(C(NC(=O)c3ccc4cc(F)ccc4c3OCc3ccc(OC(F)(F)F)cc3)C(=O)O)(CC1)CC2] | 184 |
| 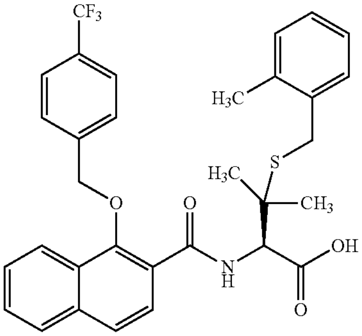 [SMILES: Cc1ccccc1CSC(C)(C)[C@H](NC(=O)c1ccc2ccccc2c1OCc1ccc(C(F)(F)F)cc1)C(=O)O] | 432 |
| 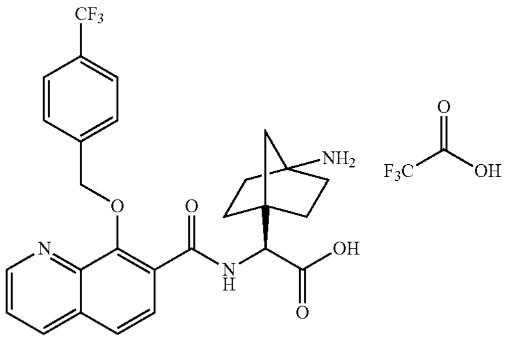 [SMILES: NC12CCC([C@H](NC(=O)c3ccc4cccnc4c3OCc3ccc(C(F)(F)F)cc3)C(=O)O)(CC1)C2 ; O=C(O)C(F)(F)F] | 433 |

TABLE 5-continued
| Compound | # |
|---|---|
| 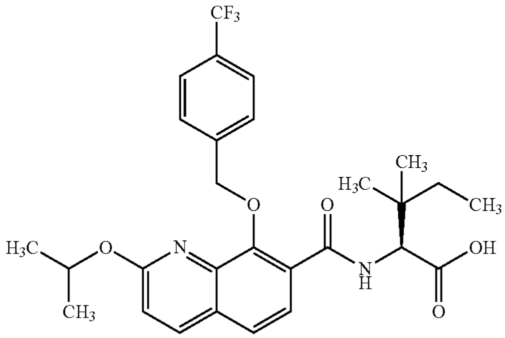 [SMILES: CCC(C)(C)[C@H](NC(=O)c1ccc2ccc(OC(C)C)nc2c1OCc1ccc(C(F)(F)F)cc1)C(=O)O] | 434 |
| 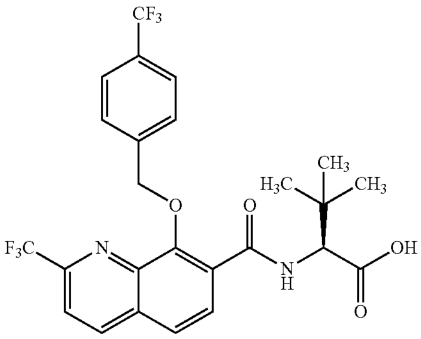 [SMILES: CC(C)(C)[C@H](NC(=O)c1ccc2ccc(C(F)(F)F)nc2c1OCc1ccc(C(F)(F)F)cc1)C(=O)O] | 435 |
| 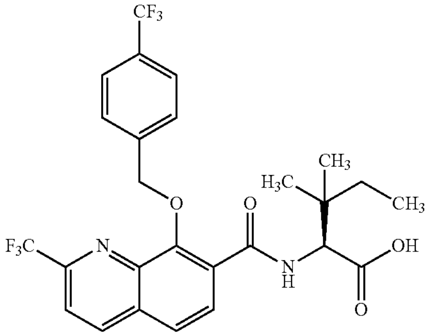 [SMILES: CCC(C)(C)[C@H](NC(=O)c1ccc2ccc(C(F)(F)F)nc2c1OCc1ccc(C(F)(F)F)cc1)C(=O)O] | 440 |
| 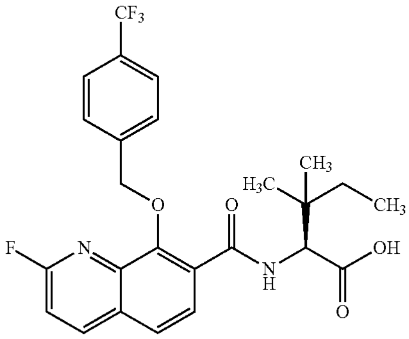 [SMILES: CCC(C)(C)[C@H](NC(=O)c1ccc2ccc(F)nc2c1OCc1ccc(C(F)(F)F)cc1)C(=O)O] | 441 |
TABLE 5-continued
| Compound | # |
|---|---|
| 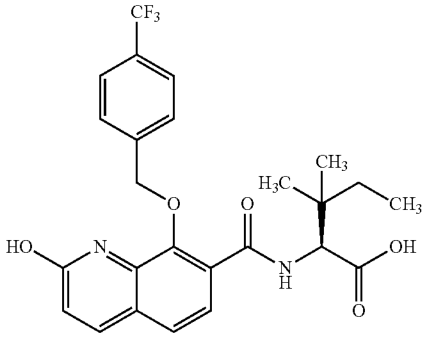 [SMILES: CCC(C)(C)[C@H](NC(=O)c1ccc2ccc(O)nc2c1OCc1ccc(C(F)(F)F)cc1)C(=O)O] | 442 |
| 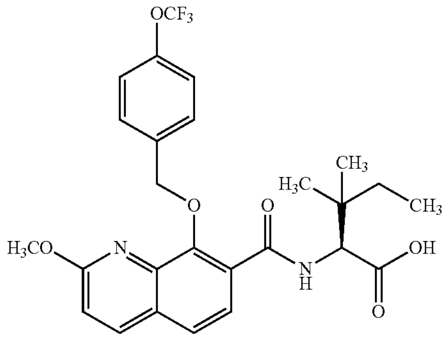 [SMILES: CCC(C)(C)[C@H](NC(=O)c1ccc2ccc(OC)nc2c1OCc1ccc(OC(F)(F)F)cc1)C(=O)O] | 443 |
| 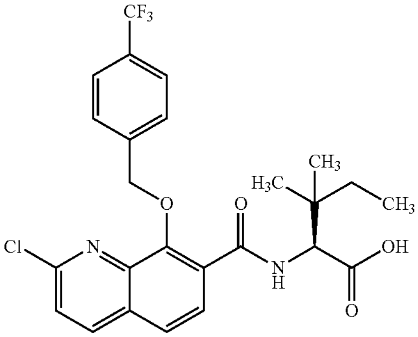 [SMILES: CCC(C)(C)[C@H](NC(=O)c1ccc2ccc(Cl)nc2c1OCc1ccc(C(F)(F)F)cc1)C(=O)O] | 444 |
| 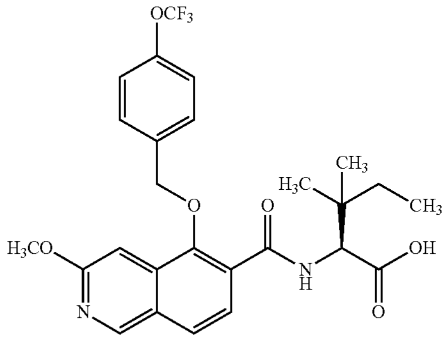 | 450 |

TABLE 5-continued
| Compound | # |
| --- | --- |
| 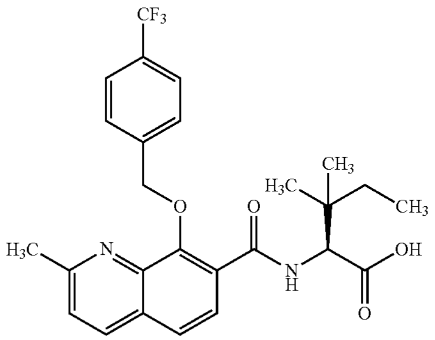 [SMILES: CCC(C)(C)[C@H](NC(=O)c1ccc2ccc(C)nc2c1OCc1ccc(C(F)(F)F)cc1)C(=O)O] | 451 |
| 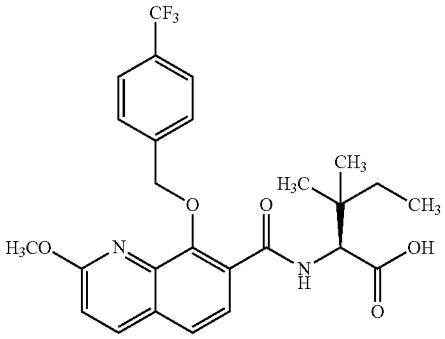 [SMILES: CCC(C)(C)[C@H](NC(=O)c1ccc2ccc(OC)nc2c1OCc1ccc(C(F)(F)F)cc1)C(=O)O] | 452 |
| 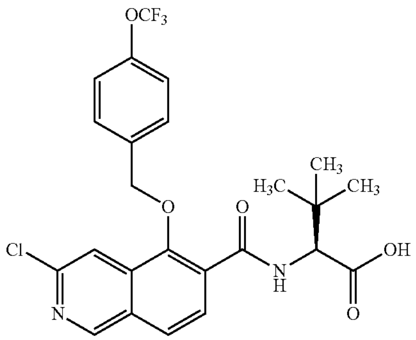 [SMILES: CC(C)(C)[C@H](NC(=O)c1ccc2cnc(Cl)cc2c1OCc1ccc(OC(F)(F)F)cc1)C(=O)O] | 453 |
| 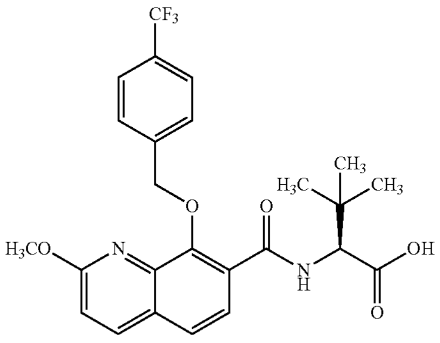 [SMILES: COc1ccc2ccc(C(=O)N[C@H](C(=O)O)C(C)(C)C)c(OCc3ccc(C(F)(F)F)cc3)c2n1] | 454 |
TABLE 5-continued
| Compound | # |
| --- | --- |
| 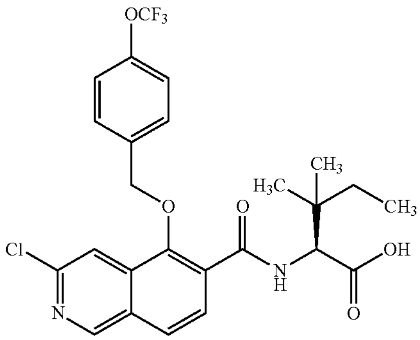 [SMILES: CCC(C)(C)[C@H](NC(=O)c1ccc2cnc(Cl)cc2c1OCc1ccc(OC(F)(F)F)cc1)C(=O)O] | 460 |
| 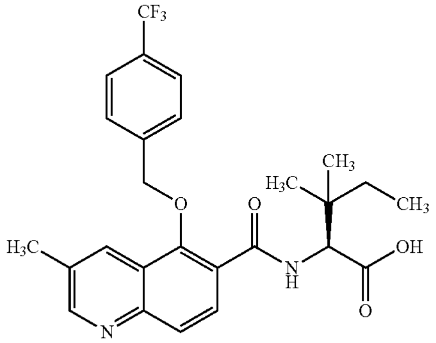 [SMILES: CCC(C)(C)[C@H](NC(=O)c1ccc2ncc(C)cc2c1OCc1ccc(C(F)(F)F)cc1)C(=O)O] | 461 |
| 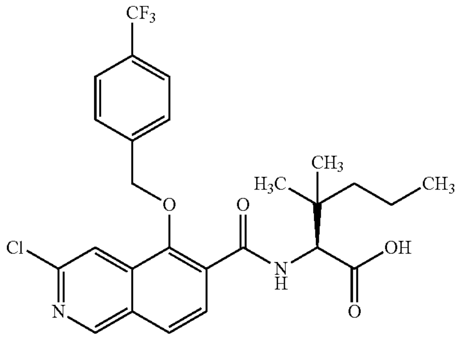 [SMILES: CCCC(C)(C)[C@H](NC(=O)c1ccc2cnc(Cl)cc2c1OCc1ccc(C(F)(F)F)cc1)C(=O)O] | 462 |
| 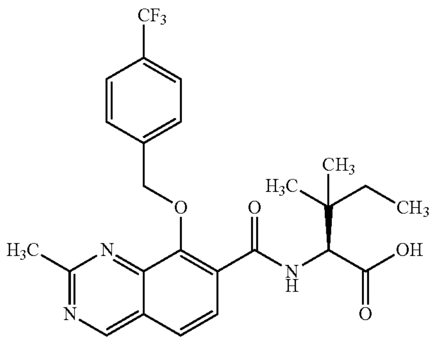 | 463 |

TABLE 5-continued
| Compound | # |
|---|---|
| 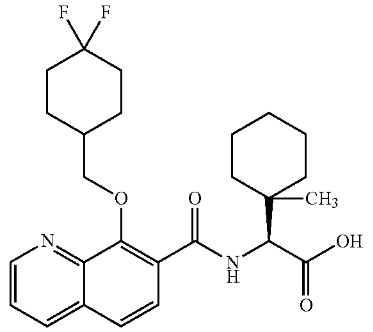 [SMILES: CC1([C@H](NC(=O)c2ccc3cccnc3c2OCC2CCC(F)(F)CC2)C(=O)O)CCCCC1] | 464 |
| 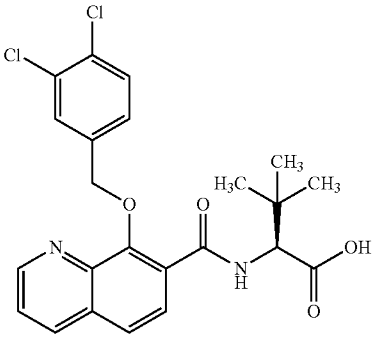 [SMILES: CC(C)(C)[C@H](NC(=O)c1ccc2cccnc2c1OCc1ccc(Cl)c(Cl)c1)C(=O)O] | 470 |
| 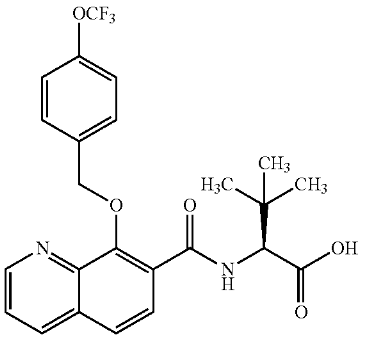 [SMILES: CC(C)(C)[C@H](NC(=O)c1ccc2cccnc2c1OCc1ccc(OC(F)(F)F)cc1)C(=O)O] | 421 |
| 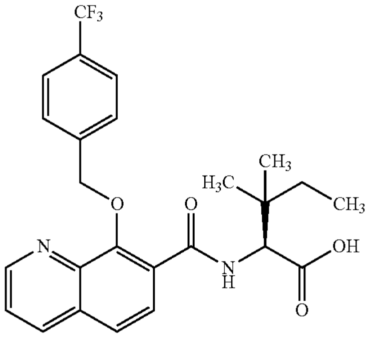 [SMILES: CCC(C)(C)[C@H](NC(=O)c1ccc2cccnc2c1OCc1ccc(C(F)(F)F)cc1)C(=O)O] | 472 |
TABLE 5-continued
| Compound | # |
|---|---|
| 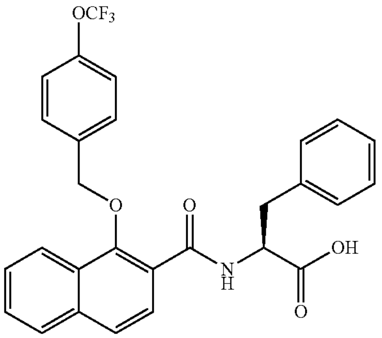 [SMILES: O=C(N[C@@H](Cc1ccccc1)C(=O)O)c1ccc2ccccc2c1OCc1ccc(OC(F)(F)F)cc1] | 90 |
| 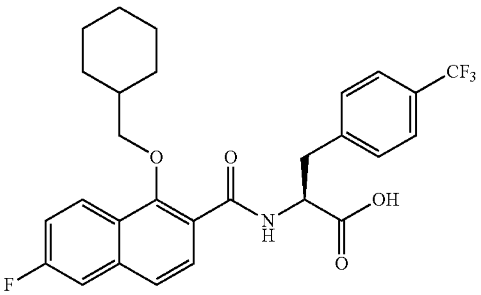 [SMILES: O=C(N[C@@H](Cc1ccc(C(F)(F)F)cc1)C(=O)O)c1ccc2cc(F)ccc2c1OCC1CCCCC1] | 204 |
| 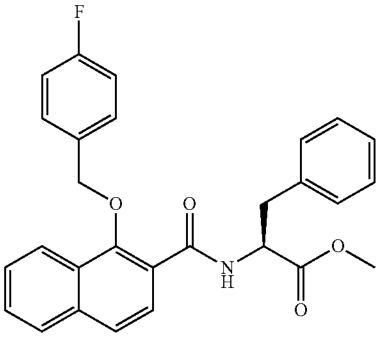 [SMILES: COC(=O)[C@H](Cc1ccccc1)NC(=O)c1ccc2ccccc2c1OCc1ccc(F)cc1] | 100 |
| 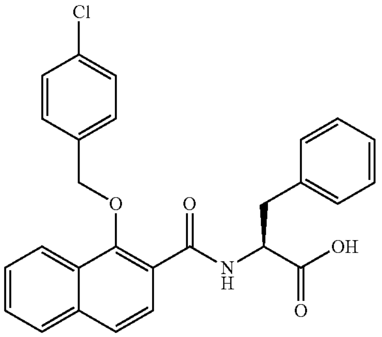 [SMILES: O=C(N[C@@H](Cc1ccccc1)C(=O)O)c1ccc2ccccc2c1OCc1ccc(Cl)cc1] | 98 |

TABLE 5-continued
| Compound | # |
|---|---|
| 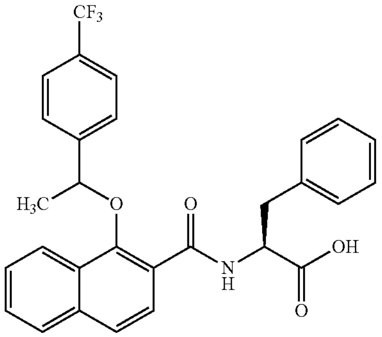 [SMILES: CC(Oc1c(C(=O)N[C@@H](Cc2ccccc2)C(=O)O)ccc2ccccc12)c1ccc(C(F)(F)F)cc1] | 124 |
| 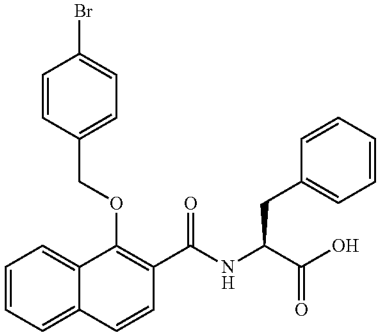 [SMILES: O=C(N[C@@H](Cc1ccccc1)C(=O)O)c1ccc2ccccc2c1OCc1ccc(Br)cc1] | 122 |
| 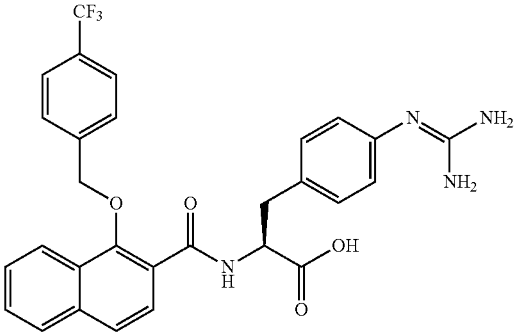 [SMILES: NC(N)=Nc1ccc(C[C@H](NC(=O)c2ccc3ccccc3c2OCc2ccc(C(F)(F)F)cc2)C(=O)O)cc1] | 105 |
| 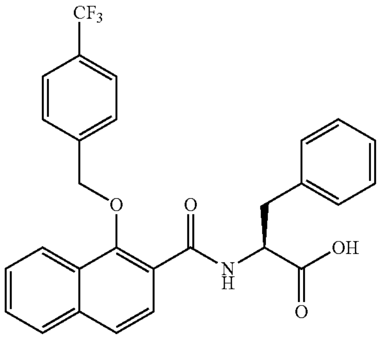 | 89 |
TABLE 5-continued
| Compound | # |
|---|---|
| 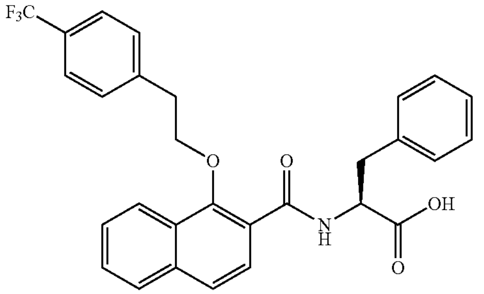 [SMILES: O=C(N[C@@H](Cc1ccccc1)C(=O)O)c1ccc2ccccc2c1OCCc1ccc(C(F)(F)F)cc1] | 97 |
| 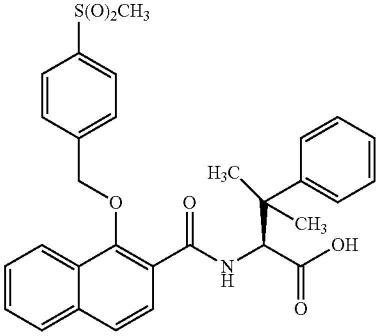 | 23 |
| 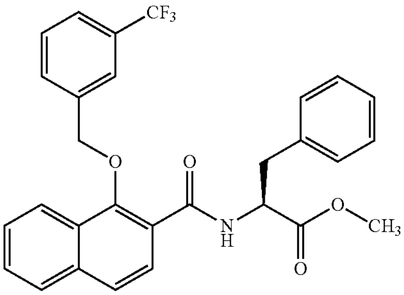 [SMILES: COC(=O)[C@H](Cc1ccccc1)NC(=O)c1ccc2ccccc2c1OCc1cccc(C(F)(F)F)c1] | 320 |
| 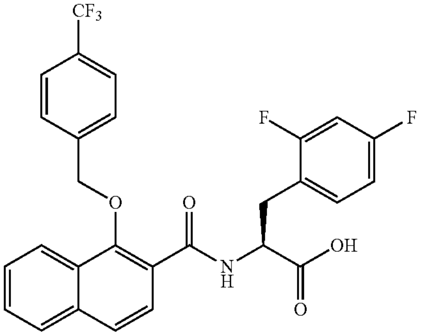 [SMILES: O=C(N[C@@H](Cc1ccc(F)cc1F)C(=O)O)c1ccc2ccccc2c1OCc1ccc(C(F)(F)F)cc1] | 321 |

TABLE 5-continued
| Compound | # |
|---|---|
| 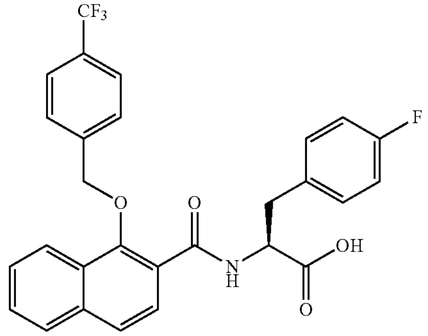 [SMILES: O=C(N[C@@H](Cc1ccc(F)cc1)C(=O)O)c1ccc2ccccc2c1OCc1ccc(C(F)(F)F)cc1] | 322 |
| 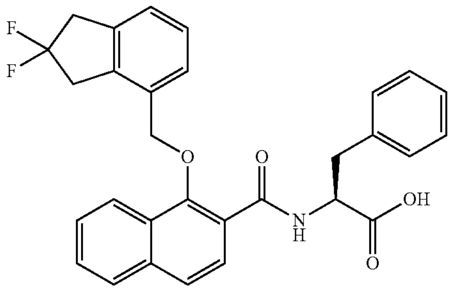 [SMILES: O=C(N[C@@H](Cc1ccccc1)C(=O)O)c1ccc2ccccc2c1OCc1cccc2c1CC(F)(F)C2] | 102 |
| 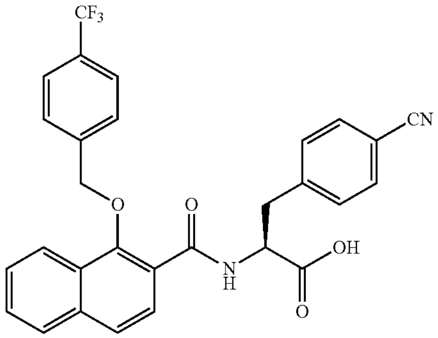 [SMILES: N#Cc1ccc(C[C@H](NC(=O)c2ccc3ccccc3c2OCc2ccc(C(F)(F)F)cc2)C(=O)O)cc1] | 107 |
| 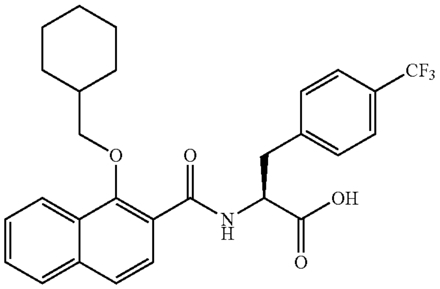 [SMILES: O=C(N[C@@H](Cc1ccc(C(F)(F)F)cc1)C(=O)O)c1ccc2ccccc2c1OCC1CCCCC1] | 200 |
| 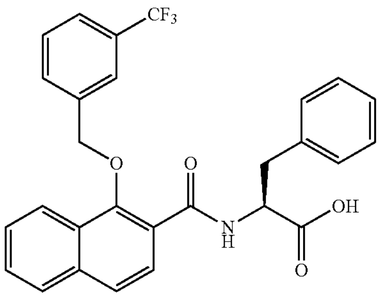 [SMILES: O=C(N[C@@H](Cc1ccccc1)C(=O)O)c1ccc2ccccc2c1OCc1cccc(C(F)(F)F)c1] | 95 |
TABLE 5-continued
| Compound | # |
|---|---|
| 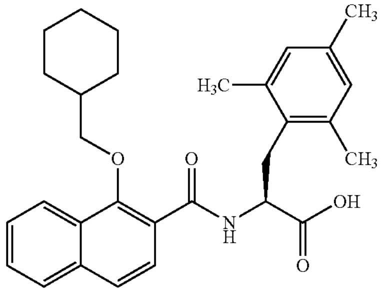 [SMILES: Cc1cc(C)c(C[C@H](NC(=O)c2ccc3ccccc3c2OCC2CCCCC2)C(=O)O)c(C)c1] | 326 |
| 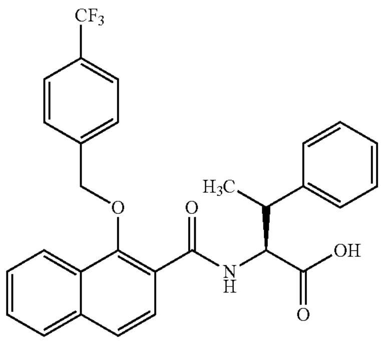 [SMILES: CC(c1ccccc1)[C@H](NC(=O)c1ccc2ccccc2c1OCc1ccc(C(F)(F)F)cc1)C(=O)O] | 127 |
| 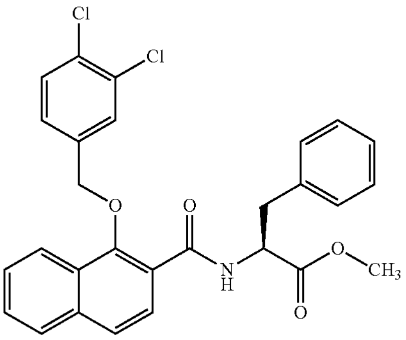 [SMILES: COC(=O)[C@H](Cc1ccccc1)NC(=O)c1ccc2ccccc2c1OCc1ccc(Cl)c(Cl)c1] | 101 |
| 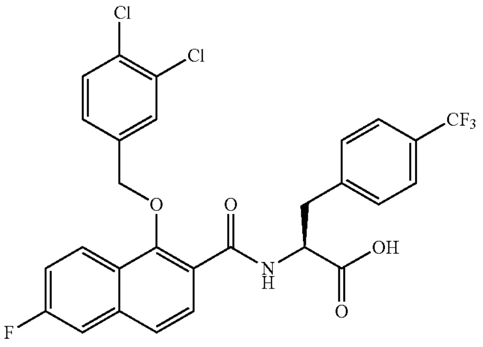 [SMILES: O=C(N[C@@H](Cc1ccc(C(F)(F)F)cc1)C(=O)O)c1ccc2cc(F)ccc2c1OCc1ccc(Cl)c(Cl)c1] | 210 |

TABLE 5-continued
| Compound | # |
| --- | --- |
| 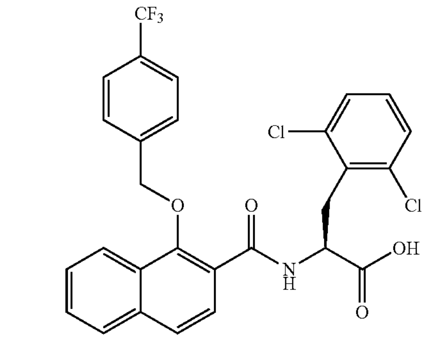 [SMILES: O=C(N[C@@H](Cc1c(Cl)cccc1Cl)C(=O)O)c1ccc2ccccc2c1OCc1ccc(C(F)(F)F)cc1] | 152 |
| 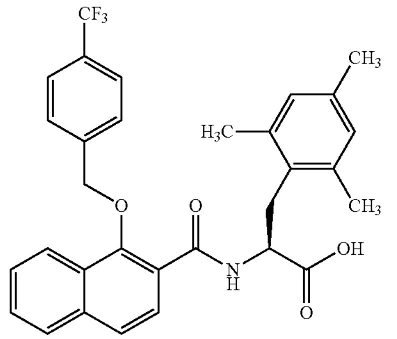 [SMILES: Cc1cc(C)c(C[C@H](NC(=O)c2ccc3ccccc3c2OCc2ccc(C(F)(F)F)cc2)C(=O)O)c(C)c1] | 178 |
| 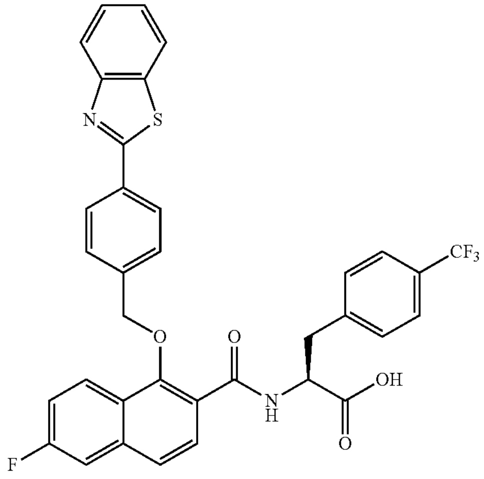 [SMILES: O=C(N[C@@H](Cc1ccc(C(F)(F)F)cc1)C(=O)O)c1ccc2cc(F)ccc2c1OCc1ccc(-c2nc3ccccc3s2)cc1] | 217 |
| 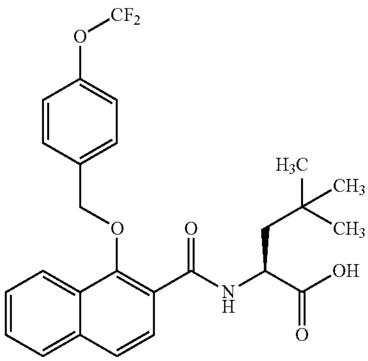 | 108 |
TABLE 5-continued
| Compound | # |
| --- | --- |
| 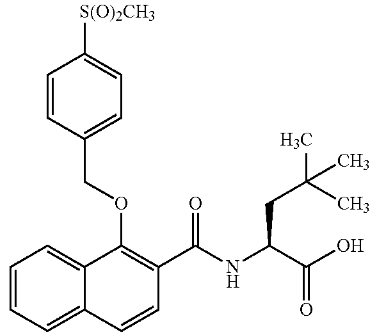 | 158 |
| 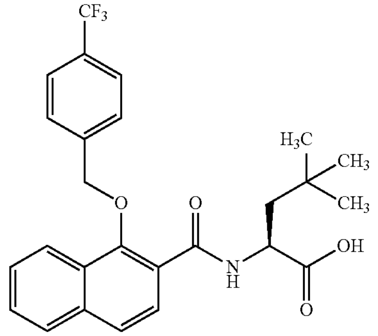 [SMILES: CC(C)(C)C[C@H](NC(=O)c1ccc2ccccc2c1OCc1ccc(C(F)(F)F)cc1)C(=O)O] | 186 |
| 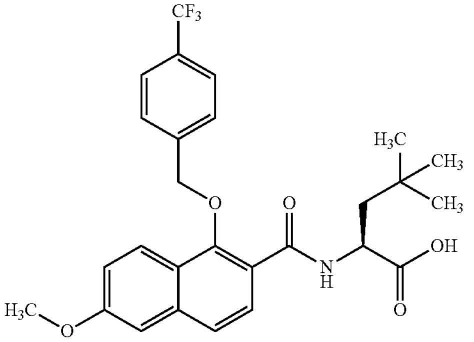 [SMILES: COc1ccc2c(OCc3ccc(C(F)(F)F)cc3)c(C(=O)N[C@@H](CC(C)(C)C)C(=O)O)ccc2c1] | 161 |
| 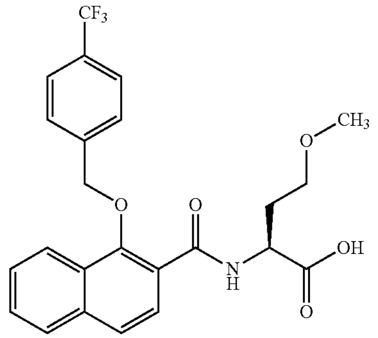 [SMILES: COCC[C@H](NC(=O)c1ccc2ccccc2c1OCc1ccc(C(F)(F)F)cc1)C(=O)O] | 137 |

TABLE 5-continued
| Compound | # |
|---|---|
| 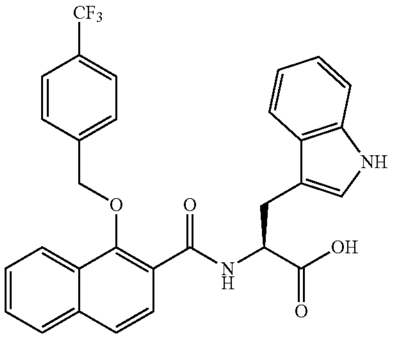 [SMILES: O=C(N[C@@H](Cc1c[nH]c2ccccc12)C(=O)O)c1ccc2ccccc2c1OCc1ccc(C(F)(F)F)cc1] | 329 |
| 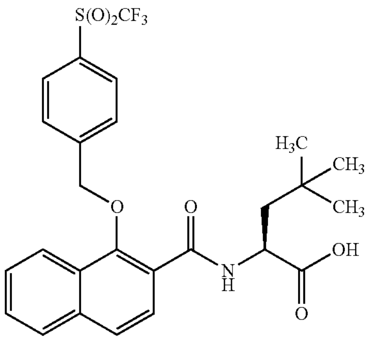 | 157 |
| 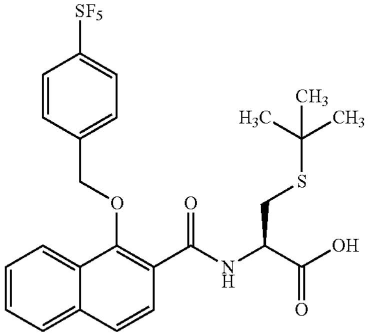 | 330 |
| 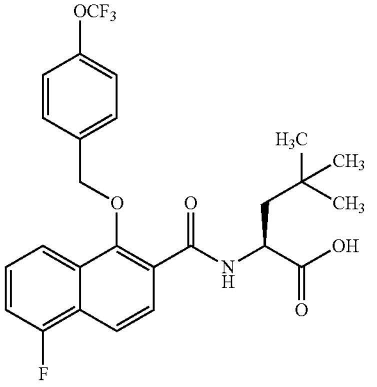 [SMILES: CC(C)(C)C[C@H](NC(=O)c1ccc2c(F)cccc2c1OCc1ccc(OC(F)(F)F)cc1)C(=O)O] | 331 |
TABLE 5-continued
| Compound | # |
|---|---|
| 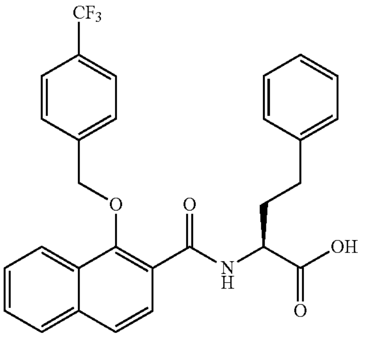 [SMILES: O=C(N[C@@H](CCc1ccccc1)C(=O)O)c1ccc2ccccc2c1OCc1ccc(C(F)(F)F)cc1] | 85 |
| 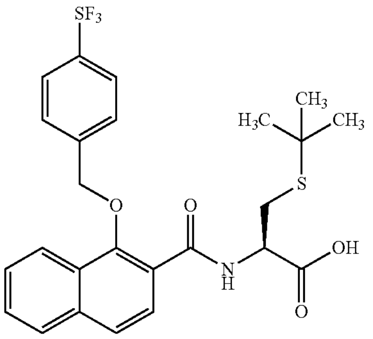 | 334 |
| 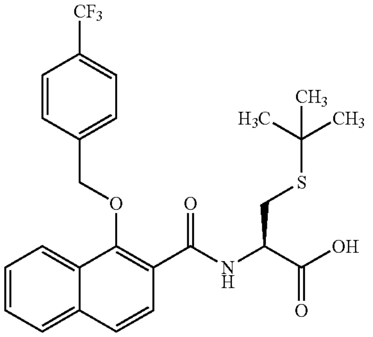 [SMILES: CC(C)(C)SC[C@H](NC(=O)c1ccc2ccccc2c1OCc1ccc(C(F)(F)F)cc1)C(=O)O] | 335 |
| 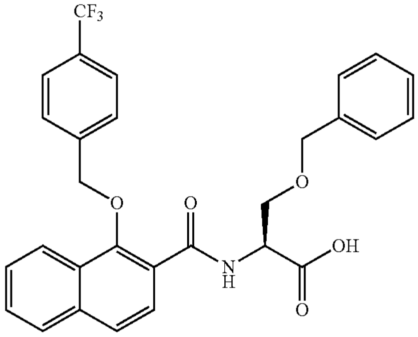 [SMILES: O=C(N[C@@H](COCc1ccccc1)C(=O)O)c1ccc2ccccc2c1OCc1ccc(C(F)(F)F)cc1] | 336 |

TABLE 5-continued
| Compound | # |
| --- | --- |
| 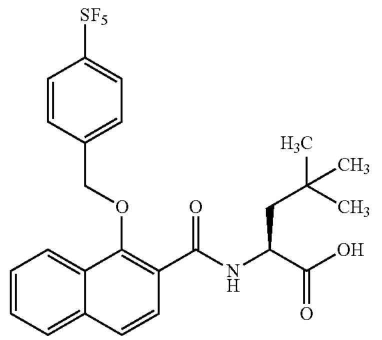 | 110 |
| 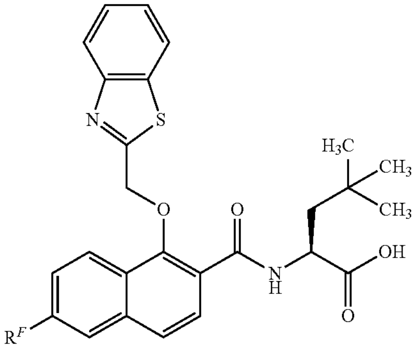 | 218 |
| 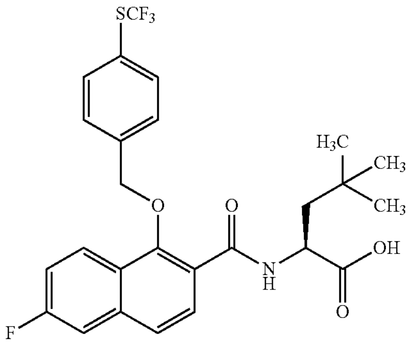 | 117 |
| 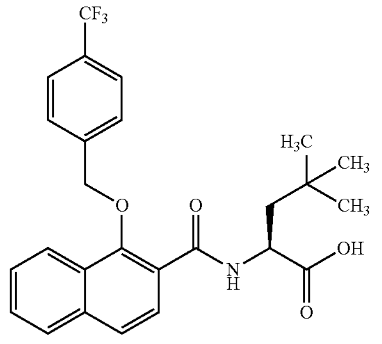 | 141 |
TABLE 5-continued
| Compound | # |
| --- | --- |
| 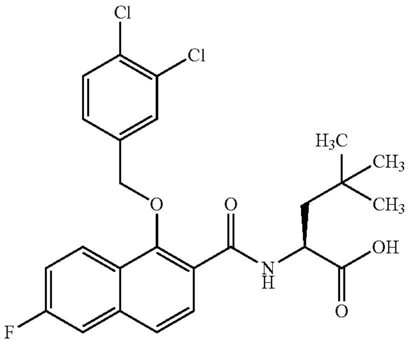 [SMILES: CC(C)(C)C[C@H](NC(=O)c1ccc2cc(F)ccc2c1OCc1ccc(Cl)c(Cl)c1)C(=O)O] | 211 |
| 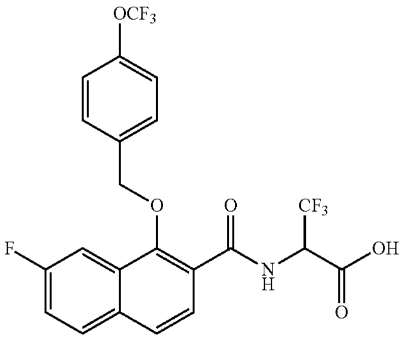 [SMILES: O=C(NC(C(=O)O)C(F)(F)F)c1ccc2ccc(F)cc2c1OCc1ccc(OC(F)(F)F)cc1] | 340 |
| 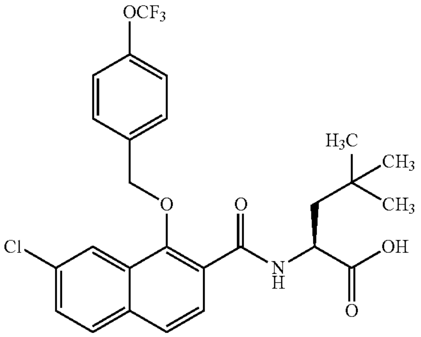 [SMILES: CC(C)(C)C[C@H](NC(=O)c1ccc2ccc(Cl)cc2c1OCc1ccc(OC(F)(F)F)cc1)C(=O)O] | 346 |
| 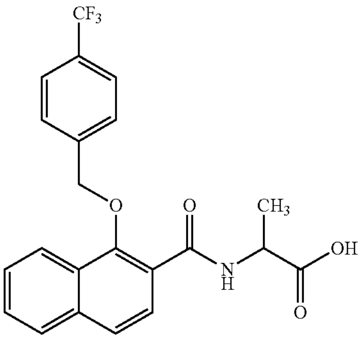 [SMILES: CC(NC(=O)c1ccc2ccccc2c1OCc1ccc(C(F)(F)F)cc1)C(=O)O] | 347 |

TABLE 5-continued
| Compound | # |
|---|---|
| 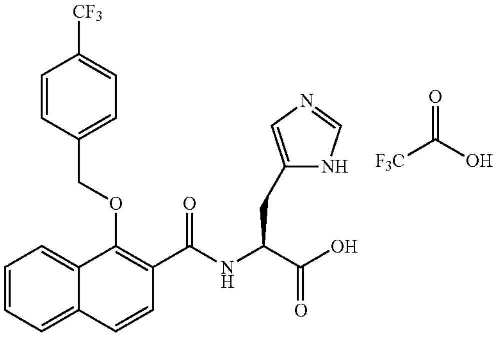 [SMILES: O=C(N[C@@H](Cc1cnc[nH]1)C(=O)O)c1ccc2ccccc2c1OCc1ccc(C(F)(F)F)cc1 ; O=C(O)C(F)(F)F] | 348 |
| 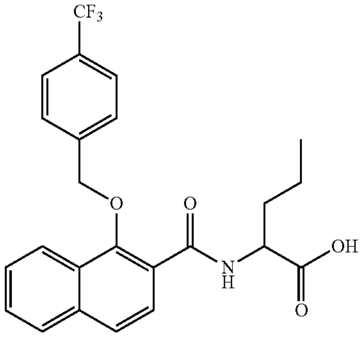 [SMILES: CCCC(NC(=O)c1ccc2ccccc2c1OCc1ccc(C(F)(F)F)cc1)C(=O)O] | 349 |
| 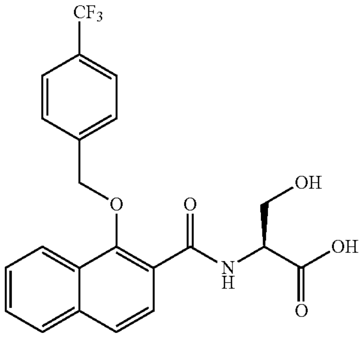 [SMILES: O=C(N[C@@H](CO)C(=O)O)c1ccc2ccccc2c1OCc1ccc(C(F)(F)F)cc1] | 350 |
| 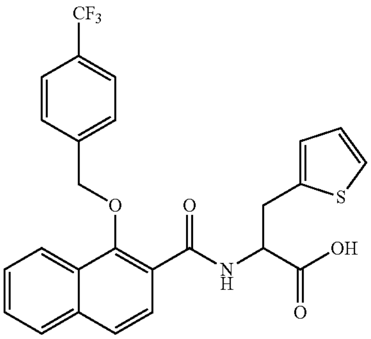 [SMILES: O=C(NC(Cc1cccs1)C(=O)O)c1ccc2ccccc2c1OCc1ccc(C(F)(F)F)cc1] | 354 |
TABLE 5-continued
| Compound | # |
|---|---|
| 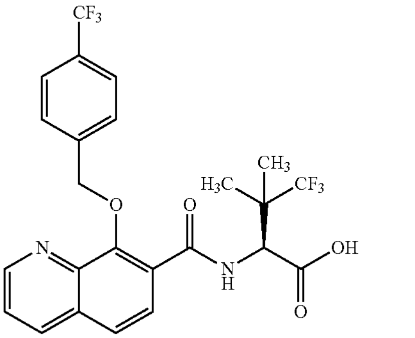 [SMILES: CC(C)([C@H](NC(=O)c1ccc2cccnc2c1OCc1ccc(C(F)(F)F)cc1)C(=O)O)C(F)(F)F] | 355 |
| 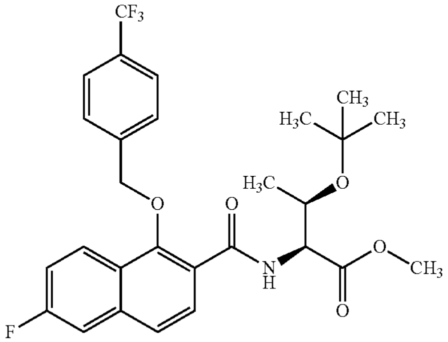 [SMILES: COC(=O)[C@@H](NC(=O)c1ccc2cc(F)ccc2c1OCc1ccc(C(F)(F)F)cc1)[C@@H](C)OC(C)(C)C] | 356 |
| 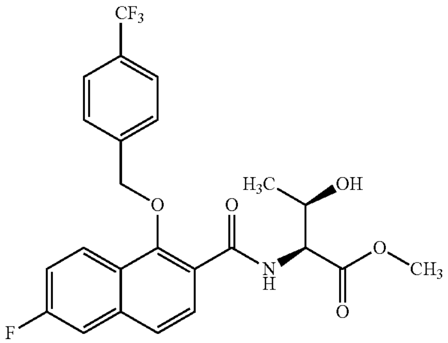 [SMILES: COC(=O)[C@@H](NC(=O)c1ccc2cc(F)ccc2c1OCc1ccc(C(F)(F)F)cc1)[C@@H](C)O] | 357 |
| 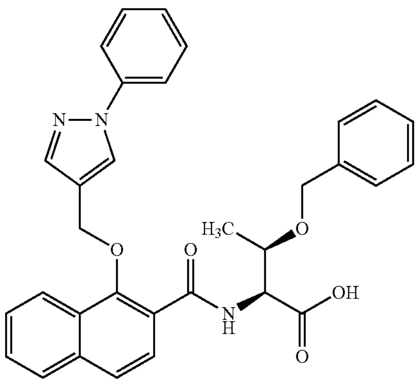 [SMILES: C[C@@H](OCc1ccccc1)[C@H](NC(=O)c1ccc2ccccc2c1OCc1cnn(-c2ccccc2)c1)C(=O)O] | 149 |

TABLE 5-continued
| Compound | # |
|---|---|
| 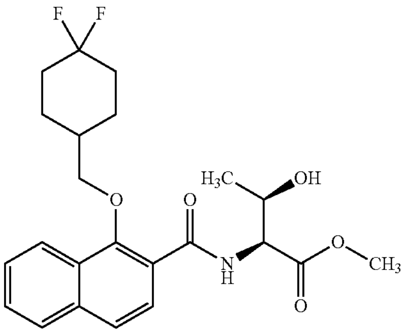 [SMILES: COC(=O)[C@@H](NC(=O)c1ccc2ccccc2c1OCC1CCC(F)(F)CC1)[C@@H](C)O] | 361 |
| 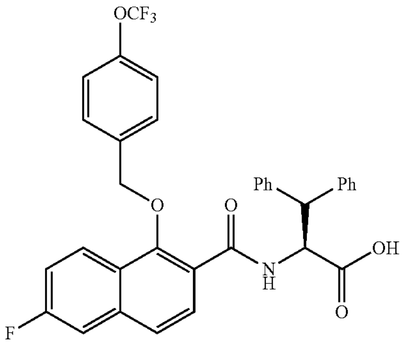 [SMILES: O=C(N[C@H](C(=O)O)C(c1ccccc1)c1ccccc1)c1ccc2cc(F)ccc2c1OCc1ccc(OC(F)(F)F)cc1] | 193 |
| 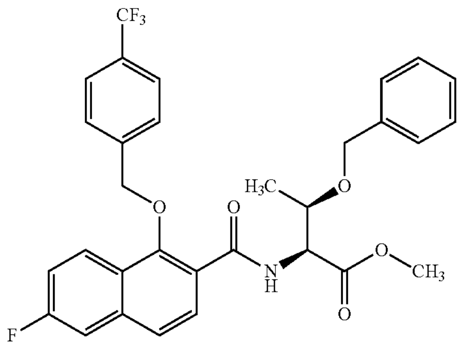 [SMILES: COC(=O)[C@@H](NC(=O)c1ccc2cc(F)ccc2c1OCc1ccc(C(F)(F)F)cc1)[C@@H](C)OCc1ccccc1] | 195 |
| 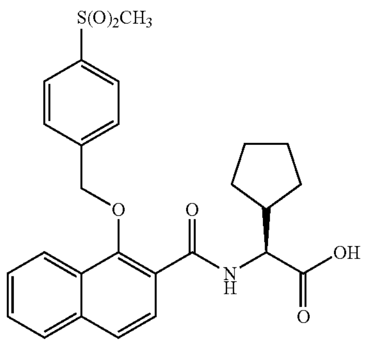 | 159 |
TABLE 5-continued
| Compound | # |
|---|---|
| 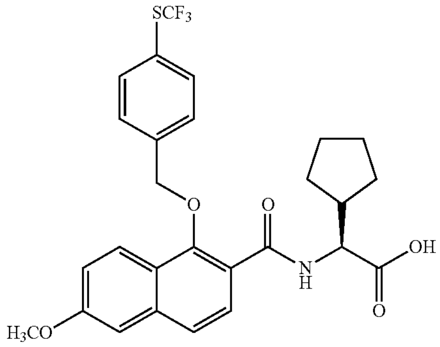 | 162 |
| 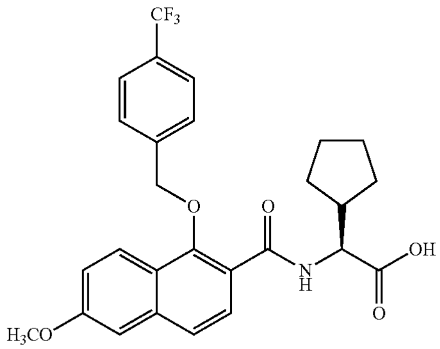 [SMILES: COc1ccc2c(OCc3ccc(C(F)(F)F)cc3)c(C(=O)N[C@H](C(=O)O)C3CCCC3)ccc2c1] | 160 |
| 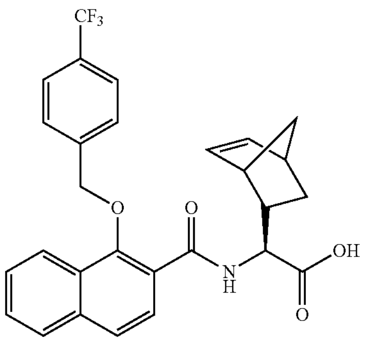 [SMILES: O=C(N[C@H](C(=O)O)C1CC2C=CC1C2)c1ccc2ccccc2c1OCc1ccc(C(F)(F)F)cc1] | 362 |
| 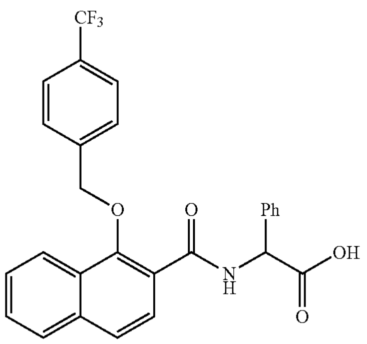 [SMILES: O=C(NC(C(=O)O)c1ccccc1)c1ccc2ccccc2c1OCc1ccc(C(F)(F)F)cc1] | 363 |

TABLE 5-continued
| Compound | # |
| --- | --- |
| 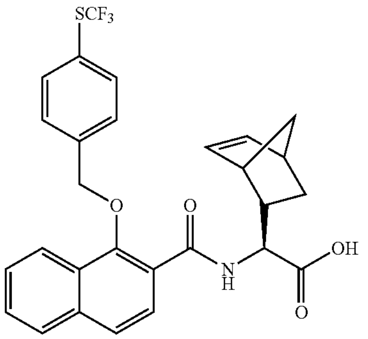 | 364 |
| 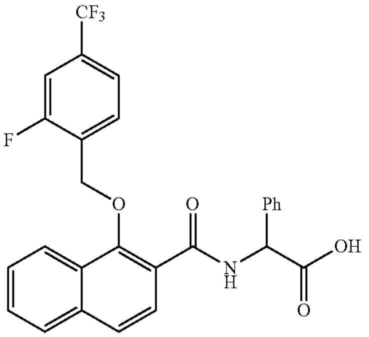 [SMILES: O=C(NC(C(=O)O)c1ccccc1)c1ccc2ccccc2c1OCc1ccc(C(F)(F)F)cc1F] | 365 |
| 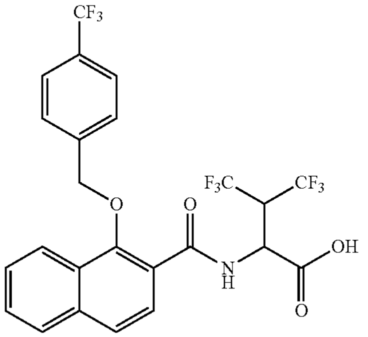 [SMILES: O=C(NC(C(=O)O)C(C(F)(F)F)C(F)(F)F)c1ccc2ccccc2c1OCc1ccc(C(F)(F)F)cc1] | 181 |
| 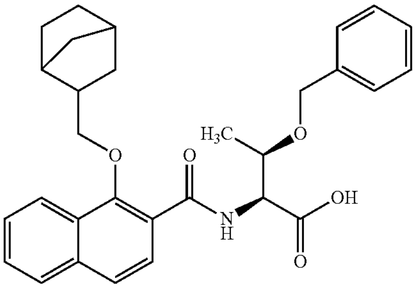 [SMILES: C[C@@H](OCc1ccccc1)[C@H](NC(=O)c1ccc2ccccc2c1OCC1CC2CCC1C2)C(=O)O] | 147 |
TABLE 5-continued
| Compound | # |
| --- | --- |
| 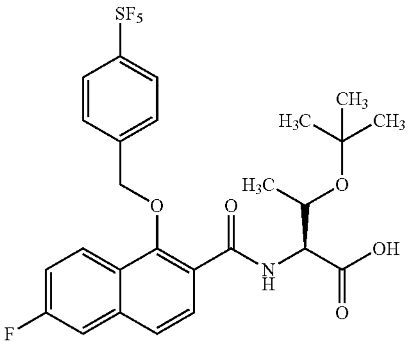 | 367 |
| 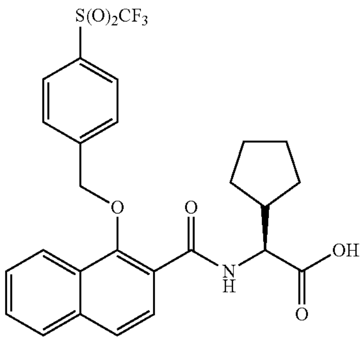 | 156 |
| 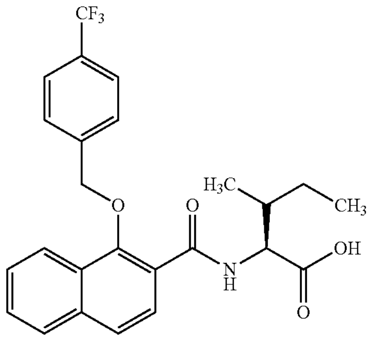 [SMILES: CCC(C)[C@H](NC(=O)c1ccc2ccccc2c1OCc1ccc(C(F)(F)F)cc1)C(=O)O] | 368 |
| 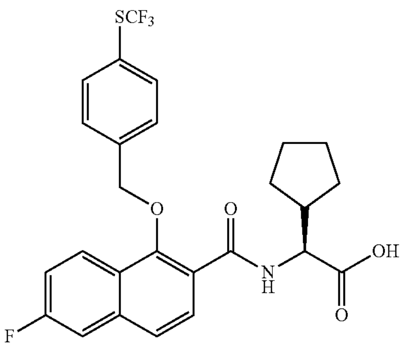 | 116 |

TABLE 5-continued
| Compound | # |
|---|---|
| 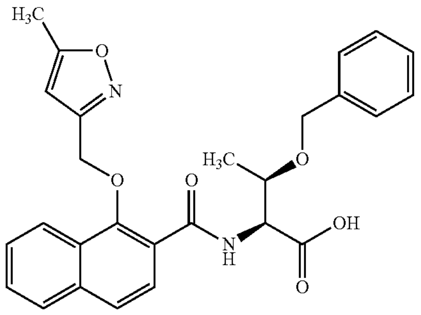 [SMILES: Cc1cc(COc2c(C(=O)N[C@H](C(=O)O)[C@@H](C)OCc3ccccc3)ccc3ccccc23)no1] | 145 |
| 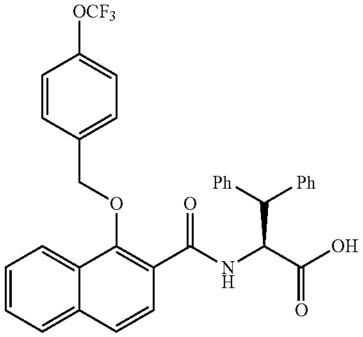 [SMILES: O=C(N[C@H](C(=O)O)C(c1ccccc1)c1ccccc1)c1ccc2ccccc2c1OCc1ccc(OC(F)(F)F)cc1] | 189 |
| 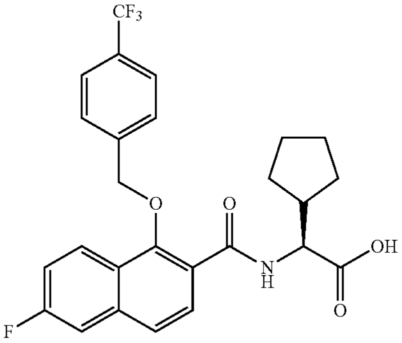 [SMILES: O=C(N[C@H](C(=O)O)C1CCCC1)c1ccc2cc(F)ccc2c1OCc1ccc(C(F)(F)F)cc1] | 153 |
| 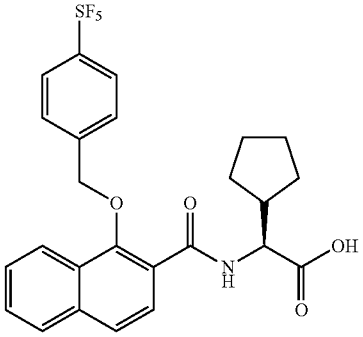 | 111 |
TABLE 5-continued
| Compound | # |
|---|---|
| 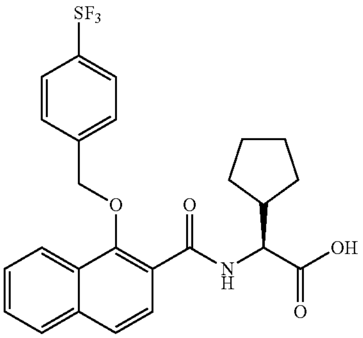 | 114 |
| 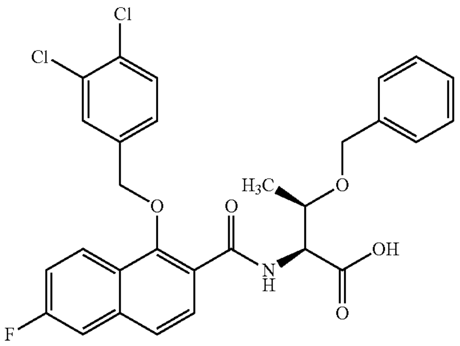 [SMILES: C[C@@H](OCc1ccccc1)[C@H](NC(=O)c1ccc2cc(F)ccc2c1OCc1ccc(Cl)c(Cl)c1)C(=O)O] | 208 |
| 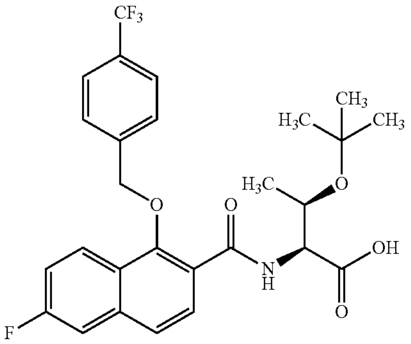 [SMILES: C[C@@H](OC(C)(C)C)[C@H](NC(=O)c1ccc2cc(F)ccc2c1OCc1ccc(C(F)(F)F)cc1)C(=O)O] | 373 |
| 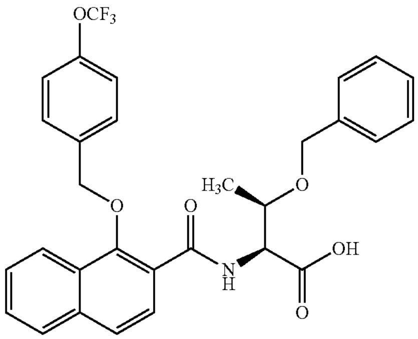 [SMILES: C[C@@H](OCc1ccccc1)[C@H](NC(=O)c1ccc2ccccc2c1OCc1ccc(OC(F)(F)F)cc1)C(=O)O] | 188 |

TABLE 5-continued
| Compound | # |
| --- | --- |
| 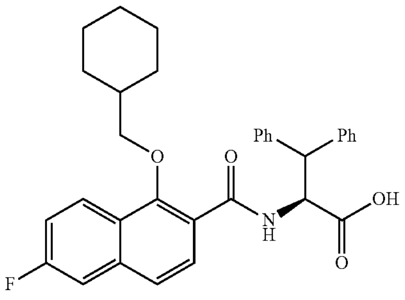 [SMILES: O=C(N[C@H](C(=O)O)C(c1ccccc1)c1ccccc1)c1ccc2cc(F)ccc2c1OCC1CCCCC1] | 203 |
| 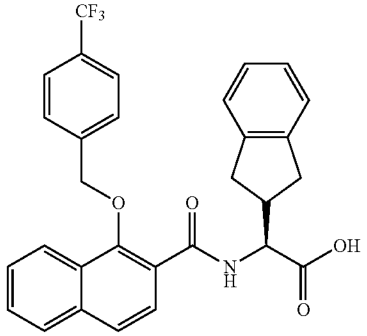 [SMILES: O=C(N[C@H](C(=O)O)C1Cc2ccccc2C1)c1ccc2ccccc2c1OCc1ccc(C(F)(F)F)cc1] | 143 |
| 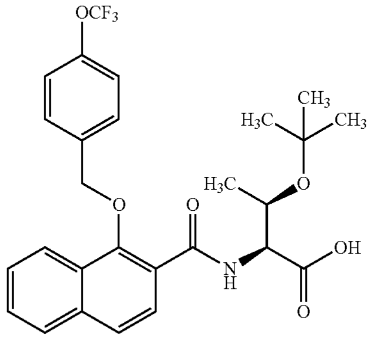 [SMILES: C[C@@H](OC(C)(C)C)[C@H](NC(=O)c1ccc2ccccc2c1OCc1ccc(OC(F)(F)F)cc1)C(=O)O] | 374 |
| 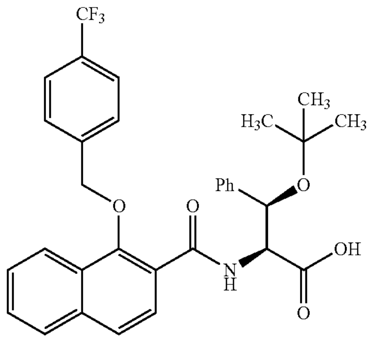 [SMILES: CC(C)(C)O[C@H](c1ccccc1)[C@H](NC(=O)c1ccc2ccccc2c1OCc1ccc(C(F)(F)F)cc1)C(=O)O] | 133 |
TABLE 5-continued
| Compound | # |
| --- | --- |
| 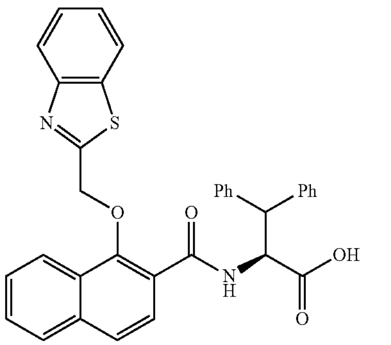 [SMILES: O=C(N[C@H](C(=O)O)C(c1ccccc1)c1ccccc1)c1ccc2ccccc2c1OCc1nc2ccccc2s1] | 212 |
| 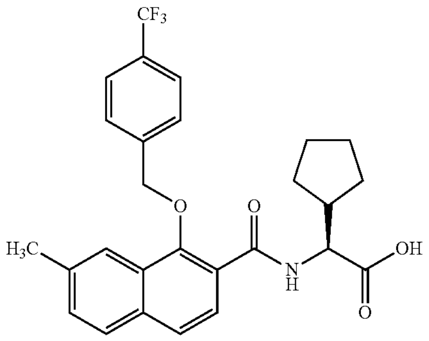 | 375 |
| 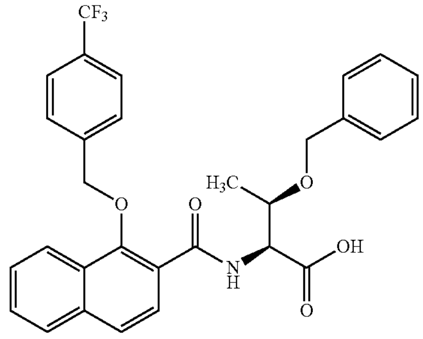 [SMILES: C[C@@H](OCc1ccccc1)[C@H](NC(=O)c1ccc2ccccc2c1OCc1ccc(C(F)(F)F)cc1)C(=O)O] | 144 |
| 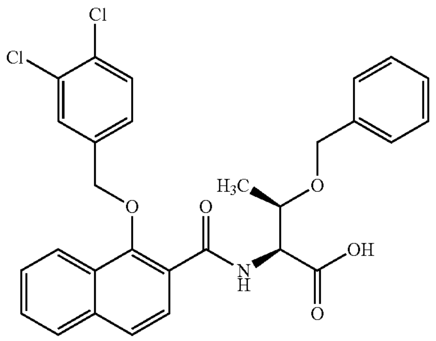 [SMILES: C[C@@H](OCc1ccccc1)[C@H](NC(=O)c1ccc2ccccc2c1OCc1ccc(Cl)c(Cl)c1)C(=O)O] | 206 |

TABLE 5-continued
| Compound | # |
|---|---|
| 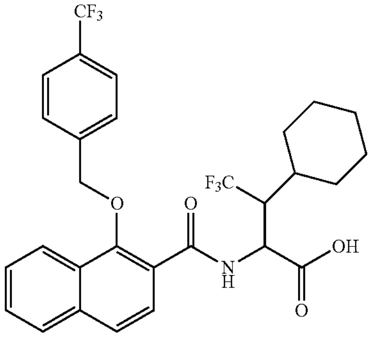 [SMILES: O=C(NC(C(=O)O)C(C1CCCCC1)C(F)(F)F)c1ccc2ccccc2c1OCc1ccc(C(F)(F)F)cc1] | 378 |
| 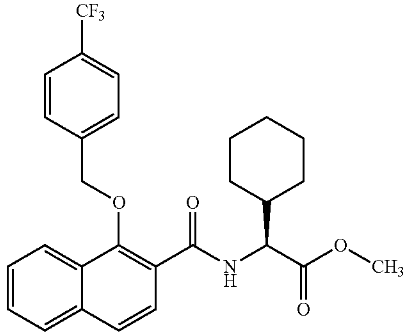 [SMILES: COC(=O)[C@@H](NC(=O)c1ccc2ccccc2c1OCc1ccc(C(F)(F)F)cc1)C1CCCCC1] | 379 |
| 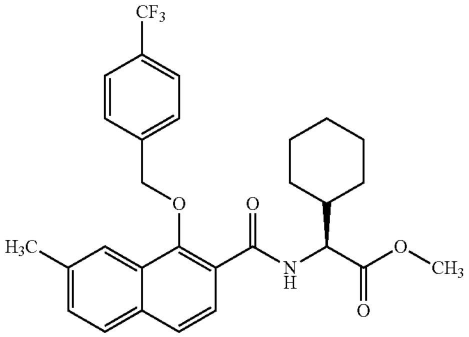 | 380 |
| 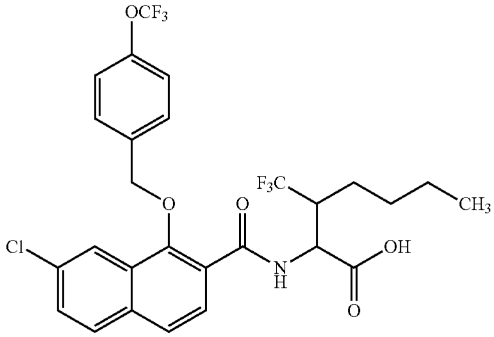 [SMILES: CCCCC(C(NC(=O)c1ccc2ccc(Cl)cc2c1OCc1ccc(OC(F)(F)F)cc1)C(=O)O)C(F)(F)F] | 386 |
TABLE 5-continued
| Compound | # |
|---|---|
| 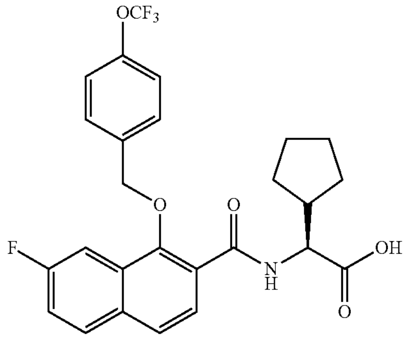 [SMILES: O=C(N[C@H](C(=O)O)C1CCCC1)c1ccc2ccc(F)cc2c1OCc1ccc(OC(F)(F)F)cc1] | 387 |
| 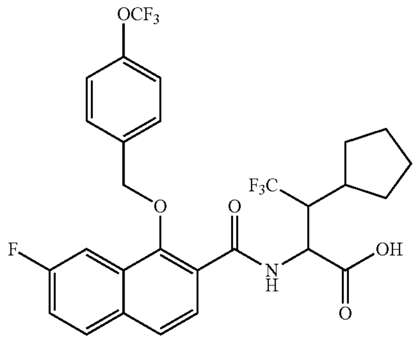 [SMILES: O=C(NC(C(=O)O)C(C1CCCC1)C(F)(F)F)c1ccc2ccc(F)cc2c1OCc1ccc(OC(F)(F)F)cc1] | 388 |
| 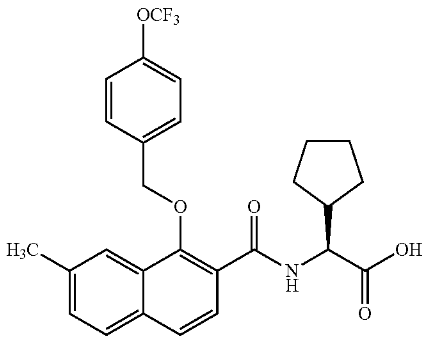 [SMILES: Cc1ccc2ccc(C(=O)N[C@H](C(=O)O)C3CCCC3)c(OCc3ccc(OC(F)(F)F)cc3)c2c1] | 389 |
| 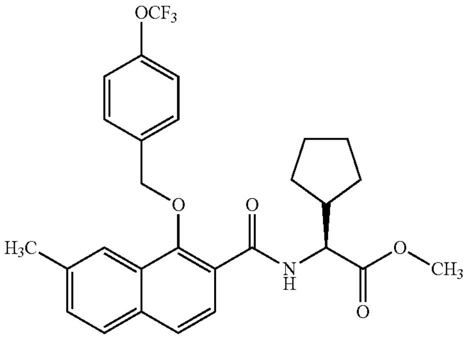 | 390 |

TABLE 5-continued
| Compound | # |
| --- | --- |
| 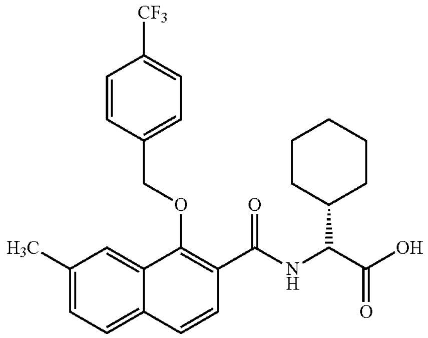 | 396 |
| 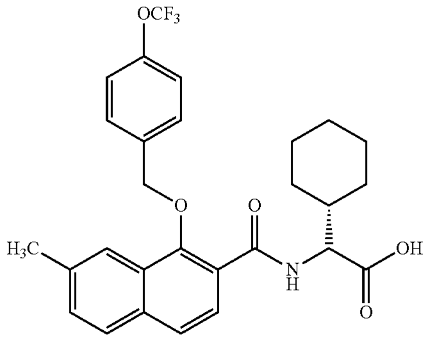 | 397 |
| 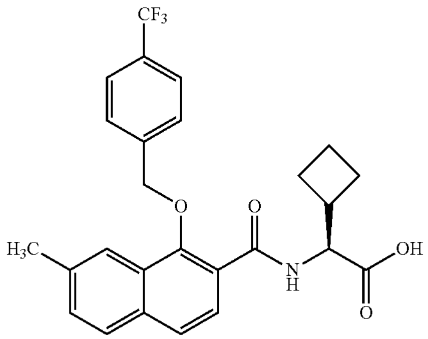 [SMILES: Cc1ccc2ccc(C(=O)N[C@H](C(=O)O)C3CCC3)c(OCc3ccc(C(F)(F)F)cc3)c2c1] | 398 |
| 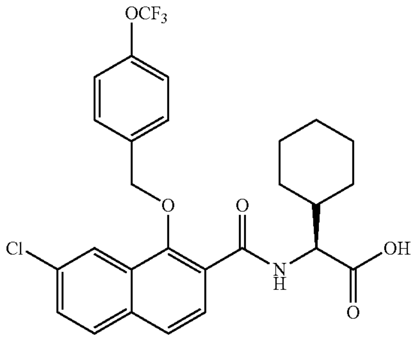 [SMILES: O=C(N[C@H](C(=O)O)C1CCCCC1)c1ccc2ccc(Cl)cc2c1OCc1ccc(OC(F)(F)F)cc1] | 399 |
TABLE 5-continued
| Compound | # |
| --- | --- |
| 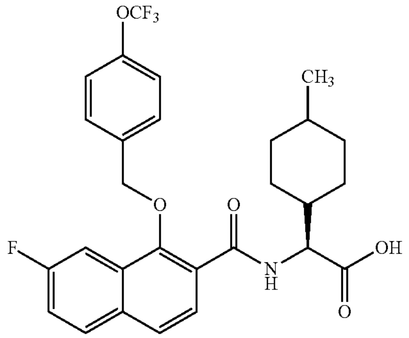 [SMILES: CC1CCC([C@H](NC(=O)c2ccc3ccc(F)cc3c2OCc2ccc(OC(F)(F)F)cc2)C(=O)O)CC1] | 400 |
| 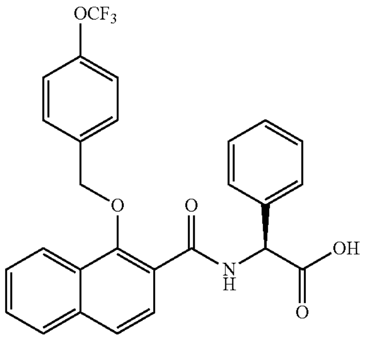 [SMILES: O=C(N[C@H](C(=O)O)c1ccccc1)c1ccc2ccccc2c1OCc1ccc(OC(F)(F)F)cc1] | 405 |
| 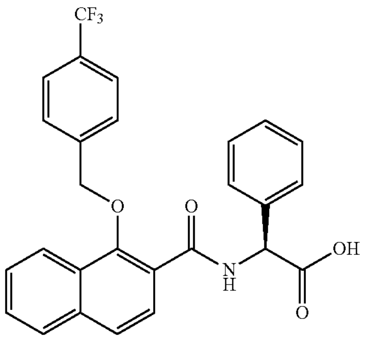 [SMILES: O=C(N[C@H](C(=O)O)c1ccccc1)c1ccc2ccccc2c1OCc1ccc(C(F)(F)F)cc1] | 140 |
| 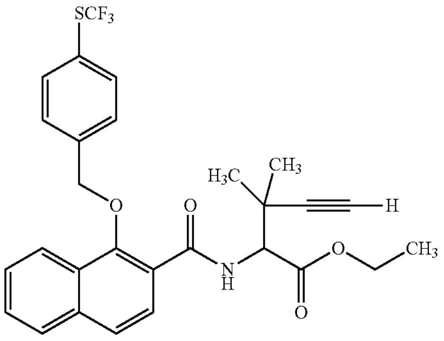 | 406 |

TABLE 5-continued
| Compound | # |
|---|---|
| 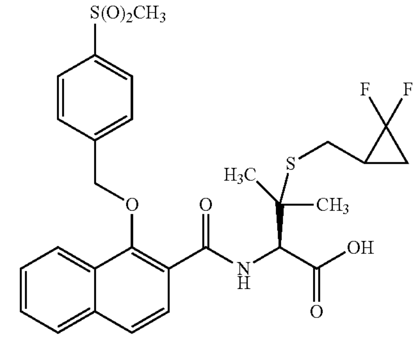 | 166 |
| 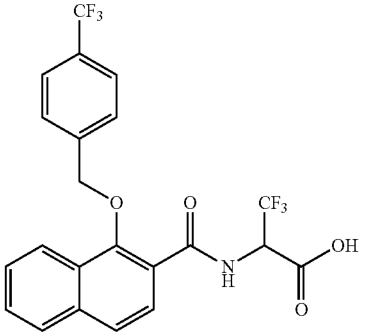 | 407 |
| 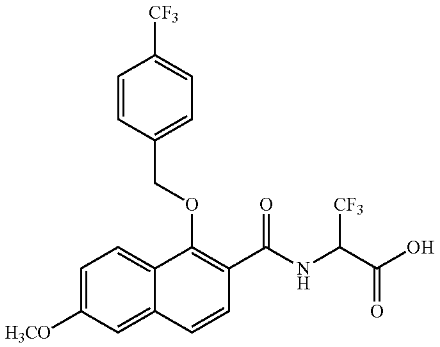 [SMILES: COc1ccc2c(OCc3ccc(C(F)(F)F)cc3)c(C(=O)NC(C(=O)O)C(F)(F)F)ccc2c1] | 411 |
| 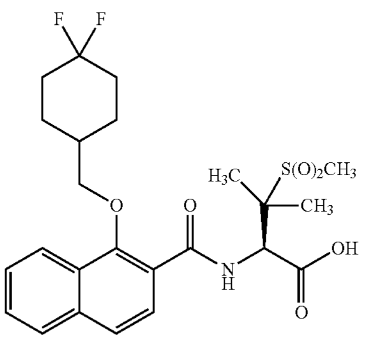 | 412 |
TABLE 5-continued
| Compound | # |
|---|---|
| 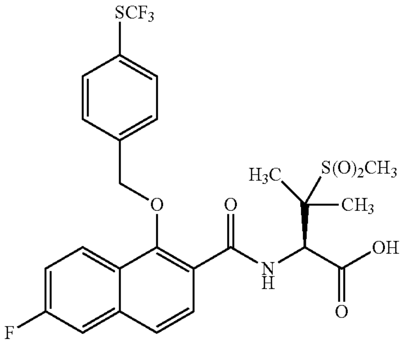 | 413 |
| 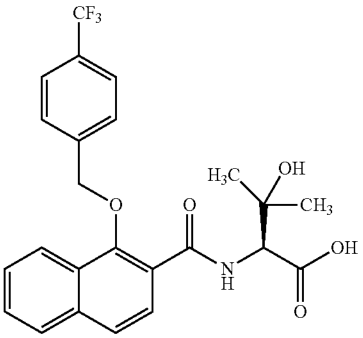 [SMILES: CC(C)(O)[C@H](NC(=O)c1ccc2ccccc2c1OCc1ccc(C(F)(F)F)cc1)C(=O)O] | 138 |
| 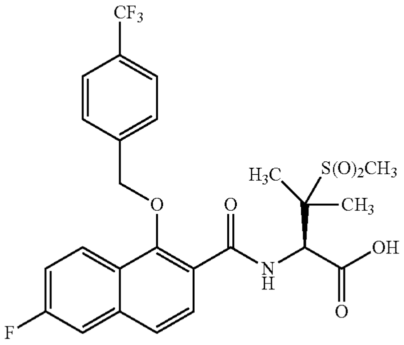 | 414 |
| 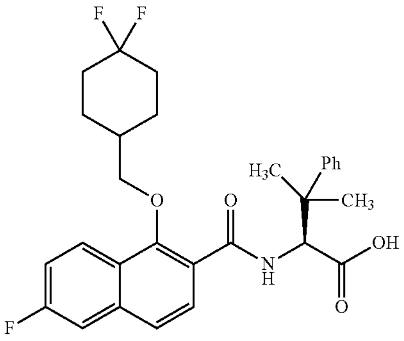 [SMILES: CC(C)(c1ccccc1)[C@H](NC(=O)c1ccc2cc(F)ccc2c1OCC1CCC(F)(F)CC1)C(=O)O] | 7 |

TABLE 5-continued
| Compound | # |
|---|---|
| 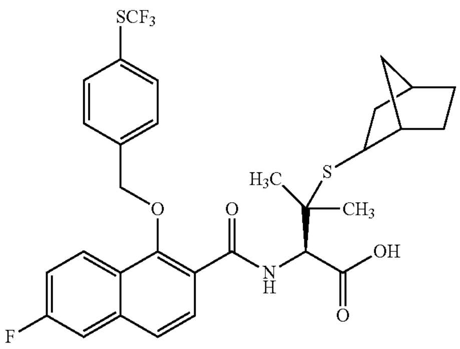 | 177 |
| 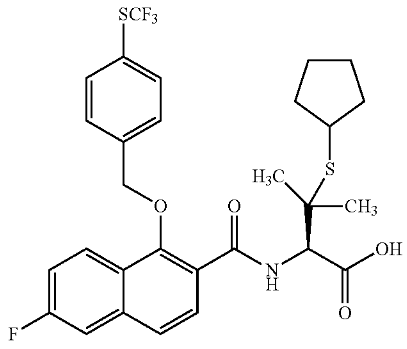 | 172 |
| 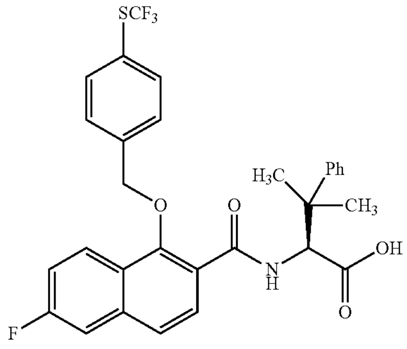 | 22 |
| 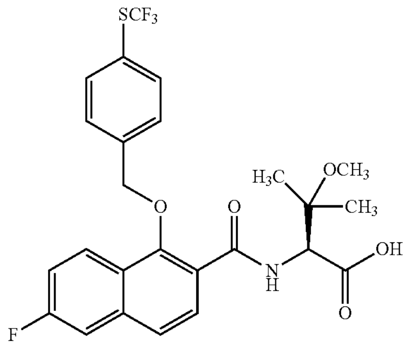 | 118 |
TABLE 5-continued
| Compound | # |
|---|---|
| 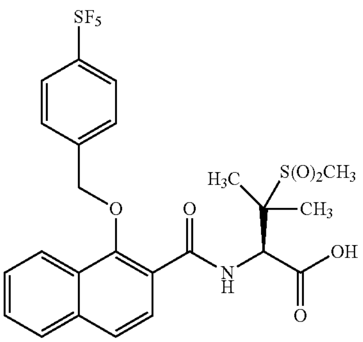 | 419 |
| 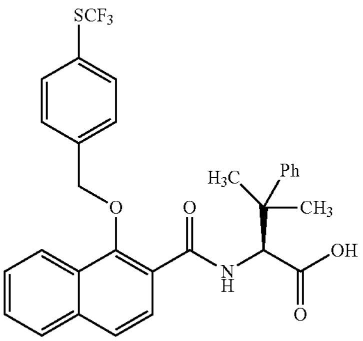 | 5 |
| 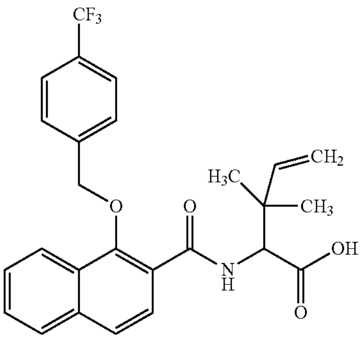 [SMILES: C=CC(C)(C)C(NC(=O)c1ccc2ccccc2c1OCc1ccc(C(F)(F)F)cc1)C(=O)O] | 223 |
| 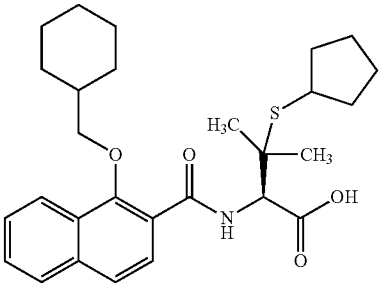 [SMILES: CC(C)(SC1CCCC1)[C@H](NC(=O)c1ccc2ccccc2c1OCC1CCCCC1)C(=O)O] | 170 |

TABLE 5-continued
| Compound | # |
|---|---|
| 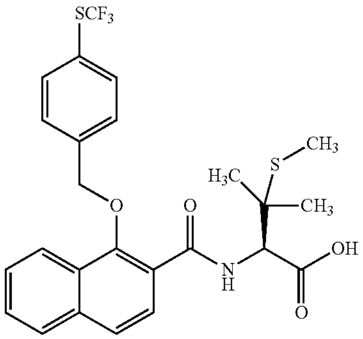 | 420 |
| 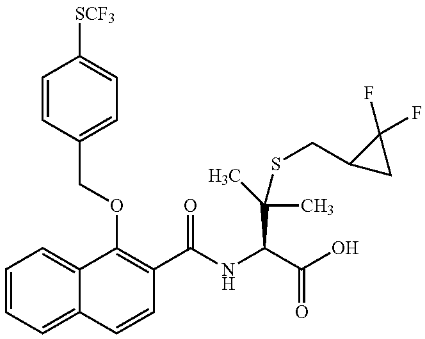 | 164 |
| 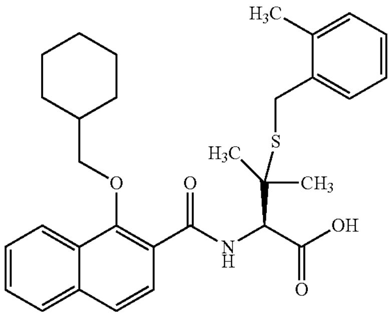 [SMILES: Cc1ccccc1CSC(C)(C)[C@H](NC(=O)c1ccc2ccccc2c1OCC1CCCCC1)C(=O)O] | 425 |
| 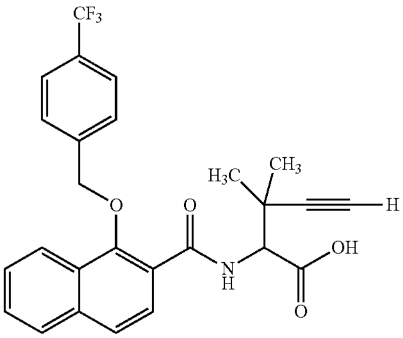 [SMILES: C#CC(C)(C)C(NC(=O)c1ccc2ccccc2c1OCc1ccc(C(F)(F)F)cc1)C(=O)O] | 228 |
TABLE 5-continued
| Compound | # |
|---|---|
| 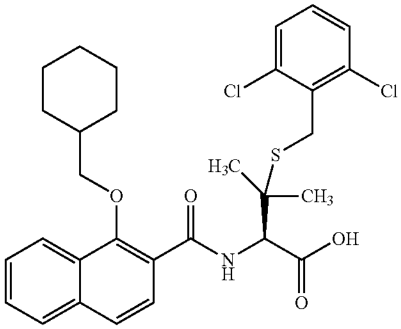 [SMILES: CC(C)(SCc1c(Cl)cccc1Cl)[C@H](NC(=O)c1ccc2ccccc2c1OCC1CCCCC1)C(=O)O] | 426 |
| 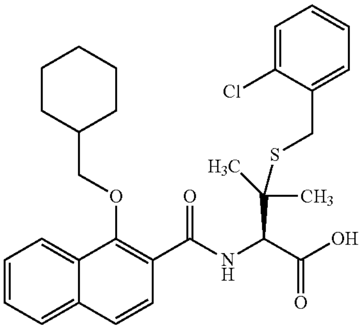 [SMILES: CC(C)(SCc1ccccc1Cl)[C@H](NC(=O)c1ccc2ccccc2c1OCC1CCCCC1)C(=O)O] | 427 |
| 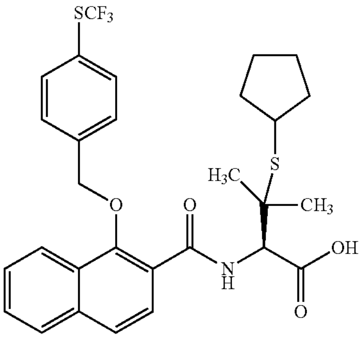 | 169 |
| 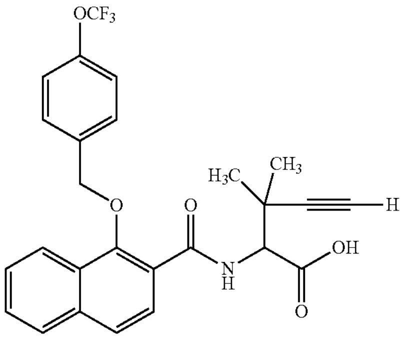 [SMILES: C#CC(C)(C)C(NC(=O)c1ccc2ccccc2c1OCc1ccc(OC(F)(F)F)cc1)C(=O)O] | 234 |

TABLE 5-continued
| Compound | # |
|---|---|
| 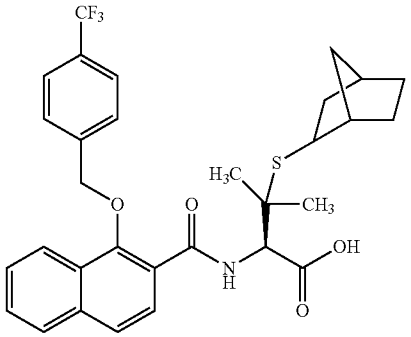 [SMILES: CC(C)(SC1CC2CCC1C2)[C@H](NC(=O)c1ccc2ccccc2c1OCc1ccc(C(F)(F)F)cc1)C(=O)O] | 173 |
| 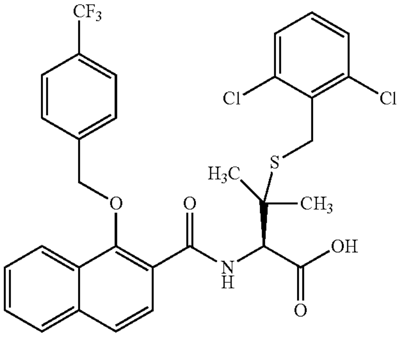 [SMILES: CC(C)(SCc1c(Cl)cccc1Cl)[C@H](NC(=O)c1ccc2ccccc2c1OCc1ccc(C(F)(F)F)cc1)C(=O)O] | 431 |
| 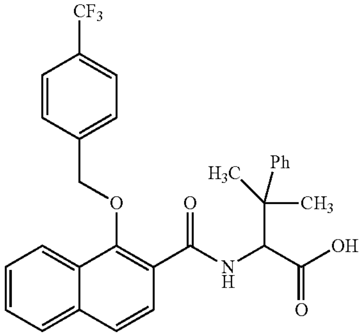 [SMILES: CC(C)(c1ccccc1)C(NC(=O)c1ccc2ccccc2c1OCc1ccc(C(F)(F)F)cc1)C(=O)O] | 16 |
| 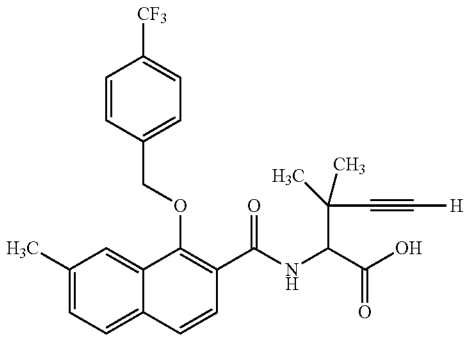 [SMILES: C#CC(C)(C)C(NC(=O)c1ccc2ccc(C)cc2c1OCc1ccc(C(F)(F)F)cc1)C(=O)O] | 219 |
TABLE 5-continued
| Compound | # |
|---|---|
| 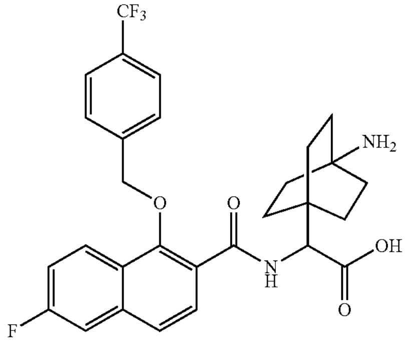 [SMILES: NC12CCC(C(NC(=O)c3ccc4cc(F)ccc4c3OCc3ccc(C(F)(F)F)cc3)C(=O)O)(CC1)CC2] | 185 |
| 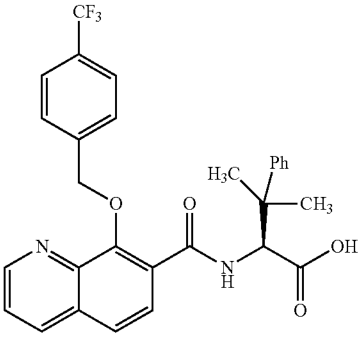 [SMILES: CC(C)(c1ccccc1)[C@H](NC(=O)c1ccc2cccnc2c1OCc1ccc(C(F)(F)F)cc1)C(=O)O] | 436 |
| 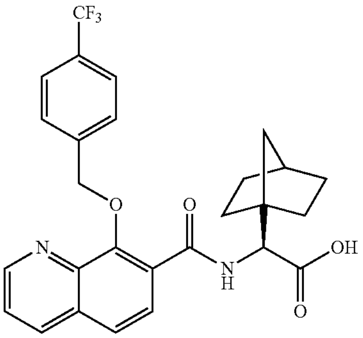 [SMILES: O=C(N[C@H](C(=O)O)C12CCC(CC1)C2)c1ccc2cccnc2c1OCc1ccc(C(F)(F)F)cc1] | 437 |
| 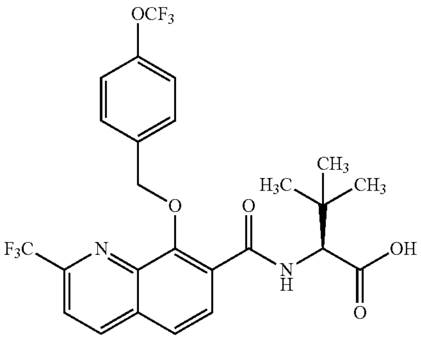 [SMILES: CC(C)(C)[C@H](NC(=O)c1ccc2ccc(C(F)(F)F)nc2c1OCc1ccc(OC(F)(F)F)cc1)C(=O)O] | 438 |

TABLE 5-continued
| Compound | # |
| --- | --- |
| 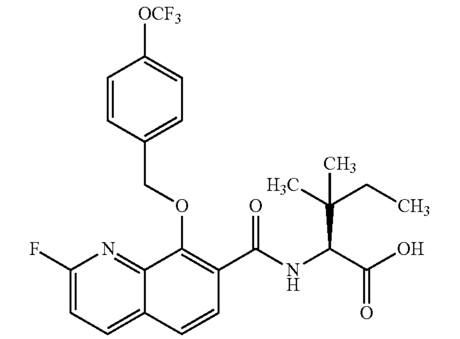 [SMILES: CCC(C)(C)[C@H](NC(=O)c1ccc2ccc(F)nc2c1OCc1ccc(OC(F)(F)F)cc1)C(=O)O] | 439 |
| 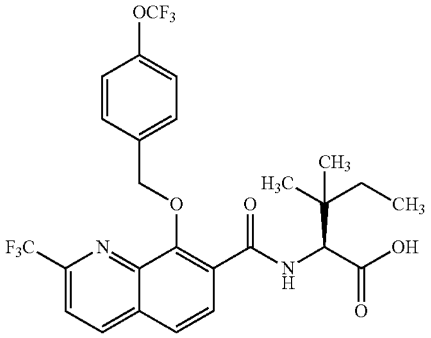 [SMILES: CCC(C)(C)[C@H](NC(=O)c1ccc2ccc(C(F)(F)F)nc2c1OCc1ccc(OC(F)(F)F)cc1)C(=O)O] | 445 |
| 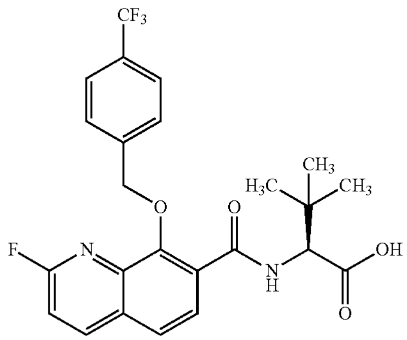 [SMILES: CC(C)(C)[C@H](NC(=O)c1ccc2ccc(F)nc2c1OCc1ccc(C(F)(F)F)cc1)C(=O)O] | 446 |
| 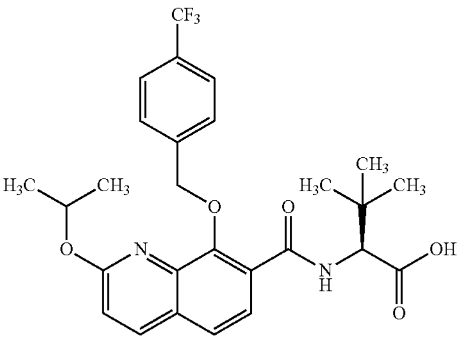 [SMILES: CC(C)Oc1ccc2ccc(C(=O)N[C@H](C(=O)O)C(C)(C)C)c(OCc3ccc(C(F)(F)F)cc3)c2n1] | 447 |
TABLE 5-continued
| Compound | # |
| --- | --- |
| 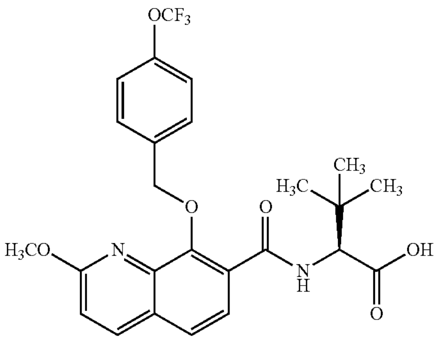 [SMILES: COc1ccc2ccc(C(=O)N[C@H](C(=O)O)C(C)(C)C)c(OCc3ccc(OC(F)(F)F)cc3)c2n1] | 448 |
| 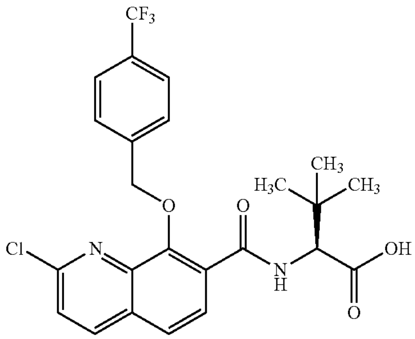 [SMILES: CC(C)(C)[C@H](NC(=O)c1ccc2ccc(Cl)nc2c1OCc1ccc(C(F)(F)F)cc1)C(=O)O] | 449 |
| 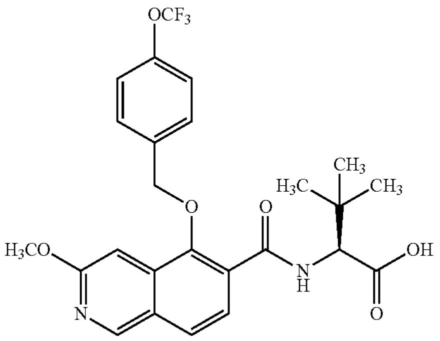 [SMILES: COc1cc2c(OCc3ccc(OC(F)(F)F)cc3)c(C(=O)N[C@H](C(=O)O)C(C)(C)C)ccc2cn1] | 455 |
| 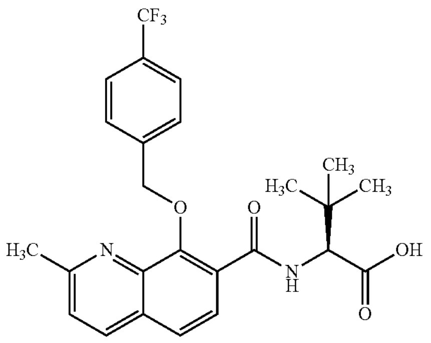 | 456 |

TABLE 5-continued
| Compound | # |
|---|---|
| 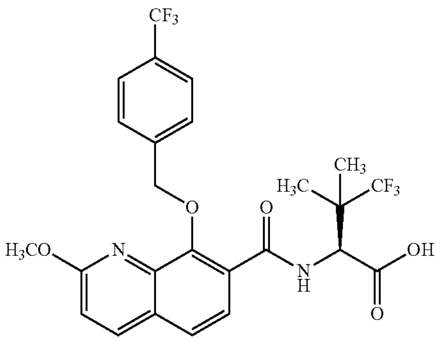 | 457 |
| 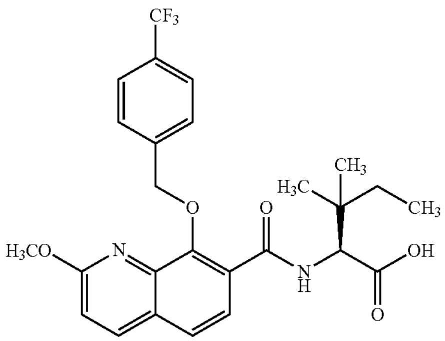 [SMILES: CCC(C)(C)[C@H](NC(=O)c1ccc2ccc(OC)nc2c1OCc1ccc(C(F)(F)F)cc1)C(=O)O] | 458 |
| 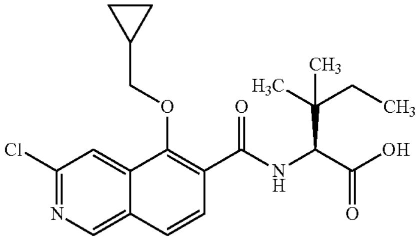 [SMILES: CCC(C)(C)[C@H](NC(=O)c1ccc2cnc(Cl)cc2c1OCC1CC1)C(=O)O] | 459 |
| 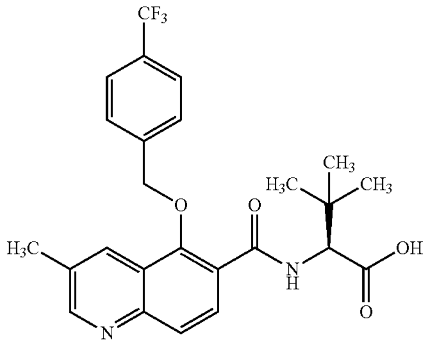 [SMILES: Cc1cnc2ccc(C(=O)N[C@H](C(=O)O)C(C)(C)C)c(OCc3ccc(C(F)(F)F)cc3)c2c1] | 465 |
TABLE 5-continued
| Compound | # |
|---|---|
| 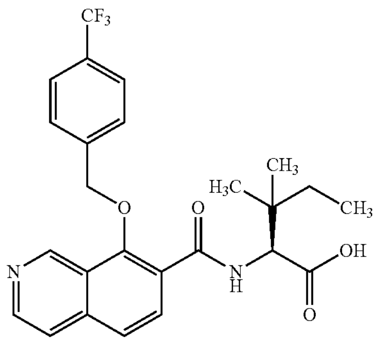 [SMILES: CCC(C)(C)[C@H](NC(=O)c1ccc2ccncc2c1OCc1ccc(C(F)(F)F)cc1)C(=O)O] | 466 |
| 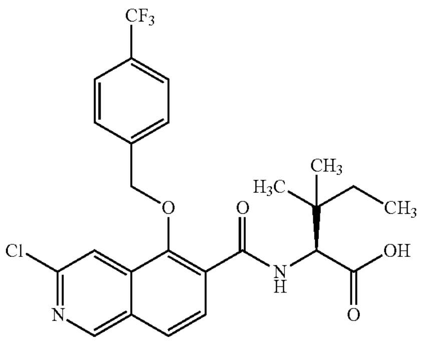 [SMILES: CCC(C)(C)[C@H](NC(=O)c1ccc2cnc(Cl)cc2c1OCc1ccc(C(F)(F)F)cc1)C(=O)O] | 467 |
| 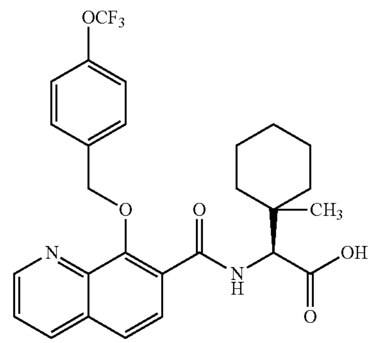 [SMILES: CC1([C@H](NC(=O)c2ccc3cccnc3c2OCc2ccc(OC(F)(F)F)cc2)C(=O)O)CCCCC1] | 468 |
| 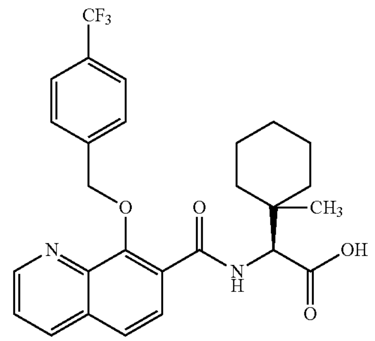 [SMILES: CC1([C@H](NC(=O)c2ccc3cccnc3c2OCc2ccc(C(F)(F)F)cc2)C(=O)O)CCCCC1] | 469 |

TABLE 5-continued

| Compound | # |
| --- | --- |
| 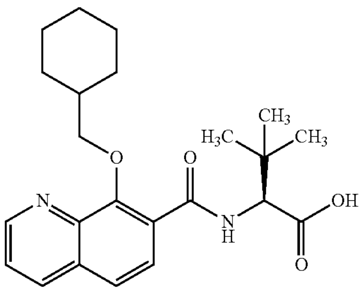 [SMILES: CC(C)(C)[C@H](NC(=O)c1ccc2cccnc2c1OCC1CCCCC1)C(=O)O] | 473 |
| 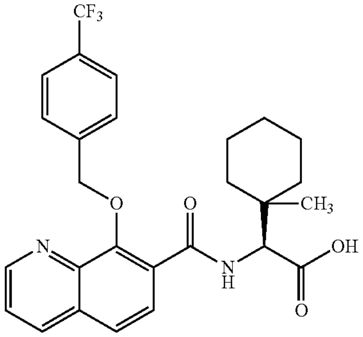 [SMILES: CC1([C@H](NC(=O)c2ccc3cccnc3c2OCc2ccc(C(F)(F)F)cc2)C(=O)O)CCCCC1] | 474 |
| 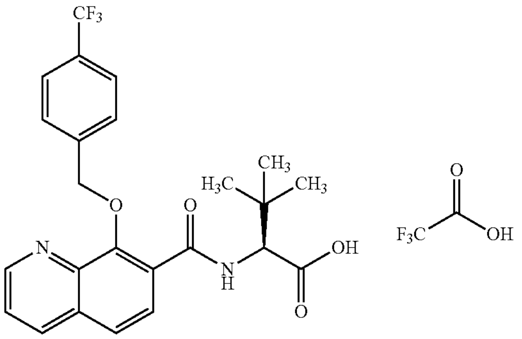 [SMILES: CC(C)(C)[C@H](NC(=O)c1ccc2cccnc2c1OCc1ccc(C(F)(F)F)cc1)C(=O)O ; O=C(O)C(F)(F)F] | 475 |

In certain embodiments, the present disclosure provides a pharmaceutical preparation suitable for use in a subject, comprising any of the compounds shown above (e.g., a compound of the disclosure, such as a compound of formula (I), and one or more pharmaceutically acceptable excipients. In certain embodiments, the pharmaceutical preparations may be for use in treating or preventing cystic fibrosis.

Any of the disclosed compounds may be used in the manufacture of medicaments for the treatment of any diseases or conditions disclosed herein.

Definitions

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Unless specifically stated or obvious from context, as used herein, the term "or" is understood to be inclusive. Unless specifically stated or obvious from context, as used herein, the terms "a", "an", and "the" are understood to be singular or plural.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10, more preferably from 1-6. unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "haloalkyl", as used herein, refers to an alkyl group in which at least one hydrogen has been replaced with a halogen, such as fluoro, chloro, bromo, or iodo. Exemplary haloalkyl groups include trifluoromethyl, difluoromethyl, fluoromethyl, 2-fluoroethyl, 2,2-difluoroethyl, and 2,2,2-trifluoroethyl.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

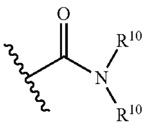

wherein each $R^{10}$ independently represents a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

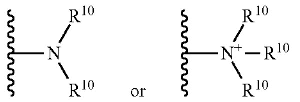

wherein each $R^{10}$ independently represents a hydrogen or a hydrocarbyl group, or two $R^{10}$ are taken together with the N atom to which they are attached complete a heterocycle having from 4 to 8 atoms in the ring structure. The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5-to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

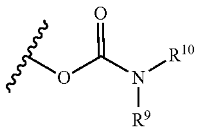

or

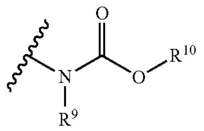

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings.

A "cycloalkenyl" group is a cyclic hydrocarbon containing one or more double bonds. The cycloalkenyl ring may have 3 to 10 carbon atoms. As such, cycloalkenyl groups can be monocyclic or multicyclic. Individual rings of such multicyclic cycloalkenyl groups can have different connectivities, e.g., fused, bridged, spiro, etc. in addition to covalent bond substitution. Exemplary cycloalkenyl groups include cyclopropenyl, cyclobutenyl, cyclopentyl, cyclohexenyl, cycloheptenyl, 1,3-cyclohexadienyl, 1,4-cyclohexadienyl and 1,5-cyclooctadienyl.

Exemplary cycloalkyl groups include cyclopropyl, cyclobutyl, cyclopentyl, cyclohexyl, norbornanyl, bicyclo[3.2.1]octanyl, octahydro-pentalenyl, spiro[4.5]decanyl, cyclopropyl, and adamantyl.

The term "carbocyclylalkyl", as used herein, refers to an alkyl group substituted with a carbocycle group.

The term "carbonate" is art-recognized and refers to a group —$OCO_2$—$R^{10}$, wherein $R^{10}$ represents a hydrocarbyl group.

The term "carboxy", as used herein, refers to a group represented by the formula —$CO_2H$.

The term "ester", as used herein, refers to a group —C(O)$OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 3- to 10-membered rings, more preferably 5- to 9-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

Individual rings of such multicyclic heteroaryl groups can have different connectivities, e.g., fused, etc. in addition to covalent bond substitution. Exemplary heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl, etc. In general, the heteroaryl group typically is attached to the main structure via a carbon atom.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

Individual rings of such multicyclic heterocycloalkyl groups can have different connectivities, e.g., fused, bridged, spiro, etc. in addition to covalent bond substitution. Exemplary heterocycloalkyl groups include pyrrolidinyl, tetrahydrofuranyl, dihydrofuranyl, tetrahydropyranyl, pyranyl, thiopyranyl, azindinyl, azetidinyl, oxiranyl, methylenedioxy, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazine-2-yl, 1,3-tetrahydrothiazine-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0]hexanyl 2-azaspiro[4.4]nonanyl, 7-oxa-1-aza-spiro[4.4]nonanyl, 7-azabicyclo[2.2.2]heptanyl, octahydro-1H-indolyl, etc. In general, the heterocycloalkyl group typically is attached to the main structure via a carbon atom or a nitrogen atom.

The term "heterocyclylalkyl", as used herein, refers to an alkyl group substituted with a heterocycle group.

The term "hydrocarbyl", as used herein, refers to a group that is bonded through a carbon atom that does not have a ═O or ═S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a ═O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —$OSO_3H$, or a pharmaceutically acceptable salt thereof.

The term "sulfonamide" is art-recognized and refers to the group represented by the general formulae

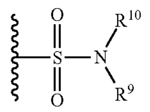

or

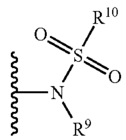

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—$R^{10}$, wherein $R^{10}$ represents a hydrocarbyl.

The term "sulfonate" is art-recognized and refers to the group $SO_3H$, or a pharmaceutically acceptable salt thereof.

The term "sulfone" is art-recognized and refers to the group —$S(O)_2$—$R^{10}$, wherein $R^{10}$ represents a hydrocarbyl.

The term "thioalkyl", as used herein, refers to an alkyl group substituted with a thiol group.

The term "thioester", as used herein, refers to a group —C(O)S$R^{10}$ or —SC(O)$R^{10}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

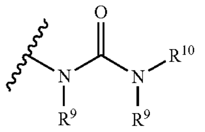

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The disclosure also includes various isomers and mixtures thereof. Certain of the compounds of the present disclosure may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. When a chiral center is not defined as R or S, either a pure enantiomer or a mixture of both configurations is present.

"Racemate" or "racemic mixture" means a compound of equimolar quantities of two enantiomers, wherein such mixtures exhibit no optical activity; i.e., they do not rotate the plane of polarized light. In certain embodiments, compounds of the disclosure may be racemic.

In certain embodiments, compounds of the disclosure may be enriched in one enantiomer. For example, a compound of the disclosure may have greater than about 30% ee, about 40% ee, about 50% ee, about 60% ee, about 70% ee, about 80% ee, about 90% ee, or even about 95% or greater ee. In certain embodiments, compounds of the disclosure may have more than one stereocenter. In certain such embodiments, compounds of the disclosure may be enriched in one or more diastereomer. For example, a compound of the disclosure may have greater than about 30% de, about 40% de, about 50% de, about 60% de, about 70% de, about 80% de, about 90% de, or even about 95% or greater de.

In certain embodiments, the therapeutic preparation may be enriched to provide predominantly one enantiomer of a compound (e.g., of Formula (I)). An enantiomerically enriched mixture may comprise, for example, at least about 60 mol percent of one enantiomer, or more preferably at least about 75, about 90, about 95, or even about 99 mol percent. In certain embodiments, the compound enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the therapeutic preparation may be enriched to provide predominantly one diastereomer of a compound (e.g., of Formula (I)). A diastereomerically enriched mixture may comprise, for example, at least about 60 mol percent of one diastereomer, or more preferably at least about 75, about 90, about 95, or even about 99 mol percent.

The compounds of the disclosure may be prepared as individual isomers by either isomer specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least about 60%, about 70%, about 80%, about 90%, about 99% or about 99.9% by weight pure relative to the other stereoisomers. When a single enantiomer is named or depicted by structure, the depicted or named enantiomer is at least about 60%, about 70%, about 80%, about 90%, about 99% or about 99.9% by weight optically pure. Percent optical purity by weight is the ratio of the weight of the enantiomer that is present divided by the combined weight of the enantiomer that is present and the weight of its optical isomer.

In the pictorial representation of the compounds given through this application, a thickened tapered line () indicates a substituent which is above the plane of the ring to which the asymmetric carbon belongs and a dotted line () indicates a substituent which is below the plane of the ring to which the asymmetric carbon belongs.

As used herein a compound of the present disclosure can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

An isotope-labelled form of a disclosed compound has one or more atoms of the compound replaced by an atom or atoms having an atomic mass or mass number different that which usually occurs in greater natural abundance. Examples of isotopes which are readily commercially available and which can be incorporated into a disclosed compound by well-known methods include isotopes of hydrogen, carbon, nitrogen, oxygen, phosphorus, fluorine and chlorine, for example, 2H, 3H, 13C, 14C, 15N, 18O, 17O, 31P, 32P, 35S, 18F and 36Cl, respectively. An isotope-labelled compound provided herein can usually be prepared by carrying out the procedures disclosed herein, replacing a non-isotope-labelled reactant by an isotope-labelled reactant.

The concentration of such a heavier isotope, specifically deuterium, may be defined by the isotopic enrichment factor. The term "isotopic enrichment factor" as used herein means the ratio between the isotopic abundance and the natural abundance of a specified isotope. If a hydrogen atom in a compound of this disclosure is replaced with deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

An isotope-labelled compound as provided herein can be used in a number of beneficial ways. Compounds having 14C incorporated are suitable for medicament and/or substrate tissue distribution assays. Tritium (3H) and carbon-14 (14C), are preferred isotopes owing to simple preparation and excellent detectability. Heavier isotopes, for example deuterium (2H), has therapeutic advantages owing to the higher metabolic stability. Metabolism is affected by the primary kinetic isotope effect, in which the heavier isotope has a lower ground state energy and causes a reduction in the rate-limiting bond breakage. Slowing the metabolism can lead to an increased in vivo half-life or reduced dosage requirements or an improvement in therapeutic index.

For a further discussion, see S. L. Harbeson and R. D. Tung, Deuterium In Drug Discovery and Development, Ann. Rep. Med. Chem. 2011, 46, 403-417, Foster, A. B., "Deuterium Isotope Effects in Studies of Drug Metabolism," Trends in Pharmacological Sciences, 5: 524-527 (1984) AND Foster, A. B., "Deuterium Isotope Effects in the Metabolism of Drugs and Xenobiotics: Implications for Drug Design," Advances in Drug Research, 14: 1-40 (1985).

Metabolic stability can be affected by the compound's processing in different organs of the body. For example, compounds with poor pharmacokinetic profiles are susceptible to oxidative metabolism. In vitro liver microsomal assays currently available provide valuable information on the course of oxidative metabolism of this type, which in turn assists in the rational design of deuterated compounds as disclosed herein. Improvements can be measured in a number of assays known in the art, such as increases in the in vivo half-life (t1/2), concentration at maximum therapeutic effect (Cmax), area under the dose response curve (AUC), and bioavailability; and in terms of reduced clearance, dose and materials costs.

Another effect of deuterated compounds can be diminishing or eliminating undesired toxic metabolites. For example, if a toxic metabolite arises through oxidative carbon-hydrogen (C—H) bond cleavage, the deuterated analogue will have a slower reaction time and slow the production of the unwanted metabolite, even if the particular oxidation is not a rate-determining step. See, e.g., Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" means to decrease, suppress, attenuate, diminish, arrest, or stabilize the development or progression of a disease (e.g., a disease or disorder delineated herein), lessen the severity of the disease or improve the symptoms associated with the disease. Treatment includes treating a symptom of a disease, disorder or condition. Without being bound by any theory, in some embodiments, treating includes augmenting deficient CFTR activity. If it is administered prior to clinical manifestation of the unwanted condition (e.g., disease or other unwanted state of the subject) then the treatment is prophylactic (i.e., it protects the subject against developing the unwanted condition), whereas if it is administered after manifestation of the unwanted condition, the treatment is therapeutic, (i.e., it is intended to diminish, ameliorate, or stabilize the existing unwanted condition or side effects thereof).

As used herein, the term "prodrug" means a pharmacological derivative of a parent drug molecule that requires biotransformation, either spontaneous or enzymatic, within the organism to release the active drug. For example, prodrugs are variations or derivatives of the compounds of the disclosure that have groups cleavable under certain metabolic conditions, which when cleaved, become the compounds of the disclosure. Such prodrugs then are pharmaceutically active in vivo, when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form. Prodrug forms often offer advantages of solubility, tissue compatibility, or delayed release in the mammalian organism (See, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, CA, 1992). Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Of course, other prodrug derivatives may be combined with other features disclosed herein to enhance bioavailability.

As such, those of skill in the art will appreciate that certain of the presently disclosed compounds having free amino, amido, hydroxy or carboxylic groups can be converted into prodrugs. Prodrugs include compounds having an amino acid residue, or a polypeptide chain of two or more (e.g., two, three or four) amino acid residues which are covalently joined through peptide bonds to free amino, hydroxy or carboxylic acid groups of the presently disclosed compounds. The amino acid residues include the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrullinehomocysteine, homoserine, ornithine and methionine sulfone. Prodrugs also include compounds having a carbonate, carbamate, amide or alkyl ester moiety covalently bonded to any of the above substituents disclosed herein.

A "therapeutically effective amount", as used herein refers to an amount that is sufficient to achieve a desired therapeutic effect. For example, a therapeutically effective amount can refer to an amount that is sufficient to improve at least one sign or symptom of cystic fibrosis.

A "response" to a method of treatment can include a decrease in or amelioration of negative symptoms, a decrease in the progression of a disease or symptoms thereof, an increase in beneficial symptoms or clinical outcomes, a lessening of side effects, stabilization of disease, partial or complete remedy of disease, among others.

As used herein, "CFTR" means cystic fibrosis transmembrane conductance regulator. Defects in the function of the CFTR ion channel result from loss of function mutations of CFTR. Such mutations lead to exocrine gland dysfunction, abnormal mucociliary clearance, and cause cystic fibrosis. The most common CFTR mutation in Cystic Fibrosis (CF) patients leads to the specific deletion of three nucleotides of the codon for phenylalanine at position 508. This mutation, which is found in ~70% of CF patients worldwide, is referred to as "ΔF508". The ΔF508 mutation decreases the stability of the CFTR NBD1 domain and limits CFTR interdomain assembly. Since CF is an autosomal recessive disease, a CF patient harboring the ΔF508 CFTR mutation must also carry a second defective copy of CFTR. Approximately 2000 different CF-causing CFTR mutations have been identified in CF patients. CF patients harboring the ΔF508 CFTR mutation can be homozygous for that mutation (ΔF508/ΔF508). CF patients can also be ΔF508 heterozygous, if the second CFTR allele such patients carry instead contains a different CFTR loss of function mutation. Such CFTR mutations include, but are not limited to, G542X, G551D, N1303K, W1282X, R553X, R117H, R1162X, R347P, G85E, R560T, A455E, A1507, G178R, S549N, S549R, G551S, G970R, G1244E, 51251N, 51255P, and G1349D.

As used herein, the term "CFTR modulator" refers to a compound that increases the activity of CFTR. In certain aspects, a CFTR modulator is a CFTR corrector or a CFTR potentiator or a dual-acting compound having activities of a corrector and a potentiator. These dual acting agents are useful when the mutations result in absence or reduced amount of synthesized CFTR protein.

As used herein, the term "CFTR corrector" refers to a compound that increases the amount of functional CFTR protein at the cell surface, thus enhancing ion transport through CFTR. CFTR correctors partially "rescue" misfolding of CFTR protein, particularly such misfolding that results from mutations within CFTR, thereby permitting CFTR maturation and functional expression on the cell surface. CFTR correctors may modify the folding environment of the cell in a way that promotes CFTR folding, and include compounds that interact directly with CFTR protein to modify its folding, conformational maturation or stability. Examples of correctors include, but are not limited to, VX-809, VX-661, VX-152, VX-440, VX-445, VX-659, VX-121, VX-983, compounds described in US20190248809A1, GLPG2222, GLPG2737, GLPG3221, GLPG2851, FDL169, FDL304, FD2052160, FD2035659, and PTI-801.

As used herein, the term "CFTR potentiator" refers to a compound that increases the ion channel activity of CFTR protein located at the cell surface, resulting in enhanced ion transport. CFTR potentiators restore the defective channel functions that results from CFTR mutations, or that otherwise increase the activity of CFTR at the cell surface. Examples of potentiators include, but are not limited to, ivacaftor (VX770), deuterated ivacaftor (CPT 656, VX-561), PTI-808, QBW251, GLPG1837, GLPG2451, ABBV-3067, ABBV-974, ABBV-191, FDL176, and genistein.

As used herein, "CFTR disease or condition" refers to a disease or condition associated with deficient CFTR activity, for example, cystic fibrosis, congenital bilateral absence of vas deferens (CBAVD), acute, recurrent, or chronic pancreatitis, disseminated bronchiectasis, asthma, allergic pulmonary aspergillosis, congenital pneumonia, intestinal malabsorption, celiac disease, nasal polyposis, non-tuberculous mycobacterial infection, pancreatic steatorrhea, intestinal atresia, smoking-related lung diseases, such as chronic obstructive pulmonary disease (COPD), rhinosinusitis, dry eye disease, protein C deficiency, A.beta.-lipoproteinemia, lysosomal storage disease, type 1 chylomicronemia, mild pulmonary disease, lipid processing deficiencies, type 1 hereditary angioedema, coagulation-fibrinolysis, hereditary hemochromatosis, CFTR-related metabolic syndrome, chronic bronchitis, constipation, pancreatic insufficiency, hereditary emphysema, and Sjogren's syndrome.

Methods of Use

Disclosed herein are methods of treating deficient CFTR activity in a cell, comprising contacting the cell with a compound of formula (I), or a pharmaceutically acceptable salt thereof. In certain embodiments, contacting the cell occurs in a subject in need thereof, thereby treating a disease or disorder mediated by deficient CFTR activity.

Also, disclosed herein are methods of treating a disease or a disorder mediated by deficient CFTR activity comprising administering a compound of Formula (I) or a pharmaceutically acceptable salt thereof. In some embodiments, the subject is a mammal, preferably a human. In some embodiments, the disease is associated with the regulation of fluid volumes across epithelial membranes, particularly an obstructive airway disease such as CF or COPD.

Such diseases and conditions include, but are not limited to, cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), congenital pneumonia, intestinal malabsorption, celiac disease, nasal polyposis, non-tuberculous mycobacterial infection, pancreatic steatorrhea, intestinal atresia, rhinosinusitis, liver disease, hereditary emphysema, hereditary hemochromatosis, coagulation-fibrinolysis deficiencies, protein C deficiency, Type 1 hereditary angioedema, lipid processing deficiencies, familial hypercholesterolemia, Type 1 chylomicronemia, abetalipoproteinemia, lysosomal storage diseases, I-cell disease/pseudo-Hurler, mucopolysaccharidoses, Sandhoff/Tay-Sachs, Crigler-Najjar type II, polyendocrinopathy/hyperinosemia, Diabetes mellitus, Laron dwarfism, myleoperoxidase deficiency, primary hypoparathyroidism, melanoma, glucanases CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Pelizaeus-Merzbacher disease, neurodegenerative diseases, Alzheimer's disease, Parkinson's disease, amyotrophic lateral sclerosis, progressive supranuclear palsy, Pick's disease, several polyglutamine neurological disorders, Huntington's, spinocerebellar ataxia type I, spinal and bulbar muscular atrophy, dentatorubral pallidoluysian, myotonic dystrophy, spongiform encephalopathies, hereditary Creutzfeldt-Jakob disease, Fabry disease, Straussler-Scheinker syndrome, COPD, dry-eye disease, Sjogren's disease, Osteoporosis, Osteopenia, bone healing and bone growth, bone repair, bone regeneration, reducing bone resorption, increasing bone deposition, Gorham's Syndrome, chloride channelopathies, myotonia congenita, Bartter's syndrome type III, Dent's disease, hyperekplexia, epilepsy, hyperekplexia, lysosomal storage disease, Angelman syndrome, Primary Ciliary Dyskinesia (PCD), PCD with situs inversus, PCD without situs inversus and ciliary aplasia.

Such diseases and conditions include, but are not limited to, cystic fibrosis, congenital bilateral absence of vas deferens (CBAVD), acute, recurrent, or chronic pancreatitis, disseminated bronchiectasis, asthma, allergic pulmonary aspergillosis, congenital pneumonia, intestinal malabsorption, celiac disease, nasal polyposis, non-tuberculous mycobacterial infection, pancreatic steatorrhea, intestinal atresia, smoking-related lung diseases, such as chronic obstructive pulmonary disease (COPD), rhinosinusitis, dry eye disease, protein C deficiency, A.beta.-lipoproteinemia, lysosomal storage disease, type 1 chylomicronemia, mild pulmonary disease, lipid processing deficiencies, type 1 hereditary angioedema, coagulation-fibrinolysis, hereditary hemochromatosis, CFTR-related metabolic syndrome, chronic bronchitis, constipation, pancreatic insufficiency, hereditary emphysema, and Sjogren's syndrome. In some embodiments, the disease is cystic fibrosis.

Provided herein are methods of treating cystic fibrosis or a symptom thereof, comprising administering to a subject in need thereof, a compound as disclosed herein or a pharmaceutically acceptable salt thereof. Also provided herein are methods of lessening the severity of cystic fibrosis or a symptom thereof, comprising administering to a subject in need thereof, a compound as disclosed herein or a pharmaceutically acceptable salt thereof. In some embodiments, the subject is a human. In some embodiments, the subject is at risk of developing cystic fibrosis, and administration is carried out prior to the onset of symptoms of cystic fibrosis in the subject.

Provided herein are compounds as disclosed herein for use in treating a disease or condition mediated by deficient CFTR activity. Also provided herein are uses of a compound as disclosed herein for the manufacture of a medicament for treating a disease or condition mediated by deficient CFTR activity.

The compounds and methods described herein can be used to treat subjects who have deficient CFTR activity and harbor CFTR mutations like ΔF508. The ΔF508 mutation impedes normal CFTR folding, stability, trafficking, and function by decreasing the stability of CFTR's NBD1 domain, the competency of CFTR domain-domain assembly, or both. Due their impact on the ICL4 interface, a CFTR corrector with an ICL4-directed mechanism can be effective in subjects harboring the following mutations: ΔF508-CFTR (>70% of all CF patients harbor at least one copy) and mutations that cause ICL4 interface instability for example: G85E, H139R, H1054D, L1065P, L1077P, R1066C and other CFTR mutations where ICL4 interface stability is compromised.

Provided herein are kits for use in measuring the activity of CFTR or a fragment thereof in a biological sample in vitro or in vivo. The kit can contain: (i) a compound as disclosed herein, or a pharmaceutical composition comprising the disclosed compound, and (ii) instructions for: a) contacting the compound or composition with the biological sample; and b) measuring activity of said CFTR or a fragment thereof. In some embodiments, the biological sample is biopsied material obtained from a mammal or extracts thereof; blood, saliva, urine, feces, semen, tears, other body fluids, or extracts thereof. In some embodiments, the mammal is a human.

Combination Treatments

As used herein, the term "combination therapy" means administering to a subject (e.g., human) two or more CFTR modulators, or a CFTR modulator and an agent such as antibiotics, ENaC inhibitors, GSNO (S-nitrosothiol s-nitroglutanthione) reductase inhibitors, and a CRISPR Cas correction therapy or system (as described in US 2007/0022507 and the like).

In certain embodiments, the method of treating or preventing a disease or condition mediated by deficient CFTR activity comprises administering a compound as disclosed herein conjointly with one or more other therapeutic agent(s). In some embodiments, one other therapeutic agent is administered. In other embodiments, at least two other therapeutic agents are administered.

Additional therapeutic agents include, for example, ENaC inhibitors, mucolytic agents, bronchodilators, antibiotics, anti-infective agents, anti-inflammatory agents, ion channel modulating agents, modulators of mucus rheology, therapeutic agents used in gene or mRNA therapy, agents that reduce airway surface liquid and/or reduce airway surface PH, CFTR correctors, and CFTR potentiators, or other agents that modulate CFTR activity. Other therapeutics include liposomal composition components such as those described in WO2012/170889, hybrid oligonucleotides that facilitate RNA cleavage such as those described in WO2016/130943, and single stranded oligonucleotides that modulate gene expression as described in WO2016/130929.

In some embodiments, at least one additional therapeutic agent is selected from one or more CFTR modulators, one or more CFTR correctors and one or more CFTR potentiators.

Non-limiting examples of additional CFTR modulators, correctors and potentiators include VX-770 (Ivacaftor), VX-809 (Lumacaftor, 3-(6-(I-(2,2-5 difluorobenzo[d][1,3]dioxol-5-yl)cyclopropanecarboxamido)-3-methylpyridin-2-yl) benzoic acid, VX-661 (Tezacaftor, I-(2,2-difluoro-1,3-benzodioxol-5-yl)-N—[I-[(2R)-2,3-dihydroxypropyl]-6-fluoro-2-(2-hydroxy-1, I-dimethylethyl)-IH-indol-5-yl]-cyclopropanecarboxamide), VX-983, VX-152, VX-440, VX-445, VX-659, VX-371, VX-121, Orkambi, compounds described in US20190248809A1, Ataluren (PTC 124) (3-[5-(2-fluorophenyl)-1,2,4-oxadiazol-3-yl]benzoic acid), PTI-130 (Proteostasis), PTI-801, PTI-808, PTI-428, N91115.74 (cavosonstat), QBW251 (Novartis) compounds described in WO2011113894, compounds N30 Pharmaceuticals (e.g., WO 2014/186704), deuterated ivacaftor (e.g., CTP-656 or VX-561), GLPG2222, GLPG3221, GLPG2451, GLPG3067, GLPG2851, GLPG2737, GLPG1837 (N-(3-carbamoyl-5,5,7,7-tetramethyl-5,7-dihydro-4H-thieno[2,3-c]pyran-2-yl)-1H-pyrazole-5-carboxamide), GLPG2665 (Galapagos), ABBV-191 (Abbvie), ABBV-974, FDL 169 (Flatley Discovery lab), FDL176, FDL438, FDL304, FD2052160, FD1881042, FD2027304, FD2035659, FD2033129, FD1860293, CFFT-Pot01, CFFT-Pot-02, P-1037, glycerol, phenylbutyrate, and the like.

Non-limiting examples of anti-inflammatory agents are N6022 (3-(5-(4-(IH-imidazol-I-yl)10 phenyl)-I-(4-carbamoyl-2-methylphenyl)-'H-pyrrol-2-yl) propanoic acid), Ibuprofen, Lenabasum (anabasum), Acebilustat (CTX-4430), LAU-7b, POL6014, docosahexaenoic acid, alpha-1 antitrypsin, sildenafil. Additional therapeutic agents also include, but are not limited to a mucolytic agent, a modifier of mucus rheology (such as hypertonic saline, mannitol, and oligosaccharide based therapy), a bronchodilator, an anti-infective (such as tazobactam, piperacillin, rifampin, meropenum, ceftazidime, aztreonam, tobramycin, fosfomycin, azithromycin, vancomycin, gallium and colistin), an anti-infective agent, an anti-inflammatory agent, a CFTR modulator other than a compound of the present disclosure, and a nutritional agent. Additional therapeutic agents can include treatments for comorbid conditions of cystic fibrosis, such as exocrine pancreatic insufficiency which can be treated with Pancrelipase or Liprotamase.

Examples of CFTR potentiators include, but are not limited to, Ivacaftor (VX-770), CTP-656, NVS-QBW251, PTI-808. ABBV-3067. ABBV-974, ABBV-191, FDL176, FD1860293, GLPG2451, GLPG837, and N-(3-carbamoyl-5,5,7,7-tetramethyl-5,7-dihydro-4H-thieno[2,3-c]pyran-2-yl)-1H-pyrazole-5-carboxamide. Examples of potentiators are also disclosed in publications: WO2005120497, WO2008147952, WO2009076593, WO2010048573, WO2006002421, WO2008147952, WO2011072241, WO2011113894, WO2013038373, WO2013038378, WO2013038381, WO2013038386, WO2013038390, WO2014180562, WO2015018823, and U.S. patent application Ser. Nos. 14/271,080, 14/451,619 and 15/164,317.

Non-limiting examples of correctors include Lumacaftor (VX-809), 1-(2,2-difluoro-1,3-benzodioxol-5-yl)-N-{1-[(2R)-2,3-dihydroxypropyl]-6-fluor-2-(1-hydroxy-2-methylpropan-2-yl)-1H-indol-5-yl}cyclopropane carboxamide (VX-661), VX-983, GLPG22222, GLPG2665, GLPG2737, GLPG3221, GLPG2851, VX-152, VX-440, VX-121, VX-445, VX-659, compounds described in 1S20190248809A1, PH-801, FDL169, FDL304, FD2052160, and FD2035659. Examples of correctors are also disclosed in US20160095858A1, and U.S. application Ser. Nos. 14/925,649 and 14/926,727.

In certain embodiments, the additional therapeutic agent is a CFTR amplifier. CFTR amplifiers enhance the effect of known CFTR modulators, such as potentiators and correctors. Examples of CFTR amplifier include PTI130 and PTI-428. Examples of amplifiers are also disclosed in publications: WO2015138909 and WO2015138934.

In certain embodiments, the additional therapeutic agent is an agent that reduces the activity of the epithelial sodium channel blocker (ENaC) either directly by blocking the channel or indirectly by modulation of proteases that lead to an increase in ENaC activity (e.g. serine proteases, channel-activating proteases). Exemplary of such agents include camostat (a trypsin-like protease inhibitor), QAU145, 552-02, ETD001, GS-9411, INO-4995, Aerolytic, amiloride, AZD5634, and VX-371. Additional agents that reduce the activity of the epithelial sodium channel blocker (ENaC) can be found, for example, in PCI Publication No. WO2009074575 and WO2013043720; and U.S. Pat. No. 8,999,976.

In one embodiment, the ENaC inhibitor is VX-371.

In one embodiment, the ENaC inhibitor is SPX-101 (S18).

In certain embodiments, the additional therapeutic agent is an agent that modulates the activity of the non-CFTR Cl-channel TMEM16A. Non-limiting examples of such agents include TMEM16A activators, denufosol, Melittin, Cinnamaldehyde, 3,4,5-Trimethoxy-N-(2-methoxyethyl)-N-(4-phenyl-2-thiazolyl)benzamide, INO-995, CLCA1, ETX001, ETD002 and phosphatidylinositol diC8-PIP2, and TMEM16A inhibitors, 10 bm, Arctigenin, dehydroandrographolide, Ani9, Niclosamide, and benzbromarone.

In certain embodiments, the combination of a compound of Formula (I), with a second therapeutic agent may have a synergistic effect in the treatment of cancer and other diseases or disorders mediated by adenosine. In other embodiments, the combination may have an additive effect.

Pharmaceutical Compositions

The compositions and methods of the present disclosure may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the disclosure and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the disclosure, with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this disclosure. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this disclosure, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered two or three times daily. In preferred embodiments, the active compound will be administered once daily.

In certain embodiments, the dosing follows a 3+3 design. The traditional 3+3 design requires no modeling of the dose-toxicity curve beyond the classical assumption for cytotoxic drugs that toxicity increases with dose. This rule-based design proceeds with cohorts of three patients; the first cohort is treated at a starting dose that is considered to be safe based on extrapolation from animal toxicological data, and the subsequent cohorts are treated at increasing dose levels that have been fixed in advance. In some embodiments, the three doses of a compound of formula (I) range from about 100 mg to about 1000 mg orally, such as about 200 mg to about 800 mg, such as about 400 mg to about 700 mg, such as about 100 mg to about 400 mg, such as about 500 mg to about 1000 mg, and further such as about 500 mg to about 600 mg. Dosing can be three times a day when taken with without food, or twice a day when taken with food. In certain embodiments, the three doses of a compound of formula (I) range from about 400 mg to about 800 mg, such as about 400 mg to about 700 mg, such as about 500 mg to about 800 mg, and further such as about 500 mg to about 600 mg twice a day. In certain preferred embodiments, a dose of greater than about 600 mg is dosed twice a day.

If none of the three patients in a cohort experiences a dose-limiting toxicity, another three patients will be treated at the next higher dose level. However, if one of the first three patients experiences a dose-limiting toxicity, three more patients will be treated at the same dose level. The dose escalation continues until at least two patients among a cohort of three to six patients experience dose-limiting toxicities (i.e., ≥about 33% of patients with a dose-limiting toxicity at that dose level). The recommended dose for phase II trials is conventionally defined as the dose level just below this toxic dose level.

In certain embodiments, the dosing schedule can be about 40 $mg/m^2$ to about 100 $mg/m^2$, such as about 50 $mg/m^2$ to about 80 $mg/m^2$, and further such as about 70 $mg/m^2$ to about 90 $mg/m^2$ by IV for 3 weeks of a 4 week cycle.

In certain embodiments, compounds of the disclosure may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds of the disclosure with one or more additional therapeutic agent(s) (e.g., one or more additional chemotherapeutic agent(s)) provides improved efficacy relative to each individual administration of the compound of the disclosure (e.g., compound of formula I or Ia) or the one or more additional therapeutic agent(s). In certain such embodiments, the conjoint administration provides an additive effect, wherein an additive effect refers to the sum of each of the effects of individual administration of the compound of the disclosure and the one or more additional therapeutic agent(s).

This disclosure includes the use of pharmaceutically acceptable salts of compounds of the disclosure in the compositions and methods of the present disclosure. In certain embodiments, contemplated salts of the disclosure include, but are not limited to, alkyl, dialkyl, trialkyl or tetra-alkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the disclosure include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Although specific embodiments of the present disclosure will now be described with reference to the preparations and schemes, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure as further defined in the appended claims.

Unless defined otherwise, all technical and scientific terms used herein have the same meaning as commonly understood by one having ordinary skill in the art to which this disclosure belongs. Although other compounds or methods can be used in practice or testing, certain preferred methods are now described in the context of the following preparations and schemes.

A number of synthetic protocols were used to produce the compounds described herein. These synthetic protocols (see schemes below) have common intersections and can be used alternatively for synthesis of the compounds described herein.

EXAMPLES

General Schemes

Scheme 1

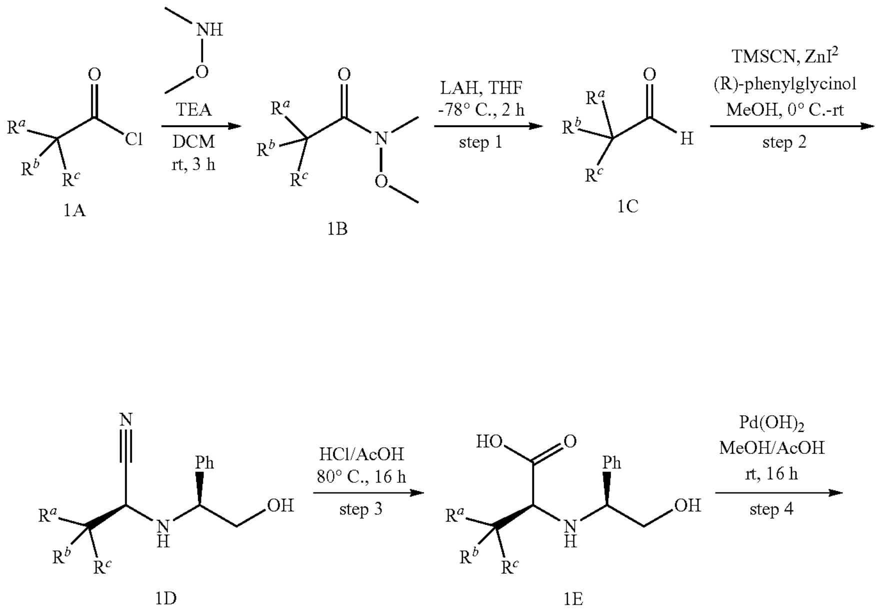

1A 1B 1C 1D 1E

-continued

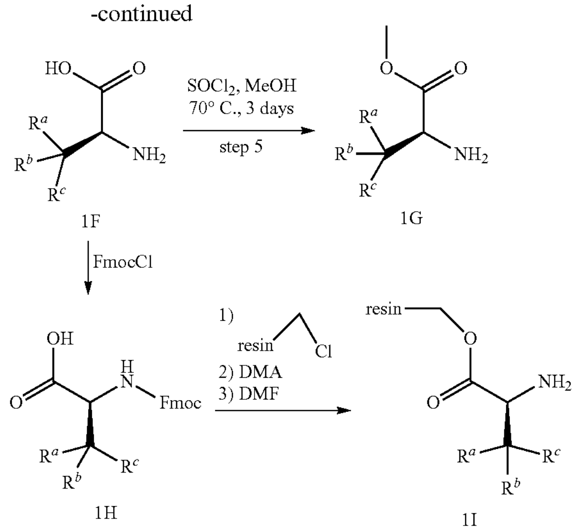

1F 1G 1H 1I

Scheme 1 provides a general scheme to arrive at the amino acids ester intermediates described herein through a 5-step process. In step 1, acid chloride 1A is condensed with N,O-dimethylhydroxylamine (step 1) to give amide 1B. The amide 1B is reduced by using a reducing agent such as LAH to give an aldehyde (1C). Aldehyde 1C is condensed with chiral auxiliary, such as (R)-phenylglycinol, and TMSCN, enantioselectively to give amino acetonitrile 1D. Hydrolysis of the nitrile under acidic conditions gives amino acid derivative 1E. The auxiliary is removed under hydrogenation conditions (step 4) to yield amino acid 1F. This building block (1F) can be converted into an ester 1G (step 5) or protected into Fmoc-protected amino acid (1H). Fmoc protected amino acid 1H can be further converted into resin linked amino acid (1I).

Scheme 2

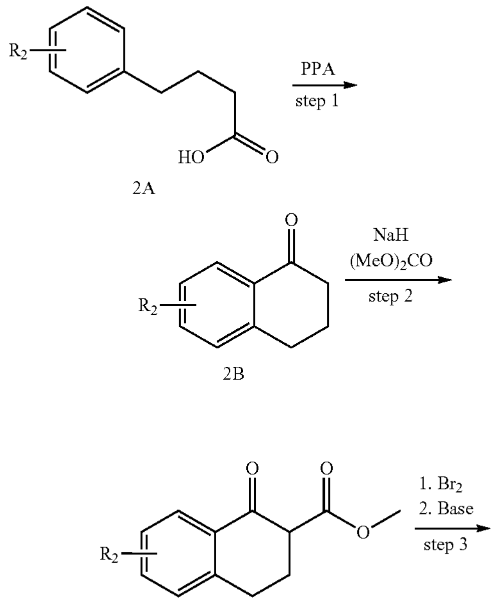

2A 2B 2C

-continued

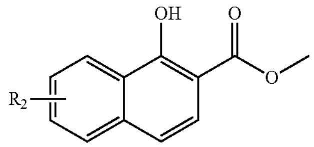

2D

Scheme 2 provides a general scheme to arrive at the compounds described herein. First, Compound 2A is cyclized with PPA as catalyst to obtain a ketone 2B. Treating intermediate 2B with a suitable base, such as NaH, captures the enolate formed with methyl carbonate to form a keto-ester 2C. This intermediate is aromatized via bromination and elimination by a base to obtain the phenol ester 2D.

Scheme 3

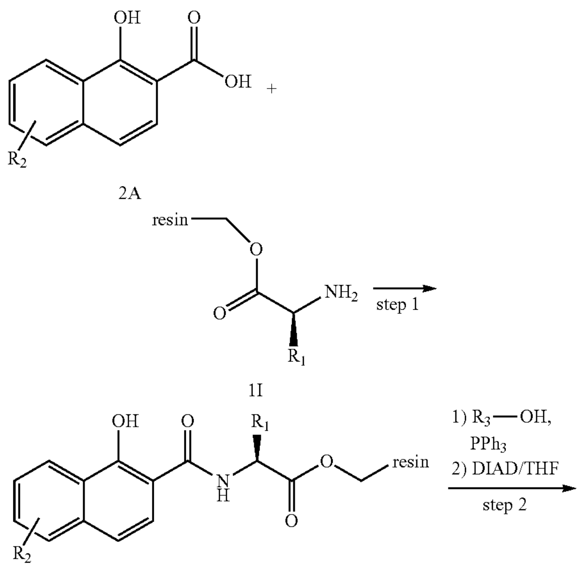

2A 1I 3A

-continued

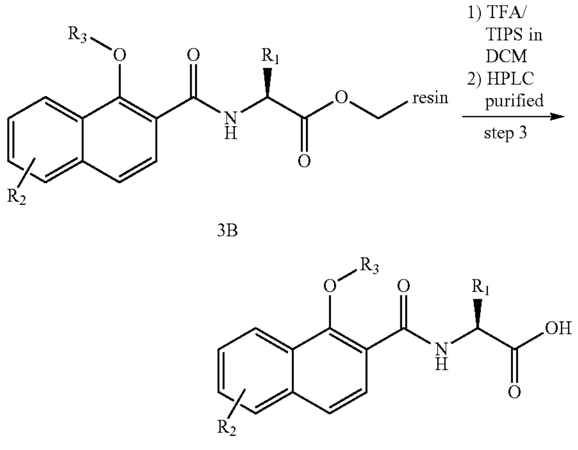

3B

3C

Scheme 3 provides a general scheme when using solid phase chemistry to arrive at the compounds described herein through a 3-step process. In step 1, Fmoc protected amino acid 1I is coupled with an appropriate aryl carboxylic acid (2D) with DIEA, followed by washing with THF and DMF to provide amide 3A. Derivatization of phenol of the amide 3A (step 2) is carried out by reacting with $R_3OH$, triphenylphosphine and DIAD to produce compound 3B. Lastly, removal of the resin is accomplished via treatment with TFA/TIPS followed by HPLC purification to produce compound 3C.

Scheme 4

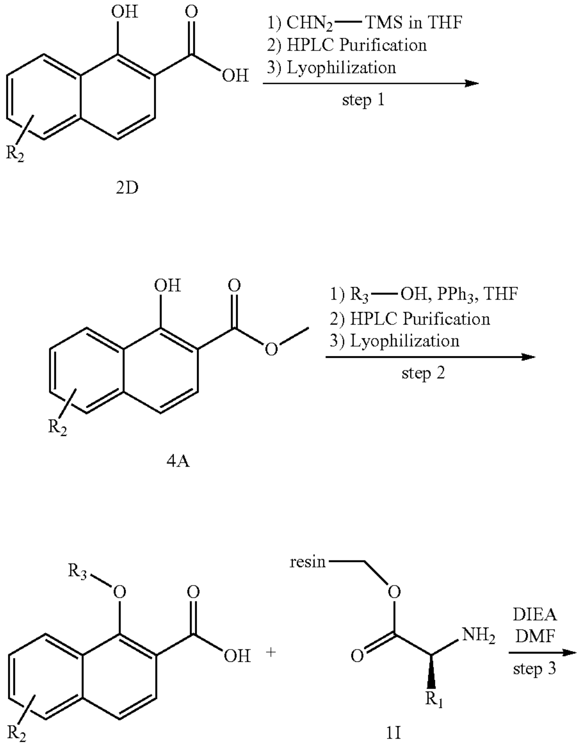

2D

4A

4B

1I

-continued

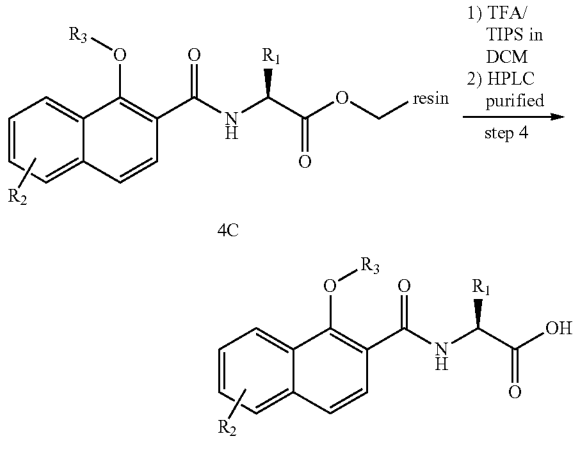

4C

3C

Scheme 4 provides a general scheme to illustrate an alternate solid phase synthetic procedure to arrive at the compounds described herein through a 4-step process. In step 1, aryl carboxylic acid 2D is reacted with TMS-$CHN_2$ followed by purification and lyophilization to provide ester 4A. Reaction of ester 4A with an appropriate alcohol in the presence of triphenylphosphine in THF is carried out to produce compound 4B. Coupling of carboxylic acid 4B with resin containing compound 1I in the presence of DIEA in DMF (step 3) produces amino acid amide 4C. Removal of the resin is carried out via treatment of 4C with TFA/TIPS followed by HPLC purification to produce compound 3C.

Scheme 5

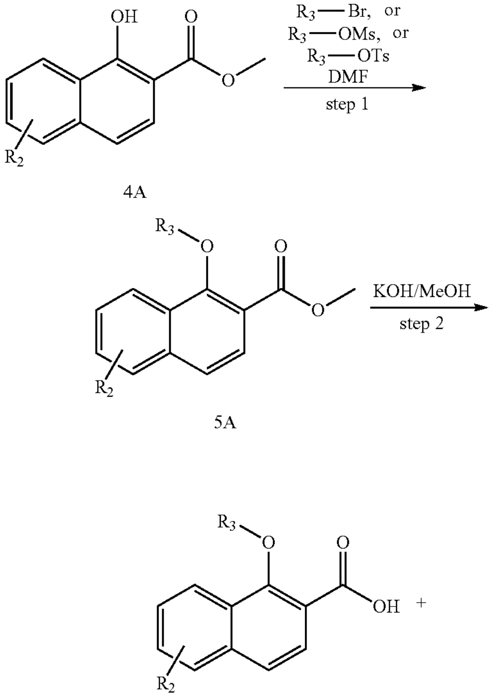

4A

5A

5B

-continued

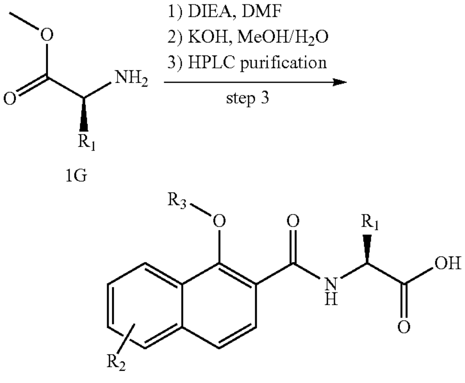

1G

3C

Scheme 5 provides a general scheme to arrive at the compounds described herein through a 3-step process. In step 1, ester 4A is treated with a base, such as sodium hydride, and then reacted with an appropriate alkylating agent, such as alkyl bromide, mesylate, or tosylate to give aryl ether carboxylic ester 5A. The ester is hydrolyzed by treatment with KOH/MeOH to produce carboxylic acid 5B. Coupling of 5B with amino acid methyl ester 1G is conducted in the presence of DIEA in DMF to produce the methyl ester. Removal of the methyl ester is carried out via treatment with KOH in a mixture of methanol and water followed by HPLC purification to produce compound 3C.

Analytical Procedures

The $^1$H NMR spectra are run at 400 MHz on a Gemini 400 or Varian Mercury 400 spectrometer with an ASW 5 mm probe, and usually recorded at ambient temperature in a de Deuterated solvent, such as D2O, DMSO-D6 or CDCl3 unless otherwise noted. Chemical shifts values (6) are indicated in parts per million (ppm) with reference to tetramethylsilane (TMS) as the internal standard.

High Pressure Liquid Chromatography-Mass Spectrometry (LCMS) experiments to determine retention times (RT) and associated mass ions were performed using one of the following methods.

Mass Spectra (MS) were recorded using a Micromass mass spectrometer. Generally, the method used was positive electro-spray ionization, scanning mass m/z from 100 to 1000. Liquid chromatography was performed on a Hewlett Packard 1100 Series Binary Pump & Degasser; Auxiliary detectors used were: Hewlett Packard 1100 Series UV detector, wavelength=220 nm and Sedere SEDEX 75 Evaporative Light Scattering (ELS) detector temperature=46° C., N2 pressure=4 bar.

LCT: Grad (AcN+0.05% TFA):(H2O+0.05% TFA)=5:95 (0 min) to 95:5 (2.5 min) to 95:5 (3 min). Column: YMC Jsphere 33×2 4 μM, 1 ml/min MUX: Column: YMC Jsphere 33×2, 1 ml/min Grad (AcN+0.05% TFA):(H2O+0.05% TFA)=5:95 (0 min) to 95:5 (3.4 min) to 95:5 (4.4 min).

LCT2: YMC Jsphere 33×2 4 μM, (AcN+0.05% TFA):(H2O+0.05% TFA)=5:95 (0 min) to 95:5 (3.4 min) to 95:5 (4.4 min)

QU: YMC Jsphere 33×2 1 ml/min, (AcN+0.08% formic acid):(H2O+0.1% formic acid)=5:95 (0 min) to 95:5 (2.5 min) to 95:5 (3.0 min)

LC-MS spectra for some of the compounds in the examples were obtained with UPLC Acquity device of Waters for liquid chromatography part, coupling with mass spectrometer ZMD of Waters. This system was piloted by MassLynx v4.1 software. Detection was made in UV at 220 nm.

Operational Conditions for Liquid Chromatography Part are the Following:

Column: Assentis Express $C_{18}$ 50×2.1 mm, 2.7μ supelco

Eluent: Way A: $H_2O$+0.02% TFA;

Way B: $CH_3CN$+0.014% TFA;

Gradient: $T_0$ min: 2% B, $T_1$ min: 98% B, $T_{1.3}$ min: 98% B, $T_{1.33}$ min: 2% B, $T_{1.5}$ min: following injection;

Flow: 1 mL/min;

Temperature: 55° C.

SQD: ESI+30V

UV: 220 nm

Injection: 0.2 μl.

Example 1: 2-(1-methylcyclohexyl)-2-[[1-[[4-(trifluoromethoxy)phenyl]methoxy]naphthalene-2-carbonyl]amino]acetic Acid

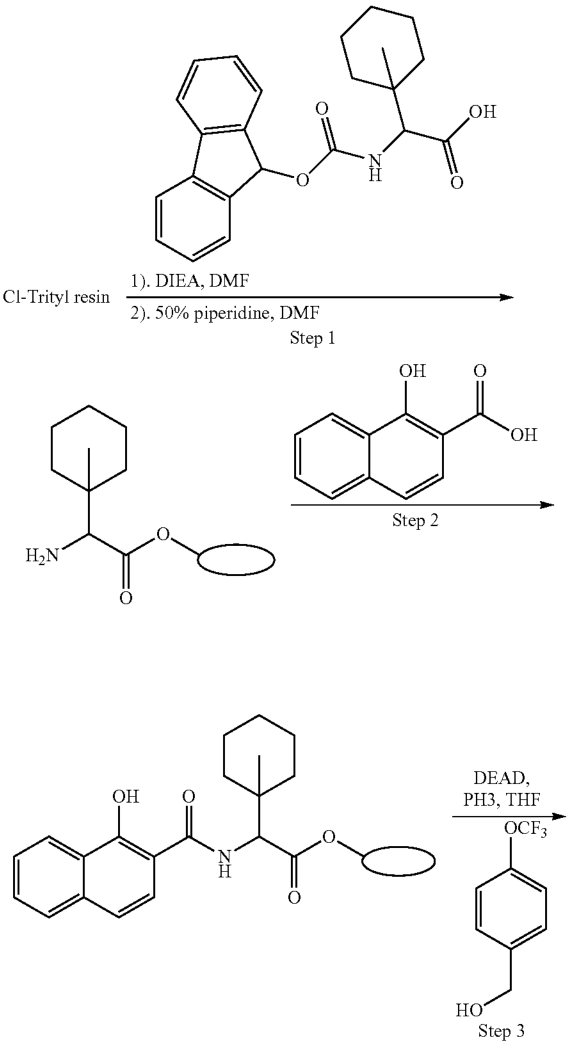

-continued

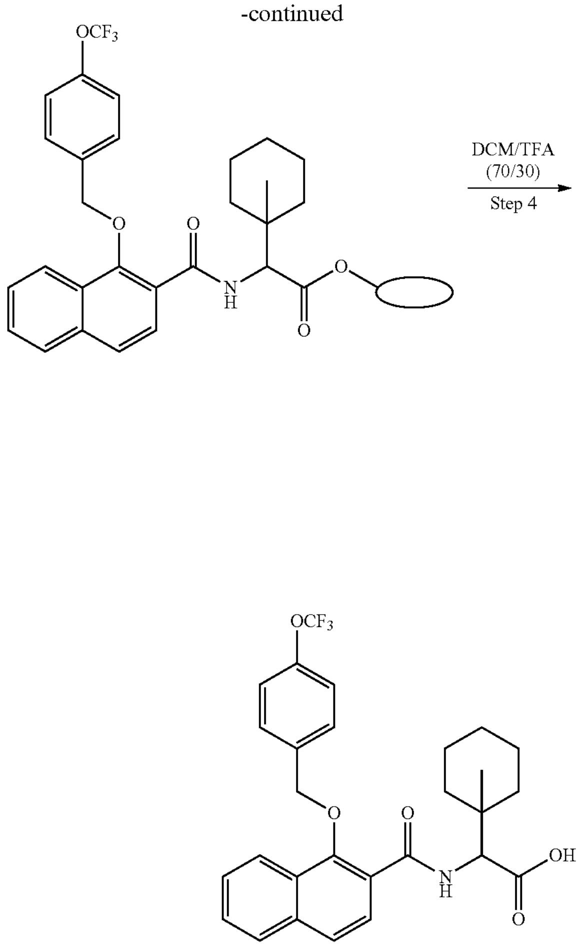

Step 1: 1 g of 2-ChloroTrityl chloride resin (100-200 mesh, Advanced ChemTech) S=1.7 mmol/g was swollen 1 h, rt in dry DMF in 20 mL syringe, then drained. Solution of 6.8 mmol (4 eq.) of L-Fmoc-AA-OH was dissolved in 8 mL dry DMF and 3.5 mL (=21 mmol) of DIEA was added, and resulting slurry in syringe was shaken 12 h at rt. Drained resin was washed 5 times using 10 mL of dry DMF via 2 minute shaking followed by draining. Fmoc deprotection was achieved via 2 times 20 min rt treatment with 12 mL of (1:1) PIP/DMF (Small sample ~40 mg of dry resin, was used in 'fmoc-reading procedure' to establish resin substitution. Usually S=0.6-0.8 mmol/g was achieved). This was followed by a washing with 10 mL of dry DMF×5 via 2 minute shaking followed by draining. The prepared AA-preloaded resin was used in next step as is.

Step 2: 0.2 g of AA-preloaded resin in a syringe, swollen in DMF, was mixed with solution of 0.64 mmol (=4 eq.) of aromatic-hydroxy-acid pre-activated via treatment of 0.64 mmol=244 mg HATU in 4 mL DMF and 0.33 mL DIEA (2 mmol). Slurry was shaken for 12 h at rt, then washed 5 times with 8 mL of DMF and 4 times with 8 mL of THF. Drained resin was dried in vacuum 12 h, and used in next step as is.

Step 3: Solution of 0.8 mmol (=5 eq.) of respective R3-alcohol, 0.8 mmol=210 mg PPh3 in 5 mL of dry THF was added to the syringe containing 0.2 g of dry resin from step 2. Capped syringe was cooled to −5 deg C. in fridge. Precooled solution of 0.8 mmol=162 mg DIAD in 0.4 mL of dry THF was added and shaken syringe was allowed to reach rt (takes 1 h). Resin in syringe was washed 8 times with 6 mL of dry THF. Drained resin was dried in vacuum 12 h, and used in next step as is.

Step 4: Syringe containing 0.2 g of resin from step 3 was shaken as slurry with mixture 2% TFA, 5% TIPS in DCM for 1 h at rt. Drained liquid was collected and resin retreated 3 more times (20 minutes each) with the same mixture. Collected extracts were evaporated with stream of nitrogen, and oily residue was dried in vacuum 12 h rt. This residue was dissolved in 2 mL of DMF and injected to HPLC, pure product containing fractions were lyophilized. Yields vary from 30 to 75%.

Example 1: LCMS: Rt=4.38 Min, m/z ($ES^+$)=516 ($M+H^+$)

The following compounds (examples 2 through 236) exemplified below were prepared in a manner analogous to Example 1 described above.

Example 2: (S)-3,3-dimethyl-2-(1-((5-(trifluoromethyl)pyridin-2-yl)methoxy)-2-naphthamido)butanoic Acid

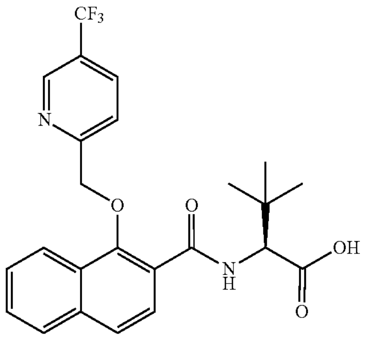

LCMS: $t_R$=3.60 min., m/z ($ES^+$)=460 ($M+H^+$).

Example 3: (S)-2-(3-(trifluoromethyl)bicyclo[1.1.1]pentan-1-yl)-2-(1-((4-((trifluoromethyl)sulfonyl)benzyl)oxy)-2-naphthamido)acetic Acid

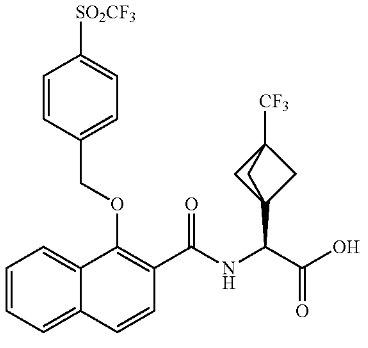

LCMS: $t_R$=2.51 min., m/z ($ES^+$)=602 ($M+H^+$).

Example 4: (S)-2-(6-fluoro-1-((4-(trifluoromethoxy)benzyl)oxy)-2-naphthamido)-2-(3-(trifluoromethyl)bicyclo[1.1.1]pentan-1-yl)acetic Acid

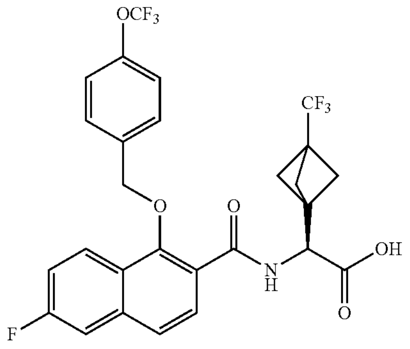 [SMILES: O=C(N[C@H](C(=O)O)C12CC(C(F)(F)F)(C1)C2)c1ccc2cc(F)ccc2c1OCc1ccc(OC(F)(F)F)cc1]

LCMS: $t_R$=2.62 min., m/z ($ES^+$)=572 ($M+H^+$).

Example 5: (S)-3-methyl-3-phenyl-2-(1-((4-((trifluoromethyl)thio)benzyl)oxy)-2-naphthamido)butanoic Acid

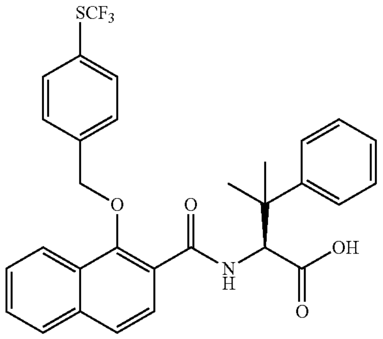

LCMS: $t_R$=4.38 min., m/z ($ES^+$)=554 ($M+H^+$).

Example 6: (S)-2-(6-fluoro-1-((4-(trifluoromethoxy)benzyl)oxy)-2-naphthamido)-2-(3-methyloxetan-3-yl)acetic Acid

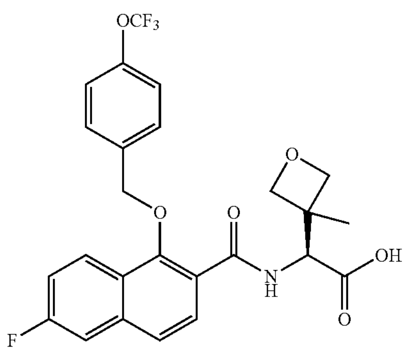 [SMILES: CC1([C@H](NC(=O)c2ccc3cc(F)ccc3c2OCc2ccc(OC(F)(F)F)cc2)C(=O)O)COC1]

LCMS: $t_R$=2.07 min., m/z ($ES^+$)=507 ($M+H^+$).

Example 7: (S)-2-(1-((4,4-difluorocyclohexyl)methoxy)-6-fluoro-2-naphthamido)-3-methyl-3-phenylbutanoic Acid

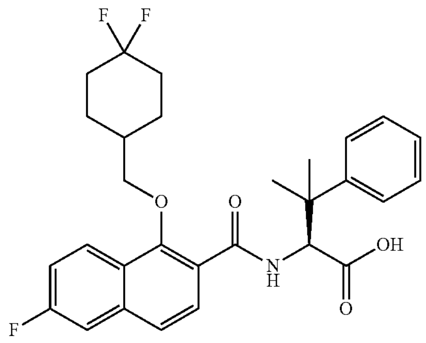 [SMILES: CC(C)(c1ccccc1)[C@H](NC(=O)c1ccc2cc(F)ccc2c1OCC1CCC(F)(F)CC1)C(=O)O]

LCMS: $t_R$=4.18 min., m/z ($ES^+$)=514 ($M+H^+$).

Example 8: (S)-2-(6-fluoro-1-((4-(trifluoromethyl)benzyl)oxy)-2-naphthamido)-2-(3-methyloxetan-3-yl)acetic Acid

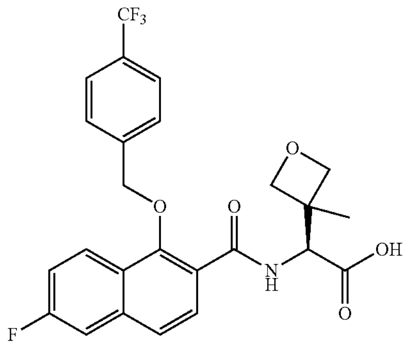 [SMILES: CC1([C@H](NC(=O)c2ccc3cc(F)ccc3c2OCc2ccc(C(F)(F)F)cc2)C(=O)O)COC1]

LCMS: $t_R$=2.04 min., m/z ($ES^+$)=491 ($M+H^+$).

Example 9: (S)-3-methyl-3-phenyl-2-(1-((4-(trifluoromethyl)benzyl)oxy)-2-naphthamido)butanoic Acid

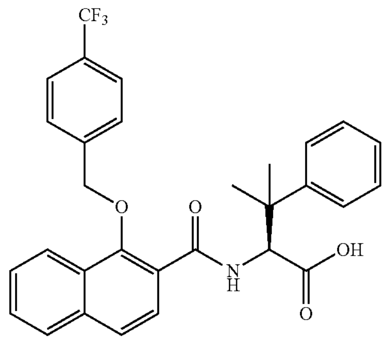 [SMILES: CC(C)(c1ccccc1)[C@H](NC(=O)c1ccc2ccccc2c1OCc1ccc(C(F)(F)F)cc1)C(=O)O]

LCMS: $t_R$=4.42 min., m/z ($ES^+$)=522 ($M+H^+$).

Example 10: (S)-2-(6-fluoro-1-((4-((trifluoromethyl)thio)benzyl)oxy)-2-naphthamido)-3-methyl-3-phenylbutanoic Acid

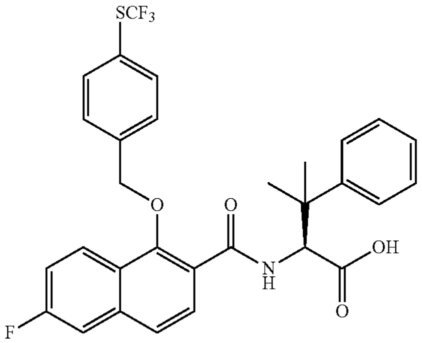

LCMS: $t_R$=4.36 min., m/z ($ES^+$)=572 ($M+H^+$).

Example 11: (S)-2-((1r,4S)-bicyclo[2.2.1]heptan-1-yl)-2-(6-fluoro-1-((4-(trifluoromethyl)benzyl)oxy)-2-naphthamido)acetic Acid

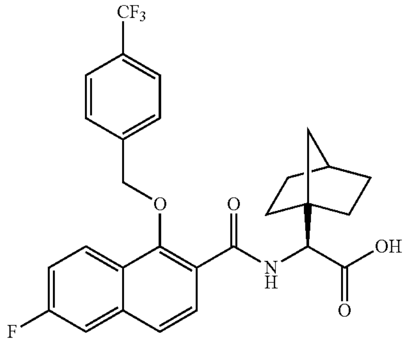 [SMILES: O=C(N[C@H](C(=O)O)C12CCC(CC1)C2)c1ccc2cc(F)ccc2c1OCc1ccc(C(F)(F)F)cc1]

LCMS: $t_R$=4.24 min., m/z ($ES^+$)=498 ($M+H^+$).

Example 12: (S)-2-(1-((4-(difluoromethoxy)benzyl)oxy)-2-naphthamido)-3,3-dimethylbutanoic Acid

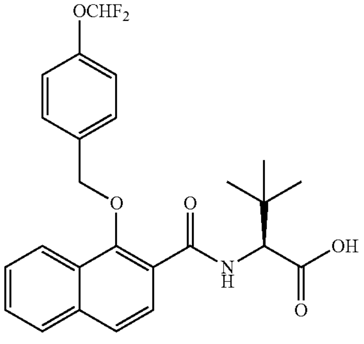 [SMILES: CC(C)(C)[C@H](NC(=O)c1ccc2ccccc2c1OCc1ccc(OC(F)F)cc1)C(=O)O]

LCMS: $t_R$=2.54 min., m/z ($ES^+$)=458 ($M+H^+$).

Example 13: (S)-2-(1-((4-(trifluoromethyl)benzyl)oxy)-2-naphthamido)-2-(3-(trifluoromethyl)bicyclo[1.1.1]pentan-1-yl)acetic Acid

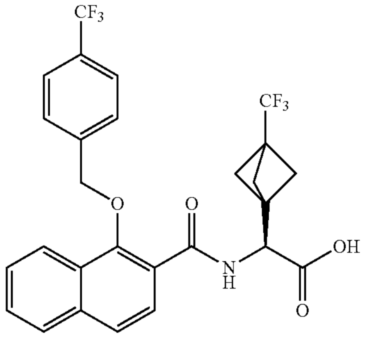 [SMILES: O=C(N[C@H](C(=O)O)C12CC(C(F)(F)F)(C1)C2)c1ccc2ccccc2c1OCc1ccc(C(F)(F)F)cc1]

LCMS: $t_R$=2.56 min., m/z ($ES^+$)=538 ($M+H^+$).

Example 14: (S)-2-((1r,4S)-bicyclo[2.2.1]heptan-1-yl)-2-(1-((4-(trifluoromethoxy)benzyl)oxy)-2-naphthamido)acetic Acid

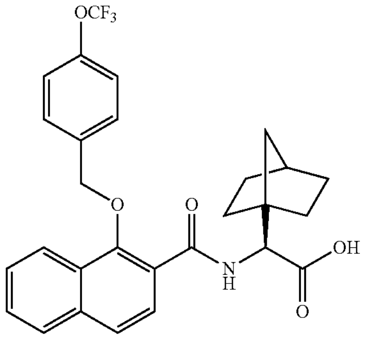 [SMILES: O=C(N[C@H](C(=O)O)C12CCC(CC1)C2)c1ccc2ccccc2c1OCc1ccc(OC(F)(F)F)cc1]

LCMS: $t_R$=4.30 min., m/z ($ES^+$)=514 ($M+H^+$).

Example 15: (S)-2-(6-fluoro-1-((4-(trifluoromethyl)benzyl)oxy)-2-naphthamido)-2-(3-(trifluoromethyl)bicyclo[1.1.1]pentan-1-yl)acetic Acid

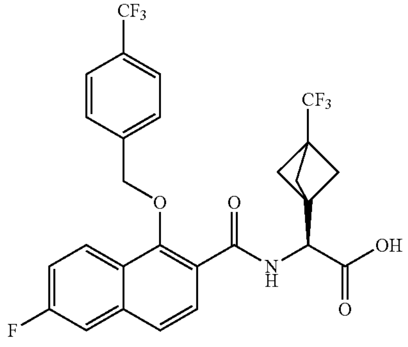 [SMILES: O=C(N[C@H](C(=O)O)C12CC(C(F)(F)F)(C1)C2)c1ccc2cc(F)ccc2c1OCc1ccc(C(F)(F)F)cc1]

LCMS: $t_R$=2.58 min., m/z ($ES^+$)=556 ($M+H^+$).

Example 16: 3-methyl-3-phenyl-2-(1-((4-(trifluoromethyl)benzyl)oxy)-2-naphthamido)butanoic Acid

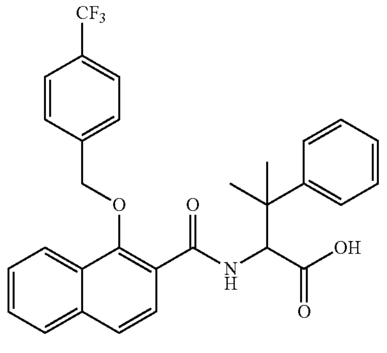 [SMILES: CC(C)(c1ccccc1)C(NC(=O)c1ccc2ccccc2c1OCc1ccc(C(F)(F)F)cc1)C(=O)O]

LCMS: $t_R$=2.55 min., m/z ($ES^+$)=556 ($M+H^+$).

Example 17: (S)-2-(3-(trifluoromethyl)bicyclo[1.1.1]pentan-1-yl)-2-(1-((4-((trifluoromethyl)thio)benzyl)oxy)-2-naphthamido)acetic Acid

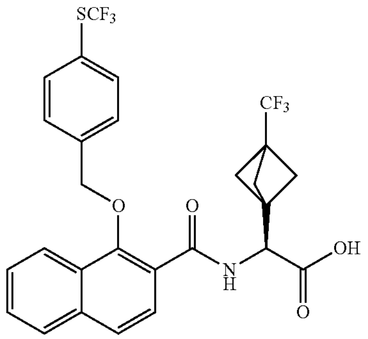

LCMS: $t_R$=2.68 min., m/z ($ES^+$)=570 ($M+H^+$).

Example 18: 2-(3-methyloxetan-3-yl)-2-(1-((4-(trifluoromethyl)benzyl)oxy)-2-naphthamido)acetic Acid

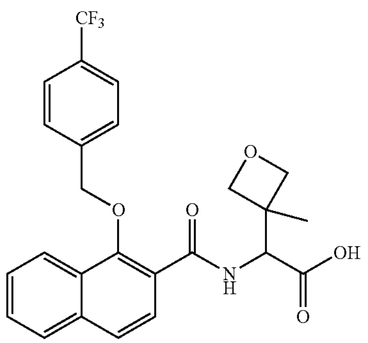

LCMS: $t_R$=2.01 min., m/z ($ES^+$)=474 ($M+H^+$).

Example 19: (S)-2-(6-fluoro-1-((4-(trifluoromethoxy)benzyl)oxy)-2-naphthamido)-3,3-dimethylbutanoic Acid

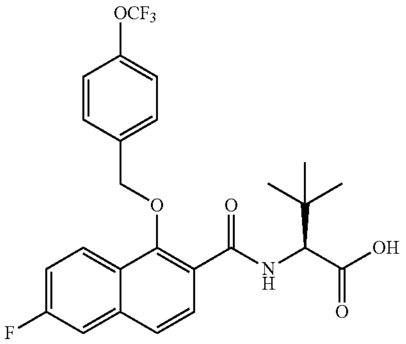

LCMS: $t_R$=2.81 min., m/z ($ES^+$)=494 ($M+H^+$).

Example 20: 2-(3-methyloxetan-3-yl)-2-(1-((4-(pentafluoro-16-sulfanyl)benzyl)oxy)-2-naphthamido)acetic Acid

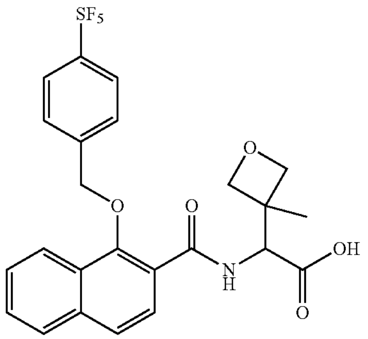 [SMILES: CC1(C(NC(=O)c2ccc3ccccc3c2OCc2ccc(C(F)(F)F)cc2)C(=O)O)COC1]

LCMS: $t_R$=2.08 min., m/z ($ES^+$)=532 ($M+H^+$).

Example 21: 2-(3-methyloxetan-3-yl)-2-(1-((4-((trifluoromethyl)thio)benzyl)oxy)-2-naphthamido)acetic Acid

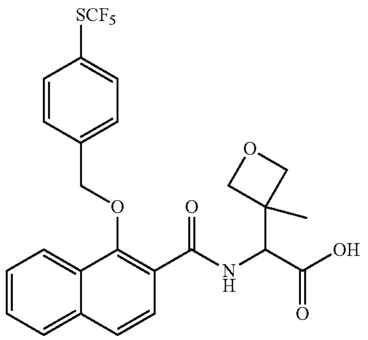

LCMS: $t_R$=2.12 min., m/z ($ES^+$)=506 ($M+H^+$).

Example 22: (S)-2-(6-fluoro-1-((4-((trifluoromethyl)thio)benzyl)oxy)-2-naphthamido)-3-methyl-3-phenylbutanoic Acid

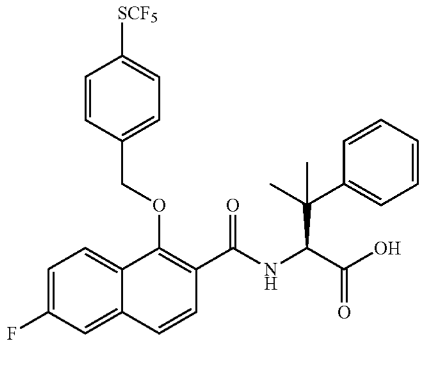

LCMS: $t_R$=2.78 min., m/z ($ES^+$)=572 ($M+H^+$).

Example 23: (S)-3-methyl-2-(1-((4-(methylsulfonyl)benzyl)oxy)-2-naphthamido)-3-phenylbutanoic Acid

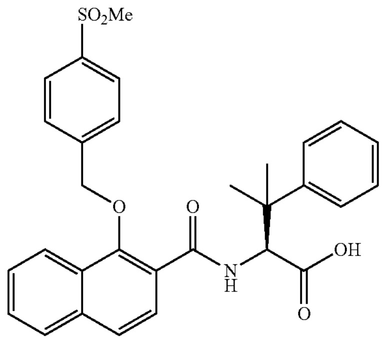 [SMILES: CC(C)(c1ccccc1)[C@H](NC(=O)c1ccc2ccccc2c1OCc1ccc(S(C)(=O)=O)cc1)C(=O)O]

LCMS: $t_R$=2.17 min., m/z ($ES^+$)=532 ($M+H^+$).

Example 24: (S)-2-(1-((4-(pentafluoro-$\lambda^6$-sulfanyl)benzyl)oxy)-2-naphthamido)-2-(3-(trifluoromethyl)bicyclo[1.1.1]pentan-1-yl)acetic Acid

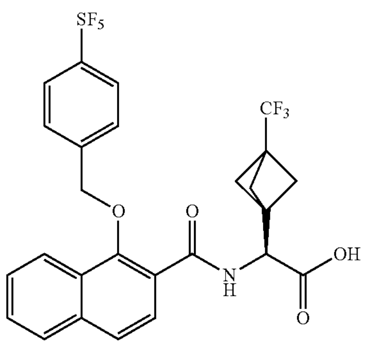

LCMS: $t_R$=2.17 min., m/z ($ES^+$)=532 ($M+H^+$).

Example 25: (S)-2-(1-((3-fluoro-4-(trifluoromethyl)benzyl)oxy)-2-naphthamido)-3,3-dimethylbutanoic Acid

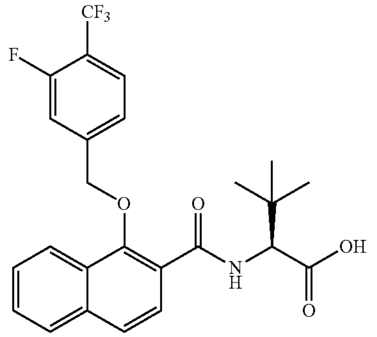 [SMILES: CC(C)(C)[C@H](NC(=O)c1ccc2ccccc2c1OCc1ccc(C(F)(F)F)c(F)c1)C(=O)O]

LCMS: $t_R$=3.99 min., m/z ($ES^+$)=478 ($M+H^+$).

Example 26: (S)-3,3-dimethyl-2-(1-(((1s,4R)-4-(trifluoromethyl)cyclohexyl)methoxy)-2-naphthamido)butanoic Acid

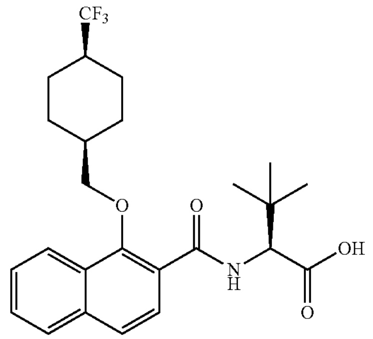 [SMILES: CC(C)(C)[C@H](NC(=O)c1ccc2ccccc2c1OC[C@H]1CC[C@@H](C(F)(F)F)CC1)C(=O)O]

LCMS: $t_R$=2.53 min., m/z ($ES^+$)=466 ($M+H^+$).

Example 27: (S)-2-(6-fluoro-1-((4-(trifluoromethyl)benzyl)oxy)-2-naphthamido)-3,3-dimethylbutanoic Acid

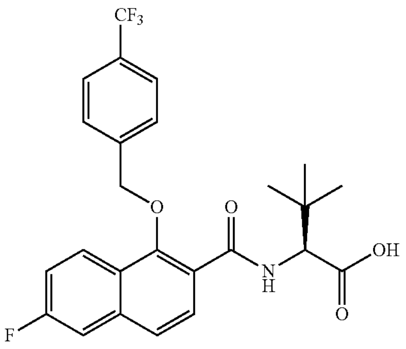

LCMS: $t_R$=4.02 min., m/z (ES)=478 ($M+H^+$).

Example 28: (S)-2-(1-((4-(methoxycarbonyl)benzyl)oxy)-2-naphthamido)-3,3-dimethylbutanoic Acid

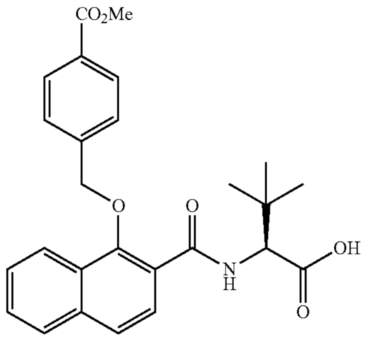

LCMS: $t_R$=3.56 min., m/z ($ES^+$)=450 ($M+H^+$).

Example 29: (S)-2-(1-((4-(hydroxymethyl)cyclohexyl)methoxy)-2-naphthamido)-3,3-dimethylbutanoic Acid

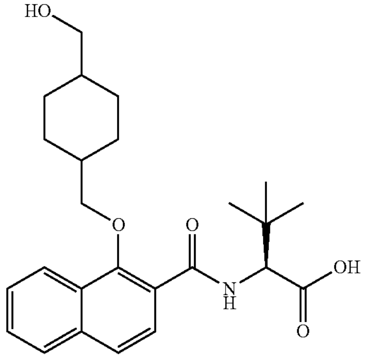 [SMILES: CC(C)(C)[C@H](NC(=O)c1ccc2ccccc2c1OCC1CCC(CO)CC1)C(=O)O]

LCMS: $t_R$=2.85 min., m/z ($ES^+$)=428 ($M+H^+$).

Example 30: (S)-2-(6-fluoro-1-((4-(trifluoromethoxy)benzyl)oxy)-2-naphthamido)-2-(1-methylcyclopropyl)acetic Acid

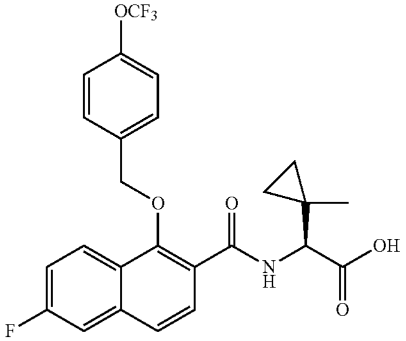 [SMILES: CC1([C@H](NC(=O)c2ccc3cc(F)ccc3c2OCc2ccc(OC(F)(F)F)cc2)C(=O)O)CC1]

LCMS: $t_R$=2.47 min., m/z ($ES^+$)=491 ($M+H^+$).

Example 31: (S)-2-(1-((4-cyanobenzyl)oxy)-2-naphthamido)-3,3-dimethylbutanoic Acid

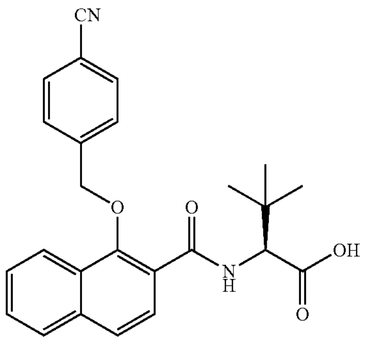

LCMS: $t_R$=3.43 min., m/z ($ES^+$)=417 ($M+H^+$).

Example 32: (S)-2-(6-methoxy-1-((4-((trifluoromethyl)thio)benzyl)oxy)-2-naphthamido)-3,3-dimethylpentanoic Acid

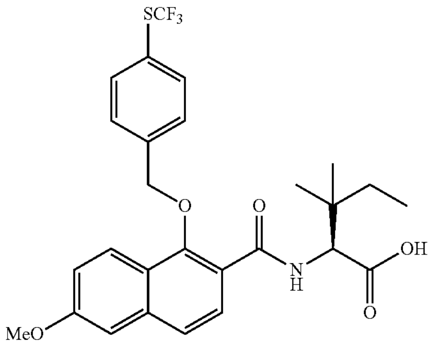

LCMS: $t_R$=3.91 min., m/z ($ES^+$)=536 ($M+H^+$).

Example 33: (S)-2-(6-fluoro-1-((4-(trifluoromethoxy)benzyl)oxy)-2-naphthamido)-2-(1-methylcyclohexyl)acetic Acid

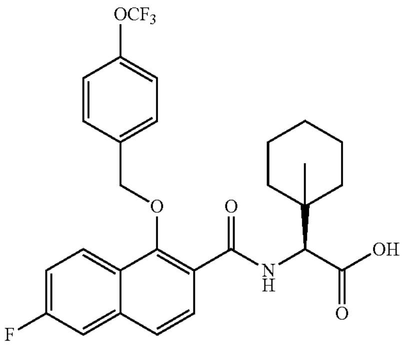

LCMS: $t_R$=4.41 min., m/z ($ES^+$)=534 ($M+H^+$).

Example 34: (S)-2-(1-((4,4-difluorocyclohexyl)methoxy)-6-fluoro-2-naphthamido)-3,3-dimethylpentanoic Acid

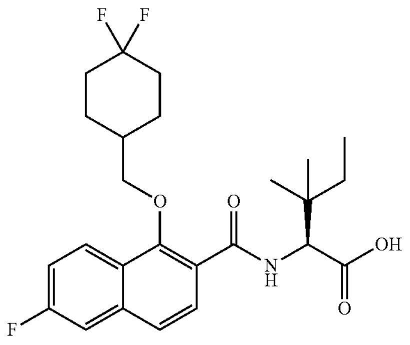 [SMILES: CCC(C)(C)[C@H](NC(=O)c1ccc2cc(F)ccc2c1OCC1CCC(F)(F)CC1)C(=O)O]

LCMS: $t_R$=4.12 min., m/z ($ES^+$)=466 ($M+H^+$).

Example 35: (S)-3,3-dimethyl-2-(1-((4-((trifluoromethyl)thio)benzyl)oxy)-2-naphthamido)butanoic Acid

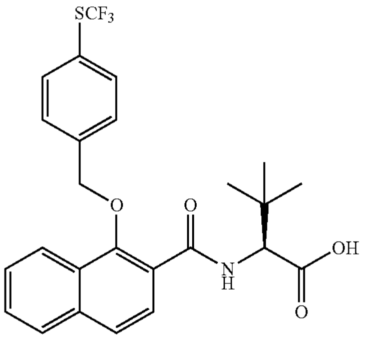

LCMS: $t_R$=4.62 min., m/z ($ES^+$)=492 ($M+H^+$).

Example 36: 2-(1-methylcyclohexyl)-2-(1-((4-((trifluoromethyl)thio)benzyl)oxy)-2-naphthamido)acetic Acid

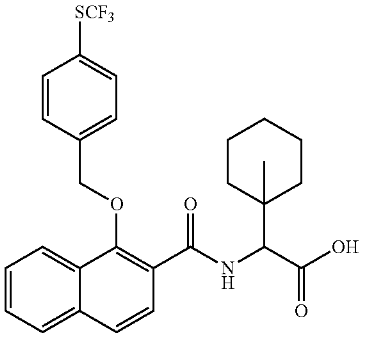

LCMS: $t_R$=4.45 min., m/z ($ES^+$)=532 ($M+H^+$).

Example 37: (S)-3,3-dimethyl-2-(1-((4-(perfluoroethyl)benzyl)oxy)-2-naphthamido)butanoic Acid

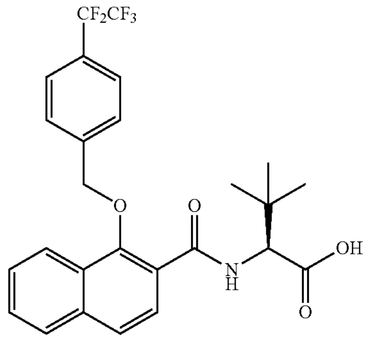

LCMS: $t_R$=4.17 min., m/z ($ES^+$)=510 ($M+H^+$).

Example 38: (S)-2-(6-methoxy-1-((4-(trifluoromethyl)benzyl)oxy)-2-naphthamido)-3,3-dimethylbutanoic Acid

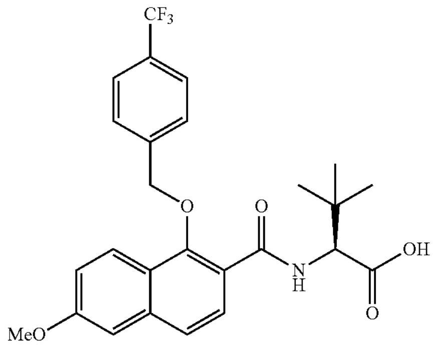 [SMILES: COc1ccc2c(OCc3ccc(C(F)(F)F)cc3)c(C(=O)N[C@H](C(=O)O)C(C)(C)C)ccc2c1]

LCMS: $t_R$=3.56 min., m/z ($ES^+$)=490 ($M+H^+$).

Example 39: 2-(1-methylcyclohexyl)-2-(1-(((1s,4s)-4-(trifluoromethyl)cyclohexyl)methoxy)-2-naphthamido)acetic Acid

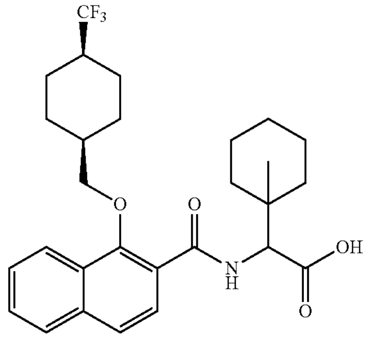

LCMS: $t_R$=2.75 min., m/z ($ES^+$)=506 ($M+H^+$).

Example 40: (S)-2-(6-fluoro-1-((4-(trifluoromethyl)benzyl)oxy)-2-naphthamido)-2-(1-methylcyclohexyl)acetic Acid

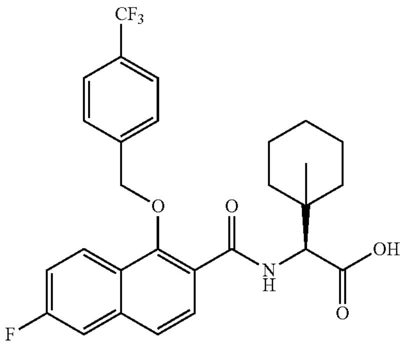

LCMS: $t_R$=4.02 min., m/z ($ES^+$)=518 ($M+H^+$).

Example 41: (2S)-2-(1-(bicyclo[2.2.1]heptan-2-ylmethoxy)-2-naphthamido)-3,3-dimethylbutanoic Acid

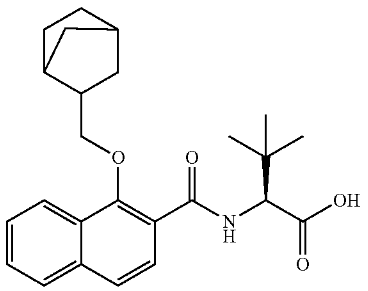 [SMILES: CC(C)(C)[C@H](NC(=O)c1ccc2ccccc2c1OCC1CC2CCC1C2)C(=O)O]

LCMS: $t_R$=3.65 min., m/z ($ES^+$)=410 ($M+H^+$).

Example 42: (2S)-2-(1-(1-(4-bromophenyl)ethoxy)-2-naphthamido)-3,3-dimethylbutanoic Acid

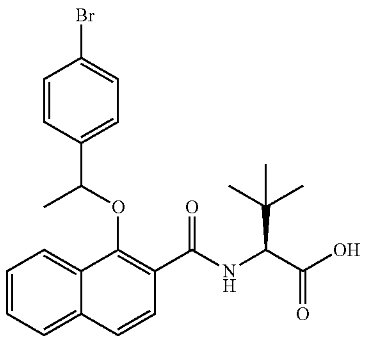 [SMILES: CC(Oc1c(C(=O)N[C@H](C(=O)O)C(C)(C)C)ccc2ccccc12)c1ccc(Br)cc1]

LCMS: $t_R$=4.29 min., m/z ($ES^+$)=484 ($M+H^+$).

Example 43: 2-(1-methylcyclohexyl)-2-(1-(((1r,4r)-4-(trifluoromethyl)cyclohexyl)methoxy)-2-naphthamido)acetic Acid

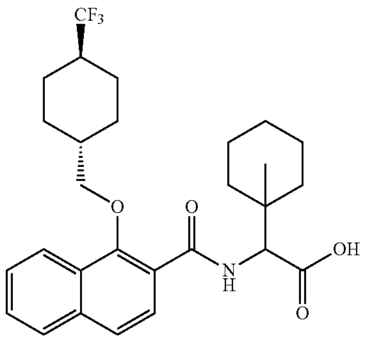

LCMS: $t_R$=2.79 min., m/z ($ES^+$)=506 ($M+H^+$).

Example 44: 2-(1-methylcyclohexyl)-2-(1-((4-(methylsulfonyl)benzyl)oxy)-2-naphthamido)acetic Acid

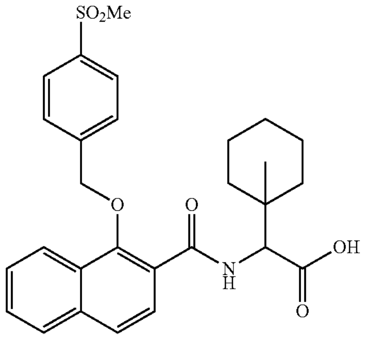

LCMS: $t_R$=2.22 min., m/z ($ES^+$)=510 ($M+H^+$).

Example 45: (S)-2-(1-(cyclohexylmethoxy)-6-fluoro-2-naphthamido)-3,3-dimethylbutanoic Acid

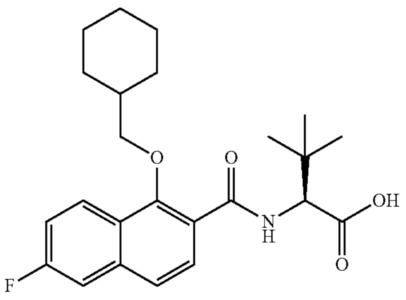 [SMILES: CC(C)(C)[C@H](NC(=O)c1ccc2cc(F)ccc2c1OCC1CCCCC1)C(=O)O]

LCMS: $t_R$=2.71 min., m/z ($ES^+$)=416 ($M+H^+$).

Example 46: (S)-2-(1-((4-bromobenzyl)oxy)-2-naphthamido)-3,3-dimethylbutanoic Acid

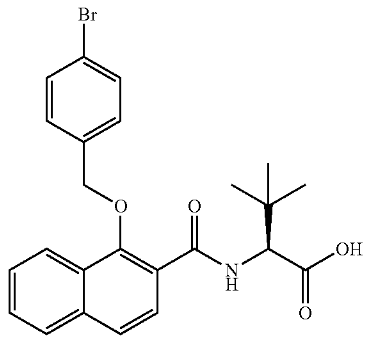 [SMILES: CC(C)(C)[C@H](NC(=O)c1ccc2ccccc2c1OCc1ccc(Br)cc1)C(=O)O]

LCMS: $t_R$=4.22 min., m/z ($ES^+$)=470 ($M+H^+$).

Example 47: (S)-2-(1-((3,4-dichlorobenzyl)oxy)-2-naphthamido)-3,3-dimethylbutanoic Acid

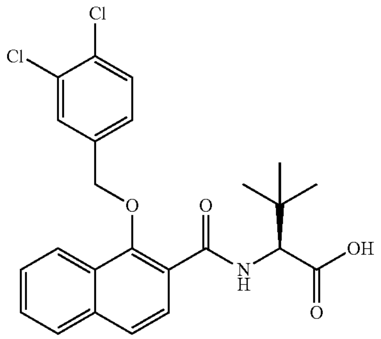 [SMILES: CC(C)(C)[C@H](NC(=O)c1ccc2ccccc2c1OCc1ccc(Cl)c(Cl)c1)C(=O)O]

LCMS: $t_R$=2.71 min., m/z ($ES^+$)=460 ($M+H^+$).

Example 48: 2-(1-methylcyclohexyl)-2-(1-((4-(pentafluoro-16-sulfanyl)benzyl)oxy)-2-naphthamido) acetic Acid

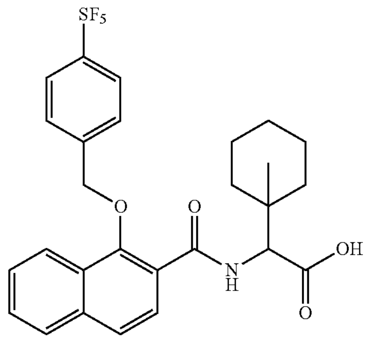

LCMS: $t_R$=4.39 min., m/z ($ES^+$)=558 ($M+H^+$).

Example 49: (2S)-3,3-dimethyl-2-(1-((4-(prop-1-en-2-yl)cyclohex-1-en-1-yl)methoxy)-2-naphthamido) butanoic Acid

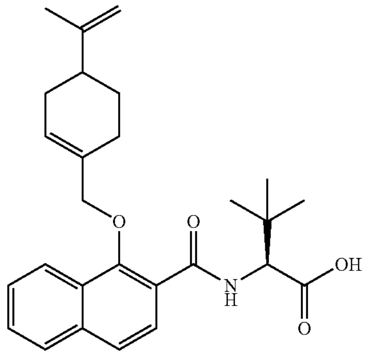 [SMILES: C=C(C)C1CC=C(COc2c(C(=O)N[C@H](C(=O)O)C(C)(C)C)ccc3ccccc23)CC1]

LCMS: $t_R$=4.05 min., m/z ($ES^+$)=436 ($M+H^+$).

Example 50: 2-(6-fluoro-1-((4-(pentafluoro-16-sulfanyl)benzyl)oxy)-2-naphthamido)-2-(1-methylcyclohexyl)acetic Acid

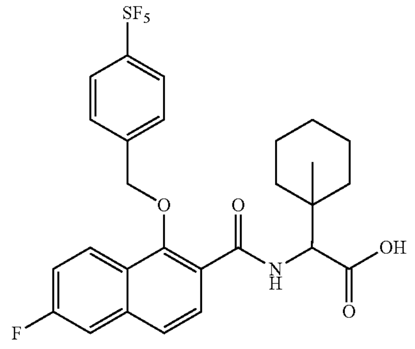

LCMS: $t_R$=4.45 min., m/z ($ES^+$)=576 ($M+H^+$).

Example 51: (S)-2-(4-bromo-1-((4-(trifluoromethyl) benzyl)oxy)-2-naphthamido)-3,3-dimethylbutanoic Acid

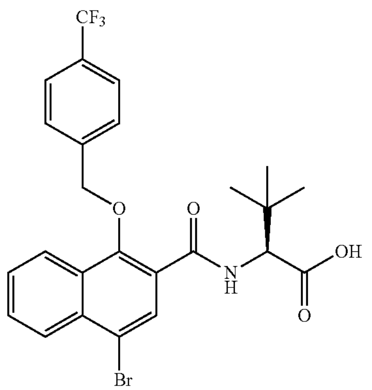 [SMILES: CC(C)(C)[C@H](NC(=O)c1cc(Br)c2ccccc2c1OCc1ccc(C(F)(F)F)cc1)C(=O)O]

LCMS: $t_R$=4.31 min., m/z ($ES^+$)=538 ($M+H^+$).

Example 52: (S)-2-(6-amino-1-((4-(trifluoromethyl)benzyl)oxy)-2-naphthamido)-3,3-dimethylbutanoic Acid

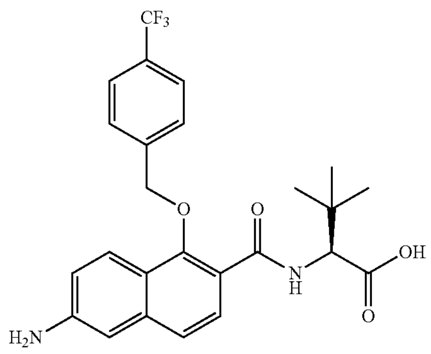 [SMILES: CC(C)(C)[C@H](NC(=O)c1ccc2cc(N)ccc2c1OCc1ccc(C(F)(F)F)cc1)C(=O)O]

LCMS: $t_R$=3.28 min., m/z ($ES^+$)=475 ($M+H^+$).

Example 53: (S)-3,3-dimethyl-2-(1-((4-(methylsulfonyl)benzyl)oxy)-2-naphthamido)pentanoic Acid

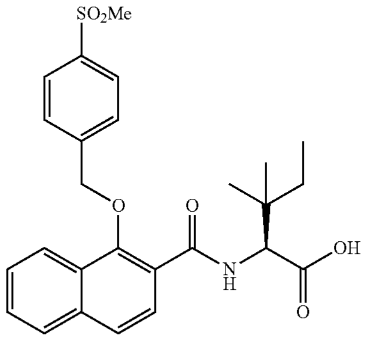 [SMILES: CCC(C)(C)[C@H](NC(=O)c1ccc2ccccc2c1OCc1ccc(S(C)(=O)=O)cc1)C(=O)O]

LCMS: $t_R$=2.10 min., m/z ($ES^+$)=484 ($M+H^+$).

Example 54: 2-(1-((4,4-difluorocyclohexyl)methoxy)-6-fluoro-2-naphthamido)-2-(1-methylcyclohexyl)acetic Acid

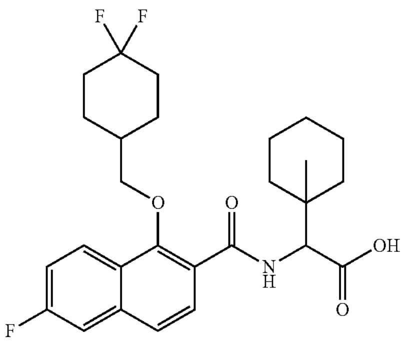

LCMS: $t_R$=4.26 min., m/z ($ES^+$)=492 ($M+H^+$).

Example 55: (S)-3,3-dimethyl-2-(1-((4-((trifluoromethyl)thio)benzyl)oxy)-2-naphthamido)pentanoic Acid

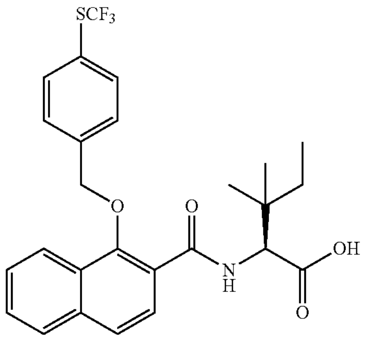

LCMS: $t_R$=4.35 min., m/z ($ES^+$)=506 ($M+H^+$).

Example 56: 2-(1-methylcyclopropyl)-2-(1-((4-(trifluoromethyl)benzyl)oxy)-2-naphthamido)acetic Acid

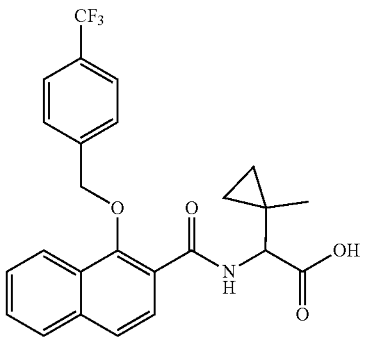 [SMILES: CC1(C(NC(=O)c2ccc3ccccc3c2OCc2ccc(C(F)(F)F)cc2)C(=O)O)CC1]

LCMS: $t_R$=2.41 min., m/z ($ES^+$)=458 ($M+H^+$).

Example 57: (S)-3,3-dimethyl-2-(1-((4-((trifluoromethyl)sulfonyl)benzyl)oxy)-2-naphthamido)butanoic Acid

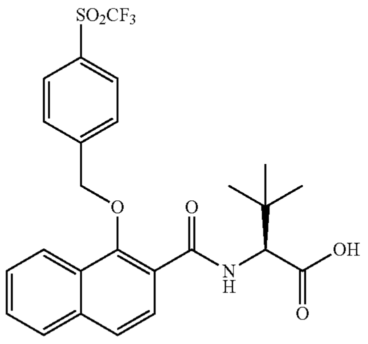

LCMS: $t_R$=2.50 min., m/z ($ES^+$)=524 ($M+H^+$).

Example 58: (S)-2-(1-(benzo[d]thiazol-2-ylmethoxy)-2-naphthamido)-3,3-dimethylbutanoic Acid

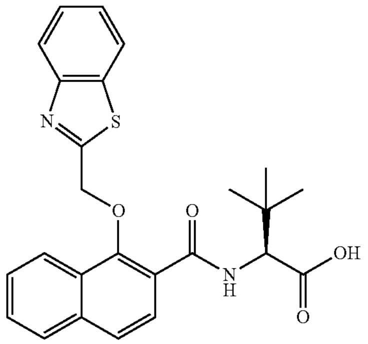 [SMILES: CC(C)(C)[C@H](NC(=O)c1ccc2ccccc2c1OCc1nc2ccccc2s1)C(=O)O]

LCMS: $t_R$=3.11 min., m/z ($ES^+$)=449 ($M+H^+$).

Example 59: (S)-2-(6-hydroxy-1-((4-(trifluoromethyl)benzyl)oxy)-2-naphthamido)-3,3-dimethylbutanoic Acid

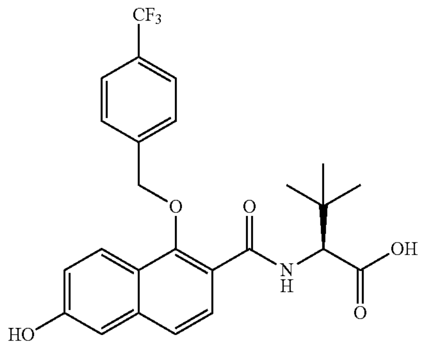

LCMS: $t_R$=3.44 min., m/z ($ES^+$)=476 ($M+H^+$).

Example 60: 2-(6-fluoro-1-((4-(trifluoromethyl)benzyl)oxy)-2-naphthamido)-2-(1-methylcyclopropyl)acetic Acid

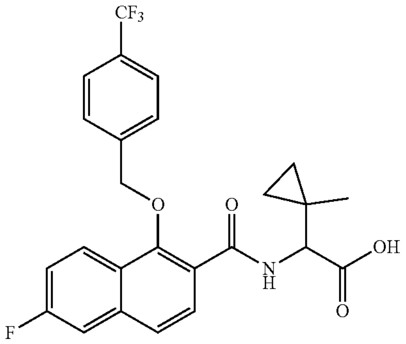 [SMILES: CC1(C(NC(=O)c2ccc3cc(F)ccc3c2OCc2ccc(C(F)(F)F)cc2)C(=O)O)CC1]

LCMS: $t_R$=2.42 min., m/z ($ES^+$)=475 ($M+H^+$).

Example 61: (S)-2-(1-(benzo[d]thiazol-2-ylmethoxy)-6-fluoro-2-naphthamido)-3,3-dimethylbutanoic Acid

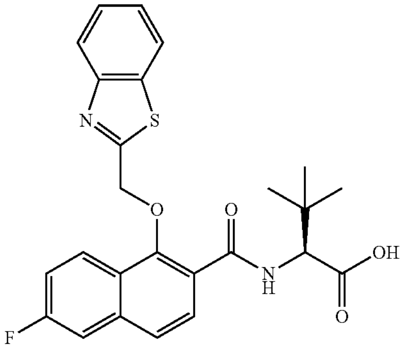 [SMILES: CC(C)(C)[C@H](NC(=O)c1ccc2cc(F)ccc2c1OCc1nc2ccccc2s1)C(=O)O]

LCMS: $t_R$=2.38 min., m/z ($ES^+$)=467 ($M+H^+$).

Example 62: (S)-3,3-dimethyl-2-(1-((1-phenyl-1H-pyrazol-4-yl)methoxy)-2-naphthamido)butanoic Acid

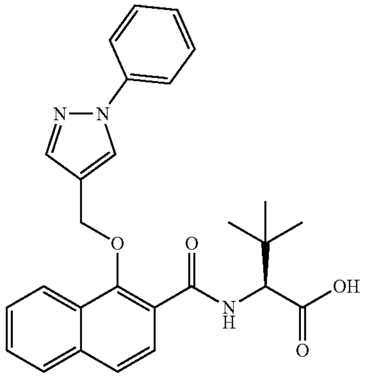 [SMILES: CC(C)(C)[C@H](NC(=O)c1ccc2ccccc2c1OCc1cnn(-c2ccccc2)c1)C(=O)O]

LCMS: $t_R$=3.36 min., m/z ($ES^+$)=458 ($M+H^+$).

Example 63: (S)-2-(6-methoxy-1-((4-((trifluoromethyl)thio)benzyl)oxy)-2-naphthamido)-3,3-dimethylbutanoic Acid

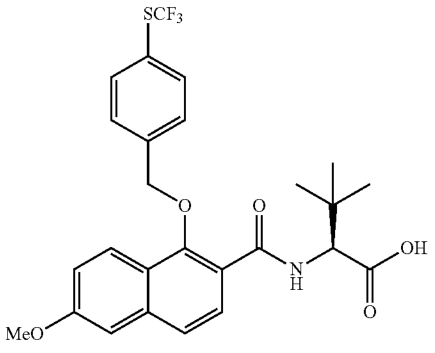

LCMS: $t_R$=3.77 min., m/z ($ES^+$)=522 ($M+H^+$).

Example 64: (S)-2-(4-fluoro-1-((4-(trifluoromethyl) benzyl)oxy)-2-naphthamido)-3,3-dimethylbutanoic Acid

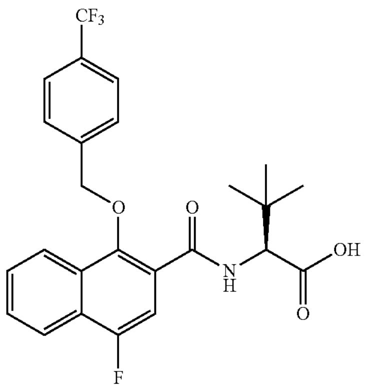 [SMILES: CC(C)(C)[C@H](NC(=O)c1cc(F)c2ccccc2c1OCc1ccc(C(F)(F)F)cc1)C(=O)O]

LCMS: $t_R$=3.73 min., m/z ($ES^+$)=478 ($M+H^+$).

Example 65: (S)-3,3-dimethyl-2-(1-((4-(trifluoromethoxy)benzyl)oxy)-2-naphthamido)butanoic Acid

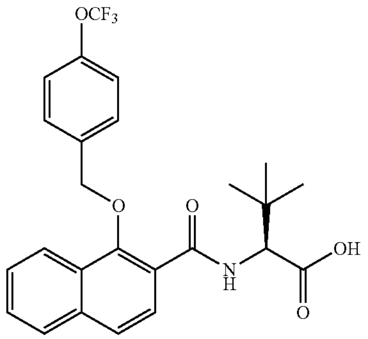 [SMILES: CC(C)(C)[C@H](NC(=O)c1ccc2ccccc2c1OCc1ccc(OC(F)(F)F)cc1)C(=O)O]

LCMS: $t_R$=2.77 min., m/z ($ES^+$)=476 ($M+H^+$).

Example 66: (S)-3,3-dimethyl-2-(1-((4-(methylsulfonyl)benzyl)oxy)-2-naphthamido)butanoic Acid

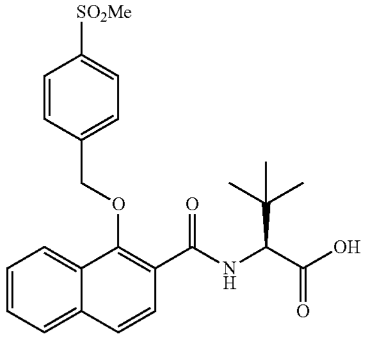 [SMILES: CC(C)(C)[C@H](NC(=O)c1ccc2ccccc2c1OCc1ccc(S(C)(=O)=O)cc1)C(=O)O]

LCMS: $t_R$=2.01 min., m/z ($ES^+$)=470 ($M+H^+$).

Example 67: (S)-3,3-dimethyl-2-(1-((4-(pentafluoro-l6-sulfanyl)benzyl)oxy)-2-naphthamido)butanoic Acid

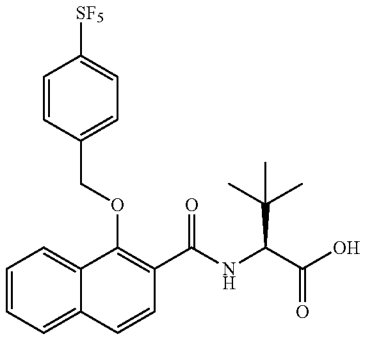

LCMS: $t_R$=4.18 min., m/z ($ES^+$)=518 ($M+H^+$).

Example 68: 2-(1-methylcyclopropyl)-2-(1-((4-(pentafluoro-l6-sulfanyl)benzyl)oxy)-2-naphthamido) acetic Acid

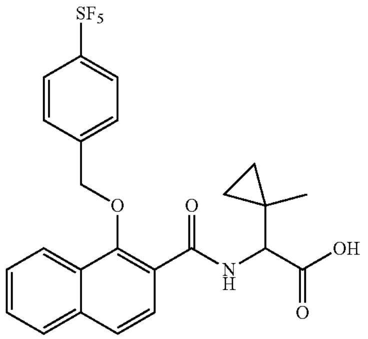

LCMS: $t_R$=2.47 min., m/z ($ES^+$)=516 ($M+H^+$).

Example 69: 2-(6-fluoro-1-((4-((trifluoromethyl) thio)benzyl)oxy)-2-naphthamido)-2-(1-methylcyclohexyl)acetic Acid

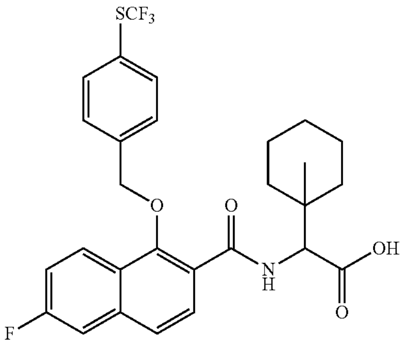

LCMS: $t_R$=4.65 min., m/z ($ES^+$)=550 ($M+H^+$).

Example 70: (S)-2-(1-((2-fluoro-4-(trifluoromethyl)benzyl)oxy)-2-naphthamido)-3,3-dimethylbutanoic Acid

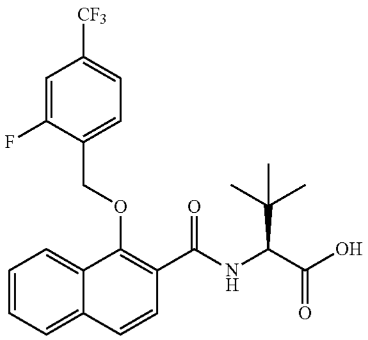 [SMILES: CC(C)(C)[C@H](NC(=O)c1ccc2ccccc2c1OCc1ccc(C(F)(F)F)cc1F)C(=O)O]

LCMS: $t_R$=3.97 min., m/z ($ES^+$)=478 ($M+H^+$).

Example 71: (2S)-3,3-dimethyl-2-(1-(1-(4-(trifluoromethyl)phenyl)ethoxy)-2-naphthamido)butanoic Acid

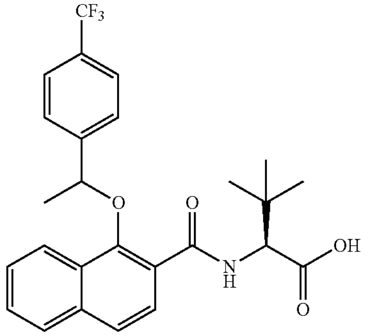 [SMILES: CC(Oc1c(C(=O)N[C@H](C(=O)O)C(C)(C)C)ccc2ccccc12)c1ccc(C(F)(F)F)cc1]

LCMS: $t_R$=4.30 min., m/z ($ES^+$)=474 ($M+H^+$).

Example 72: (S)-2-(1-(cyclohexylmethoxy)-2-naphthamido)-3,3-dimethylbutanoic Acid

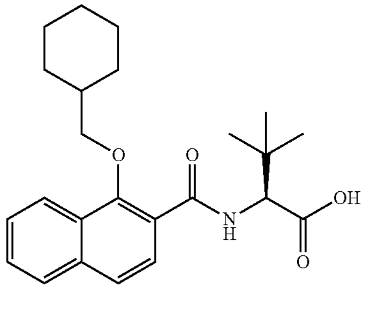 [SMILES: CC(C)(C)[C@H](NC(=O)c1ccc2ccccc2c1OCC1CCCCC1)C(=O)O]

LCMS: $t_R$=3.56 min., m/z ($ES^+$)=398 ($M+H^+$).

Example 73: (S)-3,3-dimethyl-2-(1-((4-(trifluoromethyl)benzyl)oxy)-6-(vinyloxy)-2-naphthamido)butanoic Acid

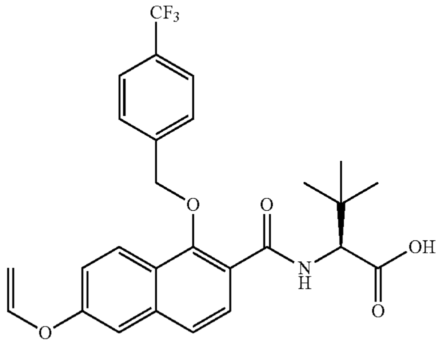 [SMILES: C=COc1ccc2c(OCc3ccc(C(F)(F)F)cc3)c(C(=O)N[C@H](C(=O)O)C(C)(C)C)ccc2c1]

LCMS: $t_R$=4.21 min., m/z ($ES^+$)=516 ($M+H^+$).

Example 74: (S)-3,3-dimethyl-2-(1-((4-(trifluoromethyl)benzyl)oxy)-6-(vinyloxy)-2-naphthamido)butanoic Acid

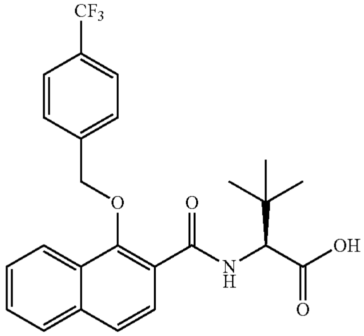

LCMS: $t_R$=4.25 min., m/z ($ES^+$)=460 ($M+H^+$).

Example 75: (S)-2-(6-fluoro-1-((4-((trifluoromethyl)thio)benzyl)oxy)-2-naphthamido)-3,3-dimethylbutanoic Acid

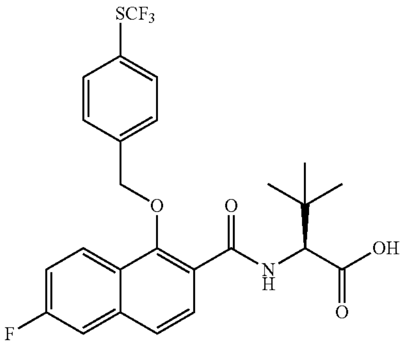

LCMS: $t_R$=4.23 min., m/z ($ES^+$)=510 ($M+H^+$).

Example 76: (S)-2-(1-((4,4-difluorocyclohexyl)methoxy)-6-fluoro-2-naphthamido)-3,3-dimethylbutanoic Acid

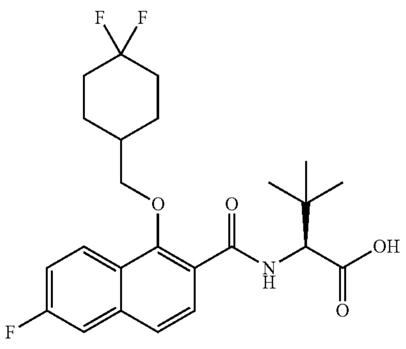

LCMS: $t_R$=4.00 min., m/z ($ES^+$)=452 ($M+H^+$).

Example 77: 2-(1-methylcyclohexyl)-2-(1-((4-((trifluoromethyl)sulfonyl)benzyl)oxy)-2-naphthamido)acetic Acid

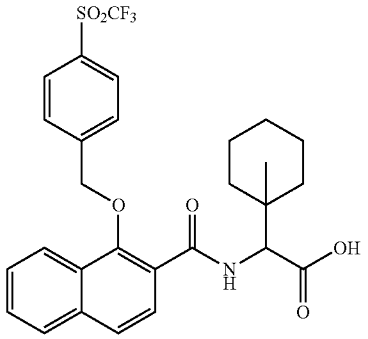

LCMS: $t_R$=2.63 min., m/z ($ES^+$)=564 ($M+H^+$).

Example 78: (S)-3,3-dimethyl-2-(1-((4-(trifluoromethyl)benzyl)oxy)-2-naphthamido)pentanoic Acid

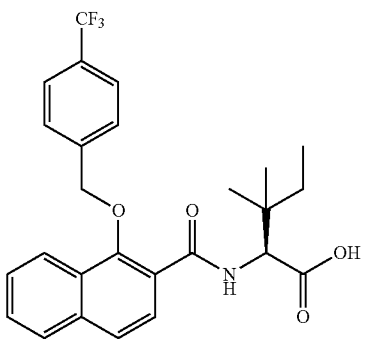 [SMILES: CCC(C)(C)[C@H](NC(=O)c1ccc2ccccc2c1OCc1ccc(C(F)(F)F)cc1)C(=O)O]

LCMS: $t_R$=4.12 min., m/z ($ES^+$)=474 ($M+H^+$).

Example 79: (S)-2-(1-(benzo[d][1,3]dioxol-5-ylmethoxy)-2-naphthamido)-3,3-dimethylbutanoic Acid

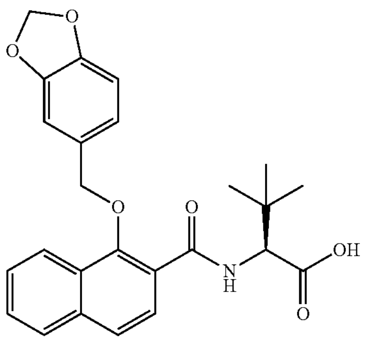 [SMILES: CC(C)(C)[C@H](NC(=O)c1ccc2ccccc2c1OCc1ccc2c(c1)OCO2)C(=O)O]

LCMS: $t_R$=3.83 min., m/z ($ES^+$)=436 ($M+H^+$).

Example 80: 2-(1-methylcyclohexyl)-2-(1-((4-(trifluoromethyl)benzyl)oxy)-2-naphthamido)acetic Acid

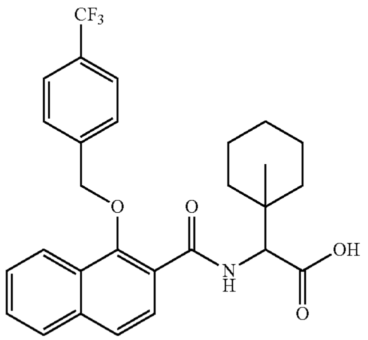

LCMS: $t_R$=4.33 min., m/z ($ES^+$)=500 ($M+H^+$).

Example 81: (S)-2-(6-fluoro-1-((4-(pentafluoro-16-sulfanyl)benzyl)oxy)-2-naphthamido)-3,3-dimethylbutanoic Acid

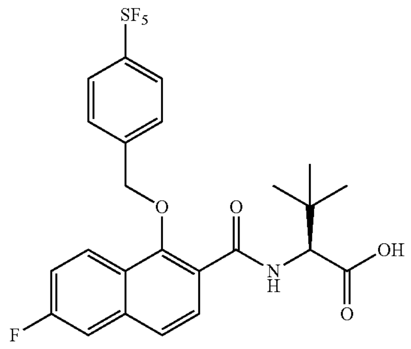

LCMS: $t_R$=4.10 min., m/z ($ES^+$)=536 ($M+H^+$).

Example 82: 2-(1-methylcyclopropyl)-2-(1-((4-((trifluoromethyl)thio)benzyl)oxy)-2-naphthamido)acetic Acid

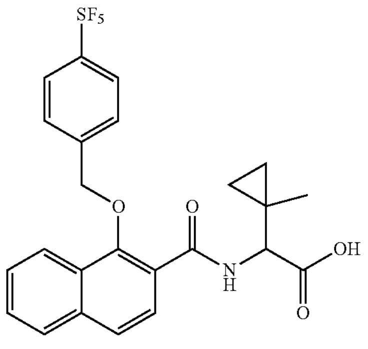

LCMS: $t_R$=2.54 min., m/z (ES$^+$)=490 (M+H$^+$).

Example 83: (S)-2-(6-methoxy-1-((4-(trifluoromethyl)benzyl)oxy)-2-naphthamido)-3,3-dimethylpentanoic Acid

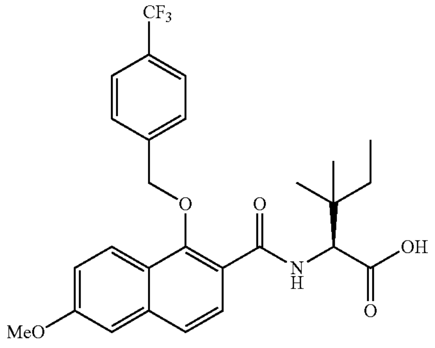 [SMILES: CCC(C)(C)[C@H](NC(=O)c1ccc2cc(OC)ccc2c1OCc1ccc(C(F)(F)F)cc1)C(=O)O]

LCMS: $t_R$=3.71 min., m/z (ES$^+$)=504 (M+H$^+$).

Example 84: (S)-2-(6-fluoro-1-((4-((trifluoromethyl)thio)benzyl)oxy)-2-naphthamido)-3,3-dimethylpentanoic Acid

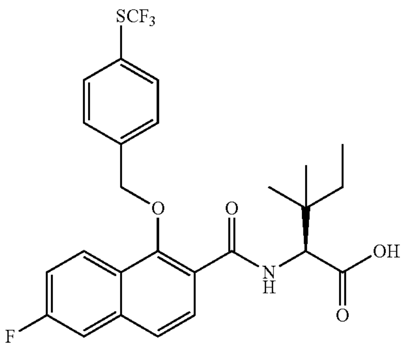

LCMS: $t_R$=4.47 min., m/z (ES$^+$)=524 (M+H$^+$).

Example 85: (S)-2-(6-(dimethylamino)-1-((4-(trifluoromethyl)benzyl)oxy)-2-naphthamido)-3,3-dimethylbutanoic Acid

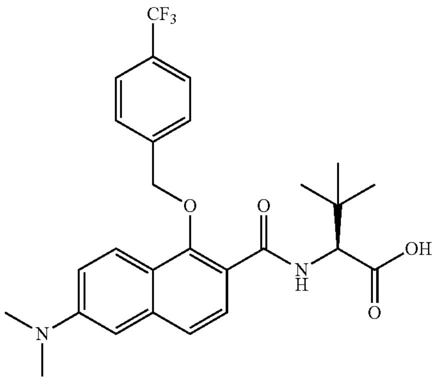 [SMILES: CN(C)c1ccc2c(OCc3ccc(C(F)(F)F)cc3)c(C(=O)N[C@H](C(=O)O)C(C)(C)C)ccc2c1]

LCMS: $t_R$=3.84 min., m/z (ES$^+$)=503 (M+H$^+$).

Example 86: (S)-3,3-dimethyl-2-(1-((5-methylisoxazol-3-yl)methoxy)-2-naphthamido)butanoic Acid

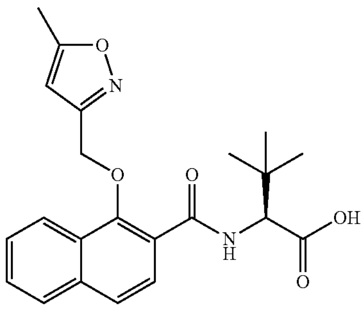 [SMILES: Cc1cc(COc2c(C(=O)N[C@H](C(=O)O)C(C)(C)C)ccc3ccccc23)no1]

LCMS: $t_R$=2.74 min., m/z (ES$^+$)=397 (M+H$^+$).

Example 87: (1-((4-(trifluoromethyl)benzyl)oxy)-2-naphthoyl)-L-phenylalanine

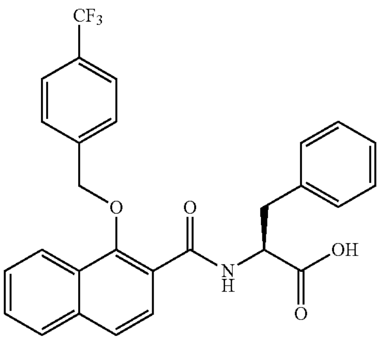

LCMS: $t_R$=3.89 min., m/z (ES$^+$)=493 (M+H$^+$).

Example 88: (S)-4-phenyl-2-(1-((4-(trifluoromethyl)benzyl)oxy)-2-naphthamido)butanoic Acid

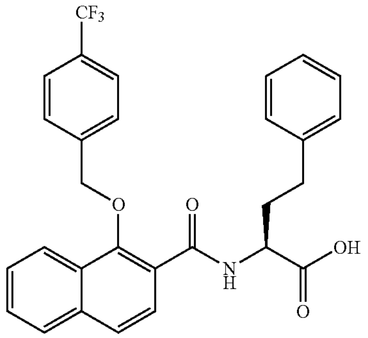 [SMILES: O=C(N[C@@H](CCc1ccccc1)C(=O)O)c1ccc2ccccc2c1OCc1ccc(C(F)(F)F)cc1]

LCMS: $t_R$=3.99 min., m/z ($ES^+$)=508 ($M+H^+$).

Example 89: (1-((4-(trifluoromethyl)benzyl)oxy)-2-naphthoyl)-D-phenylalanine

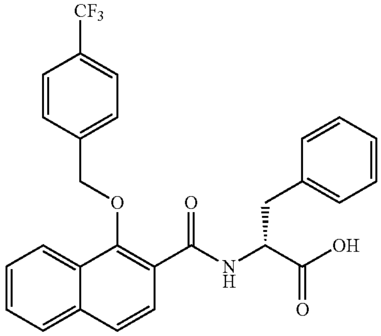 [SMILES: O=C(N[C@H](Cc1ccccc1)C(=O)O)c1ccc2ccccc2c1OCc1ccc(C(F)(F)F)cc1]

LCMS: $t_R$=3.86 min., m/z ($ES^+$)=493 ($M+H^+$).

Example 90: (1-((4-(trifluoromethoxy)benzyl)oxy)-2-naphthoyl)-L-phenylalanine

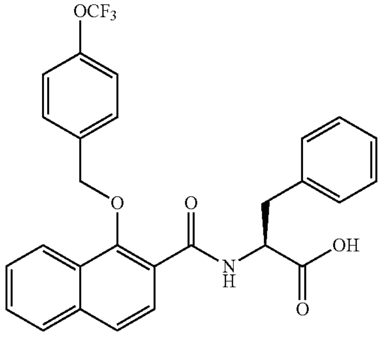

LCMS: $t_R$=4.14 min., m/z ($ES^+$)=510 ($M+H^+$).

Example 91: (1-((4-nitrobenzyl)oxy)-2-naphthoyl)-L-phenylalanine

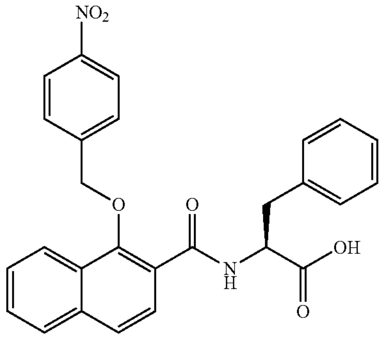

LCMS: $t_R$=3.55 min., m/z ($ES^+$)=471 ($M+H^+$).

Example 92: (S)-3-(4-(allyloxy)phenyl)-2-(1-((4-(trifluoromethyl)benzyl)oxy)-2-naphthamido)propanoic Acid

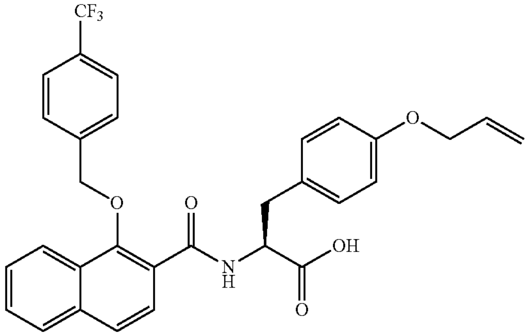 [SMILES: C=CCOc1ccc(C[C@H](NC(=O)c2ccc3ccccc3c2OCc2ccc(C(F)(F)F)cc2)C(=O)O)cc1]

LCMS: $t_R$=3.83 min., m/z ($ES^+$)=550 ($M+H^+$).

Example 93: (1-((2-(trifluoromethyl)benzyl)oxy)-2-naphthoyl)-L-phenylalanine

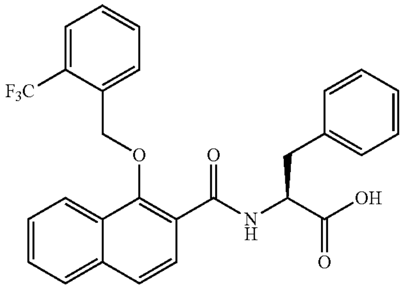 [SMILES: O=C(N[C@@H](Cc1ccccc1)C(=O)O)c1ccc2ccccc2c1OCc1ccccc1C(F)(F)F]

LCMS: $t_R$=3.77 min., m/z ($ES^+$)=494 ($M+H^+$).

Example 94: (1-((2-(trifluoromethyl)benzyl)oxy)-2-naphthoyl)-L-phenylalanine

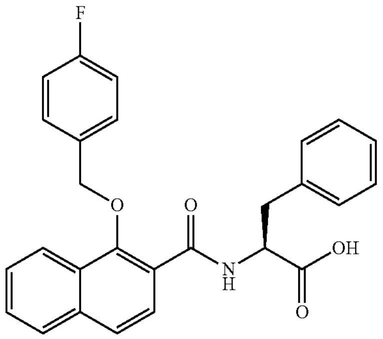

LCMS: $t_R$=3.85 min., m/z ($ES^+$)=444 ($M+H^+$).

Example 95: (1-((3-(trifluoromethyl)benzyl)oxy)-2-naphthoyl)-L-phenylalanine

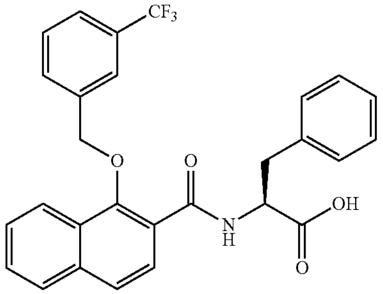 [SMILES: O=C(N[C@@H](Cc1ccccc1)C(=O)O)c1ccc2ccccc2c1OCc1cccc(C(F)(F)F)c1]

LCMS: $t_R$=3.80 min., m/z ($ES^+$)=494 ($M+H^+$).

Example 96: (1-((4-(tert-butyl)benzyl)oxy)-2-naphthoyl)-L-phenylalanine

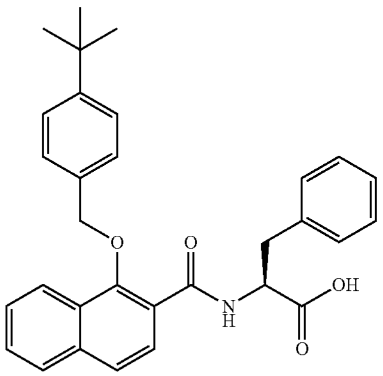 [SMILES: CC(C)(C)c1ccc(COc2c(C(=O)N[C@@H](Cc3ccccc3)C(=O)O)ccc3ccccc23)cc1]

LCMS: $t_R$=4.37 min., m/z ($ES^+$)=482 ($M+H^+$).

Example 97: (1-(4-(trifluoromethyl)phenethoxy)-2-naphthoyl)-L-phenylalanine

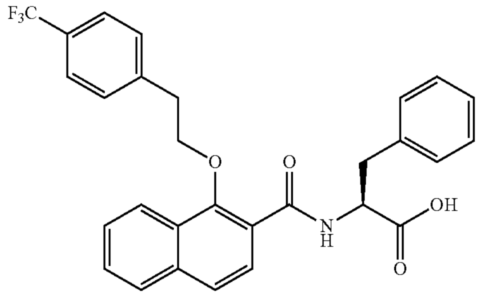 [SMILES: O=C(N[C@@H](Cc1ccccc1)C(=O)O)c1ccc2ccccc2c1OCCc1ccc(C(F)(F)F)cc1]

LCMS: $t_R$=3.96 min., m/z ($ES^+$)=508 ($M+H^+$).

Example 98: (1-((4-chlorobenzyl)oxy)-2-naphthoyl)-L-phenylalanine

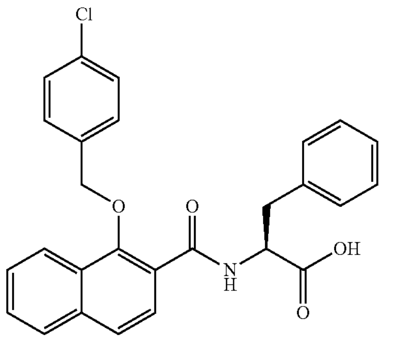

LCMS: $t_R$=4.07 min., m/z ($ES^+$)=460 ($M+H^+$).

Example 99: (1-((3,4-dichlorobenzyl)oxy)-2-naphthoyl)-L-phenylalanine

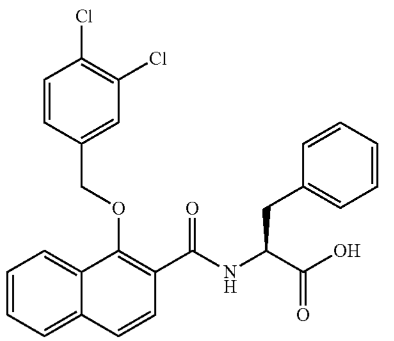 [SMILES: O=C(N[C@@H](Cc1ccccc1)C(=O)O)c1ccc2ccccc2c1OCc1ccc(Cl)c(Cl)c1]

LCMS: $t_R$=3.93 min., m/z ($ES^+$)=494 ($M+H^+$).

Example 100: Methyl (1-((4-fluorobenzyl)oxy)-2-naphthoyl)-L-phenylalaninate

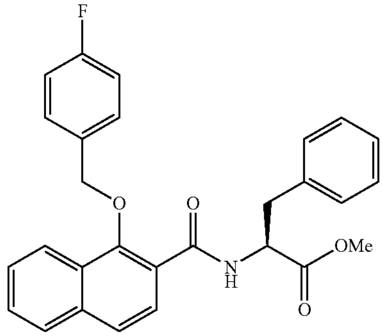 [SMILES: COC(=O)[C@H](Cc1ccccc1)NC(=O)c1ccc2ccccc2c1OCc1ccc(F)cc1]

LCMS: $t_R$=4.19 min., m/z ($ES^+$)=458 ($M+H^+$).

Example 101: Methyl (1-((3,4-dichlorobenzyl)oxy)-2-naphthoyl)-L-phenylalaninate

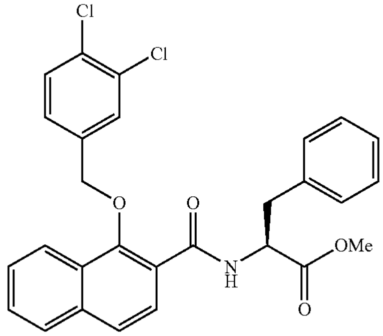

LCMS: $t_R$=4.37 min., m/z ($ES^+$)=508 ($M+H^+$).

Example 102: (1-((2,2-difluorobenzo[d][1,3]dioxol-4-yl)methoxy)-2-naphthoyl)-L-phenylalanine

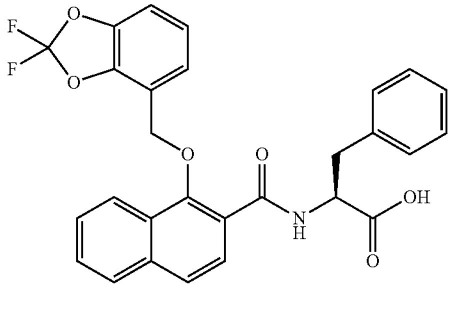

LCMS: $t_R$=3.78 min., m/z ($ES^+$)=506 ($M+H^+$).

Example 103: (S)-3-(pyridin-4-yl)-2-(1-((4-(trifluoromethyl)benzyl)oxy)-2-naphthamido)propanoic Acid

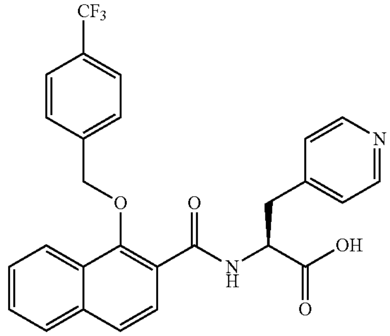 [SMILES: O=C(N[C@@H](Cc1ccncc1)C(=O)O)c1ccc2ccccc2c1OCc1ccc(C(F)(F)F)cc1]

LCMS: $t_R$=2.48 min., m/z ($ES^+$)=495 ($M+H^+$).

Example 104: (S)-2-(1-((4-(trifluoromethyl)benzyl)oxy)-2-naphthamido)-3-(4-(trifluoromethyl)phenyl)propanoic Acid

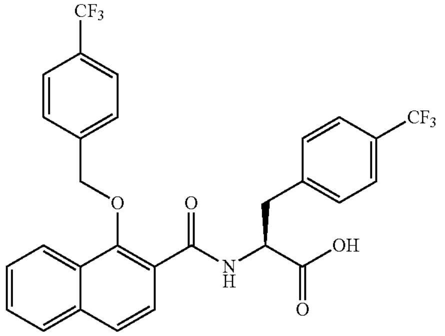 [SMILES: O=C(N[C@@H](Cc1ccc(C(F)(F)F)cc1)C(=O)O)c1ccc2ccccc2c1OCc1ccc(C(F)(F)F)cc1]

LCMS: $t_R$=3.65 min., m/z ($ES^+$)=562 ($M+H^+$).

Example 105: (R)-3-(4-((diaminomethylene)amino)phenyl)-2-(1-((4-(trifluoromethyl)benzyl)oxy)-2-naphthamido)propanoic Acid

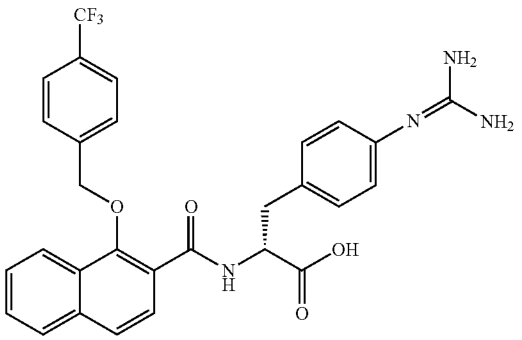 [SMILES: NC(N)=Nc1ccc(C[C@@H](NC(=O)c2ccc3ccccc3c2OCc2ccc(C(F)(F)F)cc2)C(=O)O)cc1]

LCMS: $t_R$=2.59 min., m/z ($ES^+$)=551 ($M+H^+$).

Example 106: (S)-3-(benzo[d][1,3]dioxol-5-yl)-2-(1-((4-(trifluoromethyl)benzyl)oxy)-2-naphthamido)propanoic Acid

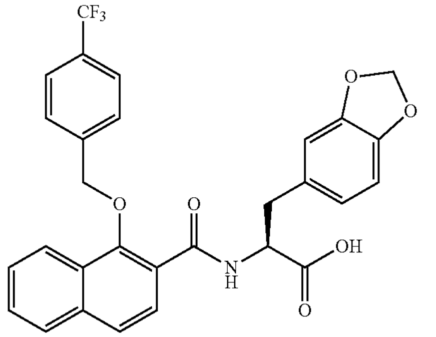 [SMILES: O=C(N[C@@H](Cc1ccc2c(c1)OCO2)C(=O)O)c1ccc2ccccc2c1OCc1ccc(C(F)(F)F)cc1]

LCMS: $t_R$=3.35 min., m/z ($ES^+$)=538 ($M+H^+$).

Example 107: (S)-3-(4-cyanophenyl)-2-(1-((4-(trifluoromethyl)benzyl)oxy)-2-naphthamido)propanoic Acid

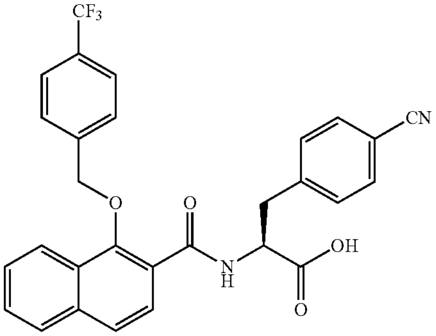 [SMILES: N#Cc1ccc(C[C@H](NC(=O)c2ccc3ccccc3c2OCc2ccc(C(F)(F)F)cc2)C(=O)O)cc1]

LCMS: $t_R$=3.25 min., m/z ($ES^+$)=519 ($M+H^+$).

Example 108: (S)-2-(1-((4-(difluoromethoxy)benzyl)oxy)-2-naphthamido)-4,4-dimethylpentanoic Acid

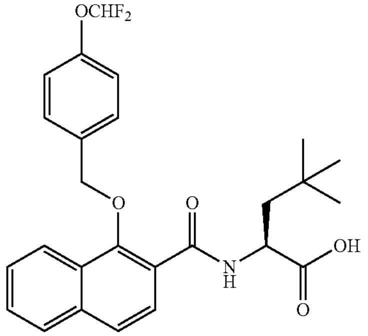 [SMILES: CC(C)(C)C[C@H](NC(=O)c1ccc2ccccc2c1OCc1ccc(OC(F)F)cc1)C(=O)O]

LCMS: $t_R$=2.58 min., m/z ($ES^+$)=472 ($M+H^+$).

Example 109: (S)-2-(1-((4,4-difluorocyclohexyl)methoxy)-6-fluoro-2-naphthamido)-4,4-dimethylpentanoic Acid

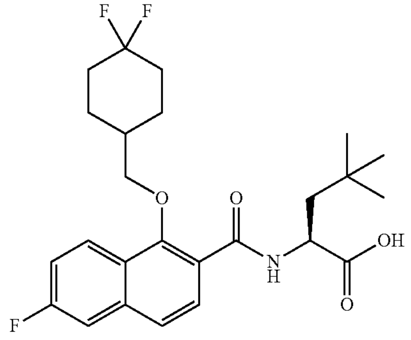 [SMILES: CC(C)(C)C[C@H](NC(=O)c1ccc2cc(F)ccc2c1OCC1CCC(F)(F)CC1)C(=O)O]

LCMS: $t_R$=4.08 min., m/z ($ES^+$)=466 ($M+H^+$).

Example 110: (S)-4,4-dimethyl-2-(1-((4-(pentafluoro-16-sulfanyl)benzyl)oxy)-2-naphthamido)pentanoic Acid

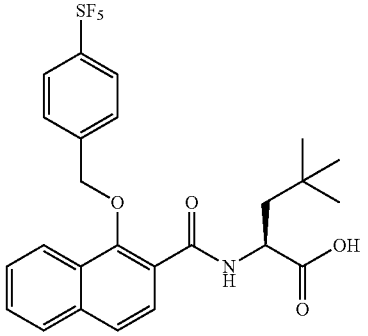

LCMS: $t_R$=4.18 min., m/z ($ES^+$)=532 ($M+H^+$).

Example 111: (S)-2-cyclopentyl-2-(1-((4-(pentafluoro-16-sulfanyl)benzyl)oxy)-2-naphthamido)acetic Acid

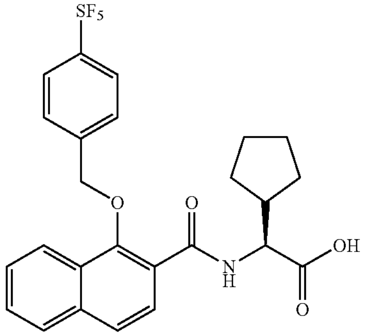

LCMS: $t_R$=4.10 min., m/z ($ES^+$)=530 ($M+H^+$).

Example 112: (S)-2-(6-fluoro-1-((4-(pentafluoro-16-sulfanyl)benzyl)oxy)-2-naphthamido)-4,4-dimethylpentanoic Acid

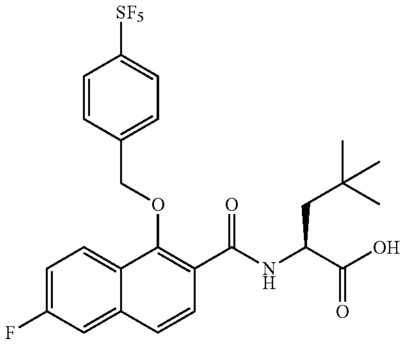

LCMS: $t_R$=4.21 min., m/z ($ES^+$)=550 ($M+H^+$).

Example 113: (S)-2-cyclopentyl-2-(6-fluoro-1-((4-(pentafluoro-16-sulfanyl)benzyl)oxy)-2-naphthamido)acetic Acid

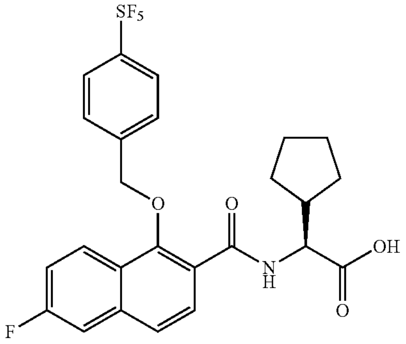

LCMS: $t_R$=4.14 min., m/z ($ES^+$)=548 ($M+H^+$).

Example 114: (S)-2-cyclopentyl-2-(1-((4-((trifluoromethyl)thio)benzyl)oxy)-2-naphthamido)acetic Acid

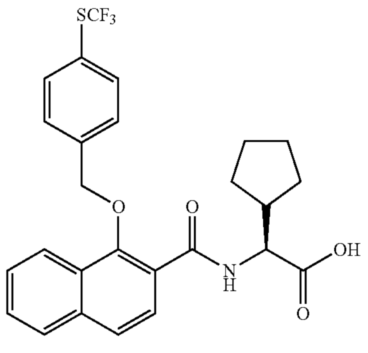

LCMS: $t_R$=4.26 min., m/z ($ES^+$)=504 ($M+H^+$).

Example 115: (S)-4,4-dimethyl-2-(1-((4-((trifluoromethyl)thio)benzyl)oxy)-2-naphthamido)pentanoic Acid

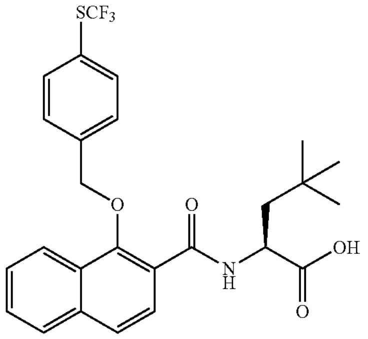

LCMS: $t_R$=4.32 min., m/z ($ES^+$)=506 ($M+H^+$).

Example 116: (S)-2-cyclopentyl-2-(6-fluoro-1-((4-((trifluoromethyl)thio)benzyl)oxy)-2-naphthamido)acetic Acid

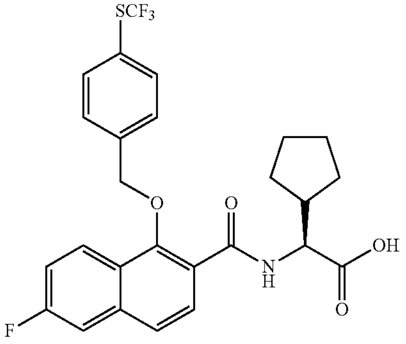

LCMS: $t_R$=4.37 min., m/z ($ES^+$)=522 ($M+H^+$).

Example 117: (S)-2-(6-fluoro-1-((4-((trifluoromethyl)thio)benzyl)oxy)-2-naphthamido)-4,4-dimethylpentanoic Acid

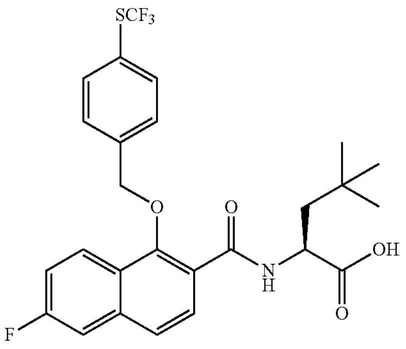

LCMS: $t_R$=4.44 min., m/z ($ES^+$)=524 ($M+H^+$).

Example 118: (S)-2-(6-fluoro-1-((4-((trifluoromethyl)thio)benzyl)oxy)-2-naphthamido)-3-methoxy-3-methylbutanoic Acid

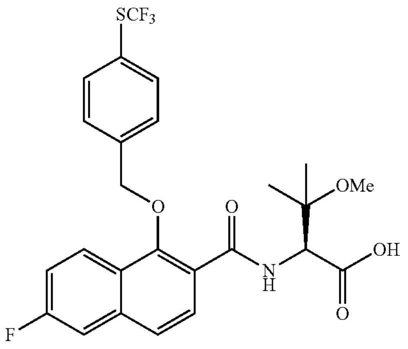

LCMS: $t_R$=4.19 min., m/z ($ES^+$)=526 ($M+H^+$).

Example 119: (S)-2-cyclopentyl-2-(6-fluoro-1-((4-(trifluoromethoxy)benzyl)oxy)-2-naphthamido)acetic Acid

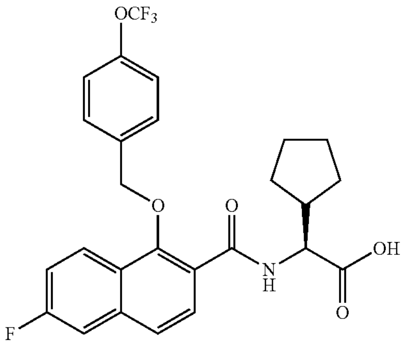 [SMILES: O=C(N[C@H](C(=O)O)C1CCCC1)c1ccc2cc(F)ccc2c1OCc1ccc(OC(F)(F)F)cc1]

LCMS: $t_R$=4.48 min., m/z ($ES^+$)=506 ($M+H^+$).

Example 120: 3,3-dimethyl-2-(1-((4-(trifluoromethoxy)benzyl)oxy)-2-naphthamido)pent-4-enoic Acid

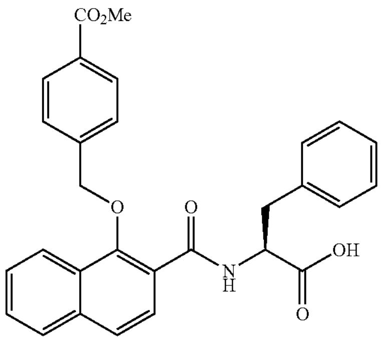 [SMILES: COC(=O)c1ccc(COc2c(C(=O)N[C@@H](Cc3ccccc3)C(=O)O)ccc3ccccc23)cc1]

LCMS: $t_R$=3.56 min., m/z ($ES^+$)=450 ($M+H^+$).

Example 121: (1-(benzo[d][1,3]dioxol-5-ylmethoxy)-2-naphthoyl)-L-phenylalanine

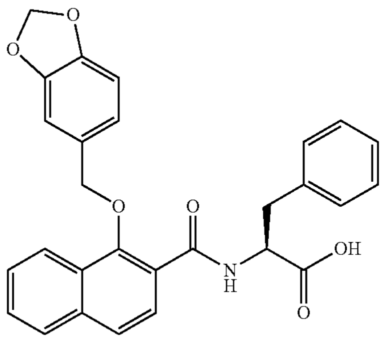 [SMILES: O=C(N[C@@H](Cc1ccccc1)C(=O)O)c1ccc2ccccc2c1OCc1ccc2c(c1)OCO2]

LCMS: $t_R$=3.76 min., m/z ($ES^+$)=470 ($M+H^+$).

Example 122: (1-((4-bromobenzyl)oxy)-2-naphthoyl)-L-phenylalanine

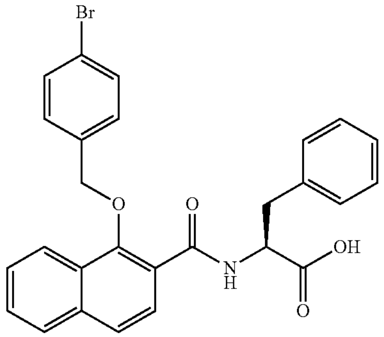

LCMS: $t_R$=4.08 min., m/z ($ES^+$)=504 ($M+H^+$).

Example 123: (1-(1-(4-bromophenyl)ethoxy)-2-naphthoyl)-L-phenylalanine

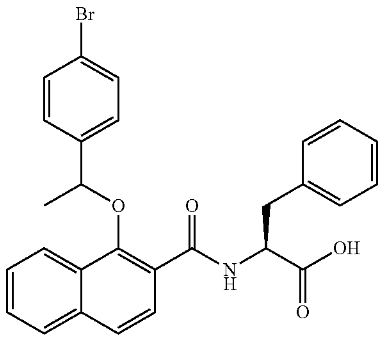 [SMILES: CC(Oc1c(C(=O)N[C@@H](Cc2ccccc2)C(=O)O)ccc2ccccc12)c1ccc(Br)cc1]

LCMS: $t_R$=4.17 min., m/z ($ES^+$)=518 ($M+H^+$).

Example 124: (1-(1-(4-(trifluoromethyl)phenyl)ethoxy)-2-naphthoyl)-L-phenylalanine

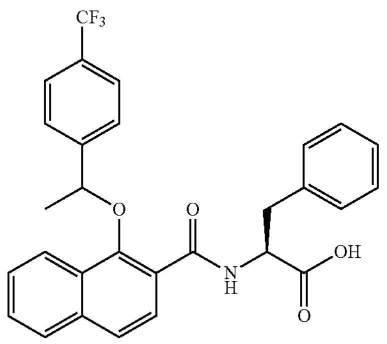

LCMS: $t_R$=4.18 min., m/z ($ES^+$)=508 ($M+H^+$).

Example 125: (1-((4-cyanobenzyl)oxy)-2-naphthoyl)-L-phenylalanine

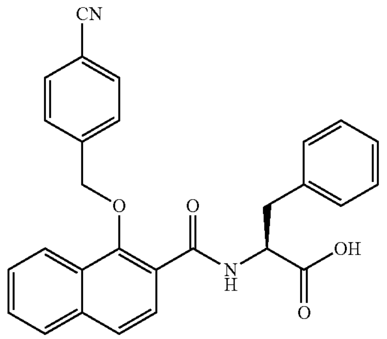

LCMS: $t_R$=3.43 min., m/z ($ES^+$)=451 ($M+H^+$).

Example 126: (S)-3,3-diphenyl-2-(1-((4-(trifluoromethyl)benzyl)oxy)-2-naphthamido)propanoic Acid

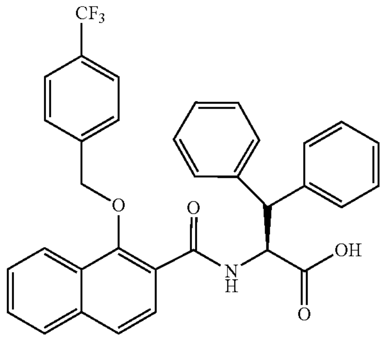 [SMILES: O=C(N[C@H](C(=O)O)C(c1ccccc1)c1ccccc1)c1ccc2ccccc2c1OCc1ccc(C(F)(F)F)cc1]

LCMS: $t_R$=4.20 min., m/z ($ES^+$)=570 ($M+H^+$).

Example 127: 3-phenyl-2-(1-((4-(trifluoromethyl)benzyl)oxy)-2-naphthamido)butanoic Acid

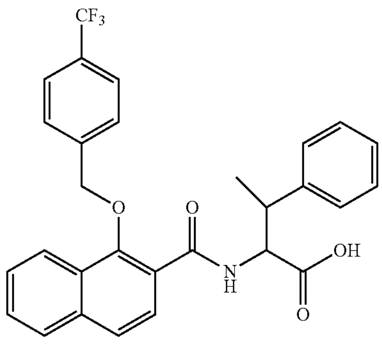 [SMILES: CC(c1ccccc1)C(NC(=O)c1ccc2ccccc2c1OCc1ccc(C(F)(F)F)cc1)C(=O)O]

LCMS: $t_R$=4.10 min., m/z ($ES^+$)=508 ($M+H^+$).

Example 128: (S)-2-cyclohexyl-2-(1-((4-(trifluoromethyl)benzyl)oxy)-2-naphthamido)acetic Acid

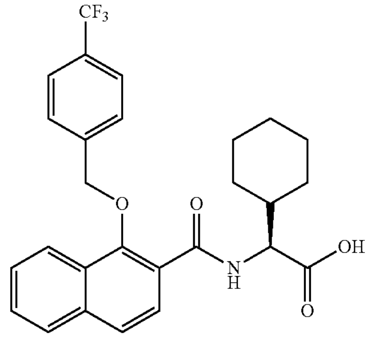 [SMILES: O=C(N[C@H](C(=O)O)C1CCCCC1)c1ccc2ccccc2c1OCc1ccc(C(F)(F)F)cc1]

LCMS: $t_R$=4.15 min., m/z ($ES^+$)=486 ($M+H^+$).

Example 129: (2S,3R)-3-hydroxy-3-phenyl-2-(1-((4-(trifluoromethyl)benzyl)oxy)-2-naphthamido)propanoic Acid

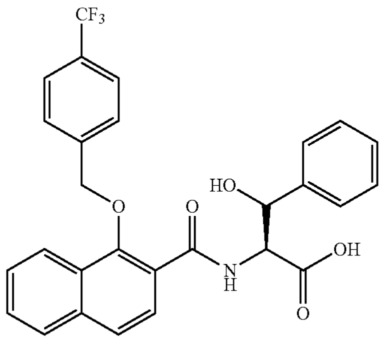

LCMS: $t_R$=2.66 min., m/z ($ES^+$)=510 ($M+H^+$).

Example 130: (S)-2-(1-((3-fluoro-4-(trifluoromethyl)benzyl)oxy)-2-naphthamido)-3,3-diphenylpropanoic Acid

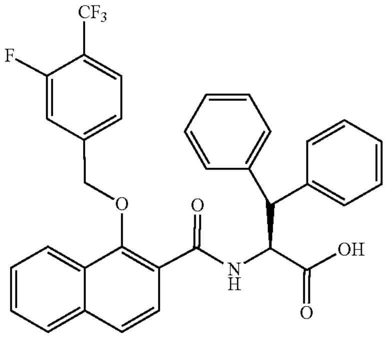 [SMILES: O=C(N[C@H](C(=O)O)C(c1ccccc1)c1ccccc1)c1ccc2ccccc2c1OCc1ccc(C(F)(F)F)c(F)c1]

LCMS: $t_R$=4.23 min., m/z ($ES^+$)=588 ($M+H^+$).

Example 131: (S)-2-(1-((4-(perfluoroethyl)benzyl)oxy)-2-naphthamido)-3,3-diphenylpropanoic Acid

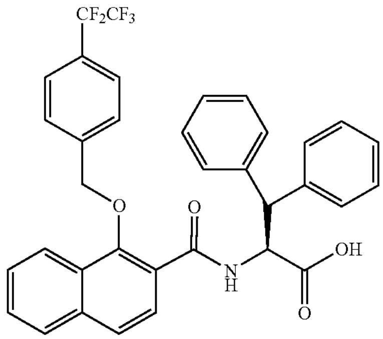

LCMS: $t_R$=4.47 min., m/z ($ES^+$)=620 ($M+H^+$).

Example 132: (S)-3,3-diphenyl-2-(1-((5-(trifluoromethyl)pyridin-2-yl)methoxy)-2-naphthamido)propanoic Acid

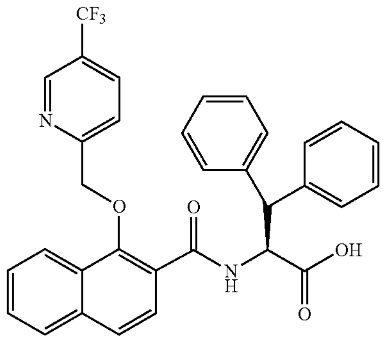 [SMILES: O=C(N[C@H](C(=O)O)C(c1ccccc1)c1ccccc1)c1ccc2ccccc2c1OCc1ccc(C(F)(F)F)cn1]

LCMS: $t_R$=3.88 min., m/z ($ES^+$)=571 ($M+H^+$).

Example 133: (3R)-3-(tert-butoxy)-2-(1-((4-(trifluoromethyl)benzyl)oxy)-2-naphthamido)butanoic Acid

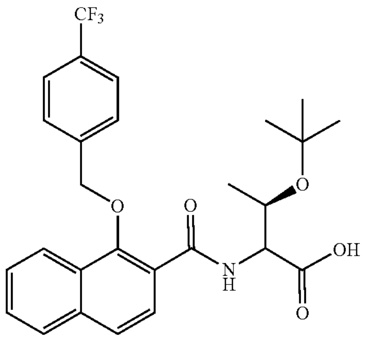 [SMILES: C[C@@H](OC(C)(C)C)C(NC(=O)c1ccc2ccccc2c1OCc1ccc(C(F)(F)F)cc1)C(=O)O]

LCMS: $t_R$=4.15 min., m/z ($ES^+$)=504 ($M+H^+$).

Example 134: (3S)-3-(tert-butoxy)-2-(1-((4-(trifluoromethyl)benzyl)oxy)-2-naphthamido)butanoic Acid

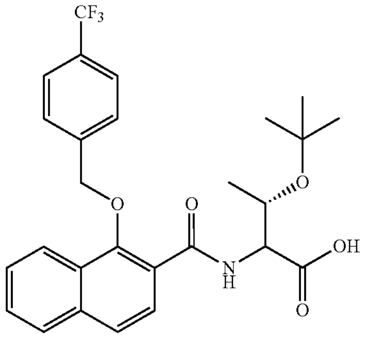 [SMILES: C[C@H](OC(C)(C)C)C(NC(=O)c1ccc2ccccc2c1OCc1ccc(C(F)(F)F)cc1)C(=O)O]

LCMS: $t_R$=4.04 min., m/z ($ES^+$)=504 ($M+H^+$).

Example 135: O-methyl-N-(1-((4-(trifluoromethyl)benzyl)oxy)-2-naphthoyl)-L-allothreonine

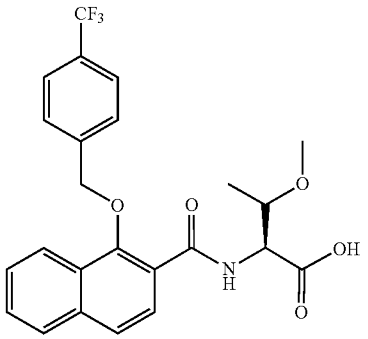 [SMILES: COC(C)[C@H](NC(=O)c1ccc2ccccc2c1OCc1ccc(C(F)(F)F)cc1)C(=O)O]

LCMS: $t_R$=3.74 min., m/z ($ES^+$)=461 ($M+H^+$).

Example 136: (S)-3-(furan-2-yl)-2-(1-((4-(trifluoromethyl)benzyl)oxy)-2-naphthamido)propanoic Acid

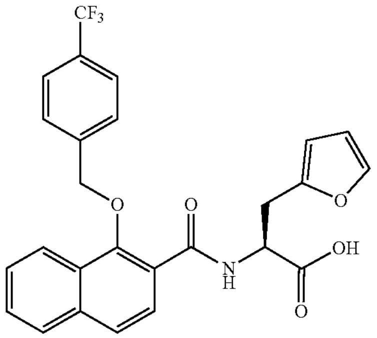 [SMILES: O=C(N[C@@H](Cc1ccco1)C(=O)O)c1ccc2ccccc2c1OCc1ccc(C(F)(F)F)cc1]

LCMS: $t_R$=3.75 min., m/z ($ES^+$)=484 ($M+H^+$).

Example 137: O-methyl-N-(1-((4-(trifluoromethyl)benzyl)oxy)-2-naphthoyl)-L-homoserine

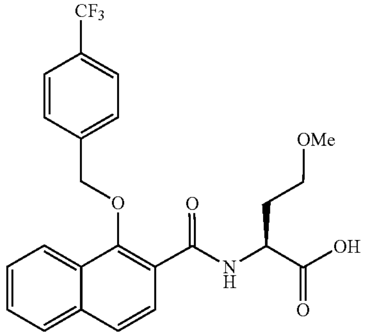 [SMILES: COCC[C@H](NC(=O)c1ccc2ccccc2c1OCc1ccc(C(F)(F)F)cc1)C(=O)O]

LCMS: $t_R$=3.55 min., m/z ($ES^+$)=461 ($M+H^+$).

Example 138: (S)-3-hydroxy-3-methyl-2-(1-((4-(trifluoromethyl)benzyl)oxy)-2-naphthamido)butanoic Acid

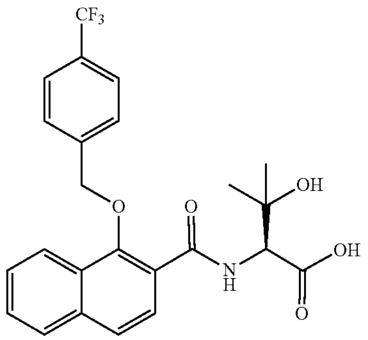 [SMILES: CC(C)(O)[C@H](NC(=O)c1ccc2ccccc2c1OCc1ccc(C(F)(F)F)cc1)C(=O)O]

LCMS: $t_R$=3.39 min., m/z ($ES^+$)=461 ($M+H^+$).

Example 139: (S)-3-methoxy-3-methyl-2-(1-((4-(trifluoromethyl)benzyl)oxy)-2-naphthamido)butanoic Acid

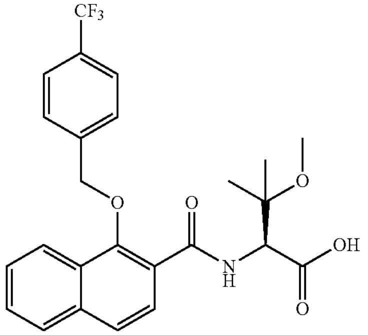 [SMILES: COC(C)(C)[C@H](NC(=O)c1ccc2ccccc2c1OCc1ccc(C(F)(F)F)cc1)C(=O)O]

LCMS: $t_R$=3.80 min., m/z ($ES^+$)=476 ($M+H^+$).

Example 140: (S)-2-phenyl-2-(1-((4-(trifluoromethyl)benzyl)oxy)-2-naphthamido)acetic Acid

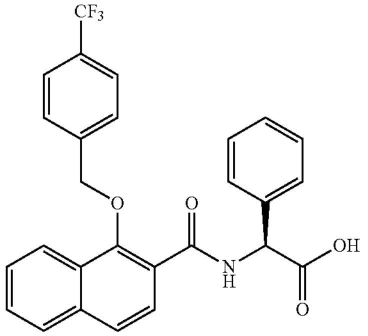 [SMILES: O=C(N[C@H](C(=O)O)c1ccccc1)c1ccc2ccccc2c1OCc1ccc(C(F)(F)F)cc1]

LCMS: $t_R$=3.95 min., m/z ($ES^+$)=480 ($M+H^+$).

Example 141: (S)-4,4-dimethyl-2-(1-((4-(trifluoromethyl)benzyl)oxy)-2-naphthamido)pentanoic Acid

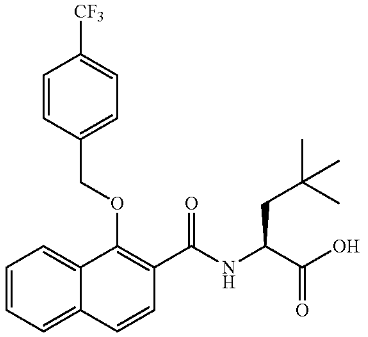 [SMILES: CC(C)(C)C[C@H](NC(=O)c1ccc2ccccc2c1OCc1ccc(C(F)(F)F)cc1)C(=O)O]

LCMS: $t_R$=4.17 min., m/z ($ES^+$)=474 ($M+H^+$).

Example 142: (S)-2-(naphthalen-1-yl)-2-(1-((4-(trifluoromethyl)benzyl)oxy)-2-naphthamido)acetic Acid

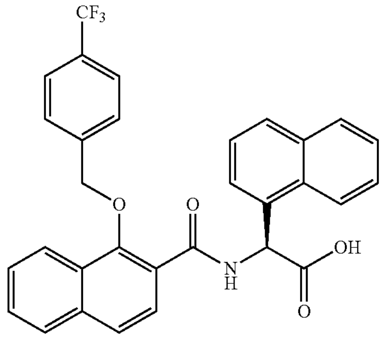 [SMILES: O=C(N[C@H](C(=O)O)c1cccc2ccccc12)c1ccc2ccccc2c1OCc1ccc(C(F)(F)F)cc1]

LCMS: $t_R$=4.19 min., m/z ($ES^+$)=530 ($M+H^+$).

Example 143: (S)-2-(2,3-dihydro-1H-inden-2-yl)-2-(1-((4-(trifluoromethyl)benzyl)oxy)-2-naphthamido) acetic Acid

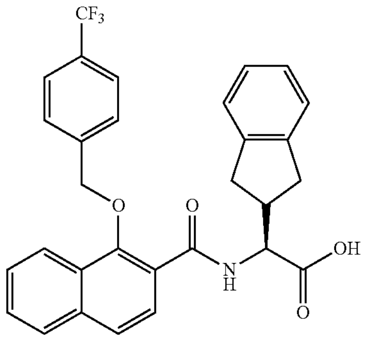 [SMILES: O=C(N[C@H](C(=O)O)C1Cc2ccccc2C1)c1ccc2ccccc2c1OCc1ccc(C(F)(F)F)cc1]

LCMS: $t_R$=4.18 min., m/z ($ES^+$)=520 ($M+H^+$).

Example 144: (3R)-3-(benzyloxy)-2-(1-((4-(trifluoromethyl)benzyl)oxy)-2-naphthamido)butanoic Acid

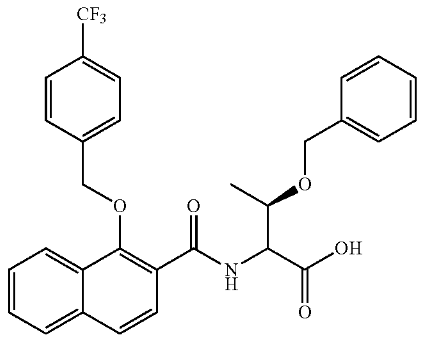 [SMILES: C[C@@H](OCc1ccccc1)C(NC(=O)c1ccc2ccccc2c1OCc1ccc(C(F)(F)F)cc1)C(=O)O]

LCMS: $t_R$=4.23 min., m/z ($ES^+$)=538 ($M+H^+$).

Example 145: (3R)-3-(benzyloxy)-2-(1-((5-methylisoxazol-3-yl)methoxy)-2-naphthamido)butanoic Acid

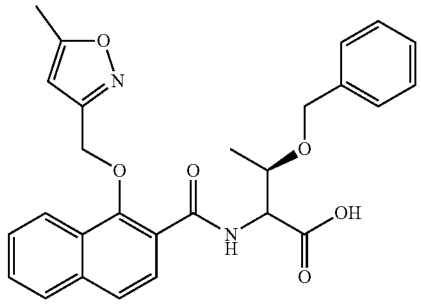 [SMILES: Cc1cc(COc2c(C(=O)NC(C(=O)O)[C@@H](C)OCc3ccccc3)ccc3ccccc23)no1]

LCMS: $t_R$=3.03 min., m/z ($ES^+$)=475 ($M+H^+$).

Example 146: (3R)-3-(benzyloxy)-2-(1-((4-(hydroxymethyl)cyclohexyl)methoxy)-2-naphthamido) butanoic Acid

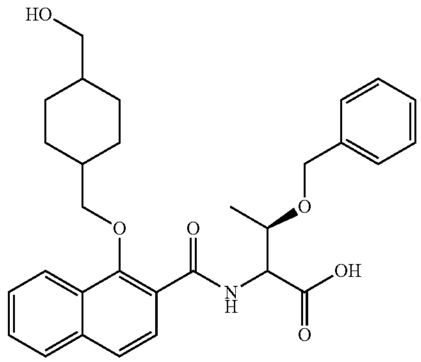 [SMILES: C[C@@H](OCc1ccccc1)C(NC(=O)c1ccc2ccccc2c1OCC1CCC(CO)CC1)C(=O)O]

LCMS: $t_R$=3.04 min., m/z ($ES^+$)=506 ($M+H^+$).

Example 147: (3R)-3-(benzyloxy)-2-(1-(bicyclo [2.2.1]heptan-2-ylmethoxy)-2-naphthamido)butanoic Acid

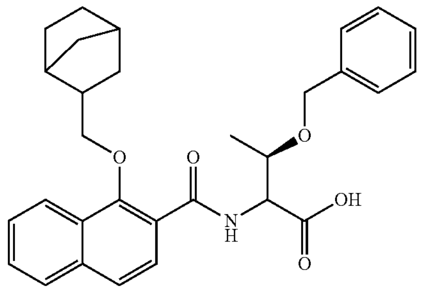 [SMILES: C[C@@H](OCc1ccccc1)C(NC(=O)c1ccc2ccccc2c1OCC1CC2CCC1C2)C(=O)O]

LCMS: $t_R$=3.75 min., m/z ($ES^+$)=488 ($M+H^+$).

Example 148: (3R)-2-(1-(benzo[d]thiazol-2-ylmethoxy)-2-naphthamido)-3-(benzyloxy)butanoic Acid

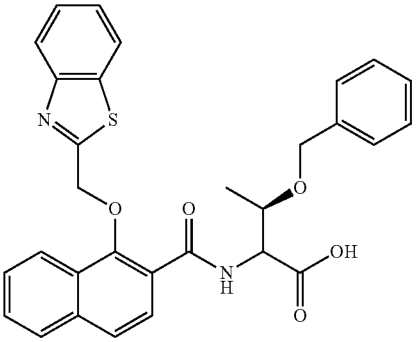 [SMILES: C[C@@H](OCc1ccccc1)C(NC(=O)c1ccc2ccccc2c1OCc1nc2ccccc2s1)C(=O)O]

LCMS: $t_R$=3.27 min., m/z ($ES^+$)=527 ($M+H^+$).

Example 149: (3R)-3-(benzyloxy)-2-(1-((1-phenyl-1H-pyrazol-4-yl)methoxy)-2-naphthamido)butanoic Acid

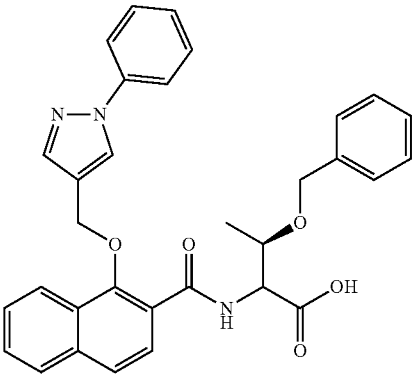 [SMILES: C[C@@H](OCc1ccccc1)C(NC(=O)c1ccc2ccccc2c1OCc1cnn(-c2ccccc2)c1)C(=O)O]

LCMS: $t_R$=3.48 min., m/z ($ES^+$)=536 ($M+H^+$).

Example 150: (3R)-3-(benzyloxy)-2-(1-(cyclohexylmethoxy)-2-naphthamido)butanoic Acid

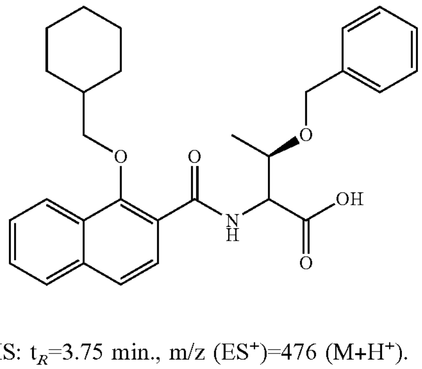

LCMS: $t_R$=3.75 min., m/z ($ES^+$)=476 ($M+H^+$).

Example 151: 4-(tert-butoxy)-4-oxo-2-(1-((4-(trifluoromethyl)benzyl)oxy)-2-naphthamido)butanoic Acid

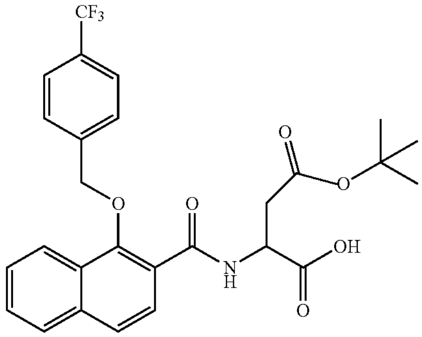

LCMS: $t_R$=4.01 min., m/z ($ES^+$)=518 ($M+H^+$).

Example 152: (S)-3-(2,6-dichlorophenyl)-2-(1-((4-(trifluoromethyl)benzyl)oxy)-2-naphthamido)propanoic Acid

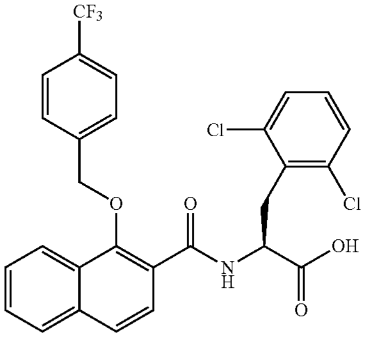 [SMILES: O=C(N[C@@H](Cc1c(Cl)cccc1Cl)C(=O)O)c1ccc2ccccc2c1OCc1ccc(C(F)(F)F)cc1]

LCMS: $t_R$=4.11 min., m/z ($ES^+$)=562 ($M+H^+$).

Example 153: (S)-2-cyclopentyl-2-(6-fluoro-1-((4-(trifluoromethyl)benzyl)oxy)-2-naphthamido)acetic Acid

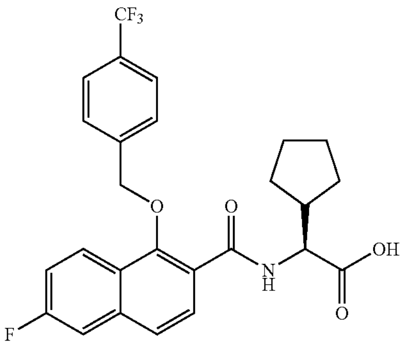

LCMS: $t_R$=2.55 min., m/z ($ES^+$)=490 ($M+H^+$).

Example 154: (S)-2-cyclopentyl-2-(1-((4-(trifluoromethyl)benzyl)oxy)-2-naphthamido)acetic Acid

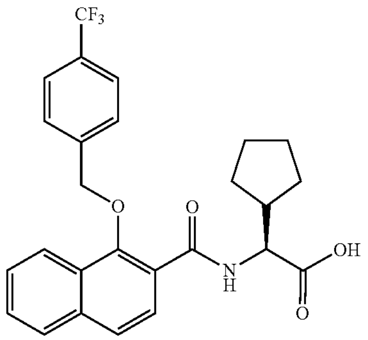 [SMILES: O=C(N[C@H](C(=O)O)C1CCCC1)c1ccc2ccccc2c1OCc1ccc(C(F)(F)F)cc1]

LCMS: $t_R$=2.54 min., m/z ($ES^+$)=472 ($M+H^+$).

Example 155: (S)-2-cyclopentyl-2-(1-((4,4-difluorocyclohexyl)methoxy)-2-naphthamido)acetic Acid

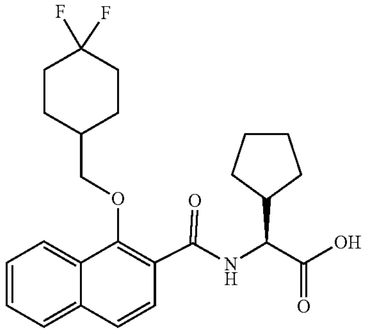 [SMILES: O=C(N[C@H](C(=O)O)C1CCCC1)c1ccc2ccccc2c1OCC1CCC(F)(F)CC1]

LCMS: $t_R$=2.45 min., m/z ($ES^+$)=446 ($M+H^+$).

Example 156: (S)-2-cyclopentyl-2-(1-((4-((trifluoromethyl)sulfonyl)benzyl)oxy)-2-naphthamido)acetic Acid

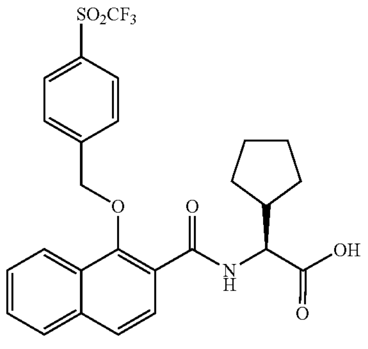

LCMS: $t_R$=2.46 min., m/z ($ES^+$)=536 ($M+H^+$).

Example 157: (S)-4,4-dimethyl-2-(1-((4-((trifluoromethyl)sulfonyl)benzyl)oxy)-2-naphthamido)pentanoic Acid

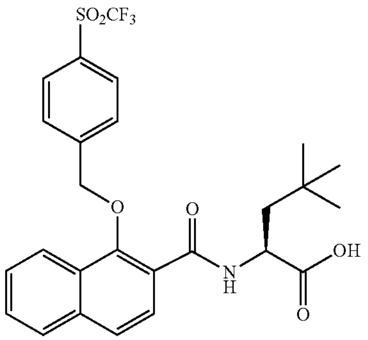

LCMS: $t_R$=2.51 min., m/z ($ES^+$)=538 ($M+H^+$).

Example 158: (S)-4,4-dimethyl-2-(1-((4-(methylsulfonyl)benzyl)oxy)-2-naphthamido)pentanoic Acid

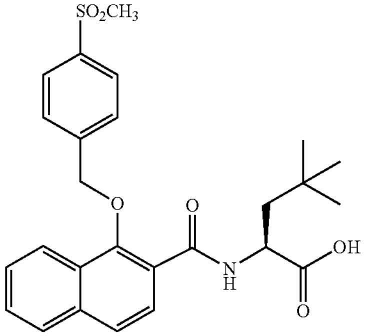 [SMILES: CC(C)(C)C[C@H](NC(=O)c1ccc2ccccc2c1OCc1ccc(S(C)(=O)=O)cc1)C(=O)O]

LCMS: $t_R$=2.11 min., m/z ($ES^+$)=484 ($M+H^+$).

Example 159: (S)-2-cyclopentyl-2-(1-((4-(methylsulfonyl)benzyl)oxy)-2-naphthamido)acetic Acid

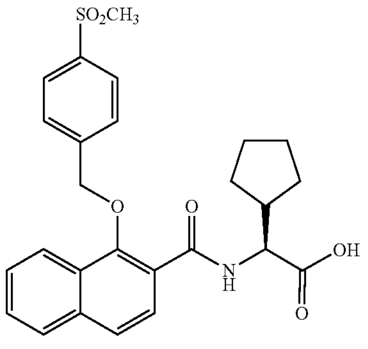 [SMILES: CS(=O)(=O)c1ccc(COc2c(C(=O)N[C@H](C(=O)O)C3CCCC3)ccc3ccccc23)cc1]

LCMS: $t_R$=2.05 min., m/z ($ES^+$)=482 ($M+H^+$).

Example 160: (S)-2-cyclopentyl-2-(6-methoxy-1-((4-(trifluoromethyl)benzyl)oxy)-2-naphthamido)acetic Acid

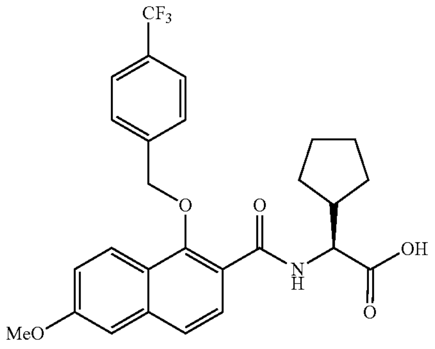 [SMILES: COc1ccc2c(OCc3ccc(C(F)(F)F)cc3)c(C(=O)N[C@H](C(=O)O)C3CCCC3)ccc2c1]

LCMS: $t_R$=3.61 min., m/z ($ES^+$)=502 ($M+H^+$).

Example 161: (S)-2-(6-methoxy-1-((4-(trifluoromethyl)benzyl)oxy)-2-naphthamido)-4,4-dimethylpentanoic Acid

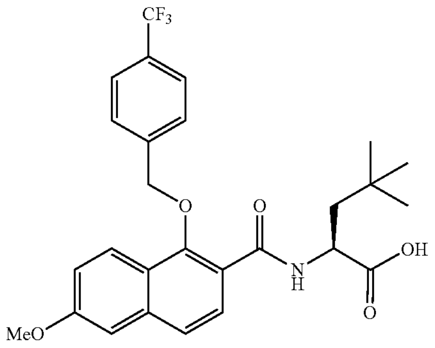 [SMILES: COc1ccc2c(OCc3ccc(C(F)(F)F)cc3)c(C(=O)N[C@@H](CC(C)(C)C)C(=O)O)ccc2c1]

LCMS: $t_R$=3.70 min., m/z ($ES^+$)=504 ($M+H^+$).

Example 162: (S)-2-cyclopentyl-2-(6-methoxy-1-((4-((trifluoromethyl)thio)benzyl)oxy)-2-naphthamido)acetic Acid

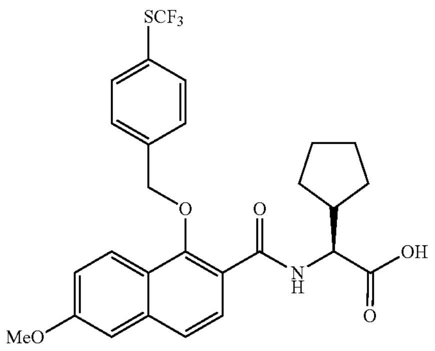

LCMS: $t_R$=3.86 min., m/z ($ES^+$)=534 ($M+H^+$).

Example 163: (2R)-3-(((2,2-difluorocyclopropyl)methyl)thio)-3-methyl-2-(1-((4-(trifluoromethyl)benzyl)oxy)-2-naphthamido)butanoic Acid

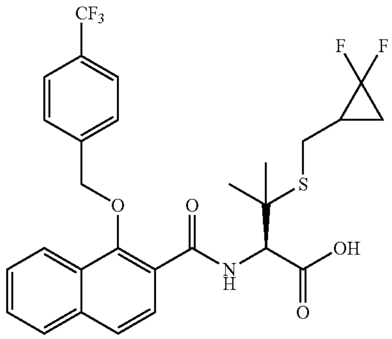 [SMILES: CC(C)(SCC1CC1(F)F)[C@H](NC(=O)c1ccc2ccccc2c1OCc1ccc(C(F)(F)F)cc1)C(=O)O]

LCMS: $t_R$=2.61 min., m/z ($ES^+$)=568 ($M+H^+$).

Example 164: (2R)-3-(((2,2-difluorocyclopropyl)methyl)thio)-3-methyl-2-(1-((4-((trifluoromethyl)thio)benzyl)oxy)-2-naphthamido)butanoic Acid

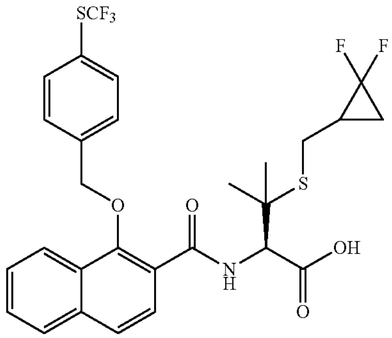

LCMS: $t_R$=2.73 min., m/z ($ES^+$)=600 ($M+H^+$).

Example 165: (2R)-2-(1-(cyclohexylmethoxy)-2-naphthamido)-3-(((2,2-difluorocyclopropyl)methyl)thio)-3-methylbutanoic Acid

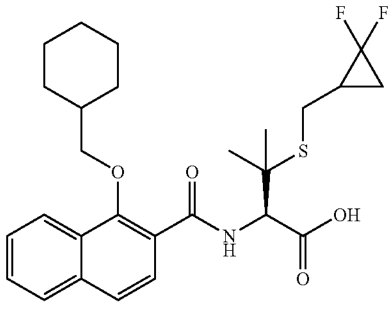 [SMILES: CC(C)(SCC1CC1(F)F)[C@H](NC(=O)c1ccc2ccccc2c1OCC1CCCCC1)C(=O)O]

LCMS: $t_R$=2.72 min., m/z ($ES^+$)=506 ($M+H^+$).

Example 166: (2R)-3-(((2,2-difluorocyclopropyl)methyl)thio)-3-methyl-2-(1-((4-(methylsulfonyl)benzyl)oxy)-2-naphthamido)butanoic Acid

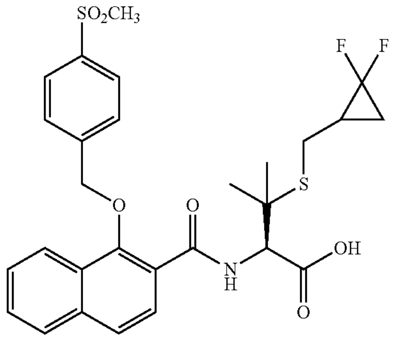 [SMILES: CC(C)(SCC1CC1(F)F)[C@H](NC(=O)c1ccc2ccccc2c1OCc1ccc(S(C)(=O)=O)cc1)C(=O)O]

LCMS: $t_R$=2.18 min., m/z (ES$^+$)=578 (M+H$^+$).

Example 167: (2R)-3-(((2,2-difluorocyclopropyl)methyl)thio)-2-(6-fluoro-1-((4-((trifluoromethyl)thio)benzyl)oxy)-2-naphthamido)-3-methylbutanoic Acid

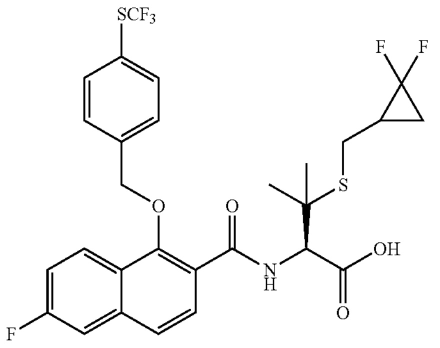

LCMS: $t_R$=2.74 min., m/z (ES$^+$)=618 (M+H$^+$).

Example 168: (R)-3-(cyclopentylthio)-3-methyl-2-(1-((4-(trifluoromethyl)benzyl)oxy)-2-naphthamido)butanoic Acid

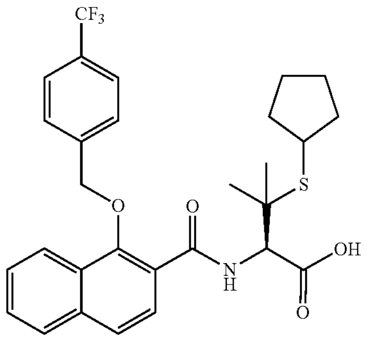 [SMILES: CC(C)(SC1CCCC1)[C@H](NC(=O)c1ccc2ccccc2c1OCc1ccc(C(F)(F)F)cc1)C(=O)O]

LCMS: $t_R$=2.80 min., m/z (ES$^+$)=546 (M+H$^+$).

Example 169: (R)-3-(cyclopentylthio)-3-methyl-2-(1-((4-((trifluoromethyl)thio)benzyl)oxy)-2-naphthamido)butanoic Acid

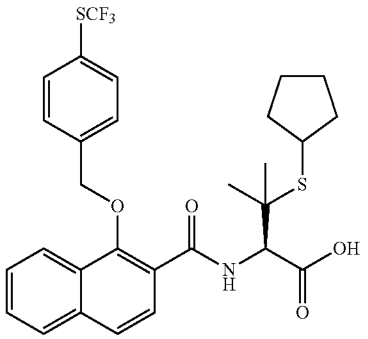

LCMS: $t_R$=2.94 min., m/z (ES$^+$)=578 (M+H$^+$).

Example 170: (R)-2-(1-(cyclohexylmethoxy)-2-naphthamido)-3-(cyclopentylthio)-3-methylbutanoic Acid

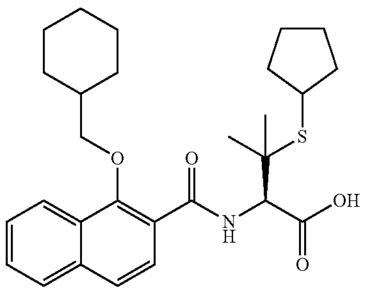 [SMILES: CC(C)(SC1CCCC1)[C@H](NC(=O)c1ccc2ccccc2c1OCC1CCCCC1)C(=O)O]

LCMS: $t_R$=2.96 min., m/z (ES$^+$)=484 (M+H$^+$).

Example 171: (R)-2-(1-(cyclohexylmethoxy)-2-naphthamido)-3-(cyclopentylthio)-3-methylbutanoic Acid

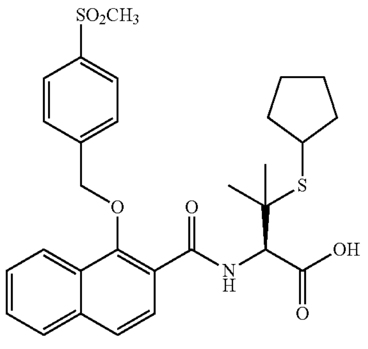 [SMILES: CC(C)(SC1CCCC1)[C@H](NC(=O)c1ccc2ccccc2c1OCc1ccc(S(C)(=O)=O)cc1)C(=O)O]

LCMS: $t_R$=2.32 min., m/z (ES$^+$)=556 (M+H$^+$).

Example 172: (R)-3-(cyclopentylthio)-2-(6-fluoro-1-((4-(methylsulfonyl)benzyl)oxy)-2-naphthamido)-3-methylbutanoic Acid

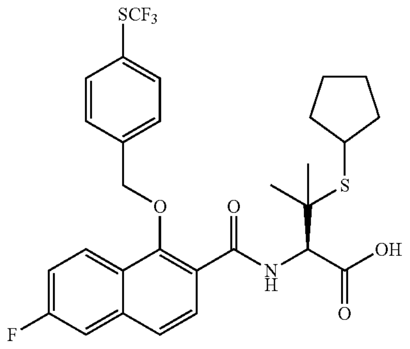

LCMS: $t_R$=2.95 min., m/z ($ES^+$)=596 ($M+H^+$).

Example 173: (R)-3-(((1S,2R,4R)-bicyclo[2.2.1]heptan-2-yl)thio)-3-methyl-2-(1-((4-(trifluoromethyl)benzyl)oxy)-2-naphthamido)butanoic Acid

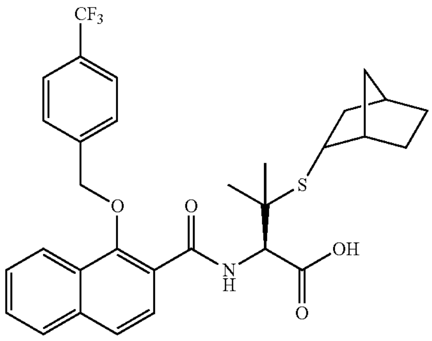 [SMILES: CC(C)(SC1CC2CCC1C2)[C@H](NC(=O)c1ccc2ccccc2c1OCc1ccc(C(F)(F)F)cc1)C(=O)O]

LCMS: $t_R$=2.91 min., m/z ($ES^+$)=572 ($M+H^+$).

Example 174: (R)-3-(((1S,2R,4R)-bicyclo[2.2.1]heptan-2-yl)thio)-3-methyl-2-(1-((4-((trifluoromethyl)thio)benzyl)oxy)-2-naphthamido)butanoic Acid

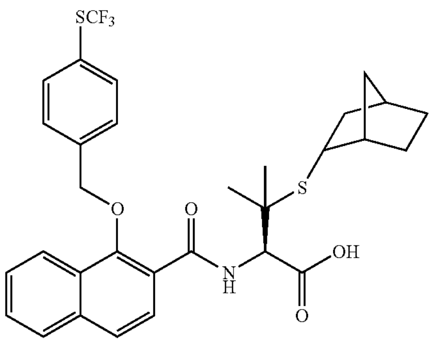

LCMS: $t_R$=3.02 min., m/z ($ES^+$)=604 ($M+H^+$).

Example 175: (R)-3-(((1S,2R,4R)-bicyclo[2.2.1]heptan-2-yl)thio)-3-methyl-2-(1-((4-((trifluoromethyl)thio)benzyl)oxy)-2-naphthamido)butanoic Acid

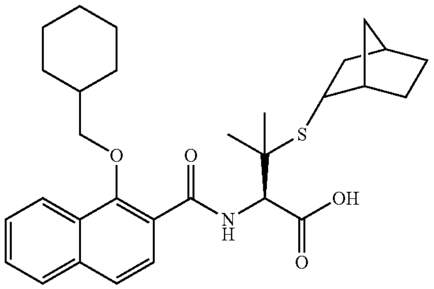 [SMILES: CC(C)(SC1CC2CCC1C2)[C@H](NC(=O)c1ccc2ccccc2c1OCC1CCCCC1)C(=O)O]

LCMS: $t_R$=3.08 min., m/z ($ES^+$)=510 ($M+H^+$).

Example 176: (R)-3-(((1S,2R,4R)-bicyclo[2.2.1]heptan-2-yl)thio)-3-methyl-2-(1-((4-(methylsulfonyl)benzyl)oxy)-2-naphthamido)butanoic Acid

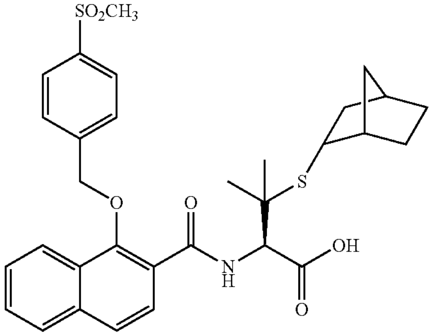 [SMILES: CC(C)(SC1CC2CCC1C2)[C@H](NC(=O)c1ccc2ccccc2c1OCc1ccc(S(C)(=O)=O)cc1)C(=O)O]

LCMS: $t_R$=2.43 min., m/z ($ES^+$)=582 ($M+H^+$).

Example 177: (R)-3-(((1S,2R,4R)-bicyclo[2.2.1]heptan-2-yl)thio)-2-(6-fluoro-1-((4-((trifluoromethyl)thio)benzyl)oxy)-2-naphthamido)-3-methylbutanoic Acid

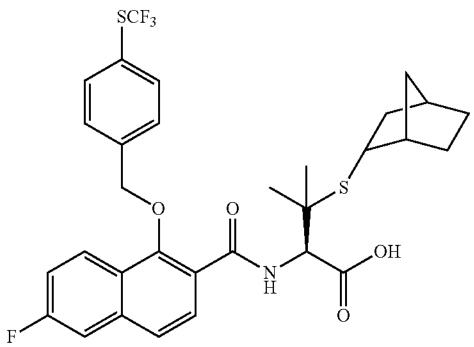

LCMS: $t_R$=3.05 min., m/z ($ES^+$)=622 ($M+H^+$).

Example 178: (S)-3-mesityl-2-(1-((4-(trifluoromethyl)benzyl)oxy)-2-naphthamido)propanoic Acid

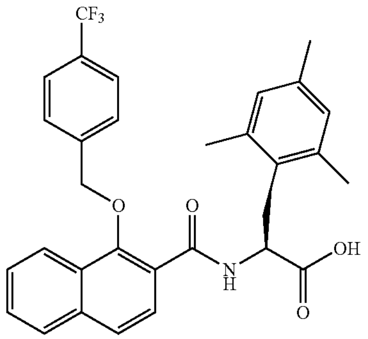 [SMILES: Cc1cc(C)c(C[C@H](NC(=O)c2ccc3ccccc3c2OCc2ccc(C(F)(F)F)cc2)C(=O)O)c(C)c1]

LCMS: $t_R$=4.33 min., m/z ($ES^+$)=536 ($M+H^+$).

Example 179: (S)-4,4-dimethyl-2-(1-(((1r,4S)-4-(trifluoromethyl)cyclohexyl)methoxy)-2-naphthamido)pentanoic Acid

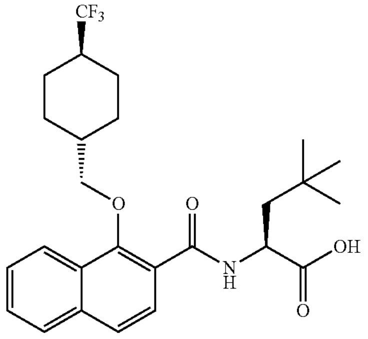

LCMS: $t_R$=2.65 min., m/z ($ES^+$)=480 ($M+H^+$).

Example 180: (S)-4,4-dimethyl-2-(1-(((1s,4R)-4-(trifluoromethyl)cyclohexyl)methoxy)-2-naphthamido)pentanoic Acid

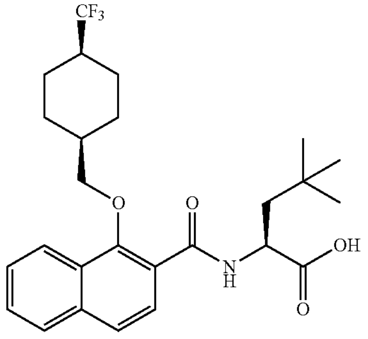 [SMILES: CC(C)(C)C[C@H](NC(=O)c1ccc2ccccc2c1OC[C@H]1CC[C@@H](C(F)(F)F)CC1)C(=O)O]

LCMS: $t_R$=2.61 min., m/z ($ES^+$)=480 ($M+H^+$).

Example 181: 4,4,4-trifluoro-3-(trifluoromethyl)-2-(1-((4-(trifluoromethyl)benzyl)oxy)-2-naphthamido)butanoic Acid

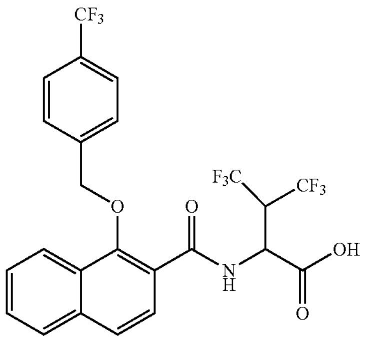 [SMILES: O=C(NC(C(=O)O)C(C(F)(F)F)C(F)(F)F)c1ccc2ccccc2c1OCc1ccc(C(F)(F)F)cc1]

LCMS: $t_R$=4.24 min., m/z ($ES^+$)=553 ($M+H^+$).

Example 182: 4,4,4-trifluoro-2-(6-fluoro-1-((4-(trifluoromethyl)benzyl)oxy)-2-naphthamido)-3-(trifluoromethyl)butanoic Acid

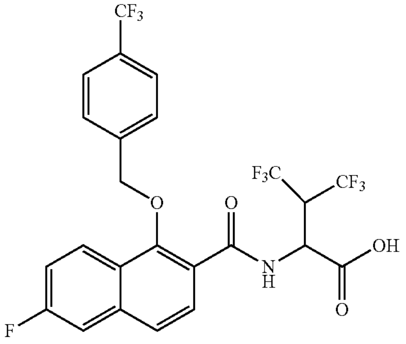 [SMILES: O=C(NC(C(=O)O)C(C(F)(F)F)C(F)(F)F)c1ccc2cc(F)ccc2c1OCc1ccc(C(F)(F)F)cc1]

LCMS: $t_R$=4.31 min., m/z ($ES^+$)=571 ($M+H^+$).

Example 183: 2-(1-(cyclohexylmethoxy)-2-naphthamido)-4,4,4-trifluoro-3-(trifluoromethyl)butanoic Acid

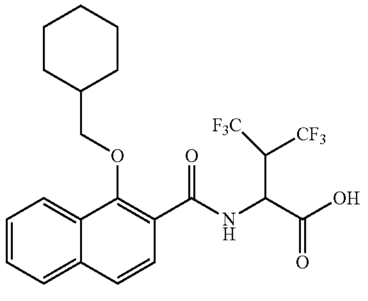 [SMILES: O=C(NC(C(=O)O)C(C(F)(F)F)C(F)(F)F)c1ccc2ccccc2c1OCC1CCCCC1]

LCMS: $t_R$=4.29 min., m/z ($ES^+$)=491 ($M+H^+$).

Example 184: 2-(4-aminobicyclo[2.2.2]octan-1-yl)-2-(6-fluoro-1-((4-(trifluoromethoxy)benzyl)oxy)-2-naphthamido)acetic Acid

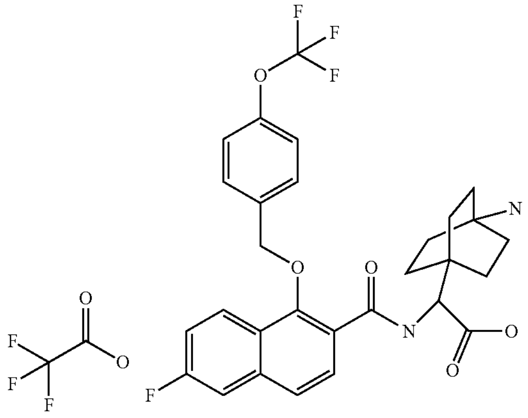

LCMS: $t_R$=3.03 min., m/z ($ES^+$)=675 ($M+H^+$).

Example 185: 2-(4-aminobicyclo[2.2.2]octan-1-yl)-2-(6-fluoro-1-((4-(trifluoromethyl)benzyl)oxy)-2-naphthamido)acetic Acid

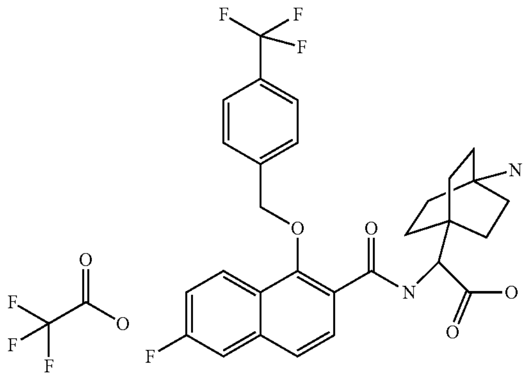

LCMS: $t_R$=2.99 min., m/z ($ES^+$)=659 ($M+H^+$).

Example 186: (S)-2-(6-amino-1-((4-(trifluoromethyl)benzyl)oxy)-2-naphthamido)-4,4-dimethylpentanoic Acid

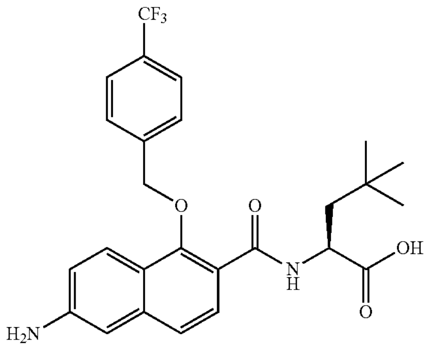 [SMILES: CC(C)(C)C[C@H](NC(=O)c1ccc2cc(N)ccc2c1OCc1ccc(C(F)(F)F)cc1)C(=O)O]

LCMS: $t_R$=3.42 min., m/z ($ES^+$)=489 ($M+H^+$).

Example 187: (S)-2-(6-amino-1-((4-(trifluoromethyl)benzyl)oxy)-2-naphthamido)-2-cyclopentylacetic Acid

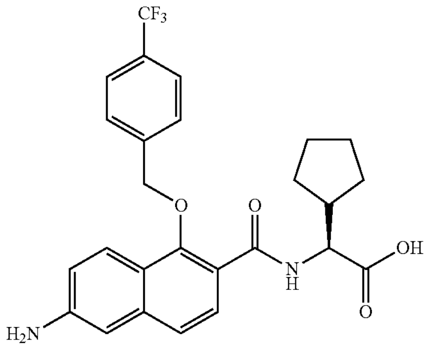 [SMILES: Nc1ccc2c(OCc3ccc(C(F)(F)F)cc3)c(C(=O)N[C@H](C(=O)O)C3CCCC3)ccc2c1]

LCMS: $t_R$=3.33 min., m/z ($ES^+$)=487 ($M+H^+$).

Example 188: O-benzyl-N-(1-((4-(trifluoromethoxy)benzyl)oxy)-2-naphthoyl)-L-allothreonine

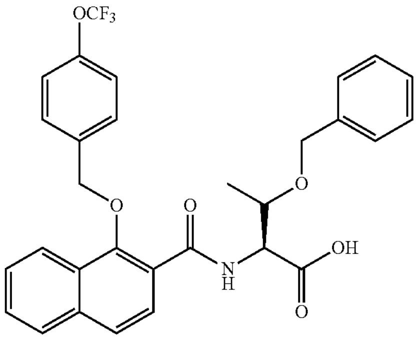 [SMILES: CC(OCc1ccccc1)[C@H](NC(=O)c1ccc2ccccc2c1OCc1ccc(OC(F)(F)F)cc1)C(=O)O]

LCMS: $t_R$=2.83 min., m/z ($ES^+$)=554 ($M+H^+$).

Example 189: (S)-3,3-diphenyl-2-(1-((4-(trifluoromethoxy)benzyl)oxy)-2-naphthamido)propanoic Acid

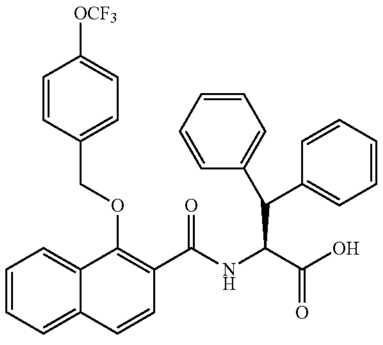 [SMILES: O=C(N[C@H](C(=O)O)C(c1ccccc1)c1ccccc1)c1ccc2ccccc2c1OCc1ccc(OC(F)(F)F)cc1]

LCMS: $t_R$=2.81 min., m/z ($ES^+$)=586 ($M+H^+$).

Example 190: (S)-2-(1-((4-(trifluoromethoxy)benzyl)oxy)-2-naphthamido)-3-(4-(trifluoromethyl)phenyl)propanoic Acid

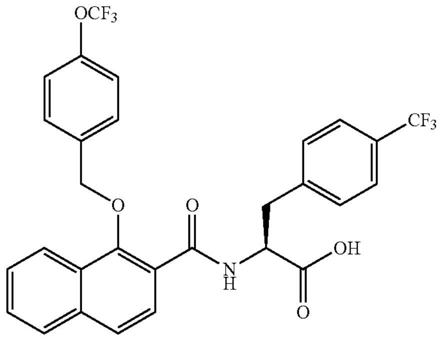 [SMILES: O=C(N[C@@H](Cc1ccc(C(F)(F)F)cc1)C(=O)O)c1ccc2ccccc2c1OCc1ccc(OC(F)(F)F)cc1]

LCMS: $t_R$=2.83 min., m/z ($ES^+$)=578 ($M+H^+$).

Example 191: (S)-4,4-dimethyl-2-(1-((4-(trifluoromethoxy)benzyl)oxy)-2-naphthamido)pentanoic Acid

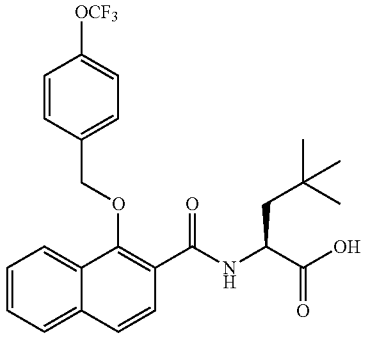

LCMS: $t_R$=2.81 min., m/z ($ES^+$)=490 ($M+H^+$).

Example 192: O-benzyl-N-(6-fluoro-1-((4-(trifluoromethoxy)benzyl)oxy)-2-naphthoyl)-L-allothreonine

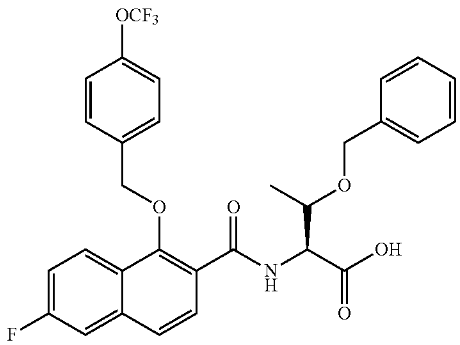 [SMILES: CC(OCc1ccccc1)[C@H](NC(=O)c1ccc2cc(F)ccc2c1OCc1ccc(OC(F)(F)F)cc1)C(=O)O]

LCMS: $t_R$=2.89 min., m/z ($ES^+$)=572 ($M+H^+$).

Example 193: (S)-2-(6-fluoro-1-((4-(trifluoromethoxy)benzyl)oxy)-2-naphthamido)-3,3-diphenylpropanoic Acid

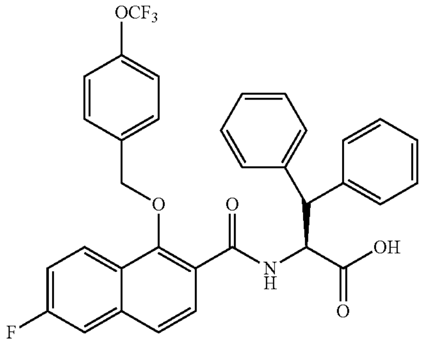 [SMILES: O=C(N[C@H](C(=O)O)C(c1ccccc1)c1ccccc1)c1ccc2cc(F)ccc2c1OCc1ccc(OC(F)(F)F)cc1]

LCMS: $t_R$=2.85 min., m/z ($ES^+$)=604 ($M+H^+$).

Example 194: (S)-2-(6-fluoro-1-((4-(trifluoromethoxy)benzyl)oxy)-2-naphthamido)-3-(4-(trifluoromethyl)phenyl)propanoic Acid

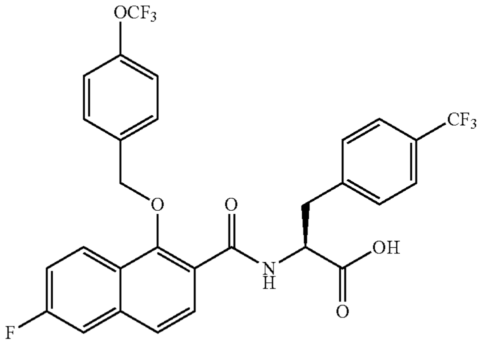 [SMILES: O=C(N[C@@H](Cc1ccc(C(F)(F)F)cc1)C(=O)O)c1ccc2cc(F)ccc2c1OCc1ccc(OC(F)(F)F)cc1]

LCMS: $t_R$=2.90 min., m/z ($ES^+$)=596 ($M+H^+$).

Example 195: O-benzyl-N-(6-fluoro-1-((4-(trifluoromethyl)benzyl)oxy)-2-naphthoyl)-L-allothreonine

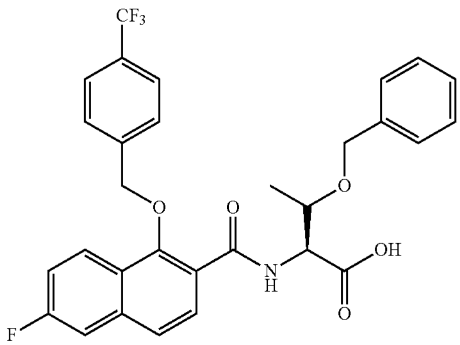 [SMILES: CC(OCc1ccccc1)[C@H](NC(=O)c1ccc2cc(F)ccc2c1OCc1ccc(C(F)(F)F)cc1)C(=O)O]

LCMS: $t_R$=2.72 min., m/z ($ES^+$)=556 ($M+H^+$).

Example 196: O-benzyl-N-(6-fluoro-1-((4-(trifluoromethyl)benzyl)oxy)-2-naphthoyl)-L-allothreonine

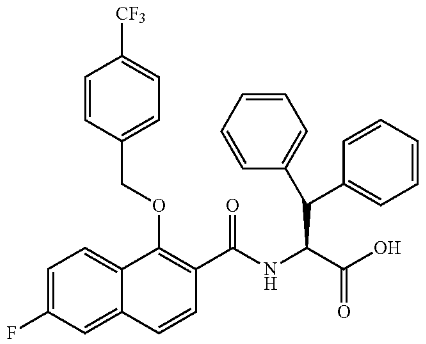 [SMILES: O=C(N[C@H](C(=O)O)C(c1ccccc1)c1ccccc1)c1ccc2cc(F)ccc2c1OCc1ccc(C(F)(F)F)cc1]

LCMS: $t_R$=2.70 min., m/z ($ES^+$)=588 ($M+H^+$).

Example 197: (S)-2-(6-fluoro-1-((4-(trifluoromethyl)benzyl)oxy)-2-naphthamido)-3-(4-(trifluoromethyl)phenyl)propanoic Acid

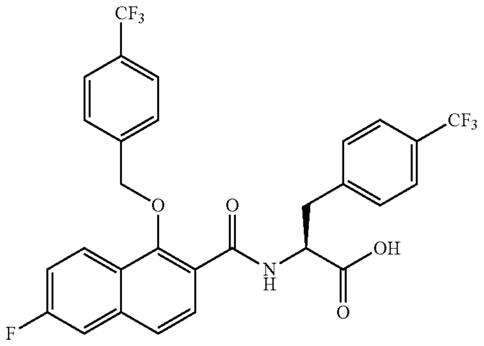 [SMILES: O=C(N[C@@H](Cc1ccc(C(F)(F)F)cc1)C(=O)O)c1ccc2cc(F)ccc2c1OCc1ccc(C(F)(F)F)cc1]

LCMS: $t_R$=2.66 min., m/z ($ES^+$)=580 ($M+H^+$).

Example 198: (S)-2-(6-fluoro-1-((4-(trifluoromethyl)benzyl)oxy)-2-naphthamido)-4,4-dimethylpentanoic Acid

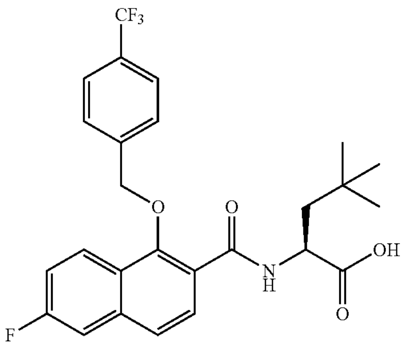

LCMS: $t_R$=2.64 min., m/z ($ES^+$)=492 ($M+H^+$).

Example 199: (S)-2-(1-(cyclohexylmethoxy)-2-naphthamido)-3,3-diphenylpropanoic Acid

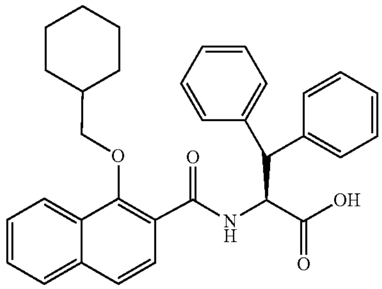 [SMILES: O=C(N[C@H](C(=O)O)C(c1ccccc1)c1ccccc1)c1ccc2ccccc2c1OCC1CCCCC1]

LCMS: $t_R$=2.83 min., m/z ($ES^+$)=508 ($M+H^+$).

Example 200: (S)-2-(1-(cyclohexylmethoxy)-2-naphthamido)-3-(4-(trifluoromethyl)phenyl)propanoic Acid

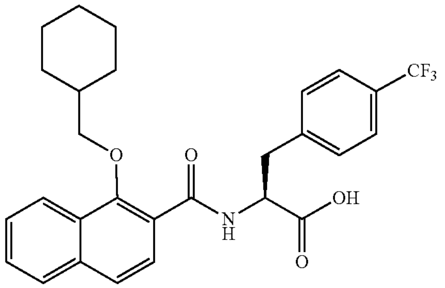 [SMILES: O=C(N[C@@H](Cc1ccc(C(F)(F)F)cc1)C(=O)O)c1ccc2ccccc2c1OCC1CCCCC1]

LCMS: $t_R$=2.77 min., m/z ($ES^+$)=500 ($M+H^+$).

Example 201: (S)-2-(1-(cyclohexylmethoxy)-2-naphthamido)-4,4-dimethylpentanoic Acid

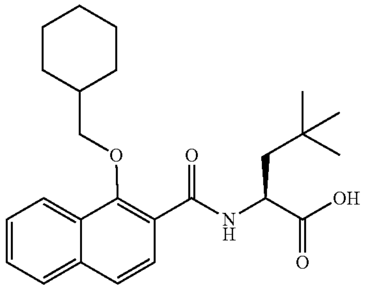 [SMILES: CC(C)(C)C[C@H](NC(=O)c1ccc2ccccc2c1OCC1CCCCC1)C(=O)O]

LCMS: $t_R$=2.78 min., m/z ($ES^+$)=412 ($M+H^+$).

Example 202: (S)-2-(1-(cyclohexylmethoxy)-2-naphthamido)-4,4-dimethylpentanoic Acid

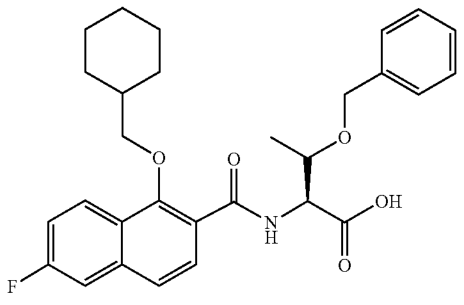 [SMILES: CC(OCc1ccccc1)[C@H](NC(=O)c1ccc2cc(F)ccc2c1OCC1CCCCC1)C(=O)O]

LCMS: $t_R$=2.82 min., m/z ($ES^+$)=494 ($M+H^+$).

Example 203: (S)-2-(1-(cyclohexylmethoxy)-2-naphthamido)-4,4-dimethylpentanoic Acid

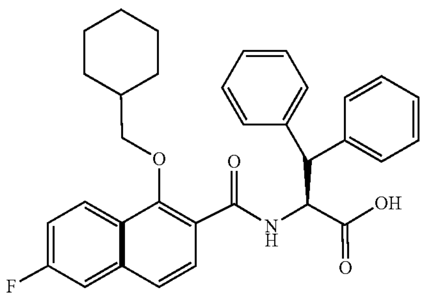

LCMS: $t_R$=2.86 min., m/z ($ES^+$)=526 ($M+H^+$).

Example 204: (S)-2-(1-(cyclohexylmethoxy)-6-fluoro-2-naphthamido)-3-(4-(trifluoromethyl)phenyl) propanoic Acid

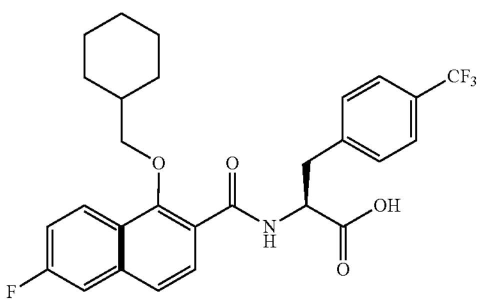

LCMS: $t_R$=2.79 min., m/z ($ES^+$)=518 ($M+H^+$).

Example 205: (S)-2-(1-(cyclohexylmethoxy)-6-fluoro-2-naphthamido)-4,4-dimethylpentanoic Acid

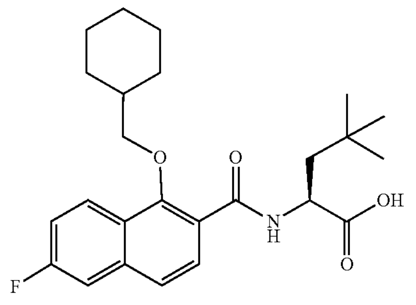 [SMILES: CC(C)(C)C[C@H](NC(=O)c1ccc2cc(F)ccc2c1OCC1CCCCC1)C(=O)O]

LCMS: $t_R$=2.80 min., m/z ($ES^+$)=430 ($M+H^+$).

Example 206: (S)-2-(1-(cyclohexylmethoxy)-6-fluoro-2-naphthamido)-4,4-dimethylpentanoic Acid

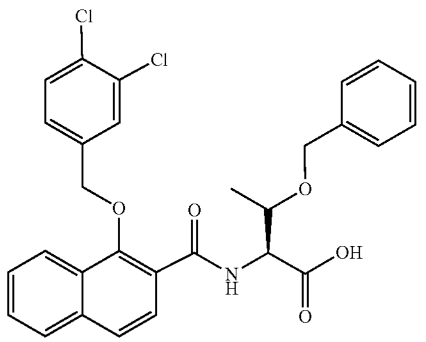 [SMILES: CC(OCc1ccccc1)[C@H](NC(=O)c1ccc2ccccc2c1OCc1ccc(Cl)c(Cl)c1)C(=O)O]

LCMS: $t_R$=2.57 min., m/z ($ES^+$)=538 ($M+H^+$).

Example 207: (S)-2-(1-((3,4-dichlorobenzyl)oxy)-2-naphthamido)-3,3-diphenylpropanoic Acid

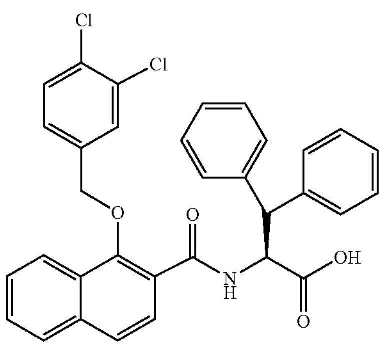 [SMILES: O=C(N[C@H](C(=O)O)C(c1ccccc1)c1ccccc1)c1ccc2ccccc2c1OCc1ccc(Cl)c(Cl)c1]

LCMS: $t_R$=2.62 min., m/z ($ES^+$)=571 ($M+H^+$).

Example 208: O-benzyl-N-(1-((3,4-dichlorobenzyl)oxy)-6-fluoro-2-naphthoyl)-L-allothreonine

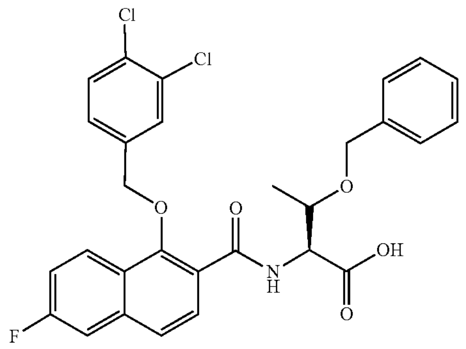 [SMILES: CC(OCc1ccccc1)[C@H](NC(=O)c1ccc2cc(F)ccc2c1OCc1ccc(Cl)c(Cl)c1)C(=O)O]

LCMS: $t_R$=2.76 min., m/z ($ES^+$)=556 ($M+H^+$).

Example 209: (S)-2-(1-((3,4-dichlorobenzyl)oxy)-6-fluoro-2-naphthamido)-3,3-diphenylpropanoic Acid

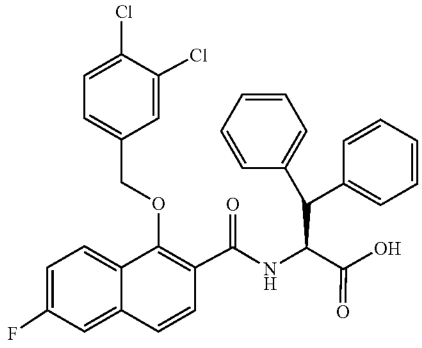 [SMILES: O=C(N[C@H](C(=O)O)C(c1ccccc1)c1ccccc1)c1ccc2cc(F)ccc2c1OCc1ccc(Cl)c(Cl)c1]

LCMS: $t_R$=2.75 min., m/z ($ES^+$)=589 ($M+H^+$).

Example 210: (S)-2-(1-((3,4-dichlorobenzyl)oxy)-6-fluoro-2-naphthamido)-3-(4-(trifluoromethyl)phenyl)propanoic Acid

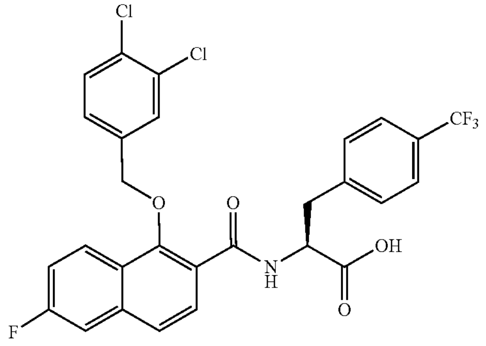 [SMILES: O=C(N[C@@H](Cc1ccc(C(F)(F)F)cc1)C(=O)O)c1ccc2cc(F)ccc2c1OCc1ccc(Cl)c(Cl)c1]

LCMS: $t_R$=2.71 min., m/z ($ES^+$)=580 ($M+H^+$).

Example 211: (S)-2-(1-((3,4-dichlorobenzyl)oxy)-6-fluoro-2-naphthamido)-4,4-dimethylpentanoic Acid

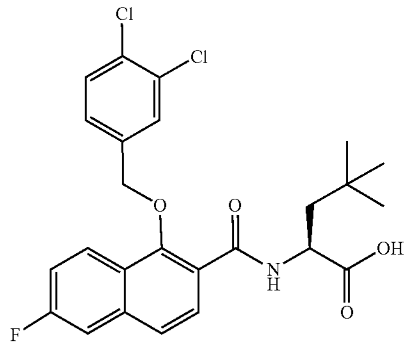 [SMILES: CC(C)(C)C[C@H](NC(=O)c1ccc2cc(F)ccc2c1OCc1ccc(Cl)c(Cl)c1)C(=O)O]

LCMS: $t_R$=2.54 min., m/z ($ES^+$)=492 ($M+H^+$).

Example 212: (S)-2-(1-(benzo[d]thiazol-2-ylmethoxy)-2-naphthamido)-3,3-diphenylpropanoic Acid

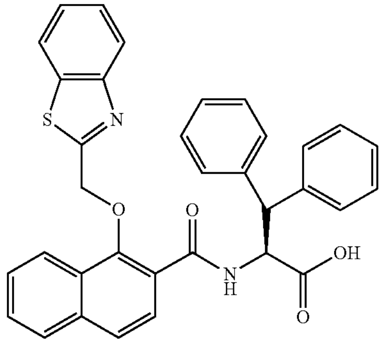 [SMILES: O=C(N[C@H](C(=O)O)C(c1ccccc1)c1ccccc1)c1ccc2ccccc2c1OCc1nc2ccccc2s1]

LCMS: $t_R$=2.51 min., m/z ($ES^+$)=559 ($M+H^+$).

Example 213: (S)-2-(1-(benzo[d]thiazol-2-ylmethoxy)-2-naphthamido)-3-(4-(trifluoromethyl)phenyl)propanoic Acid

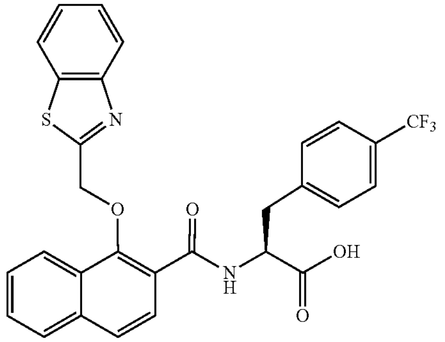 [SMILES: O=C(N[C@@H](Cc1ccc(C(F)(F)F)cc1)C(=O)O)c1ccc2ccccc2c1OCc1nc2ccccc2s1]

LCMS: $t_R$=2.49 min., m/z ($ES^+$)=551 ($M+H^+$).

Example 214: (S)-2-(1-(benzo[d]thiazol-2-ylmethoxy)-2-naphthamido)-4,4-dimethylpentanoic Acid

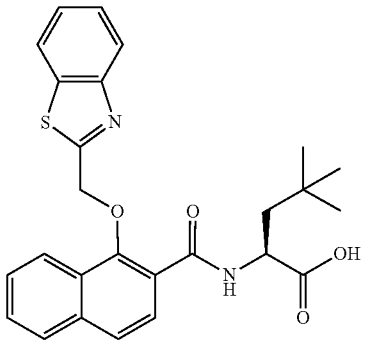 [SMILES: CC(C)(C)C[C@H](NC(=O)c1ccc2ccccc2c1OCc1nc2ccccc2s1)C(=O)O]

LCMS: $t_R$=2.44 min., m/z ($ES^+$)=463 ($M+H^+$).

Example 215: N-(1-(benzo[d]thiazol-2-ylmethoxy)-6-fluoro-2-naphthoyl)-O-benzyl-L-allothreonine

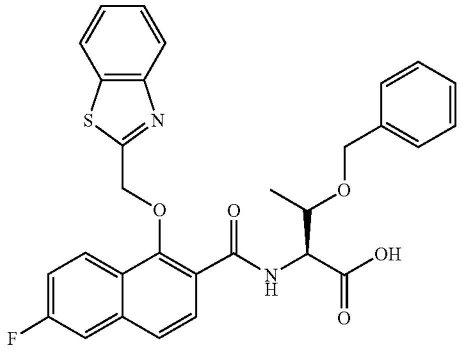 [SMILES: CC(OCc1ccccc1)[C@H](NC(=O)c1ccc2cc(F)ccc2c1OCc1nc2ccccc2s1)C(=O)O]

LCMS: $t_R$=2.52 min., m/z ($ES^+$)=545 ($M+H^+$).

Example 216: (S)-2-(1-(benzo[d]thiazol-2-ylmethoxy)-6-fluoro-2-naphthamido)-3,3-diphenylpropanoic Acid

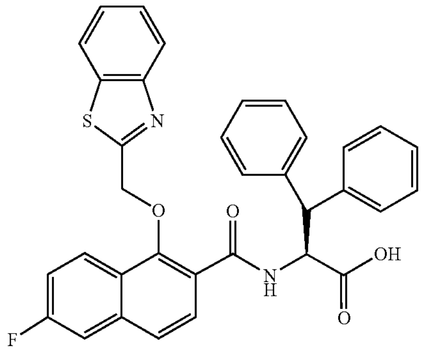 [SMILES: O=C(N[C@H](C(=O)O)C(c1ccccc1)c1ccccc1)c1ccc2cc(F)ccc2c1OCc1nc2ccccc2s1]

LCMS: $t_R$=2.54 min., m/z ($ES^+$)=577 ($M+H^+$).

Example 217: (S)-2-(1-(benzo[d]thiazol-2-ylmethoxy)-6-fluoro-2-naphthamido)-3-(4-(trifluoromethyl)phenyl)propanoic Acid

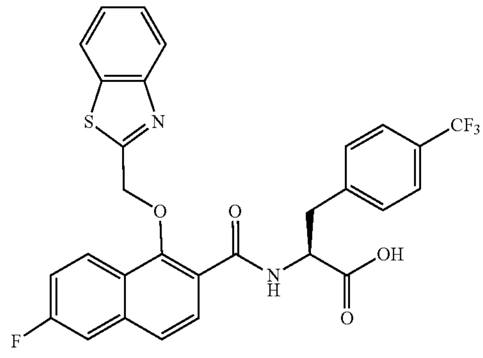 [SMILES: O=C(N[C@@H](Cc1ccc(C(F)(F)F)cc1)C(=O)O)c1ccc2cc(F)ccc2c1OCc1nc2ccccc2s1]

LCMS: $t_R$=2.51 min., m/z ($ES^+$)=569 ($M+H^+$).

Example 218: (S)-2-(1-(benzo[d]thiazol-2-ylmethoxy)-6-fluoro-2-naphthamido)-4,4-dimethylpentanoic Acid

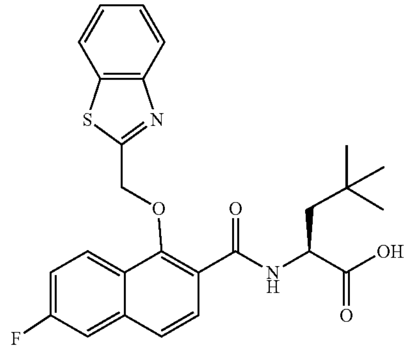 [SMILES: CC(C)(C)C[C@H](NC(=O)c1ccc2cc(F)ccc2c1OCc1nc2ccccc2s1)C(=O)O]

LCMS: $t_R$=2.46 min., m/z ($ES^+$)=481 ($M+H^+$).

Example 219: 3,3-dimethyl-2-[[7-methyl-1-[[4-(trifluoromethyl)phenyl]methoxy]naphthalene-2-carbonyl]amino]pent-4-ynoic Acid

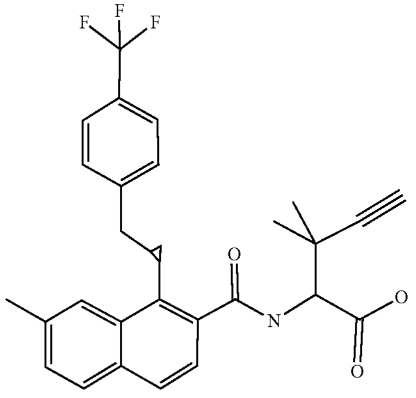

LCMS: $t_R$=4.13 min., m/z ($ES^+$)=484 ($M+H^+$).

Example 220: 3,3-dimethyl-2-[[1-[[4-(trifluoromethoxy)phenyl]methoxy]naphthalene-2-carbonyl]amino]pent-4-enoic Acid

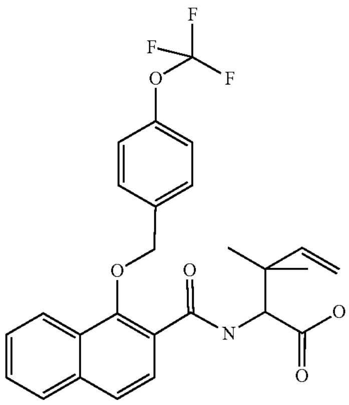

LCMS: $t_R$=4.33 min., m/z ($ES^+$)=488 ($M+H^+$).

Example 221: (2S)-2-[[5-fluoro-1-[[4-(trifluoromethoxy)phenyl]methoxy]naphthalene-2-carbonyl]amino]-3,3-dimethyl-butanoic Acid

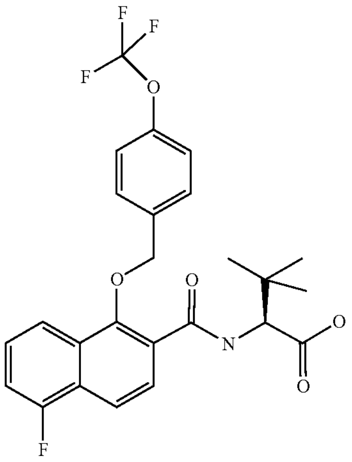

LCMS: $t_R$=4.19 min., m/z ($ES^+$)=494 ($M+H^+$).

Example 222: (2S)-3,3-dimethyl-2-[[1-[[4-(trifluoromethyl)cyclohexyl]methoxy]naphthalene-2-carbonyl]amino]butanoic Acid

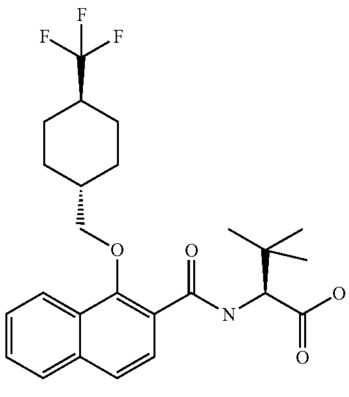

LCMS: $t_R$=2.53 min., m/z ($ES^+$)=466 ($M+H^+$).

Example 223: 3,3-dimethyl-2-[[1-[[4-(trifluoromethyl)phenyl]methoxy]naphthalene-2-carbonyl]amino]pent-4-enoic Acid

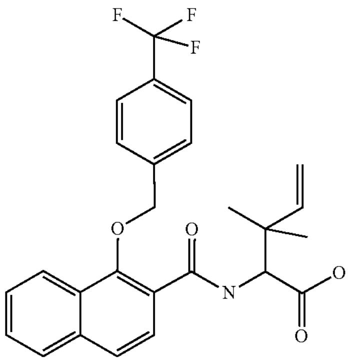

LCMS: $t_R$=4.01 min., m/z ($ES^+$)=472 ($M+H^+$).

Example 224: (2S)-2-[[6-fluoro-1-(4-methylpent-2-ynoxy)naphthalene-2-carbonyl]amino]-3,3-dimethyl-butanoic Acid

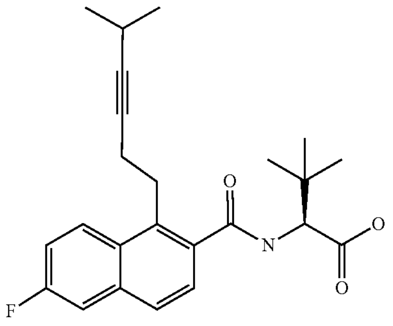

LCMS: $t_R$=3.82 min., m/z ($ES^+$)=400 ($M+H^+$).

Example 225: (2S)-3,3-dimethyl-2-[[6-methyl-1-[[4-(trifluoromethyl)phenyl]methoxy]naphthalene-2-carbonyl]amino]pentanoic Acid

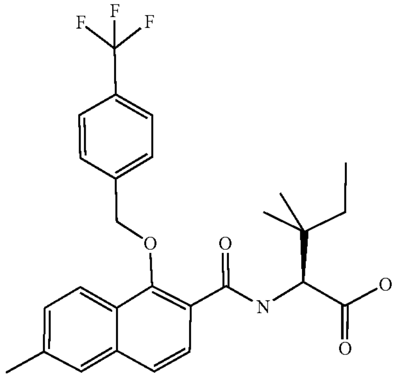

LCMS: $t_R$=4.34 min., m/z ($ES^+$)=488 ($M+H^+$).

Example 226: (2S)-2-[[5-fluoro-1-[[4-(trifluoromethoxy)phenyl]methoxy]naphthalene-2-carbonyl]amino]-3,3-dimethyl-pentanoic Acid

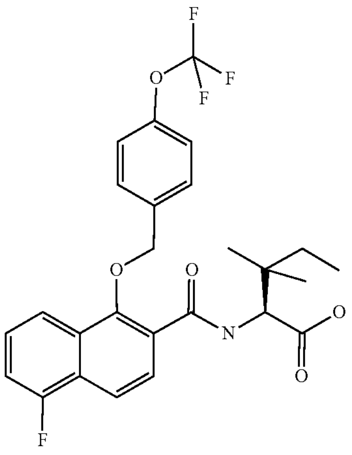

LCMS: $t_R$=4.29 min., m/z ($ES^+$)=508 ($M+H^+$).

Example 227: 3,3-dimethyl-2-[[1-[[4-(trifluoromethylsulfanyl)phenyl]methoxy]naphthalene-2-carbonyl]amino]pent-4-ynoic Acid

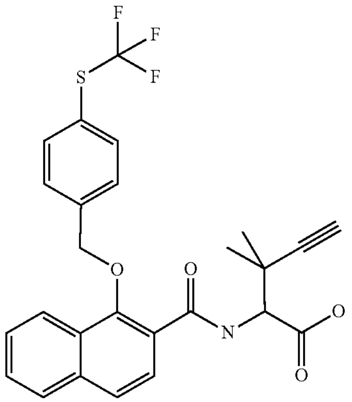

LCMS: $t_R$=4.14 min., m/z ($ES^+$)=502 ($M+H^+$).

Example 228: 3,3-dimethyl-2-[[1-[[4-(trifluoromethyl)phenyl]methoxy]naphthalene-2-carbonyl]amino]pent-4-ynoic Acid

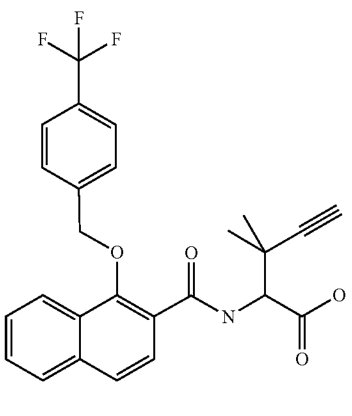

LCMS: $t_R$=4.00 min., m/z ($ES^+$)=470 ($M+H^+$).

Example 229: (2S)-2-(1-methylcyclopropyl)-2-[[7-methyl-1-[[4-(trifluoromethyl)phenyl]methoxy]naphthalene-2-carbonyl]amino]acetic Acid

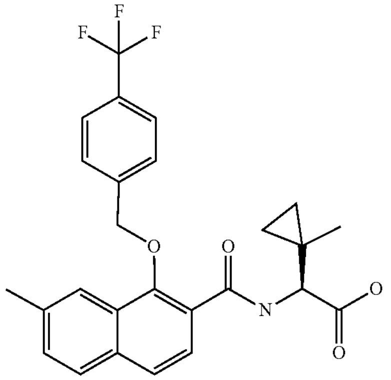

LCMS: $t_R$=4.12 min., m/z ($ES^+$)=472 ($M+H^+$).

Example 230: (2S)-2-[[5-fluoro-1-[[4-(trifluoromethyl)phenyl]methoxy]naphthalene-2-carbonyl]amino]-3,3-dimethyl-pentanoic Acid

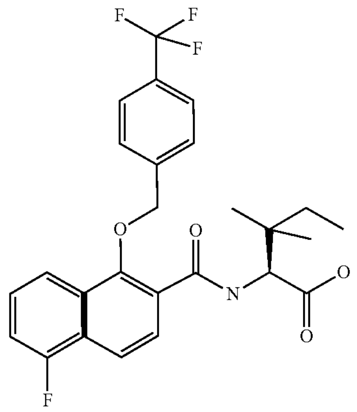

LCMS: $t_R$=4.24 min., m/z ($ES^+$)=492 ($M+H^+$).

Example 231: (2S)-3,3-dimethyl-2-[[1-[(4-nitrophenyl)methoxy]naphthalene-2-carbonyl]amino]butanoic Acid

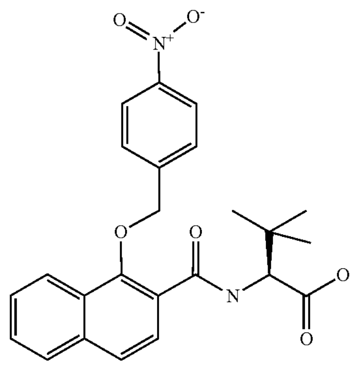

LCMS: $t_R$=3.36 min., m/z ($ES^+$)=437 ($M+H^+$).

Example 232: (2S)-3,3-dimethyl-2-[[1-(4-pyridylmethoxy)naphthalene-2-carbonyl]amino]butanoic Acid

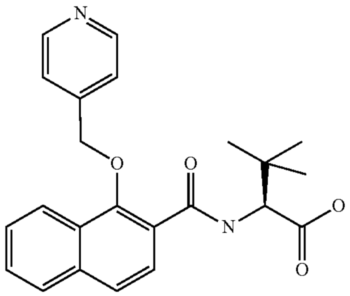

LCMS: $t_R$=3.30 min., m/z ($ES^+$)=393 ($M+H^+$).

Example 233: (2S)-3,3-dimethyl-2-[[6-methyl-1-[[4-(trifluoromethyl)phenyl]methoxy]naphthalene-2-carbonyl]amino]butanoic Acid

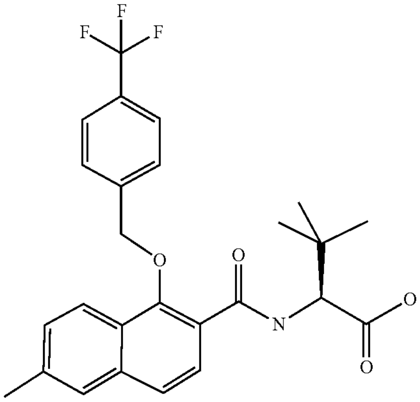

LCMS: $t_R$=4.23 min., m/z ($ES^+$)=474 ($M+H^+$).

Example 234: 3,3-dimethyl-2-[[1-[[4-(trifluoromethoxy)phenyl]methoxy]naphthalene-2-carbonyl]amino]pent-4-ynoic Acid

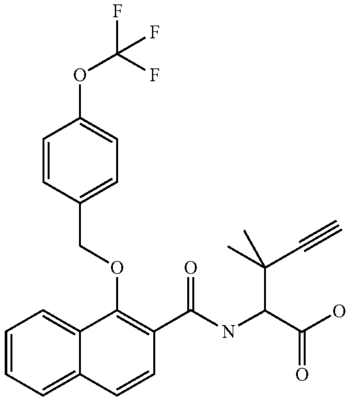

LCMS: $t_R$=4.04 min., m/z ($ES^+$)=486 ($M+H^+$).

Example 235: (2S)-3,3-dimethyl-2-[[1-(4-methylpent-2-ynoxy)naphthalene-2-carbonyl]amino]butanoic Acid

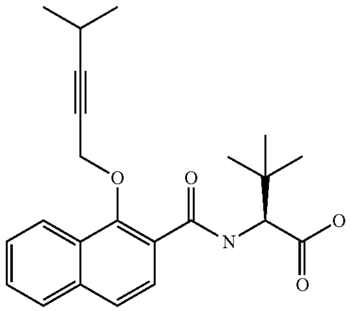

LCMS: $t_R$=3.73 min., m/z ($ES^+$)=382 ($M+H^+$).

Example 236: (2S)-2-[[5-fluoro-1-[[4-(trifluoromethyl)phenyl]methoxy]naphthalene-2-carbonyl]amino]-3,3-dimethyl-butanoic Acid

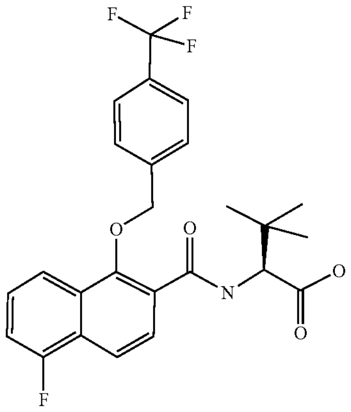

LCMS: $t_R$=4.14 min., m/z ($ES^+$)=478 ($M+H^+$).

Intermediate Syntheses

Preparation of 7-chloro-1-((4-(trifluoromethoxy)benzyl)oxy)-2-naphthoic Acid

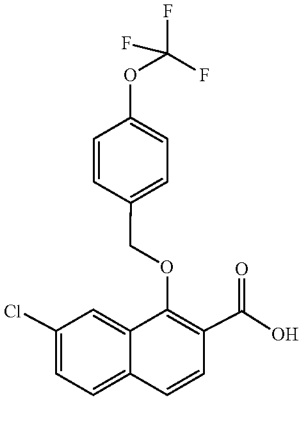 [SMILES: O=C(O)c1ccc2ccc(Cl)cc2c1OCc1ccc(OC(F)(F)F)cc1]

Step 1, preparation of ethyl 7-chloro-1-oxo-1,2,3,4-tetrahydronaphthalene-2-carboxylate

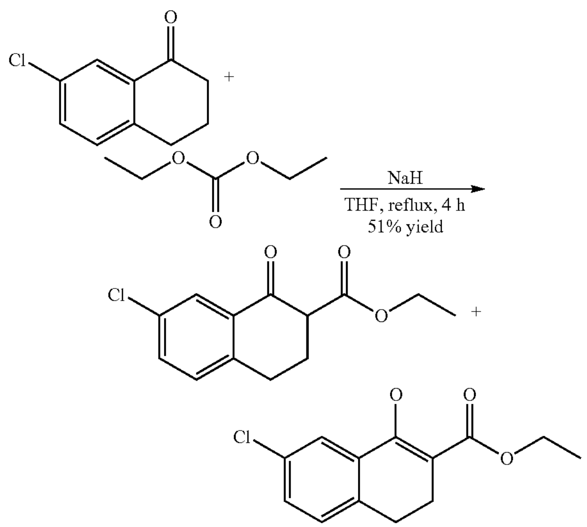

To a suspension of sodium hydride (1.87 g, 46.7 mmol) in 150 mL of THF was added diethyl carbonate (4.29 ml, 35 mmol). Then 7-chloro-1-tetralone (4.44 g, 23.35 mmol) in 75 mL of THF was added dropwise. The mixture was heated at reflux for 4 hours. The mixture was cooled at 0° C. and hydrolyzed with caution with a solution of hydrochloric acid 1 M. The crude mixture was extracted twice with diethyl ether. The organic phases were collected and dried over $Na_2SO_4$ and concentrated in vacuum. The crude product obtained was purified by column chromatography on silica gel using a mixture of heptane and ethyl acetate as eluent (gradient: 0% AcOEt-25'→50% AcOEt) to give yellow oil (3 g, 51% yield).

LCMS: $t_R$=0.79 min. & 1.05 min. (Keto/enol), m/z ($ES^+$)=253 ($M+H^+$).

Step 2, preparation of ethyl 2-bromo-7-chloro-1-oxo-1,2,3,4-tetrahydronaphthalene-2-carboxylate

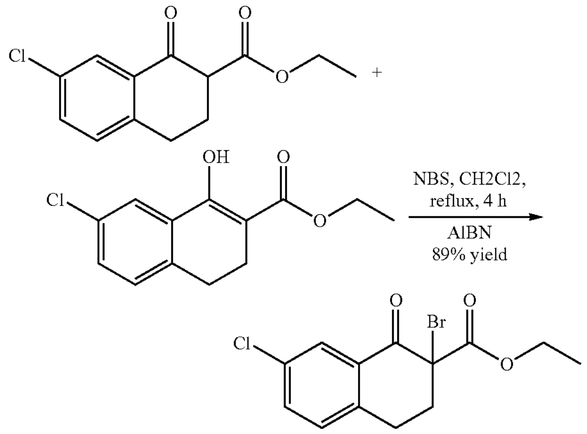

To a solution of ethyl 7-chloro-1-oxo-1,2,3,4-tetrahydronaphthalene-2-carboxylate (3 g, 11.87 mmol) in 100 mL of dichloromethane was added N-bromosuccinimide (2.35 g, 13.06 mmol) and 2,2'-azobis(2-methylpropionitrile) (99.47 mg, 593.6 μmol). The mixture was heated at reflux for 4 hours. Then, the mixture was cooled at room temperature and was concentrated in vacuum. 20 mL of heptane was added and the crude mixture was filtered and evaporated. The crude product obtained was purified by column chromatography on silica gel using a mixture of heptane and ethyl acetate as eluent (gradient: 0% to 50% AcOEt) to give a yellow oil (3.5 g, 89% yield).

LCMS: $t_R$=0.88 min., m/z ($ES^+$)=333 ($M+H^+$).

Step 3. Preparation of ethyl 7-chloro-1-hydroxy-2-naphthoate

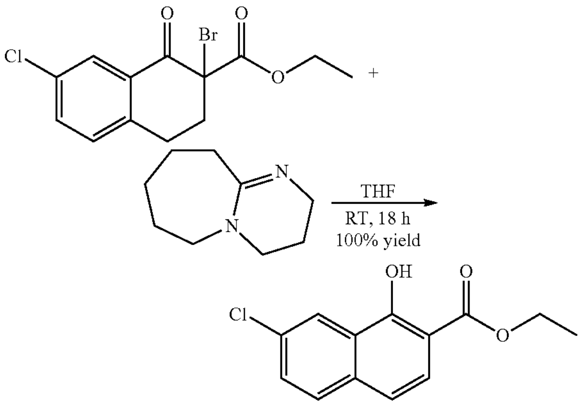

To a solution of ethyl 2-bromo-7-chloro-1-oxo-1,2,3,4-tetrahydronaphthalene-2-carboxylate (3.5 g, 10.56 mmol) in 120 mL of tetrahydrofuran was added dropwise 1,8-diazabicyclo[5.4.0]undec-7-ene (3.22 ml, 21.11 mmol). The solution was stirred at room temperature for 18 hours. Then, the crude mixture was poured on 100 mL of ice water and acidified with hydrochloric acid 1 M until pH<3. The crude mixture was extracted twice with ethyl acetate. The organic phases were collected, dried over $Na_2SO_4$ and concentrated in vacuum. The crude product obtained was a yellow solid. (2.65 g, 100% yield). The product was used without further purification.

LCMS: $t_R$=1.04 min., m/z ($ES^+$)=251 ($M+H^+$).

Step 4. Preparation of ethyl 7-chloro-1-((4-(trifluoromethoxy)benzyl)oxy)-2-naphthoate

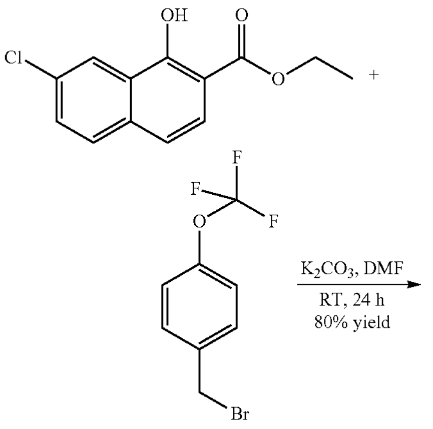

-continued

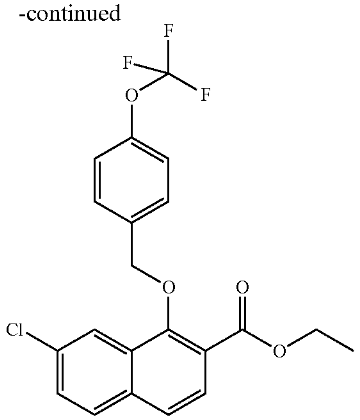

To a solution of ethyl 7-chloro-1-hydroxy-2-naphthoate (2.70 g, 10.77 mmol) in 150 mL of N,N-dimethylformamide was added potassium carbonate (1.79 g, 12.92 mmol) and 4-(trifluoromethoxy)benzyl bromide (1.93 ml, 11.85 mmol). The mixture was stirred at room temperature for 12 hours. Then, the crude was concentrated in vacuum and extracted with ethyl acetate. The organic layer was washed once with water and once with saturated aqueous solution of NaCl. The organic layers were collected, dried over $Na_2SO_4$ and concentrated in vacuum. The crude product obtained was purified by column chromatography on silica gel using a mixture of heptane and ethyl acetate as eluent (gradient: 0% to 10% AcOEt) to give yellow oil (3.63 g, 80% yield).

LCMS: $t_R$=1.10 min., m/z ($ES^+$)=425 ($M+H^+$).

Step 5. Preparation of 7-chloro-1-((4-(trifluoromethoxy)benzyl)oxy)-2-naphthoic Acid

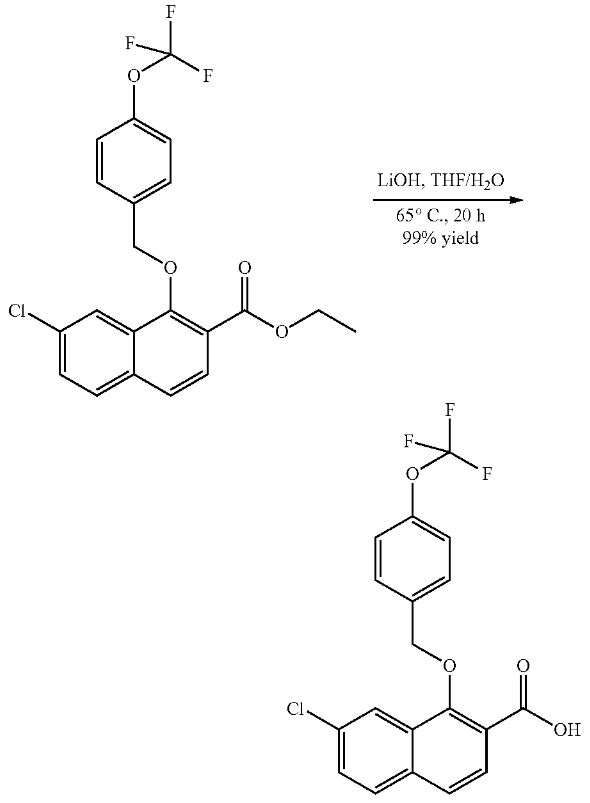

To a solution of ethyl 7-chloro-1-((4-(trifluoromethoxy)benzyl)oxy)-2-naphthoate (3.63 g, 8.55 mmol) in 16 mL of tetrahydrofuran was added lithium hydroxide (1.43 g, 34.18 mmol) and 4 mL of water. The mixture was heated at 65° C. for 20 hours. Then, the crude was concentrated in vacuum. Water was added and the mixture was extracted with ethyl acetate. The aqueous layer was acidified with HCl 1 M solution and washed once with ethyl acetate. The organic layer was collected and washed once with water and once with saturated aqueous solution of NaCl. The organic phases were dried over $Na_2SO_4$ and concentrated in vacuum. The crude product obtained was yellow oil (3.37 g, 99% yield). The product was used without purification.

LCMS: $t_R$=0.94 min., m/z ($ES^+$)=397 ($M+H^+$).

Preparation of 7-methyl-1-[[4-(trifluoromethoxy)phenyl]methoxy]naphthalene-2-carboxylic Acid

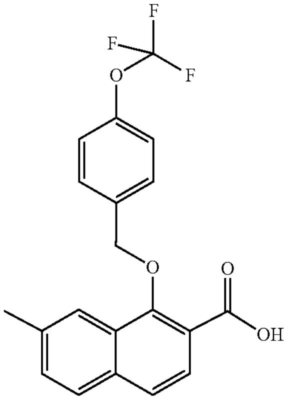 [SMILES: Cc1ccc2ccc(C(=O)O)c(OCc3ccc(OC(F)(F)F)cc3)c2c1]

Step 1. Preparation of 7-Methyl-1-oxo-1,2,3,4-tetrahydro-naphthalene-2-carboxylic Acid Methyl Ester

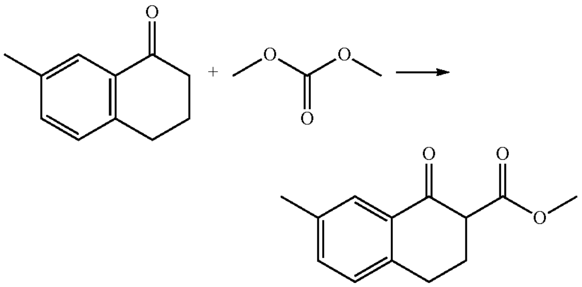

Under nitrogen atmosphere, 7-methyl-3,4-dihydronaphthalen-1(2H)-one (2.0 g, 12.5 mmol) was added to dimethyl carbonate (12.5 mL, 150 mmol). Sodium hydride (1.0 g, 60 percent in mineral oil, 25.0 mmol) and dry methanol (0.05 mL, 0.1 eq.) were added. The suspension was heated to 80° C. (bath) and stirred for 3 hours. After cooling in ice-water bath, ethyl acetate (25 mL) was added, followed by hydrochloric acid (3N, 30.0 mL) while cooling in an ice-water bath. The two layers were separated and the aqueous solution was extracted with ethyl acetate (10 mL×2) and the combined organic phases were dried over anhydrous sodium sulphate. After removing the solvent, the product was obtained as a red-brown liquid, 2.7 g, 99% yield. The compound was used immediately without further purification.

$^1H$ NMR ($CDCl_3$, 300 MHz): (mixture and enol and ketone forms) δ 12.45 (s), 7.82-7.21 (m, 3H), 3.82 (s), 3.83 (s) 3.60 (m), 3.00 (m), 2.82 (m), 2.41 (s).

LCMS: $t_R$=1.18 min and 1.49 min; m/z ($ES^+$)=219 ($M+H^+$).

Step 2. 1-Hydroxy-7-methyl-naphthalene-2-carboxylic acid methyl ester

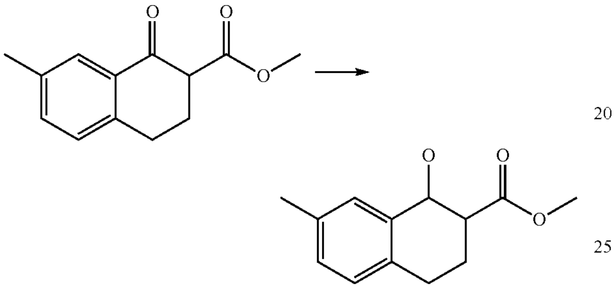

Step A. 7-Methyl-1-oxo-1,2,3,4-tetrahydro-naphthalene-2-carboxylic acid methyl ester was dissolved in chloroform and then N-bromosuccinimide and a few crystals of AIBN were added. The reaction mixture was heated under reflux for 40 minutes and the reaction was complete (TLC, 10% EtOAc in heptane). The reaction solution was diluting with heptane (5 mL), allowed to cool with ice-water bath. Succinimide precipitated out and was removed by filtration, rinsed with hexane. The filtrate was evaporated to dryness and was used immediately in the next reaction.

Step B. The residue obtained above was re-dissolved in anhydrous THF (2.5 mL). While stirring under nitrogen, DBU (0.40 mL, 3.32 mmol) was added drop wise and then the resulting solution was stirred overnight at rt. During this time a precipitate formed. The reaction mixture was cooled in ice-water bath, diluted with ether (5 mL) and water (2 mL), treated with acetic acid (17 M; 0.3 mL) and then extracted with ether. The combined extracts were dried ($MgSO_4$) and evaporated to dryness to give a brown solid. The solid was re-dissolved in EtOAc, dry loaded onto a 12-g silica gel column, eluted with 10% EtOAc in heptane to obtain a white solid after drying, 224 mg, 62% yield.

$^1H$ NMR (400 MHz, $CDCl_3$) δ 11.96 (s, 1H), 8.20 (s, 1H), 7.69 (dd, J=12.4 Hz & 8.4 Hz, 2H), 7.45 (dd, J=8.4 Hz & 1.2 Hz, 1H), 7.25 (d, J=8.8 Hz, 1H), 4.00 (s, 3H), 2.55 (s, 3H) ppm.

LCMS: $t_R$=1.49 min., m/z ($ES^+$)=217 ($M+H^+$).

Step 3. Preparation of [4-(Trifluoromethoxy)phenyl]methyl Methanesulfonate

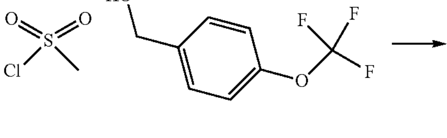

-continued

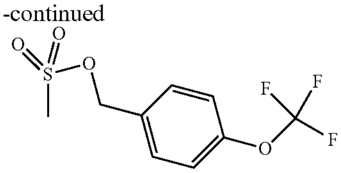

A 500-mL 3-neck RB flask equipped with mechanic stirrer, static nitrogen line was charged with 4-(trifluoromethoxy)phenyl)methanol (20.0 g, 113.5 mmol, 1.0 eq), followed by MTBE (50 mL) and triethylamine (4.7 mL, 3.44 g, 33.83 mmol, 1.3 eq.). The clear light amber solution was cooled to 1.8° C. via an ice-water bath cooling. Methanesulfonyl chloride (3.58 g, 31.23 mmol, 1.2 eq) was added dropwise using syringe. The resulting slurry was stirred at ~10° C. (bath) until in-process LCMS indicated complete reaction (40 min.). The flask was charged with either and $H_2O$ (25 mL each). The triethylamine hydrochloride dissolved to give a clear light-yellow organic layer and cloudy aqueous layer. The aqueous layer was separated. The organic layer was washed with brine (25 mL), dried with sodium sulfate then concentrated on a rotavap down to about 10 mL. To this solution was added 10 mL of heptane and concentrated further to get the title compound as a very white crystalline sample, 7.13 g (100% yield). The sample was used as such in the next step of the reaction.

Step 4. Methyl 7-methyl-1-[[4-(trifluoromethoxy) phenyl]methoxy]naphthalene-2-carboxylate

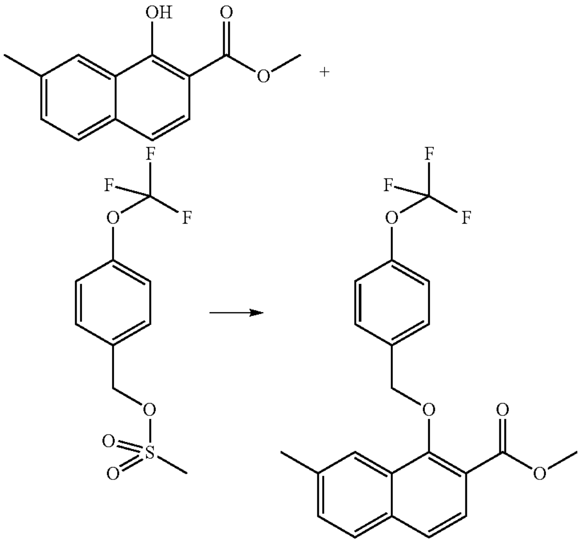

4-(trifluoromethoxy)benzyl methanesulfonate (3.08 g, 11.39 mmol, 1.1 equiv.) and methyl 1-hydroxy-7-methyl-2-naphthoate (2.24 g, 1 equiv.) were dissolved in acetone (80 mL) and potassium carbonate (3.58 g, 25.9 mmol, 2.5 equiv.) was added. The suspension was heated at 50° C. (bath) for 11 h (timer). The reaction was cooled to ambient temperature and water and EtOAc (50 mL reach) were added to form a clear solution. EtOAc work out. TLC (20% EtOAc in Heptane). The crude product was dissolved in 20% EtOAc in heptane and loaded onto a 50-g silica gel column, eluted with 10%-12% EtOAc in heptane to afford the title compound, 3.87 g (96% yield), a thick liquid, which crystalized upon standing.

$^1$H NMR ($CDCl_3$, 300 MHz): δ 7.88 (s, 1H), 7.82-7.84 (m, 2H), 7.65-7.12 (m, 3H), 7.44 (m, 1H), 7.35-7.32 (m, 2H), 5.18 (s, 2H), 3.95 (s, 3H), 2.55 (s, 3H).

LCMS: $t_R$=1.62 min., m/z ($ES^+$)=m/z ($ES^+$)=391.

Step 5. 7-Methyl-1-[[4-(trifluoromethoxy)phenyl]methoxy]naphthalene-2-carboxylic Acid

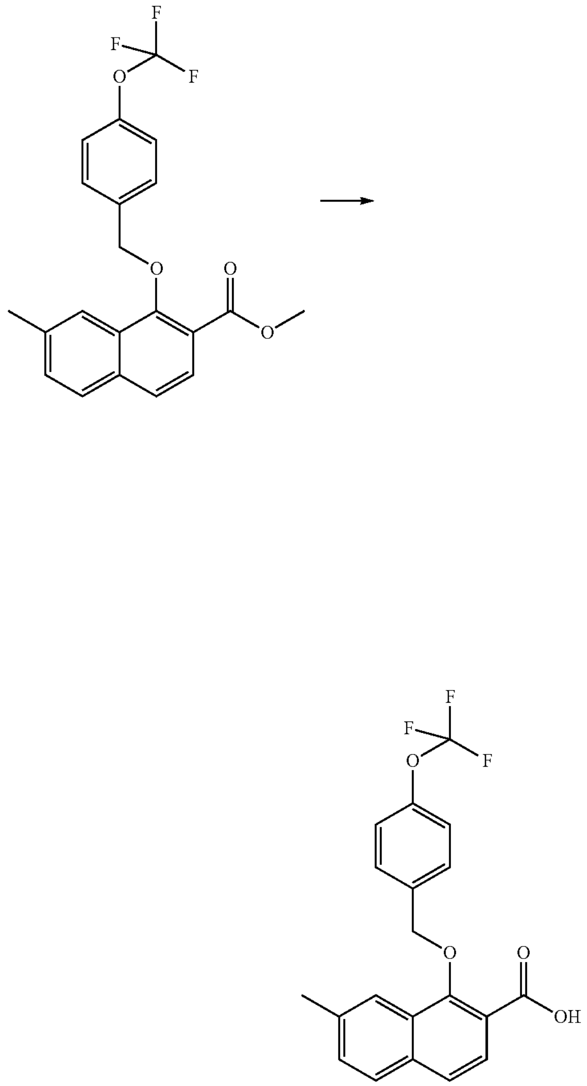

Methyl 7-methyl-1-[[4-(trifluoromethoxy)phenyl]methoxy]naphthalene-2-carboxylate (3.87 g, 9.9 mmol) was dissolved in dioxane (50 mL) and water (10 mL). To this solution was added 2 M LiOH (12 mL, 24 mmol, 2.2 equiv.) at rt. The reaction mixture was stirred at rt overnight. The solvent was evaporated and the residue was taken in EtOAc and water (20 mL each) and cooled to ice-water bath. EtOAc work up. 3N HCl (11.5 mL, 34.5 mmol, 1.01 equiv.) was added while cooling. The EtOAc solution was dried ($Na_2SO_4$ and $MgSO_4$), filtered and concentrated to obtain the title compound as a solid. The solid was used in the next step without further purification.

LCMS: $t_R$=1.46 min., m/z ($ES^+$)=m/z ($ES^+$)=377 ($M+H^+$).

Preparation of 6-Fluoro-7-methyl-1-(4-trifluoromethyl-benzyloxy)-naphthalene-2-carboxylic Acid

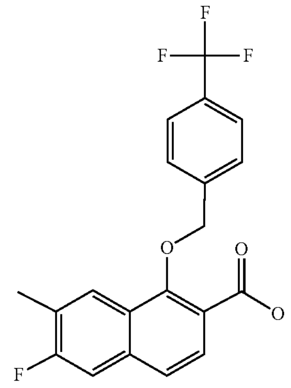

Step 1. Preparation of 4-(3-Fluoro-4-methyl-phenyl)-but-3-enoic Acid

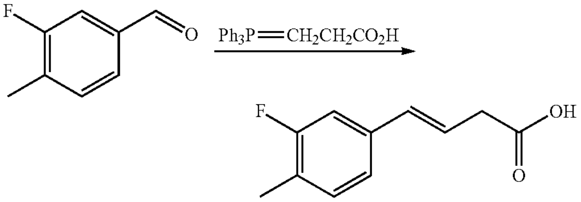

(2-Carboxyethyl)triphenylphosphonium bromide (50.5 g, 122 mmol) was added to a solution of 3-fluoro-4-methyl-benzaldehyde (12.0 g, 87.0 mmol) in anhydrous tetrahydrofuran (400 mL). The suspension was cooled to −78° C. and potassium tert-butoxide (31.2 g, 278.4 mmol) was added. The reaction mixture was allowed to warm to room temperature and stirred overnight under argon. Water (200 mL) was added, and tetrahydrofuran was removed under reduced pressure. Water (300 mL) was added to the resulting solution, and the aqueous layer was extracted with EA/PE (v/v=1/1, 3×300 mL). The aqueous layer was acidified with 37% aqueous solution of hydrochloric acid to pH=1 and extracted with ethyl acetate (3×300 mL). The organic layer was dried over anhydrous sodium sulfate, filtered and concentrated in vacuum. The crude product was purified by silica gel column chromatography (PE/EA=4/1) to afford the title compound (10 g, 59%) as a light yellow solid.

LCMS Purity: 89%; ($M+H^+$) 195.0

Step 2. Preparation of 4-(3-Fluoro-4-methyl-phenyl)-butyric Acid

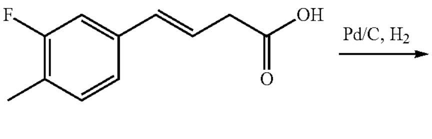

-continued

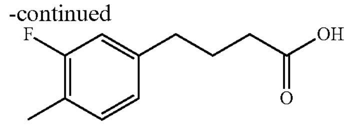

To a solution of 4-(3-fluoro-4-methyl-phenyl)-but-3-enoic acid (10 g, 51.5 mmol) in MeOH (50 mL) was added 10% Pd/C (5.0 g). The resultant mixture was stirred at room temperature under hydrogen for 2 h. The mixture was filtered, and the filtrate was concentrated in vacuo to afford of 4-(3-Fluoro-4-methyl-phenyl)-butyric acid (8.0 g, 79%) as a light yellow solid.

LCMS Purity: 62%; (M+H$^+$) 197.0;

Step 3. Preparation of 6-fluoro-7-methyl-tetralin-1-one

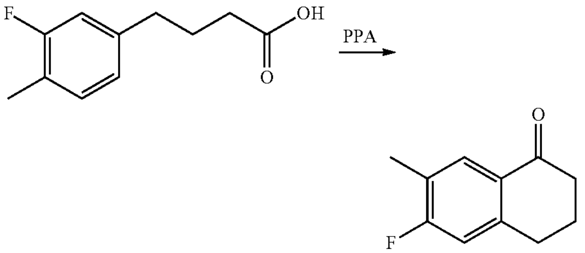

To a well stirred solution of PPA (50 mL) at 90° C. was added 4-(3-Fluoro-4-methyl-phenyl)-butyric acid (8.0 g, 40.8 mmol). The mixture was stirred at 90° C. for 3 h, diluted with $H_2O$ (300 mL), and extracted with ethyl acetate (4×200 mL). The combined organic phases were dried over anhydrous sodium sulfate, filtered, and concentrated in vacuo. The residue was purified by silica gel column chromatography (PE/EA=30/1) to afford 6-fluoro-7-methyl-tetralin-1-one (4.0 g, 55%) as a light-yellow oil.

LCMS Purity: 93%; (M+H$^+$) 179.2;

Step 4. Preparation of methyl 6-fluoro-7-methyl-1-oxo-tetralin-2-carboxylate

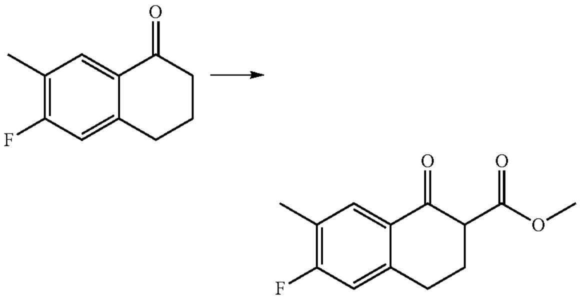

To a stirred solution of NaH (2.13 g, 53.4 mmol, 60% in oil) in dimethyl carbonate (15 mL) was added 6-fluoro-7-methyl-tetralin-1-one (1.9 g, 10.7 mmol) at room temperature. The resulting solution was heated at 80° C. for 2 hours. The mixture was cooled in ice, treated with HCl (2N) to pH=4, extracted with DCM (4×50 mL). The combined organic phases were dried over anhydrous sodium sulfate, filtered, and concentrated in vacuo. The residue was purified by silica gel column chromatography (PE/EA=40/1) to afford methyl 6-fluoro-7-methyl-1-oxo-tetralin-2-carboxylate (2.0 g, 79%) as a light yellow oil.

LCMS Purity: 79%; (M+H$^+$) 237.1.

Step 5. Preparation of methyl 6-fluoro-1-hydroxy-7-methyl-naphthalene-2-carboxylate

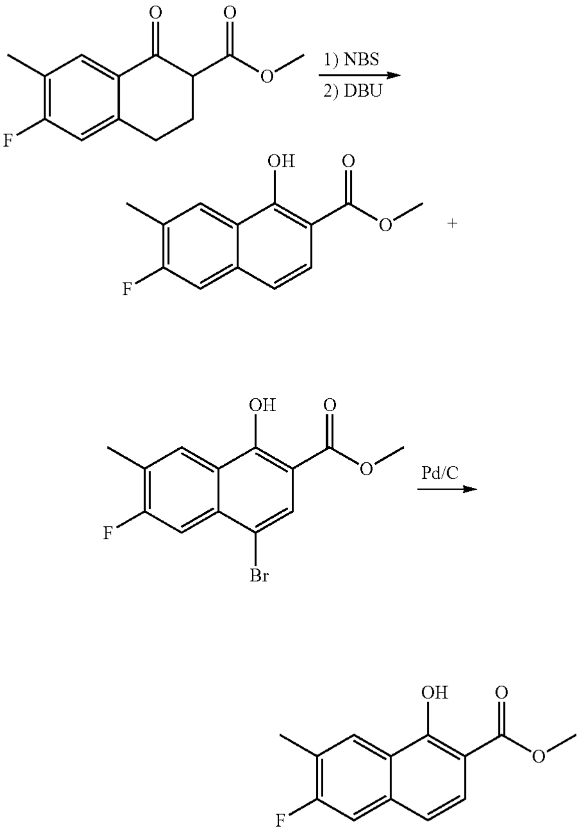

A solution of 6-fluoro-7-methyl-1-oxo-tetralin-2-carboxylate (2.0 g, 8.47 mmol) in $CHCl_3$ (25 mL) was added NBS (2.26 g, 12.7 mmol) and AIBN (139 mg, 0.847 mmol) at room temperature, then the reaction mixture was stirred under reflux for 1 hour, and concentrated to afford a residue. The residue was dissolved in THF (20 mL), DBU (6.44 g, 42.35 mmol) was added at room temperature, the solution was stirred at room temperature for 2 hours, adjusted pH to 6 with 1N HCl, extracted with EA (4×50 mL), washed with brine (100 mL), dried over $Na_2SO_4$, filtered and concentrated, then purified by silica gel chromatography (PE/EA=200/1) to afford the mixture of methyl 6-fluoro-1-hydroxy-7-methyl-naphthalene-2-carboxylate and brominated by product (1.8 g) as white solid. The mixture was dissolved in MeOH (10 mL), 10% Pd/C (1.0 g) was added, and the reaction mixture was stirred at room temperature under $H_2$ atmosphere for 1 hour. The mixture was filtered, and the filtrate was concentrated in vacuo to afford methyl 6-fluoro-1-hydroxy-7-methyl-naphthalene-2-carboxylate (1.4 g, 71%) as a light yellow solid.

LCMS Purity: 100%; (M+H$^+$) 235.1.

Step 6. Preparation of methyl 6-fluoro-7-methyl-1-[[4-(trifluoromethyl)phenyl]-methoxy]naphthalene-2-carboxylate

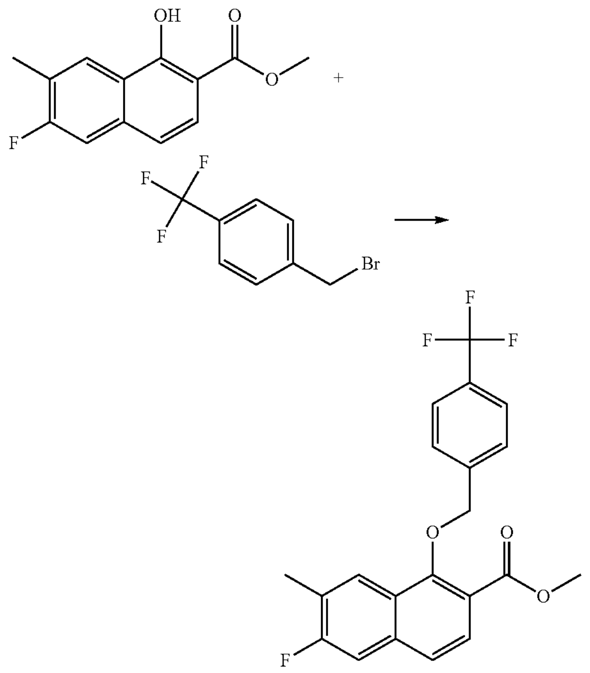

To a stirred solution of methyl 6-fluoro-1-hydroxy-7-methyl-naphthalene-2-carboxylate (600 mg, 2.56 mmol) in DMF (10 mL) was added bromide (643 mg, 2.69 mmol) and $Cs_2CO_3$ (2.5 g, 7.68 mmol). The resulting mixture was stirred at room temperature for 2 h, diluted with water (100 mL), and extracted with EA (50 mL×4). The combined organic phases were dried over anhydrous sodium sulfate, filtered, and concentrated in vacuo. The residue was purified by silica gel column chromatography (PE/EA=100/1) to afford methyl 6-fluoro-7-methyl-1-[[4-(trifluoromethyl)phenyl]methoxy]naphthalene-2-carboxylate (900 mg, 90%) as a white solid.

LCMS Purity: 100%; ($M+H^+$) 392.7.

Step 7. Preparation of 6-fluoro-7-methyl-1-[[4-(trifluoromethyl)phenyl]methoxy]naphthalene-2-carboxylic Acid

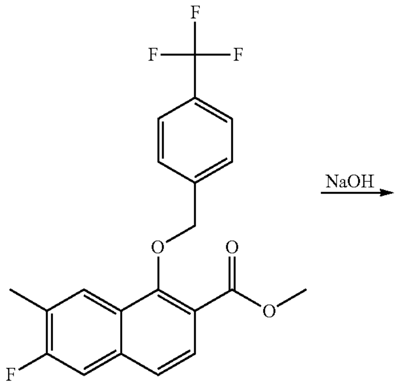

-continued

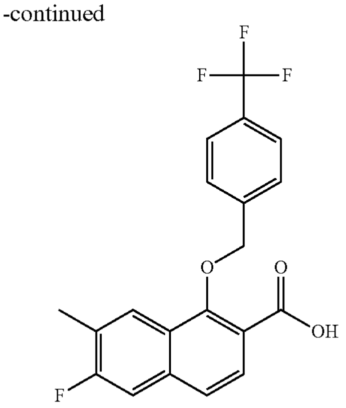

To a solution of methyl 6-fluoro-7-methyl-1-[[4-(trifluoromethyl)phenyl]methoxy]naphthalene-2-carboxylate (900 mg, 2.30 mmol) in THF/MeOH/$H_2O$ (v/v/v=1/2/1, 10 mL) was added NaOH (460 mg, 11.5 mmol). The mixture was stirred at room temperature overnight. The volatiles were removed. The residue was diluted with $H_2O$ (50 mL), acidified with aqueous HCl (2.0 M) to pH<3, and extracted with ethyl acetate (4×10 mL). The combined organic phases were dried over anhydrous sodium sulfate, filtered, and concentrated in vacuo to afford Preparation of 6-fluoro-7-methyl-1-[[4-(trifluoromethyl)phenyl]methoxy]naphthalene-2-carboxylic acid (830 mg, 96%) as a light yellow solid.

LCMS Purity: 100%; ($M+H^+$) 378;

1H NMR (400 MHz, DMSO-d6) δ 13.1 (s, 1H), 8.02 (d, J=7.6 Hz, 1H), 7.84-7.82 (m, 5H), 7.76 (d, J=10.8 Hz, 1H), 7.73 (d, J=10.8 Hz, 1H), 5.24 (s, 2H), 2.40 (s, 3H) ppm.

Preparation of 1-(4,4-dimethylpentoxy)-7-methyl-naphthalene-2-carboxylic Acid

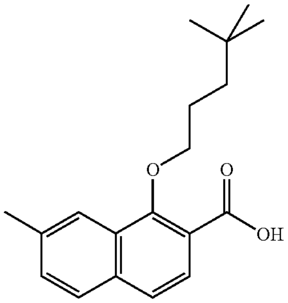 [SMILES: Cc1ccc2ccc(C(=O)O)c(OCCCC(C)(C)C)c2c1]

Step 1. Preparation of ethyl (E)-4,4-dimethylpent-2-enoate

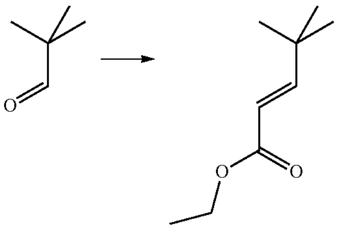

To a solution of ethyl 2-(diethoxyphosphoryl)acetate (4.5 g, 20 mmol) in THF (30 mL) at 0° C., NaH (880 mg, 22 mmol) was added slowly. After addition, the mixture was stirred at 0° C. for 20 min, and then aldehyde was added. The mixture was stirred at rt overnight. $H_2O$ (20 mL) was added, extracted with EA (30 mL×3), dried over $Na_2SO_4$, concentrated at 40° C. to give ethyl (E)-4,4-dimethylpent-2-enoate as colorless oil (2.0 g, 65%).

LCMS Purity: 100%

$^1$H NMR: ($CDCl_3$, 400 Hz): δ 6.97 (d, J=16.0 Hz, 1H), 5.73 (d, J=16.0 Hz, 1H), 4.19 (q, J=7.2 Hz, 2H), 1.30 (t, J=7.2 Hz, 3H), 1.08 (s, 9H).

Step 2. Preparation of ethyl 4,4-dimethylpentanoate

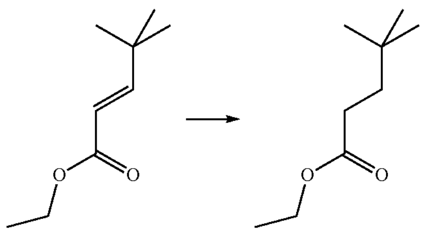

The mixture of ethyl (E)-4,4-dimethylpent-2-enoate (2.0 g, 13 mmol) and $PtO_2$ (80 mg) in EA (30 mL) was charged with $H_2$ and stirred at $H_2$ atmosphere for 12 h, filtered and concentrated to give ethyl 4,4-dimethylpentanoate as colorless oil (2.0 g, 100%).

LCMS Purity: 100%.

$^1$H NMR: ($CDCl_3$, 400 Hz): δ 4.12 (q, J=7.2 Hz, 2H), 2.27 (t, J=8.4 Hz, 2H), 1.55 (t, J=8.4 Hz, 2H), 1.26 (t, J=7.2 Hz, 3H), 0.90 (s, 9H).

Step 3. Preparation of 4,4-dimethylpentan-1-ol

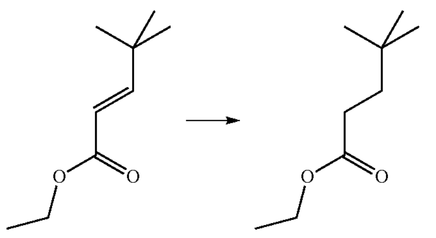

To a solution of ethyl 4,4-dimethylpentanoate (2.0 g, 13 mmol) in THF (30 mL) at 0° C., $LiAlH_4$ (988 mg, 26 mmol) was added in five portions. The mixture was stirred at 0° C. for 3 h. $H_2O$ (5 mL) was added slowly, filtered through celite, concentrated at 40° C. to give 4,4-dimethylpentan-1-ol as colorless oil (1.5 g, 100%).

LCMS Purity: 100%.

$^1$H NMR: ($CDCl_3$, 400 Hz): δ 3.31 (s, 2H), 1.24-1.20 (m, 2H), 0.92-0.89 (m, 5H), 0.87 (s, 6H).

Step 4. Preparation of methyl 1-(4,4-dimethylpentoxy)-7-methyl-naphthalene-2-carboxylate

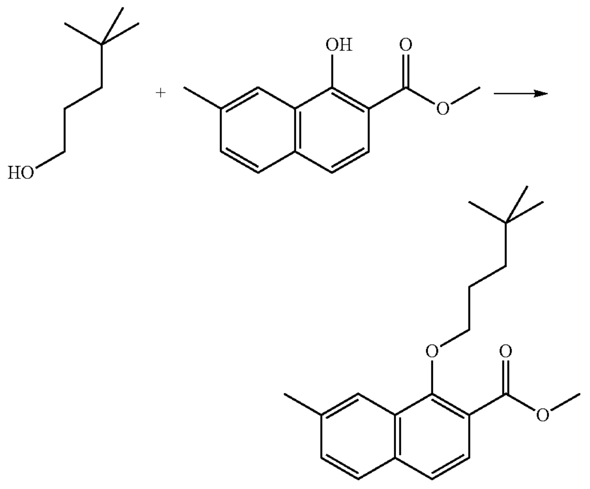

The mixture of 4,4-dimethylpentan-1-ol (348 mg, 3.0 mmol), ester (324 mg, 1.5 mmol) and $PPh_3$ (524 mg, 3.0 mmol), DEAD (344 mg, 3.0 mmol) in THF (20 mL) was stirred at 35° C. for 12 h. The reaction was detected with LCMS, concentrated and purified with flash chromatography (PE:EA=15:1) to give methyl 1-(4,4-dimethylpentoxy)-7-methyl-naphthalene-2-carboxylate (400 mg, 87%) as colorless oil.

LCMS Purity: 96%; (M+H$^+$) 315.2.

Step 5. Preparation of 1-(4,4-dimethylpentoxy)-7-methyl-naphthalene-2-carboxylic Acid

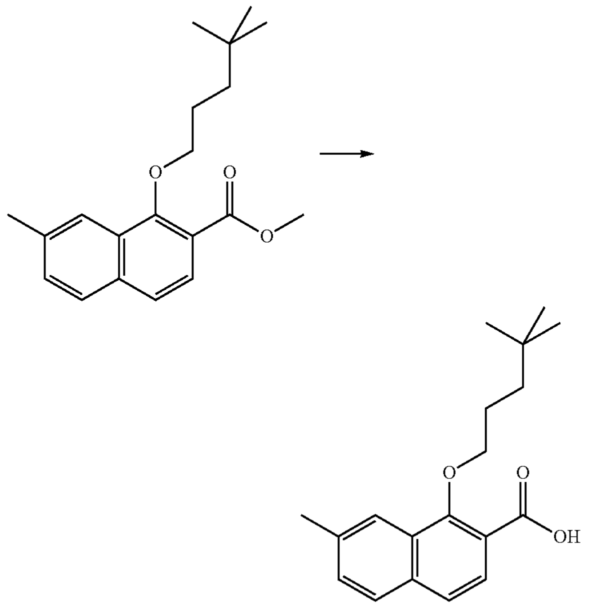

To a solution of methyl 1-(4,4-dimethylpentoxy)-7-methyl-naphthalene-2-carboxylate (400 mg, 1.27 mmol) in THF (10 mL), LiOH—$H_2O$ (160 mg, 3.8 mmol), MeOH (10 mL), $H_2O$ (1.5 mL) was added, and the mixture was stirred at rt for 6 h. $NaHSO_4$ (10% in water) was added until pH=4-5, extracted with EA (20 mL×3). The organic layer was dried over $Na_2SO_4$, concentrated and purified with flash chromatography (PE:EA=2:1) to give 1-(4,4-dimethylpentoxy)-7-methyl-naphthalene-2-carboxylic acid (380 mg, 100%) as a white solid.

LCMS Purity: 95%; $(M+H^+)$ 301.1.

Preparation of 1-[[4-(trifluoromethyl)thiazol-2-yl]methoxy]naphthalene-2-carboxylic Acid

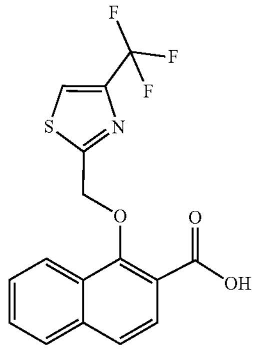 [SMILES: O=C(O)c1ccc2ccccc2c1OCc1nc(C(F)(F)F)cs1]

Step 1. Preparation of methyl 1-[[4-(trifluoromethyl)thiazol-2-yl]methoxy]naphthalene-2-carboxylate

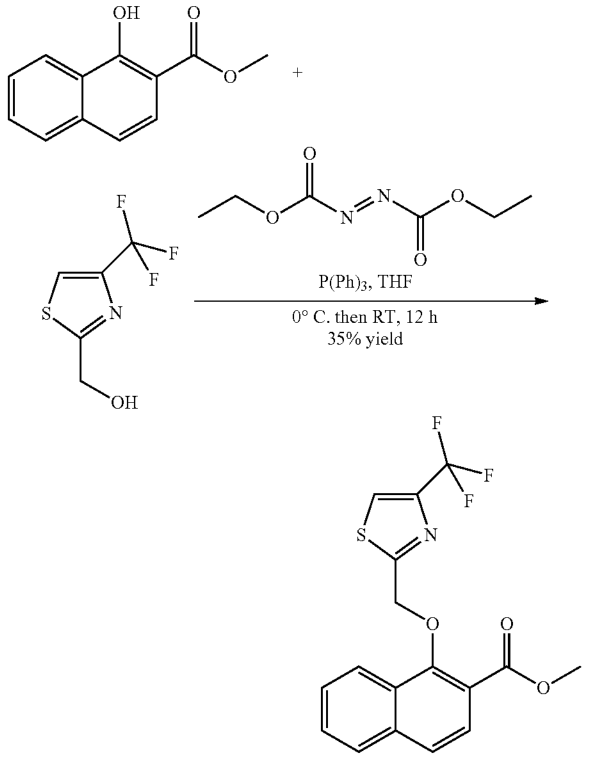

To a solution of methyl 1-hydroxy-2-naphthoate (0.90 g, 4.45 mmol) in 100 mL of tetrahydrofuran was added triphenylphosphine (1.28 g, 4.90 mmol) and 4-(trifluoromethyl)thiazol-2-yl methanol (0.95 g, 4.90 mmol). The mixture was cooled at 0° C. and diethyl azodicarboxylate (794.8 μL, 4.90 mmol) was added dropwise. The mixture was stirred at room temperature for 12 hours. Then, the crude was concentrated in vacuum and purified by column chromatography on silica gel using a mixture of heptane and ethyl acetate as eluent (gradient: 0% to 50%) to give yellow oil (0.58 g, 35% yield).

LCMS: $t_R$=0.90 min., m/z $(ES^+)$=368 $(M+H^+)$.

Step 2. Preparation of 1-[[4-(trifluoromethyl)thiazol-2-yl]methoxy]naphthalene-2-carboxylic

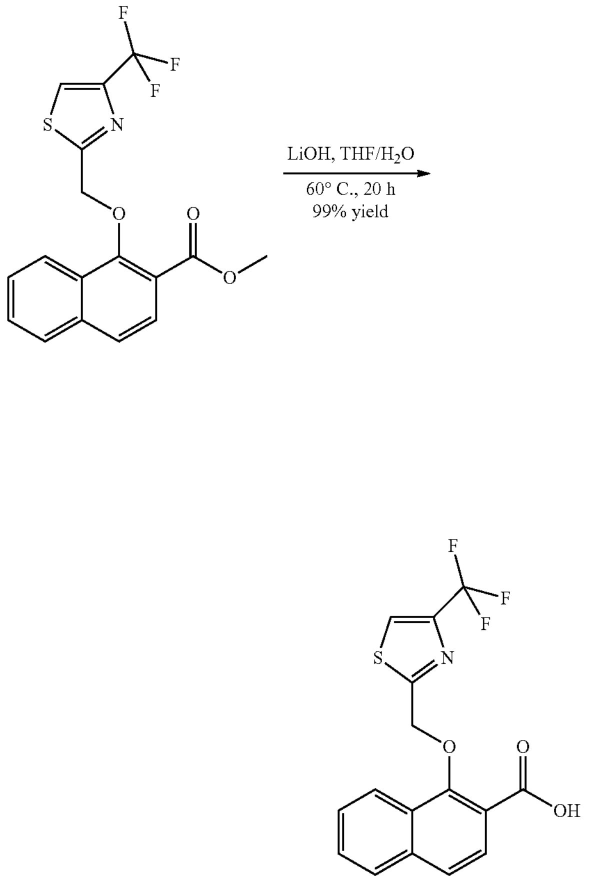

To a solution of methyl 1-[[4-(trifluoromethyl)thiazol-2-yl]methoxy]naphthalene-2-carboxylate (0.58 g, 1.58 mmol) in 16 mL of tetrahydrofuran was added lithium hydroxide (0.26 g, 6.32 mmol) dissolved in 4 mL of water. The mixture was heated at 60° C. for 20 hours. Then, the crude was concentrated in vacuum. Water was added and the mixture was extracted with ethyl acetate. The aqueous layer was acidified with HCl 1 M solution and washed once with ethyl acetate. The organic layers were collected and washed once with water and once with saturated aqueous solution of NaCl. The organic phases were dried over $Na_2SO_4$ and concentrated in vacuum. The crude product obtained was yellow (0.90 g, 99% yield). The product was used without purification.

LCMS: $t_R$=0.80 min., m/z $(ES^+)$=354 $(M+H^+)$.

Preparation of 1-(3-cyclopropylprop-2-ynoxy)naphthalene-2-carboxylic acid

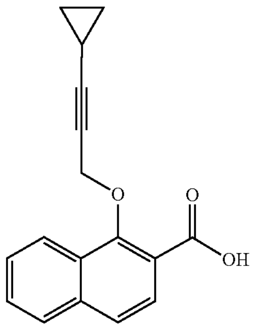 [SMILES: O=C(O)c1ccc2ccccc2c1OCC#CC1CC1]

Step 1. Preparation of 3-cyclopropylprop-2-yn-1-ol

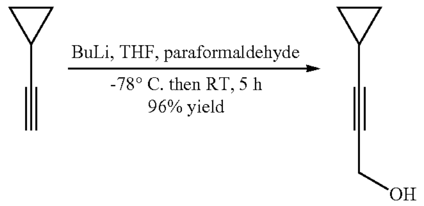

To a solution of cyclopropylacetylene (4.23 ml, 48.92 mmol) in 150 mL of tetrahydrofuran was added dropwise at −78° C., butyllithium 2.5 M (21.53 ml, 53.82 mmol). The mixture was stirred at −78° C. for 0.5 hours and then, paraformaldehyde (5.39 g, 58.82 mmol) was added. The mixture was stirred at room temperature for 5 hours. 30 ml of HCl 1N was added and the mixture was stirred at room temperature for 0.5 hours. The crude was extracted with ethyl acetate. The organic layer was washed once with saturated aqueous solution of NaCl, dried over $Na_2SO_4$ and concentrated in vacuum. The crude product obtained was yellow oil (4.50 g, 96% yield). The product was used without purification.

LCMS: $t_R$=0.38 min., m/z ($ES^+$)=97 ($M+H^+$).

Step 2. Preparation of methyl 1-(3-cyclopropylprop-2-ynoxy)naphthalene-2-carboxylate

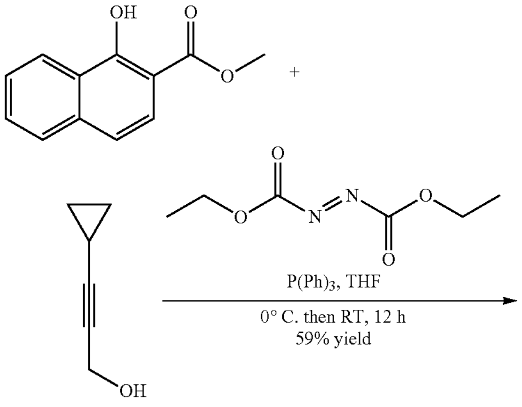

-continued

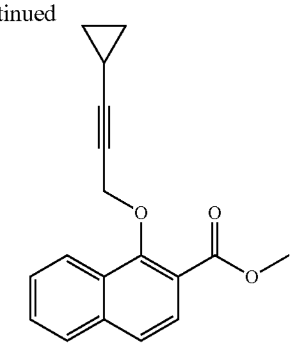

To a solution of methyl 1-hydroxy-2-naphthoate (4 g, 19.39 mmol) in 100 mL of tetrahydrofuran was added triphenylphosphine (5.59 g, 21.32 mmol) and 3-cyclopropylprop-2-yn-1-ol (2.05 g, 21.32 mmol). The mixture was cooled at 0° C. and diethyl azodicarboxylate (3.46 mL, 21.32 mmol) was added dropwise. The mixture was stirred at room temperature for 12 hours. Then, the crude was concentrated in vacuum and purified by column chromatography on silica gel using a mixture of heptane and ethyl acetate as eluent (gradient: 2%-50% of AcOEt in heptane) to give yellow oil (0.58 g, 59% yield).

LCMS: $t_R$=0.94 min., m/z ($ES^+$)=281 ($M+H^+$).

Step 3. Preparation of 1-(3-cyclopropylprop-2-ynoxy)naphthalene-2-carboxylic Acid

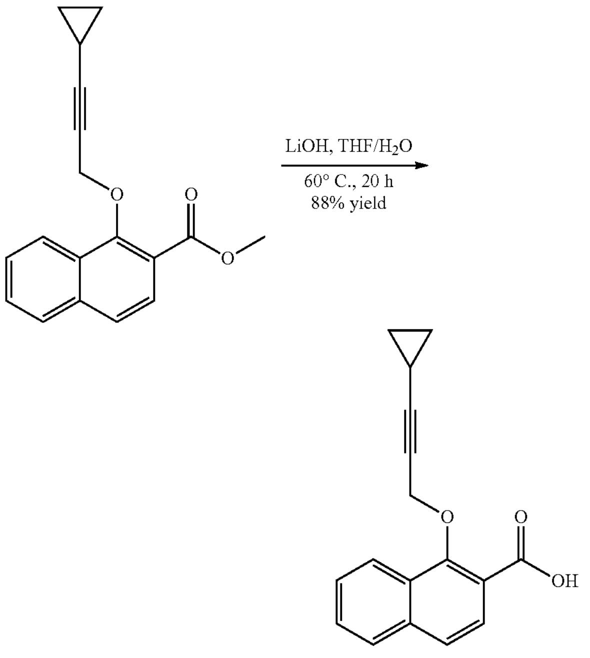

To a solution of methyl 1-(3-cyclopropylprop-2-ynoxy) naphthalene-2-carboxylate (1.80 g, 6.42 mmol) in 80 mL of tetrahydrofuran was added lithium hydroxide (1.08 g, 25.68 mmol) dissolved in 40 mL of water. The mixture was heated at 60° C. for 20 hours. Then, the crude was concentrated in vacuum. Water was added and the mixture was extracted with ethyl acetate. The aqueous layer was acidified with HCl 1 M solution and washed once with ethyl acetate. The organic layers were collected and washed once with water and once with saturated aqueous solution of NaCl. The organic phases were dried over $Na_2SO_4$ and concentrated in vacuum. The crude product obtained was white (1.50 g, 88% yield). The product was used without purification.

LCMS: $t_R$=0.77 min., m/z ($ES^+$)=267 ($M+H^+$).

Preparation of 1-[[1-(trifluoromethyl)cyclopropyl] methoxy]naphthalene-2-carboxylic Acid

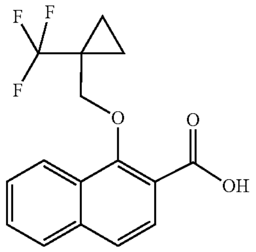 [SMILES: O=C(O)c1ccc2ccccc2c1OCC1(C(F)(F)F)CC1]

Step 1. Preparation of methyl 1-[[1-(trifluoromethyl)cyclopropyl]methoxy]naphthalene-2-carboxylate

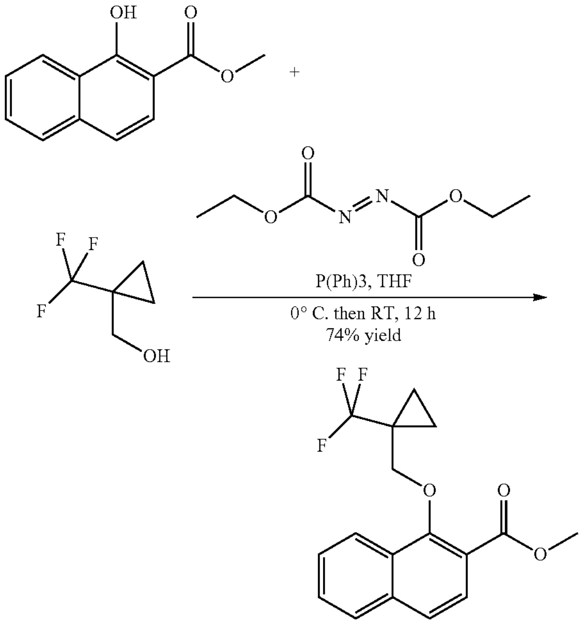

To a solution of methyl 1-hydroxy-2-naphthoate (1.50 g, 7.27 mmol) in 100 mL of tetrahydrofuran was added triphenylphosphine (2.10 g, 8.00 mmol) and 1-(trifluoromethyl) cyclopropanemethanol (1.07 g, 7.27 mmol). The mixture was cooled at 0° C. and diethyl azodicarboxylate (1.30 ml, 8.00 mmol) was added dropwise. The mixture was stirred at room temperature for 12 hours. Then, the crude was concentrated in vacuum and purified by column chromatography on silica gel using a mixture of heptane and ethyl acetate as eluent (gradient: 2% AcOEt—15'→50% AcOEt; 50% AcOEt—10'→50% AcOEt) to give a colorless oil (1.75 g, 74% yield).

LCMS: $t_R$=0.96 min., m/z ($ES^+$)=325 ($M+H^+$).

Step 2. Preparation of 1-[[1-(trifluoromethyl)cyclopropyl]methoxy]naphthalene-2-carboxylic Acid

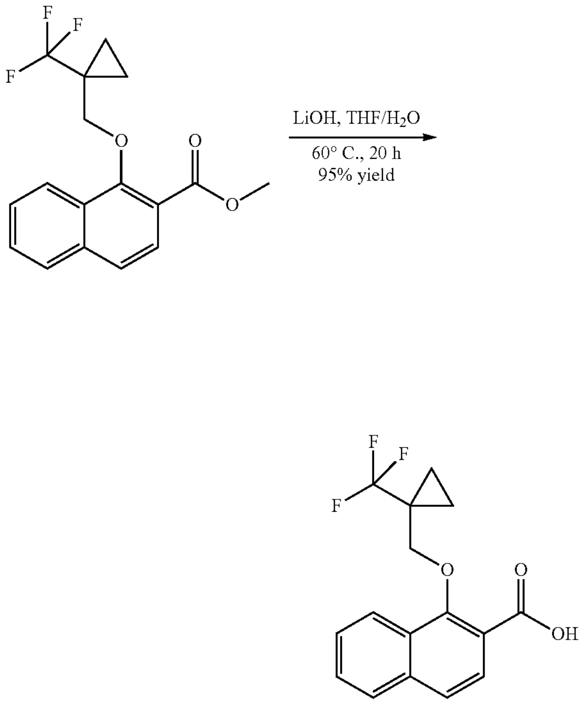

To a solution of methyl 1-[[1-(trifluoromethyl)cyclopropyl]methoxy]naphthalene-2-carboxylate (1.70 g, 5.24 mmol) in 100 mL of tetrahydrofuran was added lithium hydroxide (0.66 g, 15.73 mmol) dissolved in 30 mL of water. The mixture was heated at 60° C. for 12 hours. Then, the crude was concentrated in vacuum. Water was added and the mixture was extracted with ethyl acetate. The aqueous layer was acidified with HCl 1 M solution and washed once with ethyl acetate. The organic layers were collected and washed once with water and once with saturated aqueous solution of NaCl. The organic phases were dried over $Na_2SO_4$ and concentrated in vacuum. The crude product obtained was a white powder (1.55 g, 95% yield). The product was used without purification.

LCMS: $t_R$=0.81 min., m/z ($ES^+$)=311 ($M+H^+$).

Preparation of (S)-methyl 2-amino-3,3-dimethyl-pentanoate

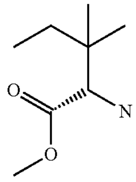

Step 1. Preparation of N-methoxy-2,2, N-trimethyl-butyramide

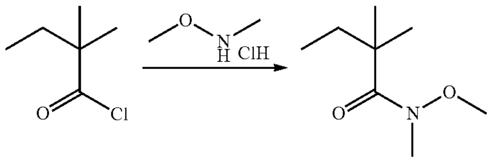

To a solution of methyl 3,3-dimethyl-pentanoyl chloride (10.0 g, 70 mmol) in $CH_2Cl_2$ (67 mL) was added N,O-dimethyl hydroxylamine hydrochloride (7.8 g, 80 mmol), then TEA (22.3 g, 0.22 mol) was added slowly at 0° C. The resulting mixture was stirred at the same temperature for 2 h until the disappearance of starting material as checked by LCMS. Then, the solid was filtered out. The solvent was concentrated in vacuo and purified by silica gel column chromatography (petroleum ether/ethyl acetate=3/1) to afford N-methoxy-2,2,N-trimethyl-butyramide as a yellow oil (10.3 g, yield 88%).

LCMS: Purity: 100%, $t_R$=1.94 min, m/z ($ES^+$)=160 ($M+H^+$).

Step 2. Preparation of 2,2-dimethylbutanal

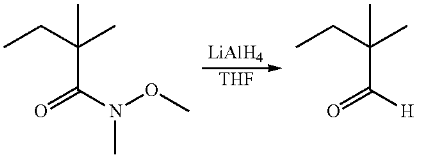

To a solution of N-methoxy-2,2, N-trimethyl-butyramide (10.0 g, 62.9 mmol) in 100 mL anhydrous THF was added of 94 mL $LiAlH_4$ (1 M in THF) slowly at −78° C. under N2 protection. The resulting mixture was stirred at the same temperature for 2 h. Then 3.6 mL water, 3.6 mL 15% aqueous NaOH and 11 mL water were added to this mixture slowly at 0° C. in sequence. The mixture was stirred at room temperature for 30 min, and filtered out the solid. The solvent was dried over $Na_2SO_4$ and the solution of the crude title compound was used in the next step directly without concentration.

GCMS: $t_R$=4.86 min, m/z ($ES^+$)=100 ($M+H^+$).

Step 3. Preparation of (2S)-2-[[(1R)-2-hydroxy-1-phenyl-ethyl]amino]-3,3-dimethyl-pentanenitrile

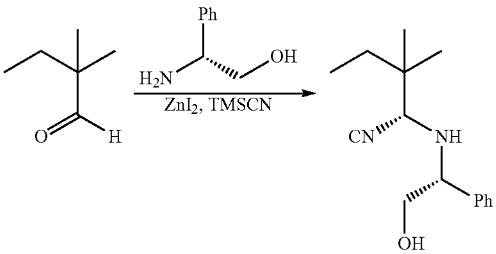

To a solution of 2,2-dimethylbutanal obtained in the previous step was added of 90 mL methanol, $ZnI_2$ (0.996 g, 3.12 mmol) and (R)-2-amino-2-phenylethanol (9.48 g, 69.1 mmol) in sequence. The mixture was stirred at room temperature for 30 min. Then the TMSCN (9.34 g, 94.14 mmol) was added dropwise at 0° C., and the mixture was stirred for 16 h at room temperature. The solvent was concentrated and purified by silica gel column chromatography (petroleum ether/ethyl acetate=5/1) to obtain 8.8 g (2S)-2-[[(1R)-2-hydroxy-1-phenyl-ethyl]amino]-3,3-dimethyl-pentanenitrile as a yellow oil, yield 57% (two steps).

LCMS: $t_R$=2.13 min, m/z ($ES^+$)=247 ($M+H^+$).

Step 4. Preparation of (2S)-2-[[(1R)-2-hydroxy-1-phenyl-ethyl]amino]-3,3-dimethyl-pentanoic Acid

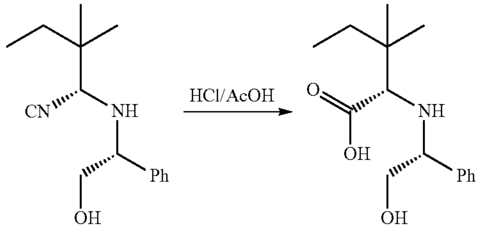

To a solution of (2S)-2-[[(1R)-2-hydroxy-1-phenyl-ethyl]amino]-3,3-dimethyl-pentanenitrile (8.5 g, 34.6 mmol) in 29.7 mL acetic acid was added of 67.8 mL conc. HCl and the mixture was stirred at 80° C. overnight. Then remove the solvent in vacuo and the residue was slurried with water (2 mL×3) to remove the other isomer and afford (2S)-2-[[(1R)-2-hydroxy-1-phenyl-ethyl]amino]-3,3-dimethyl-pentanoic acid as a white solid. (3.74 g, yield: 40.8%).

LCMS: Purity: 100%, $t_R$=1.45 min, [M+H]=266.

Step 5. Preparation of (2S)-2-amino-3,3-dimethyl-pentanoic Acid

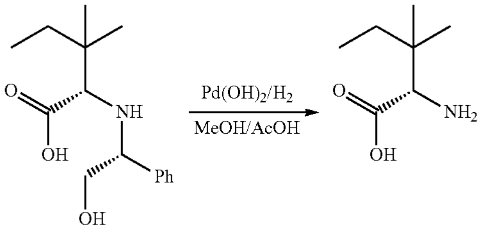

To a suspension of $Pd(OH)_2$ (1.12 g, 0.81 mmol) in 18.6 mL acetic acid and 93 mL methanol was added of (2S)-2-[[(1R)-2-hydroxy-1-phenyl-ethyl]amino]-3,3-dimethyl-pentanoic acid (3.7 g, 13.9 mmol) and the mixture was stirred at room temperature under the circumstance of hydrogen overnight. Then the $Pd(OH)_2$ was filtered out and the solvent was removed in vacuo to afford the crude product, which was washed with ethyl ether to give (2S)-2-amino-3,3-dimethyl-pentanoic acid as a white solid (1.92 g, yield: 94.8%). LCMS: m/z ($ES^+$)=146 ($M+H^+$).

Step 6. Preparation of (2S)-methyl 2-amino-3,3-dimethyl-pentanoate

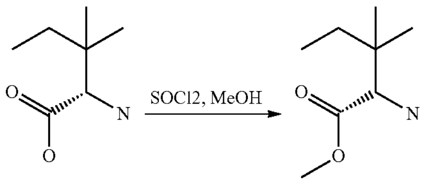

To a solution of (2S)-2-amino-3,3-dimethyl-pentanoic acid (1.72 g, 11.85 mmol) in 30 mL methanol was added of 6 mL thionyl chloride ($SOCl_2$) and the mixture was stirred at 70° C. for 24 h. Then 6 mL $SOCl_2$ and 6 mL methanol were added to this mixture which was reacted at 70° C. for another 24 h. Finally, 6 mL $SOCl_2$ and 6 mL methanol were added again to this mixture. The reaction mixture was stirred at the same temperature for 24 h. Then remove the solvent in vacuo. The residue was dissolved in ethyl acetate and washed with saturated sodium bicarbonate aqueous solution. The organic phase was concentrated and purified by silica gel column chromatography (ethyl acetate, 100%) to give compound methyl 2-amino-3,3-dimethyl-pentanoate as a yellow liquid (1.404 g, yield: 74.5%). Then, the target product was dissolved in ethyl acetate and added of 6 mL hydrochloric acid solution (4 M in 1,4-dioxane). The solvent was removed in vacuo to provide the corresponding hydrochloride as a white solid.

$^1$H NMR (400 MHz, CDCl3) δ 8.53 (br s, 3H), 3.75 (s, 3H), 3.74-3.72 (m, 1H), 1.41-1.29 (m, 2H), 0.96 (s, 3H), 0.92 (s, 3H), 0.84-0.81 (m, 3H).

LCMS: $t_R$=1.03 min., m/z ($ES^+$)=160.7 ($M+H^+$)

The above synthesis of methyl (2S)-methyl 2-amino-3,3-dimethyl-pentanoate was exemplary. If opposite stereo auxiliary is used, for example, (S)-2-amino-2-phenylethanol, the D-amino acid would be synthesized using this protocol. One of skill in the art would appreciate that other synthetic routes are known for these compounds and analogs thereof.

Example 237: (S)-2-(7-chloro-1-((4-(trifluoromethoxy)benzyl)oxy)-2-naphthamido)-3,3-dimethyl Butanoic Acid

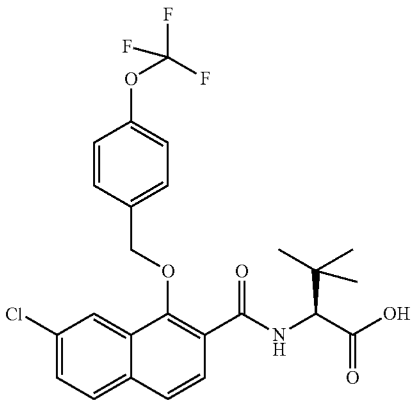 [SMILES: CC(C)(C)[C@H](NC(=O)c1ccc2ccc(Cl)cc2c1OCc1ccc(OC(F)(F)F)cc1)C(=O)O]

Step 1. Preparation of Methyl-(S)-2-(7-chloro-1-((4-(trifluoromethoxy)benzyl)oxy)-2-naphthamido)-3,3-dimethylbutanoate

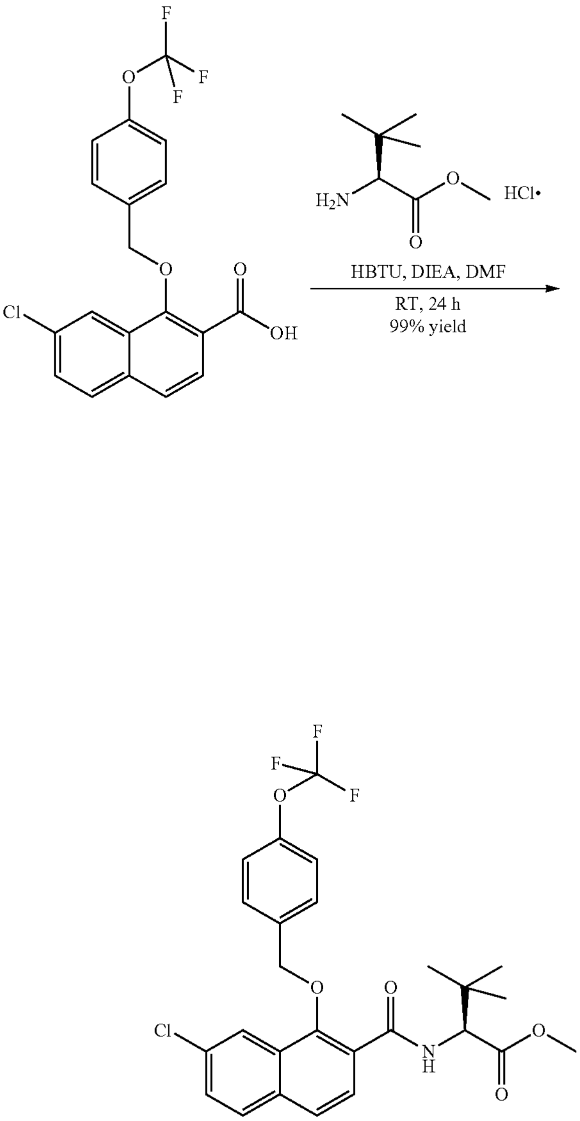

To a solution of ethyl 7-chloro-1-((4-(trifluoromethoxy)benzyl)oxy)-2-naphthoic acid (300 mg, 756.15 μmol) in 20 mL of N,N-dimethylformamide was added N-ethyl-N-isopropylpropan-2-amine (329.28 μl, 1.89 mmol) and HBTU (315.44 mg, 831.77 μmol). The mixture was stirred at room temperature for 24 hours. Then, the crude was concentrated in vacuum and extracted with ethyl acetate. The organic layer was washed once with saturated aqueous solution of $KHSO_4$ and once with saturated aqueous solution of $K_2CO_3$. The organic layers were collected, washed once with saturated aqueous solution of NaCl, dried over $Na_2SO_4$ and concentrated in vacuum. The crude product obtained was purified by column chromatography on silica gel using a mixture of heptane and ethyl acetate as eluent (gradient: 0%-50% AcOEt) to give yellow oil (395 mg, 99% yield).

LCMS: $t_R$=1.10 min., m/z ($ES^+$)=524 ($M+H^+$).

Step 2. Preparation of (S)-2-(7-chloro-1-((4-(trifluoromethoxy)benzyl)oxy)-2-naphthamido)-3,3-dimethyl Butanoic Acid

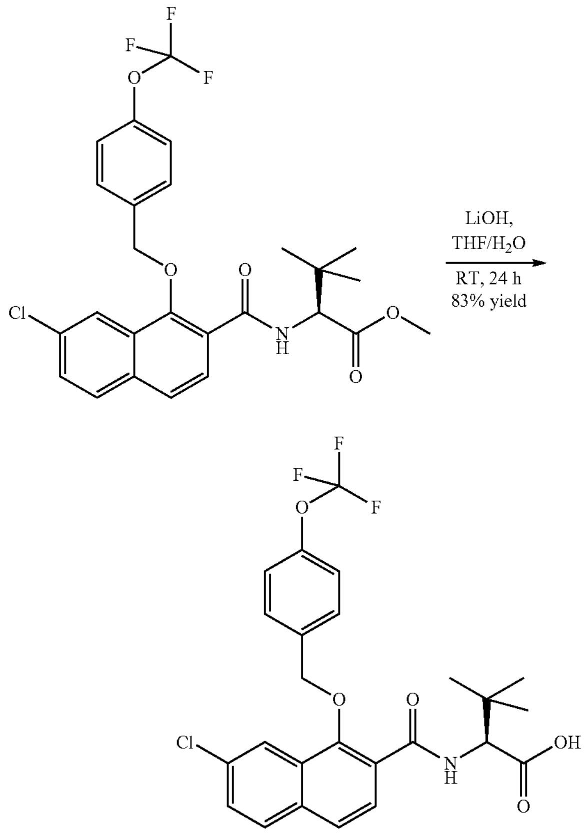

To a solution of methyl (S)-2-(7-chloro-1-((4-(trifluoromethoxy)benzyl)oxy)-2-naphthamido)-3,3-dimethylbutanoate (395 mg, 753.91 μmol) in 10 mL of tetrahydrofuran was added lithium hydroxide (190 m g, 4.53 mmol) and 3 mL of water. The mixture was heated at room temperature for 24 hours. Then, the crude was concentrated in vacuum. Water was added and the mixture was extracted with ethyl acetate. The aqueous layer was acidified with HCl 1 M solution and washed once with ethyl acetate. The organic layers were collected and washed once with water and once with saturated aqueous solution of NaCl. The organic phases were dried over $Na_2SO_4$ and concentrated in vacuum. The crude product obtained was purified by column chromatography on silica gel using a mixture of heptane and ethyl acetate as eluent (gradient: 0%-50% AcOEt) to give yellow oil (318 mg, 83% yield).

$^1$H NMR (400 MHz, DMSO-$d_6$) δ ppm 12.88-12.72 (m, 1H), 8.62 (d, J=8.51 Hz, 1H), 8.06 (d, J=8.81 Hz, 1H), 7.99 (d, J=2.12 Hz, 1H), 7.84 (d, J=8.56 Hz, 1H), 7.68-7.61 (m, 4H), 7.42 (d, J=8.03 Hz, 2H), 5.20 (dd, J=38.60, 11.68 Hz, 2H), 4.35 (d, J=8.51 Hz, 1H), 0.98 (s, 9H)

LCMS: $t_R$=1.01 min., m/z ($ES^+$)=510 ($M+H^+$)

Examples 238 through 273 exemplified below were synthesized in a manner analogous to Example 237 described above using the appropriate intermediates and starting materials/reagents.

Example 238: 2-(7-chloro-1-((4-(trifluoromethoxy)benzyl)oxy)-2-naphthamido)-2-(1-(trifluoromethyl)cyclopropyl)acetic Acid

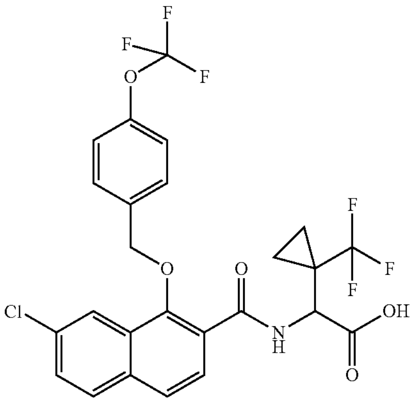 [SMILES: O=C(NC(C(=O)O)C1(C(F)(F)F)CC1)c1ccc2ccc(Cl)cc2c1OCc1ccc(OC(F)(F)F)cc1]

$^1$H NMR (400 MHz, DMSO-$d_6$) δ ppm 8.57 (d, J=8.06 Hz, 1H), 8.04 (d, J=8.81 Hz, 1H), 7.91 (d, J=2.01 Hz, 1H), 7.88-7.81 (m, 2H), 7.72 (d, J=8.58 Hz, 2H), 7.63 (dd, J=8.81, 2.01 Hz, 1H), 7.41 (d, J=8.58, 2H) 5.22 (dd, J=110.31, 12.11 Hz, 2H), 4.46 (d, J=8.06 Hz, 1H), 1.21-1.01 (m, 2H), 0.91-0.71 (m, 2H)

LCMS: $t_R$=1.01 min., m/z ($ES^+$)=562 ($M+H^+$)

Example 239: (S)-2-(7-fluoro-1-((4-(trifluoromethoxy)benzyl)oxy)-2-naphthamido)-3,3-dimethyl Butanoic Acid

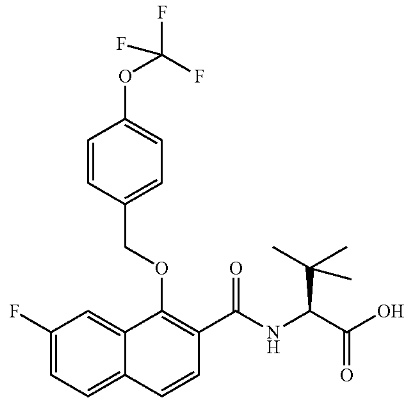 [SMILES: CC(C)(C)[C@H](NC(=O)c1ccc2ccc(F)cc2c1OCc1ccc(OC(F)(F)F)cc1)C(=O)O]

1H NMR (400 MHz, DMSO-d6) δ ppm 12.58-12.99 (m, 1H) 8.60 (d, J=8.44 Hz, 1H) 8.11 (dd, J=9.05, 5.62 Hz, 1H) 7.85 (d, J=8.44 Hz, 1H) 7.70-7.72 (m, 1H) 7.67 (d, J=8.68 Hz, 2H) 7.61 (d, J=8.44 Hz, 1H) 7.55 (td, J=8.80, 2.57 Hz, 1H) 7.42 (d, J=8.68 Hz, 2H) 5.19 (dd, J=37.90, 11.00 Hz, 2H) 4.35 (d, J=8.44 Hz, 1H) 0.93-1.03 (m, 9H)

LCMS: $t_R$=0.96 min., m/z ($ES^+$)=494 ($M+H^+$)

Example 240: 2-(7-fluoro-1-((4-(trifluoromethoxy)benzyl)oxy)-2-naphthamido)-2-(1-(trifluoromethyl)cyclopropyl)acetic Acid

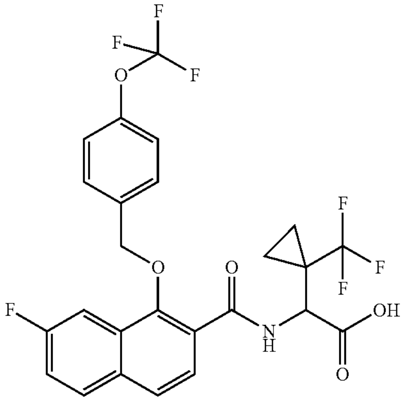 [SMILES: O=C(NC(C(=O)O)C1(C(F)(F)F)CC1)c1ccc2ccc(F)cc2c1OCc1ccc(OC(F)(F)F)cc1]

1H NMR (400 MHz, DMSO-d6) δ ppm 13.15-13.52 (m, 1H) 8.94 (d, J=7.82 Hz, 1H) 8.12 (dd, J=9.11, 5.69 Hz, 1H) 7.86 (d, J=8.44 Hz, 1H) 7.60-7.72 (m, 4H) 7.55 (td, J=9.00, 3.40 Hz, 1H) 7.40 (d, J=7.70 Hz, 2H) 5.20 (dd, J=50.60, 11.40 Hz, 2H) 4.67 (d, J=7.83 Hz, 1H) 0.75-1.48 (m, 4H)

LCMS: $t_R$=0.96 min., m/z ($ES^+$)=546 ($M+H^+$)

Example 241: (S)-2-(7-fluoro-1-((4-(trifluoromethyl)benzyl)oxy)-2-naphthamido)-3,3-dimethylbutanoic Acid

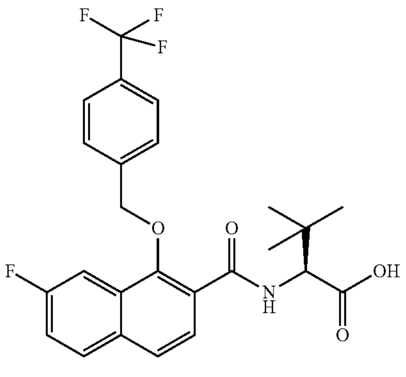 [SMILES: CC(C)(C)[C@H](NC(=O)c1ccc2ccc(F)cc2c1OCc1ccc(C(F)(F)F)cc1)C(=O)O]

1H NMR (400 MHz, DMSO-d6) δ ppm 12.54-13.02 (m, 1H) 8.62 (d, J=8.56 Hz, 1H) 8.12 (dd, J=9.11, 5.69 Hz, 1H) 7.86 (d, J=8.44 Hz, 1H) 7.75-7.83 (m, 4H) 7.71 (dd, J=10.58, 2.51 Hz, 1H) 7.61 (d, J=8.44 Hz, 1H) 7.52-7.59 (m, 1H) 5.27 (dd, J=33.00, 12.10 Hz, 2H) 4.34 (d, J=8.56 Hz, 1H) 0.98 (s, 9H)

LCMS: $t_R$=0.94 min., m/z ($ES^+$)=478 ($M+H^+$)

Example 242: (2S)-2-[[7-(difluoromethyl)-1-[[4-(trifluoromethyl)phenyl]methoxy]naphthalene-2-carbonyl]amino]-3,3-dimethyl-pentanoic Acid

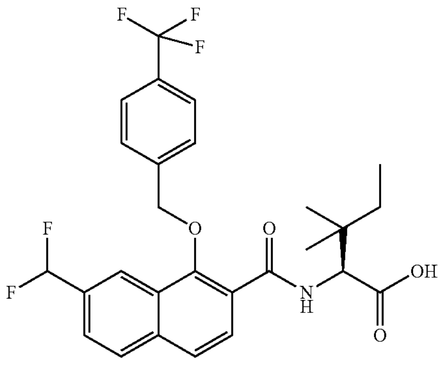 [SMILES: CCC(C)(C)[C@H](NC(=O)c1ccc2ccc(C(F)F)cc2c1OCc1ccc(C(F)(F)F)cc1)C(=O)O]

$^1$H NMR (400 MHz, DMSO-$d_6$) δ 12.85-12.68 (m, 1H) 8.63 (d, J=9.0 Hz, 1H) 8.29 (s, 1H) 8.16 (d, J=8.6 Hz, 1H) 7.89 (d, J=8.6 Hz, 1H) 7.83-7.74 (m, 5H) 7.72 (d, J=8.6 Hz, 1H) 7.23 (t, J=56.4 Hz, 1H) 5.36-5.19 (m, 2H) 4.44 (d, J=9.0 Hz, 1H) 1.44-1.22 (m, 2H) 0.93 (s, 3H), 0.90 (s, 3H) 0.78 (t, J=7.44 Hz, 3H)

LCMS: $t_R$=0.95 min., m/z ($ES^+$)=524 ($M+H^+$)

Example 243: (2S)-3,3-dimethyl-2-[[7-thiazol-4-yl-1-[[4-(trifluoromethyl)phenyl]methoxy]naphthalene-2-carbonyl]amino]butanoic Acid

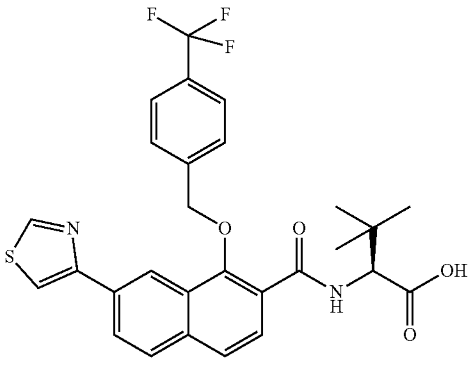 [SMILES: CC(C)(C)[C@H](NC(=O)c1ccc2ccc(-c3cscn3)cc2c1OCc1ccc(C(F)(F)F)cc1)C(=O)O]

$^1$H NMR (400 MHz, DMSO-$d_6$) δ 12.92-12.72 (m, 1H) 9.25 (d, J=1.8 Hz, 1H) 8.77 (s, 1H) 8.63 (d, J=8.9 Hz, 1H) 8.28 (d, J=1.8 Hz, 1H) 8.23 (dd, J=8.7, 1.6 Hz 1H) 8.09 (d, J=8.7 Hz, 1H) 7.87-7.79 (m, 5H) 7.67 (d, J=8.5 Hz, 1H) 5.40-5.22 (m, 2H) 4.36 (d, J=8.9 Hz, 1H) 0.98 (s, 9H)

LCMS: $t_R$=0.94 min., m/z ($ES^+$)=543 ($M+H^+$)

Example 244: (2S)-2-[[7-(difluoromethyl)-1-[[4-(trifluoromethyl)phenyl]methoxy]naphthalene-2-carbonyl]amino]-3,3-dimethyl-butanoic Acid

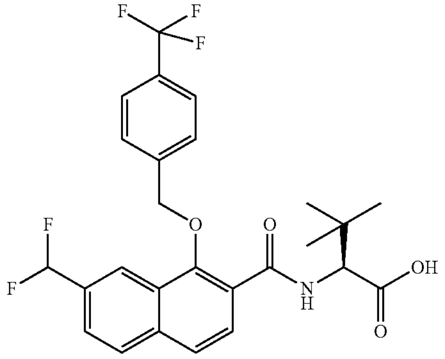 [SMILES: CC(C)(C)[C@H](NC(=O)c1ccc2ccc(C(F)F)cc2c1OCc1ccc(C(F)(F)F)cc1)C(=O)O]

$^1$H NMR (400 MHz, DMSO-$d_6$) δ 12.87-12.69 (m, 1H) 8.64 (d, J=8.7 Hz, 1H) 8.29 (s, 1H) 8.16 (d, J=8.6 Hz, 1H) 7.89 (d, J=8.6 Hz, 1H) 7.82-7.69 (m, 6H) 7.23 (t, J=55.7 Hz, 1H) 5.37-5.19 (m, 2H) 4.34 (d, J=8.7 Hz, 1H) 0.98 (s, 9H)

LCMS: $t_R$=0.92 min., m/z (ES$^+$)=510 (M+H$^+$)

Example 245: (2S)-2-[[7-(difluoromethyl)-1-[[4-(trifluoromethoxy)phenyl]methoxy]naphthalene-2-carbonyl]amino]-3,3-dimethyl-butanoic Acid

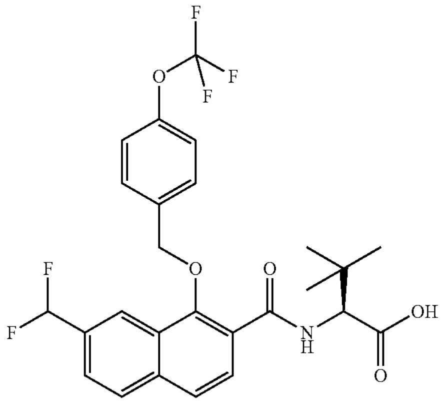 [SMILES: CC(C)(C)[C@H](NC(=O)c1ccc2ccc(C(F)F)cc2c1OCc1ccc(OC(F)(F)F)cc1)C(=O)O]

$^1$H NMR (400 MHz, DMSO-$d_6$) δ 12.92-12.66 (m, 1H) 8.62 (d, J=8.6 Hz, 1H) 8.29 (s, 1H) 8.15 (d, J=8.6 Hz, 1H) 7.88 (d, J=8.6 Hz, 1H) 7.77-7.72 (m, 2H) 7.67 (d, J=8.4 Hz, 2H) 7.41 (d, J=8.4 Hz, 2H), 7.23 (t, J=55.7 Hz, 1H) 5.29-5.12 (m, 2H) 4.34 (d, J=8.6 Hz, 1H) 0.98 (s, 9H)

LCMS: $t_R$=0.93 min., m/z (ES$^+$)=526 (M+H$^+$)

Example 246: (2S)-2-[[7-(difluoromethyl)-1-[[4-(trifluoromethyl)phenyl]methoxy]naphthalene-2-carbonyl]amino]-3,3-dimethylhexanoic Acid

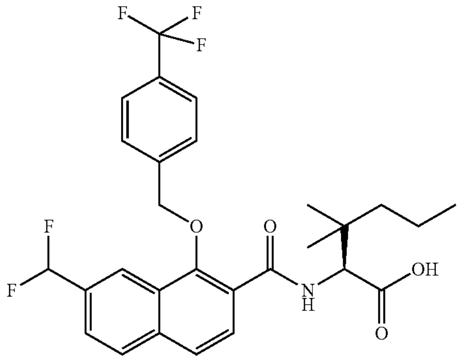 [SMILES: CCCC(C)(C)[C@H](NC(=O)c1ccc2ccc(C(F)F)cc2c1OCc1ccc(C(F)(F)F)cc1)C(=O)O]

$^1$H NMR (400 MHz, DMSO-$d_6$) δ 12.77 (s, 1H) 8.63 (d, J=8.7 Hz, 1H) 8.29 (s, 1H) 8.16 (d, J=8.6 Hz, 1H) 7.90 (d, J=8.6 Hz, 1H) 7.82-7.73 (m, 5H) 7.71 (d, J=8.6 Hz, 1H) 7.23 (t, J=55.6 Hz, 1H) 5.37-5.21 (m, 2H) 4.43 (d, J=8.7 Hz, 1H) 1.37-1.14 (m, 4H) 0.95 (s, 3H) 0.92 (s, 3H) 0.81-074 (m, 3H)

LCMS: $t_R$=0.99 min., m/z (ES$^+$)=538 (M+H$^+$)

Example 247: (2S)-2-[[7-bromo-1-[[4-(trifluoromethoxy)phenyl]methoxy]naphthalene-2-carbonyl]amino]-3,3-dimethyl-butanoic Acid

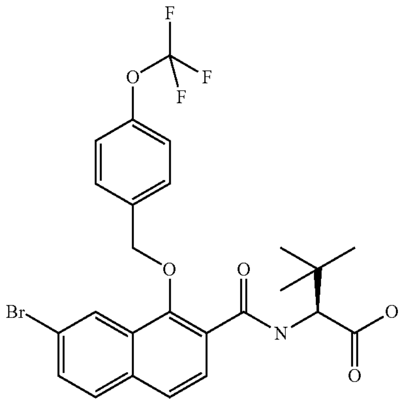 [SMILES: CC(C)(C)[C@H](NC(=O)c1ccc2ccc(Br)cc2c1OCc1ccc(OC(F)(F)F)cc1)C(=O)O]

$^1$H NMR (400 MHz, DMSO-$d_6$) δ 12.83-12.68 (m, 1H) 8.61 (d, J=8.7 Hz, 1H) 8.14 (d, J=1.8 Hz, 1H) 7.95 (d, J=8.7 Hz, 1H) 7.82 (d, J=8.5 Hz, 1H) 7.73 (dd, J=8.7, 1.8 Hz 1H) 7.67-7.59 (m, 3H) 7.41 (d, J=7.9 Hz, 2H) 5.27-5.09 (m, 2H) 4.34 (d, J=8.7 Hz, 1H) 0.98 (s, 9H)

LCMS: $t_R$=1.01 min., m/z (ES$^+$)=554 (M+H$^+$)

Example 248: (2S)-2-[[7-cyano-1-[[4-(trifluoromethyl)phenyl]methoxy]naphthalene-2-carbonyl]amino]-3,3-dimethyl-butanoic Acid

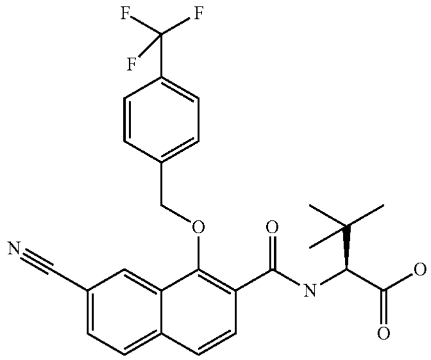 [SMILES: CC(C)(C)[C@H](NC(=O)c1ccc2ccc(C#N)cc2c1OCc1ccc(C(F)(F)F)cc1)C(=O)O]

$^1$H NMR (400 MHz, DMSO-$d_6$) δ ppm 12.99-12.69 (m, 1H) 8.68 (br d, J=8.44 Hz, 1H) 8.53 (s, 1H) 8.20 (d, J=8.56 Hz, 1H) 7.97-7.86 (m, 2H) 7.83-7.71 (m, 5H) 5.41-5.19 (m, 2H) 4.31 (d, J=8.44 Hz, 1H) 0.98 (s, 9H)

LCMS: $t_R$=0.87 min., m/z ($ES^+$)=485 ($M+H^+$)

Example 249: (2S)-3,3-dimethyl-2-[[7-methyl-1-[[4-(trifluoromethoxy)phenyl]methoxy]naphthalene-2-carbonyl]amino]butanoic Acid

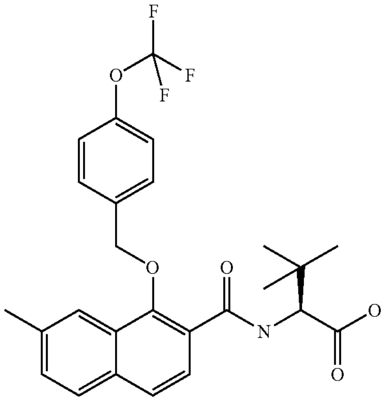 [SMILES: Cc1ccc2ccc(C(=O)N[C@H](C(=O)O)C(C)(C)C)c(OCc3ccc(OC(F)(F)F)cc3)c2c1]

$^1$H NMR (400 MHz, DMSO-$d_6$) δ ppm 12.99-12.55 (m, 1H) 8.55 (d, J=8.56 Hz, 1H) 7.91 (d, J=8.44 Hz, 1H) 7.86 (s, 1H) 7.75 (d, J=8.44 Hz, 1H) 7.70 (d, J=8.56 Hz, 2H) 7.63 (d, J=8.56 Hz, 1H) 7.50-7.40 (m, 3H) 5.29-5.04 (m, 2H) 4.40 (d, J=8.56 Hz, 1H) 2.48 (s, 3H) 0.95 (s, 9H)

LCMS: $t_R$=0.99 min., m/z ($ES^+$)=490 ($M+H^+$)

Example 250: (2S)-2-[[7-(difluoromethyl)-1-[[4-(trifluoromethoxy)phenyl]methoxy]naphthalene-2-carbonyl]amino]-3,3-dimethyl-pentanoic Acid

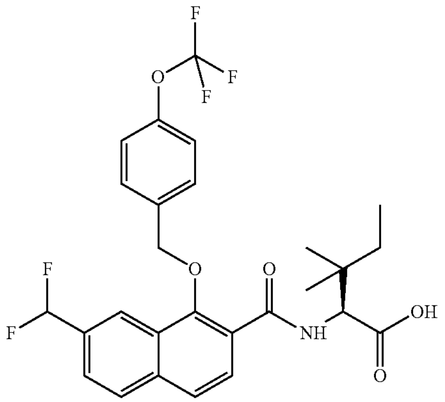 [SMILES: CCC(C)(C)[C@H](NC(=O)c1ccc2ccc(C(F)F)cc2c1OCc1ccc(OC(F)(F)F)cc1)C(=O)O]

$^1$H NMR (400 MHz, DMSO-$d_6$) δ ppm 12.98-12.59 (m, 1H) 8.61 (d, J=8.56 Hz, 1H) 8.29 (s, 1H) 8.16 (d, J=8.44 Hz, 1H) 7.88 (d, J=8.44 Hz, 1H) 7.79-7.71 (m, 2H) 7.68 (d, J=8.19 Hz, 2H) 7.42 (d, J=8.19 Hz, 2H) 7.23 (t, J=55.38 Hz, 1H) 5.30-5.12 (m, 2H) 4.44 (d, J=8.56 Hz, 1H) 1.44-1.26 (m, 2H) 0.93 (s, 3H) 0.90 (s, 3H) 0.79 (t, J=7.17 Hz, 3H)

LCMS: $t_R$=0.96 min., m/z ($ES^+$)=540 ($M+H^+$)

Example 251: (2S)-2-[[7-chloro-1-[[4-(trifluoromethoxy)phenyl]methoxy]naphthalene-2-carbonyl]amino]-3-ethyl-3-methyl-hexanoic Acid

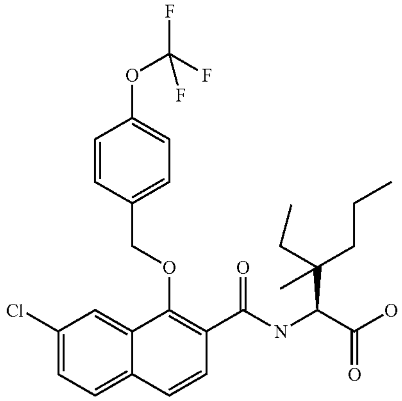 [SMILES: CCCC(C)(CC)[C@H](NC(=O)c1ccc2ccc(Cl)cc2c1OCc1ccc(OC(F)(F)F)cc1)C(=O)O]

$^1$H NMR (400 MHz, DMSO-$d_6$) δ ppm 12.98-12.58 (m, 1H) 8.63-8.55 (m, 1H) 8.06 (d, J=8.96 Hz, 1H) 7.99 (d, J=1.00 Hz, 1H) 7.84 (d, J=8.4 Hz, 1H) 7.71-7.59 (m, 4H) 7.44 (br d, J=8.07 Hz, 2H) 5.29-5.11 (m, 2H) 4.53 (dd, J=8.80, 2.20 Hz, 1H) 1.43-1.11 (m, 6H) 0.93-0.68 (m, 9H)

LCMS: $t_R$=1.11 min., m/z ($ES^+$)=552 ($M+H^+$)

Example 252: (2S)-3,3-dimethyl-2-[[7-thiazol-4-yl-1-[[4-(trifluoromethoxy)phenyl]methoxy]naphthalene-2-carbonyl]amino]butanoic Acid

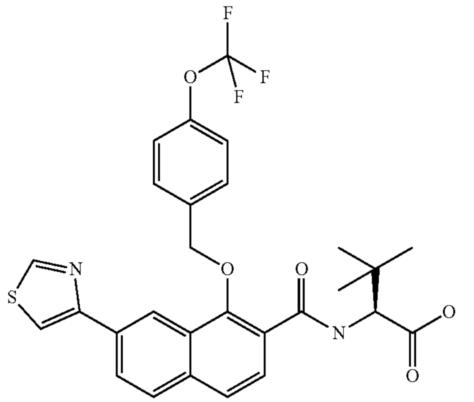 [SMILES: CC(C)(C)[C@H](NC(=O)c1ccc2ccc(-c3cscn3)cc2c1OCc1ccc(OC(F)(F)F)cc1)C(=O)O]

$^1$H NMR (400 MHz, DMSO-$d_6$) δ ppm 13.08-12.58 (m, 1H) 9.27 (d, J=1.71 Hz, 1H) 8.79 (s, 1H) 8.62 (d, J=8.56 Hz, 1H) 8.28 (d, J=1.71 Hz, 1H) 8.23 (dd, J=8.58, 1.60 Hz, 1H) 8.08 (d, J=8.58 Hz, 1H) 7.82 (d, J=8.67 Hz, 1H) 7.75 (d, J=8.51 Hz, 2H) 7.69 (d, J=8.67 Hz, 1H) 7.45 (d, J=8.51 Hz, 2H) 5.34-5.13 (m, 2H) 4.37 (d, J=8.56 Hz, 1H) 0.98 (s, 9H)

LCMS: $t_R$=0.95 min., m/z ($ES^+$)=559 ($M+H^+$)

Example 253: (2S)-2-[[7-chloro-1-[[4-(trifluoromethoxy)phenyl]methoxy]naphthalene-2-carbonyl]amino]-2-(1-ethylcyclopentyl)acetic Acid

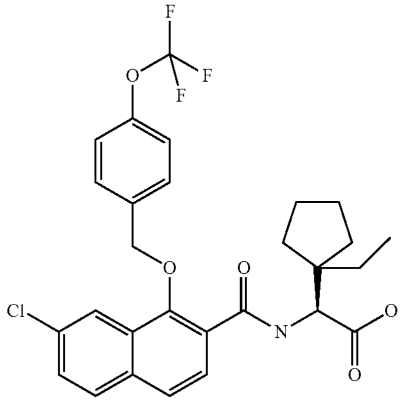 [SMILES: CCC1([C@H](NC(=O)c2ccc3ccc(Cl)cc3c2OCc2ccc(OC(F)(F)F)cc2)C(=O)O)CCCC1]

$^1$H NMR (400 MHz, DMSO-$d_6$) δ ppm 12.98-12.64 (m, 1H) 8.59 (d, J=8.56 Hz, 1H) 8.06 (d, J=8.86 Hz, 1H) 8.02-7.98 (m, 1H) 7.85 (d, J=8.43 Hz, 1H) 7.70-7.60 (m, 4H) 7.44 (d, J=8.32 Hz, 2H) 5.29-5.13 (m, 2H) 4.55 (d, J=8.56 Hz, 1H) 1.81-1.69 (m, 2H) 1.59-1.27 (m, 8H) 0.80 (t, J=7.26 Hz, 3H)

LCMS: $t_R$=1.09 min., m/z ($ES^+$)=550 ($M+H^+$)

Example 254: (2S)-2-[[7-cyano-1-[[4-(trifluoromethoxy)phenyl]methoxy]naphthalene-2-carbonyl]amino]-3,3-dimethyl-butanoic Acid

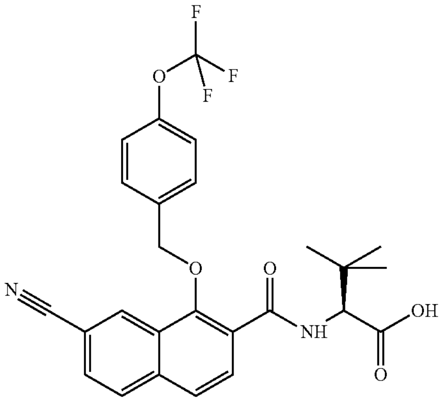 [SMILES: CC(C)(C)[C@H](NC(=O)c1ccc2ccc(C#N)cc2c1OCc1ccc(OC(F)(F)F)cc1)C(=O)O]

$^1$H NMR (400 MHz, DMSO-$d_6$) δ ppm 8.42-8.34 (m, 2H) 8.17 (d, J=8.56 Hz, 1H) 7.98 (d, J=8.67 Hz, 1H) 7.90 (d, J=8.67 Hz, 1H) 7.86 (dd, J=8.56, 1.53 Hz, 1H) 7.71 (d, J=8.19 Hz, 2H) 7.37 (d, J=8.19 Hz, 2H) 5.46-5.06 (m, 2H) 4.02 (d, J=8.37 Hz, 1H) 0.94 (s, 9H)

LCMS: $t_R$=0.88 min., m/z ($ES^+$)=501 ($M+H^+$)

Example 255: (2S)-2-[[7-chloro-1-[[4-(trifluoromethyl)phenyl]methoxy]naphthalene-2-carbonyl]amino]-3-ethyl-3-methyl-hexanoic Acid

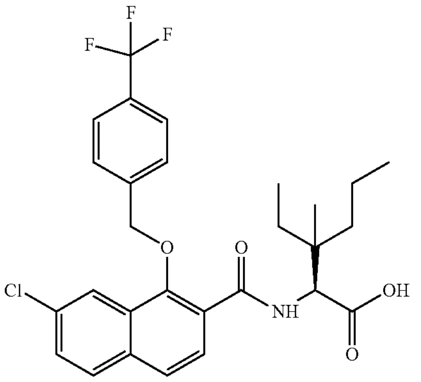 [SMILES: CCCC(C)(CC)[C@H](NC(=O)c1ccc2ccc(Cl)cc2c1OCc1ccc(C(F)(F)F)cc1)C(=O)O]

$^1$H NMR (400 MHz, DMSO-$d_6$) δ ppm 12.93-12.66 (m, 1H) 8.63-8.55 (m, 1H) 8.08 (d, J=8.80 Hz, 1H) 8.01 (d, J=1.96 Hz, 1H) 7.89-7.74 (m, 5H) 7.68-7.61 (m, 2H) 5.37-5.19 (m, 2H) 4.55-4.46 (m, 1H) 1.42-1.12 (m, 6H) 0.91-0.85 (m, 3H) 0.84-0.69 (m, 6H)

LCMS: $t_R$=1.10 min., m/z ($ES^+$)=536 ($M+H^+$)

Example 256: (2S)-2-[[7-bromo-1-[[4-(trifluoromethyl)phenyl]methoxy]naphthalene-2-carbonyl]amino]-3,3-dimethyl-butanoic Acid

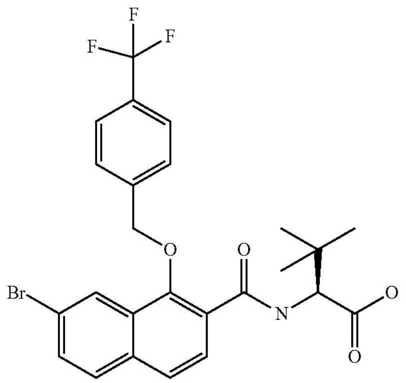 [SMILES: CC(C)(C)[C@H](NC(=O)c1ccc2ccc(Br)cc2c1OCc1ccc(C(F)(F)F)cc1)C(=O)O]

$^1$H NMR (400 MHz, DMSO-$d_6$) δ ppm 12.95-12.63 (m, 1H) 8.64 (d, J=8.44 Hz, 1H) 8.15 (d, J=1.70 Hz, 1H) 7.99 (d, J=8.80 Hz, 1H) 7.88-7.71 (m, 6H) 7.66 (d, J=8.56 Hz, 1H) 5.36-5.18 (m, 2H) 4.34 (d, J=8.44 Hz, 1H) 0.98 (s, 9H)

LCMS: $t_R$=1.00 min., m/z (ES$^+$)=538 (M+H$^+$)

Example 257: (2S)-2-[[1-(4,4-dimethylpentoxy)-7-methyl-naphthalene-2-carbonyl]amino]-3,3-dimethyl-pentanoic Acid

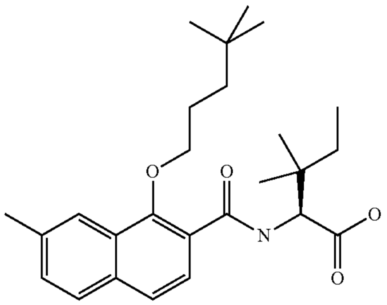 [SMILES: CCC(C)(C)[C@H](NC(=O)c1ccc2ccc(C)cc2c1OCCCC(C)(C)C)C(=O)O]

LCMS Purity: 100%; (M+H$^+$) 428.0.

1H NMR: (CDCl3, 400 Hz): ? 12.88 (s, 1H), 8.57 (d, J=13.2 Hz, 1H), 7.93 (s, 1H), 7.89 (d, J=12.4 Hz, 1H), 7.74-7.69 (m, 2H), 7.48 (d, J=12.8 Hz, 1H), 4.50 (d, J=13.2 Hz, 1H), 4.09-3.97 (m, 2H), 2.53 (s, 3H), 1.97-1.88 (m, 2H), 1.42-1.35 (m, 4H), 0.99 (s, 3H), 0.98 (s, 3H), 0.93 (s, 9H), 0.88 (t, J=7.2 Hz, 3H).

Example 258: 2S)-2-[[7-chloro-1-[[4-(trifluoromethyl)phenyl]methoxy]naphthalene-2-carbonyl]amino]-2-(1-ethylcyclopentyl)acetic Acid

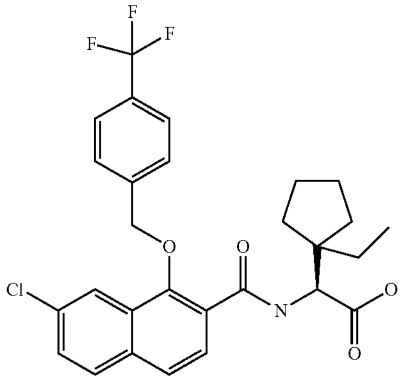 [SMILES: CCC1([C@H](NC(=O)c2ccc3ccc(Cl)cc3c2OCc2ccc(C(F)(F)F)cc2)C(=O)O)CCCC1]

$^1$H NMR (400 MHz, DMSO-$d_6$) δ ppm 13.03-12.59 (m, 1H) 8.60 (d, J=8.63 Hz, 1H) 8.07 (d, J=8.82 Hz, 1H) 8.01 (d, J=1.91 Hz, 1H) 7.89-7.73 (m, 5H) 7.70-7.61 (m, 2H) 5.38-5.19 (m, 2H) 4.53 (d, J=8.63 Hz, 1H) 1.80-1.68 (m, 2H) 1.59-1.26 (m, 8H) 0.79 (t, J=7.21 Hz, 3H)

LCMS: $t_R$=1.08 min., m/z (ES$^+$)=534 (M+H$^+$)

Example 259: (2R)-2-[[7-fluoro-1-[[4-(trifluoromethoxy)phenyl]methoxy]naphthalene-2-carbonyl]amino]-3,3-dimethyl-butanoic Acid

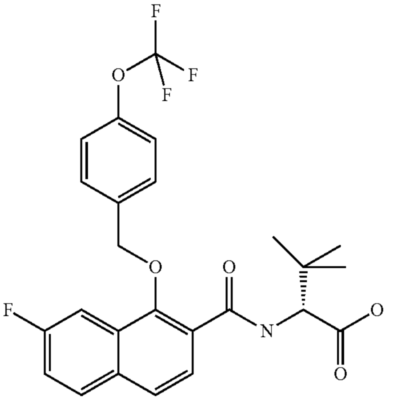 [SMILES: CC(C)(C)[C@@H](NC(=O)c1ccc2ccc(F)cc2c1OCc1ccc(OC(F)(F)F)cc1)C(=O)O]

$^1$H NMR (400 MHz, DMSO-$d_6$) δ ppm 12.90-12.61 (m, 1H) 8.61 (d, J=8.56 Hz, 1H) 8.16-8.06 (m, 1H) 7.85 (d, J=8.71 Hz, 1H) 7.74-7.63 (m, 3H) 7.61 (d, J=8.71 Hz, 1H) 7.54 (td, J=8.86, 2.67 Hz, 1H) 7.42 (d, J=8.01 Hz, 2H) 5.29-5.10 (m, 2H) 4.36 (d, J=8.56 Hz, 1H) 0.98 (s, 9H)

LCMS: $t_R$=0.95 min., m/z (ES$^+$)=494 (M+H$^+$)

Example 260: (2S)-2-[[6-isopropoxy-1-[[4-(trifluoromethyl)phenyl]methoxy]naphthalene-2-carbonyl]amino]-3,3-dimethyl-butanoic Acid

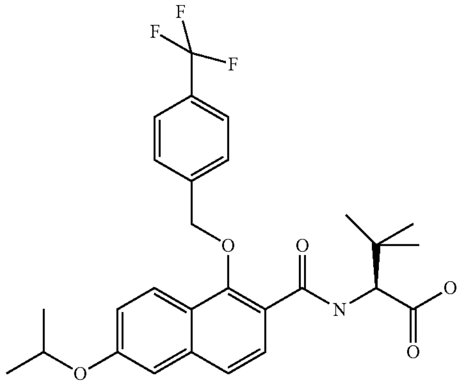 [SMILES: CC(C)Oc1ccc2c(OCc3ccc(C(F)(F)F)cc3)c(C(=O)N[C@H](C(=O)O)C(C)(C)C)ccc2c1]

$^1$H NMR (400 MHz, DMSO-$d_6$) δ ppm 13.15-12.34 (m, 1H) 8.49 (d, J=8.56 Hz, 1H) 7.99 (d, J=9.17 Hz, 1H) 7.84-7.77 (m, 4H) 7.74-7.64 (m, 2H) 7.43 (s, 1H) 7.21 (br d, J=9.17 Hz, 1H) 5.37-5.12 (m, 2H) 4.90-4.67 (m, 1H) 4.34 (d, J=8.56 Hz, 1H) 1.35 (d, J=5.87 Hz, 6H) 0.93 (s, 9H)

LCMS: $t_R$=1.03 min., m/z (ES$^+$)=518 (M+H$^+$)

Example 261: (2R)-2-[[7-fluoro-1-[[4-(trifluoromethyl)phenyl]methoxy]naphthalene-2-carbonyl]amino]-3,3-dimethyl-butanoic Acid

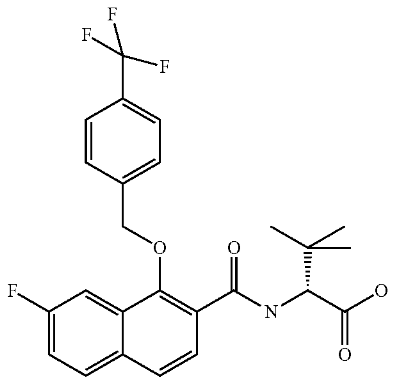 [SMILES: CC(C)(C)[C@@H](NC(=O)c1ccc2ccc(F)cc2c1OCc1ccc(C(F)(F)F)cc1)C(=O)O]

$^1$H NMR (400 MHz, DMSO-$d_6$) δ ppm 13.00-12.54 (m, 1H) 8.62 (d, J=8.56 Hz, 1H) 8.17-8.07 (m, 1H) 7.86 (d, J=8.44 Hz, 1H) 7.84-7.75 (m, 4H) 7.71 (dd, J=10.57, 2.6 Hz, 1H) 7.60 (d, J=8.44 Hz, 1H) 7.55 (td, J=8.77, 2.60 Hz, 1H) 5.35-5.18 (m, 2H) 4.35 (d, J=8.56 Hz, 1H) 0.98 (s, 9H)

LCMS: $t_R$=0.94 min., m/z (ES$^+$)=478 (M+H$^+$)

Example 262: (2R)-2-[[7-chloro-1-[[4-(trifluoromethyl)phenyl]methoxy]naphthalene-2-carbonyl]amino]-3,3-dimethyl-butanoic Acid

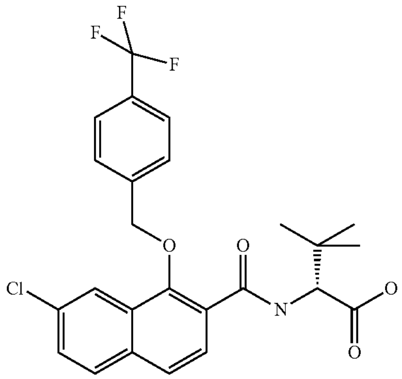 [SMILES: CC(C)(C)[C@@H](NC(=O)c1ccc2ccc(Cl)cc2c1OCc1ccc(C(F)(F)F)cc1)C(=O)O]

$^1$H NMR (400 MHz, DMSO-$d_6$) δ ppm 12.93-12.63 (m, 1H) 8.64 (d, J=8.44 Hz, 1H) 8.07 (d, J=8.73 Hz, 1H) 8.00 (d, J=2.15 Hz, 1H) 7.85 (d, J=8.48 Hz, 1H) 7.83-7.73 (m, 4H) 7.67-7.62 (m, 2H) 5.38-5.18 (m, 2H) 4.35 (d, J=8.44 Hz, 1H) 0.98 (s, 9H)

LCMS: $t_R$=0.98 min., m/z (ES$^+$)=494 (M+H$^+$)

Example 263: (2S)-2-[[5-fluoro-7-methyl-1-[[4-(trifluoromethyl)phenyl]methoxy]naphthalene-2-carbonyl]amino]-3,3-dimethyl-butanoic Acid

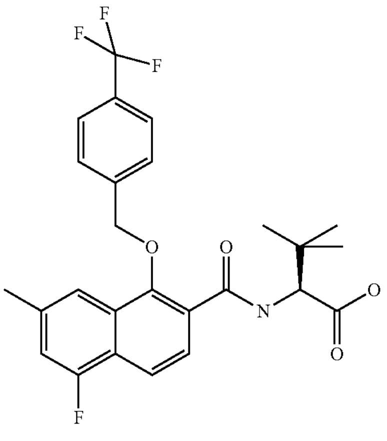 [SMILES: Cc1cc(F)c2ccc(C(=O)N[C@H](C(=O)O)C(C)(C)C)c(OCc3ccc(C(F)(F)F)cc3)c2c1]

$^1$H NMR (400 MHz, DMSO-$d_6$) δ ppm 13.02-12.57 (m, 1H) 8.63 (d, J=8.44 Hz, 1H) 7.84 (d, J=8.67 Hz, 1H) 7.82-7.73 (m, 4H) 7.69 (s, 1H) 7.62 (d, J=8.67 Hz, 1H) 7.34 (d, J=11.24 Hz, 1H) 5.32-5.18 (m, 2H) 4.33 (d, J=8.44 Hz, 1H) 2.47 (s, 3H) 0.96 (s, 9H)

LCMS: $t_R$=0.99 min., m/z (ES$^+$)=492 (M+H$^+$)

Example 264: (2R)-2-[[7-(difluoromethyl)-1-[[4-(trifluoromethoxy)phenyl]methoxy]naphthalene-2-carbonyl]amino]-3,3-dimethyl-butanoic Acid

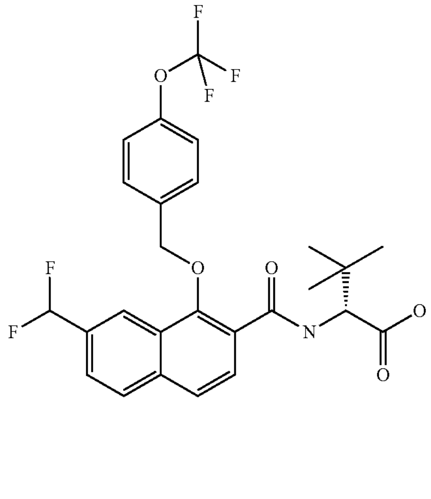 [SMILES: CC(C)(C)[C@@H](NC(=O)c1ccc2ccc(C(F)F)cc2c1OCc1ccc(OC(F)(F)F)cc1)C(=O)O]

$^1$H NMR (400 MHz, DMSO-$d_6$) δ ppm 8.51 (br d, J=7.34 Hz, 1H) 8.23 (s, 1H) 8.14 (d, J=8.63 Hz, 1H) 7.91-7.81 (m, 2H) 7.78-7.66 (m, 3H) 7.38 (d, J=8.61 Hz, 2H) 7.20 (t, J=55.69 Hz, 1H) 5.37-5.08 (m, 2H) 4.23 (br d, J=7.34 Hz, 1H) 0.96 (s, 9H)

LCMS: $t_R$=0.93 min., m/z (ES$^+$)=526 (M+H$^+$)

Example 265: (2R)-2-[[7-(difluoromethyl)-1-[[4-(trifluoromethyl)phenyl]methoxy]naphthalene-2-carbonyl]amino]-3,3-dimethyl-butanoic Acid

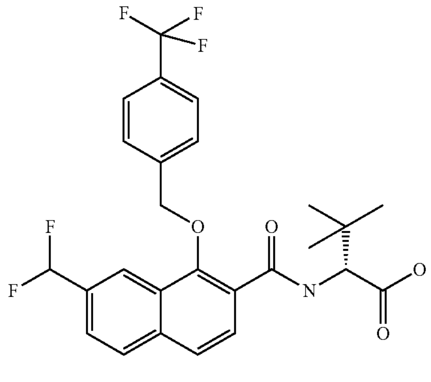 [SMILES: CC(C)(C)[C@@H](NC(=O)c1ccc2ccc(C(F)F)cc2c1OCc1ccc(C(F)(F)F)cc1)C(=O)O]

$^1$H NMR (400 MHz, DMSO-$d_6$) δ ppm 13.40-12.17 (m, 1H) 8.59 (br d, J=8.44 Hz, 1H) 8.26 (s, 1H) 8.16 (d, J=8.56 Hz, 1H) 7.89 (d, J=8.56 Hz, 1H) 7.82-7.73 (m, 6H) 7.21 (t, J=55.77 Hz, 1H) 5.40-5.18 (m, 2H) 4.30 (br d, J=8.44 Hz, 1H) 0.97 (s, 9H)

LCMS: $t_R$=0.92 min., m/z (ES$^+$)=510 (M+H$^+$)

Example 266: (2S)-2-[[1-(4,4-dimethylpent-2-ynoxy)-6-fluoro-naphthalene-2-carbonyl]amino]-3,3-dimethyl-butanoic Acid

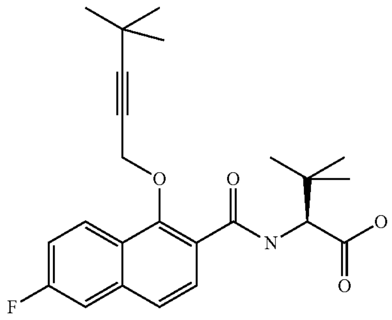 [SMILES: CC(C)(C)C#CCOc1c(C(=O)N[C@H](C(=O)O)C(C)(C)C)ccc2cc(F)ccc12]

$^1$H NMR (400 MHz, DMSO-$d_6$) δ ppm 13.15-12.58 (m, 1H) 8.45 (d, J=8.44 Hz, 1H) 8.28 (dd, J=9.23, 5.69 Hz, 1H) 7.88-7.77 (m, 3H) 7.57 (td, J=8.96, 2.63 Hz, 1H) 4.95-4.78 (m, 2H) 4.37 (d, J=8.44 Hz, 1H) 1.06 (s, 9H) 1.00 (s, 9H)

LCMS: $t_R$=0.95 min., m/z (ES$^+$)=414 (M+H$^+$)

Example 267: (2S)-2-[[1-(4,4-dimethylpent-2-ynoxy)naphthalene-2-carbonyl]amino]-3,3-dimethyl-butanoic Acid

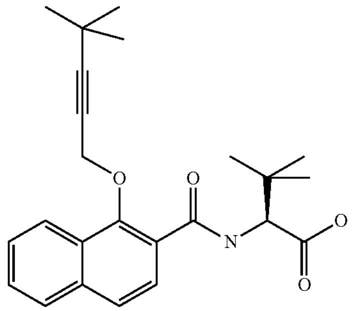 [SMILES: CC(C)(C)C#CCOc1c(C(=O)N[C@H](C(=O)O)C(C)(C)C)ccc2ccccc12]

$^1$H NMR (400 MHz, DMSO-$d_6$) δ ppm 13.10-12.66 (m, 1H) 8.49 (d, J=8.44 Hz, 1H) 8.25-8.17 (m, 1H) 8.04-7.97 (m, 1H) 7.87-7.78 (m, 2H) 7.72-7.59 (m, 2H) 4.94-4.80 (m, 2H) 4.38 (d, J=8.44 Hz, 1H) 1.07 (s, 9H) 1.02 (s, 9H)

LCMS: $t_R$=0.94 min., m/z (ES$^+$)=396 (M+H$^+$)

Example 268: (2S)-3,3-dimethyl-2-[[1-[[1-(trifluoromethyl)cyclopropyl]methoxy]naphthalene-2-carbonyl]amino]butanoic Acid

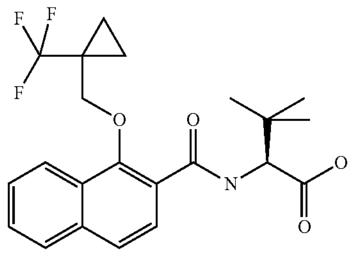 [SMILES: CC(C)(C)[C@H](NC(=O)c1ccc2ccccc2c1OCC1(C(F)(F)F)CC1)C(=O)O]

$^1$H NMR (400 MHz, DMSO-$d_6$) δ ppm 13.28-12.04 (m, 1H) 8.57 (d, J=8.44 Hz, 1H) 8.24-8.18 (m, 1H) 8.01-7.94 (m, 1H) 7.72 (d, J=8.44 Hz, 1H) 7.66-7.58 (m, 2H) 7.41 (d, J=8.44 Hz, 1H) 4.32 (d, J=8.44 Hz, 1H) 4.30-4.14 (m, 2H) 1.14-0.99 (m, 13H)

LCMS: $t_R$=0.88 min., m/z (ES$^+$)=424 (M+H$^+$)

Example 269: (2S)-3,3-dimethyl-2-[[1-[[4-(trifluoromethyl)thiazol-2-yl]methoxy]naphthalene-2-carbonyl]amino]butanoic Acid

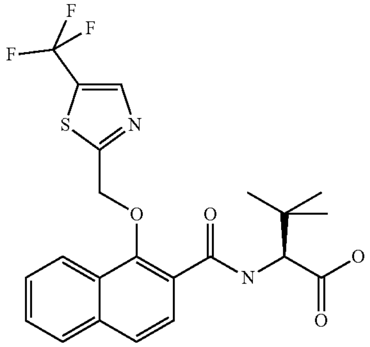 [SMILES: CC(C)(C)[C@H](NC(=O)c1ccc2ccccc2c1OCc1ncc(C(F)(F)F)s1)C(=O)O]

$^1$H NMR (400 MHz, DMSO-$d_6$) δ ppm 12.91-12.56 (m, 1H) 8.65-8.56 (m, 2H) 8.20.8.14 (m, 1H) 8.06-8.01 (m, 1H) 7.86 (d, J=8.44 Hz, 1H) 7.68-7.59 (m, 3H) 5.55-5.45 (m, 2H) 4.34 (d, J=8.44 Hz, 1H) 1.00 (s, 9H)

LCMS: $t_R$=0.86 min., m/z (ES$^+$)=467 (M+H$^+$)

Example 270: (2S)-2-[[1-(3-cyclopropylprop-2-ynoxy)naphthalene-2-carbonyl]amino]-3,3-dimethyl-butanoic Acid

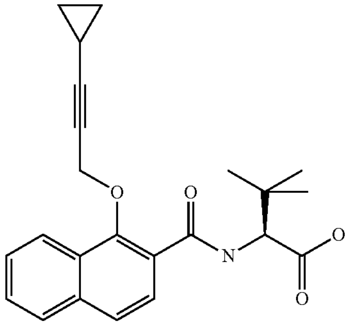 [SMILES: CC(C)(C)[C@H](NC(=O)c1ccc2ccccc2c1OCC#CC1CC1)C(=O)O]

$^1$H NMR (400 MHz, DMSO-$d_6$) δ ppm 13.02-12.69 (m, 1H) 8.46 (d, J=8.56 Hz, 1H) 8.18 (dd, J=6.42, 3.36 Hz, 1H) 8.00 (dd, J=6.42, 3.36 Hz, 1H) 7.84-7.77 (m, 2H) 7.68-7.62 (m, 2H) 4.89-4.76 (m, 2H) 4.37 (d, J=8.56 Hz, 1H) 1.27-1.09 (m, 1H) 1.06 (s, 9H) 0.74-0.69 (m, 2H) 0.50-0.42 (m, 2H)

LCMS: $t_R$=0.81 min., m/z (ES$^+$)=380 (M+H$^+$)

Example 271: (2S)-2-[[5-fluoro-7-methyl-1-[[4-(trifluoromethoxy)phenyl]methoxy]naphthalene-2-carbonyl]amino]-3,3-dimethyl-butanoic Acid

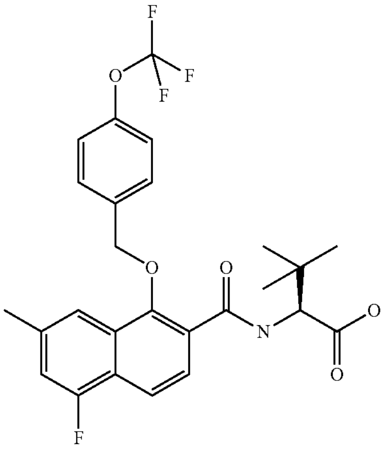 [SMILES: Cc1cc(F)c2ccc(C(=O)N[C@H](C(=O)O)C(C)(C)C)c(OCc3ccc(OC(F)(F)F)cc3)c2c1]

$^1$H NMR (400 MHz, DMSO-$d_6$) δ ppm 12.93-12.63 (m, 1H) 8.62 (d, J=8.56 Hz, 1H) 7.85 (d, J=8.68 Hz, 1H) 7.71-7.62 (m, 4H) 7.42 (d, J=8.07 Hz, 2H) 7.34 (d, J=11.62 Hz, 1H) 5.31-5.02 (m, 2H) 4.35 (d, J=8.56 Hz, 1H) 2.48 (s, 3H) 0.97 (s, 9H)

LCMS: $t_R$=1.01 min., m/z (ES$^+$)=508 (M+H$^+$)

Example 272: (2S)-2-[[5-fluoro-7-methyl-1-[[4-(trifluoromethyl)phenyl]methoxy]-naphthalene-2-carbonyl]amino]-3,3-dimethyl-pentanoic Acid

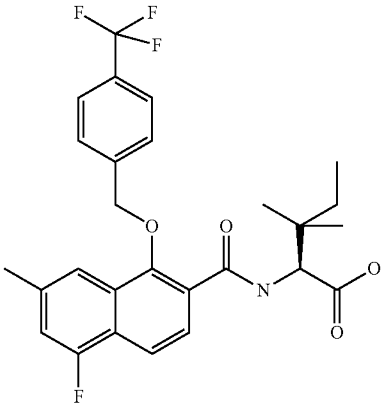 [SMILES: CCC(C)(C)[C@H](NC(=O)c1ccc2c(F)cc(C)cc2c1OCc1ccc(C(F)(F)F)cc1)C(=O)O]

$^1$H NMR (400 MHz, DMSO-$d_6$) δ ppm 12.76 (br s, 1H) 8.62 (d, J=8.68 Hz, 1H) 7.86 (d, J=8.68 Hz, 1H) 7.83-7.76 (m, 4H) 7.70 (s, 1H) 7.63 (d, J=8.68 Hz, 1H) 7.34 (d, J=11.49 Hz, 1H) 5.34-5.15 (m, 2H) 4.43 (d, J=8.68 Hz, 1H) 2.47 (s, 3H) 1.41-1.14 (m, 2H) 0.92 (s, 3H) 0.89 (s, 3H) 0.78 (t, J=7.46 Hz, 3H)

LCMS: $t_R$=1.02 min., m/z (ES$^+$)=506 (M+H$^+$)

Example 273: (2S)-2-[[5-fluoro-7-methyl-1-[[4-(trifluoromethoxy)phenyl]methoxy]naphthalene-2-carbonyl]amino]-3,3-dimethyl-pentanoic Acid

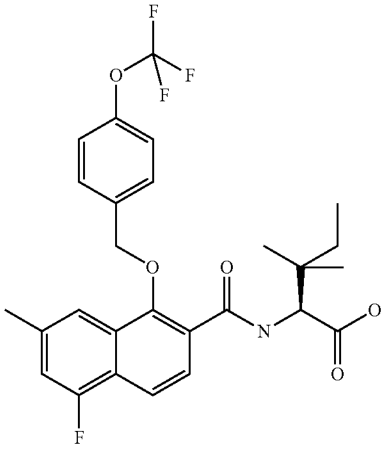 [SMILES: CCC(C)(C)[C@H](NC(=O)c1ccc2c(F)cc(C)cc2c1OCc1ccc(OC(F)(F)F)cc1)C(=O)O]

$^1$H NMR (400 MHz, DMSO-$d_6$) δ ppm 12.95-12.59 (m, 1H) 8.60 (d, J=8.68 Hz, 1H) 7.85 (d, J=8.68 Hz, 1H) 7.71-7.62 (m, 4H) 7.43 (d, J=8.07 Hz, 2H) 7.34 (d, J=11.74 Hz, 1H) 5.30.5.08 (m, 2H) 4.43 (d, J=8.68 Hz, 1H) 2.48 (s, 3H) 1.43-1.26 (m, 2H) 0.92 (s, 3H) 0.89 (s, 3H) 0.79 (t, J=7.46 Hz, 3H)

LCMS: $t_R$=1.04 min., m/z ($ES^+$)=522 ($M+H^+$)

Example 274: (2S)-2-[[7-fluoro-1-[[4-(trifluoromethyl)phenyl]methoxy]naphthalene-2-carbonyl]amino]-3,3-dimethyl-pentanoic Acid

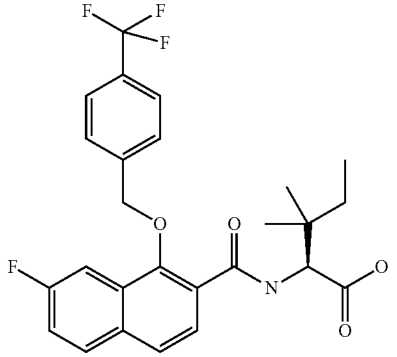 [SMILES: CCC(C)(C)[C@H](NC(=O)c1ccc2ccc(F)cc2c1OCc1ccc(C(F)(F)F)cc1)C(=O)O]

Step 1. Preparation of methyl (S)-2-(7-fluoro-1-((4-(trifluoromethyl)benzyl)oxy)-2-naphthamido)-3,3-dimethylpentanoate

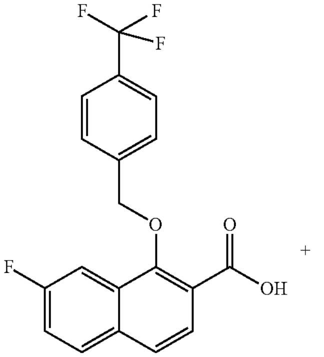

-continued

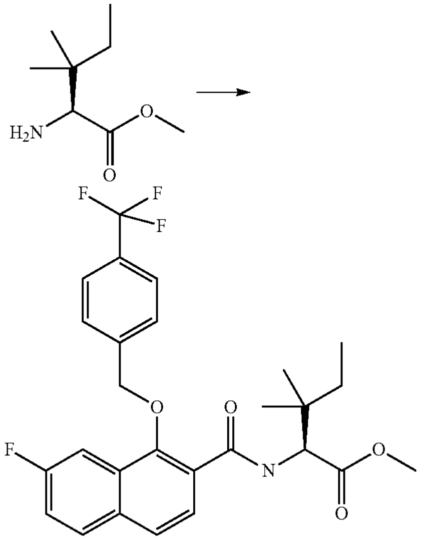

A 25-mL flask equipped with stir bar, static nitrogen line was charged with 7-fluoro-1-((4-(trifluoromethyl)benzyl)oxy)-2-naphthoic acid (182 mg, 0.5 mmol, 1.0 equiv.) and EtOAc (4 mL). To this solution was added DIPEA (0.3 mL, 185 mg, 1.435 mmol, 3.5 equiv.), followed by methyl (S)-2-amino-3,3-dimethylpentanoate ((1.15 equiv): 99 mg. 025 mmol, 1.25 equiv.). The solution was cooled in an ice-water bath to 5° C. To this solution was added 2,4,6-tripropyl-1,3,5,2,4,6-trioxatriphosphorinane-2,4,6-trioxide (T3P, 50 wt % solution in EtOAc, 636 mg, 1.0 mmol, 2.0 equiv.) drop-wise using a syringe with cooling in ice-water bath. The reaction flask was removed from the ice bath and the solution allowed to warm to rt after addition and then stirred at rt (overnight) until in-process LCMS indicated a complete reaction (<0.1 A % acid SM). The reaction was diluted with EtOAc (5 mL), washed sequentially with $H_2O$ (3 mL), 1N $H_3PO_4$ (2 mL), $H_2O$ (3 mL), $NaHCO_3$ aqueous (3 mL) and finally brine (5 mL). The organic solution was dried over $K_2CO_3$ then concentrated. The residue was loaded onto a silica gel column, eluted with 10-20% EtOAc in Heptane, to obtain the title compound as an oil, 207 mg (82% yield).

LCMS: $t_R$=1.63 min., m/z ($ES^+$)=506 ($M+H^+$).

Step 2. Preparation of (S)-2-(7-fluoro-1-((4-(trifluoromethyl)benzyl)oxy)-2-naphthamido)-3,3-dimethyl-pentanoic Acid

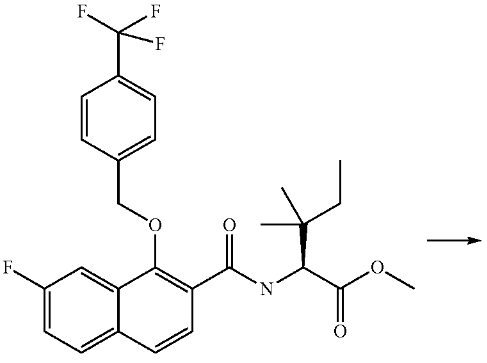

-continued

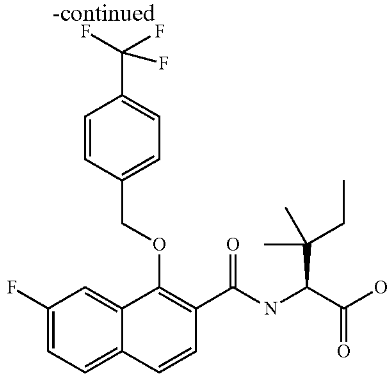

A round bottomed flask equipped with a stir bar, temperature controller, heating mantle and static nitrogen line was charged with (2S)-2-[[7-fluoro-1-[[4-(trifluoromethyl) phenyl]methoxy]naphthalene-2-carbonyl]amino]-3,3-dimethyl-pentanoic acid (207 mg, 0.409 mmol), THF (3 mL), and MeOH (1.5 mL). A clear light yellow solution formed. 1N NaOH (2.2 mL, 2.2 mmol, 5 equiv.) was added. The resulting cloudy solution was heated to 50° C. (bath 55° C.) and held until in-process TLC indicated complete reaction (6 h, timer). The solution was cooled to rt. EtOAc (5 mL) was added and the biphasic solution stirred vigorously in an ice bath. 1N HCl (2.5 mL) was added over 5 min and stirred to obtain two clear liquid phases. The aq. phase was extracted with EtOAc. The combined organics were washed with brine (5 mL) and was then dried with $Na_2SO_4$. The solution was filtered and concentrated to a gummy residue. The gummy sample was dissolved in 0.5 mL of ether. 5 mL of heptane was added. The solution was evaporated slowly till cloudiness and the solution was stirred at rt until lots of white precipitate formed. The precipitate was collected via suction filtration and further dried to obtain 200 mg (99%) of a white crystalline solid.

$^1$H NMR ($CDCl_3$, 400 MHz) δ 8.30 (m, 1H), 8.06 (m, 1H), 7.90-7.88 (m, 1H), 8.06 (m, 2H), 7.65 (m, 3H), 7.38-7.33 (m, 1H), 5.22 (dd, 1.2 Hz, 11.2 Hz, 2H), 1.33-1.27 (m, 3H), 0.92 (s, 3H), 0.88 (s, 3H), 0.81 (m, 2H).

LCMS: $t_R$=1.51 min., m/z ($ES^+$)=492 ($M+H^+$).

Examples 275 through 285 exemplified below were synthesized in a manner analogous to Example 274 described above using the appropriate intermediates and starting materials/reagents Example 275: 3,3-Dimethyl-2-{[7-methyl-1-(4-trifluoromethyl-benzyloxy)-naphthalene-2-carbonyl]-amino}-pentanoic Acid

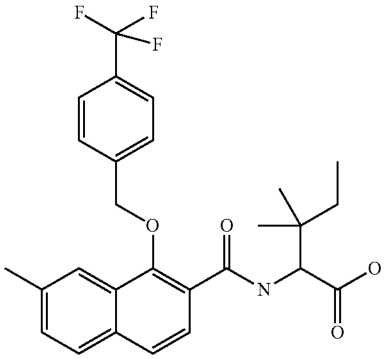 [SMILES: CCC(C)(C)C(NC(=O)c1ccc2ccc(C)cc2c1OCc1ccc(C(F)(F)F)cc1)C(=O)O]

$^1$H NMR ($CDCl_3$, 400 MHz) δ 8.43-8.41 (m, 1H), 8.06 (m, 1H), 8.05-8.03 (m, 1H), 7.89 (m, 2H), 7.71 (m, 3H), 7.42 (m, 1H), 5.24 (dd, 1.2 Hz, 11.2 Hz, 2H), 4.72 (d, 12 Hz, 1H), 2.48 (s, 3H), 1.33-1.27 (m, 2H), 0.92 (s, 3H), 0.88 (s, 3H), 0.81 (m, 3H).

LCMS: $t_R$=1.56 min., m/z ($ES^+$)=488 ($M+H^+$).

Example 276: 3,3-dimethyl-2-(7-methyl-1-((4-(trifluoromethoxy)benzyl)oxy)-2-naphthamido)pentanoic Acid

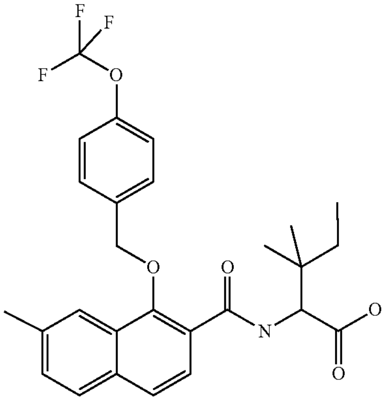

$^1$H NMR ($CDCl_3$, 400 MHz) δ 8.46-8.44 (m, 1H), 8.05-8.03 (m, 1H), 7.84-7.59 (m, 4H), 7.69-7.60 (m, 1H), 7.26-7.25 (m, 2H), 5.24 (dd, 1.2 Hz, 11.2 Hz, 2H), 4.72 (d, 12 Hz, 1H), 2.50 (s, 3H), 1.33-1.27 (m, 2H), 0.92 (s, 3H), 0.88 (s, 3H), 0.81 (m, 3H).

LCMS: $t_R$=1.58 min., m/z ($ES^+$)=504 ($M+H^+$).

Example 277: (S)-2-(7-chloro-1-((4-(trifluoromethoxy)benzyl)oxy)-2-naphthamido)-3,3-dimethylpentanoic Acid

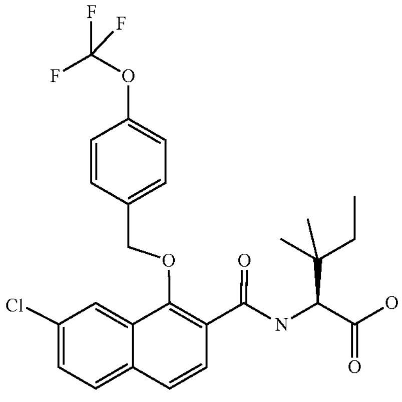

$^1$H NMR ($CDCl_3$, 400 MHz) δ 8.46-8.44 (m, 1H), 8.05-8.03 (m, 1H), 7.84-7.59 (m, 4H), 7.69-7.60 (m, 1H), 7.26-7.25 (m, 2H), 5.24 (dd, 1.2 Hz, 11.2 Hz, 2H), 4.71 (d, 8 Hz, 1H), 1.33-1.27 (m, 2H), 0.92 (s, 3H), 0.88 (s, 3H), 0.81 (m, 3H).

LCMS: $t_R$=1.60 min., m/z ($ES^+$)=524 ($M+H^+$).

Example 278: (S)-2-(6-fluoro-7-methyl-1-((4-(trifluoromethyl)benzyl)oxy)-2-naphthamido)-3,3-dimethylbutanoic Acid

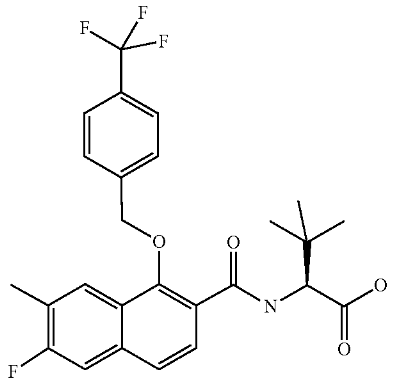

$^1$H NMR ($CDCl_3$, 400 MHz) δ 8.36 (m, 1H), 8.05 (m, 1H), 7.83 (m, 1H), 7.68 (m, 3H), 7.66 (m, 1H), 7.62 (m, 1H), 5.37 (m, 2H), 4.71 (d, 12 Hz, 1H), 2.39 (t, 4 Hz, 3H), 0.98 (s, 9H).

LCMS: $t_R$=1.53 min., m/z ($ES^+$)=492 ($M+H^+$).

Example 279: (2S)-3,3-dimethyl-2-[[7-methyl-1-[[4-(trifluoromethyl)phenyl]methoxy]naphthalene-2-carbonyl]amino]butanoic Acid

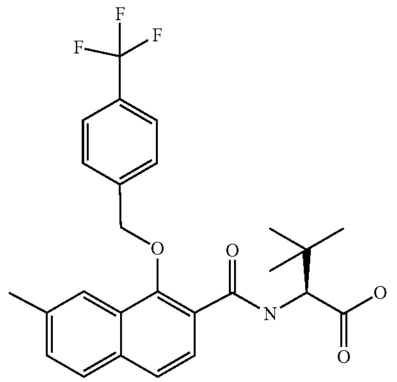

$^1$H NMR (400 MHz, DMSO-$d_6$) δ ppm 13.11-12.49 (m, 1H) 8.57 (d, J=8.56 Hz, 1H) 7.91 (d, J=8.38 Hz, 1H) 7.85 (s, 1H) 7.84-7.73 (m, 5H) 7.62 (d, J=8.44 Hz, 1H) 7.47 (dd, J=8.38, 1.41 Hz, 1H) 5.34-5.17 (m, 2H) 4.35 (d, J=8.56 Hz, 1H) 2.47 (s, 3H) 0.95 (s, 9H)

LCMS: $t_R$=0.98 min., m/z ($ES^+$)=474 ($M+H^+$)

Example 280: (S)-3,3-dimethyl-2-(7-methyl-1-((4-(trifluoromethoxy)benzyl)oxy)-2-naphthamido)pentanoic Acid

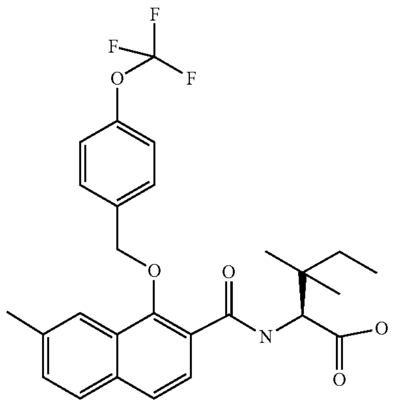

$^1$H NMR ($CDCl_3$, 400 MHz) δ 8.48 (m, 1H), 8.20 (m, 1H), 7.75-7.60 (m, 2H), 7.68 (m, 1H), 7.6 (m, 2H), 7.40 (m, 1H), 7.25 (m, 1H), 5.75-5.17 (m, 2H), 4.75 (m, 1H), 2.48 (bs, 3H), 1.49 (m, 2H), 1.09 (m, 6H), 0.94 (m, 3H)

LCMS: $t_R$=1.58 min., m/z ($ES^+$)=504 ($M+H^+$).

Example 281: (S)-2-(1-(cyclohexylmethoxy)-7-methyl-2-naphthamido)-3,3-dimethylpentanoic Acid

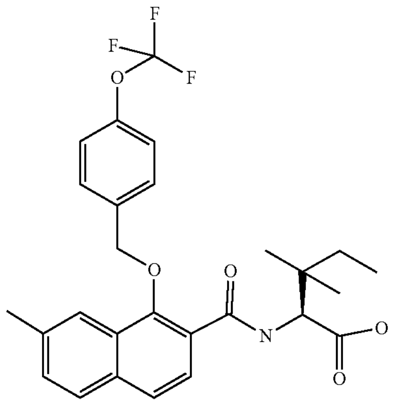

$^1$H NMR ($CDCl_3$, 400 MHz) δ 8.62 (m, 1H), 8.04-7.96 (m, 2H), 7.75 (d, 8 Hz, 1H), 7.62 (d, 8 Hz, 1H), 7.40 (m, 1H), 4.86 (m, 1H), 3.95-3.77 (m, 2H), 2.56 (s, 3H), 2.19 (m, 2H), 1.95-1.67 (m, 4H), 1.49 (m, 2H), 1.40-1.16 (m, 5H), 1.09 (m, 6H), 0.94 (m, 3H).

LCMS: $t_R$=1.67 min., m/z ($ES^+$)=426 ($M+H^+$).

Example 282: (S)-2-(1-(cyclohexylmethoxy)-7-methyl-2-naphthamido)-4-fluoro-3,3-dimethylbutanoic Acid

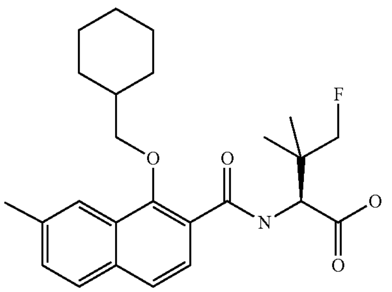

$^1$H NMR ($CDCl_3$, 400 MHz) δ8.80 (m, 1H), 8.02-7.97 (m, 2H), 7.74 (d, 8 Hz, 1H), 7.61 (d, 8 Hz, 1H), 7.41-7.38 (m, 2H), 2.55 (s, 3H), 2.17 (m, 2H), 2.01 (m, 1H) 1.90-1.66 (m, 4H), 1.17-1.11 (m, 12H), 0.87 (m, 3H).

LCMS: $t_R$=1.55 min., m/z ($ES^+$)=430 ($M+H^+$).

Example 283: (S)-2-(7-chloro-1-((4-(trifluoromethyl)benzyl)oxy)-2-naphthamido)-3,3-dimethylpentanoic Acid

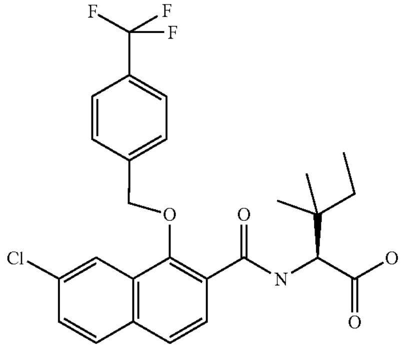

$^1$H NMR ($CDCl_3$, 400 MHz) δ8.28 (m, 1H), 8.03 (m, 2H), 7.74 (m, 1H), 7.61 (m, 4H), 7.50 (m, 1H), 5.35 (m, 1H), 5.04 (m, 1H), 1.42-1.19 (m, 4H), 0.88 (m, 6H), 0.77 (m, 3H).

LCMS: $t_R$=1.57 min., m/z ($ES^+$)=508 ($M+H^+$).

Example 284: (R)-3,3-dimethyl-2-(7-methyl-1-((4-(trifluoromethyl)benzyl)oxy)-2-naphthamido)butanoic Acid

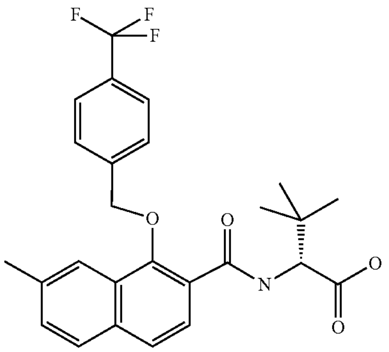

$^1$H NMR ($CDCl_3$, 400 MHz) δ 13.09 (b, 1H), 8.50 (m, 1H), 7.92-7.45 (m, 8H), 5.34-5.17 (m, 2H), 4.31 (m, 1H), 2.46 (bs, 3H), 0.95 (s, 9H).

LCMS: $t_R$=1.51 min., m/z ($ES^+$)=474 ($M+H^+$).

Example 285: (R)-2-(7-chloro-1-((4-(trifluoromethoxy)benzyl)oxy)-2-naphthamido)-3,3-dimethylbutanoic Acid

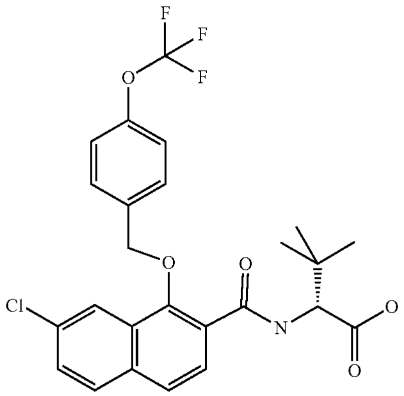

$^1$H NMR (400 MHz, DMSO-d6) δ ppm 12.88-12.72 (m, 1H), 8.62 (d, J=8.51 Hz, 1H), 8.06 (d, J=8.81 Hz, 1H), 7.99 (d, J=2.12 Hz, 1H), 7.84 (d, J=8.56 Hz, 1H), 7.68-7.61 (m, 4H), 7.42 (d, J=8.03 Hz, 2H), 5.20 (dd, J=38.60, 11.68 Hz, 2H), 4.35 (d, J=8.51 Hz, 1H), 0.98 (s, 9H)

LCMS: tR=1.01 min., m/z ($ES^+$)=510 ($M+H^+$)

Example 286: (S)-2-(7-chloro-1-((4-(trifluoromethyl)benzyl)oxy)-2-naphthamido)-3,3-dimethylbutanoic Acid

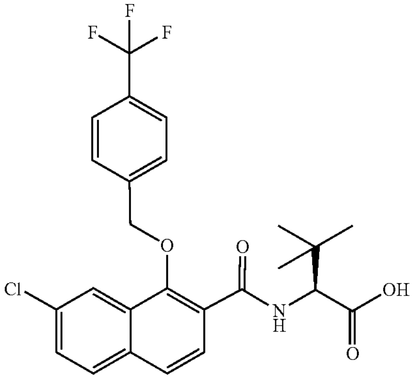 [SMILES: CC(C)(C)[C@H](NC(=O)c1ccc2ccc(Cl)cc2c1OCc1ccc(C(F)(F)F)cc1)C(=O)O]

Step 1. Preparation of methyl (S)-2-(7-chloro-1-((4-(trifluoromethyl)benzyl)oxy)-2-naphthamido)-3,3 dimethylbutanoate

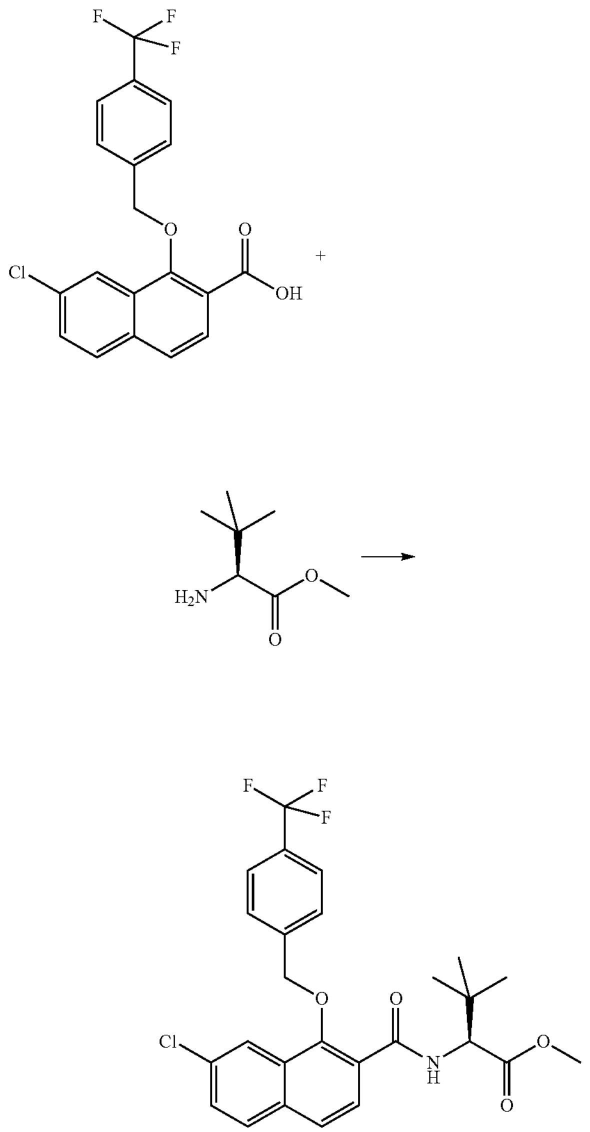

7-chloro-1-((4-(trifluoromethyl)benzyl)oxy)-2-naphthoic acid (255 mg, 669.74 μmol) was suspended in ethyl acetate (6 ml). To this was then added methyl (S)-2-amino-3,3-dimethylbutanoate (116.70 mg, 803.68 μmol) and Hunig's Base (467.90 μl, 2.68 mmol). Cooled to 5° C. and added a solution of 1-propanephosphonic anhydride (639.29 μl, 1.00 mmol). Stirred at RT overnight. LC/MS analysis indicated that the reaction was complete. Reaction was quenched with a saturated solution of $NaHCO_3$, and extracted with $CH_2Cl_2$. The combined organic extracts were washed with brine, dried over $MgSO_4$, filtered and concentrated. Purified on combiflash ($SiO_2$, 12 g) using a 0-25% Ethyl Acetate/heptanes gradient to provide methyl (S)-2-(7-chloro-1-((4-(trifluoromethyl)benzyl)oxy)-2-naphthamido)-3,3-dimethylbutanoate (296 mg, 87.0% yield) as an oil.

LCMS: tR=1.65 min., m/z ($ES^+$)=508 ($M+H^+$).

Step 2: Preparation of (S)-2-(7-chloro-1-((4-(trifluoromethyl)benzyl)oxy)-2-naphthamido)-3,3-dimethylbutanoic Acid

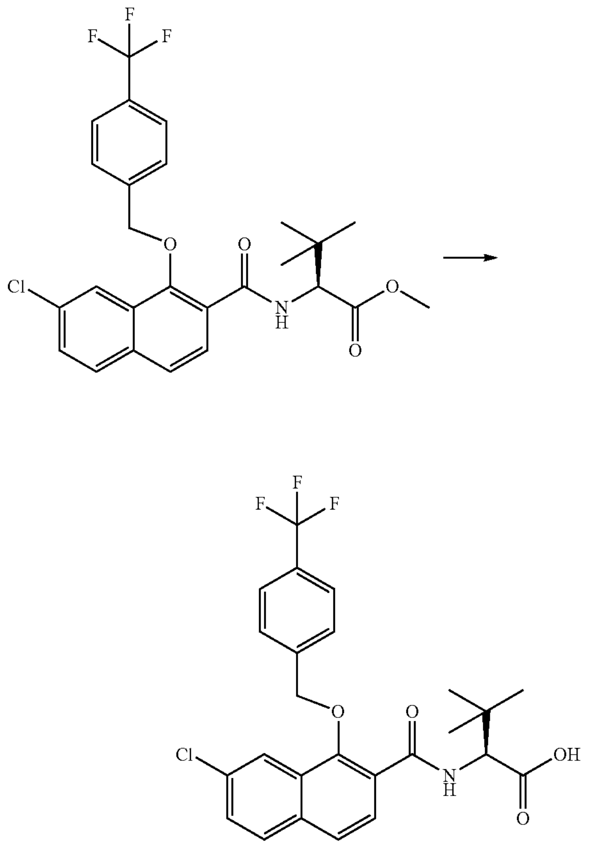 [SMILES: COC(=O)[C@@H](NC(=O)c1ccc2ccc(Cl)cc2c1OCc1ccc(C(F)(F)F)cc1)C(C)(C)C ; CC(C)(C)[C@H](NC(=O)c1ccc2ccc(Cl)cc2c1OCc1ccc(C(F)(F)F)cc1)C(=O)O]

A 2 M solution of lithium hydroxide (2.91 ml, 5.83 mmol) in water was added to a stirring solution of methyl (S)-2-(7-chloro-1-((4-(trifluoromethyl)benzyl)oxy)-2-naphthamido)-3,3-dimethylbutanoate (296 mg, 582.75 μmol) in a mixture of 1,4-dioxane (6 ml, 70.14 mmol). The reaction mixture was stirred at RT overnight. LC/MS analysis indicated that the reaction was not complete. Stirred at 50° C. for 6 hours. Cooled to RT, then neutralized with 1N HCl until pH was about 4-5, then extracted with ethyl acetate. The combined organic extracts were washed with brine, dried over $MgSO_4$, filtered and concentrate. Purified on combiflash ($SiO_2$, 12 g) using a 0-10% MeOH (1% formic acid)/$CH_2Cl_2$ gradient to provide (S)-2-(7-chloro-1-((4-(trifluoromethyl)benzyl)oxy)-2-naphthamido)-3,3-dimethylbutanoic acid (181 mg, 366.47 μmol, 62.9% yield) as a solid.

$^1H$ NMR (400 MHz, Chloroform-d) δ 8.30 (d, J=8.5 Hz, 1H), 8.06 (m, 2H), 7.83 (d, J=8.7 Hz, 1H), 7.67 (m, 4H), 7.51 (m, 1H), 5.36 (d, J=12.1 Hz, 1H), 5.08 (d, J=12.1 Hz, 1H), 4.65 (d, J=8.5 Hz, 1H), 0.98 (s, 9H).

$^{19}F$ NMR (377 MHz, $CDCl_3$) δ-62.64.

LCMS: tR=1.53 min., m/z ($ES^+$)=494 ($M+H^+$).

Examples 287 through 314 exemplified below were synthesized in a manner analogous to Example 286 described above using the appropriate intermediates and starting materials/reagents.

Example 287: (R)-3,3-dimethyl-2-(1-((4-(trifluoromethoxy)benzyl)oxy)-7-(trifluoromethyl)-2-naphthamido)butanoic Acid

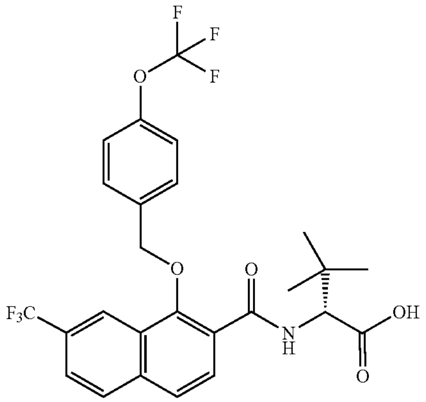 [SMILES: CC(C)(C)[C@@H](NC(=O)c1ccc2ccc(C(F)(F)F)cc2c1OCc1ccc(OC(F)(F)F)cc1)C(=O)O]

$^{1}H$ NMR (400 MHz, Chloroform-d) δ 8.47-8.29 (m, 2H), 8.23 (d, J=8.7 Hz, 1H), 7.98 (d, J=8.6 Hz, 1H), 7.84-7.77 (m, 1H), 7.72 (dd, J=8.7, 1.8 Hz, 1H), 7.52 (m, 2H), 7.21 (m, 2H), 5.34 (d, J=11.5 Hz, 1H), 4.99 (d, J=11.4 Hz, 1H), 4.69 (d, J=8.5 Hz, 2H), 1.04 (s, 9H).

$^{19}F$ NMR (377 MHz, $CDCl_3$) δ−57.9, −62.6.

LCMS: $t_R$=1.54 min., m/z ($ES^+$)=544 ($M+H^+$).

Example 288: (S)-3,3-dimethyl-2-(7-methyl-1-((4-(trifluoromethyl) benzyl)oxy)-2-naphthamido)pentanoic Acid

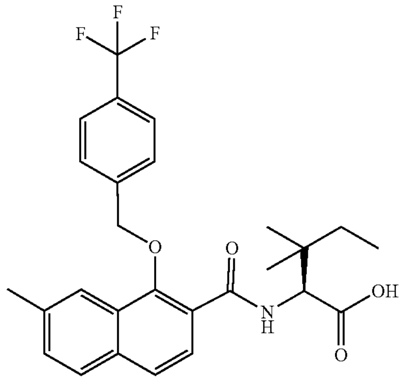 [SMILES: CCC(C)(C)[C@H](NC(=O)c1ccc2ccc(C)cc2c1OCc1ccc(C(F)(F)F)cc1)C(=O)O]

$^{1}H$ NMR (400 MHz, Chloroform-d) δ 8.42 (d, J=8.5 Hz, 1H), 8.04 (d, J=8.6 Hz, 1H), 7.74 (m, 7H), 7.41 (dd, J=8.3, 1.7 Hz, 1H), 5.35 (d, J=12.4 Hz, 1H), 5.09 (d, J=12.4 Hz, 1H), 4.71 (d, J=8.6 Hz, 1H), 2.48 (d, J=1.40-1.19 (m, 2H), 0.97-0.74 (m, 9H).

$^{19}F$ NMR (377 MHz, $CDCl_3$) δ−62.60.

LCMS: tR=1.57 min., m/z ($ES^+$)=488 ($M+H^+$)

Example 289: (R)-3,3-dimethyl-2-(7-methyl-1-((4-(trifluoromethoxy)benzyl)oxy)-2-naphthamido)butanoic Acid

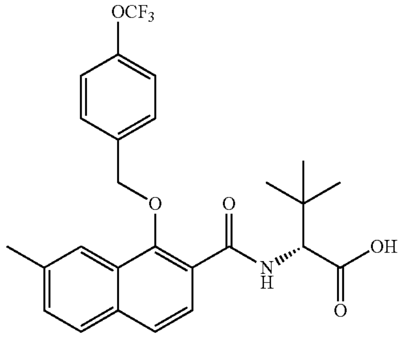 [SMILES: Cc1ccc2ccc(C(=O)N[C@@H](C(=O)O)C(C)(C)C)c(OCc3ccc(OC(F)(F)F)cc3)c2c1]

$^{1}H$ NMR (400 MHz, Chloroform-d) δ 8.48 (d, J=8.5 Hz, 1H), 8.03 (d, J=8.6 Hz, 1H), 7.82 (s, 1H), 7.78 (d, J=8.4 Hz, 1H), 7.68 (d, J=8.7 Hz, 1H), 7.57 (d, J=8.6 Hz, 2H), 7.40 (dd, J=8.4, 1.7 Hz, 1H), 7.23 (m, 3H), 5.28 (d, J=11.9 Hz, 1H), 5.02 (d, J=11.7 Hz, 1H), 4.65 (d, J=8.5 Hz, 1H), 2.48 (s, 3H), 0.98 (s, 9H).

LCMS: tR=1.59 min., m/z ($ES^+$)=524 ($M+H^+$).

Example 290: (2S)-3-ethyl-2-(7-fluoro-1-((4-(trifluoromethoxy)benzyl)oxy)-2-naphthamido)-3-methylhexanoic Acid

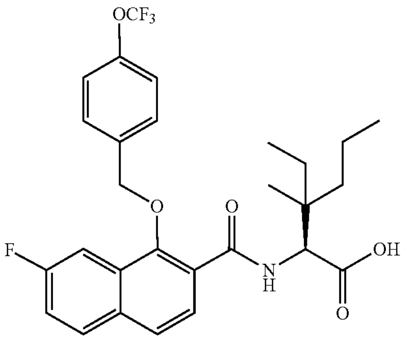

$^{1}H$ NMR (400 MHz, Chloroform-d) δ 8.35 (dd, J=8.6, 4.6 Hz, 1H), 8.07 (dd, J=8.6, 1.3 Hz, 1H), 7.89 (dd, J=9.0, 5.5 Hz, 1H), 7.69 (m, 4H), 7.31 (m, 2H), 5.29 (m, 1H), 5.01 (dd, J=11.7, 2.2 Hz, 1H), 4.81 (d, J=8.6 Hz, 1H), 1.31 (m, 7H), 0.80 (m, 8H).

$^{19}F$ NMR (377 MHz, $CDCl_3$) δ−57.9, −112.0.

LCMS: tR=1.62 min., m/z ($ES^+$)=536 ($M+H^+$).

Example 291: (2S)-3-ethyl-2-(7-fluoro-1-((4-(trifluoromethyl)benzyl)oxy)-2-naphthamido)-3-methylhexanoic Acid

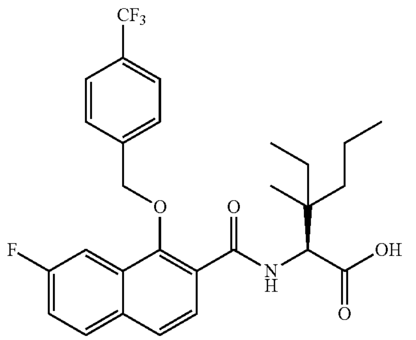 [SMILES: CCCC(C)(CC)[C@H](NC(=O)c1ccc2ccc(F)cc2c1OCc1ccc(C(F)(F)F)cc1)C(=O)O]

1H NMR (400 MHz, Chloroform-d) δ 8.31 (dd, J=8.6, 5.2 Hz, 1H), 8.07 (dd, J=8.6, 1.6 Hz, 1H), 7.90 (dd, J=9.0, 5.4 Hz, 1H), 7.71 (m, 6H), 7.36 (ddd, J=8.8, 8.2, 2.6 Hz, 1H), 5.30 (m, 1H), 5.08 (d, J=12.4 Hz, 1H), 4.81 (d, J=8.7 Hz, 1H), 1.29 (m, 7H), 0.80 (m, 8H).

$^{19}$F NMR (377 MHz, $CDCl_3$) δ−62.7, −111.8.

LCMS: tR=1.61 min., m/z ($ES^+$)=520 ($M+H^+$).

Example 292: (S)-3,3-dimethyl-2-(1-((4-(trifluoromethoxy)benzyl)oxy)-7-(trifluoromethyl)-2-naphthamido)butanoic Acid

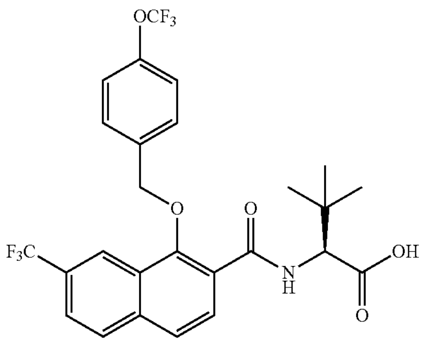

$^1$H NMR (400 MHz, Chloroform-d) δ 8.35 (m, 2H), 8.23 (d, J=8.7 Hz, 1H), 7.99 (d, J=8.6 Hz, 1H), 7.75 (m, 2H), 7.51 (m, 2H), 7.23 (m, 2H), 5.33 (t, J=11.2 Hz, 1H), 4.99 (d, J=11.5 Hz, 1H), 4.69 (d, J=8.6 Hz, 1H), 1.04 (s, 9H).

$^{19}$F NMR (377 MHz, $CDCl_3$) δ−57.9, −62.6.

LCMS: tR=1.55 min., m/z ($ES^+$)=544 ($M+H^+$).

Example 293: (S)-3,3-dimethyl-2-(7-(trifluoromethyl)-1-((4-(trifluoromethyl)benzyl)oxy)-2-naphthamido)butanoic Acid

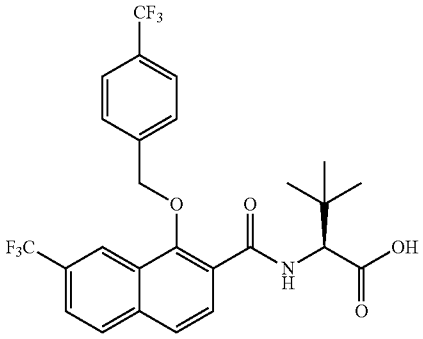

$^1$H NMR (400 MHz, Chloroform-d) δ 8.32 (t, J=4.2 Hz, 2H), 8.23 (d, J=8.7 Hz, 1H), 8.00 (d, J=8.6 Hz, 1H), 7.80 (d, J=8.6 Hz, 1H), 7.73 (dd, J=8.6, 1.8 Hz, 1H), 7.62 (m, 3H), 5.40 (d, J=11.9 Hz, 1H), 5.05 (d, J=11.9 Hz, 1H), 4.69 (d, J=8.6 Hz, 1H), 1.03 (s, 9H).

$^{19}$F NMR (377 MHz, $CDCl_3$) δ−62.6, −62.7.

LCMS: tR=1.53 min., m/z ($ES^+$)=528 ($M+H^+$).

Example 294 3,3-Dimethyl-2-{[7-methyl-1-(4-methyl-pentyloxy)-naphthalene-2-carbonyl]-amino}-pentanoic Acid

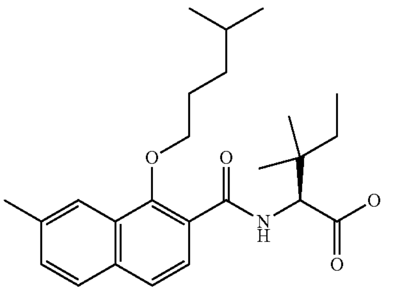 [SMILES: CCC(C)(C)[C@H](NC(=O)c1ccc2ccc(C)cc2c1OCCCC(C)C)C(=O)O]

1H NMR: (DMSO-d6, 400 Hz): 612.82 (b, 1H), 8.56 (d, J=8.8 Hz, 1H), 7.92 (s, 1H), 7.89 (d, J=4.8 Hz, 1H), 7.71 (s, 2H), 7.48 (d, J=8.4 Hz, 1H), 4.51 (d, J=8.8 Hz, 1H), 4.09-3.97 (m, 3H), 2.53 (s, 3H), 1.99-1.91 (m, 2H), 1.65-1.58 (m, 1H), 1.44-1.33 (m, 2H), 0.99 (s, 3H), 0.98 (s, 3H), 0.92 (d, J=6.4 Hz, 6H), 0.88 (t, J=7.6 Hz, 3H) ppm.

tR=1.80, m/z ($ES^+$)=414 ($M+H^+$).

Example 295: (S)-3,3-dimethyl-2-(7-(trifluoromethyl)-1-((4-(trifluoromethyl)benzyl)oxy)-2-naphthamido)pentanoic Acid

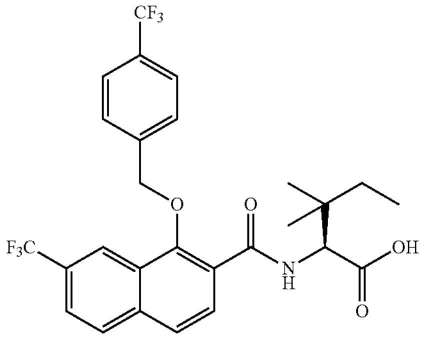 [SMILES: CCC(C)(C)[C@H](NC(=O)c1ccc2ccc(C(F)(F)F)cc2c1OCc1ccc(C(F)(F)F)cc1)C(=O)O]

$^1$H NMR (400 MHz, Chloroform-d) δ 8.38-8.17 (m, 3H), 8.00 (d, J=8.6 Hz, 1H), 7.70 (m, 5H), 5.40 (d, J=11.9 Hz, 1H), 5.04 (d, J=11.9 Hz, 1H), 4.75 (d, J=8.7 Hz, 1H), 1.33 (m, 2H), 0.91 (m, 9H).

$^{19}$F NMR (377 MHz, $CDCl_3$) δ−62.8, −62.6.

LCMS: tR=1.57 min., m/z ($ES^+$)=542 ($M+H^+$).

Example 296: (S)-3,3-dimethyl-2-(1-((4-(trifluoromethoxy)benzyl)oxy)-7-(trifluoromethyl)-2-naphthamido)pentanoic Acid

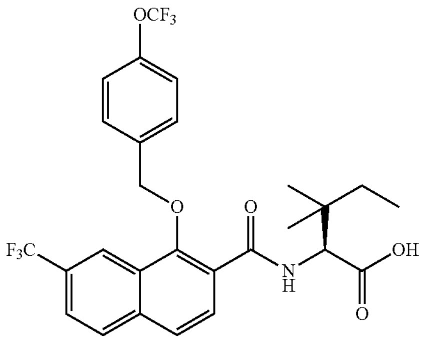 [SMILES: CCC(C)(C)[C@H](NC(=O)c1ccc2ccc(C(F)(F)F)cc2c1OCc1ccc(OC(F)(F)F)cc1)C(=O)O]

$^1$H NMR (400 MHz, Chloroform-d) δ 8.29 (m, 3H), 7.98 (d, J=8.6 Hz, 1H), 7.75 (m, 2H), 7.53 (m, 2H), 7.20 (m, 2H), 5.32 (m, 1H), 4.97 (d, J=11.4 Hz, 1H), 4.75 (d, J=8.6 Hz, 1H), 1.34 (m, 2H), 0.92 (m, 9H).

$^{19}$F NMR (377 MHz, $CDCl_3$) δ−58.0, −62.7.

LCMS: tR=1.69 min., m/z ($ES^+$)=558 ($M+H^+$).

Example 297. (S)-2-(1-methylcyclopropyl)-2-(1-((4-(trifluoromethoxy)benzyl)oxy)-7-(trifluoromethyl)-2-naphthamido)acetic Acid

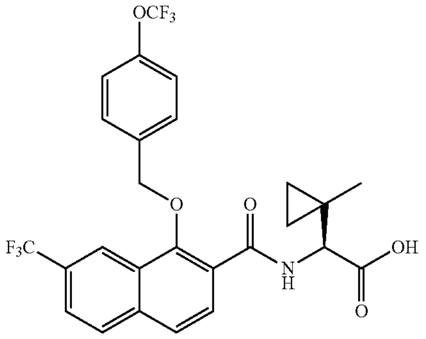 [SMILES: CC1([C@H](NC(=O)c2ccc3ccc(C(F)(F)F)cc3c2OCc2ccc(OC(F)(F)F)cc2)C(=O)O)CC1]

$^1$H NMR (400 MHz, Chloroform-d) δ 8.40 (m, 2H), 8.22 (d, J=8.7 Hz, 1H), 7.99 (d, J=8.6 Hz, 1H), 7.85-7.67 (m, 2H), 7.53 (m, 2H), 7.23 (m, 1H), 5.32 (m, 1H), 5.07 (d, J=11.5 Hz, 1H), 4.21 (d, J=7.4 Hz, 1H), 0.98 (s, 3H), 0.89 (dt, J=10.5, 5.3 Hz, 1H), 0.70 (dt, J=9.9, 5.3 Hz, 1H), 0.50 (dt, J=9.1, 5.4 Hz, 1H), 0.35 (ddd, J=9.1, 5.9, 4.7 Hz, 1H).

$^{19}$F NMR (377 MHz, $CDCl_3$) δ−57.9, −62.6.

LCMS: tR=1.51 min., m/z ($ES^+$)=542 ($M+H^+$).

Example 298: (S)-2-(1-methylcyclopropyl)-2-(7-(trifluoromethyl)-1-((4-(trifluoromethyl)benzyl)oxy)-2-naphthamido)acetic Acid

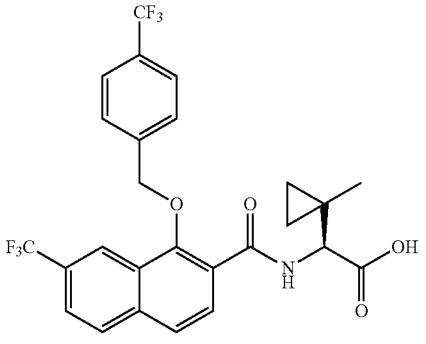 [SMILES: CC1([C@H](NC(=O)c2ccc3ccc(C(F)(F)F)cc3c2OCc2ccc(C(F)(F)F)cc2)C(=O)O)CC1]

$^1$H NMR (400 MHz, Chloroform-d) δ 8.37 (m, 2H), 8.22 (d, J=8.7 Hz, 1H), 8.00 (d, J=8.6 Hz, 1H), 7.72 (m, 5H), 5.40 (d, J=11.9 Hz, 1H), 5.13 (d, J=11.9 Hz, 1H), 4.21 (d, J=7.4 Hz, 1H), 0.90 (m, 4H), 0.70 (dt, J=10.1, 5.3 Hz, 1H), 0.50 (dt, J=9.2, 5.5 Hz, 1H), 0.33 (ddd, J=9.2, 5.9, 4.7 Hz, 1H).

$^{19}$F NMR (377 MHz, $CDCl_3$) δ−62.6, −62.7.

LCMS: tR=1.49 min., m/z ($ES^+$)=526 ($M+H^+$).

Example 299: (S)-2-(1-methylcyclobutyl)-2-(7-(trifluoromethyl)-1-((4-(trifluoromethyl)benzyl)oxy)-2-naphthamido)acetic Acid

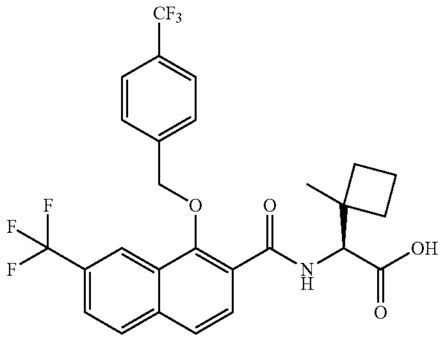 [SMILES: CC1([C@H](NC(=O)c2ccc3ccc(C(F)(F)F)cc3c2OCc2ccc(C(F)(F)F)cc2)C(=O)O)CCC1]

$^1$H NMR (400 MHz, Chloroform-d) δ 8.23 (m, 3H), 7.99 (d, J=8.6 Hz, 1H), 7.70 (m, 5H), 5.40 (d, J=11.9 Hz, 1H), 5.07 (d, J=12.0 Hz, 1H), 4.97 (d, J=8.4 Hz, 1H), 2.36 (q, J=9.1 Hz, 1H), 2.09 (m, 1H), 1.86 (m, 3H), 1.59 (ddt, J=11.7, 8.1, 3.7 Hz, 1H), 1.07 (d, J=2.5 Hz, 3H).

$^{19}$F NMR (377 MHz, $CDCl_3$) δ−62.6, −62.8.

LCMS: tR=1.54 min., m/z ($ES^+$)=540 ($M+H^+$).

Example 300: (S)-2-(7-chloro-1-((4-(trifluoromethyl)benzyl)oxy)-2-naphthamido)-2-(1-methylcyclobutyl)acetic Acid

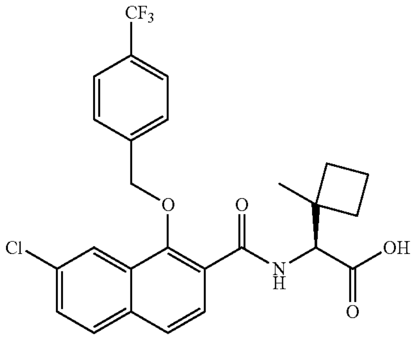 [SMILES: CC1([C@H](NC(=O)c2ccc3ccc(Cl)cc3c2OCc2ccc(C(F)(F)F)cc2)C(=O)O)CCC1]

$^1$H NMR (400 MHz, Chloroform-d) δ 8.12 (dd, J=15.4, 8.5 Hz, 2H), 8.02 (d, J=2.1 Hz, 1H), 7.83 (d, J=8.8 Hz, 1H), 7.69 (m, 4H), 7.52 (dd, J=8.7, 2.1 Hz, 1H), 5.33 (m, 1H), 5.08 (d, J=12.2 Hz, 1H), 4.93 (d, J=8.3 Hz, 1H), 2.32 (m, 1H), 2.06 (m, 1H), 1.81 (m, 3H), 1.56 (ddd, J=12.1, 8.2, 4.1 Hz, 1H), 1.01 (s, 3H).

$^{19}$F NMR (377 MHz, $CDCl_3$) δ−62.6.

LCMS: tR=1.55 min., m/z ($ES^+$)=506 ($M+H^+$).

Example 301: (S)-2-(1-methylcyclopentyl)-2-(7-(trifluoromethyl)-1-((4-(trifluoromethyl)benzyl)oxy)-2-naphthamido)acetic Acid

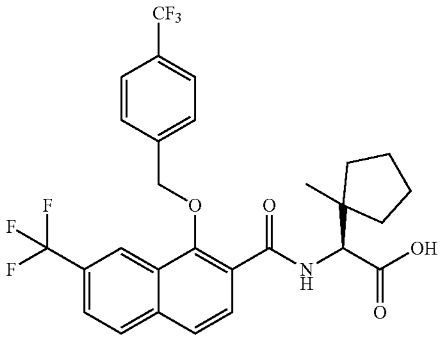 [SMILES: CC1([C@H](NC(=O)c2ccc3ccc(C(F)(F)F)cc3c2OCc2ccc(C(F)(F)F)cc2)C(=O)O)CCCC1]

$^1$H NMR (400 MHz, Chloroform-d) δ 8.28 (m, 3H), 7.99 (d, J=8.6 Hz, 1H), 7.70 (m, 6H), 5.40 (d, J=11.9 Hz, 1H), 5.06 (d, J=11.9 Hz, 1H), 4.73 (d, J=8.3 Hz, 1H), 1.83 (dt, J=12.8, 8.1 Hz, 1H), 1.64 (m, 5H), 1.35 (m, 2H), 0.93 (s, 3H).

$^{19}$F NMR (377 MHz, $CDCl_3$) δ−62.6, −62.8.

LCMS: tR=1.58 min., m/z ($ES^+$)=554 ($M+H^+$).

Example 302: (S)-2-(7-chloro-1-((4-(trifluoromethyl)benzyl)oxy)-2-naphthamido)-2-(1-methylcyclopentyl)acetic Acid

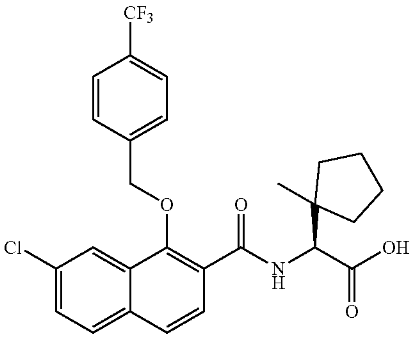 [SMILES: CC1([C@H](NC(=O)c2ccc3ccc(Cl)cc3c2OCc2ccc(C(F)(F)F)cc2)C(=O)O)CCCC1]

$^1$H NMR (400 MHz, Chloroform-d) δ 8.30 (d, J=8.3 Hz, 1H), 8.09 (d, J=8.7 Hz, 1H), 8.01 (m, 1H), 7.83 (d, J=8.7 Hz, 1H), 7.68 (m, 5H), 7.51 (dd, J=8.8, 2.1 Hz, 1H), 5.35 (d, J=12.2 Hz, 1H), 5.08 (d, J=12.1 Hz, 1H), 4.69 (d, J=8.3 Hz, 1H), 1.79 (dt, J=12.7, 8.1 Hz, 1H), 1.60 (m, 5H), 1.31 (m, 2H), 0.87 (s, 3H).

$^{19}$F NMR (377 MHz, $CDCl_3$) δ−62.6.

LCMS: tR=1.59 min., m/z ($ES^+$)=520 ($M+H^+$).

Example 303: (S)-2-(5-fluoro-1-((4-(trifluoromethyl)benzyl)oxy)-2-naphthamido)-2-(1-methylcyclopentyl)acetic Acid

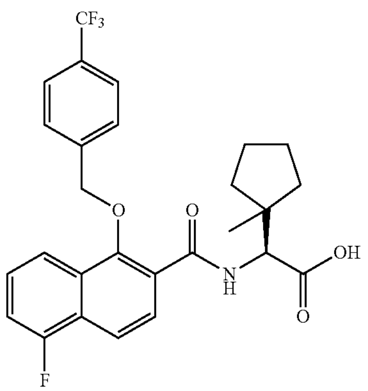 [SMILES: CC1([C@H](NC(=O)c2ccc3c(F)cccc3c2OCc2ccc(C(F)(F)F)cc2)C(=O)O)CCCC1]

$^1$H NMR (400 MHz, Chloroform-d) δ 8.29 (d, J=7.9 Hz, 1H), 8.17 (d, J=8.9 Hz, 1H), 8.00 (dd, J=8.8, 0.8 Hz, 1H), 7.90 (m, 1H), 7.69 (s, 4H), 7.47 (td, J=8.1, 5.3 Hz, 1H), 7.27 (m, 1H), 5.33 (m, 1H), 5.14 (d, J=12.2 Hz, 1H), 4.70 (m, 1H), 1.81 (tt, J=7.8, 4.0 Hz, 1H), 1.55 (m, 5H), 1.03 (m, 5H).

$^{19}$F NMR (377 MHz, $CDCl_3$) δ−62.7, −120.8.

LCMS: tR=1.54 min., m/z ($ES^+$)=504 ($M+H^+$).

Example 304: (S)-3,3-dimethyl-2-(7-(trifluoromethyl)-1-((4-(trifluoromethyl)benzyl)oxy)-2-naphthamido)hexanoic Acid

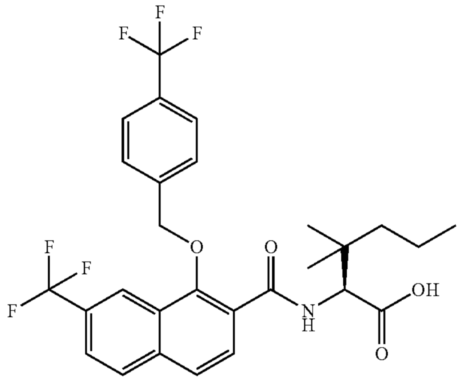 [SMILES: CCCC(C)(C)[C@H](NC(=O)c1ccc2ccc(C(F)(F)F)cc2c1OCc1ccc(C(F)(F)F)cc1)C(=O)O]

$^1$H NMR (400 MHz, Chloroform-d) δ 8.33 (m, 2H), 8.23 (d, J=8.7 Hz, 1H), 8.00 (d, J=8.6 Hz, 1H), 7.82 (m, 1H), 7.73 (dd, J=8.6, 1.8 Hz, 1H), 7.63 (m, 4H), 5.40 (d, J=11.9 Hz, 1H), 5.04 (d, J=11.9 Hz, 1H), 4.75 (d, J=8.7 Hz, 1H), 1.28 (dt, J=8.8, 4.1 Hz, 5H), 0.97 (d, J=14.4 Hz, 5H), 0.81 (t, J=6.2 Hz, 3H).

$^{19}$F NMR (377 MHz, $CDCl_3$) δ−62.7, −62.8.

LCMS: tR=1.61 min., m/z ($ES^+$)=556 ($M+H^+$).

Example 305: (R)-3,3-dimethyl-2-(7-methyl-1-((4-(trifluoromethyl)benzyl)oxy)-2-naphthamido)pentanoic Acid

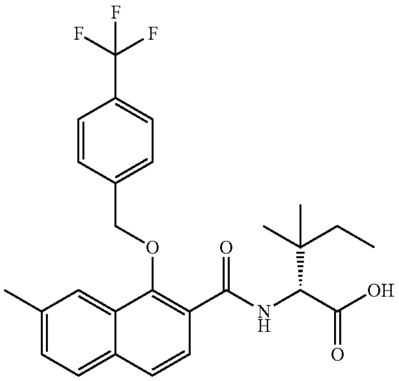 [SMILES: CCC(C)(C)[C@@H](NC(=O)c1ccc2ccc(C)cc2c1OCc1ccc(C(F)(F)F)cc1)C(=O)O]

$^1$H NMR (400 MHz, Chloroform-d) δ 8.43 (d, J=8.7 Hz, 1H), 8.03 (m, 1H), 7.81 (m, 2H), 7.67 (m, 4H), 7.41 (dd, J=8.4, 1.7 Hz, 1H), 5.37 (m, 1H), 5.08 (m, 1H), 4.71 (m, 1H), 2.48 (s, 3H), 1.28 (m, 2H), 1.00-0.65 (m, 9H).

$^{19}$F NMR (377 MHz, $CDCl_3$) δ−62.6.

LCMS: $t_R$=1.56 min., m/z ($ES^+$)=488 ($M+H^+$).

Example 306: (S)-2-(7-chloro-1-((4-(trifluoromethyl)benzyl)oxy)-2-naphthamido)-3,3-dimethylhexanoic Acid

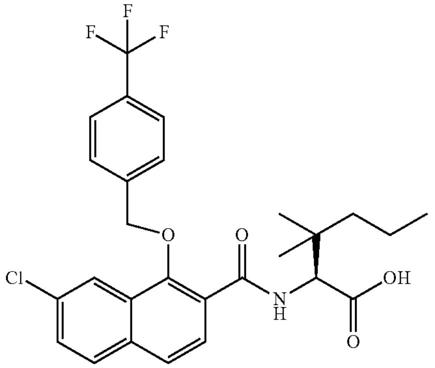 [SMILES: CCCC(C)(C)[C@H](NC(=O)c1ccc2ccc(Cl)cc2c1OCc1ccc(C(F)(F)F)cc1)C(=O)O]

$^1$H NMR (400 MHz, Chloroform-d) δ 8.30 (d, J=8.6 Hz, 1H), 8.10 (d, J=8.7 Hz, 1H), 8.03 (d, J=2.1 Hz, 1H), 7.84 (d, J=8.8 Hz, 1H), 7.68 (s, 4H), 7.52 (dd, J=8.7, 2.1 Hz, 1H), 5.36 (d, J=12.1 Hz, 2H), 5.08 (d, J=12.1 Hz, 2H), 4.72 (d, J=8.6 Hz, 1H), 1.25 (m, 5H), 0.93 (m, 5H), 0.80 (t, J=6.5 Hz, 3H).

$^{19}$F NMR (377 MHz, $CDCl_3$) δ−62.7.

LCMS: $t_R$=1.62 min., m/z ($ES^+$)=522 ($M+H^+$).

Example 307: (R)-3,3-dimethyl-2-(7-(trifluoromethyl)-1-((4-(trifluoromethyl)benzyl)oxy)-2-naphthamido)butanoic Acid

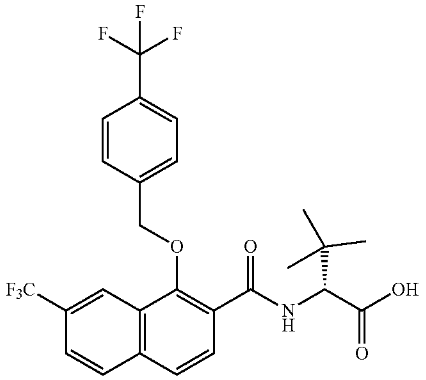 [SMILES: CC(C)(C)[C@@H](NC(=O)c1ccc2ccc(C(F)(F)F)cc2c1OCc1ccc(C(F)(F)F)cc1)C(=O)O]

$^1$H NMR (400 MHz, Chloroform-d) δ 8.31 (m, 2H), 8.23 (d, J=8.7 Hz, 1H), 8.01 (m, 1H), 7.80 (d, J=8.6 Hz, 1H), 7.65 (m, 4H), 5.41 (d, J=11.9 Hz, 1H), 5.06 (d, J=11.8 Hz, 2H), 4.70 (d, J=8.6 Hz, 2H), 1.03 (s, 9H).

$^{19}$F NMR (377 MHz, $CDCl_3$) δ−62.6, −62.8.

LCMS: $t_R$=1.52 min., m/z ($ES^+$)=528 $M+H^+$).

Example 308: (S)-2-(7-methoxy-1-((4-(trifluoromethyl)benzyl)oxy)-2-naphthamido)-3,3-dimethylbutanoic Acid

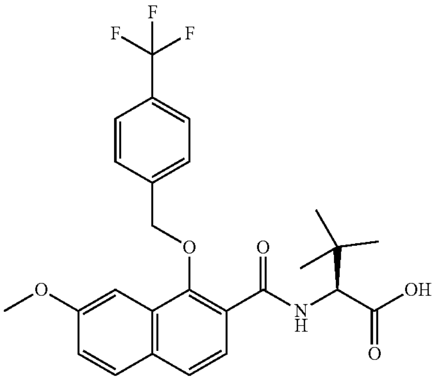 [SMILES: COc1ccc2ccc(C(=O)N[C@H](C(=O)O)C(C)(C)C)c(OCc3ccc(C(F)(F)F)cc3)c2c1]

$^1$H NMR (400 MHz, Chloroform-d) δ 8.42 (d, J=8.5 Hz, 1H), 7.95 (d, J=8.6 Hz, 1H), 7.79 (d, J=8.9 Hz, 1H), 7.68 (m, 4H), 7.25 (m, 1H), 5.39 (d, J=12.4 Hz, 1H), 5.06 (d, J=12.4 Hz, 1H), 4.68 (d, J=8.6 Hz, 1H), 3.73 (s, 3H), 1.01 (s, 9H).

$^{19}$F NMR (377 MHz, $CDCl_3$) δ−62.6.

LCMS: $t_R$=1.45 min., m/z ($ES^+$)=490 ($M+H^+$).

Example 309: (S)-2-(7-methoxy-1-((4-(trifluoromethyl)benzyl)oxy)-2-naphthamido)-3,3-dimethylpentanoic Acid

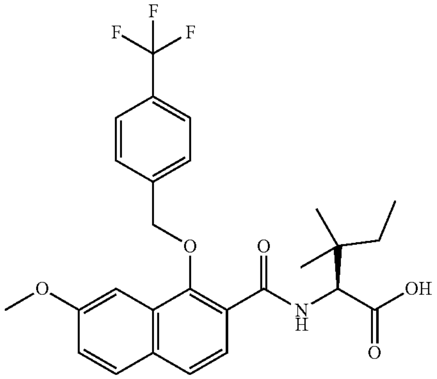 [SMILES: CCC(C)(C)[C@H](NC(=O)c1ccc2ccc(OC)cc2c1OCc1ccc(C(F)(F)F)cc1)C(=O)O]

$^1$H NMR (400 MHz, Chloroform-d) δ 8.41 (d, J=8.7 Hz, 1H), 7.95 (d, J=8.6 Hz, 1H), 7.78 (d, J=8.9 Hz, 1H), 7.67 (m, 4H), 7.25 (m, 2H), 5.39 (d, J=12.4 Hz, 1H), 5.05 (d, J=12.4 Hz, 1H), 4.73 (d, J=8.6 Hz, 1H), 3.73 (s, 3H), 1.34 (m, 2H), 0.89 (m, 9H).

$^{19}$F NMR (377 MHz, $CDCl_3$) δ−62.6.

LCMS: $t_R$=1.50 min., m/z ($ES^+$)=504 ($M+H^+$).

Example 310: (S)-2-(7-methoxy-1-((4-(trifluoromethoxy)benzyl)oxy)-2-naphthamido)-3,3-dimethylbutanoic Acid

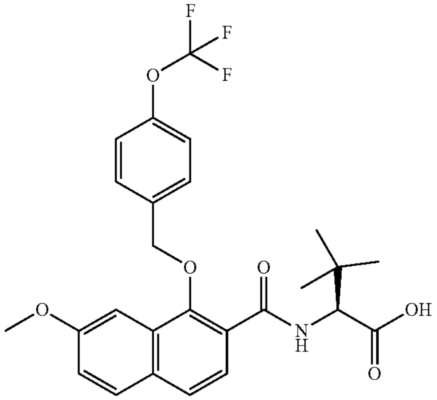 [SMILES: COc1ccc2ccc(C(=O)N[C@H](C(=O)O)C(C)(C)C)c(OCc3ccc(OC(F)(F)F)cc3)c2c1]

$^1$H NMR (400 MHz, Chloroform-d) δ 8.47 (d, J=8.6 Hz, 1H), 7.95 (d, J=8.6 Hz, 1H), 7.77 (d, J=8.9 Hz, 1H), 7.66 (m, 1H), 7.58 (m, 2H), 7.24 (m, 3H), 5.33 (d, J=11.9 Hz, 1H), 4.98 (d, J=11.9 Hz, 1H), 4.68 (d, J=8.5 Hz, 1H), 3.74 (s, 3H), 1.02 (s, 9H).

$^{19}$F NMR (377 MHz, $CDCl_3$) δ−57.9.

LCMS: $t_R$=1.47 min., m/z ($ES^+$)=506 ($M+H^+$).

Example 311: (S)-2-(7-methoxy-1-((4-(trifluoromethoxy)benzyl)oxy)-2-naphthamido)-3,3-dimethylpentanoic Acid

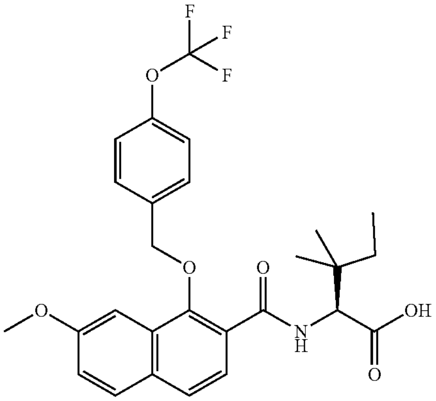 [SMILES: CCC(C)(C)[C@H](NC(=O)c1ccc2ccc(OC)cc2c1OCc1ccc(OC(F)(F)F)cc1)C(=O)O]

$^1$H NMR (400 MHz, Chloroform-d) δ 8.44 (d, J=8.6 Hz, 1H), 7.95 (d, J=8.6 Hz, 1H), 7.77 (d, J=8.9 Hz, 1H), 7.61 (m, 2H), 7.23 (m, 4H), 5.33 (d, J=11.9 Hz, 1H), 4.97 (d, J=11.9 Hz, 1H), 4.74 (d, J=8.6 Hz, 1H), 3.75 (s, 3H), 1.36 (m, 2H), 0.95 (d, J=18.1 Hz, 6H), 0.85 (t, J=7.4 Hz, 3H).

$^{19}$F NMR (377 MHz, $CDCl_3$) δ−57.9.

LCMS: $t_R$=1.52 min., m/z ($ES^+$)=520 ($M+H^+$).

Example 312: (R)-3,3-dimethyl-2-(7-methyl-1-((4-(trifluoromethoxy)benzyl)oxy)-2-naphthamido)pentanoic Acid

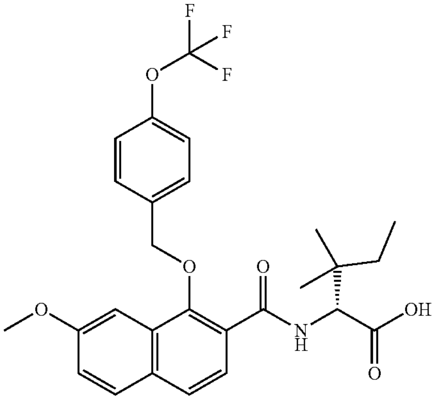 [SMILES: CCC(C)(C)[C@@H](NC(=O)c1ccc2ccc(OC)cc2c1OCc1ccc(OC(F)(F)F)cc1)C(=O)O]

$^1$H NMR (400 MHz, Chloroform-d) δ 8.45 (d, J=8.4 Hz, 1H), 8.04 (d, J=8.6 Hz, 1H), 7.85 (d, J=1.5 Hz, 1H), 7.79 (d, J=8.3 Hz, 1H), 7.68 (m, 1H), 7.60 (d, J=8.6 Hz, 2H), 7.41 (m, 1H), 7.28 (m, 1H), 5.29 (d, J=11.8 Hz, 1H), 5.05 (d, J=11.8 Hz, 1H), 4.71 (d, J=8.4 Hz, 1H), 2.49 (s, 3H), 1.32 (m, 2H), 0.90 (m, 6H), 0.81 (t, J=7.4 Hz, 3H).

$^{19}$F NMR (377 MHz, $CDCl_3$) δ−57.9

LCMS: $t_R$=1.58 min., m/z ($ES^+$)=504 ($M+H^+$).

Example 313: (S)-2-(1-ethylcyclopentyl)-2-(7-fluoro-1-((4-(trifluoromethoxy)benzyl)oxy)-2-naphthamido)acetic Acid

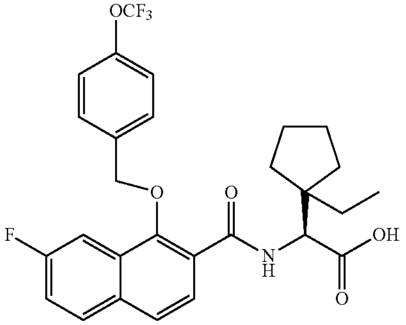 [SMILES: CCC1([C@H](NC(=O)c2ccc3ccc(F)cc3c2OCc2ccc(OC(F)(F)F)cc2)C(=O)O)CCCC1]

$^1$H NMR (400 MHz, Chloroform-d) δ 8.32 (d, J=8.1 Hz, 1H), 8.07 (d, J=8.7 Hz, 1H), 7.89 (dd, J=9.0, 5.5 Hz, 1H), 7.72 (m, 1H), 7.58 (d, J=8.6 Hz, 1H), 7.30 (m, 5H), 5.30 (d, J=11.8 Hz, 1H), 5.05 (d, J=11.8 Hz, 1H), 4.80 (d, J=8.2 Hz, 1H), 1.65 (ddd, J=22.7, 13.2, 6.3 Hz, 2H), 1.37 (p, J=6.9 Hz, 8H), 0.83 (t, J=7.4 Hz, 3H).

$^{19}$F NMR (377 MHz, $CDCl_3$) δ−57.9, −112.0.

LCMS: tR=1.60 min., m/z ($ES^+$)=534 ($M+H^+$).

Example 314: (S)-2-(1-ethylcyclopentyl)-2-(7-fluoro-1-((4-(trifluoromethyl)benzyl)oxy)-2-naphthamido)acetic Acid

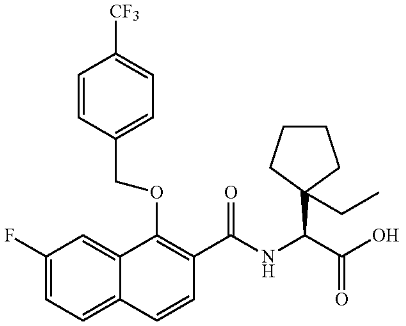 [SMILES: CCC1([C@H](NC(=O)c2ccc3ccc(F)cc3c2OCc2ccc(C(F)(F)F)cc2)C(=O)O)CCCC1]

$^1$H NMR (400 MHz, Chloroform-d) δ 8.28 (d, J=8.3 Hz, 1H), 8.07 (d, J=8.7 Hz, 1H), 7.90 (dd, J=9.0, 5.5 Hz, 1H), 7.71 (m, 6H), 7.37 (m, 1H), 5.36 (d, J=12.4 Hz, 1H), 5.11 (d, J=12.3 Hz, 1H), 4.79 (d, J=8.3 Hz, 1H), 1.48 (d, J=7.5 Hz, 6H), 1.30 (m, 4H), 0.81 (t, J=7.4 Hz, 3H).

$^{19}$F NMR (377 MHz, $CDCl_3$) δ−62.6, −111.8.

LCMS: tR=1.58 min., m/z ($ES^+$)=518 ($M+H^+$).

Biological Assays

Example 315: H441 Cell Emax and EC50

Cells

Two cell lines were used, the H441 carcinoma line and the CFHBE41o- (41o-) human bronchial epithelial line. Both cell lines expressed human Cystic Fibrosis Transmembrane Conductance Regulator (CFTR) harboring the ΔF508 mutation and with an in-frame fusion in CFTR extracellular loop 4 of Horse Radish Peroxidase (HRP) under control of the CMV promoter. In the presence of the HRP tag, ΔF508-CFTR transported to the cell surface was detectable upon addition of an HRP substrate (Luminata Forte). Both cell types were cultivated at 37° C. with $CO_2$.

The H441 cells were cultured in medium containing: 500 mls RPMI GIBCO 22400; 50 mls FBS GIBCO, 16000; 4.4 mls DPBS, no calcium, no magnesium GIBCO 14190 containing G418 AGScientific G1033 added to 50 mg/ml; and 5.5 mls Penicillin/Streptomycin 100× solution, Corning, 30-002-CL.

The 41o-cells were cultured in medium containing: 500 mls MEM (1×) GIBCO, 11095; 50 mls FBS (Tet System) Clontech 631106; 5.5 mls Hepes (1 M) GIBCO 15630; 5 mls GlutaMAX (100×) GIBCO 35050; 1.2 mls Puromycin (10 mg/ml) Invivogen ant-pr; and 2.2 mls of 50 mg/ml G418 solution.

The 41o-cells were grown on Becton/Dickinson Biocoat (collagen) T175 flasks or house-coated (see below) 2-stack or 5-stack tissue culture hotels. The house-coat contained 48 mls (240 mls) LHC Basal Medium GIBCO 12677019; 67 μls (335 μls) BSA Fraction V (7.5%) Sigma A8412-100; 1.5 mls (7.5 mls) 0.1% collagen SIGMA; and 0.5 mls (2.5 mls) human plasma fibronectin (1 mg/ml) GIBCO 3306-015 in sterile $H_2O$. The house-coat was poured on to the growing surface of the plasticware to ensure coverage, poured off and incubated at 37° C. overnight (O/N) or longer.

For both cell types, the medium was changed every other day unless the culture was at low % confluence. Cells were used for the assays at ~75% confluence.

Assay

DMSO/Compound Dilutions Plate for 15-Point Dose-Response Testing

To a polypropylene (PP) 384-well plate, 15 pls DMSO was added to all wells in columns 1-22 and 24 (low Control). 15 μls of 260 μM VX809 (Lumacaftor), Selleckchem S1565, was added to column 23 wells (high Control). 15 pls of 10 mM test compound or VX809 (control) were added to wells of row A. Serial dilutions of Row A compound were performed 2×15 pls in rows A through 0 (15-point).

Medium Dilution Plate

A PP, 384-well plate containing the appropriate cell culture medium was prepared for each assay plate with 100 pls per well. For the doxycycline-induced 41o-cells, doxycycline for both the assay plate and the medium dilution plate was added at 0.0005 mg/ml to the medium.

Assay Plate

Both cell lines were plated for the assay at 30 pls per 384-well at 3.4×10 $e^5$ cells per ml (~10K cells/well). H441 cells were plated on opaque, white, Corning plate 3704. 41o-cells were plated on collagen-coated opaque, white, Corning plate 356665. For 41o-cells, doxycycline was added to the medium.

Compound Addition/Assay Incubation

Using FX (Beckman) protocol, 10 pls diluted compound or medium was added per well to the Assay Plate as: 2 pls DMSO Dilution plate well was diluted in 100 pls of the Medium Dilution Plate well, mixed, and 10 pls was transferred to the Assay Plate.

The final assay dilution series was 24.5, 12.3, 6.1, 3.1, 1.5, 0.8, 0.4, 0.2, 0.1, 0.05, 0.02, 0.01, 0.006, 0.003, 0.001 and 0 μM. The 41o-assay plates were incubated at 37° C. w/$CO_2$, the H441 assay plates were incubated at 27° C. w/CO2, each overnight for two nights.

Assay Result Determination

After being brought to room temperature, the assay plate liquid was removed. 30 uls of Luminata Forte (Millipore ELLUF0100) was added per well and incubated at room temperature for 10 min. The plates were then read on a Topcount, protocol LumiMatti (CPS, luminescence). The data was analyzed for % of maximum, maximum VX809 signal, and EC50 using Pearl and SPEED tools.

Example 316: TECC24 AUC Fold Over DMSO @ 10 uM

The effects of a test agent on CFTR-mediated transepithelial chloride transport was measured using TECC24 recording analysis. Test agents were solubilized in DMSO. Solubilized test agents were mixed with incubation medium containing DMEM/F12, Ultroser G (2%; Crescent Chemical, catalog #67042), Hyclone Fetal Clone II (2%; GE Healthcare, catalog #SH30066.02), bovine brain extract (0.25%; Lonza, catalog #CC-4098), insulin (2.5 μg/mL), IL-13 (10 ng/mL), hydrocortisone (20 nM), transferrin (2.5 μg/mL), triiodothyronine (500 nM), ethanolamine (250 nM), epinephrine (1.5 μM), phosphoethanolamine (250 nM), and retinoic acid (10 nM). Primary human bronchial epithelial cells from a ΔF508 homozygous CF donor (CF-HBE cells; from University of North Carolina Cystic Fibrosis Tissue Procurement Center), grown on Transwell HTS 24-well cell culture inserts (Costar, catalog #3378), were exposed to test agents or controls dissolved in incubation medium. The CF-HBE cells were cultured at 36.5° C. for 48 hours before TECC24 recordings were performed in the presence or absence of test agent, a positive control or vehicle (DMSO).

Following incubation, the transwell cell culture inserts containing the test agent or control-treated CF-HBE cells were loaded onto a TECC24 apparatus (TECC v7 or MTECC v2; EP Design) to record the transepithelial voltage (VT) and resistance (TEER) using 4 AgCl electrodes per well configured in current-clamp mode. The apical and basolateral bath solutions both contained (in mM) 140 NaCl, 5 KCl, 2 $CaCl_2$), 1 $MgCl_2$, 10 Hepes, and 10 glucose (adjusted to pH 7.4 with NaOH). To inhibit basal Na+ absorption, the ENaC inhibitor benzamil (10 μM) was added to the bath. Then, the adenylate cyclase activator, forskolin (10 μM), was added to the bath to activate CFTR. The forskolin-stimulated Cl-transport was halted by addition of CFTR inhibitor-172 (20 μM) to the bath at the end of the experiment to confirm specificity. VT and TEER recordings were digitally acquired at routine intervals using TECC or MTECC software (EP Design). VT and TEER were transformed into equivalent transepithelial Cl-current (IEQ), and the Area Under the Curve (AUC) of the IEQ time course between forskolin and CFTR inhibitor-172 addition was generated using Excel (Microsoft). Efficacy is expressed as the ratio of the test agent AUC divided by vehicle AUC. EC50s based on AUC are generated using the non-linear regression log(agonist) vs. response function in Prism software (GraphPad) with Hill Slope fixed=1.

If a test agent increased the AUC of the forskolin-stimulated IEQ relative to vehicle in CF-HBE cells, and this increase was inhibited by CFTR inhibitor-172, then the test agent was considered a CFTR corrector.

Data for Examples 1-314 are provided in Table 6 below.

TABLE 6

| EXAMPLE No. | H441 cell Emax (%) | H441 cell EC50 (μM) | TECC24* AUC fold over DMSO @10 μM |
|---|---|---|---|
| 1 | 164.5 | 0.7 | B |
| 2 | 151.3 | 4.8 | C |

TABLE 6-continued

| EXAMPLE No. | H441 cell Emax (%) | H441 cell EC50 (μM) | TECC24* AUC fold over DMSO @10 μM |
|---|---|---|---|
| 3 | 18.1 | 2.2 | ND |
| 4 | 37.2 | 0.7 | ND |
| 5 | 100.0 | 0.8 | C |
| 6 | NA | ND | ND |
| 7 | 51.9 | 2.4 | ND |
| 8 | NA | ND | ND |
| 9 | 88.4 | 1.1 | C |
| 10 | ND | ND | C |
| 11 | 160.3 | 0.5 | C |
| 12 | NA | ND | ND |
| 13 | 81.3 | 1.2 | C |
| 14 | 103.4 | 0.1 | B |
| 15 | 48.4 | 1.7 | ND |
| 16 | ND | ND | C |
| 17 | 63.9 | 0.7 | C |
| 18 | NA | ND | ND |
| 19 | 48.3 | 21.9 | C |
| 20 | NA | ND | ND |
| 21 | NA | ND | ND |
| 22 | 63.6 | 0.3 | C |
| 23 | 29.2 | 9.8 | ND |
| 24 | 66.1 | 1.1 | C |
| 25 | 287.3 | 0.5 | C |
| 26 | 98.8 | 4.6 | C |
| 27 | 134.3 | 0.6 | B |
| 28 | 70.2 | 4.9 | C |
| 29 | 27.8 | 24.5 | ND |
| 30 | 57.5 | 2.0 | C |
| 31 | 77.1 | 8.0 | C |
| 32 | 44.3 | 1.5 | ND |
| 33 | NA | ND | ND |
| 34 | 78.4 | 3.8 | ND |
| 35 | 86.4 | 0.6 | A |
| 36 | 133.3 | 0.7 | B |
| 37 | 195.1 | 0.3 | C |
| 38 | 80.8 | 1.1 | ND |
| 39 | 60.7 | 15.4 | ND |
| 40 | 100.3 | 0.3 | C |
| 41 | 112.4 | 3.7 | C |
| 42 | NA | ND | ND |
| 43 | ND | ND | ND |
| 44 | 19.9 | 5.1 | ND |
| 45 | 94.7 | 1.8 | C |
| 46 | 26.9 | 3.5 | ND |
| 47 | 116.9 | 0.9 | C |
| 48 | 111.7 | 0.7 | C |
| 49 | 33.5 | 1.5 | ND |
| 50 | 57.8 | 0.4 | C |
| 51 | 199.5 | 0.4 | C |
| 52 | 91.4 | 7.3 | C |
| 53 | 19.8 | 22.9 | ND |
| 54 | 56.1 | 2.4 | ND |
| 55 | 114.9 | 0.6 | B |
| 56 | 127.1 | 1.7 | C |
| 57 | 87.9 | 1.5 | C |
| 58 | 139.0 | 2.8 | C |
| 59 | 108.2 | 1.9 | C |
| 60 | 90.3 | 1.6 | C |
| 61 | 132.1 | 2.7 | C |
| 62 | NA | ND | ND |
| 63 | 43.6 | 1.5 | ND |
| 64 | 106.0 | 0.6 | C |
| 65 | 8.7 | 4.4 | ND |
| 66 | 12.8 | 2.1 | ND |
| 67 | 111.8 | 0.8 | A |
| 68 | 104.3 | 1.9 | C |
| 69 | 57.7 | 0.4 | C |
| 70 | 272.1 | 0.8 | C |
| 71 | NA | ND | ND |
| 72 | 143.7 | 3.7 | C |
| 73 | 88.6 | 0.6 | C |
| 74 | 216.3 | 0.8 | A |
| 75 | 94.2 | 0.7 | B |
| 76 | 58.3 | 7.1 | ND |

TABLE 6-continued

| EXAMPLE No. | H441 cell Emax (%) | H441 cell EC50 (μM) | TECC24* AUC fold over DMSO @10 μM |
|---|---|---|---|
| 77 | 78.9 | 0.7 | C |
| 78 | 241.8 | 0.4 | A |
| 79 | 9.1 | 2.5 | ND |
| 80 | 194.6 | 0.4 | C |
| 81 | 91.9 | 0.7 | A |
| 82 | 90.4 | 1.3 | C |
| 83 | 58.9 | 1.4 | ND |
| 84 | 80.5 | 0.5 | B |
| 85 | 53.0 | 1.6 | ND |
| 86 | 108.1 | 5.6 | C |
| 87 | 102.7 | 2.1 | C |
| 88 | 64.4 | 7.3 | C |
| 89 | 47.6 | 1.4 | C |
| 90 | NA | ND | ND |
| 91 | 44.3 | 16.4 | ND |
| 92 | 52.6 | 14.0 | ND |
| 93 | 13.1 | ND | C |
| 94 | NA | ND | C |
| 95 | 29.3 | 16.0 | C |
| 96 | NA | ND | C |
| 97 | 1.1 | ND | C |
| 98 | 6.0 | ND | ND |
| 99 | 83.1 | 5.7 | C |
| 100 | NA | ND | ND |
| 101 | 79.1 | 6.7 | ND |
| 102 | 33.7 | 8.0 | ND |
| 103 | 22.4 | 24.5 | ND |
| 104 | 77.8 | 7.7 | C |
| 105 | 18.8 | 24.5 | ND |
| 106 | 82.1 | 10.4 | C |
| 107 | 63.4 | 10.9 | NA |
| 108 | 4.7 | ND | ND |
| 109 | 52.7 | 14.2 | ND |
| 110 | 83.1 | 2.1 | B |
| 111 | 93.1 | 2.3 | B |
| 112 | 58.1 | 1.9 | ND |
| 113 | 58.2 | 3.7 | ND |
| 114 | 86.1 | 2.6 | C |
| 115 | 84.0 | 1.1 | C |
| 116 | 51.4 | 1.2 | C |
| 117 | 47.0 | 1.6 | ND |
| 118 | 71.0 | 2.8 | ND |
| 119 | 37.1 | 0.8 | A |
| 120 | 23.1 | 24.5 | ND |
| 121 | 3.7 | 0.2 | ND |
| 122 | 24.5 | 0.3 | ND |
| 123 | 4.0 | ND | ND |
| 124 | 10.5 | 1.3 | ND |
| 125 | 31.5 | 20.3 | ND |
| 126 | 214.5 | 0.1 | B |
| 127 | 98.5 | 1.1 | C |
| 128 | 158.3 | 0.5 | A |
| 129 | 29.4 | 12.0 | C |
| 130 | 196.0 | 0.2 | C |
| 131 | 204.1 | 0.1 | C |
| 132 | 49.2 | 11.6 | ND |
| 133 | 151.2 | 1.2 | A |
| 134 | 84.9 | 1.0 | C |
| 135 | 93.5 | 4.7 | C |
| 136 | 73.6 | 8.1 | C |
| 137 | 38.4 | 16.4 | ND |
| 138 | 22.4 | 16.4 | C |
| 139 | 118.3 | 1.4 | C |
| 140 | 82.9 | 5.7 | C |
| 141 | 147.4 | 2.3 | A |
| 142 | 86.9 | 2.2 | C |
| 143 | 134.6 | 1.9 | B |
| 144 | 139.8 | 4.5 | ND |
| 145 | 72.6 | 12.0 | NA |
| 146 | 62.2 | 17.4 | ND |
| 147 | 68.9 | 16.8 | ND |
| 148 | 65.2 | 18.3 | ND |
| 149 | NA | ND | ND |
| 150 | 82.5 | 10.9 | C |
| 151 | 68.7 | 13.4 | ND |

TABLE 6-continued

| EXAMPLE No. | H441 cell Emax (%) | H441 cell EC50 (µM) | TECC24* AUC fold over DMSO @10 µM |
|---|---|---|---|
| 152 | 122.2 | 7.2 | C |
| 153 | 73.5 | 1.5 | B |
| 154 | 118.2 | 1.9 | A |
| 155 | 60.7 | 4.1 | C |
| 156 | 51.7 | 1.9 | ND |
| 157 | 55.0 | 7.1 | ND |
| 158 | 13.0 | 24.5 | ND |
| 159 | 22.8 | 6.7 | ND |
| 160 | 47.2 | 3.3 | ND |
| 161 | 47.7 | 3.2 | ND |
| 162 | 26.0 | 1.6 | ND |
| 163 | 138.0 | 0.7 | C |
| 164 | 112.1 | 0.6 | C |
| 165 | 113.4 | 3.4 | C |
| 166 | 6.6 | ND | ND |
| 167 | 63.5 | 1.2 | C |
| 168 | 156.8 | 0.8 | B |
| 169 | 137.7 | 0.4 | B |
| 170 | 142.8 | 5.0 | C |
| 171 | 16.4 | 24.5 | ND |
| 172 | 62.7 | 0.5 | C |
| 173 | 163.5 | 0.7 | B |
| 174 | 117.0 | 0.3 | C |
| 175 | 152.0 | 3.0 | C |
| 176 | 38.4 | 24.5 | ND |
| 177 | 64.7 | 0.7 | C |
| 178 | 149.6 | 0.9 | C |
| 179 | 102.6 | 3.4 | C |
| 180 | 70.7 | 10.0 | ND |
| 181 | 93.2 | 13.7 | ND |
| 182 | 31.4 | 4.0 | ND |
| 183 | 63.9 | 3.2 | ND |
| 184 | 11.7 | ND | ND |
| 185 | 14.0 | 24.5 | ND |
| 186 | 46.6 | 2.7 | ND |
| 187 | 70.8 | 11.4 | ND |
| 188 | NA | ND | C |
| 189 | 14.3 | 2.4 | C |
| 190 | 17.9 | 7.0 | ND |
| 191 | NA | ND | NA |
| 192 | 10.6 | ND | ND |
| 193 | NA | ND | ND |
| 194 | NA | ND | C |
| 195 | 214.1 | 1.5 | C |
| 196 | 100.8 | 0.3 | C |
| 197 | 80.8 | 11.5 | B |
| 198 | 94.4 | 1.5 | A |
| 199 | 129.4 | 0.5 | C |
| 200 | 65.4 | 20.5 | ND |
| 201 | 134.9 | 4.1 | C |
| 202 | 111.8 | 4.1 | C |
| 203 | 101.3 | 0.8 | C |
| 204 | 6.8 | ND | ND |
| 205 | 92.2 | 4.8 | C |
| 206 | 4.7 | ND | C |
| 207 | 40.4 | 20.4 | ND |
| 208 | 154.5 | 1.5 | C |
| 209 | 71.0 | 0.4 | C |
| 210 | 38.8 | 4.3 | C |
| 211 | NA | ND | C |
| 212 | 140.7 | 1.2 | C |
| 213 | 87.2 | 13.1 | ND |
| 214 | 112.1 | 3.4 | C |
| 215 | 89.9 | 5.7 | ND |
| 216 | 115.2 | 0.9 | C |
| 217 | 65.8 | 15.9 | C |
| 218 | 86.8 | 4.8 | C |
| 219 | 191.3 | 0.4 | A |
| 220 | 9.3 | ND | ND |
| 221 | 125.1 | 1.2 | A |
| 222 | 153.9 | 2.9 | A |
| 223 | 112.1 | 0.8 | B |
| 224 | 119.4 | 12.8 | ND |
| 225 | 97.0 | 12.2 | A |
| 226 | 138.7 | 0.4 | B |
| 227 | 160.3 | 1.3 | C |
| 228 | 214.8 | 2.0 | A |
| 229 | 176.6 | 1.8 | ND |
| 230 | 151.9 | 0.6 | A |
| 231 | 70.1 | 7.8 | C |
| 232 | 8.5 | 3.1 | ND |
| 233 | 156.5 | 12.2 | A |
| 234 | 139.9 | 1.3 | A |
| 235 | 210.7 | 15.2 | ND |
| 236 | 129.8 | 1.0 | B |
| 237 | 274.6 | 0.1 | A |
| 238 | 143.4 | 0.8 | C |
| 239 | 235.4 | 0.3 | A |
| 240 | 122.2 | 0.8 | C |
| 241 | 236.3 | 0.1 | A |
| 242 | 368.4 | 0.1 | A |
| 243 | 158.6 | 0.5 | A |
| 244 | 364.8 | 0.1 | A |
| 245 | 284.4 | 0.1 | A |
| 246 | 441.5 | 0.1 | A |
| 247 | 224.0 | 0.1 | A |
| 248 | 206.2 | 1.5 | A |
| 249 | 304.8 | 0.2 | A |
| 250 | 269.7 | 0.1 | A |
| 251 | 266.7 | 0.1 | A |
| 252 | 109.9 | 0.6 | A |
| 253 | 238.9 | 0.0 | A |
| 254 | 176.1 | 0.7 | A |
| 255 | 324.5 | 0.1 | A |
| 256 | 295.9 | 0.1 | A |
| 257 | 369.1 | 0.6 | A |
| 258 | 263.9 | 0.0 | A |
| 259 | 63.7 | 1.7 | A |
| 260 | 70.2 | 1.5 | C |
| 261 | 68.4 | 0.9 | A |
| 262 | 132.5 | 1.1 | A |
| 263 | 249.7 | 0.1 | A |
| 264 | 70.7 | 1.8 | B |
| 265 | 96.2 | 0.6 | C |
| 266 | 149.1 | 5.4 | ND |
| 267 | 287.6 | 3.4 | ND |
| 268 | 74.0 | 15.4 | ND |
| 269 | 60.6 | 8.5 | ND |
| 270 | 165.9 | 12.2 | ND |
| 271 | 261.1 | 0.2 | ND |
| 272 | 391.5 | 0.2 | ND |
| 273 | 339.4 | 0.1 | ND |
| 274 | 194.8 | 0.2 | A |
| 275 | 322.4 | 0.2 | A |
| 276 | 308.9 | 0.3 | A |
| 277 | 186.3 | 0.1 | A |
| 278 | 248.1 | 0.2 | A |
| 279 | 348.2 | 0.1 | A |
| 280 | 308.9 | 0.3 | A |
| 281 | 246.2 | 0.7 | A |
| 282 | 284.7 | 0.7 | A |
| 283 | 313.1 | 0.2 | A |
| 284 | 172.8 | 0.5 | C |
| 285 | 99.1 | 0.8 | C |
| 286 | 353.1 | 0.1 | A |
| 287 | 57.1 | 0.3 | C |
| 288 | 403.9 | 0.1 | A |
| 289 | 109.3 | 1.5 | C |
| 290 | 224.9 | 0.2 | A |
| 291 | 260.1 | 0.4 | A |
| 292 | 219.4 | 0.2 | A |
| 293 | 327.0 | 0.3 | A |
| 294 | 281.2 | 1.0 | A |
| 295 | 229.2 | 0.1 | A |
| 296 | 185.7 | 0.2 | A |
| 297 | 137.1 | 0.5 | A |
| 298 | 153.0 | 0.7 | A |
| 299 | 227.1 | 0.2 | A |
| 300 | 231.9 | 0.2 | A |
| 301 | 217.4 | 0.1 | A |

TABLE 6-continued

| EXAMPLE No. | H441 cell Emax (%) | H441 cell EC50 (μM) | TECC24* AUC fold over DMSO @10 μM |
|---|---|---|---|
| 302 | 247.9 | 0.1 | A |
| 303 | 174.3 | 0.7 | B |
| 304 | 249.1 | 0.1 | A |
| 305 | ND | ND | A |
| 306 | 417.1 | 0.1 | A |
| 307 | 81.1 | 0.6 | C |
| 308 | 407.6 | 0.5 | A |
| 309 | 349.1 | 0.3 | A |
| 310 | 298.6 | 0.6 | A |
| 311 | 344.9 | 0.5 | A |
| 312 | 127.3 | 2.2 | B |
| 313 | 152.5 | 0.3 | A |
| 314 | 232.6 | 0.4 | A |

NA = Not active
ND = Not determined;
"A" refers to AUC @10 uM >6;
"B" refers to AUC @10 uM between 4-6;
"C" refers to AUC @10 uM <4.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

The invention claimed is:

1. A compound of Formula (I):

(I)

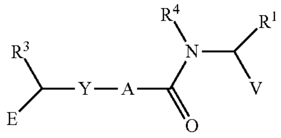

or a pharmaceutically acceptable salt thereof, wherein:

A is

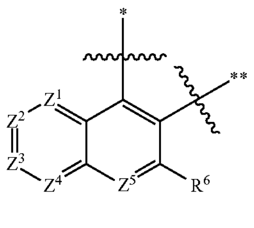

wherein * marks the point of attachment to Y and ** marks the point of attachment to-C(O)—;

$Z^1$, $Z^4$, and $Z^5$ are each independently $CR^6$;

$Z^2$ and $Z^3$ are each independently $CR^2$;

Y is —O—;

E is $C_{2-6}$-alkynyl, $C_{3-9}$-cycloalkyl, $C_{4-9}$-cycloalkenyl, $C_{6-10}$-aryl, 3-10 membered heteroaryl, or 3-9 membered heterocycloalkyl, each of which is optionally substituted with one, two, three, four, or five occurrences of $R^5$;

V is —C(O)—O—$R^7$;

$R^1$ is

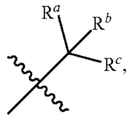

wherein $R^a$ is $C_{1-6}$ alkyl, $R^b$ is $C_{1-6}$ alkyl, or halo$C_{1-6}$ alkyl, wherein each alkyl is optionally substituted with one, two, three, four, or five occurrences of $R^9$;

$R^c$ is $C_{1-6}$ alkyl, halo$C_{1-6}$ alkyl, or $C_{6-10}$ aryl each of which is optionally and independently substituted with one, two, three, four, or five occurrences of $R^{10}$;

$R^a$ and $R^c$, taken together with the atoms to which they are attached, form a $C_{3-8}$ cycloalkyl, or a $C_{3-8}$ heterocycloalkyl ring, or $R^a$, $R^b$, and $R^c$ are taken together with the atoms to which they are attached to form a bridged $C_{5-9}$ cycloalkyl;

each $R^2$ is independently hydrogen, halo, —CN, —OH, —$NH_2$, —N—($C_{1-6}$ alkyl)$_2$, $C_{1-6}$ alkyl, halo$C_{1-6}$ alkyl, —O—$C_{1-6}$ alkyl, —O-halo$C_{1-6}$ alkyl, —O—$C_{2-6}$ alkenyl, or 3-10 membered heteroaryl;

$R^3$ is hydrogen or $C_{1-6}$ alkyl;

$R^4$ is hydrogen or $C_{1-4}$ alkyl;

each $R^5$ is independently halo, —CN, —$NO_2$, $C_{1-6}$ alkyl, hydroxy$C_{1-6}$ alkyl, $C_{1-6}$ haloalkyl, $C_{3-9}$-cycloalkyl, $C_{2-6}$-alkenyl, —O—$C_{1-6}$ alkyl, —O—$C_{1-6}$ haloalkyl, —C(O)—O—$C_{1-6}$ alkyl, —$SF_5$, —S—$C_{1-6}$ alkyl, —S—$C_{1-6}$ haloalkyl, —S(O)$_2$—$C_{1-6}$ alkyl, —S(O)$_2$—$C_{1-6}$ haloalkyl, or 3-10 membered heteroaryl; or two $R^5$ moieties, taken together with the atoms to which they are attached, form a 3-8 membered heterocycloalkyl ring, wherein each heterocycloalkyl is substituted with one, two, or three occurrences of $R^8$;

each $R^6$ is independently hydrogen, halo, or $C_{1-6}$-alkyl;

$R^7$ is hydrogen, $C_{1-6}$-alkyl, $C_{6-10}$ aryl, or benzyl;

each $R^8$ is independently hydrogen, halo or $C_{1-6}$-alkyl;

each $R^9$ is independently hydrogen, halo, $C_{1-6}$-alkyl, halo$C_{1-6}$-alkyl, or $C_{3-9}$-cycloalkyl; and each $R^{10}$ is independently hydrogen, halo, —CN, —OH, $C_{1-6}$-alkyl, halo$C_{1-6}$ alkyl, —O—$C_{1-6}$ alkyl, —O-halo$C_{1-6}$ alkyl, —O—$C_{2-6}$-alkenyl, $C_{1-4}$-alkylaryl, —O—$C_{1-6}$-alkylaryl, —O—$C_{1-6}$ alkyl-O—$C_{1-6}$ alkyl, —C(O)O$C_{1-6}$ alkyl, —S—$C_{1-6}$ alkyl, —N═($NH_2$)$_2$, $C_{6-10}$ aryl, or 3-10 membered heteroaryl.

2. The compound of claim 1, wherein $R^6$ is hydrogen or fluoro.

3. The compound of claim 1, wherein $R^6$ is hydrogen.

4. The compound of claim 1, wherein $R^6$ is fluoro.

5. The compound of claim 1, wherein $R^3$ is hydrogen or methyl.

6. The compound of claim 1, wherein $R^7$ is hydrogen, methyl, ethyl or t-butyl.

7. The compound of claim 1, wherein $R^7$ is hydrogen.

8. The compound of claim 1, wherein E is $C_{2-6}$-alkynyl, $C_{3-9}$-cycloalkyl, $C_{6-10}$-aryl, or 3-10 membered heteroaryl.

9. The compound of claim 1, wherein E is cyclopropyl, cyclohexyl, bicycloheptenyl, phenyl, benzthiazolyl, benzodioxolyl, furanyl, imidazolyl, or pyridyl.

10. The compound of claim 9, wherein E is cyclohexyl, phenyl or benzthiazolyl.

11. The compound of claim 1, wherein $R^a$ is methyl.

12. The compound of claim 1, wherein $R^b$ is methyl or ethyl.

13. The compound of claim 1, wherein $R^C$ is methyl, ethyl, butyl, t-butyl, —$CF_3$, or phenyl.

14. The compound of claim 1, wherein $R^c$ is t-butyl or phenyl.

15. The compound of claim 1, wherein $R^a$ and $R^c$, taken together with the atoms to which they are attached, form a cyclopropyl, cyclopentyl, cyclohexyl, cycloheptyl, bicyclohexyl, bicycloheptyl or dihydroindenyl.

16. The compound of claim 1, wherein $R^a$ and $R^c$, taken together with the atoms to which they are attached, form a cyclopentyl or cyclohexyl.

17. The compound of claim 1, wherein at least one $R^2$ is fluoro, chloro, methyl, —$CF_3$, —OH, —OMe, —O-isopropyl, or —$NH_2$.

18. The compound of claim 1, wherein at least one $R^2$ is fluoro, chloro, methyl, or —OMe.

19. The compound of claim 1, wherein at least one $R^5$ is fluoro, chloro, bromo, methyl, t-butyl, —$CH_2OH$, —$CF_3$, —O—$CF_3$, —$CF_2CF_3$, —CN, —$NO_2$, —$OCF_3$, —$CO_2Me$, —S—$CF_3$, —$SF_5$, —$SO_2Me$, —$SO_2CF_3$, or phenyl.

20. The compound of claim 1, wherein at least one $R^5$ is fluoro, chloro, —$CF_3$, —O—$CF_3$, —S—$CF_3$, —$SF_5$, or —$SO_2Me$.

21. The compound of claim 1, wherein at least one $R^{10}$ is fluoro, chloro, methyl, —$CF_3$, —CN, —OH, —OMe, —O-t-butyl, —O—$CF_3$, —N=$(NH_2)_2$, or phenyl.

22. The compound of claim 1, wherein at least one $R^{10}$ is chloro, methyl, —$CF_3$, or phenyl.

23. The compound of claim 1, or a pharmaceutically acceptable salt thereof, wherein at least one $R^2$ is independently halo, —CN, —N—$(C_{1-6}$ alkyl$)_2$, $C_{1-6}$ alkyl, halo$C_{1-6}$ alkyl, —O—$C_{1-6}$ alkyl, —O—$C_{2-6}$ alkenyl, or 3-10 membered heteroaryl.

24. The compound of claim 23, wherein E is phenyl, cyclohexyl, pyrazolyl, benzodioxolyl, cyclohexenyl, thiazolyl, ethynyl, pyridyl, oxazolyl, bicycloheptanyl, or benzthiazolyl.

25. The compound of claim 24, wherein E is phenyl.

26. The compound of claim 23, wherein $R^a$ is methyl.

27. The compound of claim 23, wherein $R^b$ is methyl.

28. The compound of claim 23, wherein $R^b$ is ethyl.

29. The compound of claim 23, wherein $R^b$ is —$CF_3$.

30. The compound of claim 23, wherein $R^b$ is methyl, ethyl, propyl, —$CH_2F$, or phenyl.

31. The compound of claim 23, wherein $R^c$ is methyl or ethyl.

32. The compound of claim 23, wherein $R^a$ and $R^c$, taken together with the atoms to which they are attached, form a cyclopropyl, cyclobutyl, cyclopentyl, cyclohexyl, bicyclopentyl, bicycloheptyl, or oxiranyl.

33. The compound of claim 23, wherein at least one $R^2$ is methyl, chloro, fluoro, bromo, —$CF_3$, —$CHF_2$, —OMe, —O-propenyl, —CN or thiazolyl.

34. The compound of claim 23, wherein at least one $R^2$ is methyl, chloro, —$CF_3$, —$CHF_2$, or thiazolyl.

35. The compound of claim 23, wherein at least one $R^2$ is methyl or —$CHF_2$.

36. The compound of claim 23, wherein $R^3$ is hydrogen.

37. The compound of claim 23, wherein $R^3$ is methyl.

38. The compound of claim 23, wherein $R^4$ is hydrogen.

39. The compound of claim 23, wherein $R^5$ is chloro, bromo, —OH, —CN, —$NO_2$, methyl, t-butyl, —$CH_2OH$, —O-iPr, —$CF_3$, —$CF_2CF_3$, —$OCF_3$, —$OCHF_2$, 1-propenyl, —$CO_2Me$, —S—$CF_3$, —$SF_5$, —$SO_2Me$, —$SO_2CF_3$, cyclopropyl, 1-$CF_3$-cyclopropyl, or 4,4-difluorocyclohexyl.

40. The compound of claim 23, wherein $R^5$ is t-butyl, —$CF_3$, —$OCF_3$, —S—$CF_3$, or —$SF_5$.

41. The compound of claim 23, wherein $R^6$ is hydrogen or fluoro.

42. The compound of claim 23, wherein $R^7$ is hydrogen.

43. The compound of claim 1, wherein $R^1$ is in the α-configuration.

44. The compound of claim 43, where the compound of Formula (I) has the structure (IA):

(IA)

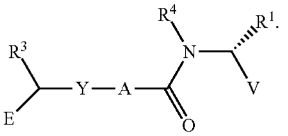

45. The compound of claim 1, wherein $R^1$ is in the β-configuration.

46. The compound of claim 45, where the compound of Formula (I) has the structure (IB):

(IB)

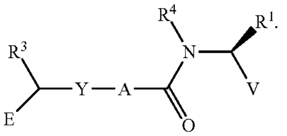

47. A compound selected from:

| | # |
|---|---|
| 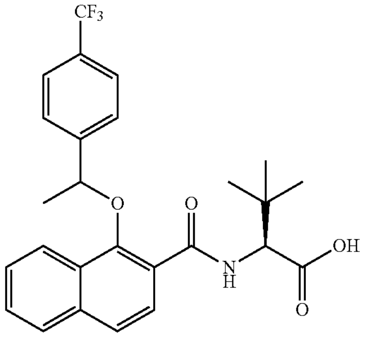 | |

| # |
| --- |
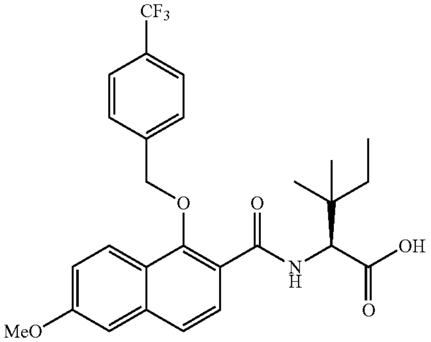 [SMILES: CCC(C)(C)[C@H](NC(=O)c1ccc2cc(OC)ccc2c1OCc1ccc(C(F)(F)F)cc1)C(=O)O]
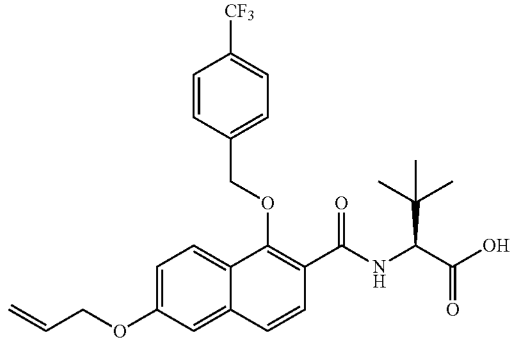 [SMILES: C=CCOc1ccc2c(OCc3ccc(C(F)(F)F)cc3)c(C(=O)N[C@H](C(=O)O)C(C)(C)C)ccc2c1]
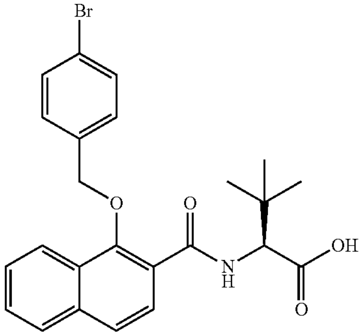 [SMILES: CC(C)(C)[C@H](NC(=O)c1ccc2ccccc2c1OCc1ccc(Br)cc1)C(=O)O]
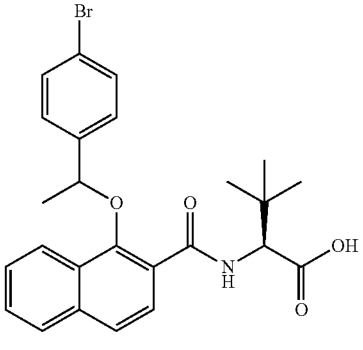 [SMILES: CC(Oc1c(C(=O)N[C@H](C(=O)O)C(C)(C)C)ccc2ccccc12)c1ccc(Br)cc1]
| # |
| --- |
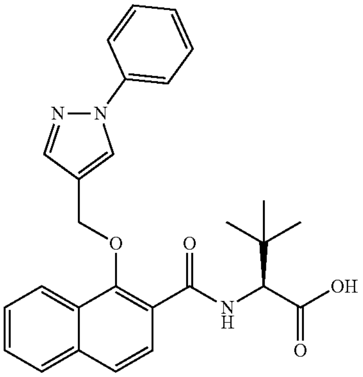 [SMILES: CC(C)(C)[C@H](NC(=O)c1ccc2ccccc2c1OCc1cnn(-c2ccccc2)c1)C(=O)O]
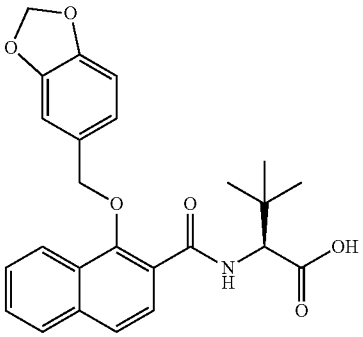 [SMILES: CC(C)(C)[C@H](NC(=O)c1ccc2ccccc2c1OCc1ccc2c(c1)OCO2)C(=O)O]
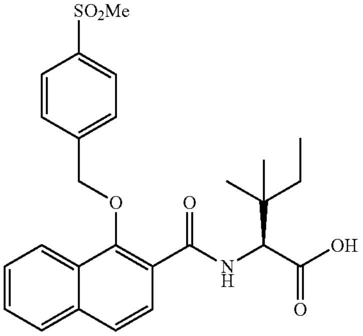 [SMILES: CCC(C)(C)[C@H](NC(=O)c1ccc2ccccc2c1OCc1ccc(S(C)(=O)=O)cc1)C(=O)O]
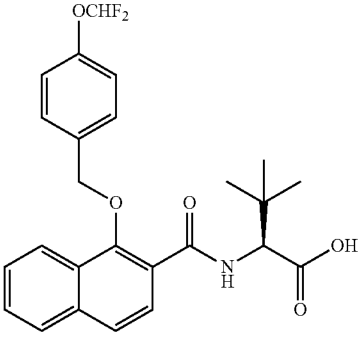

-continued
| # |
|---|
| 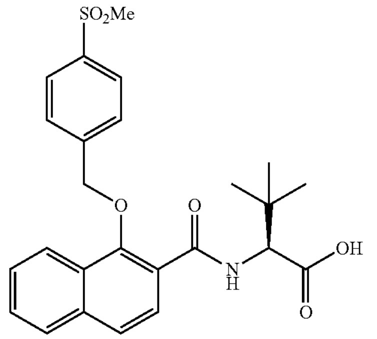 |
| 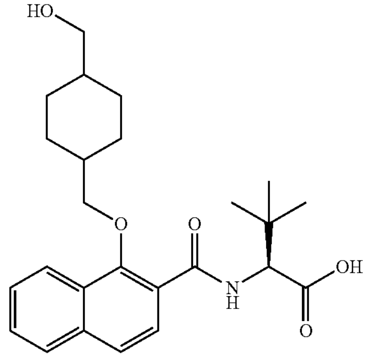 [SMILES: CC(C)(C)[C@H](NC(=O)c1ccc2ccccc2c1OCC1CCC(CO)CC1)C(=O)O] |
| 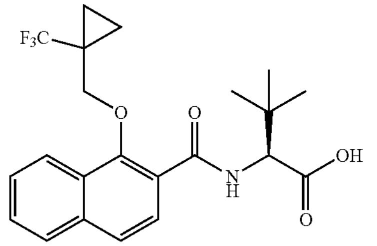 [SMILES: CC(C)(C)[C@H](NC(=O)c1ccc2ccccc2c1OCC1(C(F)(F)F)CC1)C(=O)O] |
| 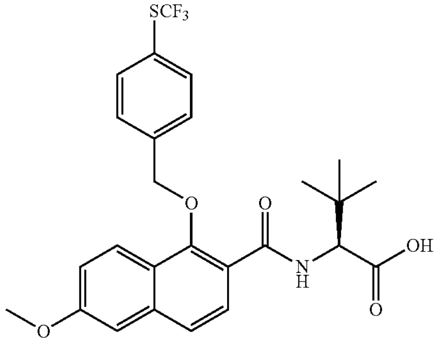 |
-continued
| # |
|---|
| 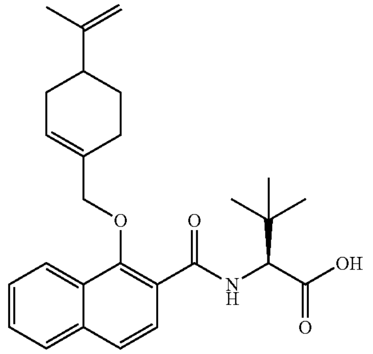 [SMILES: C=C(C)C1CC=C(COc2c(C(=O)N[C@H](C(=O)O)C(C)(C)C)ccc3ccccc23)CC1] |
| 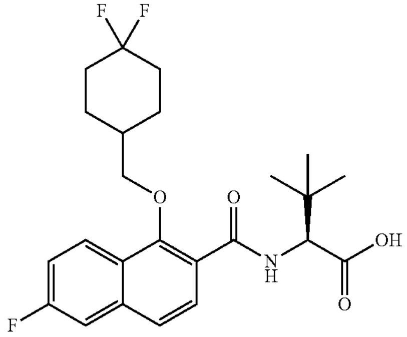 [SMILES: CC(C)(C)[C@H](NC(=O)c1ccc2cc(F)ccc2c1OCC1CCC(F)(F)CC1)C(=O)O] |
| 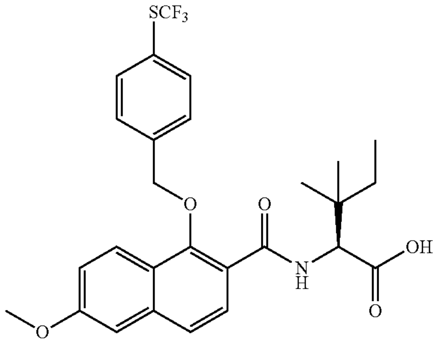 |
| 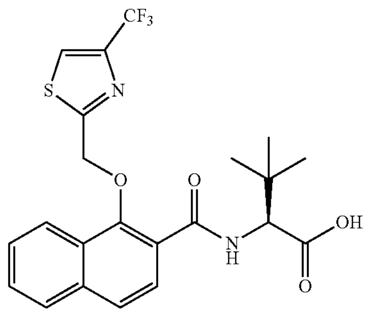 [SMILES: CC(C)(C)[C@H](NC(=O)c1ccc2ccccc2c1OCc1nc(C(F)(F)F)cs1)C(=O)O] |

-continued
| | # |
|---|---|
| 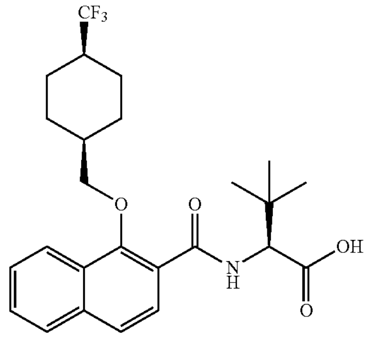 [SMILES: CC(C)(C)[C@H](NC(=O)c1ccc2ccccc2c1OC[C@H]1CC[C@@H](C(F)(F)F)CC1)C(=O)O] | |
| 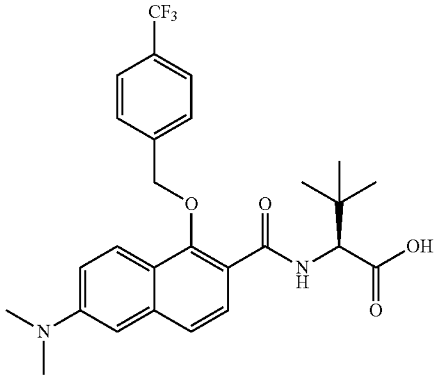 [SMILES: CN(C)c1ccc2c(OCc3ccc(C(F)(F)F)cc3)c(C(=O)N[C@H](C(=O)O)C(C)(C)C)ccc2c1] | |
| 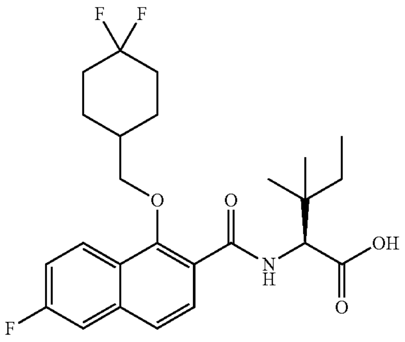 [SMILES: CCC(C)(C)[C@H](NC(=O)c1ccc2cc(F)ccc2c1OCC1CCC(F)(F)CC1)C(=O)O] | |
| 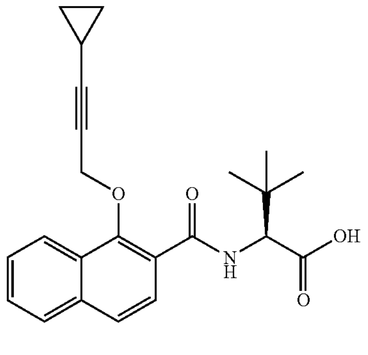 [SMILES: CC(C)(C)[C@H](NC(=O)c1ccc2ccccc2c1OCC#CC1CC1)C(=O)O] | |
-continued
| | # |
|---|---|
| 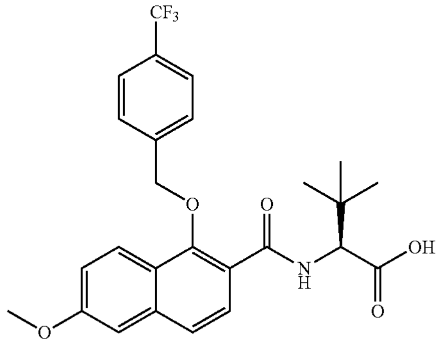 [SMILES: COc1ccc2c(OCc3ccc(C(F)(F)F)cc3)c(C(=O)N[C@H](C(=O)O)C(C)(C)C)ccc2c1] | |
| 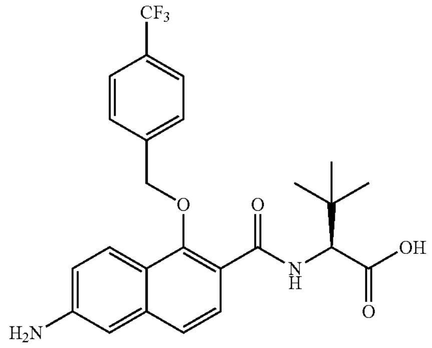 [SMILES: CC(C)(C)[C@H](NC(=O)c1ccc2cc(N)ccc2c1OCc1ccc(C(F)(F)F)cc1)C(=O)O] | |
| 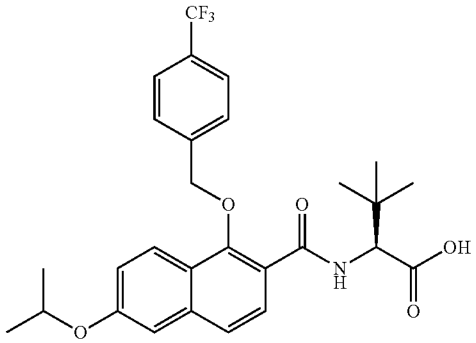 [SMILES: CC(C)Oc1ccc2c(OCc3ccc(C(F)(F)F)cc3)c(C(=O)N[C@H](C(=O)O)C(C)(C)C)ccc2c1] | |
| 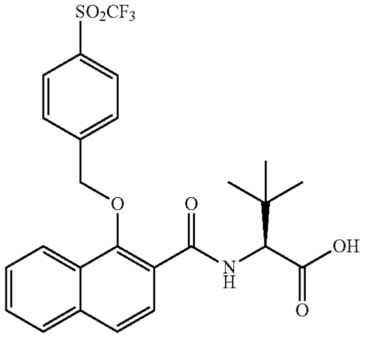 | |

-continued
| # |
|---|
| 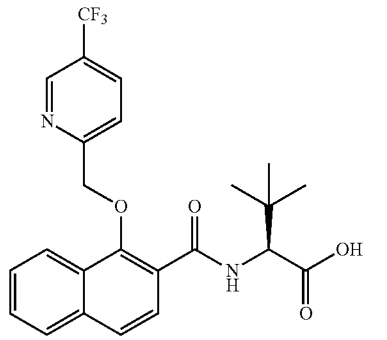 [SMILES: CC(C)(C)[C@H](NC(=O)c1ccc2ccccc2c1OCc1ccc(C(F)(F)F)cn1)C(=O)O] |
| 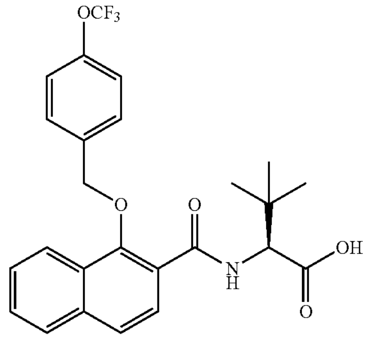 [SMILES: CC(C)(C)[C@H](NC(=O)c1ccc2ccccc2c1OCc1ccc(OC(F)(F)F)cc1)C(=O)O] |
| 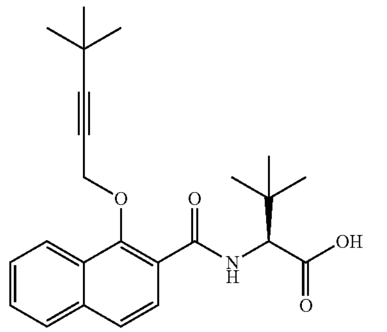 [SMILES: CC(C)(C)C#CCOc1c(C(=O)N[C@H](C(=O)O)C(C)(C)C)ccc2ccccc12] |
| 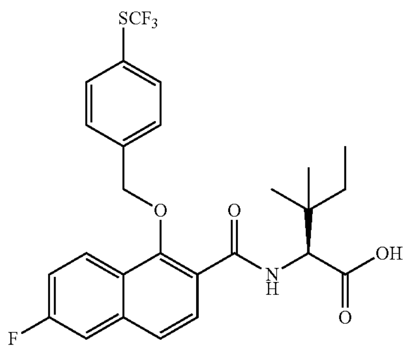 |
-continued
| # |
|---|
| 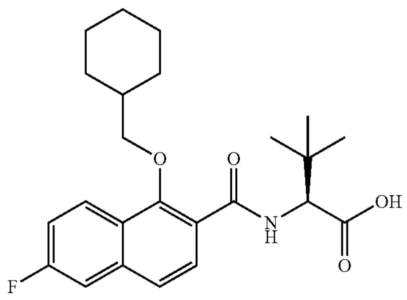 [SMILES: CC(C)(C)[C@H](NC(=O)c1ccc2cc(F)ccc2c1OCC1CCCCC1)C(=O)O] |
| 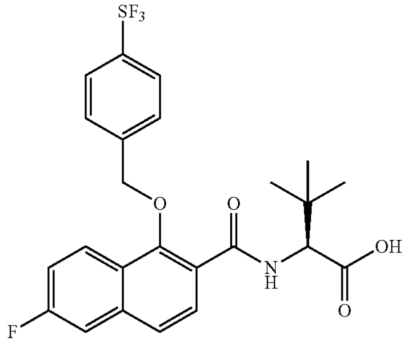 |
| 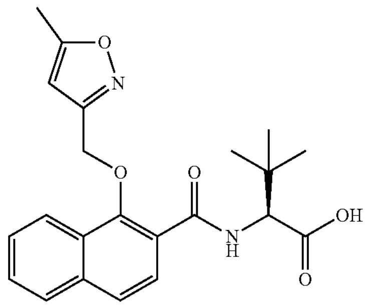 [SMILES: Cc1cc(COc2c(C(=O)N[C@H](C(=O)O)C(C)(C)C)ccc3ccccc23)no1] |
| 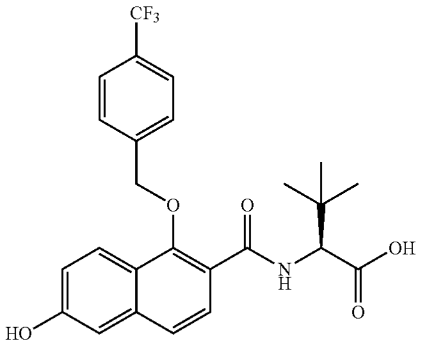 [SMILES: CC(C)(C)[C@H](NC(=O)c1ccc2cc(O)ccc2c1OCc1ccc(C(F)(F)F)cc1)C(=O)O] |

-continued
| # |
|---|
| 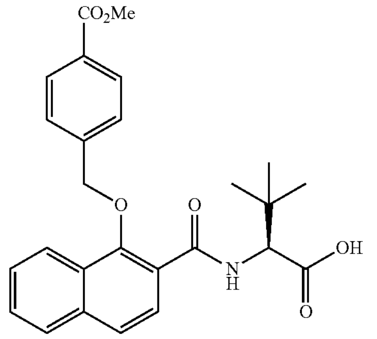 |
| 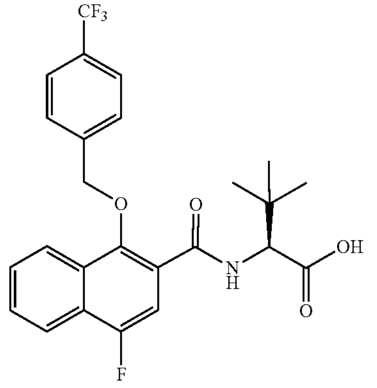 |
| 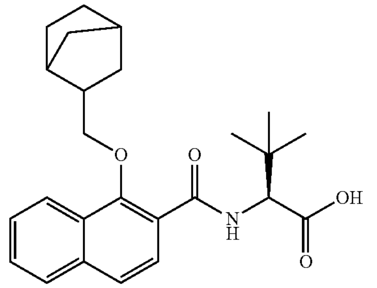 [SMILES: CC(C)(C)[C@H](NC(=O)c1ccc2ccccc2c1OCC1CC2CCC1C2)C(=O)O] |
| 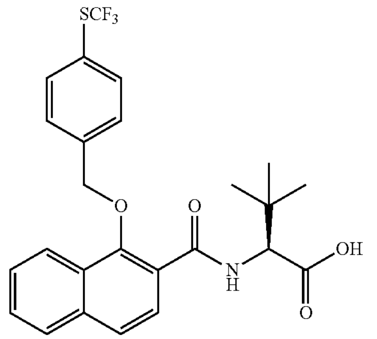 |
-continued
| # |
|---|
| 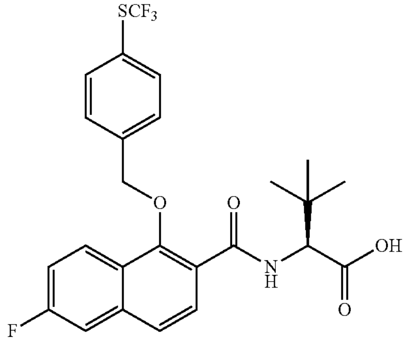 |
| 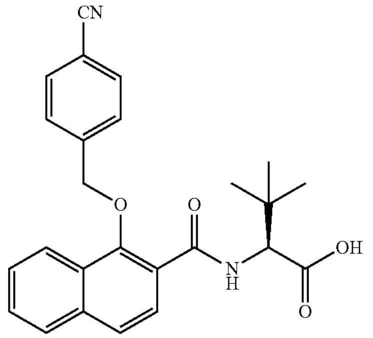 |
| 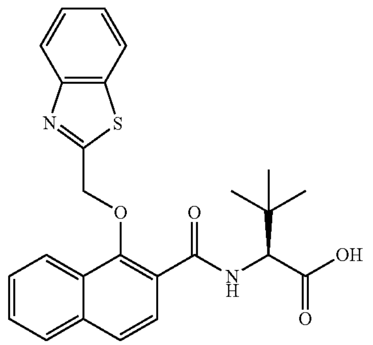 [SMILES: CC(C)(C)[C@H](NC(=O)c1ccc2ccccc2c1OCc1nc2ccccc2s1)C(=O)O] |
| 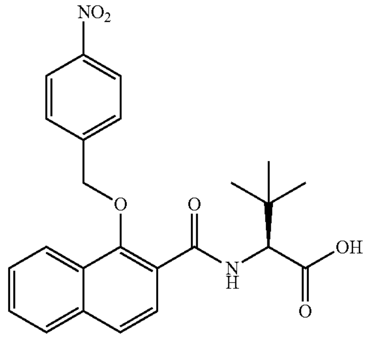 |

-continued
| | # |
|---|---|
| 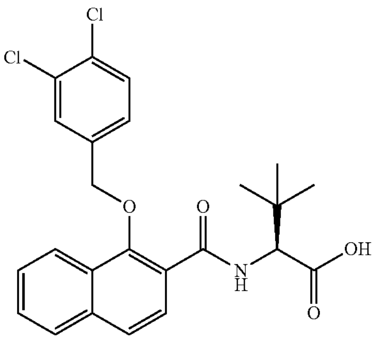 [SMILES: CC(C)(C)[C@H](NC(=O)c1ccc2ccccc2c1OCc1ccc(Cl)c(Cl)c1)C(=O)O] | |
| 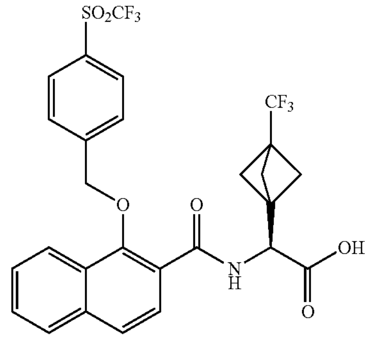 | |
| 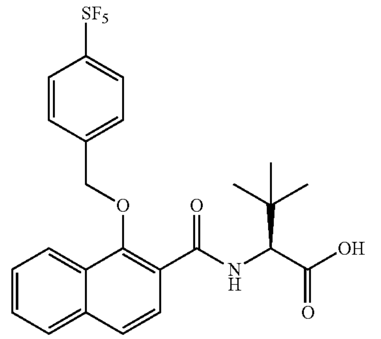 | |
| 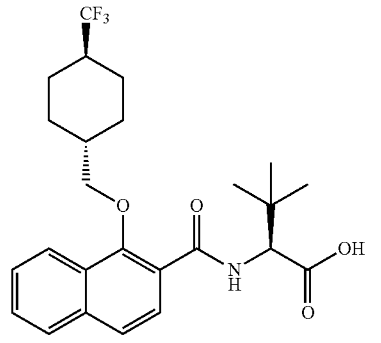 [SMILES: CC(C)(C)[C@H](NC(=O)c1ccc2ccccc2c1OC[C@H]1CC[C@H](C(F)(F)F)CC1)C(=O)O] | |
-continued
| | # |
|---|---|
| 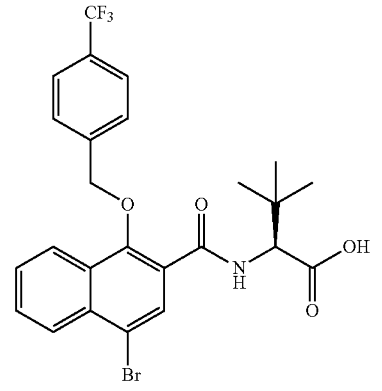 | |
| 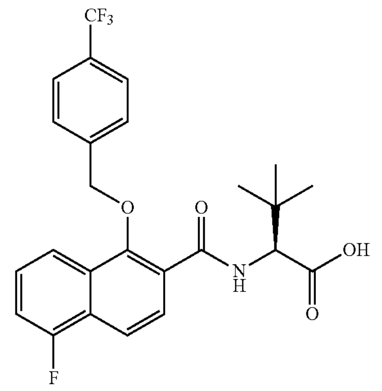 [SMILES: CC(C)(C)[C@H](NC(=O)c1ccc2c(F)cccc2c1OCc1ccc(C(F)(F)F)cc1)C(=O)O] | |
| 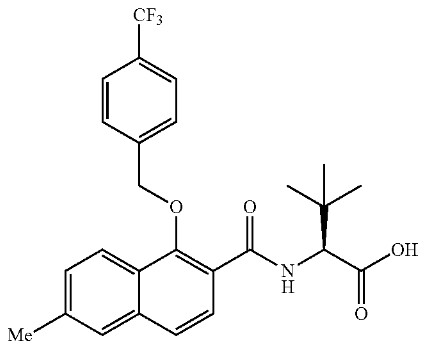 | |
| 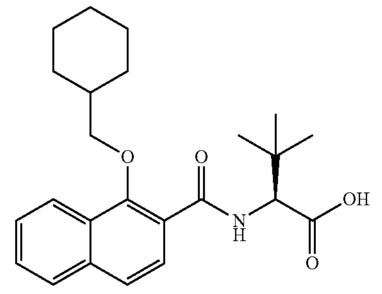 [SMILES: CC(C)(C)[C@H](NC(=O)c1ccc2ccccc2c1OCC1CCCCC1)C(=O)O] | |

-continued
| # |
| --- |
| 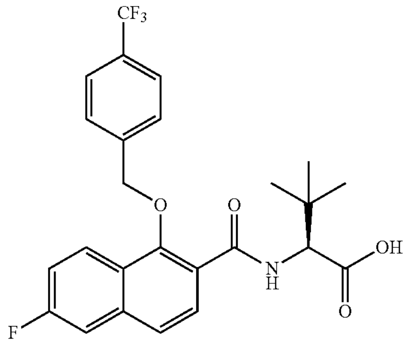 |
| 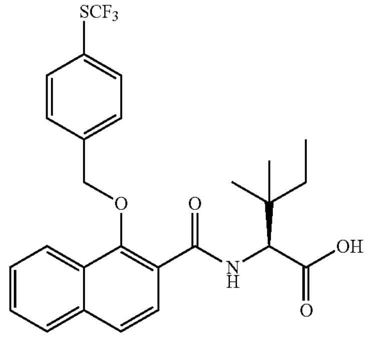 |
| 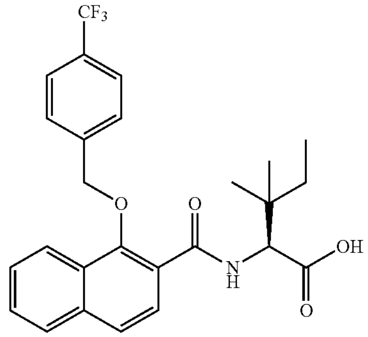 [SMILES: CCC(C)(C)[C@H](NC(=O)c1ccc2ccccc2c1OCc1ccc(C(F)(F)F)cc1)C(=O)O] |
| 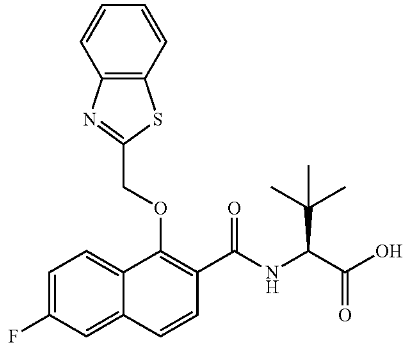 [SMILES: CC(C)(C)[C@H](NC(=O)c1ccc2cc(F)ccc2c1OCc1nc2ccccc2s1)C(=O)O] |
-continued
| # |
| --- |
| 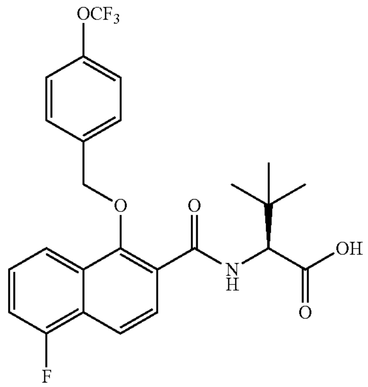 [SMILES: CC(C)(C)[C@H](NC(=O)c1ccc2c(F)cccc2c1OCc1ccc(OC(F)(F)F)cc1)C(=O)O] |
| 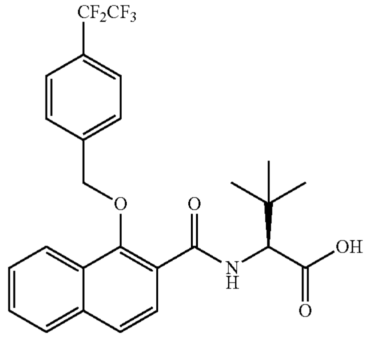 |
| 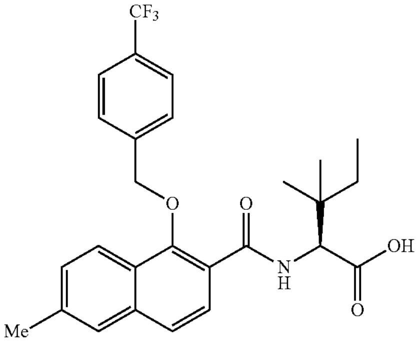 [SMILES: CCC(C)(C)[C@H](NC(=O)c1ccc2cc(C)ccc2c1OCc1ccc(C(F)(F)F)cc1)C(=O)O] |
| 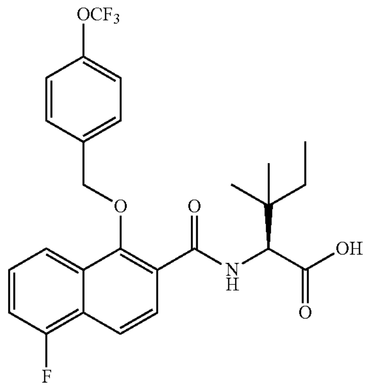 [SMILES: CCC(C)(C)[C@H](NC(=O)c1ccc2c(F)cccc2c1OCc1ccc(OC(F)(F)F)cc1)C(=O)O] |

-continued
| # |
|---|
| 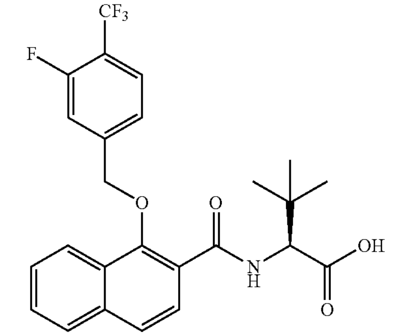 [SMILES: CC(C)(C)[C@H](NC(=O)c1ccc2ccccc2c1OCc1ccc(C(F)(F)F)c(F)c1)C(=O)O] |
| 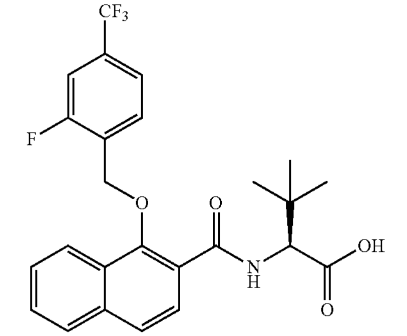 [SMILES: CC(C)(C)[C@H](NC(=O)c1ccc2ccccc2c1OCc1ccc(C(F)(F)F)cc1F)C(=O)O] |
| 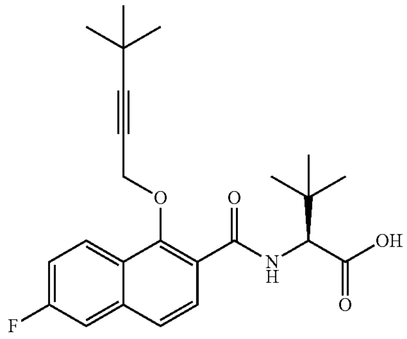 [SMILES: CC(C)(C)C#CCOc1c(C(=O)N[C@H](C(=O)O)C(C)(C)C)ccc2cc(F)ccc12] |
| 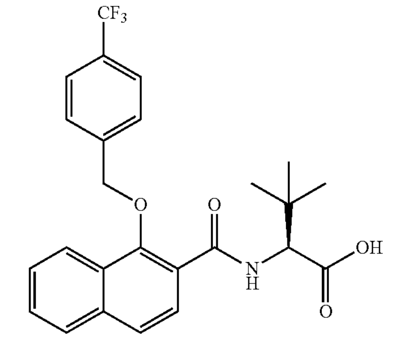 |
-continued
| # |
|---|
| 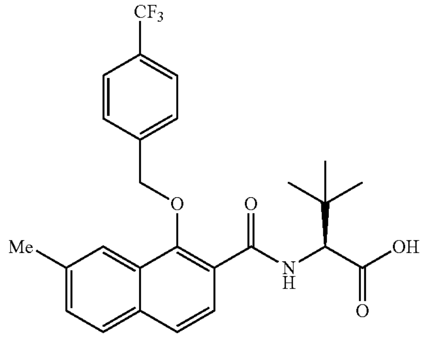 |
| 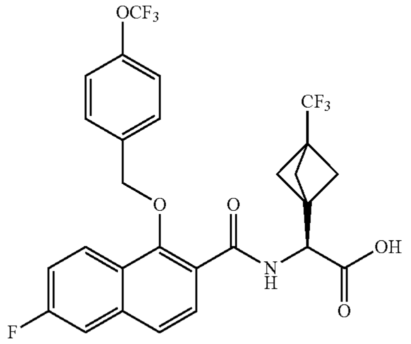 |
| 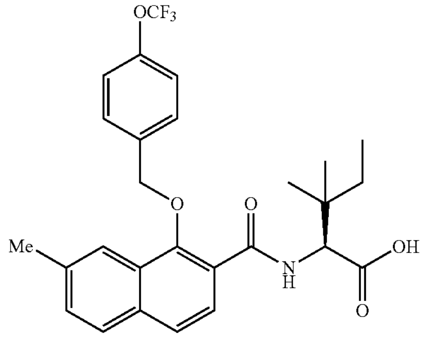 [SMILES: CCC(C)(C)[C@H](NC(=O)c1ccc2ccc(C)cc2c1OCc1ccc(OC(F)(F)F)cc1)C(=O)O] |
| 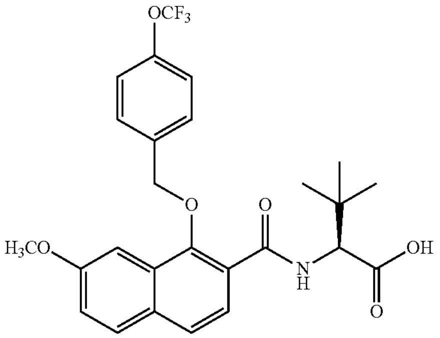 |

-continued
| # |
|---|
| 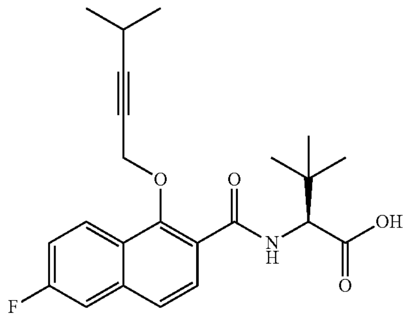 [SMILES: CC(C)C#CCOc1c(C(=O)N[C@H](C(=O)O)C(C)(C)C)ccc2cc(F)ccc12] |
| 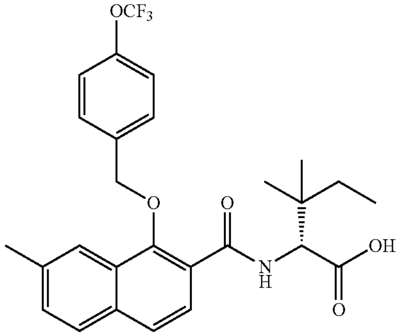 |
| 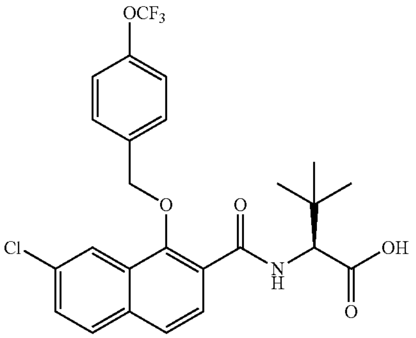 [SMILES: CC(C)(C)[C@H](NC(=O)c1ccc2ccc(Cl)cc2c1OCc1ccc(OC(F)(F)F)cc1)C(=O)O] |
| 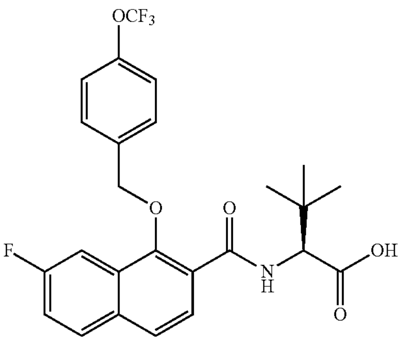 [SMILES: CC(C)(C)[C@H](NC(=O)c1ccc2ccc(F)cc2c1OCc1ccc(OC(F)(F)F)cc1)C(=O)O] |
-continued
| # |
|---|
| 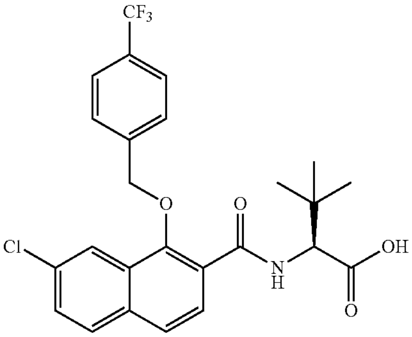 |
| 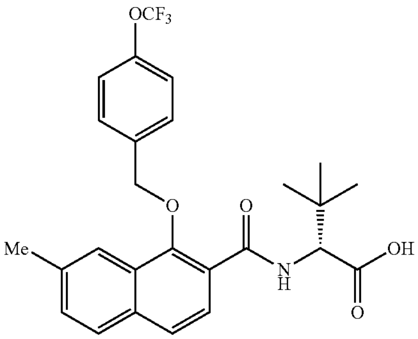 [SMILES: Cc1ccc2ccc(C(=O)N[C@@H](C(=O)O)C(C)(C)C)c(OCc3ccc(OC(F)(F)F)cc3)c2c1] |
| 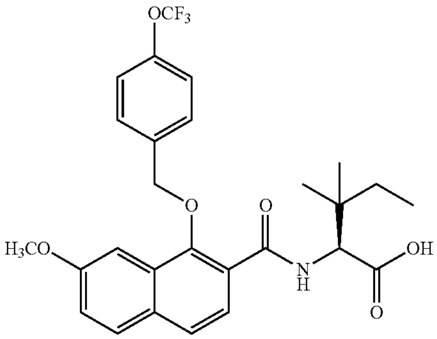 [SMILES: CCC(C)(C)[C@H](NC(=O)c1ccc2ccc(OC)cc2c1OCc1ccc(OC(F)(F)F)cc1)C(=O)O] |
| 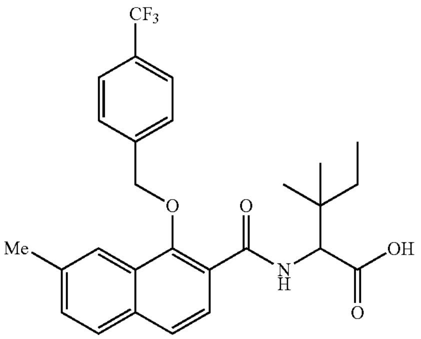 [SMILES: CCC(C)(C)C(NC(=O)c1ccc2ccc(C)cc2c1OCc1ccc(C(F)(F)F)cc1)C(=O)O] |

-continued
| | # |
|---|---|
| 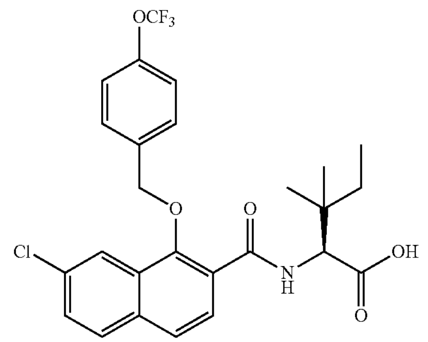 | |
| 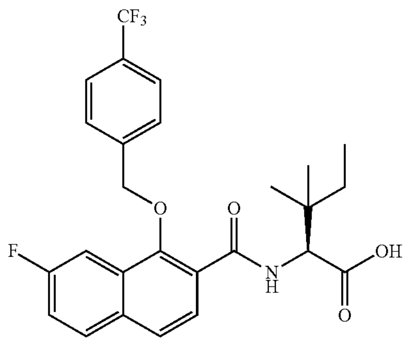 [SMILES: CCC(C)(C)[C@H](NC(=O)c1ccc2ccc(F)cc2c1OCc1ccc(C(F)(F)F)cc1)C(=O)O] | |
| 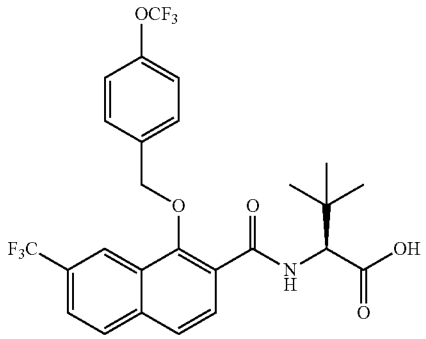 | |
| 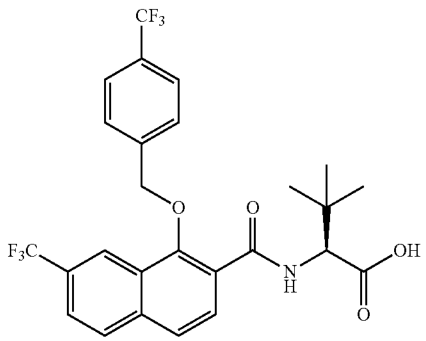 | |
-continued
| | # |
|---|---|
| 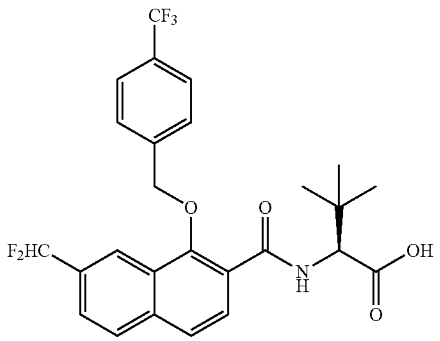 [SMILES: CC(C)(C)[C@H](NC(=O)c1ccc2ccc(C(F)F)cc2c1OCc1ccc(C(F)(F)F)cc1)C(=O)O] | |
| 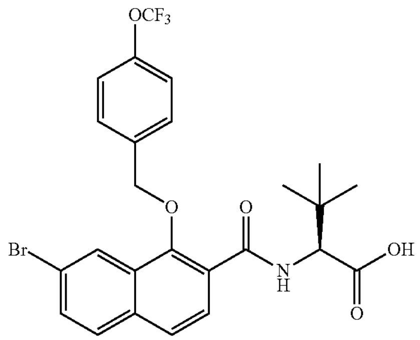 | |
| 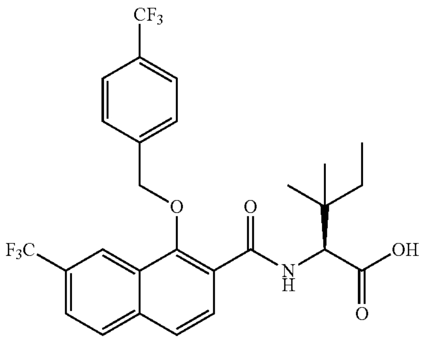 | |
| 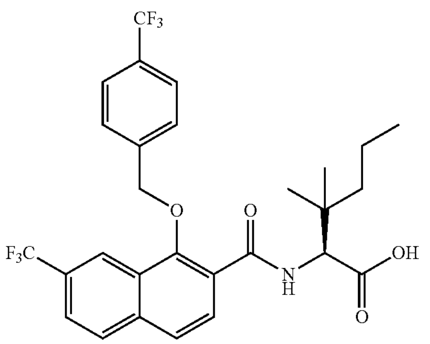 | |

-continued
| # |
|---|
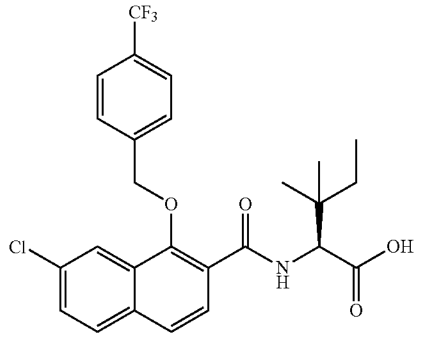
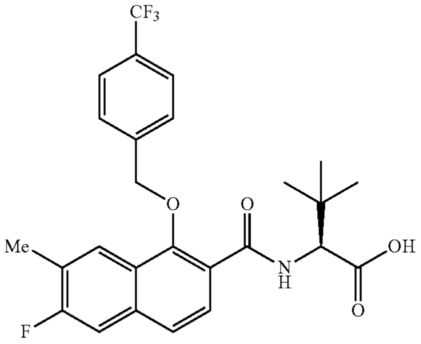 [SMILES: Cc1cc2c(OCc3ccc(C(F)(F)F)cc3)c(C(=O)N[C@H](C(=O)O)C(C)(C)C)ccc2cc1F]
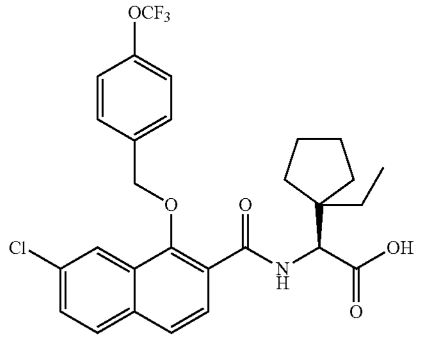
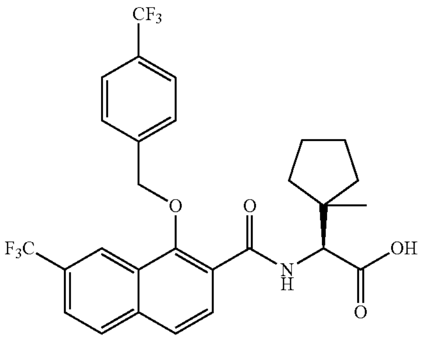 [SMILES: CC1([C@H](NC(=O)c2ccc3ccc(C(F)(F)F)cc3c2OCc2ccc(C(F)(F)F)cc2)C(=O)O)CCCC1]
-continued
| # |
|---|
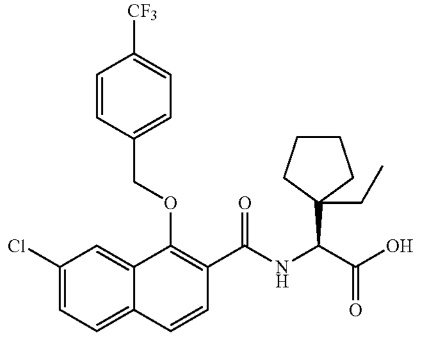 [SMILES: CCC1([C@H](NC(=O)c2ccc3ccc(Cl)cc3c2OCc2ccc(C(F)(F)F)cc2)C(=O)O)CCCC1]
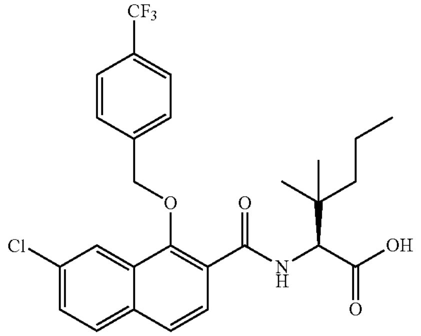 [SMILES: CCCC(C)(C)[C@H](NC(=O)c1ccc2ccc(Cl)cc2c1OCc1ccc(C(F)(F)F)cc1)C(=O)O]
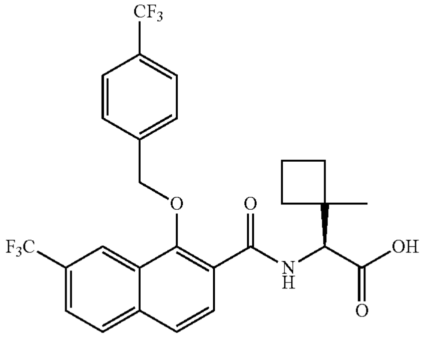 [SMILES: CC1([C@H](NC(=O)c2ccc3ccc(C(F)(F)F)cc3c2OCc2ccc(C(F)(F)F)cc2)C(=O)O)CCC1]
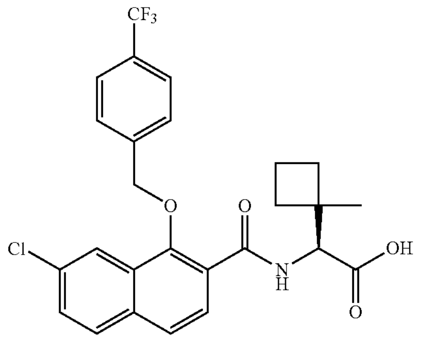 [SMILES: CC1([C@H](NC(=O)c2ccc3ccc(Cl)cc3c2OCc2ccc(C(F)(F)F)cc2)C(=O)O)CCC1]

-continued
| | # |
|---|---|
| 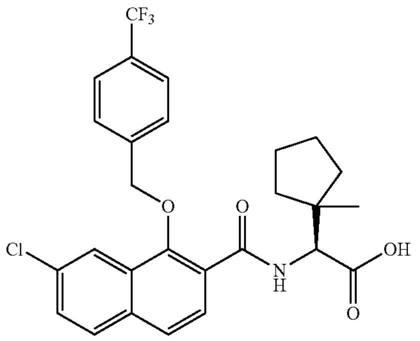 [SMILES: CC1([C@H](NC(=O)c2ccc3ccc(Cl)cc3c2OCc2ccc(C(F)(F)F)cc2)C(=O)O)CCCC1] | |
| 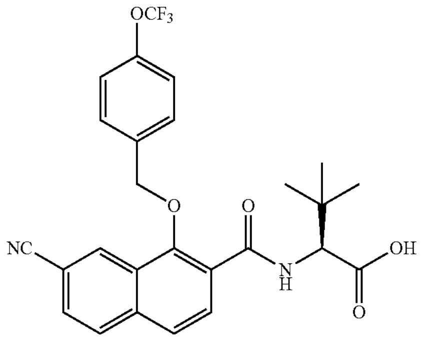 | |
| 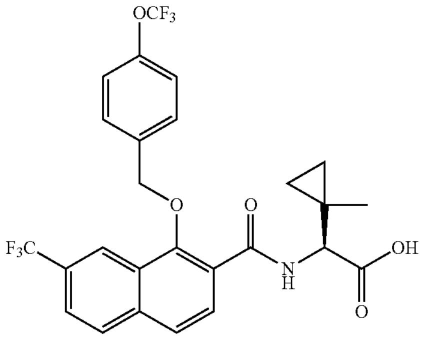 [SMILES: CC1([C@H](NC(=O)c2ccc3ccc(C(F)(F)F)cc3c2OCc2ccc(OC(F)(F)F)cc2)C(=O)O)CC1] | |
| 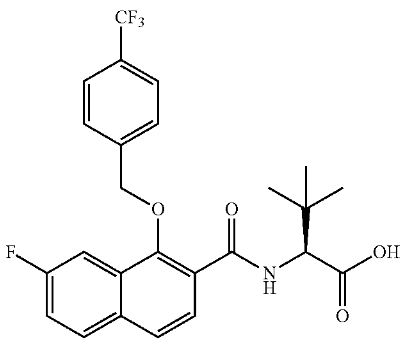 [SMILES: CC(C)(C)[C@H](NC(=O)c1ccc2ccc(F)cc2c1OCc1ccc(C(F)(F)F)cc1)C(=O)O] | |
-continued
| | # |
|---|---|
| 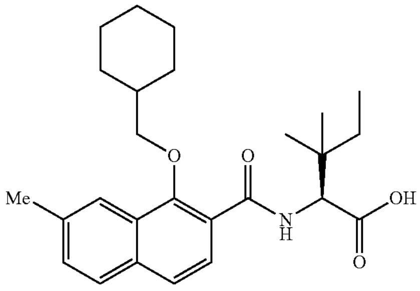 [SMILES: CCC(C)(C)[C@H](NC(=O)c1ccc2ccc(C)cc2c1OCC1CCCCC1)C(=O)O] | |
| 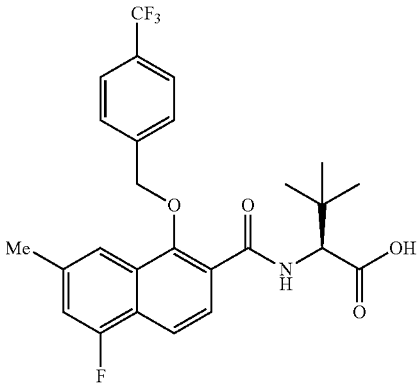 [SMILES: Cc1cc(F)c2ccc(C(=O)N[C@H](C(=O)O)C(C)(C)C)c(OCc3ccc(C(F)(F)F)cc3)c2c1] | |
| 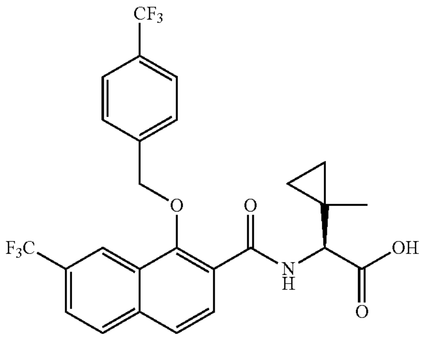 [SMILES: CC1([C@H](NC(=O)c2ccc3ccc(C(F)(F)F)cc3c2OCc2ccc(C(F)(F)F)cc2)C(=O)O)CC1] | |
| 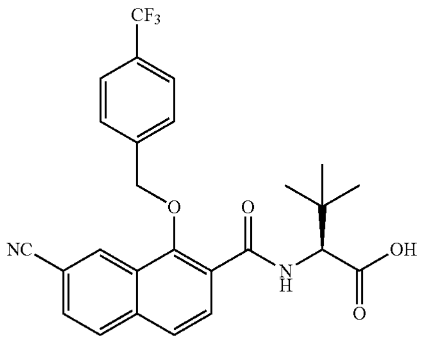 | |

-continued
| # |
| --- |
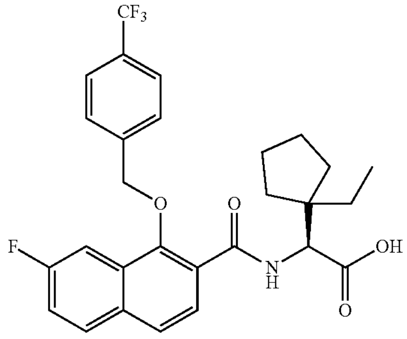 [SMILES: CCC1([C@H](NC(=O)c2ccc3ccc(F)cc3c2OCc2ccc(C(F)(F)F)cc2)C(=O)O)CCCC1]
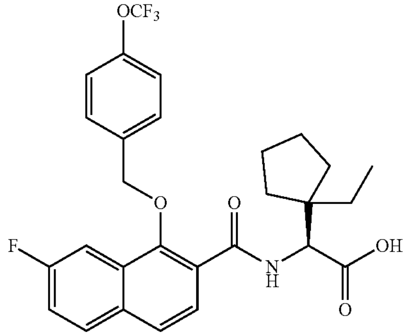 [SMILES: CCC1([C@H](NC(=O)c2ccc3ccc(F)cc3c2OCc2ccc(OC(F)(F)F)cc2)C(=O)O)CCCC1]
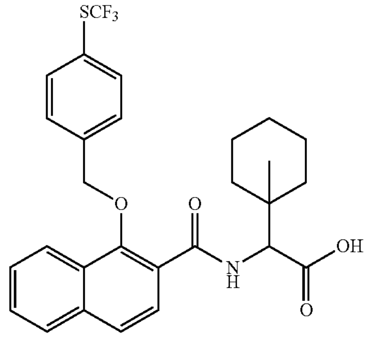
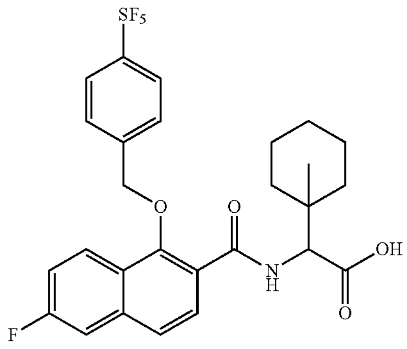
-continued
| # |
| --- |
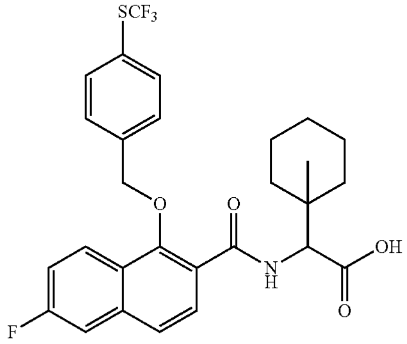
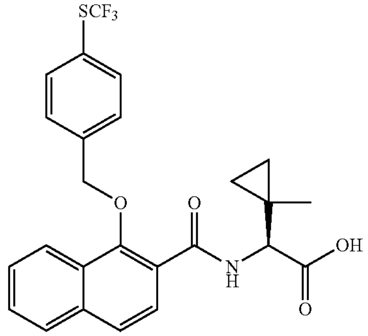
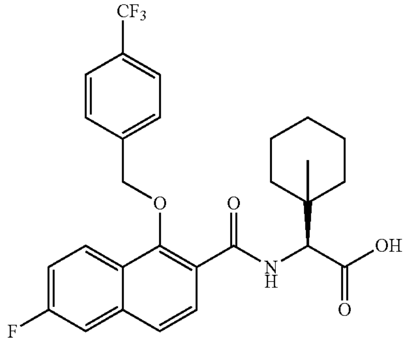
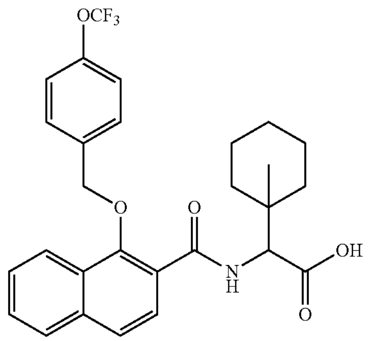

-continued
| # |
|---|
| 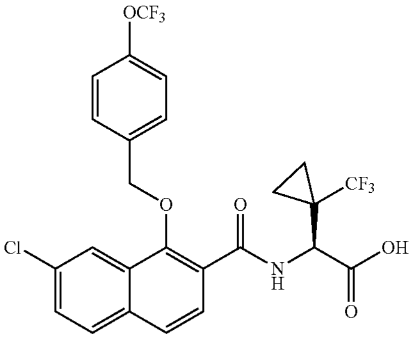 [SMILES: O=C(N[C@H](C(=O)O)C1(C(F)(F)F)CC1)c1ccc2ccc(Cl)cc2c1OCc1ccc(OC(F)(F)F)cc1] |
| 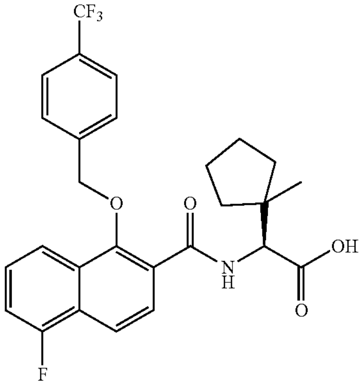 [SMILES: CC1([C@H](NC(=O)c2ccc3c(F)cccc3c2OCc2ccc(C(F)(F)F)cc2)C(=O)O)CCCC1] |
| 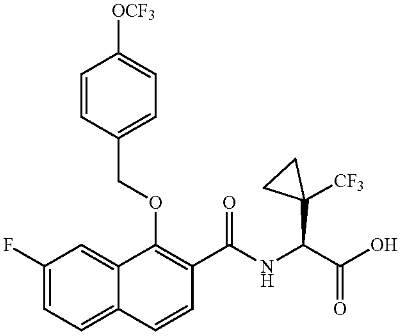 [SMILES: O=C(N[C@H](C(=O)O)C1(C(F)(F)F)CC1)c1ccc2ccc(F)cc2c1OCc1ccc(OC(F)(F)F)cc1] |
| 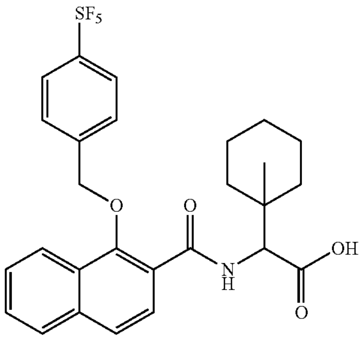 |
-continued
| # |
|---|
| 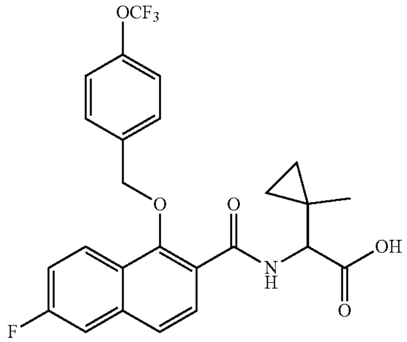 [SMILES: CC1(C(NC(=O)c2ccc3cc(F)ccc3c2OCc2ccc(OC(F)(F)F)cc2)C(=O)O)CC1] |
| 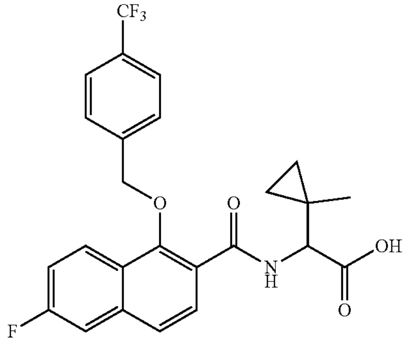 [SMILES: CC1(C(NC(=O)c2ccc3cc(F)ccc3c2OCc2ccc(C(F)(F)F)cc2)C(=O)O)CC1] |
| 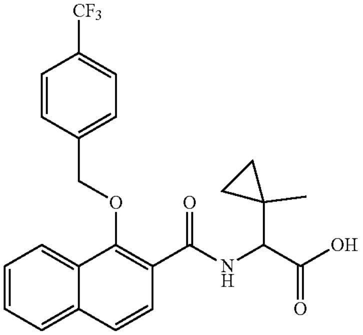 [SMILES: CC1(C(NC(=O)c2ccc3ccccc3c2OCc2ccc(C(F)(F)F)cc2)C(=O)O)CC1] |
| 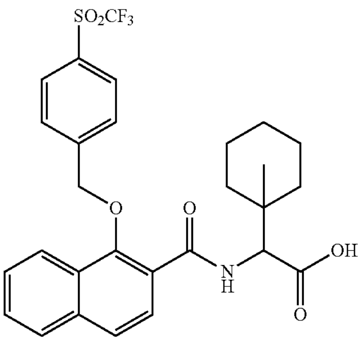

-continued

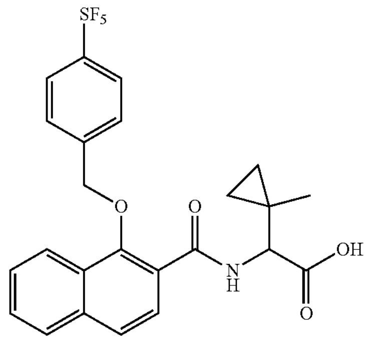
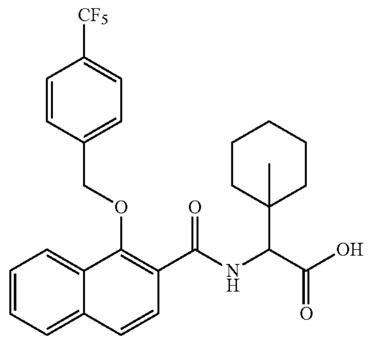
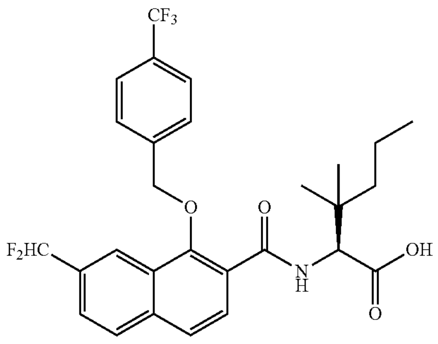 [SMILES: CCCC(C)(C)[C@H](NC(=O)c1ccc2ccc(C(F)F)cc2c1OCc1ccc(C(F)(F)F)cc1)C(=O)O]
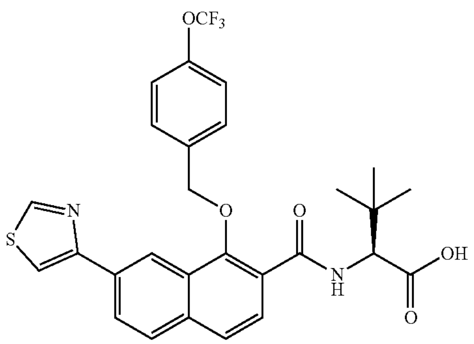
-continued

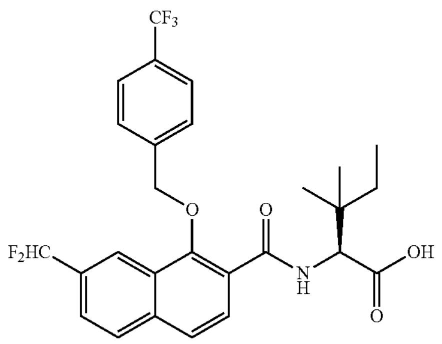
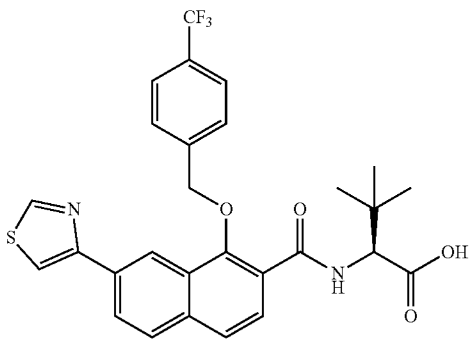 [SMILES: CC(C)(C)[C@H](NC(=O)c1ccc2ccc(-c3cscn3)cc2c1OCc1ccc(C(F)(F)F)cc1)C(=O)O]
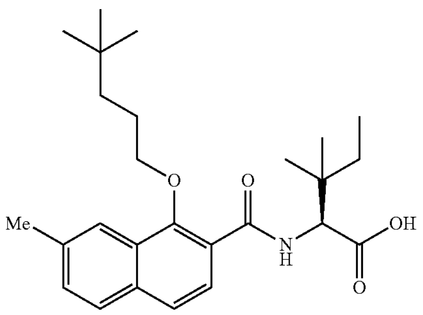 [SMILES: CCC(C)(C)[C@H](NC(=O)c1ccc2ccc(C)cc2c1OCCCC(C)(C)C)C(=O)O]
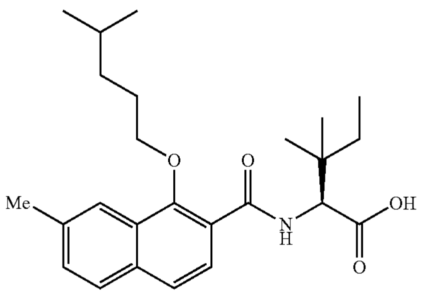 [SMILES: CCC(C)(C)[C@H](NC(=O)c1ccc2ccc(C)cc2c1OCCCC(C)C)C(=O)O]

-continued
| # |
|---|
| 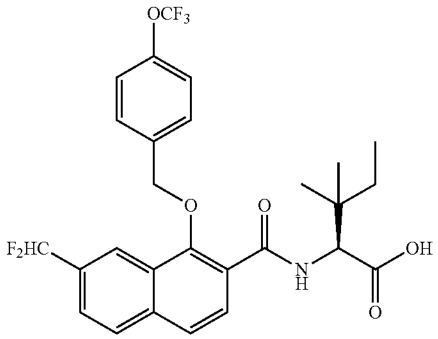 [SMILES: CCC(C)(C)[C@H](NC(=O)c1ccc2ccc(C(F)F)cc2c1OCc1ccc(OC(F)(F)F)cc1)C(=O)O] |
| 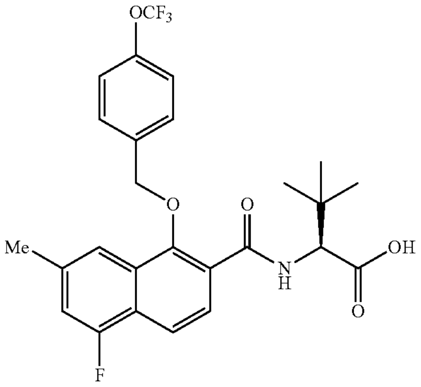 |
| 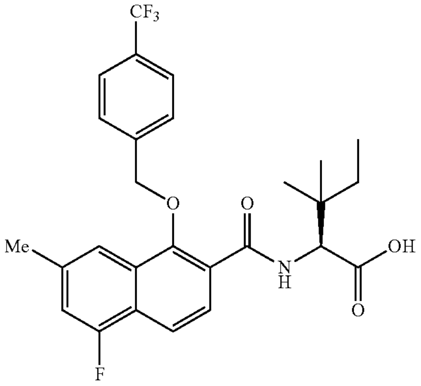 |
| 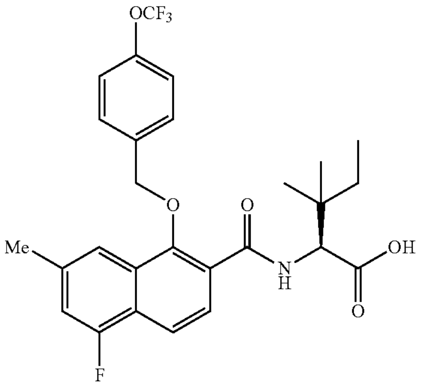 |
-continued
| # |
|---|
| 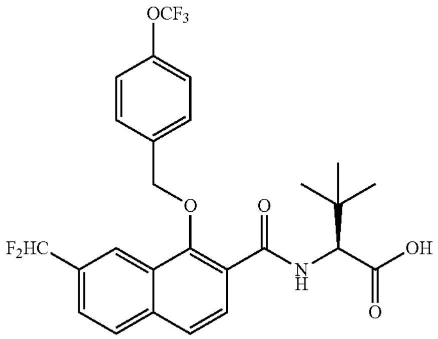 |
| 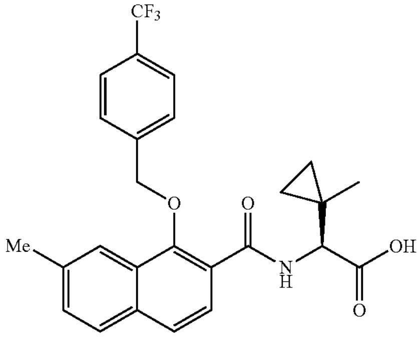 [SMILES: Cc1ccc2ccc(C(=O)N[C@H](C(=O)O)C3(C)CC3)c(OCc3ccc(C(F)(F)F)cc3)c2c1] |
| 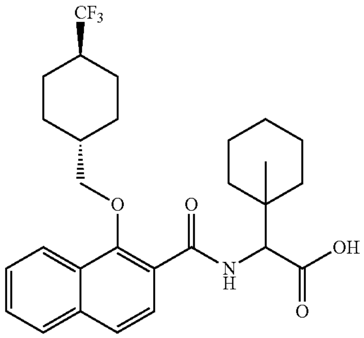 |
| 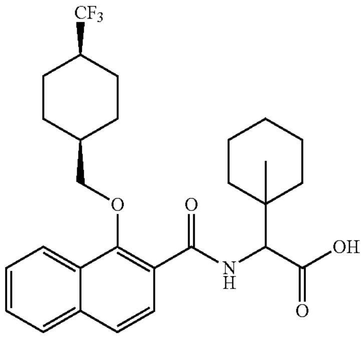 |

| # |
|---|
| 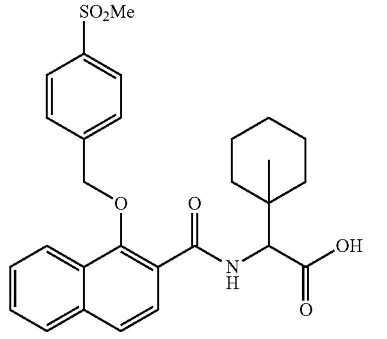 |
| 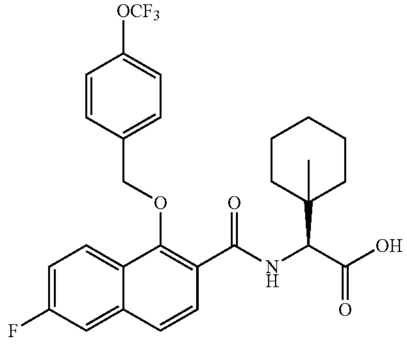 |
| 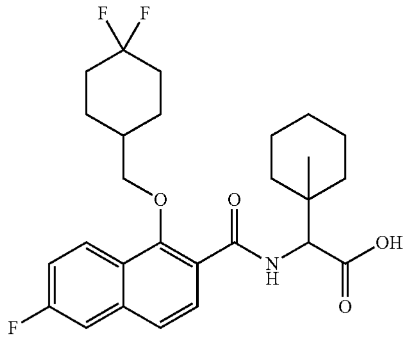 |
| 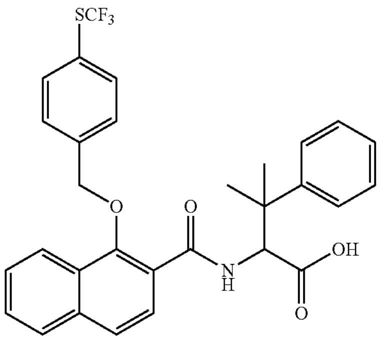 |
| # |
|---|
| 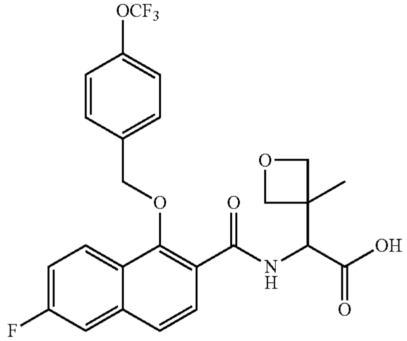 [SMILES: CC1(C(NC(=O)c2ccc3cc(F)ccc3c2OCc2ccc(OC(F)(F)F)cc2)C(=O)O)COC1] |
| 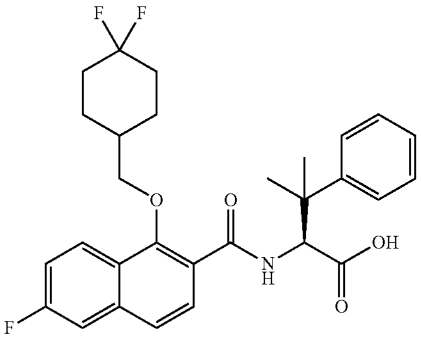 [SMILES: CC(C)(c1ccccc1)[C@H](NC(=O)c1ccc2cc(F)ccc2c1OCC1CCC(F)(F)CC1)C(=O)O] |
| 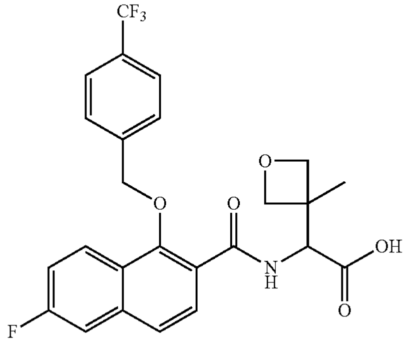 [SMILES: CC1(C(NC(=O)c2ccc3cc(F)ccc3c2OCc2ccc(C(F)(F)F)cc2)C(=O)O)COC1] |
| 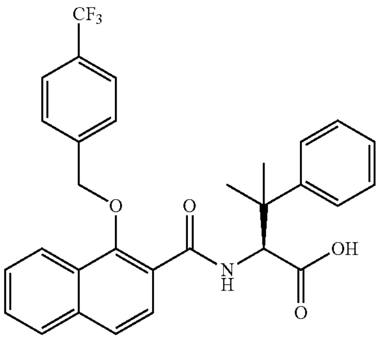 [SMILES: CC(C)(c1ccccc1)[C@H](NC(=O)c1ccc2ccccc2c1OCc1ccc(C(F)(F)F)cc1)C(=O)O] |

-continued
| # |
|---|
| 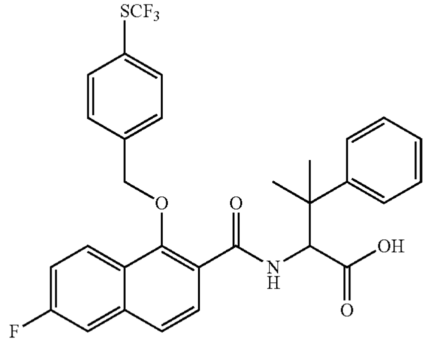 |
| 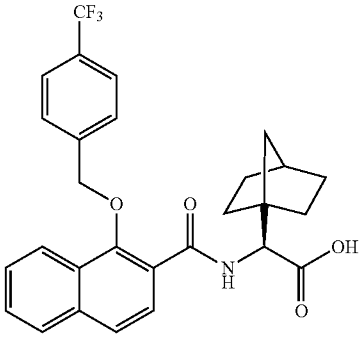 [SMILES: O=C(N[C@H](C(=O)O)C12CCC(CC1)C2)c1ccc2ccccc2c1OCc1ccc(C(F)(F)F)cc1] |
| 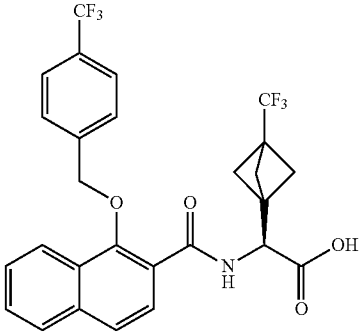 [SMILES: O=C(N[C@H](C(=O)O)C12CC(C(F)(F)F)(C1)C2)c1ccc2ccccc2c1OCc1ccc(C(F)(F)F)cc1] |
| 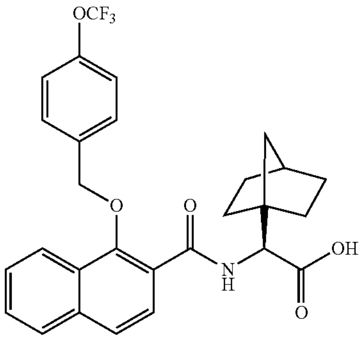 [SMILES: O=C(N[C@H](C(=O)O)C12CCC(CC1)C2)c1ccc2ccccc2c1OCc1ccc(OC(F)(F)F)cc1] |
-continued
| # |
|---|
| 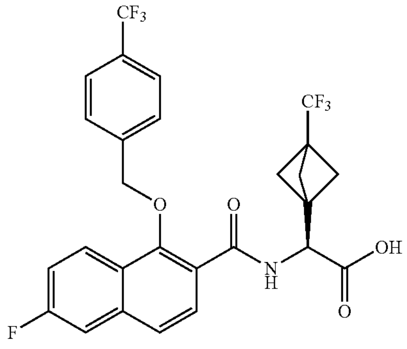 |
| 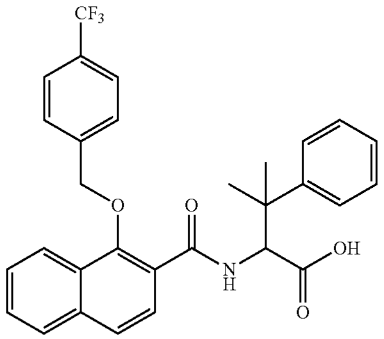 [SMILES: CC(C)(c1ccccc1)C(NC(=O)c1ccc2ccccc2c1OCc1ccc(C(F)(F)F)cc1)C(=O)O] |
| 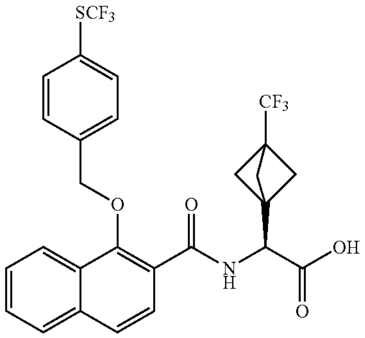 |
| 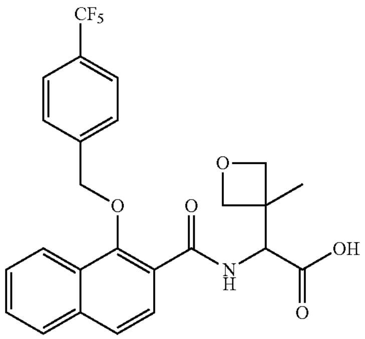 |

-continued
| # |
|---|
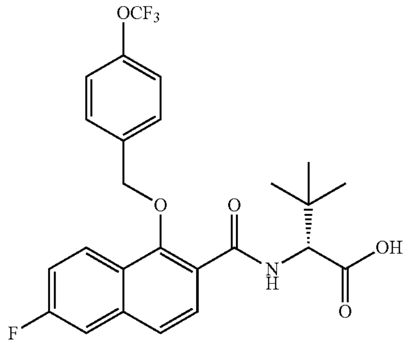 [SMILES: CC(C)(C)[C@@H](NC(=O)c1ccc2cc(F)ccc2c1OCc1ccc(OC(F)(F)F)cc1)C(=O)O]
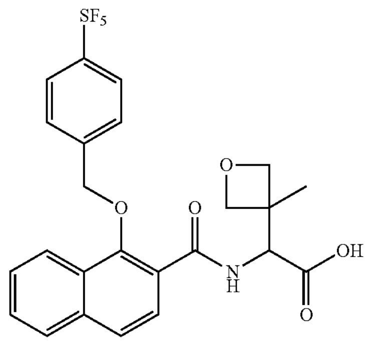
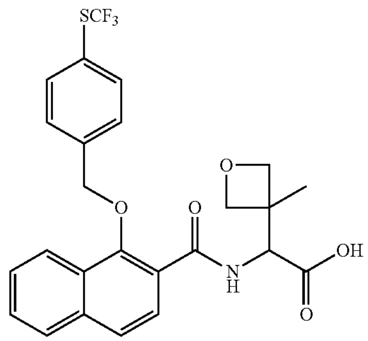
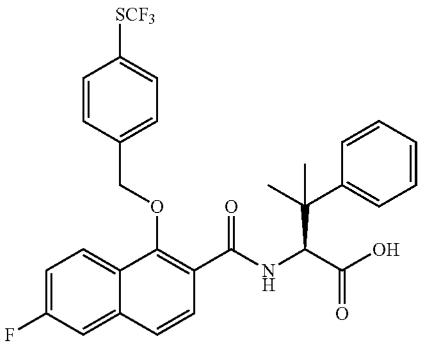
-continued
| # |
|---|
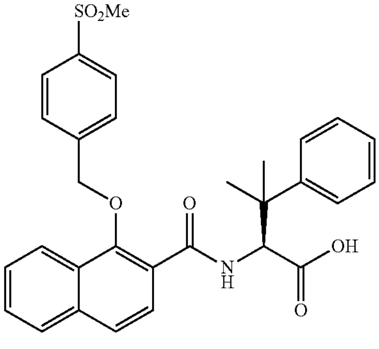 [SMILES: CC(C)(c1ccccc1)[C@H](NC(=O)c1ccc2ccccc2c1OCc1ccc(S(C)(=O)=O)cc1)C(=O)O]
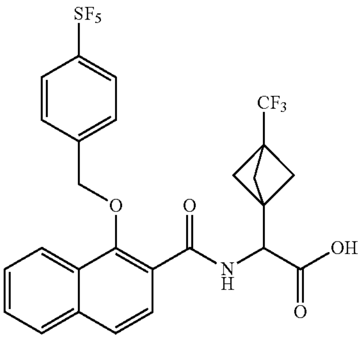
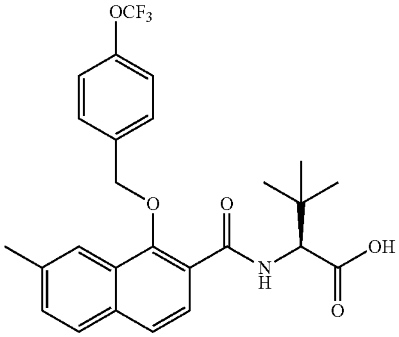 [SMILES: Cc1ccc2ccc(C(=O)N[C@H](C(=O)O)C(C)(C)C)c(OCc3ccc(OC(F)(F)F)cc3)c2c1]
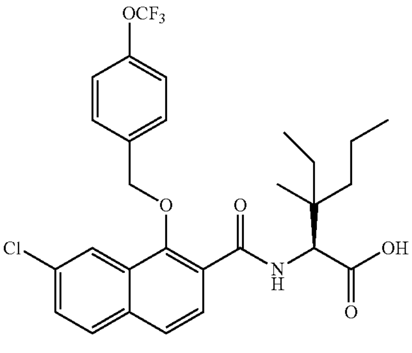 [SMILES: CCCC(C)(CC)[C@H](NC(=O)c1ccc2ccc(Cl)cc2c1OCc1ccc(OC(F)(F)F)cc1)C(=O)O]

-continued
| # |
|---|
| 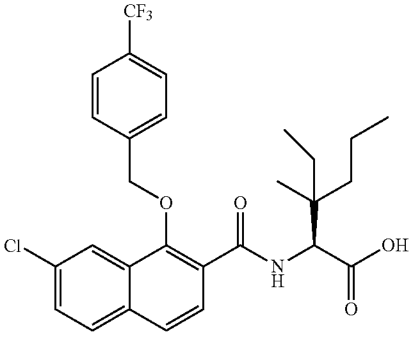 |
| 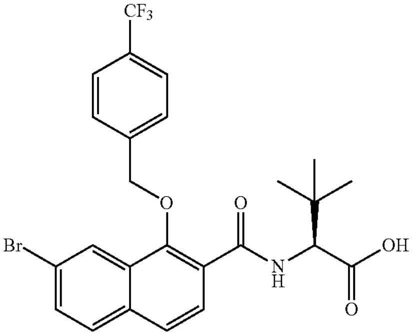 [SMILES: CC(C)(C)[C@H](NC(=O)c1ccc2ccc(Br)cc2c1OCc1ccc(C(F)(F)F)cc1)C(=O)O] |
| 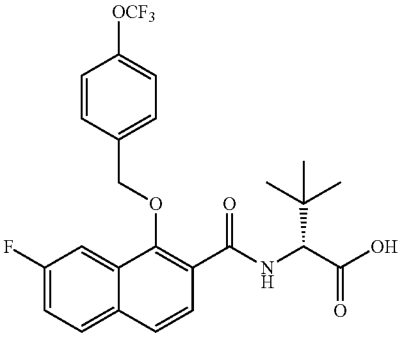 [SMILES: CC(C)(C)[C@@H](NC(=O)c1ccc2ccc(F)cc2c1OCc1ccc(OC(F)(F)F)cc1)C(=O)O] |
| 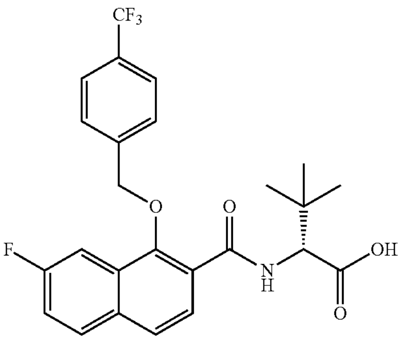 [SMILES: CC(C)(C)[C@@H](NC(=O)c1ccc2ccc(F)cc2c1OCc1ccc(C(F)(F)F)cc1)C(=O)O] |
-continued
| # |
|---|
| 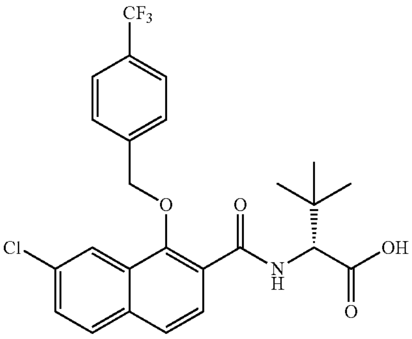 |
| 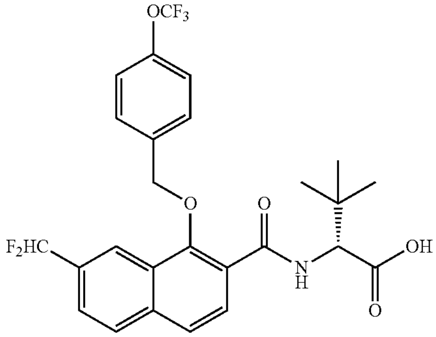 [SMILES: CC(C)(C)[C@@H](NC(=O)c1ccc2ccc(C(F)F)cc2c1OCc1ccc(OC(F)(F)F)cc1)C(=O)O] |
| 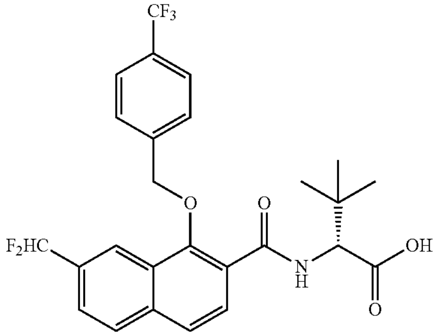 [SMILES: CC(C)(C)[C@@H](NC(=O)c1ccc2ccc(C(F)F)cc2c1OCc1ccc(C(F)(F)F)cc1)C(=O)O] |
| 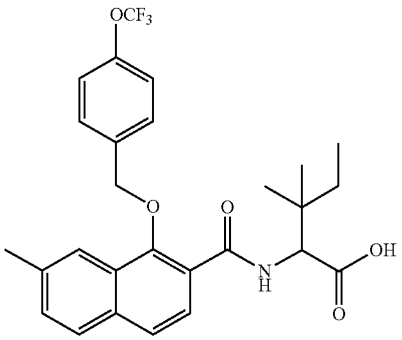 |

-continued
| # |
|---|
| 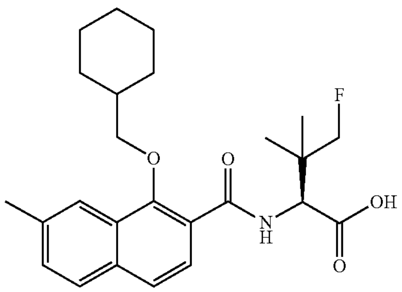 [SMILES: Cc1ccc2ccc(C(=O)N[C@H](C(=O)O)C(C)(C)CF)c(OCC3CCCCC3)c2c1] |
| 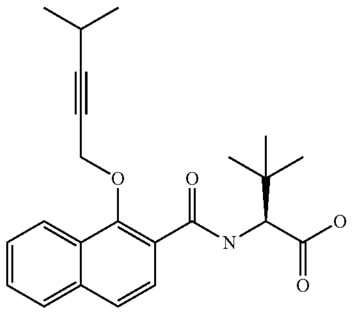 [SMILES: CC(C)C#CCOc1c(C(=O)N[C@H](C(=O)O)C(C)(C)C)ccc2ccccc12] |
| 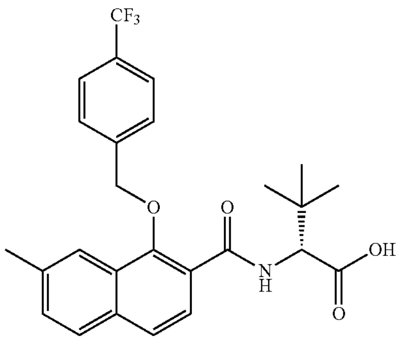 [SMILES: Cc1ccc2ccc(C(=O)N[C@@H](C(=O)O)C(C)(C)C)c(OCc3ccc(C(F)(F)F)cc3)c2c1] |
| 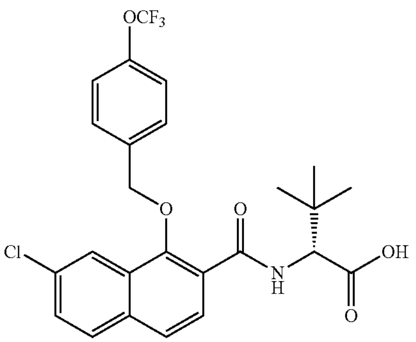 [SMILES: CC(C)(C)[C@@H](NC(=O)c1ccc2ccc(Cl)cc2c1OCc1ccc(OC(F)(F)F)cc1)C(=O)O] |
-continued
| # |
|---|
| 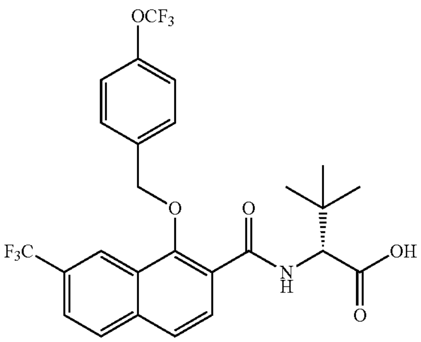 [SMILES: CC(C)(C)[C@@H](NC(=O)c1ccc2ccc(C(F)(F)F)cc2c1OCc1ccc(OC(F)(F)F)cc1)C(=O)O] |
| 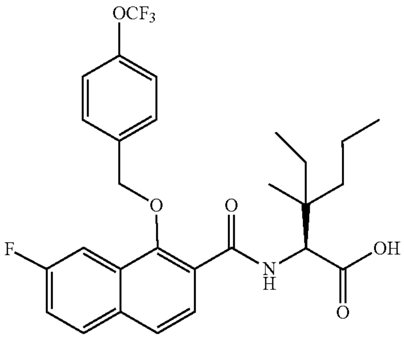 [SMILES: CCCC(C)(CC)[C@H](NC(=O)c1ccc2ccc(F)cc2c1OCc1ccc(OC(F)(F)F)cc1)C(=O)O] |
| 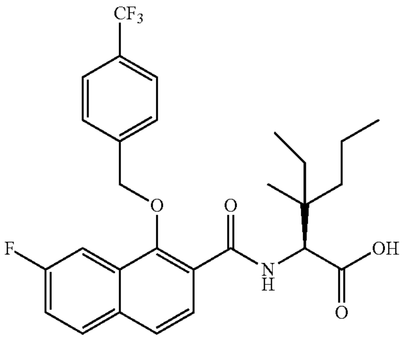 [SMILES: CCCC(C)(CC)[C@H](NC(=O)c1ccc2ccc(F)cc2c1OCc1ccc(C(F)(F)F)cc1)C(=O)O] |
| 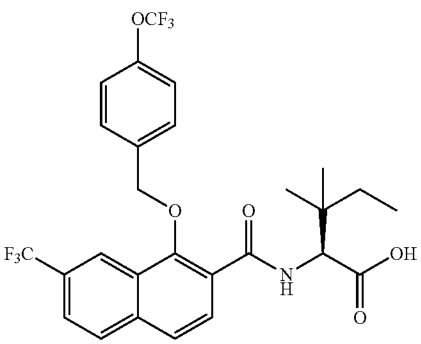 [SMILES: CCC(C)(C)[C@H](NC(=O)c1ccc2ccc(C(F)(F)F)cc2c1OCc1ccc(OC(F)(F)F)cc1)C(=O)O] |

-continued
| # |
|---|
| 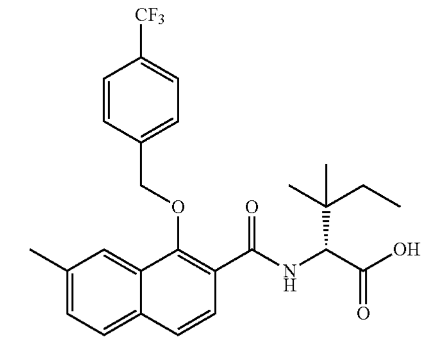 |
| 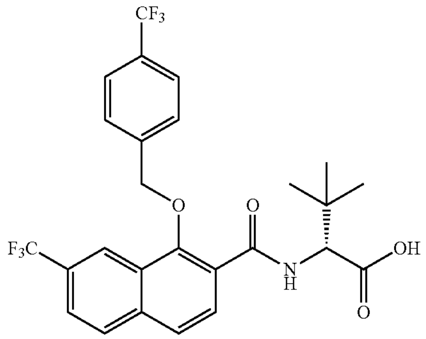 [SMILES: CC(C)(C)[C@@H](NC(=O)c1ccc2ccc(C(F)(F)F)cc2c1OCc1ccc(C(F)(F)F)cc1)C(=O)O] |
| 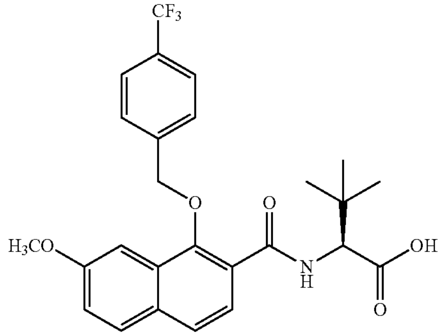 |
| 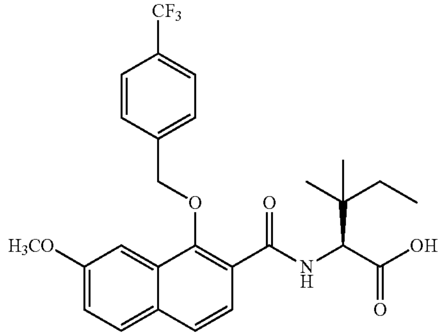 [SMILES: CCC(C)(C)[C@H](NC(=O)c1ccc2ccc(OC)cc2c1OCc1ccc(C(F)(F)F)cc1)C(=O)O] |
-continued
| # |
|---|
| 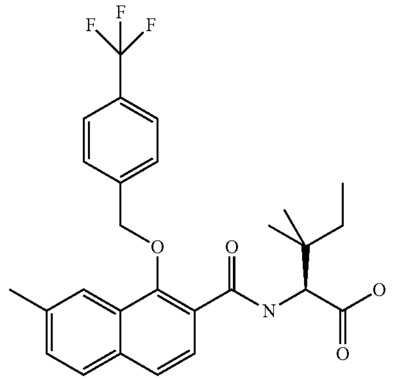 [SMILES: CCC(C)(C)[C@H](NC(=O)c1ccc2ccc(C)cc2c1OCc1ccc(C(F)(F)F)cc1)C(=O)O] |
| 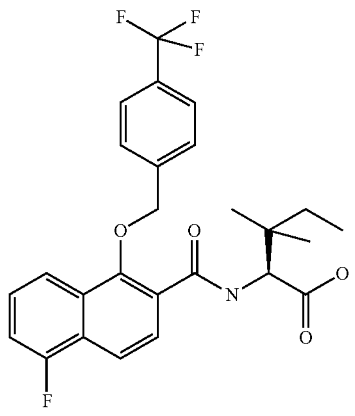 [SMILES: CCC(C)(C)[C@H](NC(=O)c1ccc2c(F)cccc2c1OCc1ccc(C(F)(F)F)cc1)C(=O)O] |
| 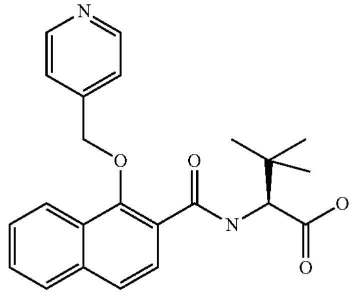 |
| 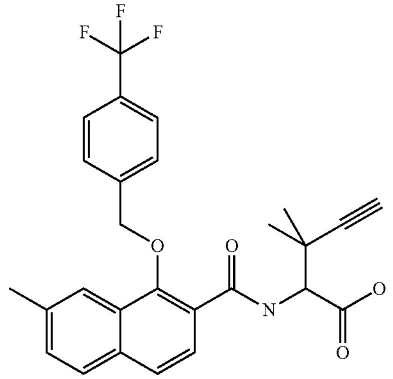 [SMILES: C#CC(C)(C)C(NC(=O)c1ccc2ccc(C)cc2c1OCc1ccc(C(F)(F)F)cc1)C(=O)O] |

-continued
| # |
|---|
| 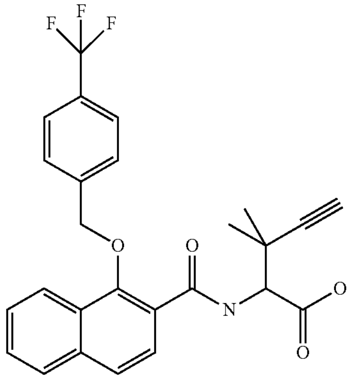 [SMILES: C#CC(C)(C)C(NC(=O)c1ccc2ccccc2c1OCc1ccc(C(F)(F)F)cc1)C(=O)O] |
| 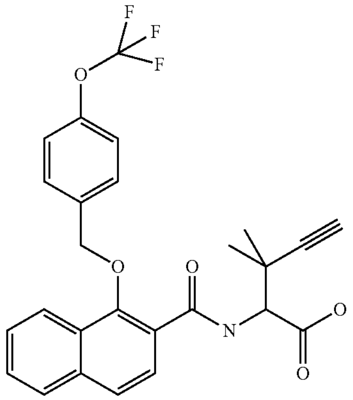 |
| 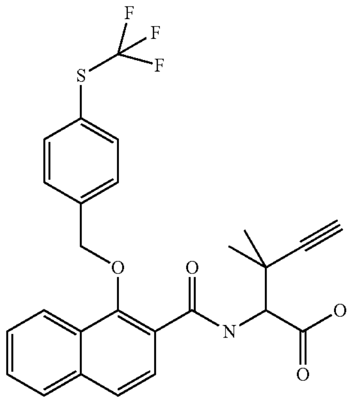 |
| 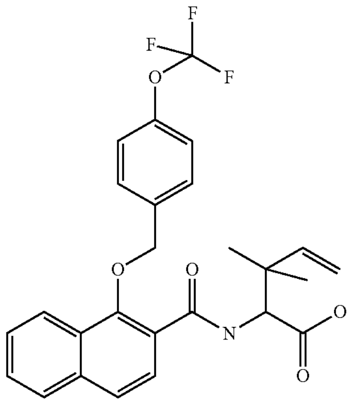 [SMILES: C=CC(C)(C)C(NC(=O)c1ccc2ccccc2c1OCc1ccc(OC(F)(F)F)cc1)C(=O)O] |
-continued
| # |
|---|
| 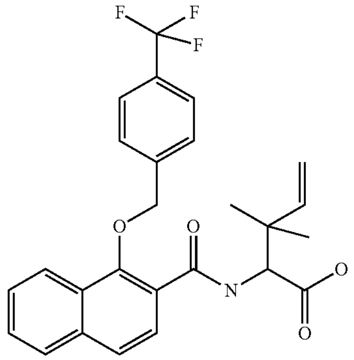 [SMILES: C=CC(C)(C)C(NC(=O)c1ccc2ccccc2c1OCc1ccc(C(F)(F)F)cc1)C(=O)O] |
| 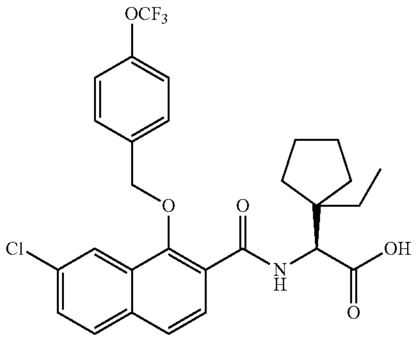 |
| 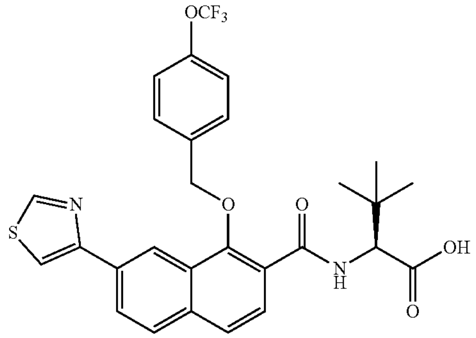 |
| 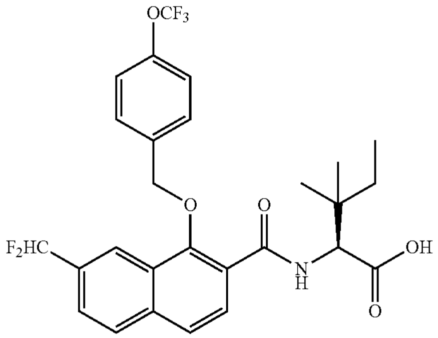 |

-continued

| | # |
|---|---|
| 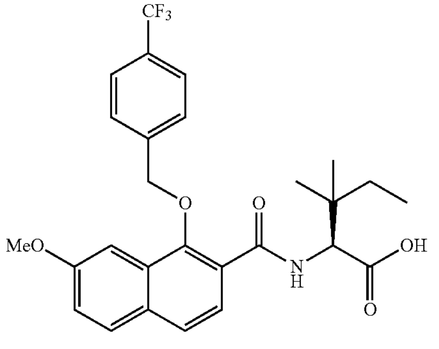 [SMILES: CCC(C)(C)[C@H](NC(=O)c1ccc2ccc(OC)cc2c1OCc1ccc(C(F)(F)F)cc1)C(=O)O] | |
| 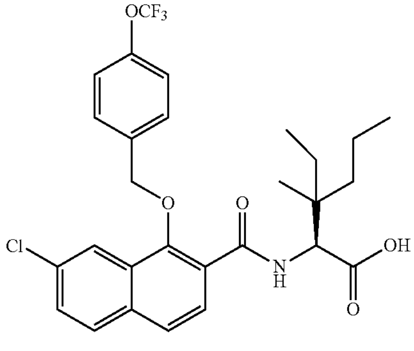 [SMILES: CCCC(C)(CC)[C@H](NC(=O)c1ccc2ccc(Cl)cc2c1OCc1ccc(OC(F)(F)F)cc1)C(=O)O] | |
| 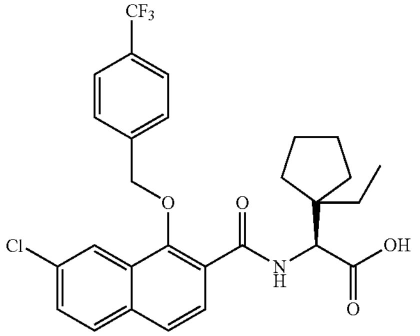 [SMILES: CCC1([C@H](NC(=O)c2ccc3ccc(Cl)cc3c2OCc2ccc(C(F)(F)F)cc2)C(=O)O)CCCC1] | |

or a pharmaceutically acceptable salt thereof.

48. A pharmaceutical composition comprising a compound of claim 1, and a pharmaceutically acceptable carrier or excipient.

49. The pharmaceutical composition of claim 48, further comprising one or more CFTR therapeutic agents.

50. A method of treating deficient CFTR activity in a cell, comprising contacting the cell with a compound of claim 1.

51. The method of claim 50, wherein contacting the cell occurs in a subject in need thereof, thereby treating a CFTR-mediated condition and/or disease.

52. The method of claim 51, wherein the CFTR-mediated condition and/or disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), congenital pneumonia, intestinal malabsorption, celiac disease, nasal polyposis, non-tuberculous mycobacterial infection, pancreatic steatorrhea, intestinal atresia, liver disease, hereditary emphysema, hereditary hemochromatosis, coagulation-fibrinolysis deficiencies, protein C deficiency, Type 1 hereditary angioedema, lipid processing deficiencies, familial hypercholesterolemia, Type 1 chylomicronemia, abetalipoproteinemia, lysosomal storage diseases, I-cell disease/pseudo-Hurler, mucopolysaccharidoses, Sandhoff/Tay-Sachs, Crigler-Najjar type II, polyendocrinopathy/hyperinosemia, Diabetes mellitus, Laron dwarfism, myleoperoxidase deficiency, primary hypoparathyroidism, melanoma, glucanases CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Pelizaeus-Merzbacher disease, neurodegenerative diseases, Alzheimer's disease, Parkinson's disease, amyotrophic lateral sclerosis, progressive supranuclear palsy, Pick's disease, several polyglutamine neurological disorders, Huntington's, spinocerebellar ataxia type I, spinal and bulbar muscular atrophy, dentatorubral pallidoluysian, myotonic dystrophy, spongiform encephalopathies, hereditary Creutzfeldt-Jakob disease, Fabry disease, Straussler-Scheinker syndrome, COPD, dry-eye disease, Sjogren's disease, Osteoporosis, Osteopenia, bone healing and bone growth, bone repair, bone regeneration, reducing bone resorption, increasing bone deposition, Gorham's Syndrome, chloride channelopathies, myotonia congenita, Bartter's syndrome type III, Dent's disease, hyperekplexia, epilepsy, hyperekplexia, lysosomal storage disease, Angelman syndrome, Primary Ciliary Dyskinesia (PCD), PCD with situs *inversus*, PCD without situs *inversus* and ciliary aplasia.

53. The method of claim 51, wherein the CFTR-mediated condition and/or disease is selected from cystic fibrosis, congenital bilateral absence of vas deferens (CBAVD), acute, recurrent, or chronic pancreatitis, disseminated bronchiectasis, asthma, allergic pulmonary aspergillosis, chronic obstructive pulmonary disease (COPD), congenital pneumonia, intestinal malabsorption, celiac disease, nasal polyposis, non-tuberculous mycobacterial infection, pancreatic steatorrhea, intestinal atresia, rhinosinusitis, dry eye disease, protein C deficiency, abetalipoproteinemia, lysosomal storage disease, type 1 chylomicronemia, mild pulmonary disease, lipid processing deficiencies, type 1 hereditary angioedema, coagulation fibrinolysis, hereditary hemochromatosis, CFTR-related metabolic syndrome, chronic bronchitis, constipation, pancreatic insufficiency, hereditary emphysema, and Sjogren's syndrome.

54. The method of claim 51, wherein the CFTR-mediated condition and/or disease is cystic fibrosis.

55. A method of treating cystic fibrosis or a symptom thereof in a subject, comprising administering to the subject a therapeutically effective amount of a compound of claim 1.

56. The method of claim 55, wherein the subject is human.

57. The method according to claim 55, wherein said subject is at risk of developing cystic fibrosis, and wherein said administering step is carried out prior to the onset of symptoms of cystic fibrosis in said subject.

* * * * *